United States Patent [19]

Ménard et al.

[11] 4,378,314

[45] Mar. 29, 1983

[54] ANTIBACTERIAL AGENTS AND METAL CONTAINING AZETIDINONE INTERMEDIATES THEREFORE

[75] Inventors: Marcel Ménard, Aberdeen; Alain Martel, Monette, both of Canada

[73] Assignee: Bristol Myers Company, New York, N.Y.

[21] Appl. No.: 200,362

[22] Filed: Oct. 24, 1980

Related U.S. Application Data

[60] Division of Ser. No. 77,888, Sep. 21, 1979, Pat. No. 4,272,437, which is a continuation-in-part of Ser. No. 968,663, Dec. 18, 1978, abandoned.

[51] Int. Cl.$^3$ ............................................. C07D 205/08
[52] U.S. Cl. ................................................. 260/239 A
[58] Field of Search ..................................... 260/239 A

[56] References Cited

U.S. PATENT DOCUMENTS

| | | | |
|---|---|---|---|
| 3,950,357 | 4/1976 | Kahan | 195/80 R |
| 4,070,477 | 1/1978 | Ernest | 260/239 A |
| 4,155,912 | 5/1979 | Menard | 260/239 A |
| 4,168,314 | 9/1979 | Christensen | 260/239 A |
| 4,182,711 | 1/1980 | Ueda | 424/270 |

FOREIGN PATENT DOCUMENTS

| | | |
|---|---|---|
| 846933 | 4/1977 | Belgium . |
| 2210 | 6/1979 | European Pat. Off. . |
| 3415 | 8/1979 | European Pat. Off. . |
| 3892 | 9/1979 | European Pat. Off. . |
| 10358 | 4/1980 | European Pat. Off. . |
| 13067 | 7/1980 | European Pat. Off. . |
| 13662 | 7/1980 | European Pat. Off. . |
| 2819655 | 11/1978 | Fed. Rep. of Germany . |
| 54-66695 | 8/1977 | Japan . |
| 1467413 | 4/1967 | United Kingdom . |
| 2005246 | 4/1979 | United Kingdom . |
| 2013674 | 8/1979 | United Kingdom . |
| 2037277 | 7/1980 | United Kingdom . |

OTHER PUBLICATIONS

Woodward et al. Acta Pharm. Suecica 14 (Supl) 23 (1977).
Fisher et al. Ann. Reports Med. Chem. 13 239, 243, 244, 248.
Eglington et al. J.C.S. Chem. Comm. 1967, 720.
Brown et al. J.C.S. Chem. Comm. 1977, 359-360.
Sankyo, Derwent 50702C/29 for Japan 55-73684.
Sankyo, Derwent 486480/28 for Japan 55-69591
Sankyo, Derwent 15713C/09 for Japan 55-9034.

*Primary Examiner*—Mark L. Berch
*Attorney, Agent, or Firm*—David M. Morse

[57] ABSTRACT

This invention relates to 2-substituted and 2,6-disubstituted penem compounds of the formula

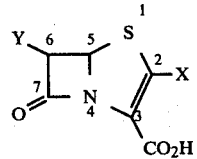

wherein Y is hydrogen, halo or certain organic substituents and X represents certain organic substituents. Also included in the invention are pharmaceutically acceptable salts of the above compounds and derivatives of the above compounds in which the carboxyl group at the 3-position is protected as by an easily removable ester protecting group. The compounds of the present invention are potent antibacterial agents or are of use as intermediates in the preparation of such agents.

4 Claims, No Drawings

ANTIBACTERIAL AGENTS AND METAL CONTAINING AZETIDINONE INTERMEDIATES THEREFORE

CROSS-REFERENCE TO RELATED APPLICATION

This application is a division of our co-pending application Ser. No. 77,888 filed Sept. 21, 1979, now U.S. Pat. No. 4,272,437 which is a continuation-in-part application of application Ser. No. 968,663 filed Dec. 18, 1978, now abandoned.

BACKGROUND OF THE INVENTION

1. Field of the Invention

Novel 2-substituted and 2,6-disubstituted penem compounds are prepared by totally synthetic chemical processes and found to be potent β-lactam antibiotics.

2. Description of the Prior Art

Penicillins and cephalosporins comprise a group of well-known antibacterial agents commonly grouped together as a class called β-lactam antibiotics. Most of the work in this field has been done, broadly speaking, with 6-aminopenicillanic acid (6-APA), 7-aminocephalosporanic acid (7-ACA) and derivatives thereof produced by fermentation or chemical transformation of the natural products. Despite the extensive progress made in preparing active derivatives of 6-APA and 7-ACA, there is a continuing search for synthetic and semi-synthetic routes to new families of β-lactam antibiotics which may possess more advantageous properties than those derived from the known penicillin and cephalosporin nuclei.

Considerable work has been done on total chemical synthesis of both known β-lactams and nuclear analogs of such knowm compounds. Literature publications relating to non-conventional bicyclic β-lactams include the following:

(a) Belgian Pat. No. 846,933 discloses the compound of the formula

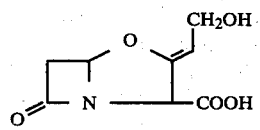

which has been isolated from fermentation of *Streptomyces clavuligerus*. This compound, named clavulanic acid, possesses a low order of antibacterial activity but inhibits the action of certain β-lactamases and reportedly enhances the in vitro and in vivo activity of some penicillins and cephalosporins.

(b) U.K. Pat. No. 1,467,413 discloses the fermentation product having the formula

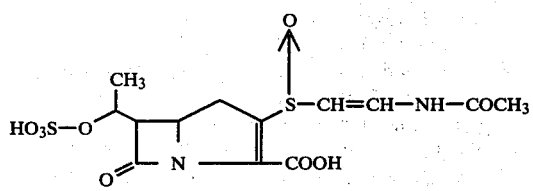

which is reported to possess some antibacterial activity and to be a β-lactamase inhibitor.

(c) Brown, et al. in J.C.S, Chem. Comm., 359–360 (1977) disclose preparation of the compound of the formula

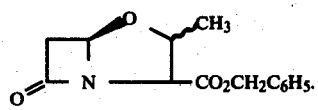

There is no indication from the publication that the compound possesses any antibacterial activity.

(d) Eglington in J.C.S. Chem. Comm., 720 (1977) discloses preparation of the ester of the formula

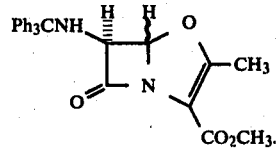

The compound is reported to be a weak inhibitor of β-lactamases.

(e) U.S. Pat. No. 3,950,357 describes a fermentation process for producing thienamycin, the compound of the formula

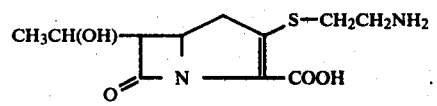

Thienamycin is reported to be a highly potent broad-spectrum antibiotic.

(f) Belgian Pat. No. 849,118 (equivalent U.S. Pat. No. is 4,118,566) discloses a series of 6-amino-2-penem-3-carboxylic acid derivatives of the formula

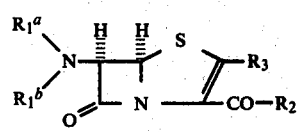

wherein $R_1{}^a$ is hydrogen or an N-protecting group, $R_1{}^b$ is hydrogen or acyl (or $R_1{}^a$ and $R_1{}^b$ taken together are a divalent N-protecting group), —CO—$R_2$ is carboxyl or a protected carboxyl group and $R_3$ is hydrogen or a C-bonded organic group. The compounds and their salts are said to possess antibacterial activity. No compounds are disclosed which do not contain the amino or acylamido moiety at the 6-position of the β-lactam ring.

(g) Acta Pharmaceutica Suecica, 14 (Suppl.), 23–25 (1977) discloses 2,6-disubstituted penems of the formula

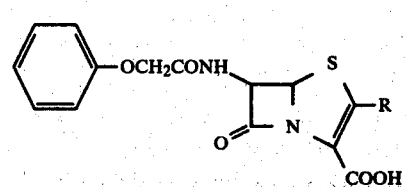

(R not defined)

and reports such penems to be considerably less active than the penicillin and cephalosporin analogs. Also disclosed as antibacterial agents (again without definition of R) are 2-substituted penems of the formula

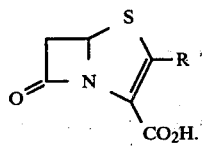

(h) Annual Reports in Medicinal Chemistry, 13, 239–248 (1978) discloses the unsubstituted penem of the formula

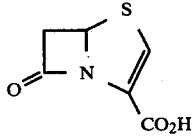

as having no β-lactamase inhibitory activity.

(i) South African Patent 77/6594 discloses 1-carba-2-penem-3-carboxylic acids of the formula

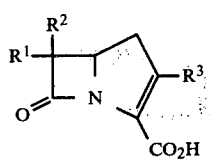

wherein $R^1$, $R^2$ and $R^3$ are independently selected from the group consisting of hydrogen, substituted and unsubstituted; alkyl, alkenyl, cycloalkyl, cycloalkylalkyl, alkylcycloalkyl, aryl, aralkyl, aralkenyl, aralkynyl, heteroaryl, heteroaralkyl, heterocycyl and heterocycylalkyl wherein the substituent or substituents relative to the above-named radicals are selected from the group consisting of amino, hydroxy, alkoxyl, mercapto, alkylthio, arylthio, sulfamoyl, amidino, guanidino, nitro, chloro, bromo, fluoro, cyano and carboxy and wherein the hetero atom in the above-named heterocyclic moiety is selected from the group consisting of oxygen, nitrogen and sulfur. The compounds are reported to have antibiotic activity.

(j) Belgian Pat. No. 866,845 discloses 2-penem compounds of the formula

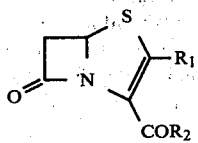

wherein $R_1$=hydrogen or an organic radical (bonded to the ring carbon atom via a carbon atom) or an etherified mercapto group and $R_2$ is hydrogen or a group $R_2^A$ which forms with CO a protected carboxylic group. The disclosed compounds are reported to be antibacterial agents and β-lactamase inhibitors.

SUMMARY OF THE INVENTION

The present invention provides certain novel 2-substituted and 2,6-disubstituted penem compounds which possess potent antibiotic activity. Also provided are various novel intermediates useful in preparing the biologically active penem derivatives and various processes for the production of the intermediates and active compounds.

The penem ring system has the formula

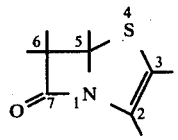

and systematically can be designated as 7-oxo-4-thia-1-azabicyclo[3.2.0]hept-2-ene. For the sake of simplicity, it is named "2-penem" in the present application and the numbering system used is as follows:

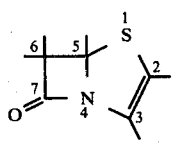

There is thus provided by the present invention the novel penem compounds having the formula

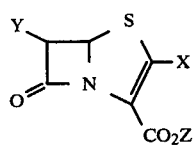

wherein Z is hydrogen or an easily removable ester protecting group; X is
(a) a radical of the formula
 (i) —$OR_a$ in which $R_a$ is hydrogen;
 (ii) —$COR_b$ in which $R_b$ is hydrogen, hydroxy, optionally substituted (lower)alkyl or optionally ring-substituted phenyl or heterocyclic, the substituents on the alkyl group being one or more (preferably 1 or 2) or halo, hydroxy, oxo, carboxy, carb(lower)alkoxy, carbamoyl, (lower)alkoxy, amino, (lower)alkylamino, di(lower)alkylamino, (lower)alkanoylamino or optionally substituted phenyl or heterocyclic and the substituents on the phenyl or heterocyclic rings being one or more (preferably 1 or 2) of hydroxy, (lower)alkoxy, halo, (lower)alkyl, halo(lower)alkyl, methanesulfonyl, oxo, (lower)alkylthio, amino, (lower)alkylamino, di(lower)alkylamino, (lower)alkanoylamino, (lower)alkanoyloxy, carboxy, carboxy(lower)alkyl, sulfo or sulfo(lower)alkyl; or
 (iii) —$OCOR_c$ in which $R_c$ is amino, (lower)alkylamino, di(lower)alkylamino or optionally substituted (lower)alkyl in which the substituents are as defined under (ii); or
(b) a substituted (lower)aliphatic, (lower)cycloaliphatic or (lower)cycloaliphatic(lower)aliphatic radical or a ring-substituted phenyl, phenyl(lower)alkyl, heterocyclic, heterocyclic (lower)alkyl or heterocyclicthio(lower)alkyl radical, substituents for the above-mentioned aliphatic, cycloaliphatic, phenyl or heterocyclic groups being
 (i)

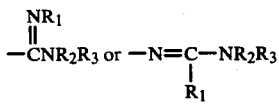

in which $R_1$ is hydrogen, (lower)alkyl or phenyl and $R_2$ and $R_3$ are each independently hydrogen, (lower)alkyl, phenyl or benzyl;

(ii) —$OR_d$ in which $R_d$ is amino, (lower)alkylamino, di(lower)alkylamino, substituted (lower)alkyl, (lower)alkenyl or optionally ring-substituted phenyl, phenyl(lower)alkyl, heterocyclic or heterocyclic (lower)alkyl, the substituents on the alkyl, phenyl and heterocyclic groups being as defined under (a) (ii);

(iii) —$O(CH_2)_nOR_r$ in which n is an integer from 1 to 6 and $R_r$ is optionally substituted (lower)alkyl or optionally ring-substituted phenyl or heterocyclic, the substituents on the alkyl, phenyl or heterocyclic groups being as defined under (a) (ii);

(iv) —$OCOR_r{}'$ in which $R_r{}'$ is amino, (lower)alkylamino, di(lower)alkylamino or $R_r$, with the proviso that $R_r{}'$ may not be unsubstituted (lower)alkyl;

(v) —$OSO_3H$;

(vi)

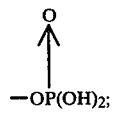

(vii) —$OSO_2R_r$ in which $R_r$ is as defined under (b) (iii);

(viii)

in which $R_e$ is (lower)alkyl and $R_r$ is as defined under (b) (iii);

(ix) —$S(O)_nR_d$ in which n is 0, 1 or 2 and $R_d$ is as defined under (b) (ii) or is in the case where n=0

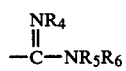

in which $R_4$ is hydrogen or (lower)alkyl and $R_5$ and $R_6$ are each independently hydrogen or (lower)alkyl, with the proviso that $R_d$ may not be unsubstituted phenyl;

(x) —$COR_f$ in which $R_f$ is amino(lower)alkyl, (lower)alkylamino(lower)alkyl, di(lower)alkylamino(lower)alkyl, —$NHNH_2$,

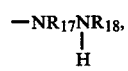

—$NHOR_{19}$, —$S$—$R_{17}$, —$O(CH_2)_n$—$A$—$R_e$ or —$N$—$R_eR_g$ in which $R_{17}$, $R_{18}$ and $R_e$ are (lower)alkyl, $R_{19}$ is hydrogen or (lower)alkyl, A is O, S, NH or $NCH_3$ and n and $R_g$ are as defined under (b) (iii) and (b) (viii);

(xi) —$PO(OR_w)_2$ in which $R_w$ is hydrogen or (lower)alkyl;

(xii) —$NHR_h$ in which $R_h$ is optionally substituted phenyl, optionally substituted heterocyclic, —CH=NH, —$SO_3H$, —OH, (lower)alkoxy, amino, (lower)alkylamino, di(lower)alkylamino, —$NHCOCH_3$, —$CS_2CH_3$, —$SO_2CH_3$,

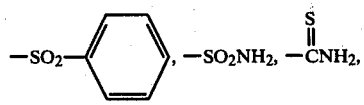

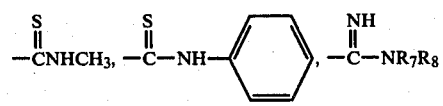

in which $R_7$ and $R_8$ are each independently (lower)alkyl, phenyl or phenyl(lower)alkyl,

in which $R_9$ is (lower)alkyl, phenyl or phenyl(lower)alkyl, or

in which $R_i$ is amino(lower)alkyl, —$NH_2$, (lower)alkylamino, di(lower)alkylamino,

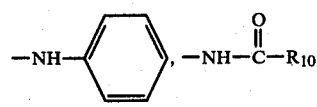

in which $R_{10}$ is (lower)alkyl or optionally substituted phenyl or heterocyclic, the phenyl and heterocyclic substituents being defined under (a) (ii),

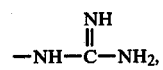

(lower)alkoxy,

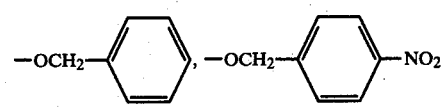

or —$O(CH_2)_2Si(CH_3)_3$;

(xiii)

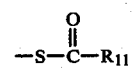

in which $R_{11}$ is (lower)alkyl substituted by amino, (lower)alkylamino or di(lower)alkylamino;

(xiv) —$NR_jR_k$ in which $R_j$ is (lower)alkyl and $R_k$ is (lower)alkyl, (lower)alkoxy, heterocyclic, amino, or

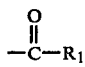

in which $R_i$ is as defined under (b) (xii) or, when taken together with the nitrogen, $R_j$ and $R_k$ represent

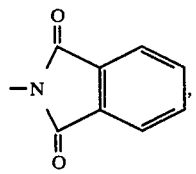

providing that when $R_k$ is amino or —CH$_2$CH$_2$NH$_2$, $R_j$ is methyl and also providing that $R_j$ and $R_k$ may not both be (lower)alkyl;

(xv) —NR$_j'$R$_k'$ in which R$_j'$ is (lower)alkoxy and R$_k'$ is (lower)alkyl, heterocyclic, amino(lower)alkyl, (lower)alkylamino(lower)alkyl, di(lower)alkylamino(lower)alkyl or

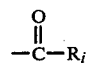

in which $R_i$ is as defined under (b) (xii) or, when taken together with the nitrogen, $R_j'$ and $R_k'$ represent

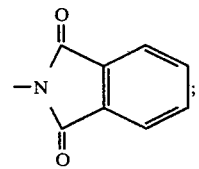

(xvi) —N$^\oplus$R$_l$R$_m$R$_n$ in which R$_l$, R$_m$ and R$_n$ are each independently (lower)alkyl or when taken together with the nitrogen, represent

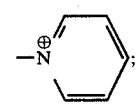

(xvii) —N=CH—R$_x$ in which R$_x$ is (lower)alkyl or optionally ring-substituted phenyl or heterocyclic, the substituents on the phenyl or heterocyclic ring being as defined under (a) (ii);

(xviii) —N=CR$_x$R$_y$ in which R$_y$ is (lower)alkyl or optionally ring-substituted phenyl or heterocyclic, the phenyl and heterocyclic substituents being as defined under (a) (ii), and R$_x$ is as defined under (b) (xvii);

(xix) =N—R$_p$ in which R$_p$ is hydroxy, (lower)alkoxy, amino, di(lower)alkylamino or

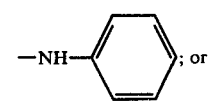

(xx)

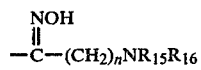

in which n is an integer from 1 to 6 and $R_{15}$ and $R_{16}$ are each independently hydrogen or (lower)alkyl; and Y is hydrogen or a radical selected from the group consisting of (a) optionally substituted (lower)aliphatic, (lower)cycloaliphatic or (lower)cycloaliphatic(lower)aliphatic, the substituents being one or more of hydroxy, (lower)alkoxy, optionally substituted phenyloxy, optionally substituted heterocyclicoxy, optionally substituted (lower)alkylthio, optionally substituted phenylthio, optionally substituted heterocyclicthio, mercapto, amino, (lower)alkylamino, di(lower)alkylamino, (lower)alkanoyloxy, (lower)alkanoylamino, optionally substituted phenyl, optionally substituted heterocyclic, carboxy, carb(lower)alkoxy, carbamoyl, N-(lower)alkylcarbamoyl, N,N-di(lower)alkylcarbamoyl, halo, cyano, oxo, thioxo, —SO$_3$H, —OSO$_3$H, —SO$_2$—(lower)alkyl, (lower)alkylsulfinyl, nitro, phosphono or

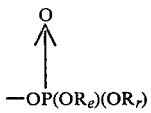

in which R$_e$ and R$_r$ are as defined above, the substituents on the (lower)alkylthio group being one or more of halo, hydroxy, (lower)alkoxy, amino, (lower)alkanoylamino or optionally substituted phenyl or heterocyclic and the phenyl or heterocyclic substituents above being one or more of hydroxy, (lower)alkoxy, halo, (lower)alkyl, halo(lower)alkyl, methanesulfonyl, (lower)alkylthio, amino, (lower)alkanoylamino, (lower)alkanoyloxy, carboxy, carboxy(lower)alkyl, sulfo or sulfo(lower)alkyl;

(b) —OR$_s$ in which R$_s$ is optionally substituted (lower)alkyl or (lower)alkanoyl or optionally substituted phenyl or heterocyclic, the substituents on the alkyl and alkanoyl being one or more of halo, hydroxy, (lower)alkoxy, (lower)alkylamino, di(lower)alkylamino, amino, oxo, (lower)alkanoylamino or optionally substituted phenyl or heterocyclic and the substituents on the phenyl or heterocyclic being one or more of hydroxy, (lower)alkoxy, halo, (lower)alkyl, halo(lower)alkyl, methanesulfonyl, (lower)alkylthio, (lower)alkylamino, di(lower)alkylamino, amino, (lower)alkanoylamino, (lower)alkanoyloxy, carboxy, carboxy(lower)alkyl, sulfo or sulfo(lower)alkyl;

(c) —S(O)$_n$R$_s$ in which n is 0, 1 or 2 and R$_s$ is as defined above;

(d) halo; and (e) optionally substituted phenyl or heterocyclic in which the substituents are one or more of hydroxy, (lower)alkoxy, halo, (lower)alkyl, halo(lower)alkyl, methanesulfonyl, (lower)alkylthio, amino, (lower)alkylamino, di(lower)alkylamino, (lower)alkanoylamino, (lower)alkanoyloxy, carboxy, carboxy(lower)alkyl, sulfo or sulfo(lower)alkyl; or a pharmaceutically acceptable salt thereof, with the proviso that when Y is hydrogen, X may not be —CH$_2$OCH$_2$CH$_2$OCH$_3$.

The compounds of formula I wherein Z is hydrogen (and their pharmaceutically acceptable salts and physiologically hydrolyzed esters) are potent antibacterial agents. The remaining compounds are useful intermediates for preparation of the biologically active penems.

Substituent groups disclosed above for the 2- and 6-positions of the penem ring may be further defined as follows:

(a) Halo includes chlorine, bromine, fluorine and iodine. Preferred halo substituents are chlorine and fluorine;

(b) (Lower)alkyl includes both straight and branched chain saturated aliphatic hydrocarbon radicals having from 1-6 carbon atoms inclusive, e.g. methyl, ethyl, n-propyl, isopropyl, n-butyl, isobutyl, sec-butyl, tert-butyl, n-pentyl, isopentyl, n-hexyl, etc. Preferred (lower)alkyl substituents have from 1-4 carbons and most preferably 1-2 carbons;

(c) (Lower)aliphatic is intended to include acyclic straight and branched chain saturated and unsaturated hydrocarbon radicals having from 1-6 carbon atoms inclusive. The unsaturated radicals may contain one or more double or triple bonds, but preferably contain either one double bond or one triple bond. Examples of (lower)aliphatic are methyl, ethyl, n-propyl, isopropyl, n-butyl, t-butyl, sec-butyl, n-pentyl, isobutyl, vinyl, 1-propenyl, 2-propenyl, isopropenyl, 2-methyl-2-propenyl, ethynyl and 2-propynyl. The most preferred aliphatic radicals are (lower)alkyl as in (b);

(d) (Lower)cycloaliphatic is intended to represent alicyclic saturated and unsaturated hydrocarbon radicals having from 3-8 ring carbon atoms, preferably 3-6 carbon atoms. The unsaturated ring may contain one or more (preferably one) double bond. Examples of this group include cyclopropyl, cyclobutyl, cyclopentyl, cyclohexyl, cycloheptyl, cyclooctyl, cyclopropenyl, cyclopentenyl, 1,3-cyclohexadienyl and cyclohexenyl;

(e) (Lower)cycloaliphatic(lower)aliphatic represents cycloaliphatic-aliphatic radicals having 3-8 carbon atoms (preferably 3-6) in the cycloaliphatic ring and 1-6 carbon atoms (preferably 1-4 and most preferably 1-2) in the aliphatic portion. Examples include cyclopropylmethyl, cyclopropylethyl, cyclopropylpentyl, cyclobutylethyl, cyclopentylmethyl, cyclohexylmethyl, cyclopenylmethyl, cyclopentenylethyl, cyclopropylethenyl, cyclopropylethynyl, etc. The most preferred radicals of this type are cycloalkyl-alkyl in which the cycloalkyl portion contains 3-6 carbons and the alkyl portion contains 1-2 carbons;

(f) (Lower)alkoxy includes C$_1$-C$_6$ alkoxy radicals, the alkyl portion of which being defined as in (b). Examples include methoxy, ethoxy, n-propoxy, isopropoxy, n-butoxy, isobutoxy, sec-butoxy, n-pentyloxy, etc. Preferred are C$_1$-C$_4$ alkoxy and most preferred are C$_1$-C$_2$ alkoxy;

(g) (Lower)alkylthio includes C$_1$-C$_6$ alkylthio radicals in which the alkyl portion is as defined under (b). Examples include methylthio, ethylthio and n-butylthio;

(h) (Lower)alkylamino includes C$_1$-C$_6$ alkylamino radicals in which the alkyl portion is as under (b). Examples are methylamino, ethylamino, n-propylamino and n-butylamino;

(i) Di(lower)alkylamino represents di C$_1$-C$_6$ alkylamino in which each alkyl is as defined under (b). Examples are dimethylamino and diethylamino;

(j) (Lower)alkanoyloxy represents radicals of the formula $$\text{(lower)alkyl}-\overset{\overset{\displaystyle O}{\|}}{C}-O-$$

in which alkyl is as defined under (b);

(k) (Lower)alkanoylamino includes radicals of the formula $$\text{(lower)alkyl}-\overset{\overset{\displaystyle O}{\|}}{C}-NH-$$

in which alkyl is as under (b);

(l) Carb(lower)alkoxy represents $$-\overset{\overset{\displaystyle O}{\|}}{C}-\text{(lower)alkoxy}$$

in which (lower)alkoxy is as under (f);

(m) Halo(lower)alkyl represents alkyl radicals in which one or more hydrogen atoms are replaced by a halogen atom;

(n) Sulfo(lower)alkyl represents —(CH$_2$)$_n$SO$_3$H in which n is 1-6;

(o) Carboxy(lower)alkyl represents —(CH$_2$)$_n$COOH in which n is 1-6;

(p) Phenyl(lower)alkyl represents $$-(CH_2)_n-\!\!\!\!\bigcirc$$

in which n is 1-6;

(q) (Lower)alkylamino(lower)alkyl represents —(CH$_2$)$_n$NH—(lower)alkyl in which n is 1-6 and alkyl is as defined under (b);

(r) Di(lower)alkylamino(lower)alkyl represents $$-(CH_2)_nN\begin{matrix}\nearrow\text{(lower)alkyl}\\ \searrow\text{(lower)alkyl}\end{matrix}$$

in which n is 1-6 and each alkyl is as defined under (b);

(s) (Lower)alkanoyl represents $$\text{(lower)alkyl}-\overset{\overset{\displaystyle O}{\|}}{C}-$$

in which alkyl is as under (b);

(t) N-(Lower)alkylcarbamoyl represents $$\text{(lower)alkyl}-HN-\overset{\overset{\displaystyle O}{\|}}{C}-$$

in which alkyl is as under (b);

(u) N,N-Di(lower)carbamoyl represents

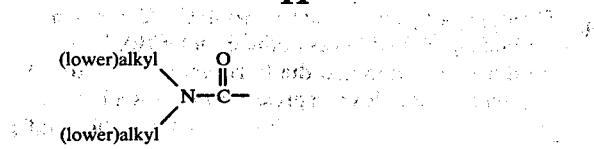

in which each alkyl is as under (b);
(v) Amino(lower)alkyl represents —(CH$_2$)$_n$NH$_2$ in which n is 1-6;
(w) Hydroxyamino(lower)alkyl represents —(CH$_2$)$_n$N-HOH in which n is 1-6;
(x) (Lower)alkylsulfinyl represents

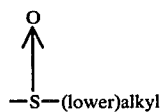

in which (lower)alkyl is as defined above under (b); and
(y) (lower)alkenyl represents straight or branched unsaturated aliphatic hydrocarbon radicals containing one double bond and having from 2-6 carbon atoms inclusive, e.g. vinyl, allyl, isopropenyl, 2- or 3-methallyl or 3-butenyl.

The term "heterocyclic" as used herein is intended to include heteromonocyclic and heterobicyclic residues of aromatic character as well as appropriate partially or wholly saturated residues, said heterocyclic residues containing at least one heteroatom selected from oxygen, sulfur and nitrogen and being bonded to the penem ring carbon atom via a ring carbon atom. The preferred heterocyclic groups are either 5- or 6-membered monocyclic radicals or fused 6,6 or 5,6 bicyclic radicals. Illustrative of suitable heterocyclic radicals are the following:

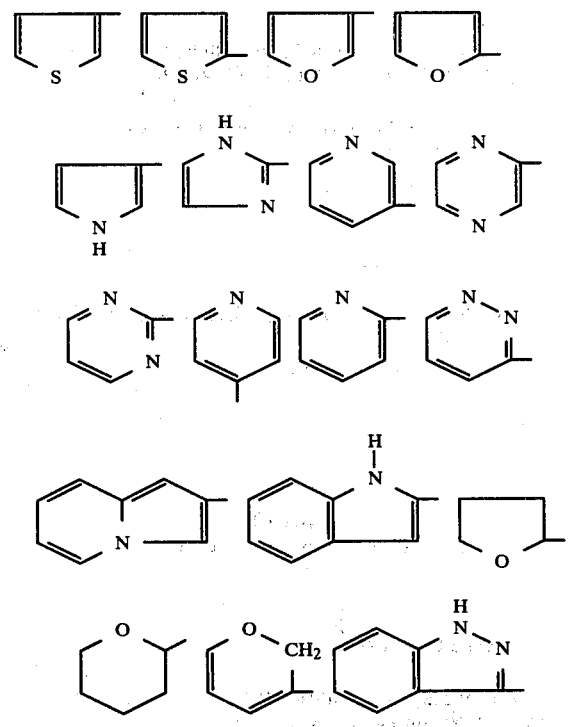

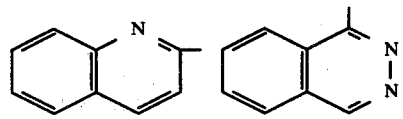

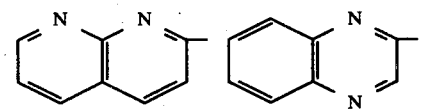

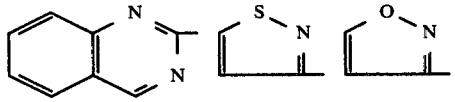

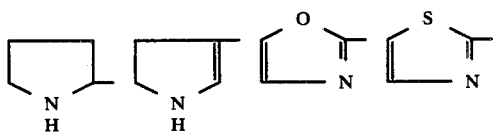

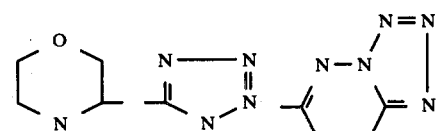

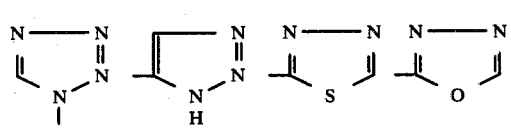

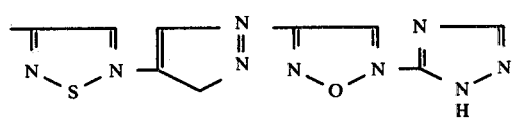

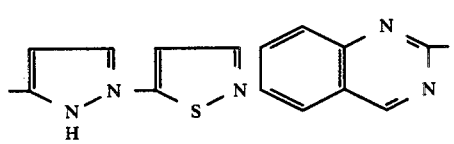

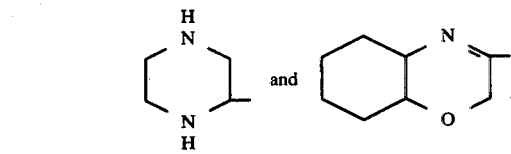

Similarly, the terms heterocyclic-(lower)alkyl, heterocyclicthio-(lower)alkyl, heterocyclicoxy and heterocyclic-thio represent —(CH$_2$)$_n$—Heterocyclic, —(CH$_2$)$_n$—S—Heterocyclic, —O—Heterocyclic and —S—Heterocyclic, respectively, in which n is 1∝6 (preferably 1 or 2).

Since an asymmetric carbon atom is present in the 2-substituted compounds of formula I, such compounds may exist either in the form of racemic mixtures (R,S form) or as the individual dextrorotatory and levorotatory (R- and S- forms) optical isomers. Preferred are the compounds in which the configuration of the 5-carbon atom corresponds to that of natural penicillin (5R-configuration). Substituents at the 5- and 6-positions of the 2,6-disubstituted penems may be in the cis or trans position in relation to one another. Where the penem 6-substituent contains an asymmetric carbon atom, the resulting isomers are identified herein as isomers A, B, C and D (see Example 58 for stereochemistry). The preferred isomer in compounds of this type is isomer B. Separation of the various optical and geometric isomers may be carried out by conventional separation and resolution procedures well-known to those skilled in the art.

The present invention is intended to include the compounds of formula I in the form of isomer mixtures and also in the form of the individual separated and resolved isomers.

The pharmaceutically acceptable salts referred to above include the nontoxic carboxylic acid salts, e.g. nontoxic metallic salts such as sodium, potassium, calcium, aluminum and magnesium, the ammonium salt and salts with nontoxic amines such as trialkylamines (triethylamine), procaine, dibenzylamine, N-benzyl-$\beta$-phenethylamine, 1-ephenamine, N,N'-dibenzylethylenediamine, N-alkylpiperidine and other amines which have been used to form salts of penicillins and cephalosporins. When a basic group is present, the present invention also includes the pharmaceutically acceptable acid addition salts, e.g. salts with mineral acids such as hydrochloric, hydrobromic, hydroiodic, phosphoric, sulfuric or with suitable organic carboxylic acids or sulfonic acids such as trifluoroacetic, p-toluenesulfonic, maleic, acetic, citric, oxalic, succinic, benzoic, tartaric, fumaric, mandelic, ascorbic and malic. Compounds containing an acid group and a basic group can also be in the form of inner salts, i.e. a zwitterion. Preparation of the above-described salts may be carried out according to conventional procedures for forming salts of $\beta$-lactam antibiotics such as penicillins and cephalosporins.

The term "easily removable ester protecting group" is one which has acquired a definite meaning within the $\beta$-lactam and peptide art. Many such groups are known which are used to protect the carboxyl group during subsequent chemical reactions and which may later be removed by standard methods to give the free carboxylic acid. Known ester protecting groups include 2,2,2-trichloroethyl, tertiary alkyl of from 4–6 carbon atoms, tertiary alkenyl of from 5–7 carbon atoms, tertiary alkynyl of from 5–7 carbon atoms, alkoxymethyl, alkanoylmethyl of from 2–7 carbon atoms, N-phthalimidomethyl, benzoylmethyl, halobenzoylmethyl, benzyl, p-nitrobenzyl, o-nitrobenzyl, benzhydryl, trityl, trimethylsilyl, triethylsilyl, $\beta$-trimethylsilylethyl, and the like. Choice of an ester protecting group is dependent on the subsequent reaction conditions the group must withstand and the conditions desired for removing it. Selection of a suitable group is well within the ability of one skilled in the art. For use as a chemical intermediate the most preferred ester is the p-nitrobenzyl ester which can be readily removed by catalytic hydrogenation. For preparation of compounds containing functional groups reducible under such removal conditions, a preferred alternative is the $\beta$-trimethylsilylethyl ester removable by treatment with fluoride ions. Also included within the scope of easily removable ester protecting groups are physiologically cleavable esters, i.e. those esters known in the penicillin and cephalsporin art to be easily cleaved within the body to the parent acid. Examples of such physiologically cleavable esters include indanyl, phthalidyl, methoxymethyl, glycyloxymethyl, phenylglycyloxymethyl, thienylglycyloxymethyl or acyloxymethyl of the formula $$-CH_2C-Y'$$
$$\parallel$$
$$O$$

in which Y' is $C_1$–$C_4$ alkyl or phenyl. Particularly preferred esters of this type are methoxymethyl, acetoxymethyl, pivaloyloxymethyl, phthalidyl and indanyl.

It will be appreciated that the compounds of formula I may exist in various states of solvation and the anhydrous as well as solvated (including hydrates) forms are intended to be within the scope of the invention.

With respect to the compounds of formula I, the preferred compounds are those wherein Y is hydrogen or (lower)alkyl optionally substituted (preferably at the $\alpha$-carbon) by hydroxy. More preferred compounds within the above group are those wherein Y is hydroxy, ethyl or $\alpha$-hydroxyethyl. Still more preferred compounds of formula I are those wherein Y is hydrogen or $\alpha$-hydroxyethyl. The most preferred compounds are those wherein Y is $\alpha$-hydroxyethyl.

A preferred embodiment of the present invention consists of the compounds of formula I wherein substituent X is a substituted (lower)aliphatic, (lower)cycloaliphatic or (lower)cycloaliphatic(lower)aliphatic radical or a ring-substituted phenyl, phenyl(lower)alkyl, heterocyclic, heterocyclic(lower)alkyl or heterocyclicthio(lower)alkyl radical, the substituents for the above-named aliphatic, cycloaliphatic, cycloaliphatic-aliphatic, phenyl, phenylalkyl, heterocyclic, heterocyclicalkyl and heterocyclicthioalkyl radicals being $$\begin{array}{c} NR_1 \\ \parallel \\ -CNR_2R_3 \text{ or } -N=C-NR_2R_3 \\ | \\ R_1 \end{array}$$

in which $R_1$ is hydrogen, (lower)alkyl or phenyl and $R_2$ and $R_3$ are each independently hydrogen, (lower)alkyl, phenyl or benzyl. Within this class, the preferred compounds are those wherein Y is hydrogen, ethyl or $\alpha$-hydroxyethyl, especially those wherein Y is hydrogen or $\alpha$-hydroxyethyl and most especially those wherein Y is $\alpha$-hydroxyethyl.

Another preferred embodiment of the present invention consists of the compounds of formula I wherein X is a substituted (lower)aliphatic, (lower)cycloaliphatic or (lower)cycloaliphatic(lower)aliphatic radical or a ring-substituted phenyl, phenyl(lower)alkyl, heterocyclic, heterocyclic(lower)alkyl or heterocyclicthio(lower)alkyl radical, the substituents on the above-mentioned aliphatic, cycloaliphatic, cycloaliphatic-aliphatic, phenyl, phenylalkyl, heterocyclic, heterocyclicalkyl or heterocyclicthioalkyl radicals being $$-COR_f$$

in which $R_f$ is amino(lower)alkyl, (lower)alkylamino(lower)alkyl, di(lower)alkylamino(lower)alkyl, $-NHNH_2$, $-NR_{17}NR_{18}$, $-NHOR_{19}$, $-SR_{17}$, $-O(CH_2)_n-A-R_e$ or $-NR_eR_g$ in which $R_{17}$, $R_{18}$, $R_e$ and $R_g$ are (lower)alkyl, $R_{19}$ is hydrogen or (lower)alkyl, A is O, S, NH or $NCH_3$ and n is an integer from 1 to 6. Within this class, the preferred compounds are those wherein Y is hydrogen, ethyl or $\alpha$-hydroxyethyl, especially those wherein Y is hydrogen or $\alpha$-hydroxyethyl and most especially those wherein Y is α-hydroxyethyl.

Still another preferred embodiment of the present invention consists of the compounds of formula I wherein X is (a)

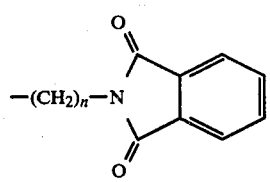

in which n is an integer from 1 to 6, preferably 1 to 4;

(b) —(CH₂)ₙNHOH in which n is an integer from 1 to 6, preferably 1 to 4;

(c) —(CH₂)ₙPO(O—C₁–C₆ alkyl)₂ in which n is an integer from 1 to 6, preferably 1 to 4 and alkyl is preferably methyl, ethyl or isopropyl;

(d)

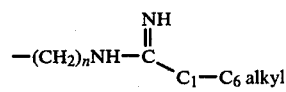

in which n is an integer from 1 to 6, preferably 1 to 4, and alkyl is preferably methyl or ethyl;

(e)

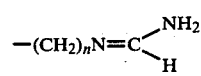

in which n is an integer from 1 to 6, preferably 1 to 4;

(f)

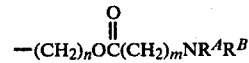

in which n and m are each independently 1 or 2 and $R^A$ and $R^B$ are each independently hydrogen or (lower)alkyl; or (g)

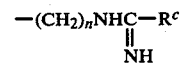

in which n is an integer of 1 to 6, preferably 1 to 4, and $R^c$ is C₁–C₄ alkyl (preferably methyl or ethyl), phenyl or

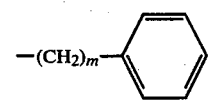

in which m is 1 or 2.

Within this class of compounds, the preferred members are those wherein Y is hydrogen, ethyl or α-hydroxyethyl, preferably those wherein Y is hydrogen or α-hydroxyethyl and most preferably those wherein Y is α-hydroxyethyl.

Other preferred embodiments of the present invention include the intermediates of the formulae:

(a)

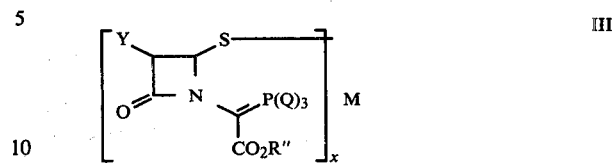

wherein Y is hydrogen or as defined above in regard to compounds of formula I, Q is phenyl or (lower)alkyl, R" is an easily removable ester protecting group, X is 1 or 2 and M is Cu(II), Pb(II) or Hg(II) when x is 2 or Ag(I) when x is 1;

(B)

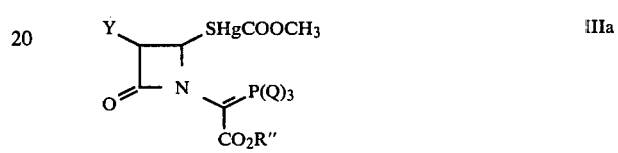

in which Y, Q and R" are as defined above under (A); and (C)

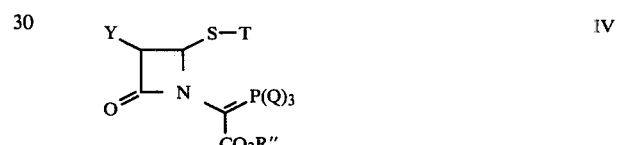

wherein Y is as defined above in regard to compounds of formula I, Q is phenyl or (lower)alkyl, R" is an easily removable ester protecting group and T is

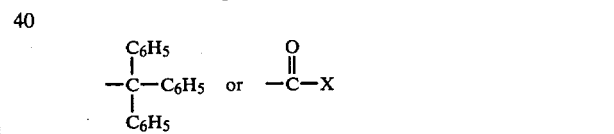

wherein X is as defined above in regard to compounds of formula I.

In the intermediates of formulae III, IIIₐ and IV, Q is preferably phenyl, R" is preferably p-nitrobenzyl and X and Y are preferably those substituent groups mentioned as being preferred in connection with the compounds of formula I. Reactive functional groups such as mercapto, amino and hydroxy in substituents Y and X may be protected by conventional blocking groups during conversion of the intermediates to biologically active end-products.

Compound I may be prepared by one or more of the reaction routes discussed below. The various synthetic routes may be divided into three main processes depending on the stage of incorporation of the 6-substituent, i.e. Y. Thus, in Process I, the 6-substituent is incorporated in the basic starting material; Process II involves incorporation of Y at the end of the synthesis and in Process III substituent Y is incorporated in mid-synthesis. Each of the three main processes in turn can vary in the procedure for incorporating the desired 2-substituent, i.e. X. In general, it is preferred to incorporate substituent Y in mid-synthesis and to incorporate substituent X by acylation of mercaptide intermediate III or III$_a$ shown below since these procedures have been found to be the most generally useful.

The steps of Process I may be seen from the following scheme:

Process I (Variation 1): Early incorporation of 2-substituent

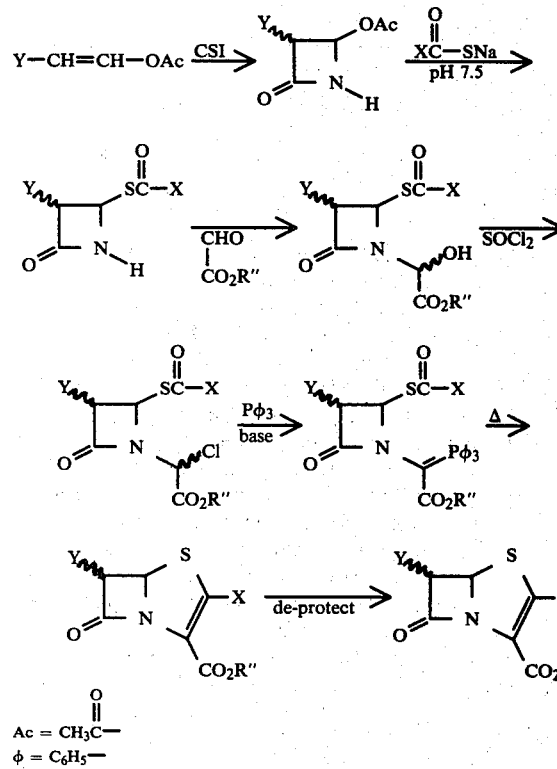

Ac = CH$_3$C—
$\phi$ = C$_6$H$_5$—

Process I (Variation 2): Late incorporation of 2-substituent

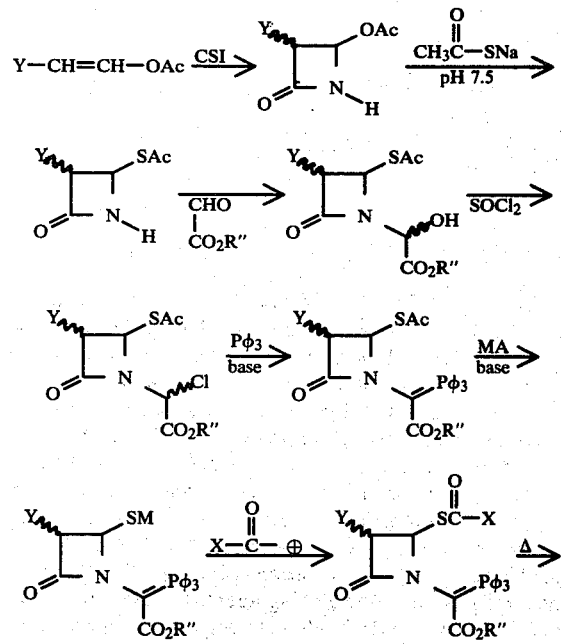

Process I (Variation 2): Late incorporation of 2-substituent -continued

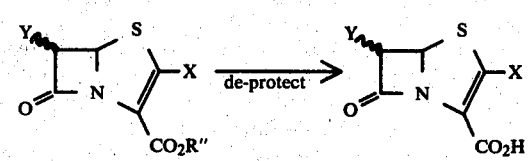

X—C—⊕ = acylating agent
MA = heavy metal salt

Process I (Variation 3): Late incorporation of 2-substituent

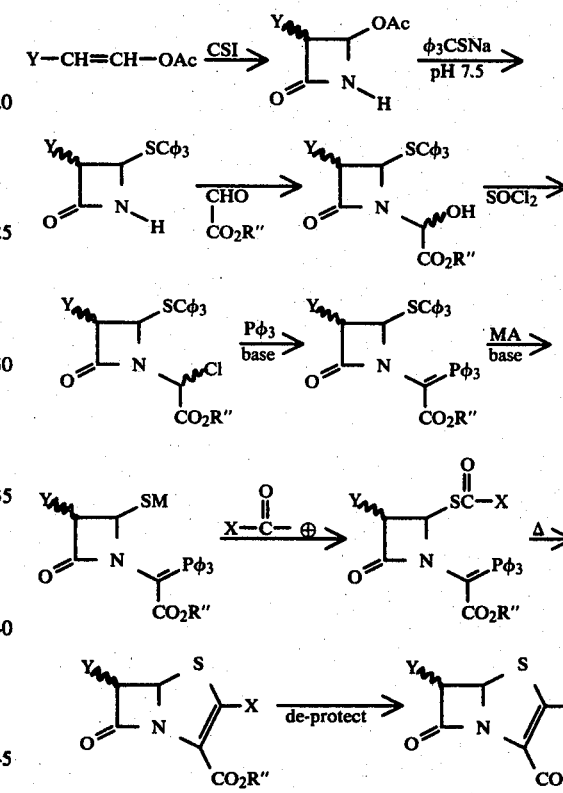

In Process I a vinyl ester (Y=H or a radical as defined in connection with compounds I) containing the desired 6-substituent is converted to the optionally 1-substituted 4-acetoxy-2-azetidinone by a cycloaddition reaction with chloro sulfonyl isocyanate (CSI) followed by reduction with an organic reducing agent such as sodium sulfite. The CSI reaction is conveniently carried out in an inert organic solvent such as diethyl ether at a temperature of 0° C. or below. The reduction step may be conducted in an aqueous or aqueous-organic reaction mixture at a temperature of 0° or below and at a slightly basic pH.

Following formation of the 4-acetoxy-2-azetidinone, Process I may be separated into three different paths. In one route (Variation 1) the azetidinone is reacted with a thiolic acid

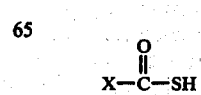

wherein X is as defined in connection with compounds I, or a salt thereof, in a suitable solvent (e.g. aqueous or aqueous organic). Displacement of the acetoxy group results in incorporation of the desired 2-substituent in the azetidinone at this stage. The displacement reaction is preferably carried out at room temperature or below and at a slightly basic pH (~7.5). When Y≠H, cis and trans isomers of the resulting azetidinone are preferably separated (e.g. by chromatography) at this point in the process. Variations 2 and 3 depicted above convert the 4-acetoxy-2-azetidinone into the 4-acetylthio-2-azetidinone and 4-tritylthio-2-azetidinone products, respectively, by nucleophic displacement with thioacetic acid or triphenylmethyl mercaptan (or a salt thereof such as the sodium salt), respectively.

The 4-thio azetidinone is next reacted with a glyoxylate ester

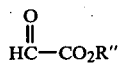

wherein R" is an easily removable ester protecting group such as p-nitrobenzyl or trimethylsilylethyl, or a reactive oxo derivative thereof such as a hydrate, in an inert organic solvent (e.g. benzene, toluene, xylene, and the like) and preferably at an elevated temperature (e.g. 50° C. up to most preferably reflux temperature). When a hydrate of the ester is employed, resulting water may be removed azeotropically or with molecular sieves. The hydroxy ester product is formed as a mixture of epimers which can be optionally purified as by chromatography or used directly in the next step.

Conversion of the hydroxy ester to the corresponding chloro ester is achieved by reaction with a chlorinating reagent (e.g. SOCl$_2$, POCl$_3$, PCl$_5$, and the like) in an inert organic solvent (e.g. tetrahydrofuran, diethyl ether, methylene chloride, dioxane, and the like) in the presence or absence of a base, preferably in aliphatic tertiary amine (e.g. triethylamine) or a heterocyclic tertiary amine (e.g. pyridine or collidine). The reaction is advantageously run at from about −10° C. to room temperature. Chloro ester product is obtained as a mixture of epimers which can optionally be purified before use in the next step.

The phosphorane intermediate may be obtained by reaction of the chloro ester with a suitable phosphine (preferably triphenylphosphine or a tri(lower)alkyl phosphine such as triethylphosphine or tri-n-butyl phosphine) in an inert organic solvent such as dimethylformamide, dimethylsulfoxide, tetrahydrofuran, dimethoxyethane, dioxane or an aliphatic, cycloaliphatic or aromatic hydrocarbon (e.g. hexane, cyclohexane, benzene, toluene, and the like) in the presence of a base, preferably an organic tertiary amine such as triethylamine, pyridine or 2,6-lutidine. The reaction is advantageously carried out at temperatures from room temperature to the reflux temperature of the solvent system.

At this stage the process again diverges into two routes. In Variation I (where the 2-substituent has already been incorporated), the phosphorane intermediate is converted to the desired penem by thermally cyclizing in an inert organic solvent at a temperature of from just above room temperature to the reflux temperature of the solvent system. Most conveniently, the cyclization is carried out under reflux conditions. Suitable inert organic solvents include aliphatic, cycloaliphatic or aromatic hydrocarbons (e.g. benzene, toluene, hexane, cyclohexane), halogenated hydrocarbons (e.g. methylene chloride, chloroform, carbon tetrachloride), ethers (diethyl ether, dioxane, tetrahydrofuran, dimethoxyethane), carboxylic acid amides (e.g. dimethylformamide), di C$_1$–C$_6$ alkylsulfoxides (e.g. dimethylsulfoxide) or a C$_1$–C$_6$ alkanol (e.g. methanol, ethanol, t-butanol), or a mixture thereof.

In variations 2 and 3 the phosphorane is converted to a heavy metal mercaptide of the formula

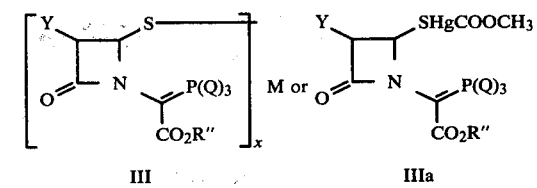

wherein Y is as defined above with respect to compounds of formula I, R" is an easily removable ester group, Q is preferably phenyl or (lower)alkyl, x is 1 or 2 and M is Cu(II), Pb(II) or Hg(II) when x is 2 or Ag(I) when x is 1. Mercaptide formation is accomplished by reaction of the phosphorane with a salt of Hg(II), Pb(II), Cu(II) or Ag(I) or with (methoxycarbonyl)mercury(II) acetate in a methanol-containing solvent and in the presence of an organic or inorganic base such as aniline, pyridine, collidine, 2,6-lutidine, an alkali metal carbonate, and the like. A preferred base is pyridine. The reaction may be carried out at room temperature or, if desired, with moderate cooling or heating. The anion (A) of the heavy metal salt may be any anion which gives a soluble salt in the selected solvent, e.g. NO$_3^-$, CH$_3$COO$^-$, BF$_4^-$, F$^-$, ClO$_4^-$, NO$_2^-$, CNO$^-$, etc. The mercaptide intermediate is then reacted with an acylating agent capable of introducing the moiety

wherein X is the desired penem 2-substituent. The acylating agent

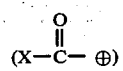

may be the acid

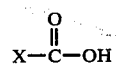

or a reactive functional derivative thereof such as an acid halide (preferably acid chloride), acid azide, acid anhydride, mixed acid anhydride, active ester, active thioester, etc. Acylation is conducted in an inert solvent (e.g. a halogenated hydrocarbon such as methylene chloride or an ether such as dioxane, tetrahydrofuran or diethyl ether) and, when an acid derivative is used, in the presence of an acid acceptor such as a tri(lower)alkylamine (e.g. triethylamine) or a tertiary organic base such as pyridine, collidine or 2,6-lutidine. When the free acid is employed, the acylation is conducted in the presence of a suitable condensing agent, for example a carbodiimide such as N,N'-dicyclohexylcarbodiimide. Acylation of the mercaptide can be achieved over a wide temperature range, but is preferably carried out from about −20° to +25° C. Following acylation, the resulting phosphorane is cyclized as described above to give the desired penem ester.

Formation of the phosphorane via the mercaptide intermediate (Variations 2 and 3) has been found to result in product of much better purity than that obtained by the more conventional route of Variation 1.

Once the carboxyl-protected penem is formed, the protecting group may be removed by conventional de-blocking procedures (e.g. hydrolysis, hydrogenation or photolysis) to give the de-blocked penem. Removal of the p-nitrobenzyl ester, for example, may be achieved by catalytic hydrogenation in the presence of a noble metal catalyst such as palladium or rhodium, including derivatives thereof such as oxides, hydroxides or halides, said catalyst being optionally supported on a conventional carrier such as carbon or diatomaceous earth. A non-reducible aqueous or non-aqueous inert solvent such as water, ethanol, methanol, ethyl acetate, tetrahydrofuran, diethyl ether or dioxane is used. Hydrogenation may be conducted at atmospheric or elevated pressure and is conveniently run at room temperature for a period of from about 1–5 hours depending on the solvent and catalyst used. If an equivalent weight of a base such as an alkali metal or alkaline earth metal hydroxide or an amine is employed during the hydrogenation, the product may be recovered in the form of a carboxylic acid salt. Removal of the β-trimethylsilylethyl ester, another useful protecting group, is conveniently achieved by treatment with a source of fluoride ions. Other ester protecting groups can be similarly removed by methods well-known to those skilled in the art.

In a second main process (Process II), the reaction sequence is as shown below:

Process II (Variation 1): Early incorporation of 2-substiutuent

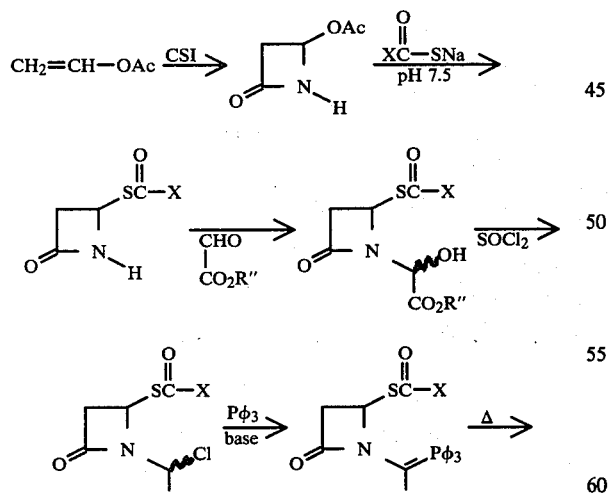

-continued
Process II (Variation 1): Early incorporation of 2-substiutuent

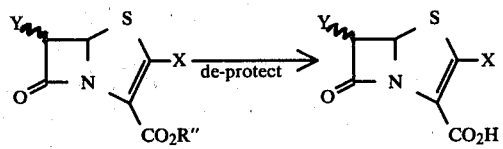

Process II (Variation 2): Late incorporation of 2-substituent

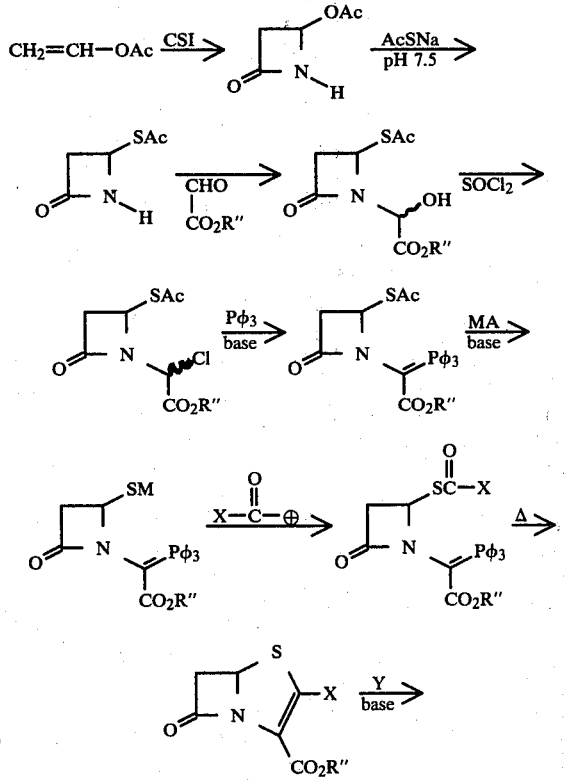

Process II (Variation 3): Late incorporation of 2-substituent

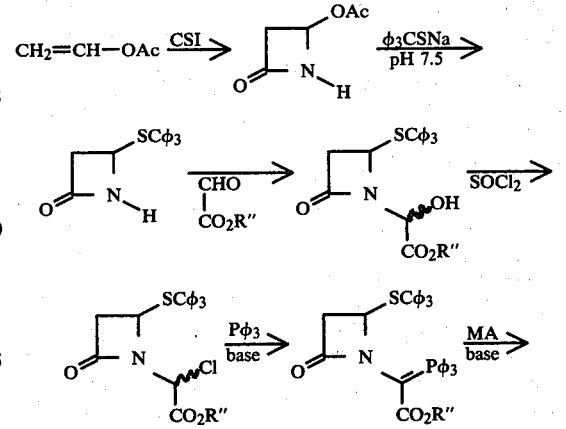

-continued
Process II (Variation 3): Late incorporation of 2-substituent

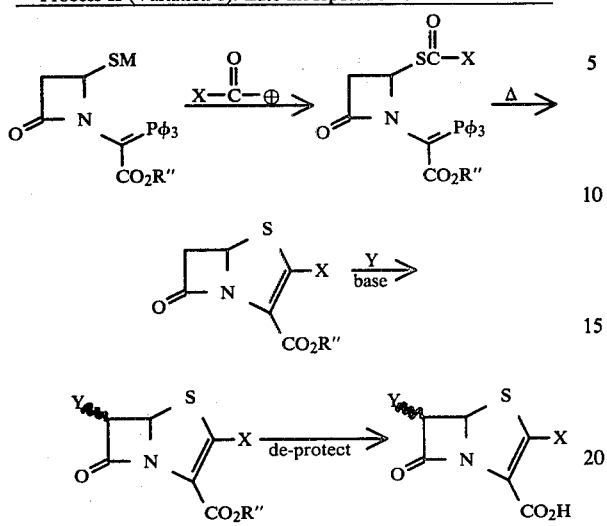

As can be seen Process II is substantially the same as Process I (except that Y must be H) up through the thermal cyclization step which produces the 2-substituted penem. A 6-substituent, however, if desired, is now incorporated at this stage by reaction of the 2-penem with a suitable electrophile in an inert solvent (e.g. tetrahydrofuran, diethyl ether, dimethoxyethane, and the like) and in the presence of a strong base. In this procedure the 2-penem can be reacted in the form of the free acid (obtained by de-blocking as described above) in the presence of about two equivalents of base or, alternatively, a suitable 2-penem ester may be used in the presence of about one equivalent of base. Any ester inert to anion chemistry (the reaction involves anion formation with base followed by reaction of the electrophile with the penem anion) may be employed, e.g. (lower)alkyl such as methyl, ethyl, n-propyl or t-butyl, phenyl, trichloroethyl, methoxymethyl, silyl such as trimethylsilyl or t-butyldimethylsilyl, and the like. Penem esters having activated methylene groups such as p-nitrobenzyl are not suitable and, if the 2-penem ester is of this type, it must be first de-blocked and either used as the free acid or converted to a suitable ester. The particular base used is not critical and the usual strong bases such as sodium hydride, phenyl lithium or butyl lithium are suitable. Most preferably, however, a lithium disilylamide or a lithium dialkylamide such as lithium dicyclohexylamide (LDCA), lithium diethylamide, lithium dimethylamide or lithium di-isopropylamide (LDA) is used. The electrophile is selected so as to generate the desired Y-substituent upon reaction with the anion and may be, for example, a halogen (e.g. $Br_2$, $I_2$), an alkyl halide (e.g. $CH_3I$) or a similar halide such as an aliphatic, cycloaliphatic, cycloaliphatic-aliphatic, phenyl(lower)alkyl, heterocyclic, heterocyclic-thio, heterocyclic-thio-(lower)alkyl, or heterocyclic-(lower)alkyl, halide, a tosylate or mesylate (e.g.

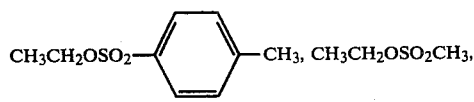, $CH_3CH_2OSO_2CH_3$,

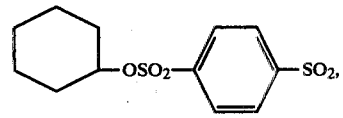

$\phi CH_2CH_2CH_2OSO_2CH_3$, etc.), an epoxide (e.g. 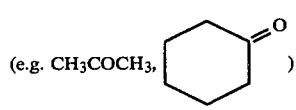), an episulfide (e.g. ), an aldehyde (e.g. $CH_3CHO$, $C_6H_5CH_2CHO$), a ketone (e.g. $CH_3COCH_3$, )

or an ester (e.g. $CH_3CH_2COOCH_3$ or $C_6H_5COOCH_3$). Representative examples of other suitable electrophiles are shown below:

$CH_2=CH-CH_2Br$

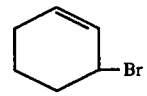     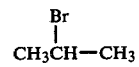

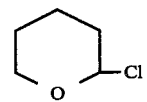     $\underset{\underset{CH_3}{|}}{CH_3CH-CH_3}$ with Br $CH_3\overset{Br}{CH}-CH_3$

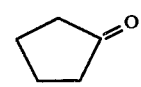     $\phi CH_2Br$ $HCHO$     $\phi C\equiv CCH_2Br$

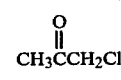     $CH_2SCH_2Cl$ $CH_3SSO_2CH_3$     $\phi OCH_2Cl$ $\phi CH=CHCHO$     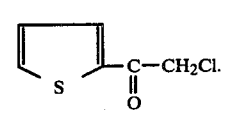

$CH_3\overset{O}{\overset{\|}{C}}CH_2Cl$

A most preferred electrophile is acetaldehyde which gives rise to the hydroxyethyl 6-substituent. Introduction of the 6-substituent by this process is preferably carried out with cooling (e.g. $-80°$ to $0°$ C.) according to the general procedure described in *Canadian Journal of Chemistry*, 50(19), 3196–3201 (1972).

After formation of the desired 2,6-penem, any ester protecting group may be removed as discussed above to give the de-protected product.

The third main reaction process (Process III) can be understood from the following scheme:

Process III (Variations 1 and 2):

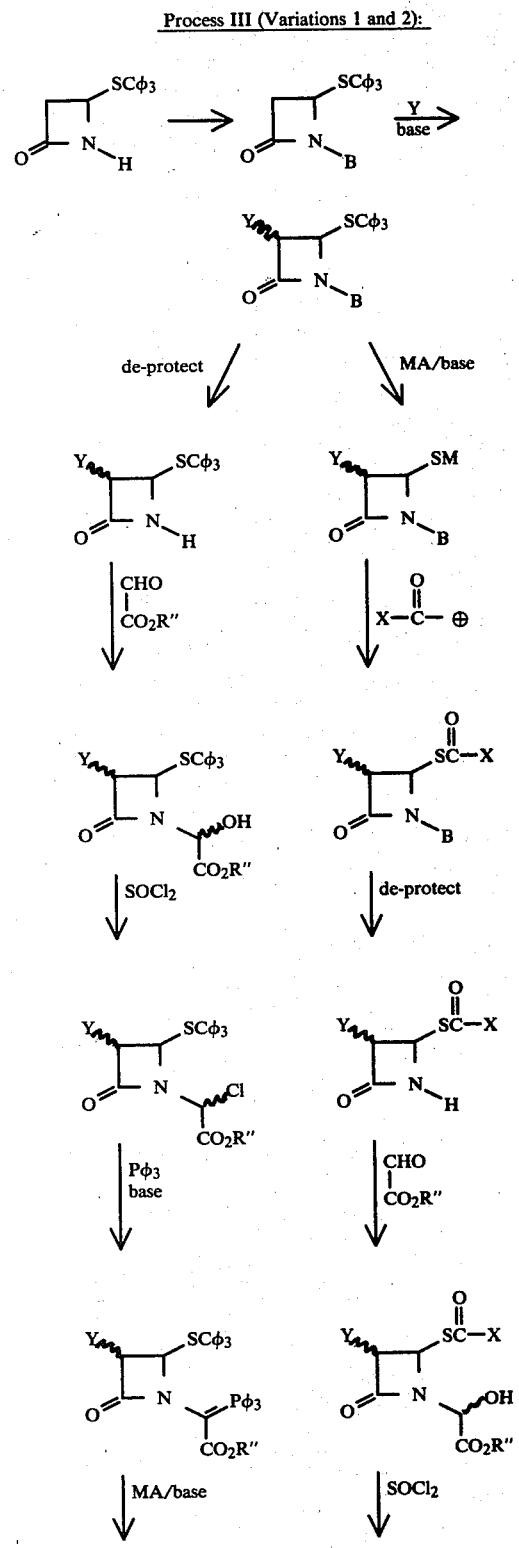

Process III (Variations 1 and 2): -continued

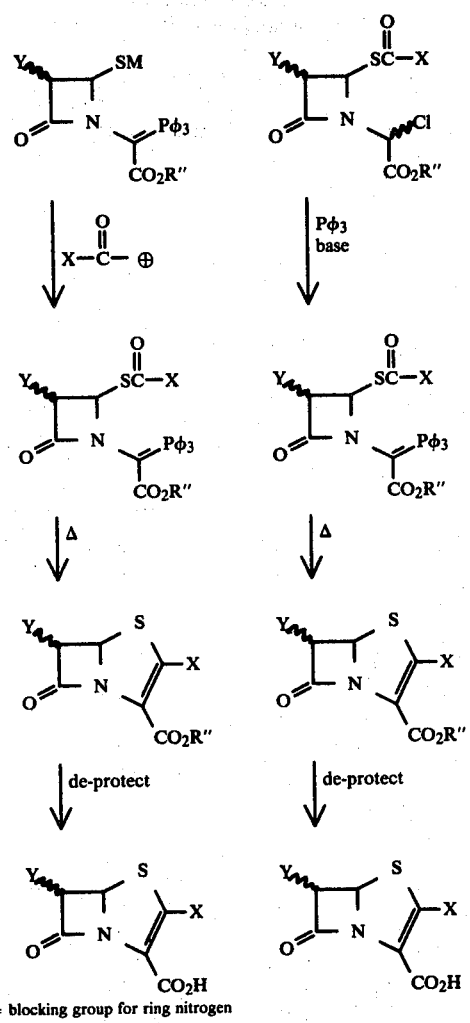

B = blocking group for ring nitrogen

The 4-tritylthio-2-azetidinone of Process III is formed as described in Process II (Variation 3). The ring nitrogen of the azetidinone is then protected by a conventional easily removable blocking group such as triorganosilyl (e.g. trimethylsilyl or t-butyldimethylsilyl), methoxymethyl, methoxyethoxymethyl, tetrahydropyranyl, and the like. Introduction of the desired Y-substituent at the 1-position of the azetidinone is then achieved by reaction of an appropriate electrophile with the N-protected azetidinone in the presence of a strong base (reaction conditions as described above in connection with Process II). At this point the process diverges into two routes depending on the time of deblocking the azetidinone.

In one route the N-protected intermediate is deblocked by conventional procedures (e.g. acid hydrolysis) and then converted to the 2,6-penem via ester formation, chlorination of the hydroxy ester, conversion of the chloro ester to a phosphorane, conversion of the phosphorane to a heavy metal mercaptide, acylation of the mercaptide with

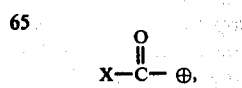

thermal cyclization of the resulting phosphorane to give the 2,6-penem ester and removal of the carboxyl-protecting group. Reaction conditions for these steps are as disclosed in connection with Process II (Variation 3).

An alternative route involves the steps of converting the N-protected azetidinone to a heavy metal mercaptide, acylating the mercaptide with the moiety

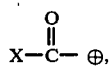

removing the N-protecting group, reacting the deprotected azetidinone with the glyoxylate ester, chlorinating, reacting the chloro ester with the phosphine to give the phosphorane, cyclizing the phosphorane to give the penem ester and removing the carboxyl-protecting group to give the 2,6-penem. Reaction conditions for these steps are as disclosed previously.

In preparing the 2-penem or 2,6-penem compounds according to the above processes, free functional groups in substituents X or Y which do not participate in the reaction may be temporarily protected in a manner which is itself known, such as free amino groups by acylation, tritylation or silylation, free hydroxyl groups, for example, by etherification or esterification, mercapto groups by esterification, and free carboxyl or sulfo groups, for example, by esterification, including silylation. After the reaction has taken place, these groups can, if desired, be liberated, individually or jointly, in a manner which is itself known.

Additionally, it is possible in compounds of formula I to functionally modify the 2- and/or 2,6-substituents during or at the conclusion of the reaction procedures according to known processes to obtain other substituents included within the scope of the present invention. Thus, for example, carbonyl groups can be reduced to alcohol groups, unsaturated aliphatic groups can be halogenated, amino groups can be alkylated or acylated, nitro groups can be converted to hydroxyamino and amino groups, hydroxyl groups can be etherified or esterified, etc.

The penem free acid compounds may be converted to pharmaceutically acceptable salts thereof or to easily removable esters thereof (particularly physiologically cleavable esters). Salts may be formed by reaction of the free acid with a stoichiometric amount of a suitable non-toxic acid or base in an inert solvent followed by recovery of the desired salt as by lyophilization or precipitation. Esters (in particular physiologically cleavable esters) may be prepared in an analogous manner to preparation of the corresponding esters of penicillins and cephalosporins. Resulting mixtures of isomers can be separated into the individual isomers according to known methods. Mixtures of diastereomeric isomers, for example, can be separated by fractional crystallization, adsorption chromatography (column or thin-layer) or other suitable separation methods. Resulting racemates can be resolved into the antipodes in the customary manner, for example by forming a mixture of diastereomeric salts with optically active salt-forming reagents, separating the diastereomeric salts and converting the salts into the free compounds, or by fractional crystallization from optically active solvents.

The present invention also comprises those embodiments according to which compounds used as intermediate products are used as starting materials and the remaining process steps are carried out with these, or the process is discontinued at any stage. Furthermore, starting materials can be used in the form of derivatives or can be formed during the reaction.

The free acid penem compounds provided by the present invention and pharmaceutically acceptable salts and physiologically cleavable esters of said acids have been found to be potent broad-spectrum antibacterial agents useful in the treatment of infectious diseases in animals, including man, caused by both Gram-negative and Gram-positive organisms. The compounds are also of value as nutritional supplements in animal feeds and as agents for the treatment of mastitis in cattle.

The 2-penem acids (and physiologically cleavable esters and pharmaceutically acceptable salts thereof) provided according to the present invention (i.e. compounds of general formula I wherein Y=H) possess antibacterial activity per se and are also useful intermediates (preferably in their carboxyl-protected form) for preparing the 2,6-disubstituted penems I via anion formation and reaction with an electrophile.

The active compounds provided by the present invention may be formulated as pharmaceutical compositions comprising, in addition to the active ingredient, a pharmaceutically acceptable carrier or diluent. The compounds may be administered both orally and parenterally. The pharmaceutical preparations may be in solid form such as capsules, tablets or dragees, or in liquid form such as solutions, suspensions or emulsions. In the treatment of bacterial infections in man, the active compounds of this invention may be administered orally or parenterally in an amount of from about 5 to 200 mg./kg./day and preferably about 5 to 20 mg./kg./day in divided dosage, e.g. three or four times a day. They are administered in dosage units containing, for example, 125, 250 or 500 mg. of active ingredient with suitable physiologically acceptable carriers or diluents.

The present invention also provides a method of combatting bacterial infections in animals, particularly warm-blooded animals, which comprises administering an acid of formula I or a physiologically cleavable ester thereof or a pharmaceutically acceptable salt thereof, or a pharmaceutical composition thereof, to an infected host in an amount sufficient to combat such infection.

Illustrative examples of the preparation of starting materials and end-products of the present invention follow. All temperatures are in degrees Centigrade. For the sake of convenience, certain abbreviations are employed in the examples. Definitions of the less obvious of these abbreviations are as follows:

| | |
|---|---|
| CSI | chloro sulfonyl isocyanate |
| pet. ether | petroleum ether |
| b.p. | boiling point |
| n.m.r. | nuclear magnetic resonance |
| h | hour |
| ether | diethyl ether (unless otherwise indicated) |
| Celite | Trademark of Johns-Manville Products Corporation for diatomaceous earth |
| psi | pounds per square inch |
| r.t. | room temperature |
| PNB | p-nitrobenzyl |
| m.p. | melting point |
| LAH | lithium aluminum hydride |
| n-BuLi | n-butyl lithium |
| MIBK | methyl isobutyl ketone |
| Et | $C_2H_5-$ |
| Tr | $-C(C_6H_5)_3$ |
| Me | $CH_3-$ |
| THF | tetrahydrofuran |

| | |
|---|---|
| Ph | phenyl |
| DMF | dimethylformamide |
| TEA | triethylamine |
| PNBG | p-nitrobenzylglyoxylate |
| THP | tetrahydropyranyl |
| TFA | trifluoroacetic acid |
| HMPT (or HMPA) | hexamethylphosphorus triamide |
| EtOAc | ethyl acetate |
| DMSO | dimethylsulfoxide |
| Ac | $CH_3CO-$ |
| Ms | $CH_3SO_2-$ |
| DMAP | 4-dimethylaminopyridine |
| Py | pyridine |
| LDA | lithium diisopropyl amide |

PREPARATION OF STARTING MATERIALS

Preparation 1

4-Acetylthio-2-azetidinone

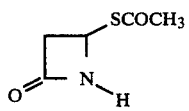

A. To a cold (0°–5° C.) oxygen-free 1N NaOH solution (27.5 ml.) was added thioacetic acid (2.09 g., 27.5 mmole) at such a rate that the temperature was maintained between 0°–5° C. The resulting solution was added dropwise (over 20 min.) to a cold (0.5° C.) oxygen-free aqueous solution (11 ml.) of 4-acetoxy-2-azetidinone (3.23 g., 25 mmole) [prepared in *Liebigs Ann. Chem.*, 539 (1974)]. The reaction mixture was stirred under a nitrogen atmosphere for 0.5 hr. at 0°–5° C. and for 2–2.5 hr. at 23°–25° C. before being extracted with chloroform (4×25 ml.). The organic extracts were combined, washed with water (10 ml.), dried over anhydrous $Na_2SO_4$ and concentrated to a yellow syrup, 3.3 g., 91% yield. The title product was found to be identical to the sample prepared by Clauss in *Liebigs Ann. Chem.*, 539 (1974). δ(ppm, $CDCl_3$), 7.2 (1H, NH), 5.23 (1H, dd, $J_{trans}=2.8$, $J_{cis}=5.0$, H-4), 3.55 (1H, ddd, $J_{gem}=15.2$, $J_{HNH}=2.0$, H-3 cis), 2.95 (1H, ddd, $J_{gem}=15.2$, $J_{trans}=2.8$, $J_{HNH}=1$, H-3 trans) and 2.36 (3H, s, methyl).

B. (Preferred Process)

To a cold (0°–5°) oxygen-free 1N NaOH solution (803 ml.) was added over 20 minutes thioacetic acid (57 ml., 61 g., 0.803 mole). The resulting solution was added in ca 20 minutes to a cold (10°) oxygen-free solution of 4-acetoxyazetidinone (94 g., 0.730 mole) in water (300 ml.). The pH of the resulting solution was immediately adjusted to 7.4 with solid $NaHCO_3$. The cooling bath was removed and the solution was stirred for 2.75 hours. The mixture was then extracted with chloroform, the combined organic extracts washed with water (150 ml.) and dried over sodium sulfate. Concentration on a rotary evaporator left a yellow oil (95.3 g., 90%) which solidified to a yellow solid on cooling and seeding. This solid was found identical (by IR, NMR and TLC) to the product obtained in Preparation 1.

Preparation 2

2-methylpenem-3-carboxylic Acid

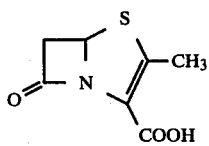

A. Preparation of p-Nitrobenzyl 2-methylpenem-3-carboxylate 1. p-Nitrobenzyl 2-(4-Acetylthio-2-oxo-1-azetidinyl)-2-hydroxyacetate

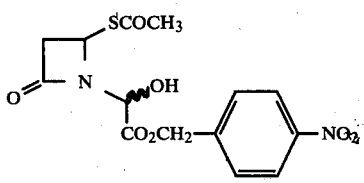

A solution of 4-acetylthio-2-azetidinone (3.33 g., 23 mmole) and p-nitrobenzyl glyoxylate (5.25 g., 25 mmole) in benzene (250 ml.) was heated under reflux for 18 hours. Evaporation of the solvent left an oil which was purified by filtration through a pad of silica gel. There was obtained 8.2 g. (100% yield) of the title intermediate. $R_f=0.8$ (ethyl acetate:$CHCl_3$, 4:1 v/v). δ(ppm, $CDCl_3$): 7.9 (4H, m, aromatic), 5.4 (4H, m, two benzylic H, H-4 and H of glyoxylate), 4.7 (1H, hydroxyl), 3.32 (2H, m, H-3), 2.4 (3H, two s, $CH_3$). $\nu_{c=o}=1775$, 1760, 1695 $cm^{-1}$, mixture of two epimers.

2. p-Nitrobenzyl 2-(4-Acetylthio-2-oxo-1-azetidinyl)-2-chloroacetate

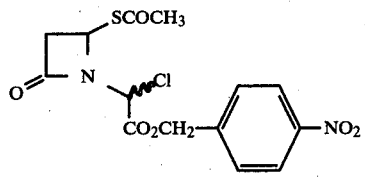

To a cooled (0°) and stirred solution of p-nitrobenzyl 2-(4-acetylthio-2-oxo-1-azetidinyl)-2-hydroxyacetate (3.79 g., 10.7 mmole) in tetrahydrofuran (40 ml.) and dioxane (40 ml.) was added pyridine (0.97 ml., 12 mmole) followed by $SOCl_2$ (1.43 g., 0.88 ml., 12 mmole). The mixture was stirred 30 minutes at 0°, the precipitate was removed and washed with toluene, and the combined filtrates were concentrated on a rotary evaporator to leave a yellow oil. Partial purification was achieved by filtering the residue over a silica gel pad and washing with chloroform. δ(ppm, $CDCl_3$): 8.2 (2H, m, aromatic), 7.55 (2H, m, aromatic), 6.12 (1H, s, CHCl), 5.65 (1H, m, H-4), 5.35 (2H, two s, benzylic H), 3.62 (1H, dd, $J_{3-3}=16$, $J_{3-4 \, cis}=6$, H-3), 3.08 (1H, m, H-3), 2.35 (3H, two s, $CH_3$). The product was obtained as a mixture of two epimers.

3. p-Nitrobenzyl 2-(4-Acetylthio-2-oxo-1-azetidinyl)-2-triphenylphosphoranylideneacetate

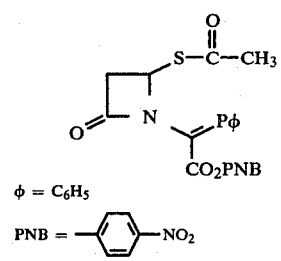

φ = C₆H₅

PNB = —⟨⟩—NO₂

2,6-Lutidine (2.14 g., 20 mmole) was added to a solution of p-nitrobenzyl 2-(4-acetylthio-2-oxo-1-azetidinyl)-2-chloroacetate (5.9 g., 16 mmole) and triphenylphosphine (5.8 g., 22 mmole) in dioxane (80 ml.). The solution was kept at 55° for 18 hours and then concentrated on a rotary evaporator. The residue was partitioned between brine and ethyl acetate and the organic phase was washed with brine, dried and concentrated. The residue was purified by chromatography over silica gel (ethyl acetate:petroleum ether, 1:2 v/v) to give 4.64 g. (48%) of the title ester.

4. p-Nitrobenzyl 2-Methylpenem-3-carboxylate

A solution of p-nitrobenzyl 2-(4-acetylthio-2-oxo-1-azetidinyl)-2-triphenylphosphoranylideneacetate (2.4 g., 4.0 mmole) in tolune (35 ml.) was heated under reflux for 4 hours. Chromatography over silica gel afforded 689 mg. (53% yield) of title product as a yellow solid, m.p. 129°-131° C. $R_f$=0.7 (ethyl acetate:petroleum ether, 1:1 v/v). $\nu_{c=o}$=1785, 1710 cm$^{-1}$. δ(ppm, CDCl₃): 8.3, 8.17, 7.67, 7.52 (4H, m, aromatic), 5.62 (1H, q, H-5), 5.30 (2H, d, benzylic H), 3.82 (1H, dd, $J_{6-6}$=16, $J_{5-6\ cis}$=4, H-6), 3.42 (1H, dd, $J_{6-6}$=16, $J_{5-6\ trans}$=2), 2.39 (3H, s, CH₃).

B. Preparation of Trimethylsilylethyl 2-Methylpenem-3-carboxylate

Using exactly the procedure described in preparations 2A1 through 2A4, but substituting trimethylsilylethyl glyoxylate for p-nitrobenzyl glyoxylate in preparation 2A1, trimethylsilylethyl 2-methylpenem-3-carboxylate was obtained. Yellow oil: $\nu_{c=o}$ 1818, 1750 cm$^{-1}$; δ(ppm, CDCl₃): 5.62 (1H, dd, H-5), 4.33 (2H, t, CO₂CH₂), 3.82 (1H, dd, H-6a), 3.41 (1H, dd, H-6B), 2.37 (3H, s, CH₃), 1.10 (2H, t, CH₂-Si), 0.05 (9H, s, CH₃).

C. 2-Methylpenem-3-carboxylic Acid

1. A mixture of p-nitrobenzyl 2-methylpenem-3-carboxylate (305.5 mg., 0.954 mmoles) in tetrahydrofuran (27 ml.), diethyl ether (42 ml.) and NaHCO₃ (81 mg., 0.964 mmole) in water (20 ml.) was hydrogenated with 30% Pd on Celite (330 mg.) for 3 hours at 30 p.s.i. H₂ on a Parr shaker. The catalyst was removed by filtration and the aqueous phase was washed twice with diethyl ether. The aqueous layer was carefully acidifed (pH 2-2.5) with cold 1% HCl and extracted with ethyl acetate (10×20 ml.). The organic extracts were combined, washed three times with brine and dried over Na₂SO₄. Solvent evaporation afforded a crystalline material which was triturated with diethyl ether to give the tital acid (105.8 mg., 60%, decomp. 134° C.). δ(ppm, DMSOd₆): 5.64 (1H, dd, $J_{5-6\ cis}$=4, $J_{5-6\ trans}$=2, H-5), 3.82 (1H, dd, $J_{gem}$=16.5, $J_{6-5\ cis}$=4, H-6), 3.37 (1H, dd, $J_{gem}$=16.5, $J_{6-5\ trans}$=2, H-6), 2.28 (3H, s, CH₃). $\nu_{c=o}$=1795 and 1775, 1670. UV(EtOH)λ$_{max}$ 308 (ε=6400), 263 (λ=4200).

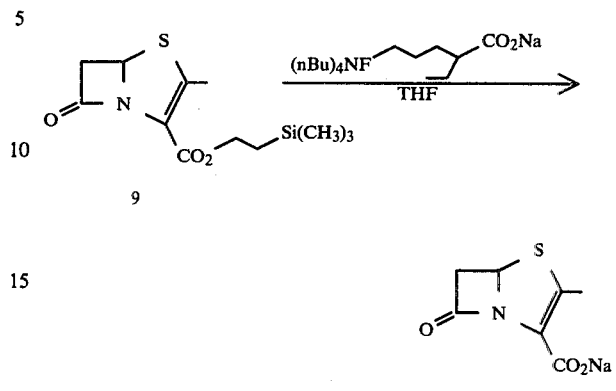

Compound 9 (260 mg, 0.911 mmole) was dissolved in a molar solution of tetrabutylammonium fluoride in THF (3.64 ml. 3.64 mmoles) under a nitrogen atmosphere. Sodium 2-ethylhexanoate (151 mg, 0.911 mmole) and ether (3.5 ml) were added. The reaction mixture was stirred at room temperature for 30 minutes. The solvents were evaporated. The residue was triturated with ether (10 ml) and filtered. The solid was dissolved in water (5 ml), treated with charcoal and filtered on celite. The filtrate was filtered on millipore and lyophilized to afford a residue (123 mg, 66%) which spectral data were in agreement with compound 10 obtained by the previous route.

Preparation 3

2-Methylpenem-3-carboxylic Acid

A. p-Nitrobenzyl 2-Methylpenem-3-carboxylate

1. p-Nitrobenzyl 2-(4-acetylthio-2-oxo-1-azetidinyl)-2-hydroxyacetate p-Nitrobenzyl glyoxylate hydrate (63.4 g., 0.278 mole) was added to a solution of 4-acetylthio-2-azetidinone (36.2 g., 0.250 mole) in 1200 ml. of benzene. The mixture was refluxed for 17 hours in a Dean-Stark apparatus. The solution was concentrated on a rotary evaporator to give the title product as a yellow oil (102 g., 100%). This oil was found to be identical with the product of Preparation 2A-1.

2. p-Nitrobenzyl 2-(4-Acetylthio-2-oxo-1-azetidinyl)-2-chloroacetate

To a cooled (−10°) and stirred solution of p-nitrobenzyl 2-(4-acetylthio-2-oxo-1-azetidinyl)-2-hydroxyacetate (102 g., 0.250 mole) in tetrahydrofuran (2000 ml.) were added in succession pyridine (27.1 ml., 0.287 mole) and thionyl chloride (25.2 ml., 0.287 mole); the thionyl chloride addition was done over ca 15 minutes. The mixture was stirred for 30 minutes at −10° and filtered. Concentration of the filtrate left a yellow oil which was partially purified by absorption on a pad of silica gel (800 ml.) and elution with chloroform (ca 3000 ml.). Concentration of the eluates gave an oil (92.9 g., 100%) which was found to contain a minimum of 90% of the title ester as a mixture of epimers.

3. p-Nitrobenzyl 2-(4-Acetylthio-2-oxo-1-azetidinyl)-2-triphenylphosphoranylideneacetate To a solution of crude p-nitrobenzyl 2-(4-acetylthio-2-oxo-1-azetidinyl)-2-chloroacetate (92.9 g., 0.249 mole) in dioxane (1200 ml.) were added in succession 2,6-lutidine (31 ml., 0.274 mole) and triphenylphosphine (71.7 g., 0.274 mole). The resulting mixture was stirred at 45°-47° for 18 hours, cooled to 23° and filtered. The filtrate was concentrated on a rotary evaporator to leave a yellow oil which was purified as follows: absorption on a column of silica gel[1] and elution with petroleum ether (4000 ml.), methylene chloride (4000 ml.) and ethyl acetate (4000 ml.). The petroleum-ether fraction was discarded since it contained only impurities. The ethyl acetate fraction was concentrated on a rotary evaporator and the oily residue was triturated with diethyl ether to give the title product as a white solid (74.5 g.), m.p. 162°-165°. The methylene chloride eluate was concentrated to dryness and the oily residue again purified by chromatography as above to give 15.0 g. of title product. The combined solids were dissolved in methylene chloride, treated with activated charcoal, concentrated and recrystallized in diethyl ether to give a total of 87 g. (58%) of title product.

[1] 100 ml. of Mallinkrodt No. 2847 Silicic Acid, 100 mesh, and 1000 ml. of BDH No. 7734 (E. M. Reagents) Silica Gel 60, 70-230 mesh Anal. Calc'd for $C_{32}H_{27}N_2O_6PS$: C, 64.20; H, 4.54; N, 4.68; S, 5.35. Found: C, 63.81; H, 4.55; N, 4.68; S, 6.86.

4. p-Nitrobenzyl 2-Methylpenem-3-carboxylate

A solution of p-nitrobenzyl 2-(4-acetylthio-2-oxo-1-azetidinyl)-2-triphenylphosphoranylideneacetate (38.6 g.) in toluene (500 ml.) was kept at reflux temperature for 3.5 hours. Concentration left a semi-solid which was purified by absorption on silica gel[1] (700 ml.) and elution with methylene chloride. The pertinent fractions were combined and concentrated and the residue triturated in diethyl ether to give the title product as a yellow crystalline solid, m.p. 125°-130° (15.0 g., 73%).

B. 2-Methylpenem-3-carboxylic Acid

The p-nitrobenzyl ester intermediate of Part A4 above may be converted to the title acid by following the procedure of Preparation 2B above.

Preparation 4
Resolution of d,l-2-Methylpenem-3-carboxylic Acid

A. (+)-2-Methylpenem-3-carboxylic Acid

To a suspension of crude d,l-2-methylpenem-3-carboxylic acid (0.925 g., 5 mmole) in isopropanol (10 ml.) was added with stirring d-(+)-α-methylbenzylamine (0.61 g., 5 mmole). The mixture was allowed to stand at room temperature for 0.5 hours. The solid was removed by filtration to give 0.7 g.; $[\alpha]_D$+120.7 (c, 0.058; CHCl₃, free acid). This was recrystallized from methanol (6 ml.) to give 0.1 g. of a white solid which was converted to free acid by treatment with cold 1N HCl. Extraction with CHCl₃ gave 40 mg. of the title isomer; $[\alpha]_D$+305.6 (c, 0.036, CHCl₃). The proton NMR spectrum of the compound was consistent with the expected structure.

B. (−)-2-Methylpenem-3-carboxylic Acid

To a hot solution of crude d,l-2-methylpenem-3-carboxylic acid (1.85 g., 10 mmole) in isopropanol (40 ml.) was added a solution of 1-(−)-α-methylbenzylamine (1.22 g., 10 mmole) in isopropanol (1 ml.). The solution was allowed to crystallize at room temperature for 0.5 hour. The crystalline solid was separated by filtration to give 0.71 g.; $[\alpha]_D$−280.8 (c, 0.12, CHCl₃, free acid). The salt was recrystallized from CH₃OH (8 ml.) to give 0.27 g. of white solid. This was treated with cold 1N HCl and extracted with CHCl₃ to give 0.13 g. of the levorotatory free acid as a white solid, $[\alpha]_D$−304.4 (c, 0.068, CHCl₃).

Preparation 5
Sodium 2-(Acetoxymethyl)penem-3-carboxylate

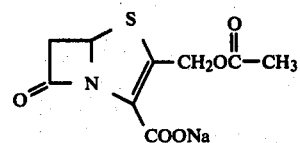

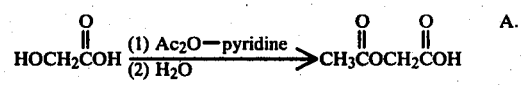

A solution of glycolic acid (38 g, 0.5 mole) in dry pyridine (380 ml) was cooled in an ice-water bath and treated dropwise (10-15 min) with acetic anhydride (60 ml 0.63 mole). The ice-water bath was removed and the reaction mixture was stirred at 23°-25° C. for 18-20 h. The solvents were evaporated under reduced pressure giving a slightly yellow oil from which traces of acetic anhydride, acetic acid and pyridine were removed by codistillation with toluene. The resulting oil was treated with water (100 ml) which was evaporated under reduced pressure at 40°-45° C.; this operation was repeated three times. The pure acetoxyacetic acid was obtained by distillation under a high vacuum 58 g, 98%, Bp₀.₄: 104°-106° C. δ(ppm, CDCl₃), 12.42 (1H, s, carboxylic acid), 4.62 (2H, s, methylene) and 2.15 (3H, s, methyl). This compound is identical to the one described by R. Anschutz and W. Bertram, Ber., 36, 466(1903) and by J. C. Micheau, A. Lattes, Bull. Soc. Chim. France, (11), 4018(1970).

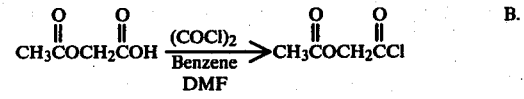

A solution of acetoxyacetic acid (5.9 g, 0.05 mole) in dry benzene (55 ml) containing one drop of N,N-dimethylformamide was treated dropwise (5-10 min) with oxalyl chloride (8.55 ml, 0.10 mole) and stirred at 23°-25° C. for 1.5 h. After 1.5 h of stirring, the same amount of oxalyl chloride was added and stirring was continued for another 1.5 h. The solvents were evaporated under reduced pressure at 27° C. and traces of oxalyl chloride were removed by codistillation with benzene leaving a yellow liquid mixed with some solid; 6.8 g, 100%. δ(ppm,CDCl₃):5.0(2H,s, methylene) and 2.17(3H,s, methyl). ν(cm⁻¹): 1806 (carbonyl of acylhalide) and 1757 (carbonyl of ester). This compound was identical to the one described by R. Anschütz and W. Bertram, Ber. 36, 446(1903).

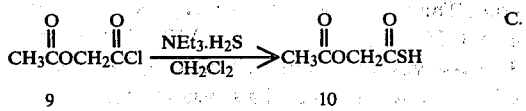

C.

A solution of triethylamine (8.0 ml, 0.057 mole) in dichloromethane (200 ml) was cooled to 7° C. in an ice-water bath and hydrogen sulfide was bubbled through during 30 min. The temperature was held between 7°-10° C. A solution of acetoxyacetyl chloride (4.9 g, 0.036 mole) in dichloromethane (70 ml) was added dropwise (10–15 min) to the preceeding solution cooled at 5° C. and the resulting reaction mixture was stirred at 23°-25° C. for 2 h under a nitrogen atmosphere. The reaction mixture was diluted with dichloromethane (125 ml), washed with 10% hydrochloric acid solution (2×15 ml) and water (2×15 ml), dried over anhydrous sodium sulfate and concentrated to a yellow liquid, 4.17 g, 86%. δ(ppm,CDCl3):4.70(s, methylene), 4.63 (s, SH) and 2.20(3H, s, methyl).

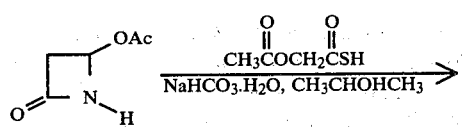

D.

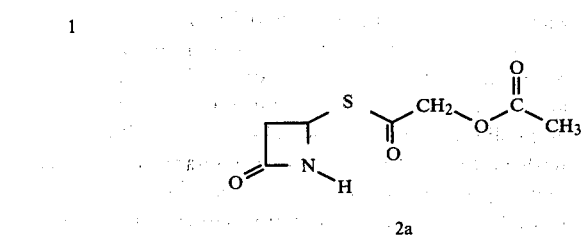

2a

A solution of acetoxythioacetic acid (10.73 g, 0.08 mole) in isopropanol (37 ml) was treated with an aqueous solution (213 ml) of sodium bicarbonate (6.72 g, 0.08 mole), stirred at 23°-25° C. under a nitrogen atmosphere until evolution of carbon dioxide was completed (~10 min) and added (5–10 min) to an aqueous solution (100 ml) of 4-acetoxyazetidinone (7.75 g 0.06 mole). The reaction mixture was stirred under a nitrogen atmosphere for 2–3 h., treated with a solution of acetoxythioacetic acid sodium salt (Thioacid 1.07 g, 0.008 mole; sodium bicarbonate 0.67 g, 0.008 mole), stirred for 0.5–1 h., and extracted with dichloromethane (7×70 ml). The organic extracts were combined, dried over anhydrous sodium sulfate and concentrated to a yellow syrup, 8.7 g, 71%. δ(ppm, CDCl3):7.1(1H, NH), 5.31 (1H,dd, J$_{cis}$=2.8, J$_{trans}$=5.0,H-4) 4.77 (2H, s, methylene), 3.56 (1H, ddd, J$_{gem}$=15.2, J$_{trans}$=5.0, J$_{trans}$=2.0,H-3trans) 2.99 (1H, ddd, J$_{gem}$=15.2, J$_{cis}$=2.8, J$_{cis}$=1.0,H-3cis) and 2.21 (3H, s, methyl of acetoxy). ν(cm$^{-1}$):1690 (thioester), 1755 (ester) shoulder at 1775 (β-lactam).

E.

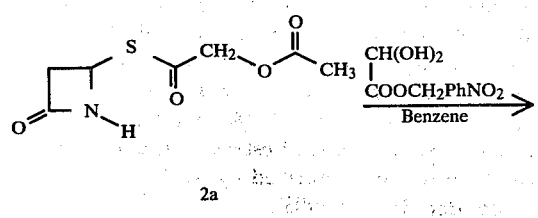

2a

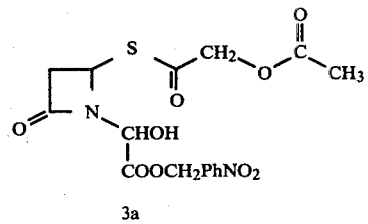

3a

A suspension of 4-S-(acetoxyacetyl)azetidinone 2a (1 g, 0.0049 mole) and p-nitrobenzylglyoxylate hydrate (1.15 g, 0.0051 mole) in benzene (100 ml) was refluxed for 21 h through a soxhlet containing 4Å molecular sieves. The reaction mixture was cooled to 23°-25° C. and the benzene was evaporated under reduced pressure leaving a yellow syrup, 1.94 g, 96%. δ(ppm, CDCl3):8.23 (2H,d,J=8.6, Hm of phenyl), 7.53(2H,d,J=8.6,Ho of phenyl), 5.5 (1H,m,H-4), 5.36 and 5.28 (3H,2s,CH2 of p-nitrobenzyl, and H of glyoxylate), 4.7 and 4.66 (2H, 2s, methylene of acetoxyacetyl), 4.3(1H,m,OH), 3.56(1H,dd,J$_{gem}$=15.6, J$_{trans}$=5.0,H-3 trans), 3.03 (1H,dd, J$_{gem}$=15.6, J$_{cis}$=2.2, H-3 cis), 2.16 and 2.13 (3H,2s, methyl of acetoxyacetyl).

F.

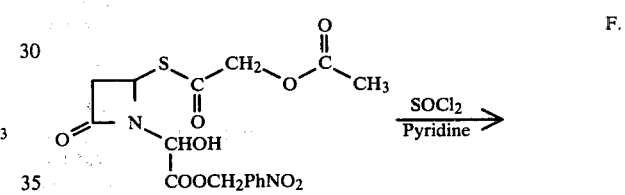

3a

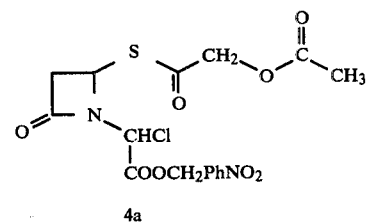

4a

A solution of 3a (0.785 g,0.0019 mole) in dry tetrahydrofuran (7.8 ml) protected from moisture by a stream of nitrogen was cooled to 0° C. in an ice-water bath and, successively treated with pyridine (0.184 ml, 0.0023 mole) and thionyl chloride (0.150 ml, 0.0023 mole). The reaction mixture was stirred at 0° C. for 50 min and concentrated under reduced pressure to a yellow semi crystalline syrup which was absorbed on a silica gel (silica gel GF60 for dry column) pad. Elution with chloroform after evaporation of the solvent gave 4a as a yellow syrup, 0.66 g, 80%. This compound was used for the next step without any further purification. δ(ppm,CDCl3):8.24(2H,d,J:9.0, Hm of p-nitrobenzyl), 7.60(2H,d,J=9.0, Ho of p-nitrobenzyl), 6.17(1H,s,H of glyoxylate), 5.7(1H,m H-4), 5.42and 5.36(2H,2s, methylene of p-nitrobenzyl), 4.77 and 4.75(2H,2s, methylene of acetoxyacetyl), 3.75(1H,dd, J$_{gem}$=15.6 J$_{trans}$=5.4, H-3 trans) 3.19(1H,m,H-3 cis), 2.19 and 2.17(3H,2s methyl of acetoxyacetyl).

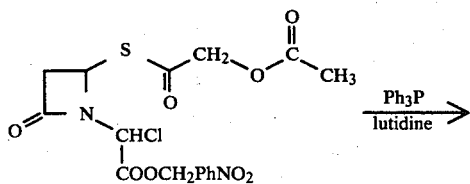

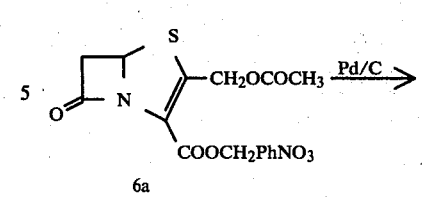

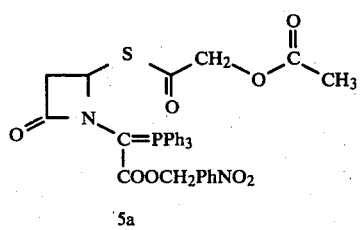

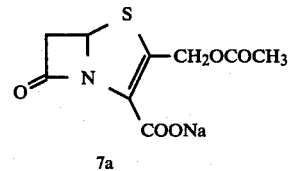

To a solution of 4a (0.655 g, 0.0015 mole) in benzene (25 ml) was added triphenylphosphine (0.577 g, 0.0022 mole) and 2,6-lutidine (0.256 ml 0.0022 mole). The reaction mixture was stirred at 45°–55° C. for 21 h, cooled to 23°–25° C. and concentrated to a semi-crystalline syrup which was chromatographed (25 g of silica gel GF60 for dry column, column size: 2.7×8.5 cm). The column was eluted with ether (310 ml) and ethyl acetate (250 ml) which gave, after combination and evaporation of the appropriate fractions, a yellow syrup, 0.40 g, 40%. This compound was used in the next step without any further purification.

H.

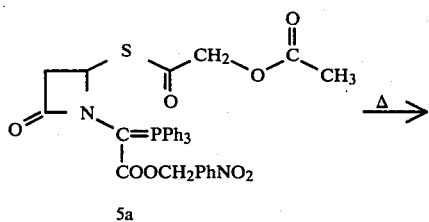

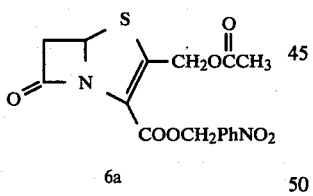

A solution of crude 5a (0.400 g, 0.0006 mole) in toluene (25 ml) was refluxed for 2.5 h, cooled to 23°–25° C. and concentrated under reduced pressure to a yellow solid. Purification of this solid was achieved by column chromatography (10 g of silica gel GF60 for dry column, column size 2.3×6 cm). Elution with ether (150 ml) gave after evaporation of the appropriate fractions, a slightly yellow solid which was triturated in ether and filtered, 0.10 g, M.P.: 119°–121° C., 44%. Analysis: Calc'd for $C_{16}H_{14}N_2O_7S$: C 50.79, H 3.73, N 7.40. Found: C 50.62, H 3.57, N 7.28. δ(ppm, CDCl$_3$): 8.15 (3H, d, J=8.8, Hm p-nitrobenzyl), 7.62 (2H, d, J=8.8, Ho p-nitrobenzyl), 5.66 (1H, dd, J$_{cis}$=2, J$_{trans}$=3.7, H-5), 5.38 (2H, s, methylene of p-nitrobenzyl), 5.31 and 5.16 (2H, 2s, methylene on C-2), 3.87 (1H, dd, J$_{gem}$=16.5, J=3.7, H-6 trans), 3.5 (1H, dd, J$_{gem}$=16.5, J=2.0, H-6 cis), 2.1 (3H, s, methyl). $\nu_{c=o}$=1795, 1757, 1705 cm$^{-1}$.

To a solution of 6a (81 mg. 0.214 mmole) in ethyl acetate (10 ml) was successively added water (5 ml), sodium bicarbonate (20 mg 0.238 mmole) and 10% palladium on charcoal (29 mg). The reaction mixture was hydrogenated at 23°–25° C. for 3 h. under 30 p.s.i. and filtered over a celite pad; the pad was washed with water and ethyl acetate. The filtrate and washings were combined and the organic phase was separated; the aqueous solution was washed with ethyl acetate and lyophilized giving a slightly yellow powder, 31 mg, 55%. The solid was a mixture (83:17) of compound 7a and sodium acetate. δ(ppm, D$_2$O): 5.73 (1H, dd, J$_{trans}$=3.5, J$_{cis}$=2.0, H-5), 5.36 and 5.16 (2H, 2s, methylene), 3.9 (1H, dd, J$_{gem}$=16.8, J=3.5, H-6 trans), 3.5 (1H, dd, J$_{gem}$=16.8 J=2.0, H-6 cis) 2.15 (3H, s, methyl of acetate). $\nu_{c=o}$=1818, 1835, 1615, 1585 cm$^{-1}$. λ(max)=254 ε 4160; 303 ε 4340.

Preparation 6

Sodium 2-methoxymethylpenem-3-carboxylate

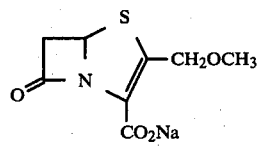

To a solution of triethylamine hydrosulfide, previously prepared by bubbling H$_2$S gas through a methylene chloride (50 cc) solution of triethylamine (6.95 g, 9.6 cc, 68.6 mmoles), was added dropwise a methylene chloride (15 cc) solution of methoxyacetyl chloride (6.0 g 55.5 mmoles), at 0° over a 30 min period. The mixture was stirred at 0° for 15 min, and allowed to warm up at room temperature. Stirring was continued for 2.5 h. The organic solution was diluted with ether, washed with 10% HCl, H$_2$O and brine. It was dried over MgSO$_4$ and the solvent was flashed down. (5.24 g, 89%). δ(ppm, CDCl$_3$) 5.30 (1H, s, S-H), 4.26 (2H, s, CH$_2$), 3.48 (3H, s, CH$_3$).

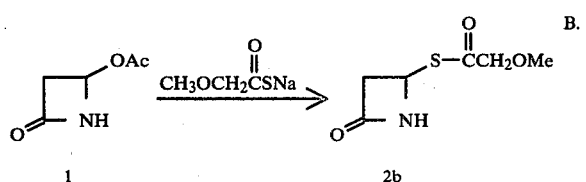
B.

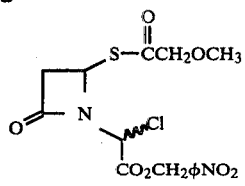
4b

A cold (0.5° C.) solution of 4-acetoxy-2-azetidinone (3.80 g, 29.5 mmoles) in water (60 cc) was treated dropwise under nitrogen atmosphere with an aqueous solution (60 cc) of the sodium salt of methoxythio acetic acid (3.91 g, 36.9 mmoles) over a 30 minute period. At the end of the addition, the mixture was stirred for 15 min at 0° C. and 2.5 h at room temperature. The aqueous solution was extracted with methylene chloride (5×50 cc). The organic phases were combined, washed with water-brine, brine and dried over MgSO$_4$. The residue (3.52 g) was passed through a silica gel (50 g) column (benzene-ether 4:1) 1.85 g, 33%, Rf=0.35 (ether benzene 1:1.5). δ(ppm, CDCl$_3$): 7.02 (1H, b.s., NH), 5.17 (1H, dd, J$_{4\text{-}3\text{-}cis}$=5, J$_{4\text{-}3\text{ }trans}$=3, C$_4$-H), 4.1 (2H, s, CH$_2$), 3.5 (1H, ddd, J$_{3\text{-}4\text{ }cis}$=5, J$_{gem}$=15, J$_{3\text{-}NH}$=2), 3.48 (3H, s, CH$_3$), 2.95 (1H,ddd, J$_{3\text{-}4\text{ }trans}$=3, J$_{gem}$=15, J$_{3\text{-}NH}$=1.5). $\nu_{c=o}$: 1775, 1690, $\nu_{NH}$: 3420.

Azetidinone glyoxylate 3b (789 mg, 2.05 mmoles) was treated at 0° C. under a dry atmosphere with thionyl chloride (9 ml) for 1.5 hr. The yellow solution was diluted with benzene and flashed down. This process was repeated and the resulting brown residue was used as such in the following reaction. δ(ppm, CDCl$_3$) 8.25 (2H, d, J=9, Ho. aromatic), 7.58 (2H, d, J=9, Hm, aromatic), 6.12 (1H, bs, CHCl), 5.70 (1H, m, H-4), 5.40 (2H, 2s, benzylic H), 4.08 (2H, s, CH$_2$), 3.48 (s, 3H, CH$_3$), 3.60-3.00 (2H, m, 2H-3). Mixture of two epimers.

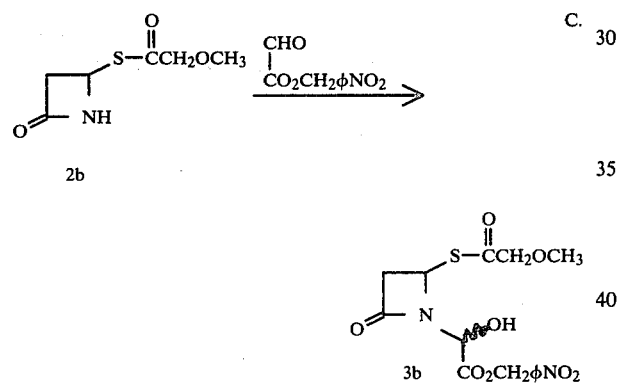
C.

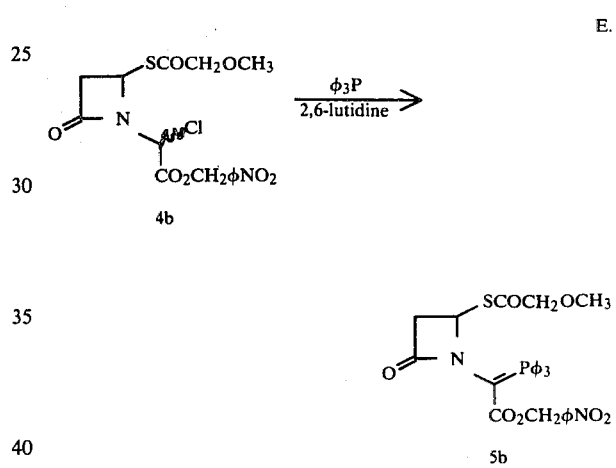
E.

A benzene (40 cc) solution of 4-methoxy acetyl thio-2-azetidinone (1.72 g, 9.82 mmoles) and p-nitrobenzyl glyoxylate (2.28 g, 10.2 mmoles) was refluxed through a Dean-Stark condenser filled with 3Å molecular sieves for 40 hrs. Evaporation of the solvent afforded an oily residue (3.82 g, 100%) in quantitative yield. δ(ppm, CDCl$_3$) 8.22 (2H, d, J=9, Ho aromatic), 7.52 and 7.57 (3H, 2 doublets, J=9,Hm aromatic) 5.2–5.7 (4H, two benzylic H, H-4 and H of glyoxylate), 4.32 (1H, b.s., OH) 4.08 and 4.02 (2H, 2s, CH$_2$) 3.68 (1H, dd, J$_{gem}$=15, J$_{3\text{-}4\text{-}cis}$=5), 3.45 and 3.42 (3H, 2s, CH$_3$), 3.03 (1H, dd, J$_{gem}$=15, J$_{3\text{-}4\text{-}trans}$=3). Mixture of two epimers, $\nu_{c=o}$: 1775, 1755, 1695 $\nu_{OH}$: 3500-3100, $\nu_{NO_2}$: 1525.

A solution of 4b (from 2.05 mmoles of 3b) in THF (20 cc, distilled over LAH) was treated with triphenyl phosphine (890 mg, 3.39 mmoles) and 2,6-lutidine (250 mg, 0.27 cc, 2.34 mmoles) for 6 h at 55°-60° C., under nitrogen atmosphere. The mixture was diluted with ether, washed with water, 10% HCl, saturated NaHCO$_3$, brine, and dried over MgSO$_4$. The residue obtained upon solvent evaporation was passed through a silica gel (5 g) column (ether:benzene, 2:8), to give 5b, 865 mg (67.5%).

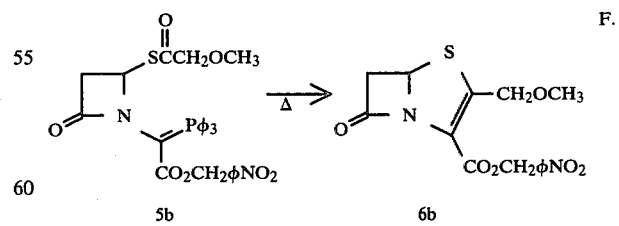
F.

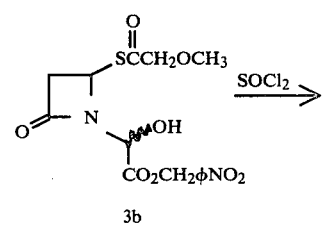
D.

A solution of phosphorane 5b (865 mg, 1.375 mmole) in toluene (15 cc) was refluxed for 1.75 h. Evaporation of the solvent gave a residue which was passed through a silica gel (9 g) column. It gave on elution with benzene a crystalline compound (191 mg, 40%) which was recrystallized from chloroformpet. ether (m.p. 109°–110°

). Rf=0.7 (benzene/ether: 1:1). δ(ppm, CDCl₃) 8.22 (2H, d, J=9, Ho. aromatic), 7.62 (2H, d, J=9, Hm. aromatic), 5.67 (1H, dd, $J_{5-6\,cis}$=4, $J_{5-6\,trans}$=2, H-5) 5.32 (2E, ABq, benzylic H), 4.63 (2H, ABq, CH₂) 3.89 (1H, dd, $J_{gem}$=16, $J_{6-5\,trans}$=2, H-6), 3.40 (3H, s, CH₃). $\nu_{c=o}$: 1795, 1710, $\nu_{NO_2}$1525, UV(EtOH) $\lambda_{max}$: 264 (ε=12,000), 320 (ε=9,680).

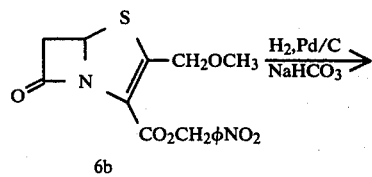

6b

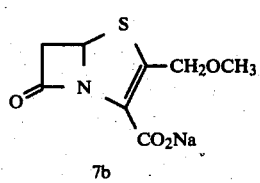

7b

A two phase mixture made of ester 6b (101 mg, 0.29 mmole) in ethyl acetate (15 cc) and sodium bicarbonate (24.2 mg, 0.29 mmole) in water (7 cc) was hydrogenated on 10% Palladium on charcoal (107 mg) in a Parr shaker at 30 p.s.i. H₂ for 3 h. The catalyst was removed and ethyl acetate was decanted. The aqueous phase was washed with ether and lyophilized to give a yellowish solid (72 mg, hydrated) NMR data indicated a mixture containing 10% sodium acetate. δ(ppm, D₂O) 5.72 (1H, m, H-5), CH₂ at C-2 (hidden by HOD signal), 3.77 (2H, m, H-6), 3.37 (3H, s, CH₃), 1.90 (S, CH₃CO₂Na). $\nu_{c=o}$, 1770, 1600, 1400. UV (EtOH) $\lambda_{max}$262 (ε=1342), 300 (ε=1623).

Preparation 7

Sodium 2-Phenylpenem-3-carboxylate

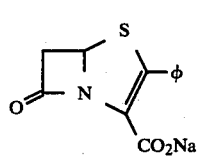

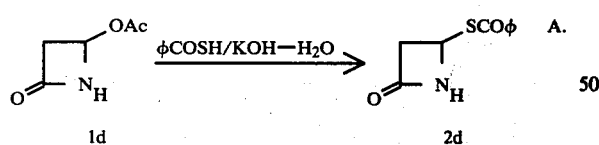

Thiobenzoic acid (4.63 g, 31.8 mmole; 95% pure) was dissolved in 1N KOH (32 ml) at ca. 20° C. and insoluble materials were removed by decantation. To this clear solution was added at 0°–2° C. (ice-bath) under nitrogen atmosphere 4-acetoxy-2-azetidinone (1d) (1.29 g, 10.0 mmole; K. Clauss et al., Liebigs Ann. Chem., 539, (1974). The reaction mixture was stirred (0.2° C., N₂) for 2 hrs and the resultant precipitates were filtered, yielding 2.13 g of yellowish solid. This was crystallized from EtOH-H₂O to obtain 4-thiobenzoyloxy 2-azetidinone (2d) (2.01 g, 9.73 mmole; yield 97.3%) as yellowish crystals: m.p. 97°–99° C.; n.m.r. (CDCl₃) δppm 2.8–3.7 (2H, m, H-3), 5.39 (1H, dd $J_{3-4\,cis}$=5Hz, $J_{3-4\,trans}$=2Hz, H-4), 6.82 (br.s.—NH), 7.3–8.0 (5H, m, aromatic H); i.r. (Nujol) 3200 cm⁻¹ ($\nu_{n-h}$), 1760 ($\nu_{c=o}$ β-lactam), 1665 and 1655 (ν-SCOφ); t.l.c. (benzene:diethylether=1:1), Rf=0.36.

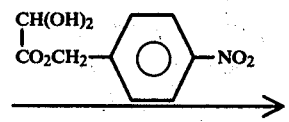

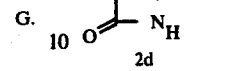

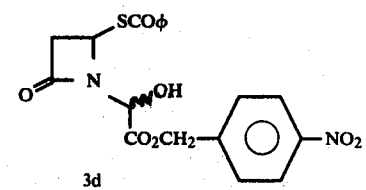

A mixture (suspension) of 4-thiobenzoyloxy-2-azetidinone (2d) (414 mg, 2.00 mmole) and p-nitrobenzyl glyoxylate hydrate (477 mg, 2.10 mmole) in benzene (70 ml) was heated at reflux with a Dean-Stark trap for 43 h. After evaporation of the solvent, the residue was purified by column chromatography (SiO₂, 20 g; eluent, benzene-diethylether=9:1), yielding 3d (671 mg, 1.61 mmole; yield 80.5%) as an oil: n.m.r. (CDCl₃) δppm 2.8–3.7 (2H, m, H-3) 5.0–5.5 (2H, m, H of glyoxylate and OH), 5.17 and 5.37 (2H, s, benzylic H) 5.70 (1H, dd, $J_{3-4\,trans}$=3Hz, $J_{3-4\,cis}$=5Hz, H-4), 7.2–8.2 (9H, m, aromatic H); i.r. (neat) 3400 cm⁻¹ ($\nu_{o-h}$), 1770 (br. $\nu_{c=o}$), 1660 ($\nu_{SCO\phi}$); t.l.c. (benzene:diethylether=1:1) Rf=0.26.

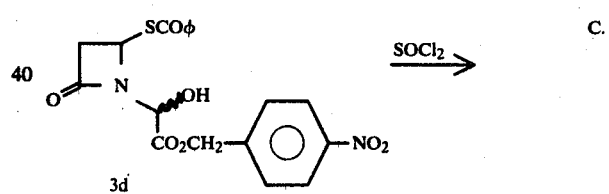

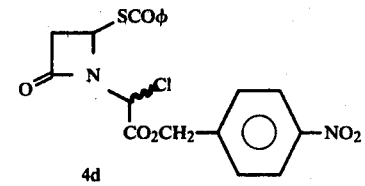

A mixture of the hydroxy ester 3d (671 mg, 1.61 mmole) and thionyl chloride (3 ml) was left at room temperature under N₂ atmosphere for 50 min and then the volatile materials were removed by water pump. The residue dissolved in methylene chloride was filtered to remove the insoluble materials. Evaporation of the solvent gave the chloro ester 4d (0.71 g, 1.6 mmole; yield 100%), as a coloured oil: n.m.r. (CDCl₃) δppm 3.20 (1H, m, H-3), 3.74 (1H, dd, $J_{3-3\,cis}$=5.5, H3),5.25 and 5.43 (2H, 2S, benzylic H), 5.85 (1H, m, H-4) 6.16 and 6.19 (1H, 2S -CHCl), 7.2–8.3 (9H, m, amomatic H); i.r. (neat) 1670 (br, $\nu_{c=o}$), 1665 ($\nu_{sco\phi}$), t.l.c. (benzene:diethylether=1:1) Rf=0.58.

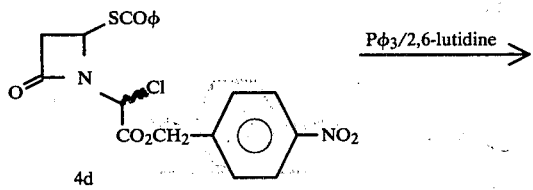
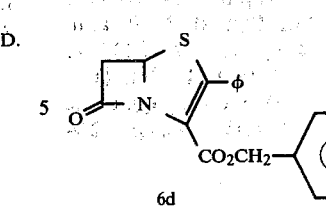
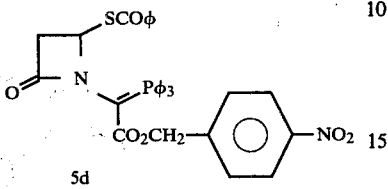
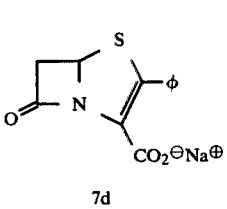

To a solution of the chloro ester 4d (0.71 g, 1.6 mmole) and triphenylphosphine (593 mg, 2.26 mmole) in benzene (50 ml, dried over molecular sieves) was added at 60°–65° C. 2,6-lutidine (0.24 ml=0.22 g, 2.1 mmole) and the mixture was heated at 60°–65° C. under $N_2$ atmosphere for 33 h and at 70°–75° C. ($N_2$) for 36 h. The cooled mixture diluted with ethyl acetate (50 ml) was washed with water, then saturated sodium chloride solution, dried ($Na_2SO_4$) and evaporated, yielding a crude oil. This oil was purified by column chromatography ($SiO_2$, 20 g; eluent, benzene: diethylether = 1:1), yielding the phosphorane 5d (625 mg, 0.945 mmole; yield, 59%) as a brownish oil: t.l.c. (benzene: diethylether = 1:1) Rf=0.16.

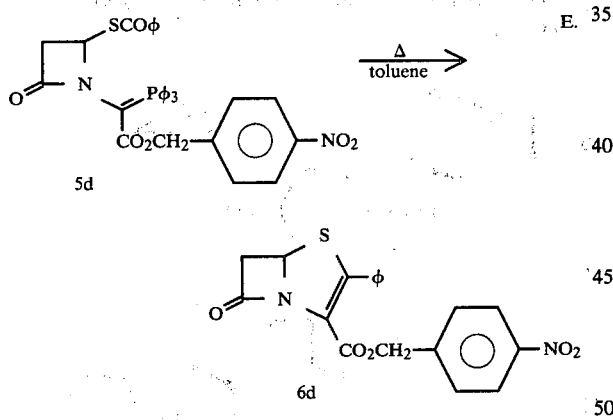

A solution of the phosphorane 5d (0.62 g, 0.94 mmole) in toluene (150 ml, dried over molecular sieves) was heated at reflux for 18 h. Evaporation of the solvent gave brown oil which was rinsed with benzene, yielding yellowish solid (0.21 g). This solid was crystallized from benzene, yielding the bicyclic ester 6d (166 mg, 0.435 mmole; yield, 46%) as light yellow crystals: m.p. 154°–161° C. (dec), n.m.r. ($CDCl_3$) δppm 3.55 (1H, AB of ABX type, $J_{6-6}$=16Hz, $J_{5-6\ trans}$=2Hz, H-6), 3.94 (1H, AB of ABX type, $J_{6-6}$=16Hz, $J_{5-6\ cis}$=4Hz, H-6), 5.20 (2H, AB type $J_{ab}$=14Hz, benzylic H), 5.79 (1H, X of ABX type, $J_{5-6\ cis}$=4Hz, $J_{5-6\ trans}$=2Ha, H-5), 7.23, 7.38, 8.07, 8.22 (4H, $A_2'B_2'$ type, aromatic H), 7.42 (5H, S, aromatic H); i.r. ($CHCl_3$) $1790_{cm^{-1}}$ ($\nu_{c=o}$ β-lactam), 1715 ($\nu_{c=o}$ ester); t.l.c. (benzene: diethylether = 1:1) Rf=0.54.

To a solution of the cyclic ester 6d (154 mg, 0.400 mmole) in ethyl acetate (30 ml) was added a solution of sodium bicarbonate (33.6 mg, 0.400 mmole) in water (15 ml) and then 10% palladium on charcoal (100 mg). The mixture was hydrogenated in the Parr shaker at room temperature and at an initial pressure of 30 psi of hydrogen. After 4 h. the catalyst was removed by filtration. The aqueous layer (decanted) was washed once with diethyl ether and filtered again through a Millipore filter paper to obtain a yellowish solution which was lyophilized, yielding sodium 3-phenyl-7-oxo-4-thia-1-azabicyclo[3,2,0]hept-2-ene-2-carboxylate 7d (59.4 mg, 0.221 mmole; yield: 55.2%) as a light yellow powder. This powder was contaminated with 11% of sodium acetate by weight): n.m.r. ($D_2O$) δppm 1.92 (1.2H, S, $CH_3CO_2Na$), 3.4–4.1 (2H, AB of ABX type, H-6), 4.8 (x H,S, $H_2$), 5.8–5.9 (1H, x of ABX, H-5), 7.5 (5H, S, aromatic H); U.V. $\lambda_{max}^{H_2O}$ 258 mu (ε=3500), 314 mu (ε=2000); i.r. 1760, 1600 cm$^{-1}$.

PREPARATION 8

2-(2'-Thienyl)methyl-penem-3-carboxylic Acid

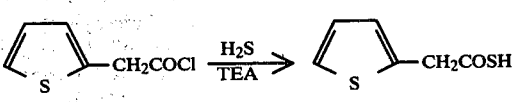

To a cold (0° C.) solution of oxalyl chloride (25 ml) was added thienylacetic acid (10.0 g, 0.0703 mole) under nitrogen atmosphere. The mixture was allowed to warm up slowly to room temperature and stirred for 16 h. Complete evaporation of oxalyl chloride gave the desired acid chloride (11.16 g, 98.8%). δ(ppm $CDCl_3$) 7.30–6.90 (3H, m, thienyl), 4.30 (2H, s, $CH_2$).

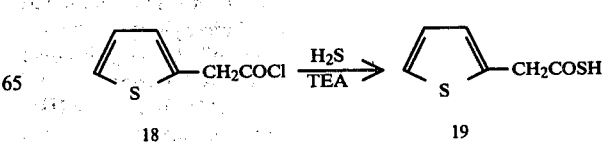

To a cold (0° C.) solution of triethylamine hydrosulfide, previously prepared by passing a stream of H₂S gas in an anhydrous methylene chloride (90 cc) solution of triethylamine (6.97 g, 9.6 ml, 68.9 mmole), was added dropwise a solution of thienylacetyl chloride (10.35 g, 64.4 moles) in methylene chloride (90 cc, dried over 3Å molecular sieves). The mixture was stirred at 0° C. for 15 min, then allowed to warm up to room temperature and stirred for 2.5 hrs. The organic solution was diluted with ether, washed with 10%, HCl, H₂O and brine. It was dried over MgSO₄ and the solvent evaporated. (10.33 g, 100%). δ(ppm CDCl₃) 7.35–6.90 (3H, m, thienyl), 4.46 (1H, b.s., SH), 4.03 (2H, s, CH₂). $\nu_{SH}$(CHCl₃): 3600–2700, $\nu_{c=o}$1705,

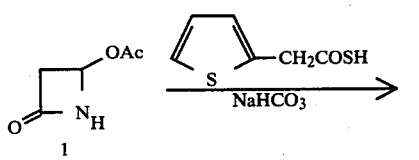

A benzene (50 cc) solution of azetidinone 2e (3.0 g, 13.2 mmoles) and p-nitrobenzyl glyoxylate (3.3 g, 14.5 mmoles) was refluxed through a Dean Stark filled with 3A molecular sieves for 48 hours. Evaporation of benzene gave an oily residue (6.74, 100%) as a mixture of 2 epimers. Anal. Calc'd for $C_{18}H_{16}N_2O_7S_2$: C, 49.53; H, 3.69; N, 6.42; S, 14.69 Found; C, 49.24; H, 3.65; N, 6.23; S, 14.63. δ(ppm, CDCl₃) 8.20 (2H, d, J=8, Hm aromatic), 7.60–6.80 (5H, m, Ho aromatic, thienyl), 5.58–5.15 (1H, m, H-4),5.32, 5.17 (2H, 2s, CH₂—PNB), 4.52 (1H, bs, OH), 3.98, 4.03 (2H, 2s, CH₂-thienyl), 3.47 (1H, d.d, $J_{gem}$=16, $J_{3-4\ cis}$=5, H-3), 2.95(1H, d.d, $J_{gem}$=16, $J_{3-4\ trans}$=3, H-3). $\nu_{c=o}$ (CHCl₃) 1780, 1760, 1695, $\nu_{NO_2}$ 1530.

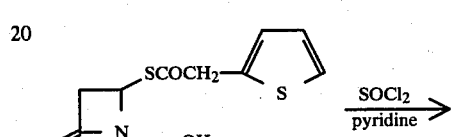

A cold (0°–5° C.) solution of 4-acetoxy-2-azetidinone (7.66 g, 59.3 mmoles) in water (120 cc) was treated dropwise (rapidly) with an aqueous solution (120 cc) of sodium 2-thienylthio acetate freshly prepared from 2-thienylthioacetic acid (10.33 g, 65.28 mmoles) and NaHCO₃ (5.76 g, 68.56 mmoles). The mixture was stirred at 0° C. for 15 min, then allowed to warm up to room temperature and stirred for 1.5 h. The aqueous solution was extracted with CH₂Cl₂ (5×50 cc). The organic phases were combined, washed twice with H₂O-brine, brine and dried over MgSO₄. The residue was crystallized from ether (m.p.: 73.5°–74°, 11.78 g, 87.4%). Analysis: Calc'd for $C_9H_9N_1O_2S_2$: C,47.56; H,3.99; N,6.16; S,28.21. Found: C,47.47; H,3.88; N,6.04; S, 28.21. δ(ppm CDCl₃) 7.38–6.92 (3H, m, thienyl), 6.78 (1H, b.s., N—H), 5.19 (1H,d.d., $J_{4-3\ trans}$=2.5, $J_{4-3\ cis}$=5, H-4), 4.03 (2H,s,CH₂), 3.42 (1H, d.d.d., $J_{gem}$=15.5, $J_{3-4\ cis}$=5, $J_{3-NH}$=2,H-3), 2.89 (1H, d.d.d., $J_{gem}$=15.5, $J_{3-4\ trans}$=2.5, $J_{3-NH}$=1,H-3). $\nu_{c=o}$ (CHCl₃) 1780, 1695, $\nu_{NH}$3420.

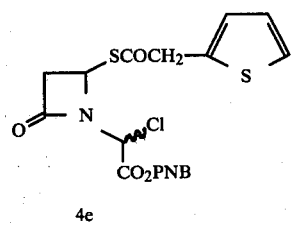

A cold (0°–5° C.) THF solution (20 cc, freshly distilled over LAH) of azetidinone 3e (3.81 g, 8.73 mmoles) was treated with thionyl chloride (0.72 cc, 9.60 mmoles, 1.1 eq) and pyridine (0.78 cc, 9.60 mmoles, 1.1 eq). It was stirred for 1 h at 0° C. and 1 h at room temperature. THF was evaporated and the dark brown oil was filtered through silica gel (40 g) using CHCl₃ as eluant (3.11 g, 78.3%, mixture of 2 epimers). δ(ppm, CDCl₃) 8.17 (2H, d, J=8, Hm aromatic), 7.52, 7.47 (2H, 2d, J=8, Ho aromatic), 7.32–7.13 (1H, m, H-5' thienyl), 6.96 (2H, d, J=4, H-3',4' thienyl),6.11 (1H, s, CHCl), 5.63 (1H, m, H-4), 5.37, 5.20 (2H, 2s, CH₂—PNB), 4.04 (2H, s, CH₂-thienyl), 3.59 (1H, d.d., $J_{gem}$=16, $J_{3-4\ cis}$=6, H-3), 3.05 (1H, 2d.d., $J_{gem}$=16, $J_{3-4\ trans}$=2, H-3). $\nu_{c=o}$ (CHCl₃) 1785, 1765 (shoulder), 1700, $\nu_{NO_2}$ 1525.

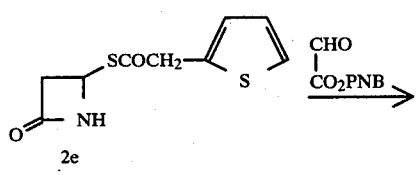

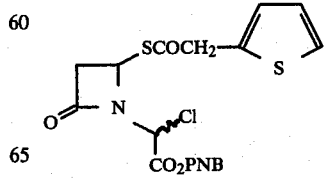

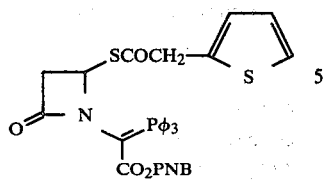

5e

To a solution of chloro-azetidinone 4e (3.11 g, 6.84 mmoles) in THF (30 cc distilled over LAH) was added triphenyl phosphine (2.72 g, 10.20 mmoles, 1.5 eq) and 2,6-lutidine (0.83 cc, 6.84 mmoles, 1 eq). The mixture was stirred for 16 h at room temperature under a nitrogen atmosphere. THF was evaporated and the residue was suspended in benzene. Lutidine hydrochloride was filtered off. The filtrate was passed through a silica gel column (45 g) and phosphorane 5e was eluted with ether and ethyl acetate (3.69 g, 67.3%).

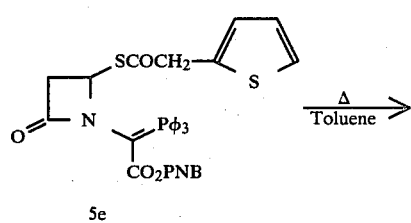

5e

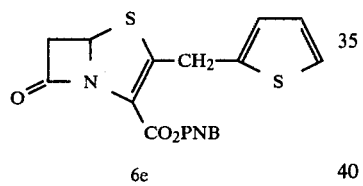

6e

Phosphorane 5e (3.69 g, 5.46 mmoles) in toluene was refluzed for 1.75 h. Toluene was evaporated.

The cyclized material was purified through a silica gel (45 g) column and came out with benzene (1.27 g, 58%, m.p. 116°-116.5° ). Analysis: Calc'd for $C_{13}H_{14}N_2O_5S_2$: C, 53.72; H, 3.51; N, 6.96; S, 15.93. Found: C, 53.82; H, 3.56; N, 6.97; S, 16.12. δ(ppm CDCl$_3$) 8.22 (2H, d, J=9, Hm aromatic), 7.59 (2H, d, J=9, Ho aromatic), 7.18 (1H, m, H-5' thienyl), 6.92 (2H, d, J=4, H-4', 3' thienyl), 5.62 (1H, d.d, J$_{5-6}$trans=2, J$_{5-6}$ cis=3.6, H—5), 5.35 (2H, center of ABq, J=14, CH$_2$-PNB), 4.37 (2H, center of ABq, J=16, CH$_2$-thienyl), 3.82 (1H, d.d., J$_{gem}$=16.5J$_{5-6}$ cis=3.6, H—6) 3.42 (1H, d.d., J$_{gem}$=16.5, J$_{6-5}$ trans=2.0, H—6). $\nu_{c=o}$(CHCl$_3$) 1795, 1715, $\nu V_{NO2}$ 1525. U.V. (EtOH) λ$_{max}$320 (ε=9,340),265 (ε=14,200), 235 (ε=14,400).

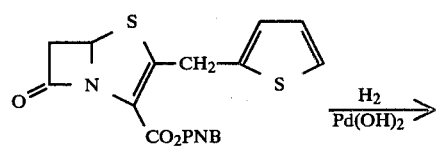

6e

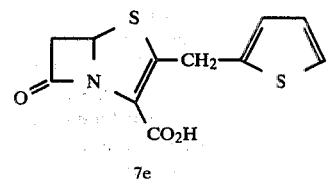

7e

A mixture of ester 6e (100 mg, 0.248 mmoles) in THF (60 cc) and water (30 cc) was shaken on a Parr hydrogenator for 24 h at 30 p.s.i. H$_2$, with Pd(OH)$_2$(100 mg). The catalyst was filtered off and the filtrate was diluted with ether (≈60 cc). The aqueous phase was separated and washed again with ether. Acidification of the aqueous layer gave a very poor yield (≈8 mg) of a mixture of desired acid plus something else. The organic phases were combined, washed with aqueous HCl, H$_2$O, brine and dried over MgSO$_4$. Upon solvent evaporation, the desired acid crystallized out and it was triturated with ether (24 mg, 42%, m.p. 119°-120° C. 120° C. decomp). δ(ppm DMSOd$_6$) 7.45 (1H, d, J=4, H-5' thienyl), 7.15 (2H, d, J=4, H-4', 3' thienyl), 5.77 (1H, d.d., J$_{6-5}$ trans=2, J$_{6-5}$ cis=4, H-5), 4.95 (2H, center of ABq, J=16, CH$_2$-thienyl), 3.95 (1H, d.d., J$_{gem}$=16, J$_{6-5 cis}$=4, H-6), 3.50 (1H, d.d., J$_{gem}$=16, J$_{6-5}$ trans=2, H-6), 3.50 (b.s., OH). $\nu_{c=o}$(CHCl$_3$) 1792, 1715 shoulder, 1685. $\nu_{OH}$ 3400-2500. U.V. (EtOH) λ$_{max}$ 312 (ε=6,000), 237 (ε=9,700).

Preparation 9

2-Methylthiomethylpenem-3-carboxylic Acid

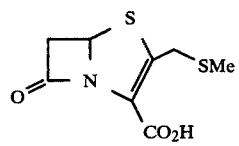

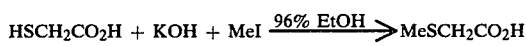

Thioglycolic acid (Aldrich; 92.12 g; 69.15 ml; 1 mole) was slowly added under nitrogen to a stirring solution of potassium hydroxide (168.3 g; 3 moles) in 1 l of 95% ethanol contained in a round-bottomed flask equipped with a reflux condenser. Methyl iodide (156.134 g; 68.5 ml; 1.1 mole) was then added over 45 min. The reaction mixture was refluxed for 5 h and then allowed to stand overnite at room temperature.

The ethanol was evaporated off in vacuo, ca. 1 l of water was added; the mixture was acidified with conc. HCl to pH 2 and extracted 3×'s with ether (250 ml). The combined ether extracts were washed 2×'s with brine, dried (Na$_2$SO$_4$), and evaporated to dryness in vacuo to give 75.5 g of a yellow-brown liquid. (70%). δ(ppm, CDCl$_3$): 2.1 (3H, s, CH$_3$S), 3.3 (2H, s, CH$_2$), 11.6 (1H, s, CO$_2$H).

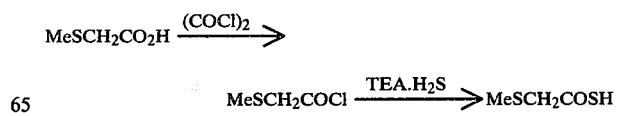

A mixture of thiomethyl acetic acid (45.5 g; 0.429 mole), oxalyl chloride (freshly distilled, 40 ml) and two drops of DMF was stirred under a reflux condenser equipped with a gas outlet for 2 h at room temperature. The excess oxalyl chloride was evaporated off in vacuo leaving the desired acid chloride as a brown liquid. 48.96 g (93.75%). δ(ppm, (COCl)₂): 2.55 (3H,s, CH₃s), 4.1 (2H, s, CH₂).

A solution of crude thiomethyl acetyl chloride (7.06 g; 65.26 mmoles) in CH₂Cl₂(20 ml) was slowly added to an ice-cold solution of TEA (9.89 g; 13.7 ml; 97.9 mmoles; 1.5 eq) in CH₂Cl₂ (125 ml) which had been saturated with H₂S. The mixture was stirred for 1 h at ice-bath temperature, then the bath was removed and the mixture was stirred another hour at ambient temperature.

Mixture was washed 3×'s with 3% HCl (50 ml), 1×brine (75 ml), dried (Na₂SO₄) and evaporated to dryness in vacuo to give 8.47 g of a brown liquid. δ(ppm, CDCl₃): 2.23 (3H, s, CH₃S, 3.45 (2H, s, CH₂), 4.95 (1H, bs, SH).

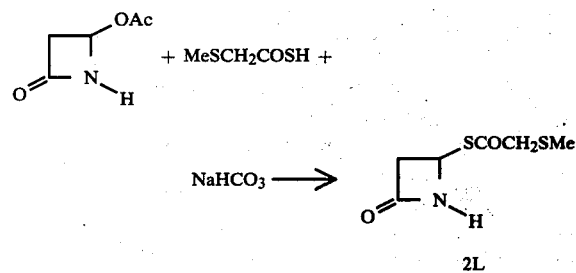

A solution of NaHCO₃ (5.82 g; 69.31 mmoles) in 50 ml H₂O was added with stirring to a solution of thioacid (8.47 g; 69.31 mmoles) in 50 ml CH₂Cl₂. After ca. 25 min, CO₂evolution had stopped. A solution of azetidinone acetate (9.32 g; 76.24 mmoles; 1.1 eq) in ca. 15 ml water was added and the reaction mixture was stirred overnite under N₂. Washed with CH₂Cl₂ (∼100 ml). Washed CH₂Cl₂ phase 2×'s 50 ml brine, dried (Na₂SO₄) and evaporated to dryness in vacuo to give 9.21 g (69.5%) of a brown oil. δ(ppm, CDCl₃): 6.78 (1H, bs, NH), 5.12 (1H, dd, J₃,₄ ₜᵣₐₙₛ=2.8 Hz, J₄,₃ ₖᵢₛ=5.0 Hz, H-4), 3.67 (1H, ddd, J₃, ₙₕ=2.0 Hz, J₃,₄ ₖᵢₛ=5.0 Hz, Jgₑₘ=15.2 Hz, H-3 cis), 3.4 (2H, s, CH₂-S), 2.95 (1H, ddd, J₃, ₙₕ=1.0 Hz, J₃,₄ ₜᵣₐₙₛ=2.8 Hz, Jgₑₘ=15.2 Hz, H-3 trans), 2.22 (3H, s, CH₃S).

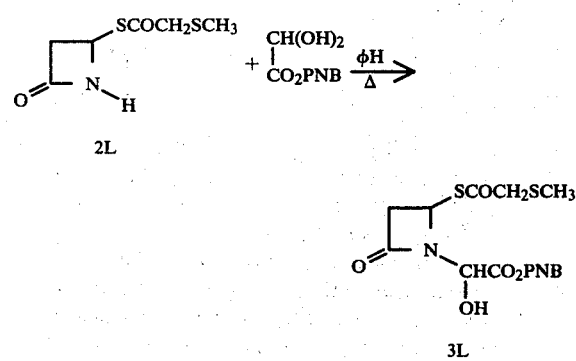

A mixture of azetidinone-2L (9.40 g; 49.14 mmoles), p-nitrobenzylglyoxylate hydrate (12.28 g; 54.05 mmoles; 1.1 eq), and 250 ml benzene was refluxed through a Dean-Stark trap overnite. The benzene was evaporated off in vacuo to give 22.60 g of a brown oil. This was used as such in the next step.

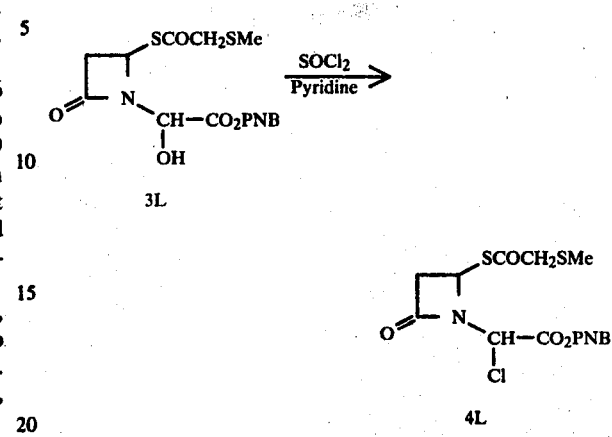

Thionyl chloride (7.39 g; 4.47 ml; 62.08 mmoles; 1.1 eq) was added dropwise to a solution of 31 (22.60 g; 56.44 mmoles) and pyridine (4.91 g; 5 ml; 62.08 mmoles; 1.1 eq) in 500 ml of THF at 5°-10°. The reaction mixture was stirred at 5°-10° for 2 h and then at ambient temperature overnite. It was evaporated to dryness in vacuo, the residue taken up in 100 ml of CHCl₃ and filtered through a pad of silica gel. The pad was washed with 850 ml of CHCl₃. The combined CHCl₃ washings were evaporated to dryness in vacuo leaving 19.08 g (80.7%) of a dark brown oil. This was used as such in the next step.

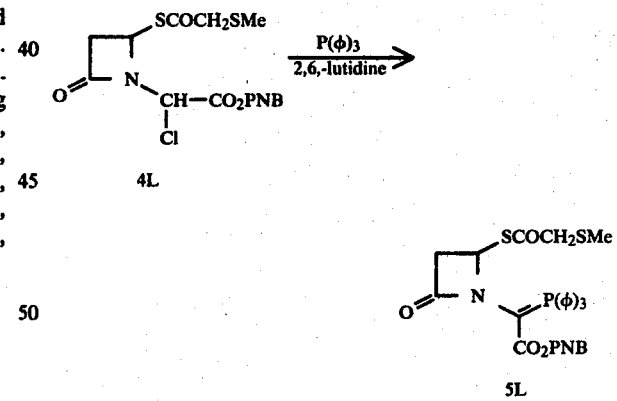

A mixture of 4L (18.98 g; 45.31 mmoles), P(ø)₃(13.07 g; 49.84 mmoles; 1.1 eq), and 2,6-lutidine (5.33 g; 5.66 ml; 49.84 mmoles; 1.1 eq) in 500 ml. THF was stirred at room temperature for 20 h. The THF was evaporated off in vacuo. NMR on the residue showed complete reaction of 4L.

The residue was dry column chromatographed on silica gel, eluting with 500 ml benzene, 5×250 ml ether, and 5×250 ml EtOAC. The EtOAC fractions were evaporated to dryness to give 14.38 g of a brown foam (49.2%). This was used as such in the next step.

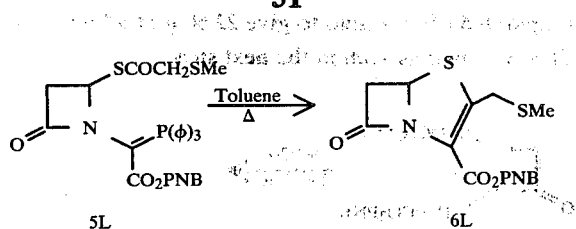

A mixture of phosphorane 5L (500 mg; 0.755 mmole) in 30 ml toluene was refluxed for 3 h, then allowed to stand at ambient temperature overnite. The toluene was evaporated off in vacuo and the residue dissolved in 5 ml chloroform and filtered through a pad of silica gel. The pad was washed with 30 ml ether. Evaporating the filtrate gave 0.28 g of a light yellow oil which crystallized on standing (98.6%).

A sample was recrystallized from ether-hexane to give a white solid, m. 102°-3°. Anal. calc'd for $C_{15}H_{14}N_2O_5S_2$: C, 49.17; H, 3.85; N, 7.65; S, 17.50. Found: C, 49.77; H, 3.91; N, 7.53; S, 17.07. NMR: (CDCl$_3$) δppm: 8.13 (2H, d, $J_{Hm-Ho}$=8.8 Hz, Hm of PNB), 7.52 (2H, d, $J_{Ho-Hm}$=8.8 Hz, Ho of PNB), 5.58 (1H, dd, $J_{5-6\,trans}$=2.0 Hz, $J_{5-6\,cis}$=3.8 Hz, H5), 5.27 (2H, AB, $J_{AB}$=13.5 Hz, CH$_2$ of PNB), 3.85 (2H, AB, $J_{AB}$=16.1 Hz, CH$_2$SMe), 3.78 (1H, dd, $J_{6,5\,cis}$=3.8 Hz, $J_{gem}$=16.1 Hz, H-6 cis), 3.43 (1H, dd, $J_{6,5\,trans}$=2.0 Hz, $J_{gem}$=16.1 Hz, H-6 trans), 2.12 (3H, s, SMe). IR (CHCl$_3$) cm$^{-1}$: 1790 (c=o of β-lactam), 1708 (c=o of PNB ester). UV (Abs. EtOH): λ265 mμ (ε=12,400), λ321 mμ (ε=7,200).

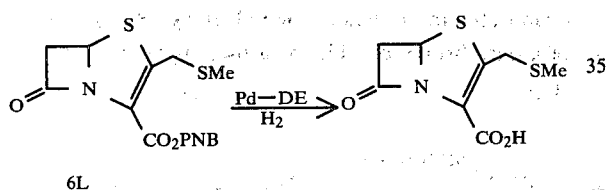

A mixture of penem ester 6L (301 mg; 0.822 mmole) in 15 ml THF, NaHCO$_3$ (69 mg; 0.822 mmole) in 15 ml water, 30% Pd-DE (300 mg), and 30 ml ether was hydrogenated for 3.5 h in a Parr apparatus starting at 50 p.s.i. The catalyst was filtered off through a celite pad which was then washed with water (ca.10 ml) and ether ca.10 ml). The aqueous phase was separated, washed twice with ether (15 ml), and then passed through a Millipore filter to remove traces of catalyst. Lyophilization gave 99.3 mg of a light brown powder. NMR showed that the title sodium salt plus approximately five other compounds were present in this powder. The powder was dissolved in ca. 10 ml water, ca. 20 ml EtOAC was added, and then 800 mg of methanol washed Dowex 50W-X8 acid resin was added. After stirring for ca. 5 min, the EtOAC phase was separated. The aqueous phase was re-extracted with EtOAC. The combined EtOAC phases were washed with water, dried (CaSO$_4$), and evaporated to dryness to give 55 mg of an orange solid. NMR and HPLC examination of this showed two compounds. The solid was triturated 3 times with cold Et$_2$O (10 ml). Et$_2$O traces were removed from the insoluble solid, 11 mg (5.8%). HPLC indicated >90% purity. NMR: (DMSO-D6) δppm: 5.33 (1H, dd, $J_{5-6\,trans}$=2.0 Hz, $J_{5-6\,cis}$=3.8 Hz, H5), 3.58 (2H, AB, $J_{gem}$=13.5, CH$_2$SCH$_3$), 3.48 (1H, dd, $J_{5-6\,cis}$=3.8 Hz, $J_{gem}$=16.1 Hz, H6 cis), 3.10 (1H, dd, $J_{5-6\,trans}$=2.0 Hz, $J_{gem}$=16.1 Hz, H6 trans), 2.63 (bs, CO$_2$H+H$_2$O), 1.75 (3H, s, SCH$_3$). IR (Nujol) cm$^{-1}$: 1780 (c=o of β-lactam), 1657 (c=o of hydrated—CO$_2$H). UV (abs. EtOH): λ260 (ε=3600), λ315 (ε=5600).

Preparation 10

2-Ethylpenem-3-carboxylic Acid

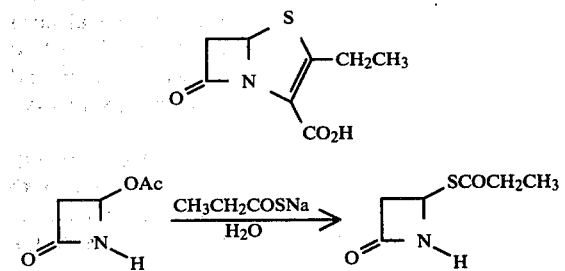

To a cold (0°-5° C.) oxygen-free 1N NaOH solution (55 ml) was added thiopropionic acid (4.96 g, 55 mmoles) at such a rate that the temperature was maintained at 0°-5° C. The resulting solution was added dropwise (20 min) to a cold (0° C.) oxygen-free solution of 4-acetoxy-2-azetidinone (6.46 g; 50 mmoles) in 22 ml of H$_2$O. The reaction mixture was stirred under a nitrogen atmosphere for 30 minutes at 0°-5° C. and 2 hours at room temperature before being extracted with chloroform (4×50 ml). The organic extracts were combined, washed with H$_2$O (2×10 ml), dried over anhydrous sodium sulfate and concentrated to a slightly yellow oil. Yield 5.20 g (65%). δ(ppm, CDCl$_3$): 7.16 (1H, b.s., NH), 5.21 (1H, dd, $J_{4,3\,trans}$=3.0 Hz, $J_{4,3\,cis}$=5.0 Hz, H-4), 3.5 (1H, ddd, $J_{3,\,NH}$=2.0 Hz, $J_{3,4\,cis}$=5.0 Hz, $J_{gem}$15.2 Hz, H$_3$cis) 2.90 (1H, ddd, $J_{3,NH}$=1.0 Hz, $J_{3,4\,trans}$=3.0 Hz, $J_{gem}$=15.2 Hz, H-3trans), 2.60 (2H, q, J=8Hz, CH$_2$), 1.08 (3H, t, J=8Hz, CH$_3$).

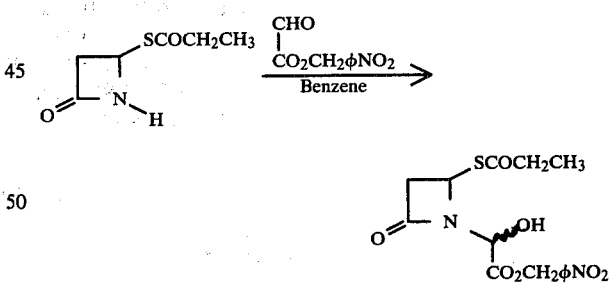

A solution of 4-propionylthio-2-azetidinone (3.18 g, 20 mmoles) and p-nitrobenzyl glyoxylate (5.0 g, 22 mmoles) in benzene (250 ml) was refluxed through a Dean-stark condenser filled with 3Å molecular sieves. After 18 h, the solvent was evaporated. The resulting yellow oil was filtered through a pad of silica gel (activity III; 100 g) using benzene: ether 3:1. This procedure yielded a slightly yellow oil. Yield 7.41 g (100%) Mixture of two epimers. δ (ppm, CDCl$_3$) 8.2(2H, d, J=9, Hm arom.), 7.6 (2H, d, J=9, Ho arom), 5.4 (4H, m, two benzylic H, H-4 and H of glyoxylate) 4.6 (1H, br. m, hydroxyl), 3.4 (2H, m, H-3), 2.6 (2H, 2q, —CH$_2$), 1.1 (3H, 2t, CH$_3$).

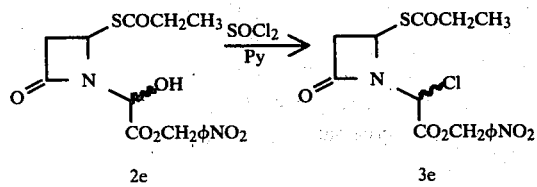

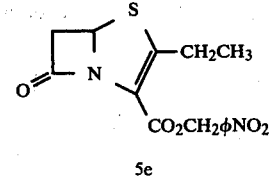

Azetidinone glyoxylate (2e) (3.92 g, 10.6 mmoles) was dissolved in CH$_2$Cl$_2$(40 ml) and pyridine (0.97 ml, 12 mmoles) was added to the solution. The mixture was cooled to 0° C. and SOCl$_2$ (0.88 ml, 12 mmoles) in CH$_2$Cl$_2$(5 ml) was slowly added. The mixture was stirred 30 minutes at 0° C. The solvent was then evaporated under reduced pressure to yield a yellow oil. This material was dry-chromatographed on 50 g of silica gel using CH$_2$Cl$_2$as eluent. This procedure yielded a faintly yellow oil. Yield 3.08 g (75%). Mixture of two epimers. δ(ppm, CDCl$_3$) 8.2 (2H, d, J=9, Hm aromatic), 7.6 (2H, d, J=9, Ho aromatic), 6.06, 6.10 (1H, 2s, CHCl), 5.8 (1H, m, H-4), 5.43, 5.30 (2H, 2s, benzylic), 3.7 (1H, dd, J$_{gem}$=16, J$_{3,4}$ cis=5, H-3), 3.2 (1H, dd, J$_{gem}$=16, J$_{3,4}$ trans=3, H-3), 2.6 (2H, 2q, J=8, —CH$_2$), 1.16 (3H, t, J=8, —CH$_3$).

The phosphorane 4e (3.15 g, 5.1 mmoles) was dissolved in 50 ml of toluene and the solution was refluxed for 3 hours. The solvent was evaporated in vacuo and the residue was chromatographed over 40 g of silica gel using benzene: ether 95:5 as eluent. This procedure afforded 658 mg of colorless cyclic compound. Subsequent elution with ethyl acetate gave 1.8 g of unreacted phosphorane. The whole procedure (cyclization-purification) was repeated twice more. Total yield: 1.42 g (83%) m.p. 110°–112° C. δ(ppm, CDCl$_3$), 8.25 (2H, d, J=9, Hm aromatic), 7.65 (2H, d, J=9, Ho aromatic), 5.65 (1H, dd, J$_{4,3}$ cis=3.6, J$_{4,3}$ trans=2.2 H-4), 3.75 (1H, dd, J$_{gem}$=16, J$_{3,4}$ cis=5, H-3) 3.2 (1H, dd, J$_{gem}$=16, J$_{3-4}$ trans=2.2, H-3), 2.88, 2.85, (2H, 2q, J=8Hz, —CH$_2$), 1.2 (3H, t, J=8Hz, —CH$_3$), ν$_{c=o}$=1785, 1710. ν$_{NO_2}$=1525.

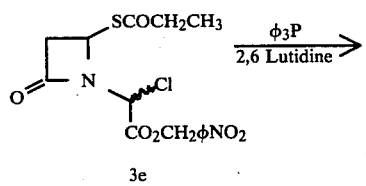

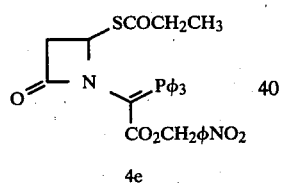

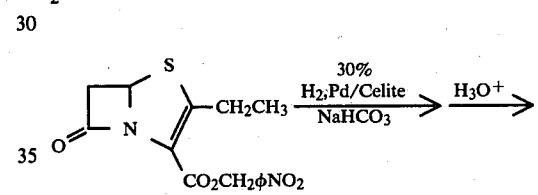

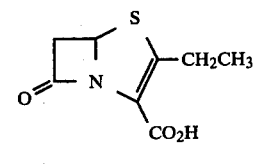

Chloro compound 3e (11.3 g, 29 mmoles) and triphenyl phosphine (7.8 g, 30 mmoles) were dissolved in 300 ml of anhydrous ether. 2,6 Lutidine (3.6 ml, 30 mmoles) was then added to the solution which was stirred at room temperature for 36 hours. At the end of this time, an abundant white precipitate had formed. It was collected by filtration, dissolved in benzene and the solution filtered to remove lutidine hydrochloride. The benzene solution was then evaporated to yield a yellow oil which on trituration with ether afforded the desired plhosphorane as a white crystalline material. It was recrystallized from CH$_2$Cl$_2$: ether to afford pure phosphorane. Yield 11.6 g (64%) - m.p. 143.5°–145 ° C.

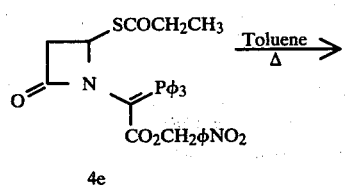

The p-nitrobenzyl ester (1.002 g, 3 mmoles) was dissolved in THF (81 ml) and ether (126 ml). NaHCO$_3$ (276 mg, 3.3 mmoles) H$_2$O) (60 ml) and 30% palladium on Celite (1.05 g) were added and the mixture was hydrogenated 4 hours at room temperature and 30 p.s.i. The catalyst was removed and the organic phase was decanted. The aqueous layer was washed with ether, then cooled to 0° C. and carefully acidified with 3.3 ml of 1N HCl. The aqueous layer was extracted with ethyl acetate (10×20 ml) and the ethyl acetate solution was dried and evaporated to give the desired acid as colorless crystals. Yield 293 mg (49%). δ (ppm, CDCl$_3$), 9.1 (1H, br.s, carboxyl), 5.65 (1H, dd, J$_{4,3}$ cis=3.6, J$_{4-3}$ trans=2.2, H-4), 3.75 (1H, dd, J$_{gem}$=16, J$_{4-3}$ cis=3.6, H-3), 3.2 (1H, dd, J$_{gem}$=16, J$_{3-4}$ trans=2.2 H-3), 2.88, 2.85 (2H, 2q, J=8Hz, —CH$_2$), 1.2 (3H, t, J=8Hz, —CH$_3$). ν$_{c=o}$=1790, 1680 UV (EtOH) λ$_{max}$320 (ϵ=5075), 285 (ϵ=3900).

Preparation 11

Disodium 2-(2-carboxyethyl)penem-3-carboxylate

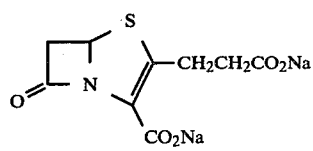

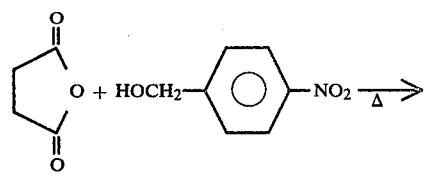

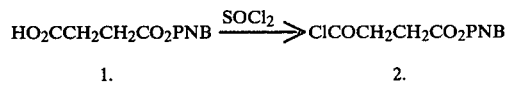

A mixture of succinic anhydride (20 g) and p-nitrobenzyl alcohol (30.6 g) was stirred together with heating until all had melted (about 140°), then maintained at 130°–150° for 1 h. The melt was allowed to cool a little (but not solidify) and 450 ml of ethyl acetate was carefully added with stirring. The solution was cooled to 23° and extracted with sodium bicarbonate solution (200+2×50 ml, containing 21 g of NaHCO₃). The aqueous extract was washed with ethyl acetate (200 ml) and then acidified with 210 ml of 1.2 M hydrochloric acid. The acidified aqueous mixture was extracted with ethyl acetate (400+100 ml) and the extracts were washed with water and saturated sodium chloride solutions (400 ml each). The ethyl acetate extract was dried (Na₂SO₄) and the solvent was evaporated in vacuo to give acid 1. as an off-white solid, 37.2 g (72% yield).

$$\text{HO}_2\text{CCH}_2\text{CH}_2\text{CO}_2\text{PNB} \xrightarrow{\text{SOCl}_2} \text{ClCOCH}_2\text{CH}_2\text{CO}_2\text{PNB}$$
<p style="text-align:center">1.            2.</p>

A solution of acid 1 (19.36 g), thionyl chloride (40 ml) and dichloromethane (200 ml) was stirred at 23° for 18 h. The solvent and excess thionyl chloride were evaporated in vacuo at 23° to give acid chloride 2 as an off-white solid, 20.5 g (99% yield).

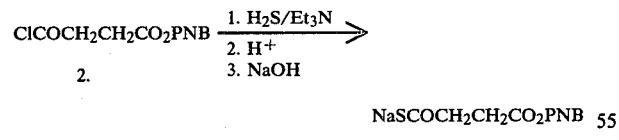

Hydrogen sulfide was bubbled into a solution of triethylamine (26 ml) in dichloromethane (350 ml) at 0° until saturated (about 10 min). A solution of acid chloride 2 (20.5 g) in dichloromethane (350 ml) was added over 30 min to the hydrogen sulfide solution at 0°. The solution was maintained at 0° for 1 h, then the solvent was evaporated in vacuo. The residue was mixed with water and ethyl acetate (250 ml each), cooled to 0°, nitrogen bubbled through the mixture and 120 ml of 1.6 M hydrochloric acid was added. The mixture was shaken and separated. The ethyl acetate layer was washed with 250 ml dilute sodium chloride solution, then extracted with 300 ml of 0.25 M NaOH. About 1 ml more of sodium hydroxide solution was added to bring the solution to pH 8. The aqueous extract was freeze-dried to give salt 3 as a yellow powder, 24.2 g, 100% yield.

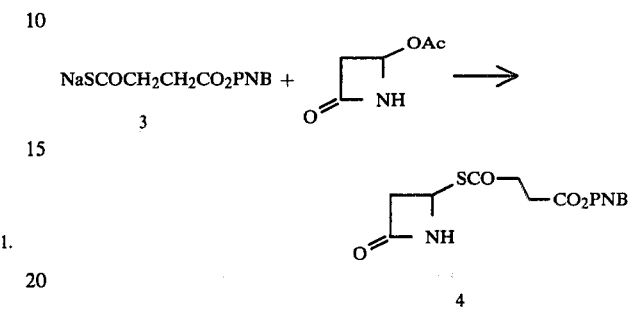

A solution of 4-acetoxy azetidinone (8.15 g) in 80 ml of water was added to a solution of salt 3 (24 g) in 240 ml of water plus 240 ml of acetone. The solution was stirred at 23° for 5 h. The resulting mixture was diluted to 1000 ml with water and extracted with dichloromethane (2×500 ml). The combined organic extract was washed with 0.5% hydrochloric acid and 2% sodium bicarbonate (500 ml each), then dried (Na₂SO₄) and absorbed onto 200 g of silica gel. The silica was extracted with 3 l of diethyl ether. The solvent was evaporated from the extracts to give compound 4 as a faintly yellow solid, 17.5 g (92% yield.) Compound 4 was recrystallized from benzene, m.p. 88°–89°. Anal. Calc'd for $C_{14}H_{14}N_2O_6S$: C, 49.70; H, 4.17; N, 8.28; S, 9.48. Found: C, 49.74; H, 4.22; N, 8.18;, S, 9.42.

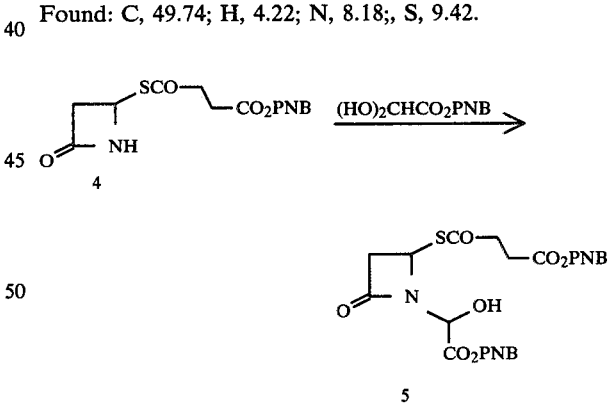

A mixture of compound 4 (10.3 g), p-nitrobenzylglyoxylate (8.8 g) and benzene (200 ml) was heated under reflux under a Dean-Stark trap for 6 h. The solvent was evaporated in vacuo and the residue was redissolved in 200 ml of dichloromethane. The dichloromethane solution was washed with dilute sodium chloride, dried (Na₂SO₄) and absorbed onto 170 g of silica gel. The silica was extracted with 1700 ml of ethyl acetate. The ethyl acetate was evaporated in vacuo to give crude hydroxy compound 5, as a pale yellow tar, 18.6 g.

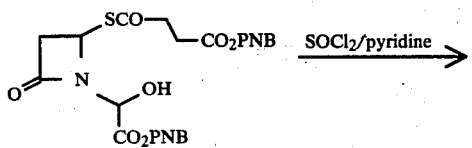 SOCl₂/pyridine → 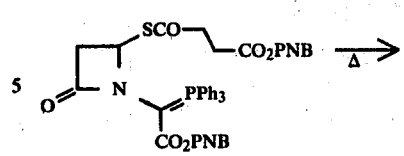 Δ →

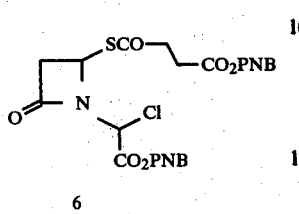

6

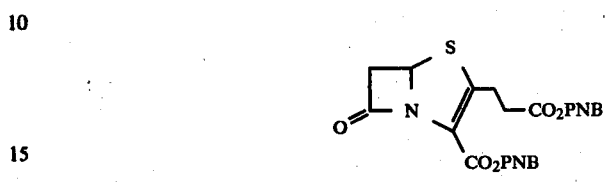

8.

A solution of thionyl chloride (2.5 ml) in tetrahydrofuran (25 ml) was added dropwise with stirring to a solution of crude compound 5 (18.6 g), pyridine (2.8 ml) and tetrahydrofuran (200 ml) at 0°. The resulting mixture was stirred at 0° for 4 h. A precipitate was removed by filtration and the solvent was evaporated in vacuo. The residue was dissolved in 200 ml of dichloromethane, treated with charcoal, filtered and the solvent was evaporated in vacuo to give the crude chloro derivative 6 as an orange tar, 17.5 g.

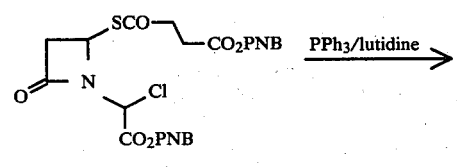 PPh₃/lutidine →

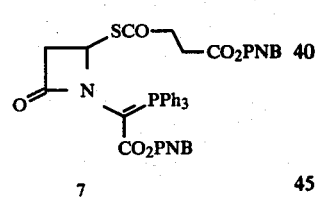

A mixture of the crude chloro compound 6 (17.4 g), 2,6-lutidine (3.3 g), triphenylphosphine (8.1 g) and tetrahydrofuran (175 ml) was stirred together at 23° for 20 h. A precipitate was removed by filtration and the solvent was evaporated in vacuo. The residue was dissolved in dichloromethane (300 ml) and absorbed onto 300 g of silica gel. The silica was eluted with dichloromethane (600 ml), then with ethyl acetate (1500 ml). The ethyl acetate was evaporated in vacuo. The residue was dissolved in dichloromethane (150 ml) and absorbed onto 75 g of silica gel. The solvent was evaporated in vacuo and the silica was placed on a 400 g silica gel column. The column was eluted with dichloromethane, gradually switching to ethyl acetate (total about 11 l). TLC of the column fractions (125 ml each) (silica gel, dichloromethane: ethyl acetate 1:1) showed a major spot (with near impurities) at Rf 0.34 for fractions 22 to 26. These fractions were combined and the solvent was evaporated in vacuo to give impure phosphorane 7 as a brown tar, 6.97 g.

A mixture of crude phosphorane 7 (6.97 g) in 210 ml of toluene was heated under reflux with stirring for 4 h. Silica gel (35 g, activity III) was added to the cooled solution, the solvent was evaporated in vacuo and the silica was placed on a 70 g silica gel column. The column was eluted with diethyl ether. The first fraction was 50 ml; the remaining were 100 ml each. TLC (silica gel, ether) showed fractions 3 to 11 to produce a single spot at Rf 0.38. The solvent was evaporated in vacuo from these fractions to give diester 8 as a pale yellow solid, 2.37 g. Overall yield from 4 to 8: 15.2%. Compound 8 was recrystallized from benzene/ethyl acetate, m.p. 138°–140°.

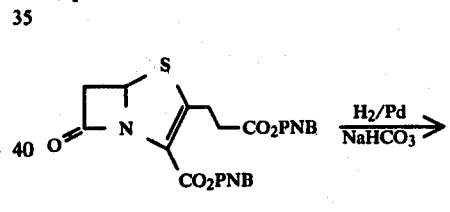 H₂/Pd / NaHCO₃ →

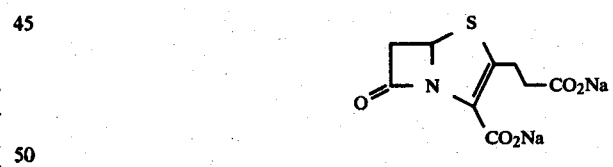

9.

A slurry of 514 mg of diester 8, 168 mg of sodium bicarbonate, 500 mg of 30% palladium-on-diatomaceous-earth and 25 ml each of water, diethyl ether and tetrahydrofuran was hydrogenated with a Parr shaker at 23° and 45 p.s.i. for 5 h. The catalyst was removed by filtration through Celite and the filter cake was extracted with 25 ml each of water and ethyl acetate. The combined filtrates were allowed to separate and the aqueous layer was freeze-dried to give disodium salt 9 as a light brown powder, 228 mg, 80% yield. $\lambda_{max}^{H_2O}$ 225 ($\epsilon=3300$), 301 ($\epsilon=4100$). Estimated purity of product: 70% (plus 10% each of NaHCO₃, H₂O and organic byproducts).

Preparation 12

2-Phenoxymethylpenem-3-carboxylic Acid

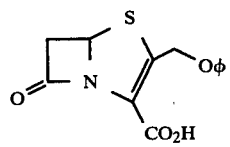

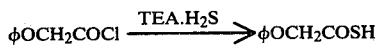

A solution of phenoxyacetyl chloride (Aldrich; 1.70 g; 10 mmoles) in 15 ml of methylene chloride (molecular sieve dried) was slowly added to a cooled (ice bath) solution of triethylamine (1.52 g; 2.17 ml; 15 mmoles) in 50 ml of methylene chloride which had been saturated with H₂S for 20 minutes. The mixture was stirred for 10 minutes at 0°–10° and then at 25° for 1 h. Approximately 50 ml of methylene chloride was added and the reaction mixture was washed successively with 3% HCl (1×30 ml) and brine (2×30 ml), dried (Na₂SO₄) and evaporated to dryness in vacuo. This gave 1.6 g of a yellow liquid. δ (ppm, CDCl₃): 4.43 (2H, s, CH₂), 4.78 (1H, s, S—H), 6.73–7.43 (5H, m, φ). i.r. (liq. film): 1690 ($v_{C=O}$), 2555 ($v_{S-H}$).

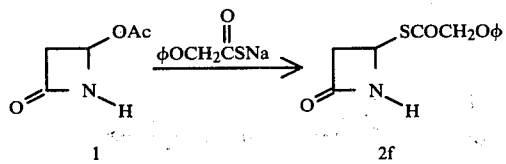

A solution of thioacid (1.38 g; 8.01 mmoles) in 5 ml water was added to a solution of NaHCO₃ (673 mg; 8.01 mmoles) in water (5 ml) at 0°–10°. After CO₂ evolution had stopped (ca. 4 min), a solution of azetidinone acetate (906 mg; 7.01 mmoles) in water (15 ml) was added and the mixture allowed to stir at 25° for 2 h. It was extracted with methylene chloride (3×20 ml). The extract was washed with brine (2×10 ml), dried (Na₂SO₄) and evaporated in vacuo to yield 1.6 g of yellow oil which crystallized on standing.

An analytical sample was prepared by crystallizing from ether and then from CCl₄. White solid; m.p. 87.5°–88°. Anal. Calc'd for C₁₁H₁₁NO₃S: C 55.68; H 4.67; N 5.90; S 13.51. Found: C 55.43; H 4.68; N 5.92; S 13.78. NMR: (CDCl₃)

7.47–6.77 1H, bs, NH
        (5H, m, φ), 5.17 (1H, dd, J₄₋₃ cis=3 cps, J₄₋₃ trans=5 cps C₄-4), 4.65 (2H, s, CH₂), 3.5 (1H, ddd, J₃₋₄ cis=5 cps, J_gem=15 caps, J₃₋NH=2 cps), 2.87 (1H, ddd, J₃₋₄ trans=3 cps, J_gem=15 cps, J₄₋NH=1.5 cps).

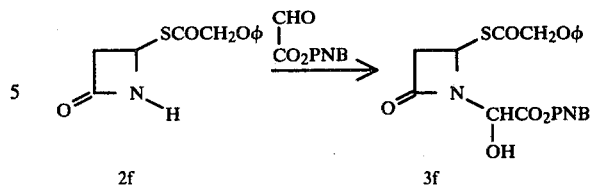

A mixture of azetidinone 2f (4.74 g; 20 mmoles), glycidic ester (4.77; 21 mmoles) and 200 ml of benzene was refluxed overnight through a Dean-Stark trap filled with 3A molecular sieves. Evaporation to dryness gave a thick brown oil (9.39 g; 105%) which was used in the next step without further purification.

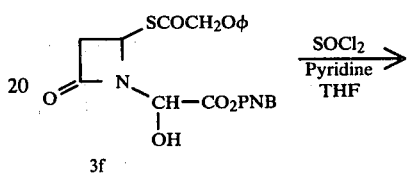

Thionyl chloride (2.02 g; 1.22 ml; 16.973 mmoles; 1.1 equiv) was added to a stirring solution of 3f (6.89 g; 15.43 mmoles), pyridine (Karl fisher grade; 1.34 g; 1.36 ml; 16.973 mmoles, 1.1 equiv), and 100 ml of THF (molecular sieve dried) at ice bath temp. under N₂. The reaction mixture was stirred at 5°–10° for 1 h, then the bath was removed and stirring was continued for another hour. The THF was removed in vacuo, the residue dissolved in 200 ml of CHCl₃ and filtered through a pad of silica gel (act. 3, 70 g). The pad was washed with CHCl₃ (2×75 ml). Combined filtrates were evaporated to dryness in vacuo. 7.09 g (99%) of an orange oil. This material was used as such to prepare 5f. NMR (CDCl₃): δ 8.23 (2H, d, J=11 cps, H-o-NITRO); δ 7.63–6.80 (7H, m, aromatic); δ6.10 (1H, s, CHCl); δ 5.70 (1H, dd, J=6 cps, 2 cps, C₄H); δ 5.27 (2H, dd, benzylic CH₂ [AB]); δ 4.67 (2H, 2S, benzylic CH₂); δ 3.65 (1H, dd, C₂H); δ 3.1 (1H, ddd, C₂-4). IR (film): 1788 (β-lactam $v_{C=O}$); 1764 (ester $v_{C=O}$); 1695 (thioester $v_{C=O}$).

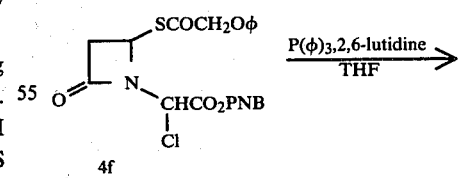

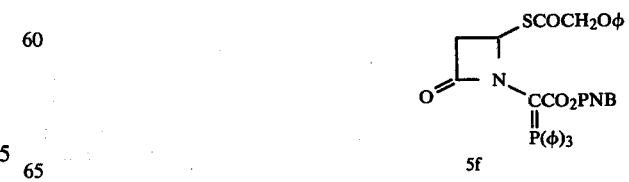

A mixture of 4f (4.03 g; 8.67 mmoles), P(φ)₃ (2.5 g; 9.54 mmoles; 1.1 equiv.), 2,6-lutidine (1.02 g; 1.08 ml;

9.54 mmoles; 1.1 equiv) and 100 ml of THF (molecular sieve dried) was stirred under N$_2$ overnite at room temperature. The THF was evaporated off in vacuo and the residue dry column chromatographed on silica gel eluting with 200 ml benzene, 200 ml benzene: ether (1:1), 200 ml ether, and 300 ml EtOAc. The ether and ethyl acetate fractions combined weighed 2.54 g (42.4%) and NMR showed the presence of 5f. This material was used as such to prepare 6f.

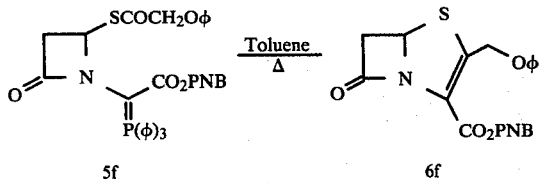

5f            6f

A solution of 5f (0.57 g; 0.82 mmoles) and 50 ml Toluene was refluxed for 1.5 h. At this point the TLC (Et$_2$O) showed complete disappearance of 5f and the formation of a new less polar spot. The toluene was evaporated off in vacuo and the residue filtered through a pad of silica gel with 50 ml of benzene and 50 ml of benzene: ether (1:1). Evaporation of the filtrates gave 0.23 g of a yellow oil (68%) which crystallized on standing.

An analytical sample was prepared by triturating the crude solid with ether, white solid, mp. 124°–125°. Anal. calc'd for C$_{20}$H$_{16}$N$_2$O$_6$S: C, 58.24; H, 3,91; N, 6.79; S, 7.77. Found: C, 57.47; H, 4.02; N, 6.79; S, 7.65. NMR: (CDCl$_3$) δ ppm 3.45 (1H, AB of ABX type, J$_{6-6}$=16.5 Hz, J$_{5-6\ trans}$=2 Hz, H-6), δ 3.75 (1H, AB of ABX type, J$_{6-6}$=16.5 Hz, J$_{5-6\ cis}$=3.8 Hz, H-6), δ 5.02–5.4 (4H, complex multiplet, benzylic and allylic H), δ 5.63 (1H,X of ABX type, J$_{5-6\ trans}$=2 Hz, J$_{5-6\ cis}$=3.8 Hz, H-5), δ 6.7–7.7 (7H, complex multiplet, phenyl and meta-H in p-nitrobenzyl), δ 8.15 (2H, d, J$_{ortho}$=9 Hz, ortho-H in p-nitrobenzyl). i.r (CHCl$_3$) 1798 cm$^{-1}$ (ν$_{c=o}$β-lactam), 1712 (ν$_{c=o}$ester). U.V. (abs. EtOH) λ 264 mu (ε=14,000), 322 (ε=9,000).

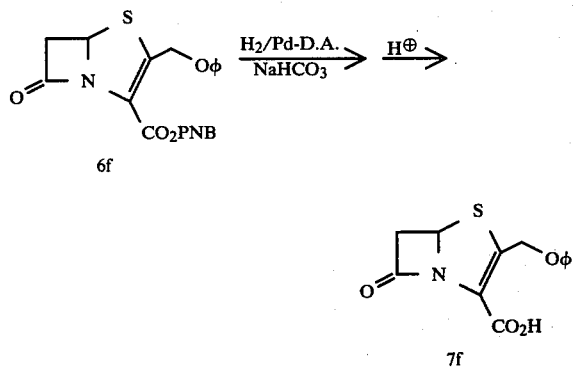

6f

7f

A mixture of 6f (103 mg; 0.2497 mmole) dissolved in THF (7 ml), sodium bicarbonate (21 mg; 0.2497 mmole dissolved in H$_2$O (7 ml), 30% Pd-diatomaceous earth (103 mg) and Et$_2$O (14 ml) was hydrogenated in a Parr apparatus for 24 h, starting at 40 psig. The catalyst was filtered off through a pad of celite, which was then washed with H$_2$O and Et$_2$O. The H$_2$O phase in the filtrate was washed twice with Et$_2$O (~15 ml each), acidified with 3% HCl, and extracted with EtOAc (3×25 ml). The EtOAc extract was washed with H$_2$O (1×10 ml), dried (Na$_2$SO$_4$) and evaporated to dryness to give 40 mg of a yellow solid. (57.9%). This material was triturated with Et$_2$O (3×10 ml), leaving 20 mg of a cream colored solid, m.p. 126°–131° dec. NMR: (DMSO-d$_6$) δ ppm 3.40 (9.6H, CO$_2$H and 4.3 H$_2$O), 3.63 (1H, AB of ABX type, J$_{6-6}$=16.7 Hz, J$_{5-6\ trans}$=2 Hz, H-6), 4.00 (1H, AB of ABX type, J$_{6-6}$=16.7 Hz, J$_{5-6\ cis}$=3.8 Hz, H-6), 5.42 (2H, J$_{gem}$=15 Hz, CH$_2$O), 5.85 (1H, X of ABX type, J$_{5-6\ cis}$=3.8 Hz, J$_{5-6\ trans}$=2 Hz, H-5), 6.85–7.55 (5H, complex multiplet, aromatic). i.r. (Nujol) 1792 cm$^{-1}$ (ν$_{c=o}$ β-lactam), 1662 (ν$_{c=o}$ acid hydrated). U.V. (abs. EtOH) λ 315 (ε=5600).

Preparation 13

2-(2'-Furyl)penem-3-carboxylic Acid

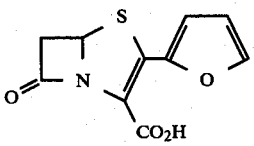

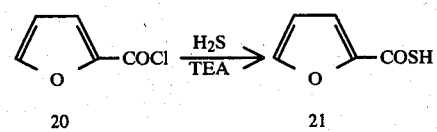

20       21

To a cold (0° C.) solution of triethylamine hydrosulfide, previously prepared by passing a stream of H$_2$S gas (15 min) in a deoxygenated anhydrous methylene chloride (180 cc) solution of triethylamine (17 cc, 12.3 g 0.122 mole), was added dropwise a methylene chloride (30 cc) solution of furoyl chloride (13.0 g, 0.099 mole) over a 15 min period. The mixture was allowed to react at room temperature for 20 h. The organic solution was diluted with ether, washed with 10% HCl, H$_2$O and brine. It was dried over MgSO$_4$ and gave 21 (11.77 g, 92%) upon solvent evaporation. δ(ppm CDCl$_3$) 7.56 (1H, d, J$_{5-4}$=2, H-5), 7.20 (1H, d, J$_{3-4}$=4, H-3), 6.57 (1H, dd, J$_{4-5}$=2, J$_{4-3}$=4, H-4), 4.72 (1H, b.s., S—H), Ref: S. Patton New Compounds, 71, 3571-72(1949)

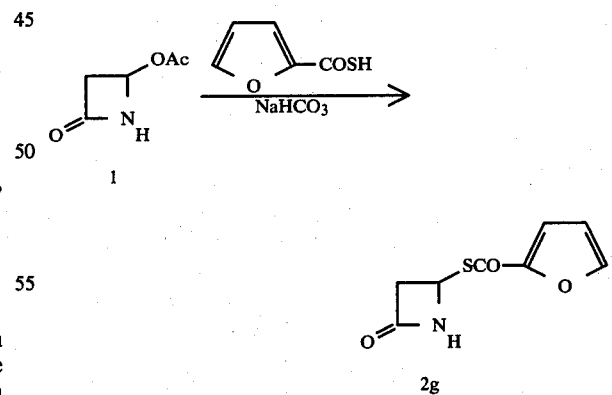

1

2g

A cold (0°–5° C.) solution of 4-acetoxy-2-azetidinone (10 g, 77.4 mmoles) in water (100 cc) was treated very rapidly with an aqueous solution (100 cc) of sodium 2-thiofuroate, freshly prepared from 2-thiofuroic acid (11.77 g, 91.8 mmoles) and NaHCO$_3$ (8.0 g, 95.2 mmoles). The mixture was stirred for 2 h and more aqueous (30 cc) sodium 2-thiofuroate [from 2-thiofuroic acid (2 g, 15.6 mmoles) and NaHCO$_3$ (1.3 g, 15.5 mmoles)] was added. A further 2 h stirring brought the reaction to completion. The aqueous mixture was extracted with CH₂Cl₂ (4×50 cc). The methylene chloride extracts were combined, washed with H₂O (3×30 cc), brine and dried over MgSO₄. It yielded a crystalline material (13.8 g, 90.4%, m.p.: 93.5°–94.5°). Anal. Calc'd for $C_8H_7N_1O_3S_1$: C, 48.72; H, 3,58; N, 7.10; S, 16.26. Found: C, 48.67; H, 3.60; N, 7.17; S, 16.16. δ(ppm, CDCl₃) 7.52 (1H, dd, $J_{5'-3'}=0.8$, $J_{5'-4'}=1.8$, H-5' furoyl), 7.25 (1H, dd, $J_{3'-5'}=0.8$, $J_{3'-4'}=3.6$, H-3' furoyl), 6.55 (1H, dd, $J_{4'-5'}=1.8$, $J_{4'-3'}=3.6$, H-4' furoyl), 7.14 (1H, bs, N-H), 5.39 (1H, dd, $J_{4-3\ trans}=2.8$, $J_{4-3\ cis}=5$, H-4), 3.53 (1H, ddd, $J_{gem}=15.6$, $J_{3-4\ cis}=5$, $J_{3-NH}=2$, H-3), 3.03 (1H, ddd, $J_{gem}=15.6$, $J_{3-4\ trans}=2.8$, $J_{3-NH}=1.2$, H-3). $\nu_{c=o}$(CHCl₃) 1780, 1655, $\nu_{NH}$3425.

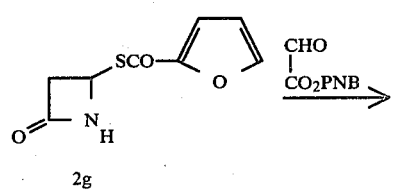

2g

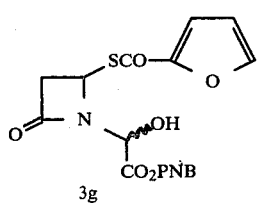

3g

A benzene solution (40 cc) of azetidinone 2 g (1.95 g, 9.89 mmoles) and hydrated p-nitrobenzyl glyoxylate 2.51 g, 11.0 mmoles) was refluxed through a Dean Stark condenser filled with 3A molecular sieves for 26 h. Evaporation of benzene gave an oily residue (4.34 g, 100%) as a mixture of 2 epimers. δ (ppm CDCl₃) 8.20, 8.15 (2H, 2d, J=8, Hm aromatic), 7.75–7.15 (4H, m, Ho aromatic, H-5', 3' furoyl), 6.58 (1H,dd, $J_{4'5'}=2$, $J_{4'-3'}=4$, H-4' furoyl), 5.61 (2H, 1s and 1m, $J_{4-3\ trans}=3$, H-4 and CHOH), 5.40, 5.21 (2H, 2s, CH₂—PNB), 4.21 (1H, bs, OH), 3.64, 3.60 (1H, 2dd, $J_{gem}=16$, $J_{3-4\ cis}=5$, H-3), 3.10 (1H, dd, $J_{gem}=16$, $J_{3-4\ trans}=3$, H-3). $\nu_{c=o}$(CHCl₃) 1780, 1760 (shoulder), 1655, $\nu_{NO_2}$1525, $\nu_{OH}$=3600–3400.

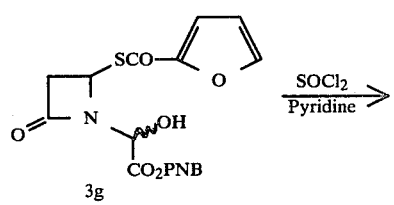

3g

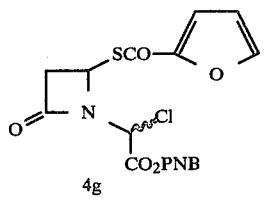

4g

A cold (0°–5° C.) THF solution (15 cc, freshly distilled over LAH) of azetidinone 3 g (1.0 g, 2.46 mmoles) was treated, under nitrogen atmosphere, with thionyl chloride (355 mg, 0.235 cc, 2.98 mmoles, 1.2 eq) and pyridine (2.38 mg, 0.242 cc, 3.01 mmoles, 1.2 eq). The mixture was stirred for 1.5 h at 0°. The precipitate was filtered off and washed with dry benzene. Evaporation of the combined benzene and THF solution afforded a residue which was redissolved in warm benzene and treated with activated charcoal. Filtration and evaporation of benzene gave 4 g (1 g, 96%) as an epimeric mixture. δ (ppm CDCl₃) 8.25 (2H, d, J=8, Hm aromatic), 7.20–7.70 (4H, m, Ho aromatic and H-3', 5' furoyl), 6.60 (1H, m, H-4' furoyl), 6.16, 6.13 (1H, 2s, CHCl), 5.85 (1H, m, H-4), 5.40, 5.27 (2H, 2s, CH₂–$_{PNB}$), 3.70 (1H, dd, $J_{gem}=16$, $J_{3-4\ cis}=5$, H-3), 3.17 (1H, dd, $J_{gem}=16$, $J_{3-4\ trans}=3$, H-3). $\nu_{c=o}$ (film) 1787, 1760 (shoulder, 1655, $\nu_{NO_2}$1525.

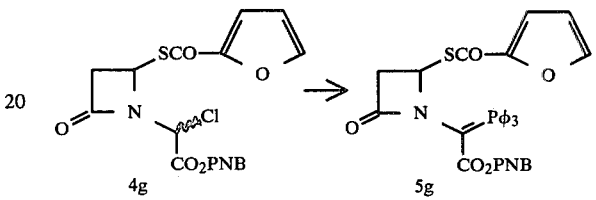

4g    5g

To a solution of chloroazetidinone 4 g (1.0 g, 2.35 mmoles) in THF (15 cc, distilled over LAH) was added triphenyl phosphine (980 mg, 3.74 mmoles, 1.5 eq) and 2,6-lutidine (0.294 g, 0.32 cc, 2.74 mmoles, 1.16 eq). The mixture was stirred for 4 days at room temperature under nitrogen atmosphere. Lutidine hydrochloride was filtered off and washed with ether. THF and ether fractions were combined, washed with 5% HCl, saturated aqueous NaHCO₃, water and brine. Evaporation of solvent gave a residue which was purified through a silica gel (20 g) column and eluted with 20% benzene ether, ether and ethyl acetate (932 mg, 61%). $\nu_{c=o}$(KBr film) 1760, 1705, 1675, $\nu_{NO_2}$1520.

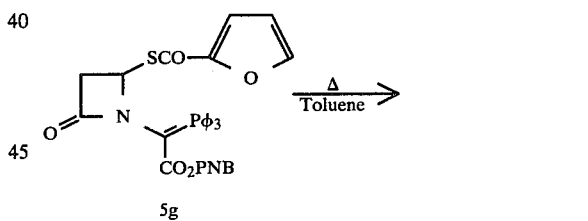

5g    6g

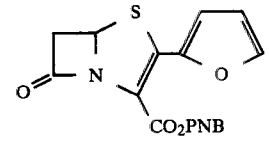

Phosphorane 5 g (932 mg, 1.43 mmole) in toluene was refluxed for 3.75 h. Evaporation of toluene afforded a semicrystalline residue which as crystallized from ether (m.p. 153°–153.5°, 323 mg, 61%). Anal. Calc'd for $C_{17}H_{12}N_2O_6S_1$:C, 54.84; H, 3.25; N, 7.52; S, 8.61. Found: C, 54.96; H, 3.28; N, 7.60; S, 8.38. δ(ppm, CDCl₃) 8.25 (2H, d, J=8, Hm aromatic), 7.80–7.45 (4H, m, Ho aromatic, H-5', 3' furyl), 6.57 (1H, dd, $J_{4'-5'}=1.8$, $J_{4'-3'}=3.8$, H-4' furyl), 5.66 (1H, dd, $J_{5-6\ trans}=2$, $J_{5-6\ cis}=4$, H-5), 5.37 (2H, center of ABq, J=14, CH₂-PNB), 3.85 (1H, dd, $J_{gem}=16$, $J_{6-5\ cis}=4$, H-6) 3.50 (1H, dd, $J_{gem}=16$, $J_{6-5\ trans}=2$, H-6). $\nu_{c=o}$ (CHCl₃) 1790, 1710, $\nu_{NO_2}$1525. U.V. (EtOH) $\lambda_{max}$364 ($\epsilon$=13,100), 313 ($\epsilon$=10,000), 299 ($\epsilon$=11,400), 265 ($\epsilon$=13,400).

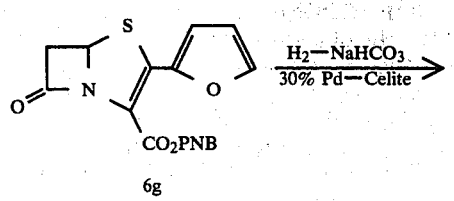

6g

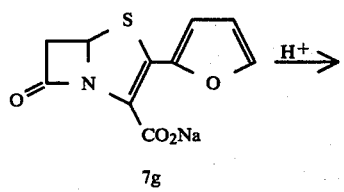

7g

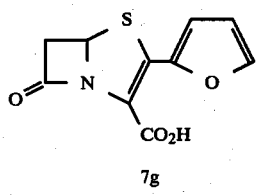

7g

A mixture of ester 6 g (102 mg, 0.274 mmoles) in THF, (10 cc) ether (20 cc) and NaHCO$_3$ (23 mg, 0.274 mmoles) in water (10 cc) was shaken on a Parr hydrogenator for 3 h at 30 p.s.i. H$_2$, using 30% Pd on celite (110 mg) as catalyst. The catalyst was removed and washed with ether and water. The aqueous phase was carefully shaken with ether (3×50 cc) and lyophilized to yield the sodium salt 7 g. $\delta$(ppm, D$_2$O) 7.60 (1H, d, J$_{5'-4'}$=2, H-5' furyl), 7.10 (1H, d, J$_{3'-4'}$=4, H-3' furyl), 6.58 (1H, dd, J$_{4'5'}$=2, J$_{4'3'}$=4, H-4' furyl), 5.72 (1H, m, H-5), 3.87 (1H, dd, J$_{gem}$ = 16, J$_{6-5\ cis}$=4, H-6), 3.50 (1H, b.d., J$_{gem}$ =16, H-6).

The sodium salt 7gwas dissolved in H$_2$O (5 cc) and slowly acidified portionwise with 1% cold HCl. It was extracted with EtOAc after each HCl addition. The ethyle acetate extracts were combined, washed with brine (3×20 cc) and dried over Na$_2$SO$_4$. (15.1 mg, 23%, decomp. 100°). $\delta$)ppm, DMSOd6) 7.98 (1H, d, J$_{5'-4'}$=1.8, H-5' furyl), 7.68 (1H, d, J$_{3'-4'}$=4, H-3' furyl), 6.82 (1H, dd, J$_{4'-5'}$=1.8,J$_{4'-3'}$=4, H-4' furyl), 5.83 (1H, dd, J$_{5-6\ cis}$=3.5, J$_{5-6\ trans}$=1.5 H-5), 4.03 (1H, dd, J$_{gem}$ =16.5, J$_{6-5\ cis}$=3.5, H-6), 3.63 (1H, dd, J$_{gem}$=16.5, J$_{6-5\ trans}$=1.5, H-6), 3.40 (b.s., OH). $\nu_{C=O}$(Nujol mull) 1785, 1675, $\nu_{OH}$ 3500-2500. UV (EtOH) $\lambda_{max}$ 349 ($\epsilon$=7470), 306 ($\epsilon$=6050), 298 ($\epsilon$=6170), 230 ($\epsilon$=4860).

PREPARATION 14

Sodium 2-(Benzyloxymethyl) penem-3-carboxylate and Potassium 2-(benzyloxymethyl) penem-3-carboxylate

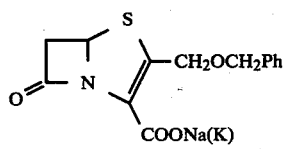

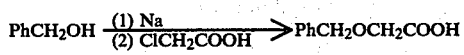

The benzyloxyacelic acid has been prepared following the procedure described in U.S. Pat. No. 4,068,075; column 50, lines 30-51.

NMR (CDCl$_3$) $\delta$: 9.48(1H, s, H of carboxylic acid), 7.34 (5H, s, H of phenyl), 4.62 (2H, s, CH$_2$ of benzyl) and 4.12 (2H, s, CH$_2$ of acetyl).

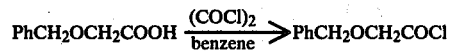

A solution of benzyloxyacetic acid (3.0 g, 18.1 mmoles) in dry (molecular sieve, 4Å) benzene (30 ml) containing one drop of N,N -dimethylformamide was treated dropwise (5-10 min) with oxalyl chloride (3.06 ml, 35.9 mmoles) and stirred at 23-25° C. for 2 h. The solvents were evaporated under reduced pressure at 30° C. and the traces of oxalyl chloride were removed by codistillation with benzene leaving a yellow liquid; 3.3 g, 99%. NMR(CDCl$_3$) $\delta$: 7.30 (5H, s, H of phenyl), 4.56 (2H, s, CH$_2$ of benzyl) and 4.33 (2H, s, CH$_2$ of acetyl). IR (neat) cm$^{-1}$: 1797 (C=O of acyl choloride).

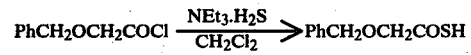

A solution of triethylamine (2.8 ml, 20.0 mmoles) in dichloromethane (100 ml) was cooled to 7° C. in an ice-water bath and hydrogen sulfide was bubbled through during 0.5 h at such a rate that the temperature was kept between 7-10° C. A solution of benzyloxyacetyl chloride (3.3 g, 17.9 mmoles) in dichloromethane (30 ml) was added dropwise (10-15 min) to the preceding solution cooled at 5° C. and the resulting reaction mixture was stirred at 23°-25° C. for 2 h under a nitrogen atmosphere. The reaction mixture was diluted with dichloromethane (60 ml), washed with 10% hydrochloric acid solution (2×10 ml) and water 2×10 ml), dried over anhydrous sodium sulfate and concentrated to a yellow liquid, 3.20 g, 98%. NMR (CDCl$_3$) $\delta$: 7.33 (5H, s, H of phenyl), 4.82 (1H, bs, SH), 4.60 (2H, s, CH$_2$ of benzyl) and 3.99 (2H, s, CH$_2$ of acetyl). IR (neat) cm$^{-1}$:2560 (SH) and 1700 (C=O of thio acid).

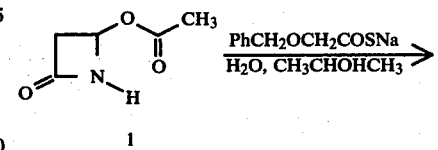

1

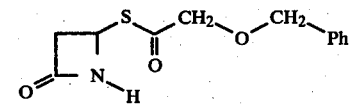

2h

To a solution of benzyloxythioacetic acid (11.99 g, 65.8 mmoles) in isopropyl alcohol (44 ml) was added (10 min) an oxygen free aqueous solution (200 ml) of sodium bicarbonate (5.53 g, 65.8 mmoles). The soution was stirred vigorously for 1-1.5 h at 23°-25°C. and added (10 min) to an oxygen free aqueous solution (110 ml) of 4-acetoxyazetidinone (7.11 g, 55.1 mmoles); the pH of the later solution was adjusted to 6.3-6.5 by the addition of sodium bicarbonate. The pH of the reaction mixture was adjusted to 7.4-7.5 by the addition of sodium bicrbonate, and the solution was stirred for 2.75 h at 23°–25° C. and extracted with chloroform (8×100 ml). The organic extracts were combined, washed with water (40 ml), dried over anhydrous sodium sulfate and concentrated under reduced pressure to a slightly yellow syrup, 13.67 g, 99% NMR (CDCl₃) δ:7.35 (5H, s, H of phenyl), 6.94 (1H, bs, NH), 5.18 (1H, dd, J₄₋₃ cis =5.0 Hz, J₄₋₃ trans =2.6 Hz, H-4), 4.61 (2H, s, CH₂ of benzyl), 4.14 (2H, s, CH₂ of acetyl), 3.46 (1H, ddd, J_gem =15.2 Hz, J₃₋₄ cis =5.0 Hz, J₃₋NH =2.0 Hz, H-3 cis) and 2.93 (1H, ddd, J_gem =15.2 Hz, H₃₋₄ trans =2.6 Hz, J₃₋NH =1.0 Hz, H-3 trans). Ir (neat) cm⁻¹ 1765 (C=O of β lactam). 1689 (c=o of thioester) and 3280 (NH).

of the solvent, a yellow syrup, 5.47 g, 76%, which is a mixture of isomers. This compound (purity ≧80% by NMR) was used for the next step without any further purification. NMR (CDCl₃) δ: 8.18 and 8.16 (2H, 2d, J_Hm-Ho=8.7 Hz, Hm of p-nitrobenzyl), 7.7–7.2 (7H, Ho of p-nitrobenzyl and H of phenyl), 6.11 (s, H of glyoxylate), 5.7 (1H, m, H-4), 5.36 and 5.22 (2H, 2s, CH₂ of p-nitrobenzyl), 4.63 (2H, s, CH₂ of benzyl), 4.14 (2H, s, CH₂ of acetyl), 3.63 (1H, dd, J_gem=15.8 Hz, J₃₋₄ cis=5.5 Hz, H-3 cis) and, 3.10 and 3.06 (1H, 2dd, J_gem=15.8 Hz, J₃₋₄ trans=3.0 Hz, H-3 trans).

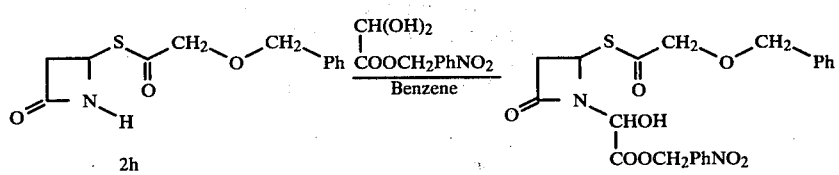

A suspension of 4-S-(benzyloxyacetyl) azetidinone 2h (10.04 g, 40.0 mmoles) and p-nitrobenzylglyoxylate hydrate (9.8 g, 43.0 mmoles) in benzene (350 ml) was refluxed for 2 h through a Dean-Stark trap after which the Dean-Start trap was replaced by a Soxhlet containing molecular sieves (4Å) and the reflux was continued for 19 h more. The solution was decanted from an orange insoluble sticky residue, cooled to 23°–25° C. and concentrated under reduced pressure to a yellow syrup, 18.4 g, 100%, which is a mixture of two isomers. NMR (CDCl₃) δ: 8.15 and 8.12 (2H, 2d, J_Hm-Ho=8.7 Hz, Hm of p-nitrobenzyl), 7.7–7.2 (7H, Ho of p-nitrobenzyl and H of phenyl), 5.7–5.1 (4H, H of glyoxylate, H-4 and CH₂ of p-nitrobenzyl), 4.61 and 4.58 (2H, 2s, CH₂ of benzyl), 4.3 (1H, bs, OH), 4.14 and 4.12 (2H, 2s, CH₂ of acetyl), 3.52 (1H, dd, J_gem=15.1 Hz, J₃₋₄ cis=5.4 Hz, H-3 cis) 3.05 and 2.99 (1H, 2dd, J_gem=15.1 Hz, J₃₋₄ trans=3.0 Hz, H-3 trans).

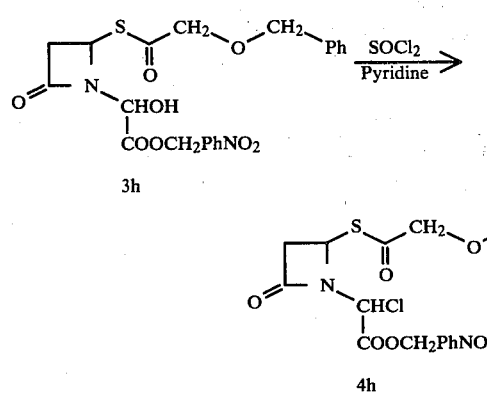

A solution of compound 3h (6.90 g, 0.015 mole) in dry tetrahydrofuran (70 ml) protected from moisture by a stream of nitrogen was cooled to 0° C. in an ice-water bath and, successively treated with pyridine (1.53 ml, 0.019 mole) and thionyl chloride (1.36 ml, 0.019 mole). The reaction mixture was stirred at 0°–5° C. for 1 h and filtered. The solid was washed with benzene and the filtrate and the washings were combined and concentrated under reduced pressure to a dark orange syrup which was absorbed on a silica gel (40 g of silica gel 60 for dry column) pad. Elution with chloroform gave after treatment of eluates with charcoal and evaporation

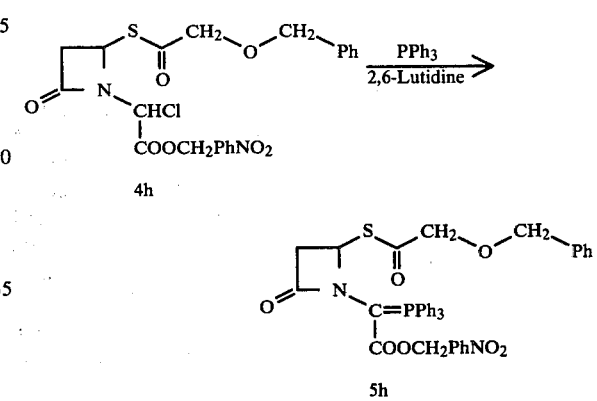

A solution of compound 4h (5.47 g, 0.011 mole), triphenylphosphine (4.08 g, 0.015 mole) and 2,6-lutidine (1.81 ml 0.015 mole) in benzene (120 ml) was stirred at 45° C. for 20 h, cooled to 23°–25° C. and filtered. The solid was washed with some benzene; the filtrate and the washings were combined and concentrated under reduced pressure to a dark orange syrup which was chromatographed on silica gel column (200 g of silica gel 60 dry column, column size: 4.5×21 cm). Elution of the column was done with benzene-ether mixture (1:4, 2.25 l; 1:9, 500 ml), ether (500 ml) and ether-ethyl acetate mixture (1:9, 1.5 l) and 25 ml fractions were taken. The fractions 44–130 were combined and the solvents were evaporated under reduced pressure leaving the pure compound 5h, 4.0 g, 50%, as a light yellow syrup which solidified partially on standing. Evaporation of fractions 131–171 gave the impure compound 5h, 0.62 g, 7.7%, which could be used for the next step without any further purification.

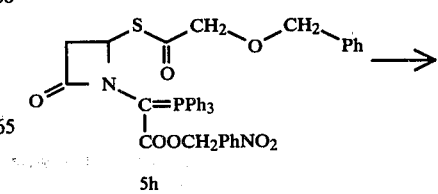

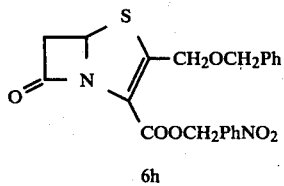

6h

A solution of compound 5h (4.0 g, 5.7 mmoles) in toluene (75 ml) was heated at 100° C. for 4 h, cooled to 23°–25° C. and concentrated to an orange solid which was chromatographed on a silica gel column (80 g of silica gel 60, column size: 3.5×16 cm) Elution was done with benzene (500 ml) and benzene-ether mixture (95:5, 500 ml). The fractions (25 ml) 34–50 were combined and concentrated under reduced pressure to a yellow solid; 1.76 g, M.P. 96°–7° C., 73%. An analytical sample was obtained after one crystallization from $CH_2Cl_2$, M.P. 105°–7° C.; calc'd for $C_{21}H_{18}N_2O_6S$: C 59.15, H 4.25, N 6.57, S 7.52; found: C 58.93, H 4.25, N 6.53, S 7.89. NMR ($CDCl_3$) δ: 8.13 (2H, d, $J_{Hm-Ho}$=8.8 Hz, Hm of p-nitrobenzyl), 7.49 (2H, d, $J_{Ho-Hm}$=8.8 Hz, Ho of p-nitrobenzyl), 7.30 (5H, s, H of phenyl), 5.53 (1H, dd, $J_{5-6\ cis}$=3.5 Hz, $J_{5-6\ trans}$=2.0 Hz, H-5), 5.22 (center of ABq, $CH_2$ of p-nitrobenzyl), 4.68 (center of ABq, $CH_2$ on C-2), 4.52 (2H, s, $CH_2$ of benzyl), 3.73 (1H, dd, $J_{gem}$=16.5 Hz, $J_{6-5\ cis}$=3.5 Hz, H-6 cis) and 3.37 (1H, dd, $J_{gem}$=16.5 Hz, $J_{6-5\ trans}$=2.0 Hz, H-6 trans). IR (nujol) $cm^{-1}$: 1791 (C=O of β-lactam), 1699 (C=O of p-nitrobenzyl ester), 1607 and 1587 (C=C of benzyl and p-nitrobenzyl) and 1517 ($NO_2$).

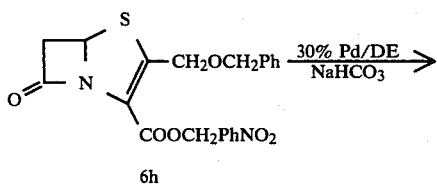

6h

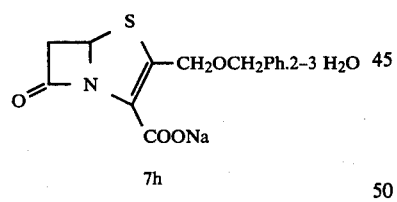

7h

To a solution of compound 6h (0.106 g, 0.25 mmole) in tetrahydrofuran-ether mixture (1:2, 27 ml) was added water (7 ml), sodium bicarbonate (0.021 g, 0.25 mmole) and 30% palladium on diatomaceous earth (0.106 g). The reaction mixture was hydrogenated under 30 psi for 16 h at 23°–25° C., filtered over celite pad and diluted with ether (40 ml). Aqueous solution was separated, washed with ether (30 ml) and lyophilized; the compound 7h (0.070 g, 91%, contained 2–3 mmoles of water by NMR) was obtained as a yellowish powder. NMR (DMSOd-6,80 MHz) δ: 7.44 (5H, s, H of phenyl), 5.62 (1H, dd, $J_{5-6\ cis}$=3.7 Hz, $J_{5-6\ trans}$=1.7 Hz, H-5), 4.84 (center of ABq, $J_{ab}$=13.7 Hz, $CH_2$ on C-2), 4.56 (2H, s, $CH_2$ of benzyl), 3.74 (1H, dd, $J_{gem}$=15.9 Hz, $J_{6-5\ cis}$=3.7 Hz, H-6 cis) and 3.34 (1H, dd, $J_{gem}$=15.9 Hz, $J_{6-5\ trans}$=1.7 Hz, H-6 trans). IR (nujol) $cm^{-1}$: 1765 (C=O of β-lactam) and 1595 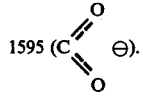.

UV $\lambda_{max}^{H_2O}$ mμ: 254 (ε 3910) and 304 (ε 5480).

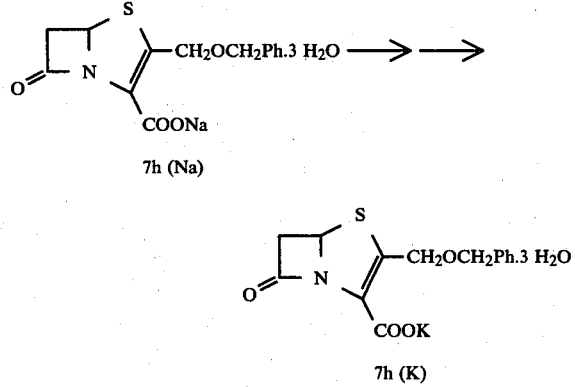

7h (Na)

7h (K)

A solution of 7h (Na) (50 mg, 0.16 mmole) in distilled water (15 ml) was treated with resin 50w-x8H+ form (5 ml) and extracted with ethyl acetate (4×40 ml). Ethyl acetate extracts were combined, dried over anhydrous sodium sulfate and concentrated to an orange thick syrup which was dissolved in methyl isobutyl ketone (2 ml); insoluble material was filtered off and washed with some methyl isobutyl ketone while the filtrate and washing were combined, cooled in ice-water bath and treated with 50% solution of potassium 2-ethyl-hexanoate in n-butanol. The solid was filtered off, washed with some methylisobutyl ketone and dried under high vacuum, 6 mg, 11%. NMR (DMSOd-6, 80 MHz) δ: 7.41 (5H, s, H of phenyl), 5.61 (1H, dd, $J_{5-6\ cis}$=3.8 Hz, $J_{5-6\ trans}$=1.8 Hz, H-5), 4.82 (center of ABq, $J_{ab}$=13.5 Hz, $CH_2$ on C-2), 4.55 (2H, s, $CH_2$ of benzyl) and 3.72 (1H, dd, $J_{gem}$=16.0 Hz, $J_{6-5\ cis}$=3.8 Hz, H-6 cis). UV $\lambda_{max}^{H_2O}$ mμ: 255 (ε 1760) and 303 (ε 1820).

Preparation 15

2-Propylpenem-3-carboxylic Acid

To a solution of triethylamine hydrosulfide, previously prepared by bubbling $H_2S$ gas through a methylene chloride (125 ml) solution of triethylamine (27 ml; 192 mmoles) was added dropwise a solution of butyryl chloride (16 g, 150 mmoles) in $CH_2Cl_2$ (50 ml). The addition was conducted at 0° C. over a 30 minute period. The mixture was stirred 15 minutes at 0° C., then allowed to warm-up to room temperature. Stirring was continued for 1 h. The organic solution was diluted with ether, washed with 10% HCl, $H_2O$ and brine. It was dried over $Na_2SO_4$ and evaporated. Yield 15.6 g (100%) Purity 70% (N.M.R.) 4.6 (1H, s, —SH), 2.6 (2H, t, J=8, αCH₂), 1.65 (2H, m, J$_{α-β}$=8, J$_{β-γ}$=6, βCH₂) 1.0 (3H, t, J=6, —CH₃).

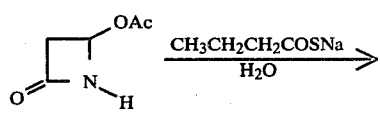

To a cold (0°–5° C.) oxygen free solution of 1 N sodium hydroxide solution (120 ml) was added in 20 minutes thiobutyric acid (12.5 g 120 mmoles). The resulting solution was added in 20 minutes to a cold (10° C.) oxygen-free solution of 4-acetoxyazetidinone (10.3 g 80 mmoles) in water (40 ml). The pH of the resulting solution was immediately adjusted to 7.4 with solid NaHCO₃ The cooling bath was removed and the solution stirred for 3 hours. The mixture was then extracted with chloroform and the organic extracts were washed with water (30 ml) and dried over sodium sulfate. Concentration on a rotary evaporator left a yellow oil. Yield 9.37 g (68%), δ (ppm, CDCl₃) 7.6 (1H, br.s. —NH), 5.2 (1H, dd, J$_{4-3\ cis}$=5, J$_{4-3\ trans}$=2.2, H-4) 3.5 (1H, ddd, J$_{gem}$=15.15 J$_{4-3\ cis}$=5, J$_{3-NH}$=2; H-3), 3.0 (1H, ddd, J$_{gem}$=15.5 J$_{4-3\ trans}$=2.2, J$_{3-NH}$=1.0), 2.6 (2H, t, J=8, α CH₂), 1.65 (2H, m, J$_{α-β}$=8, J$_{β-γ}$=6, β—CH₂), 1.0 (3H, t, J=6, CH₃).

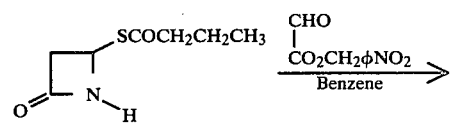

A solution of 4 butyrylthio-2-azetidinone (4.22 g; 25 mmoles) and p-nitrobenzylglyoxylate (6.24 g; 27.5 mmoles) in benzene (200 ml) was refluxed 18 hours through a Dean-stark condenser filled with 3 Å molecular sieves. Evaporation of the solvent gave a yellow oil Yield 10.1 g (100%). δ (ppm, CDCl₃) 8.25 (2H, d, J=9, Hm, arom.), 7.6 (2H, d, J=9, Ho arom.), 5.4 (4H, m, two benzylic H, H-4 and H of glyoxylate), 4.5 (1H, br. s., hydroxyl), 3.5 (1H, dd, J$_{gem}$=16, J$_{4-3\ cis}$=5, H-3), 3.0 (1H, dd, J$_{gem}$=16, J$_{4-3\ trans}$=3, H-3), 2.5 (2H, m, α CH₂), 1.65 (2H, m, β—CH₂), 1.0 (3H, t, J=6, —CH₃).

2f

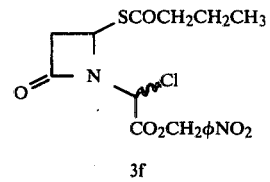

3f

Azetidinone glyoxylate 2f (10.1 g; 26 mmoles) was dissolved in methylene chloride (80 ml) and pyridine (2.4 ml, 30 mmoles) was added to the solution. The mixture was cooled to 0° C. and SOCl₂ (2.2 ml, 30 mmoles) in 20 ml of CH₂Cl₂ was slowly added. The mixture was stirred 30 minutes at 0° C. The solvent was then evaporated to give a dark brown residue. Filtration of this material over a pad of silica gel gave a slightly yellow oil. Yield 9.3 g (89%). Mixture of two epimers. δ (ppm, CDCl₃) 8.25 (2H, d, J=9, Hm arom.), 7.55 (2H, d, J=9, Ho arom), 6.07, 6.10 (1H, 2s, —C$\underline{H}$Cl) 5.65 (1H, dd, J$_{4-3\ cis}$=5, J$_{4-3\ trans}$=2.2, H-4), 5.3, 5.4 (2H, 2s, benzylic —CH₂), 3.5 (1H, dd, J$_{gem}$=16, J$_{4-3\ cis}$=5, H-3) 3.1 (1H, dd, J$_{gem}$=16, J$_{4-3\ trans}$=2.2, H-3), 2.5 (2H, m, α—CH₂) 1.7 (2H, m β—CH₂), 0.95 (3H, t, J=6, —CH₃).

3f

4f 2,6 Lutidine (3.0 ml, 25 mmoles) was added to a solution of chloro compound 3f (9.3 g, 23 mmoles) and triphenyl phosphine (6.5 g, 25 mmoles) in ether (200 ml). After stirring 36 hours at room temperature, the reaction mixture was diluted with benzene, filtered to get rid of lutidine hydrochloride and evaporated to give a gummy residue. Purification of this residue by chromatography on a silica gel column gave a faintly yellow foam which crystallized readily on trituration with ether. Yield: 4.8 g (33%) m.p. 158°–159° C.

4f

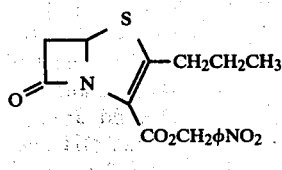
5f

A solution of phosphorane 4f (3.15 g, 5 mmoles) in toluene (100 ml) was refluxed for 5 hours. The solvent was evaporated and the residue was chromatographed over 40 g of silica gel, eluting with benzene. This procedure afforded 403 mg of the desired cyclic compound. Subsequent elution with ethyl acetate gave 1.92 g of unreacted phosphorane. The whole procedure was repeated twice more. Total yield 873 mg (50%) m.p. 100°–102° C. δ (ppm, CDCl$_3$) 8.3 (2H, d, J=9, Hm arom.), 5.65 (1H, dd, J$_{4-3}$ $_{cis}$=4, J$_{4-3}$ $_{trans}$=2, H-4), 5.4, 5.3 (2H, 2s, benzylic—CH$_2$), 3.7 (1H, dd J$_{gem}$=16, J$_{4-3}$ $_{cis}$=4, H-3), 3.5 (1H, dd, J$_{gem}$=16, J$_{4-3}$ $_{trans}$=2, H-3), 3.80, 3.75 (2H, 2t, J=8, α CH$_2$), 1.5 (2H, m, β CH$_2$), 0.95 (3H, t, J=6,—CH$_3$), ν$_{C=O}$=1790, 1715, ν$_{NO_2}$=1525.

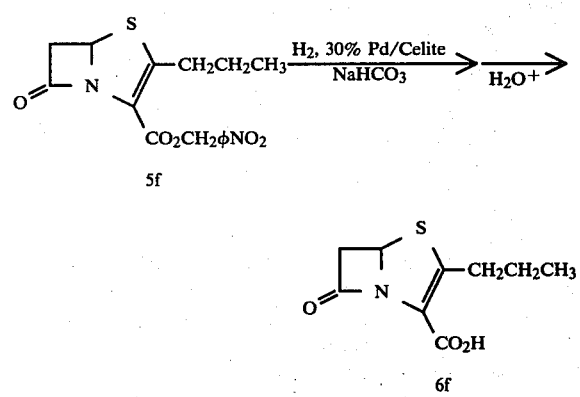
5f

6f

To a solution of the p-nitrobenzyl ester (348 mg, 1 mmole) in ethyl acetate (50 ml) were added: water (25 ml) sodium bicarbonate (84 mg, 1 mmole) and 30% Palladium on Celite (350 mg). The reaction mixture was hydrogenated at room temperature under 30 p.s.i. for 4 hours. It was filtered over a Celite pad. The ethyl acetate layer was decanted and the aqueous layer washed with ether (2×10 ml). The aqueous solution was carefully acidified at 0° C. with 1N HCl and extracted with ethyl acetate (10×10 ml). The organic extracts were dried over sodium sulfate and evaporated to give the desired acid. Yield 64 mg. (31%). δ (ppm, CDCl$_3$) 9.8 (1H, br.s., carboxyl), 5.65 (1H, dd, J$_{4-3}$ $_{-cis}$=4, J$_{4-3}$ $_{trans}$=2, H-4), 3.75 (1H, dd, J$_{gem}$=16, J$_{4-3}$ $_{cis}$=4, H-3), 3.5 (1H, dd, J$_{gem}$=16, J$_{4-3}$ $_{trans}$=2, H-3), 2.76, 2.83 (1H, 2t, J=8, αCH$_2$), 1.6 (2H, m, β-CH$_2$), 1.0 (3H, t, J=6, CH$_3$).

Preparation 16

Potassium 2-Pentylpenem-3-carboxylate

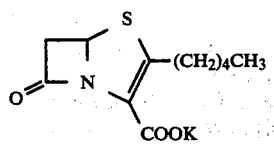

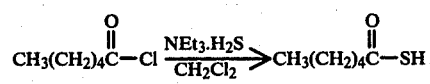

A solution of triethylamine (13.36 ml, 0.096 mole) in dichloromethane (320 ml) was cooled in ice-water bath to 5° C. under nitrogen atmosphere and hydrogen sulfide was bubbled through for 0.5 h at such a rate that the temperature was kept between 7°–10° C. A solution of hexanoyl chloride (10.88 g, 0.08 mole) in dichloromethane (160 ml) was added dropwise (20 min) to the preceeding solution cooled at 5° C. and the resulting solution was stirred at 23°–25° C. for 1 h under a nitrogen atmosphere. The reaction mixture was washed with 3 N hydrochloric acid solution (2×48 ml) and water (2×48 ml), dried over anhydrous sodium sulfate and concentrated to a yellow liquid; 0.88 g, 93%. NMR(CDCl$_3$) δ: 4.48 (1H, s, H of thioacid), 2.62 (2H, t, J=7.0 Hz, α methylene) and 2.0–0.7 (9H, β,γ,δ methylene and methyl). IR (neat) cm$^{-1}$: 2560 (SH of thioacid) and 1705 (C=O of thioacid).

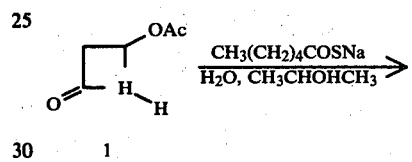

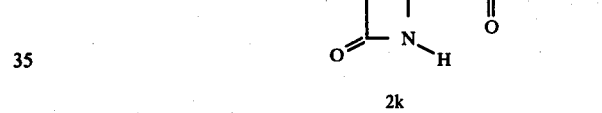
2k

To a solution of thiohexanoic acid (9.78 g, 74 mmoles) in isopropyl alcohol (24 ml) was added (15 min) an aqueous solution (250 ml) of sodium bicarbonate (6.22 g, 74 mmoles). The solution was stirred at 23°–25° C. for 1 h and added (15 min) to an aqueous solution (250 ml) of 4-acetoxy-2-azetidinone (7.75 g, 60 mmoles); the pH of the latter solution being adjusted to 6.5 with solid sodium bicarbonate. The pH of the reaction mixture was adjusted to 7.3 by the addition of solid sodium bicarbonate and the solution was stirred for 3 h at 23°–25° C. and extracted with chloroform (200 ml, 4×100 ml). The chloroform extracts were combined, washed with water (2×40 ml), dried over anhydrous sodium sulfate and concentrated under reduced pressure to a yellow syrup; 12.07 g, 100%. NMR (CDCl$_3$) δ: 7.0 (1H, bs, NH), 5.27 (1H, dd, J$_{4,3}$ $_{cis}$=5.1 Hz, J$_{4,3}$ $_{trans}$=2.7 Hz, H-4), 3.50 (1H, ddd, J$_{3,NH}$=2.0 Hz, J$_{3,4}$ $_{cis}$=5.1 Hz, J$_{gem}$=15.2 Hz, H-3 cis), 2.93 (1H, ddd, J$_{3,NH}$=1.2 Hz, J$_{3,4}$ $_{trans}$=2.7 Hz, J$_{gem}$=15.2 Hz, H-3 trans), 2.61 (2H, α methylene of thioester) and 2.0–0.6 (9H, β,γ,δ methylene of thioester and methyl). IR (neat) cm$^{-1}$: 1770 (C=O of β lactam), 1690 (C=O of thioester) and 3300 (NH).

2k

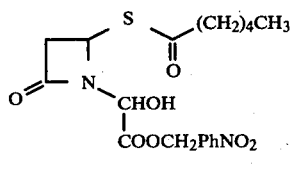

3k

A suspension of 4-S-hexanoyl-2-azetidinone 2k (12.07 g, 0.06 mole) and p-nitrobenzylglyoxylate hydrate (15.75 g, 0.069 mole) in benzene (700 ml) was refluxed for 2 h through a Dean-Stark trap after which the Dean-Stark trap was replaced by a Soxhlet filled with molecular sieves 4 Å and the reflux was continued for 22 h more. The solution was decanted from orange insoluble sticky residue, cooled to 23°–25° C. and concentrated under reduced pressure to a yellow syrup; 24.6 g, 100%. NMR (CDCl$_3$) δ: 8.28 and 8.24 (2H, 2d, $J_{Hm, Ho}$=8.8 Hz, Hm of p-nitrobenzyl), 7.60 and 7.57 (2H, 2d, $J_{Ho,Hm}$=8.8 Hz, Ho of p-nitrobenzyl), 5.8–5.2 (4H, H-4, CH$_2$ of p-nitrobenzyl and H of glyoxylate), 4.3 (1H, bs, OH), 3.52 and 3.50 (1H, 2dd, $J_{3,4\,cis}$=5.2 Hz, $J_{gem}$=15.4 Hz, H-3 cis), 3.01 and 2.99 (1H, 2dd, $J_{3,4\,trans}$=3.0 Hz, $J_{gem}$=15.4 Hz, H-3 trans), 2.8–2.3 (2H, α methylene of thioester) and 2.0–0.6 (9H, β,γ,δ methylene of thioester and methyl). The yellow syrup was solubilized in a large amount of ether and, on standing a few days while some ether slowly evaporated off, a small amount of compound 3k crystallized out: M.P. 64°–9° C. Recrystallization from ether using the same technique gave analytical sample; M.P. 72–3° C. Analysis calc'd for C$_{18}$H$_{22}$N$_2$O$_7$S: C 52.67, H 5.40, N 6.83, S 7.81. Found C: 52.40, H 5.34, N 7.03, S 7.92.

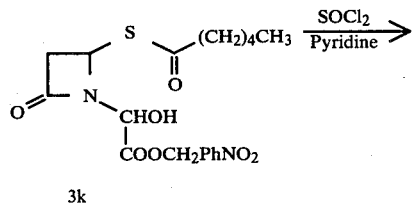

3k

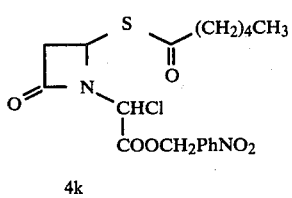

4k

A solution of compound 3k (2.95 g, 7.2 mmoles) in dry tetrahydrofuran (30 ml) protected from moisture by a stream of nitrogen was cooled to 0° C. in an ice-water bath and successively treated with pyridine (0.725 ml, 9.0 mmoles) and thionyl chloride (0.647 ml, 9.0 mmoles) at such a rate that the temperature was kept between 2°–3° C. The reaction mixture was stirred at 2°–3° C. for ¾ h and filtered. The solid was washed with benzene and the filtrate and the washings were combined and concentrated under reduced pressure to a dark orange syrup which was absorbed on a silica gel (20 g of silica gel 60 for dry column) pad. Elution with chloroform (180 ml) gave after evaporation of the solvent a yellow syrup; 2.87 g, 92% which is a mixture of isomers. This compound (purity>87% by NMR) was used for the next step without any further purification. NMR (CDCl$_3$) δ: 8.26 (2H, bd, $J_{Hm, Ho}$=8.8 Hz, Hm of p-nitrobenzyl), 7.60 (2H, bd, $J_{Ho, Hm}$=8.8 Hz, Ho of p-nitrobenzyl), 6.12 and 6.07 (2s, H of glyoxylate, 5.66 (1H, m, H-4), 5.42 and 5.33 (2H, 2s, CH$_2$ of p-nitrobenzyl), 3.68 (1H, dd, $J_{3,4\,cis}$=5.6 Hz, $J_{gem}$=15.6 Hz, H-3 cis), 3.04 and 3.02 (1H, 2dd, $J_{3,4\,trans}$=3.2 Hz, $J_{gem}$=15.6 Hz, H-3 trans), 2.8–2.4 (2H, α methylene of thioester) and 2.1–0.5 (9H, β,γ,δ methylene of thioester and methyl).

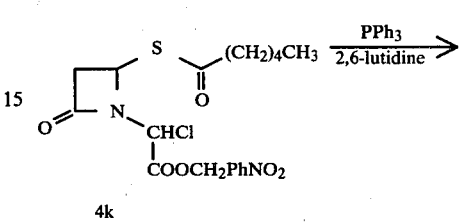

4k

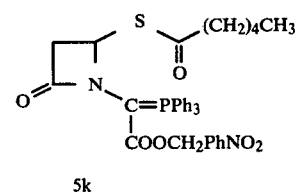

5k

A solution of compound 4k (5.66 g, 13.1 mmoles), triphenylphosphine (4.20 g, 16 mmoles) and 2,6-lutidine (1.86 ml, 16 mmoles) in benzene (100 ml) was stirred at 65° C. for 24 h. The reaction mixture was cooled to 23°–25° C. and the solids were filtered off and washed with benzene; the filtrate and the washings were combined and concentrated under reduced pressure to a semi-crystalline substance which was triturated with ether and filtered; 4.5 g, 52%. The pure phosphorane was obtained by column chromatography (120 g of silica gel 60 for dry column, column size: 4.5×16 cm). Elution of the column was done with benzene-ether mixture (3:1) and ether. Evaporation of the fractions containing the phosphorane gave a white powder, 3.99 g, 46%, after trituration with ether and filtration. Analytical sample was obtained after recrystallization from benzene-ether mixture; M.P. 176°–8° C., calc'd for C$_{36}$H$_{35}$N$_2$O$_6$SP: C 66.04, H 5.39, N 4.28, S 4.90; found: C 65.84, H 5.50, N 4.29, S 4.93.

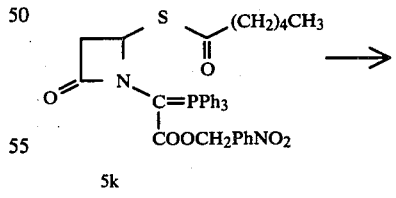

5k

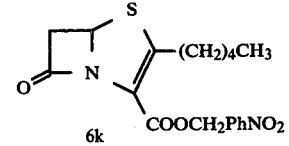

6k

A solution of compound 5k (1.87 g, 2.86 mmoles) in toluene (25 ml) was refluxed for 4 h, cooled to 23°–25° C. and concentrated under reduced pressure to an orange syrup which crystallized slowly. The solid was triturated with benzene-ether mixture (3:1) and filtered off. The solid which was pure unreacted phosphorane was treated as before; the cyclization reaction was done three times. The three filtrates were combined and concentrated under reduced pressure to an orange syrup which was chromatographed on silica gel (25 g of silica gel 60) column (2.6×12 cm). Elution with benzene-ether mixture (3:1) gave after evaporation of fractions (4 ml) 9–12 a slightly yellow syrup; 635 mg, 59%. NMR (CDCl$_3$) δ: 8.23 (2H, d, J$_{Hm, Ho}$=8.8 Hz, Hm of p-nitrobenzyl), 7.65 (2H, d, J$_{Ho, Hm}$=8.8 Hz, Ho of p-nitrobenzyl), 5.65 (1H, dd, J$_{5,6\ cis}$=3.5 Hz, J$_{5,6\ trans}$=2.0 Hz, H-5), 5.34 (2H, center of ABq, J$_{a,b}$=14.3 Hz, CH$_2$ of p-nitrobenzyl), 3.86 (1H, dd, J$_{6,5\ cis}$=3.5 Hz, J$_{gem}$=16.4 Hz, H-6 cis), 3.44 (1H, dd, J$_{6,5\ trans}$=2.0 Hz J$_{gem}$=16.4 Hz, H-6 trans), 2.7 (2H, m, α methylene on C-2) and 1.9–0.6 (9H, α,γ,δ methylene on C-2 and methyl). IR (neat) cm$^{-1}$: 1790 (C=O of β lactam), 1712 (C=O of p-nitrobenzylester), 1607 and 1578 (C=C of benzyl and p-nitrobenzyl) and 1524 (NO$_2$).

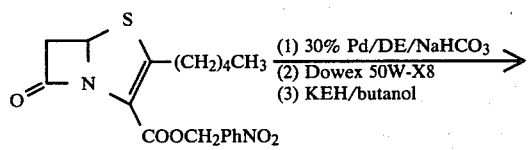

6k

7k

To a solution of compound 6k (0.180 g, 0.48 mmole) in tetrahydrofuran-ether mixture (1:1, 24 ml) was added water (10 ml), sodium bicarbonate (0.040 g, 0.48 mmole) and 30% palladium on diatomaceous earth (0.180 g). The reaction mixture was hydrogenated in a Parr apparatus at 30 p.s.i. for 6 h at 23°–25° C., filtered over celite pad and diluted with ether (30 ml). The aqueous phase was separated and washed twice with ether. Lyophilization of the aqueous solution gave a slightly yellow powder; 74 mg, 58% (An NMR spectrum showed the presence of water). The sodium salt 7k was dissolved in water (10 ml), treated with a resin (Dowex 50W-X8 H+ form) and extracted with ethyl acetate (5×5 ml). The ethyl acetate extracts were combined, dried over anhydrous sodium sulfate and evaporated to dryness leaving a yellow solid; 24 mg, 21% (An NMR spectrum showed the presence of water) NMR (DMSOd-6,80 MHz) δ: 5.7 (dd, J$_{5,6\ trans}$=1.8 Hz, J$_{5,6\ cis}$=3.8 Hz, H-5), 3.92 (dd, J$_{6,5\ cis}$=3.8 Hz, J$_{gem}$=16.3 Hz, H-6 cis) and 1.9–0.7 (β,γ,δ methylene on C-2 and methyl. IR (nujol) cm$^{-1}$: 1775 (C=O of β-lactam) and 1675 (C=O of acid). UV λ$_{max}^{EtOH}$ mμ: 256 (ε 4675) and 307 (ε 5850). The free acid 7k was solubilized in ether and insoluble material was filtered off. The filtrate was concentrated to dryness leaving a yellow solid (17 mg) which was solubilized in methyl isobutylketone; the solution was cooled in ice-water bath and treated with a n-butanol solution of potassium 2-ethylhexanoate. The precipitate was filtered off, washed several times with methyl isobutylketone and dried under high vacuum; 12 mg, 9%. NMR (DMSO d-6, 80 MHz) δ: 5.58 (dd, J$_{5,6}$ trans=1.7 Hz, J$_{5,6\ cis}$=3.6 Hz, H-5), 3.73 (dd, J$_{6,5\ cis}$=3.6 Hz, J$_{gem}$=16.0 Hz, H-6 cis), 3.29 (dd, J$_{6,5\ trans}$=1.7 Hz, J$_{gem}$=16.0 Hz, H-6 trans), 2.88 (m, α methylene on C-2) and 1.9–0.7 (β,γ,δ methylene on C-2 and methyl). IR (KBr) cm$^{-1}$: 1765 (C=O of β-lactam), 1605 (C=C) and 1575 

Preparation 17

Sodium 2-Methoxypenem-3-carboxylate

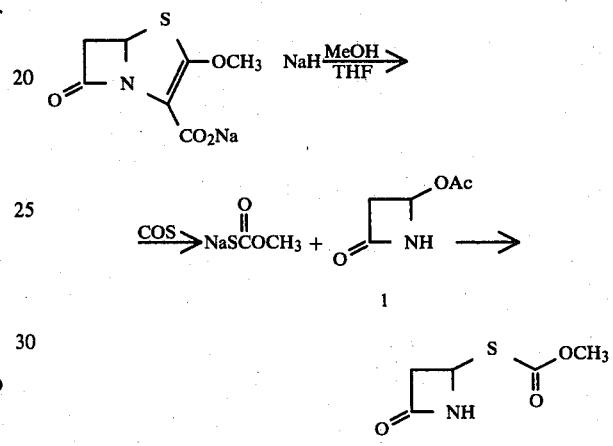

PROCEDURE:

To a suspension of NaH (0.96 g of 50%, 20 mmoles, washed twice with pet. ether) in THF (5 ml) was added dropwise at r.t., under N$_2$, methanol (10 ml). After gas evolution had ceased, the resulting solution was cooled (ice bath) and COS gas was bubbled in. The resulting mixture was evaporated in vacuo to give an oil, which was treated with 1 (2.58 g, 20 mmoles) and water (10 ml). The mixture was stirred at r.t. for 2 h. This was extracted with CHCl$_3$, and the extract dried (Na$_2$SO$_4$) and evaporated to give 3.1 g (96%) of 2, as a yellow oil, which crystallized on standing. NMR (CDCl$_3$) δ: 6.83 (1H, NH), 5.23 (1H, dd, J$_{4,3\ trans}$=2.8 Hz, J$_{4,3\ cis}$=5.0 Hz, H-4), 3.50 (1H, ddd, J$_{3, NH}$=2.0 Hz, J$_{3,4\ cis}$=5.0 Hz, J$_{gem}$=15.2 Hz, H-3 cis), 2.95 (1H, ddd, J$_{3, NH\ trans}$ 1.-Hz, J$_{3,4\ trans}$=2.8 Hz, J$_{gem}$=15.2 Hz, H-3 trans) and 3.87 (3H, s, CH$_3$). m.p. 72°–73° C.

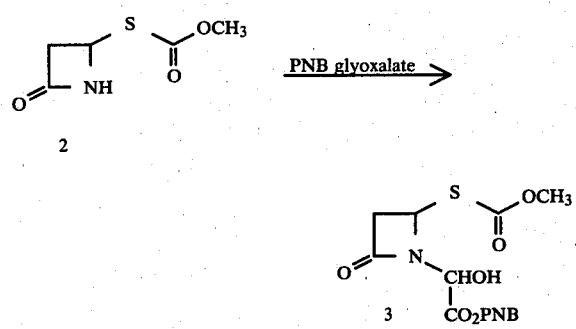

PROCEDURE:

A solution of 2 (3.0 g, 18.63 mmoles) and PNBG (4.23 g, 18.63 mmoles) in benzene (60 ml) was refluxed for 20 h. It was concentrated to dryness to give 3 as an oil in quantitative yield, (6.89 g), NMR (CDCl$_3$) δ: 7.5-8.5 (4H, m, aromatic) 5.2-5.7 (4H, m, benzylic CH$_2$, H$_4$ and H of glyoxalate) 4.15 (H, hydroxyl) 3.9 (3H, s, CH$_3$) 2.8-3.9 (2H, m, H$_3$).

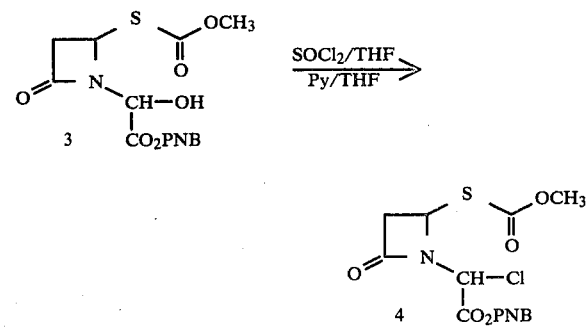

PROCEDURE:

To a cooled (ice bath) solution 3 (6.89 g, 18.6 mmoles) in 1 M pyridine in THF (19 ml) was added dropwise 1 M SOCl$_2$ solution in THF (19 ml) and the mixture stirred in the cold for 5 min and at room temperature for 10 min. Then it was diluted with benzene (25 ml), stirred at room temperature for a further 15 min and filtered over celite-charcoal. The filtrate was evaporated to dryness to give 4, as an oil, quantitative yield (7.30 g) NMR (CDCl$_3$) δ: 7.5-8.25 (4H, m, aromatic) 6.08 (1H, 2s, CH—Cl) 5.56 (1H, m, H$_4$) 5.3 (2H, two S, benzylic CH$_2$) 3.77 (3H, s, CH$_3$) 2.9-3.6 (2H, m, H$_3$).

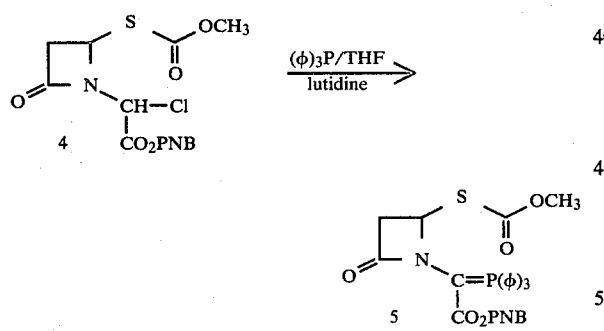

PROCEDURE:

Triphenylphosphine (4.8 g, 18.63 mmoles) was added to a solution of 4 (7.247 g, 18.63 mmoles) and lutidine (1.006 g, 18.63 mmoles) in THF (60 ml). The mixture was allowed to stand at room temperature for 6 days. It was partitioned between water and ether pet. ether. The layers were separated and the organic layer was washed with 1N HCl followed by 1 M NaHCO$_3$ solution and water. It was dried and evaporated to give an oil which crystallized from ether to give 5.2 g of solid 5. All the aqueous solutions were reextracted with CH$_2$Cl$_2$ to give an oil which on treatment with ether gave a further 2.4 g of solid 5 for a total yield of 7.6 g (66.43%). NMR (CDCl$_3$) δ: 7.2-8.35 (19H, m) 4.6-5.3 (3H, m, H$_4$ and benzylic CH$_2$) 3.8 (3H, s, CH$_3$) 2.4-3.3 (2H, m, H$_3$).

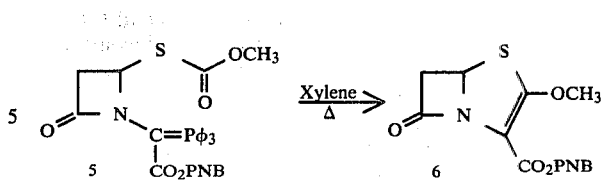

PROCEDURE:

A solution of phosphorane 5 (2.0 g, 3.25 mmoles) in xylene (400 ml) was refluxed for 18 h. Distillation of the solvent followed by concentration to dryness afforded 2.5 g of a brown oil. Purification by a column chromatography and two preparative TLC's gave 6 (20 mg) as a light yellow oil. NMR (CDCl$_3$) δ: 8.23 (2H, d, J=9 Hz), 7.52 (2H, d, J=9 Hz), 5.48 (1H, dd J$_{cis}$=5 Hz, J$_{trans}$=3 Hz), 3.83 (3H, s), 5.57 (1H, dd J$_{cis}$=5 Hz, J$_{gem}$=15 Hz), 3.0 (1H, dd J$_{trans}$=3 Hz, J$_{gem}$=15 Hz).

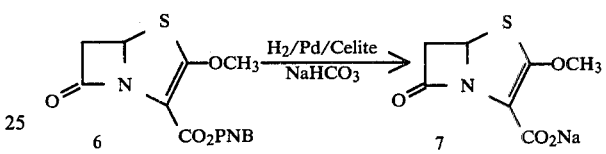

PROCEDURE:

A two phase mixture of ester 6 (50 mg, 0.15 mmole) in ether (2 ml)/tetrahydrofuran (4 ml) and sodium bicarbonate (10 mg, 0.12 mmole) in water (2 ml) was hydrogenated on 30% palladium on diatomaceous earth (50 mg) in a Parr shaker at 40 p.s.i. H$_2$. After 4 h, it was filtered over celite and the cake was washed well with water and tetrahydrofuran. The filtrate and washings were combined and the aqueous phase was washed with ethyl acetate (3×5 ml); it was then lyophilized to give 7 (22.5 mg) as a yellow solid.

PREPARATION 18

Sodium 2-(2-Furylmethyl)penem-3-carboxylate

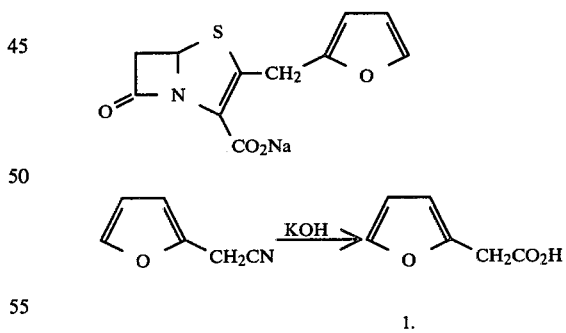

1.

A mixture of furanacetonitrile (26.5 g, 0.248 mole), ethanol (100 ml) and 20% potassium hydroxide in water (100 ml) was heated under reflux with stirring for 17 h. The ethanol was evaporated in vacuo. The remaining solution was diluted with 100 ml of water and washed with ether (2×50 ml). The aqueous layer was treated with charcoal, filtered, cooled to 0° and acidified with 100 ml of cold 10% hydrochloric acid. This mixture was extracted with dichloromethane (4×100 ml). The extract was decanted from a tarry precipitate, treated with charcoal, filtered and the solvent was evaporated in vacuo to give the furyl acetic acid 1 as a light yellow solid, 22.9 g (73% yield).

Procedure of: J. Plucker and E. Amstutz. J. Amer. Chem. Soc. 62, 1512 (1940)

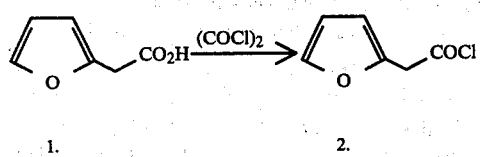

1.  2.

To a mixture of acid 1 (10.0 g, 79 mmoles) in 100 ml of oxalyl chloride was added one drop of dimethylformamide. The mixture was stirred for 1.15 h at 23° and then the excess oxalyl chloride was distilled off at 23° and 10–20 torr to give acid chloride 2 as a brown oil, 11.4 (100%).

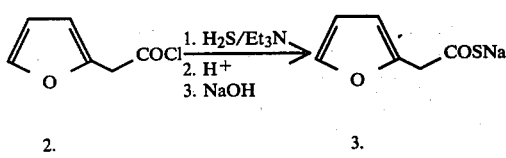

2.  3.

A solution of triethylamine (27.5 ml, 197 mmoles) in 350 ml of dichloromethane was cooled to 0° and hydrogen sulfide was passed in for ½ h. A solution of acid chloride 2 (11.4 g, 79 mmoles) in 150 ml of dichloromethane was added dropwise with stirring. The solution was stirred at 0° for one h and then nitrogen was blown in to remove the excess hydrogen sulfide while the temperature was allowed to rise to 23°. The solvent was evaporated in vacuo and the residue was dissolved in 250 ml each of ethyl acetate and water. A solution of 17 ml of 12 M hydrochloric acid diluted with 100 ml of water was added while nitrogen was passed through the solution. The mixture was shaken and separated. The organic layer was washed with another 100 ml of water (under nitrogen) and then extracted with 163 ml of 0.5 M sodium hydroxide (aqueous extract about pH 7.5). This aqueous extract containing 3 was used directly in the next step. A small portion of the aqueous extract was evaporated in vacuo to give a brown tar on which spectral data were obtained.

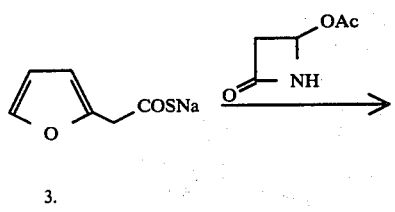

3.  4.

The aqueous solution of 3 obtained from the last step (about 160 ml; containing theoretically 79 mmoles of 3) was mixed with a solution of 4-acetoxy azetidinone (10.2 g, 79 mmoles) in 100 ml of water. Dilute sodium bicarbonate was added until the solution was pH 7.5 to 8.0. After being stirred for 5 h at 23°, the mixture was extracted with 350 ml of ethyl acetate (a difficult to separate emulsion formed). The ethyl acetate extract was washed with 200 ml each of very dil. sodium bicarbonate and sat. sodium chloride solutions, dried and filtered through 160 g of silica gel using 1.5 l of ethyl acetate. The solvent was evaporated in vacuo to a red tar, 4.87 g. The tar was absorbed onto 25 g of silica gel and placed on a 100 g silica gel column. The column was eluted with ether. Fractions 3 to 10 (25 ml fractions) were combined and the solvent evaporated in vacuo to give 4 as a light brown solid, 3.41 g (20.5% yield).

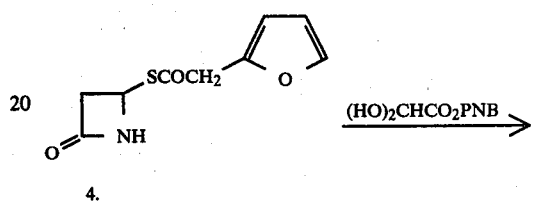

4.

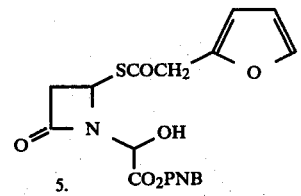

5.

A mixture of 4 (3.35 g, 15.8 mmoles) and p-nitrobenzylglyoxylate (4.5 g, 20 mmoles) in 80 ml of benzene was stirred and heated under reflux for 6 h under a Dean-Stark trap which had been filled with 3Å molecular sieve. The solvent was evaporated in vacuo and the residue was re-dissolved in dichloromethane (80 ml). This solution was washed with dilute sodium chloride solution, dried (Na₂SO₄) and absorbed onto 80 g of silica gel. The silica was extracted with 700 ml of ethyl acetate. The solvent was evaporated in vacuo to give compound 5 as a reddish-brown tar, 7.69 g, with ≦85% purity. The product was used as such in subsequent reactions.

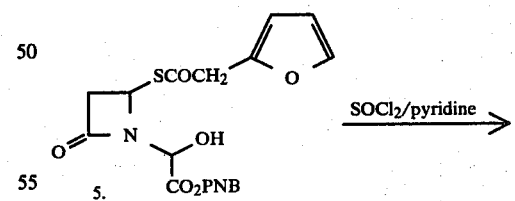

5.

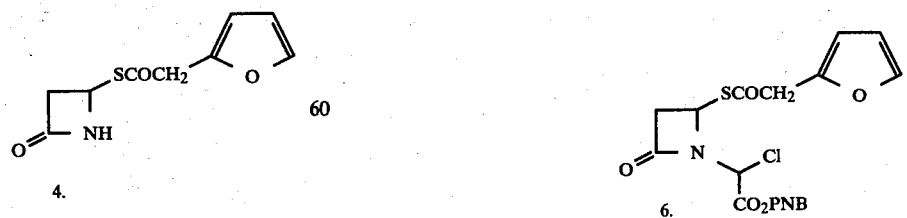

6.

A solution of thionyl chloride (1.5 ml, 20.8 mmoles) in 15 ml of tetrahydrofuran was added dropwise with stirring to a solution of compound 5 (7.65 g, 18 mmoles), pyridine (1.7 ml, 21 mmoles) and tetrahydrofuran (120 ml) at 0°. The mixture was stirred at 0° for 4 h. The precipitate was removed by filtration and the solvent was evaporated in vacuo at 30°. The residue was dissolved in 250 ml of dichloromethane, treated with charcoal and filtered. The solvent was evaporated in vacuo at 30° to give compound 6 as an orange tar, 7.22 g, with about 80% purity. The product* was used as such in subsequent reactions.

*The product proved to be relatively unstable so that it was necessary that it be used immediately in the next reaction.

silica gel was placed on a 50 g silica gel column and eluted with ether. The first few fractions contained impure compound 8 (2 g). The fractions were absorbed onto 10 g of silica gel and re-chromatographed on a 40 g silica gel column (elution with ether/cyclohexane 1:1, then 3:1). A major component was isolated from middle fractions and crystallized from ether to give compound 8, 1.08 g (17.7% overall yield from 4). A portion was recrystallized from benzene/cyclohexane, m.p. 105°–106°. Anal. calc'd for $C_{18}H_{14}N_2O_6S$: C, 55.95; H, 3.65; N, 7.25; S, 8.30. Found: C, 56.13; H, 3.81; N, 7.37; S, 8.48.

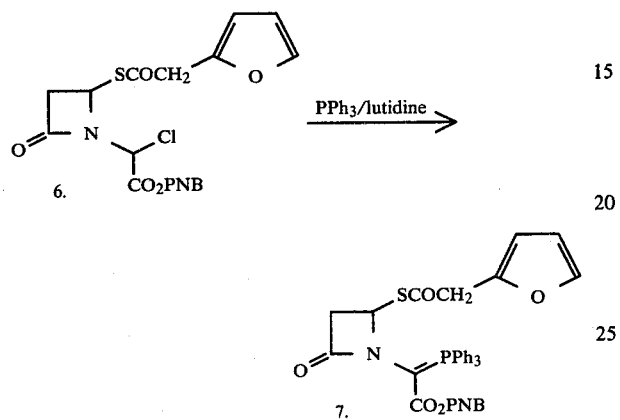

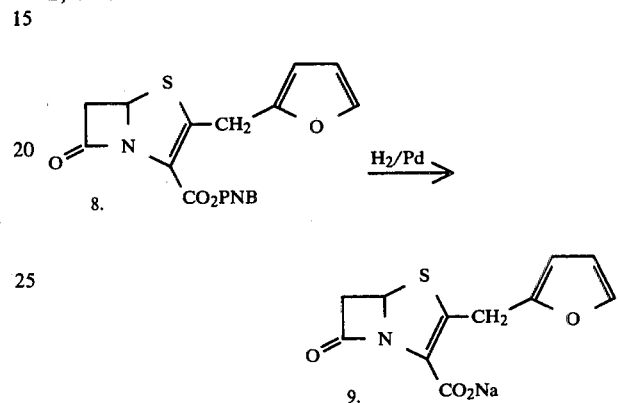

A mixture of compound 6 (7.2 g, 16.4 mmoles), triphenylphosphine (5.76 g, 22 mmoles), 2,6-lutidine (2.6 ml, 22 mmoles) and tetrahydrofuran (72 ml) was stirred at 23° for 17 h. The precipitate was removed by filtration and the solvent was evaporated in vacuo. The residue was dissolved in 280 ml of dichloromethane and absorbed onto 140 g of silica gel. The silica gel was washed with a further 100 ml of dichloromethane (discarded). The silica gel was then extracted with 1.5 l of dichloromethane/ethyl acetate 1:1. The solvent was evaporated in vacuo to give a tar, 8.3 g. The tar was dissolved in dichloromethane and absorbed onto 40 g of silica gel which was placed (dry) on a 160 g silica gel column. The column was eluted with gradually increasing ratios of ethyl acetate in dichloromethane (up to 1:1). A major component was isolated from later fractions and proved to be compound 7, 4.7 g, in <50% purity.

A mixture of compound 8 (386 mg, 1.00 mmole) sodium bicarbonate (84 mg, 1.00 mmole), 30% palladium on diatomaceous earth (400 mg) and tetrahydrofuran, ether, water (25 ml each) was hydrogenated on a Parr apparatus at 50 p.s.i. and 23° for 4 h. The catalyst was removed by filtration and the liquid phases were separated. The aqueous layer was washed with ethyl acetate, filtered and freeze-dried to give compound 9 as a pale yellow powder, 160 mg (59% yield), and in 70-80% purity. $\lambda_{max}/H_2O$ 255 ($\epsilon$=3790), 301 ($\epsilon$=4360).

Preparation 19

2-(3'-Indole)methylpenem-3-carboxylic acid

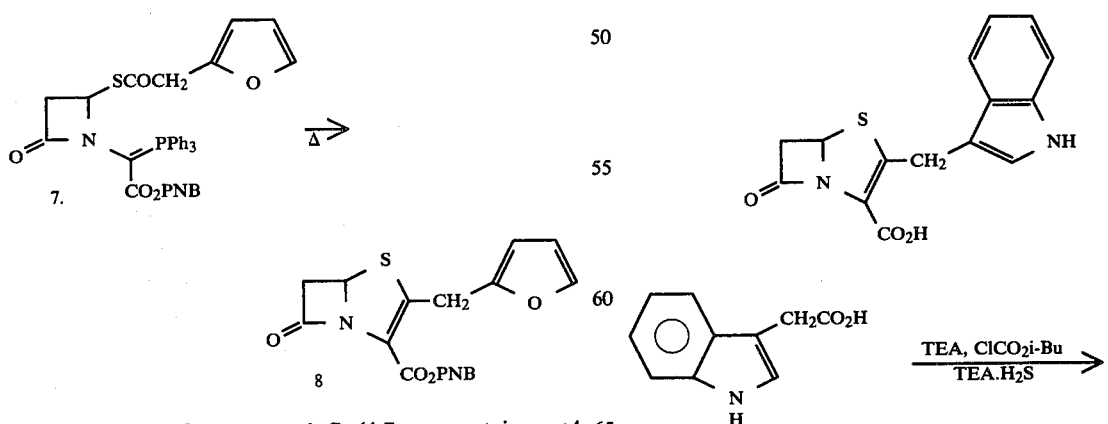

A solution of compound 7 (4.7 g, contains <4 mmoles) in toluene (140 ml) was stirred and heated under reflux for 4 h. On cooling, 25 g of silica gel was added, the solvent was evaporated in vacuo and the

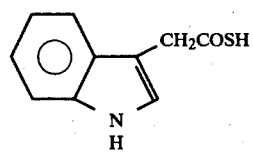

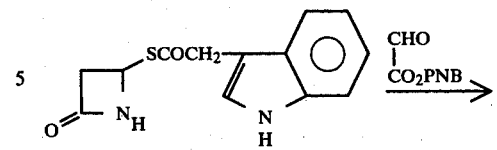

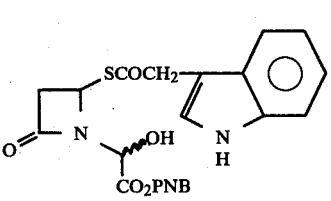

A cold (0° C.) methylene chloride (50 cc) suspension of 3-indole acetic acid (3.00 g, 17.1 mmoles) was treated with triethyl amine (1.74 g, 17.2 mmoles, 2.4 cc) and stirred for 15 min. The resulting solution was treated at −15° C. with i-butyl chloroformate (2.36 g, 173 mmole, 2.24 cc) and stirred for 10-15 min at −15° C. A previously prepared methylene chloride (50 cc) solution of triethyl amine-(3.62 g, 35.9 mmoles, 5.00 cc) $H_2S$ at −78° C. was poured in the mixed anhydride mixture. It was then stirred for 10 to 20 min at −15° C. or lower, diluted with ether and washed with 10% HCl and water. The solution was extracted with 10% $NaHCO_3$ (3×10 cc). The aqueous extracts were combined, washed with ether and ethyl acetate. They were acidified with 10% HCl and extracted with ethyl acetate (5×20 cc). The organic extracts were combined, washed with water (3×20 cc), brine and dried over magnesium sulfate. (1.83 g, 56%). δ (ppm, $CDCl_3$) 8.22 (1H, b.s., N—H), 7.73-7.00 (5H, m, H-indole), 4.63 (1H, s, S—H), 3.95 (2H, s, $CH_2$). $\nu_{c=o}$(KBr film) 1700, $\nu_{SH}$2550, $\nu_{NH}$3400.

Hydrated p-nitrobenzyl glyoxylate (544 mg, 2.40 mmoles) was refluxed in benzene (100 cc) through a Dean Stark condenser filled with 3Å molecular sieves for 1 h. Azetidinone 4 (520 mg, 2.0 mmoles) in acetone (25 cc) was added to the refluxing benzene solution of glyoxylate. Acetone was distilled off and the benzene solution was refluxed for 3 more h. Evaporation of benzene afforded a quantitative yield of 5 (1.06 g) as a mixture of 2 epimers. δ (ppm, $C_2D_6CO$) 10.20 (1H, b.s., N—H), 8.10 (2H, 2d, J=8, Hm aromatic), 7.75-6.97 (7H, m, H-indole and Ho aromatic), 5.70-4.67 (4H, $CH_2$—PNB, and H—C—OH), 4.00 (2H, s, $CH_2$ - indole), 3.50 (1H, dd, $J_{gem}$=15, $J_{3-4\ cis}$=5, H-3), 2.90 (1H, 2dd, $J_{gem}$=15, $J_{3-4\ trans}$=2.5, H-3). $\nu_{c=o}$ (KBr film) 1770, 1755, 1690, $\nu_{NO_2}$ 1525, $\nu_{OH,\ NH}$ 3,700 - 3200.

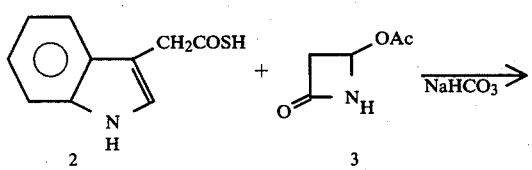

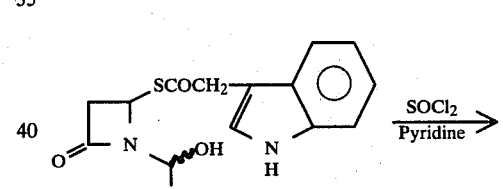

A solution of indole-3-thioacetic acid (1.83 g, 9.58 mmoles) in THF (6 cc) and water (10 cc) was treated with an aqueous solution (10 cc) of $NaHCO_3$ (860 mg, 10.24 mmoles) for 5 min at room temperature. Then 4-acetoxy azethidinone (1.40 g, 10.85 mg) in water (10 cc) was poured in the thiolate solution. The resulting mixture was stirred for 2 h. Filtration of the precipitate yielded the desired derivative 4 which was dried under high vacuum (2 g, 80.3%, m.p.: 153°-154°). Anal. calc'd for $C_{13}H_{12}N_2O_2S$: C, 59.98; H, 4.65; N, 10.76; S, 12.32. Found: C,60.20; H, 4.69; N, 10.79; S, 12.29. δ(ppm, $C_2D_6CO$) 10.35 (1H, b.s., N—H), 7.90-6.97 (6H, m, H-indole and N—H), 5.20 (1H, dd, $J_{4-3\ trans}$=2.5, $J_{4-3\ cis}$=5, H-4), 4.02 (2H, s, $CH_2$), 3.40 (1H, ddd, $J_{gem}$=15, $J_{3-4\ cis}$=5, $J_{3-NH}$=1.5, H-3), 3.80 (1H, dd, $J_{gem}$=15, $J_{3-4\ trans}$=2.5, H-3). $\nu_{c=o}$ (Nujol Mull), 1757, 1655, $\nu_{NH}$ 3290, 3230.

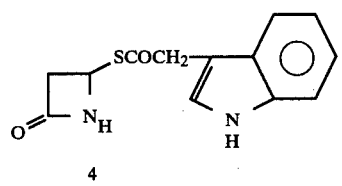

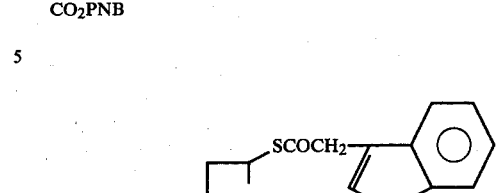

A cold (−15° C.) THF (3cc, freshly distilled over LAH) solution of azetidinone 5 (105 mg, 0.224 mmole) was treated under nitrogen atmosphere with pyridine (17.2 mg, 0.220 mmole, 17.8 μl) and thionyl chloride (25.8 mg, 0.220 mmole, 15.8 μl). The mixture was stirred for 15 min at −15° C. The filtrate was filtered off and washed with benzene. Evaporation of solvent gave a residue which was filtered through a small silica gel pad. Elution of the pad with methylene chloride gave 6 (75 mg, 68.8%) as an epimeric mixture. δ (ppm, $CDCl_3$) 8.32 (1H, b.s., N—H), 8.19 (2H, d, Hm aromatic), 7.65-7.05 (7H, m, H-indole and Ho aromatic), 6.07 (1H, s, Cl—C—H), 5.62 (1H, dd, $J_{4-3\ trans}$ =3, $J_{4-3\ cis}$ =5, H-4), 5.32 (1.3 H, s, CH$_2$—PNB), 4.93 (0.7 H, ABq, CH$_2$—PNB), 4.00 (2H, s, CH$_2$—indole), 3.57, 3.52 (1H, 2dd, J$_{gem}$=10, J$_{3\text{-}4\ cis}$=5, H-3), 3.00, 2.95 (1H, 2dd, J$_{gem}$=16, J$_{3\text{-}4\ trans}$=3, H-3). $\nu_{c=o}$ 1780, 1760, 1695, $\nu_{No_2}$ 1525, $\nu_{NH}$ 3420.

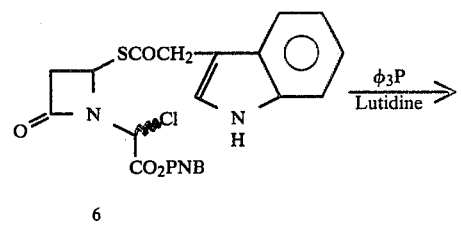

6

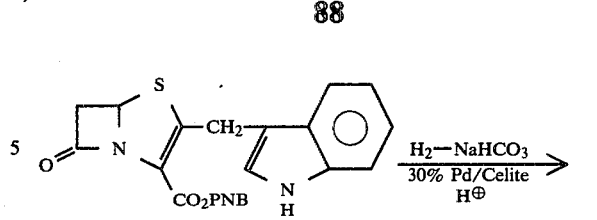

8

A THF (10 cc, distilled over LAH) solution of chlorazetidinone 6 (530 mg, 1.07 mmole) was treated with 2,6-lutidine (129 mg, 1.20 mmole, 0.140 cc) and triphenyl phosphine (425 mg, 1.58 mmole, 1.5 eq). The mixture was heated at $\approx$ 60°-65° C. for 50 h. The crude phosphorane was purified on silica gel (5 g) column (ether-ethyl acetate) and gave 7 (680 mg, 86.4%). $\nu_{c=o}$ (KBr film) 1760, 1690, 1630, $\nu_{NO_2}$ 1520, $\nu_{NH}$ 3400-3100.

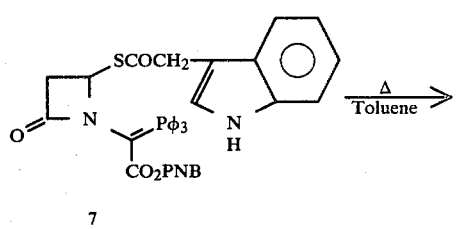

7

A mixture of ester 8 (142 mg, 0.326 mmole) in THF (20 cc), ether (40 cc) and NaHCO$_3$ (27.4 mg, 0.366 mmole) in water (20 cc) was shaken on a Parr hydrogenator for 3 h at 30 p.s.i., using 30% Pd on celite (300 mg) as catalyst. The catalyst was filtered off and washed with water and ether. The aqueous phase was carefully washed with ether (3×50 cc) and then acidified portion wise with 1% HCl while extracting with EtOAc between each HCl addition. The ethyl acetate extracts were combined, washed with H$_2$O-brine, brine and dried over Na$_2$SO$_4$. The residue upon solvent evaporation was triturated with ether (28 mg, 28.6%, decomp.$\approx$145° C.). $\delta$ (ppm DMSO) 7.70-6.95 (6H, m, H-indole), 5.70 (1H, dd, J$_{5\text{-}6\ cis}$=4.0, J$_{5\text{-}6\ trans}$=1.5, H-5), 4.40 (2H, center of ABq, J=15.5, CH$_2$-indole), 3.90 (1H, dd, J$_{gem}$=16.5, J$_{6\text{-}5\ cis}$=4, H-6), 3.45 (1H, dd, J$_{gem}$=16.5, J$_{6\text{-}5\ trans}$=1.5, H-6).$\nu_{c=o}$(nujol mull) 1770, 1655, $\nu_{NH}$=3395, $\nu_{OH}$3300-2500. UV (H$_2$O) $\lambda_{max}$307 ($\epsilon$=13,000), 289 ($\epsilon$=17,500), 281 ($\epsilon$=17,500), 273 ($\epsilon$=16,500).

Preparation 20

Sodium 2-Hydroxymethylpenem-3-carboxylate

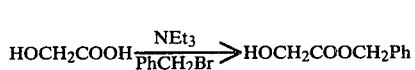

A solution of glycolic acid (40.0 g, 0.526 mole) in N,N-dimethylformamide (400 ml) was first treated with triethylamine (73.9 ml, 0.53 mole) before the dropwise addition of benzylbromide (63 ml, 0.53 mole) over a 1 h period. The reaction mixture was stirred at 23° C. for 60 h and poured into water (4 l). The aqueous solution was extracted with ether (3×1 l and 14×500 ml): the extracts were combined, washed with water, dried over anhydrous magnesium sulfate and concentrated under reduced pressure to a slightly yellow oil; 65.8 g, 75%. NMR (CDCl$_3$) $\delta$:7.37 (5H, s, phenyl), 5.20 (2H, s, CH$_2$ of benzyl), 4.19 (2H, s, $\alpha$ methylene) and 3.13 (1H, b.s., OH).

Phosphorane 7 (680 mg, 0.937 mmole) was refluxed in toluene for 20 h. Toluene evaporation afforded a residue which was passed through a silica gel (7 g) column (benzene). It yielded 8 as a foam (325 mg, 79.6%). Anal. calc'd for C$_{22}$H$_{17}$N$_3$O$_5$S: C, 60.68; H, 3.94; N, 9.65; S, 7.36. Found: C, 60.46; H, 3.89, N, 9.35; S, 7.10. $\delta$ (ppm, CDCl$_3$ 8.20 (2H, d, J=8, Hm aromatic), 8.14 (1H, b.s., N-H ), 7.58 (2H, d, J=8, Ho aromatic), 7.74-7.00 (5H, m, H-indole), 5.51 (1H, dd, J$_{5\text{-}6\ trans}$=2.0, J$_{5\text{-}6\ cis}$3.6, H-5), 5.38 (2H, center of ABq, J=14, CH$_2$-PNB), 4.32 (2H, s, CH$_2$-indole), 3.75 (1H, dd, J$_{gem}$=16.2, J$_{6\text{-}5\ cis}$=3.6, H-6), 3.35 (1H, dd, J$_{gem}$=16.2, J$_{6\text{-}5\ trans}$=2.0, H-6). $\nu_{c=o}$(KBr film) 1783, 1705, $\nu_{No_2}$ 1520, $\nu_{NH}$ 3400. U.V. (EtOH) $\lambda_{max}$ 314 ($\epsilon$=10,000), 290 ($\epsilon$=13,500), 269 ($\epsilon$=18,000).

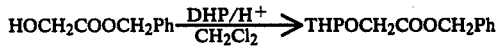

To a solution of benzyl glycolate (65.8 g, 0.395 mole) in dichloromethane (650 ml) was successively added dihydropyran (54.7 ml, 0.60 mole) and a solution of hydrochloric acid in dichloromethane (prepared from acetyl chloride (0.7 ml), ethanol (0.58 ml) and CH$_2$Cl$_2$ (3 ml)). The reaction mixture was stirred at 23° C. for 4 h, then diluted with dichloromethane (100 ml). The organic solution was washed with sodium bicarbonate solution (pH∼7.1), dried over anhydrous magnesium sulfate and concentrated under reduced pressure to a slightly yellow oil; 94.6 g, 95%. NMR (CDCl$_3$) δ:7.37 (5H, s, phenyl hydrogen), 5.18 (2H, s, CH$_2$ of benzyl), 4.73 (1H, m, H-2 of tetrahydropyranyl), 4.26 (2H, s, α-methylene), 4.2–3.3 (2H, m, Hs-5 of tetrahydropyranyl) and 2.2–1.1 (6H, Hs-3, Hs-4, Hs-5 of tetrahydropyranyl).

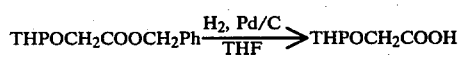

To a solution of benzyl O-tetrahydropyranyl glycolate (36.5 g, 0.146 mole) in dry tetrahydrofuran (650 ml) was added 10% palladium on charcoal (1.0 g). The mixture was hydrogenated in a Parr Shaker apparatus at 23° C. under 15 p.s.i. for 24 h. The catalyst was filtered off on a pad of celite and washed with some tetrahydrofuran. The filtrate and washings were combined and concentrated under reduced pressure to a slightly yellow oil; 23.4 g, 100%. NMR (CDCl$_3$) δ: 9.6 (1H, OH), 4.70 (1H, m, H-2 of tetrahydropyranyl), 4.28 (2H, s, α-methylene), 4.3–3.4 (2H, m, Hs-6 of tetrahydropyranyl) and 2.1–1.2 (6H, Hs-3, Hs-4, Hs-5 of tetrahydropyranyl).

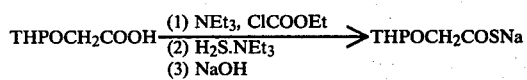

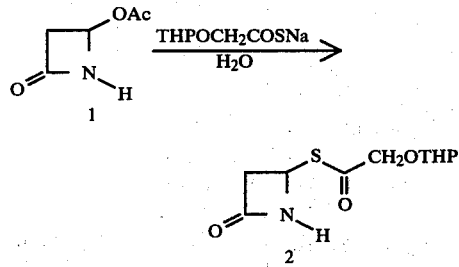

A solution of O-tetrahydropyranylglycolic acid (10.0 g, 62.4 mmoles) in dichloromethane (300 ml) kept under nitrogen atmosphere was cooled at −30° C. and successively treated with triethylamine (8.70 ml, 62.4 mmoles) and ethylchloroformate (5.97 ml, 62.4 mmoles); the ethylchloroformate was added over a period of 10 min. The reaction mixture was stirred at −25° C. for 0.5 h and treated dropwise (20 min) with a solution of triethylamine-hydrogen sulfide in dichloromethane; this solution was prepared by bubbling hydrogen sulfide in dichloromethane (300 ml) containing triethylamine (9.15 ml, 65.6 mmoles). The reaction mixture was stirred at −25° C. for 0.5 h then warmed up slowly to 23° C. over a period of 1 h. The solution was concentrated to half volume and 0.5 N sodium hydroxide solution (256 ml) was added. The two phase mixture was vigourously stirred for 1 h and the organic phase was removed; the aqueous solution was washed with dichloromethane (2×20 ml) and the pH was adjusted to 7.5 by the addition of some acetic acid. The aqueous solution of sodium O-tetrahydropyranyl thioglycolate was rapidly added to aqueous solution (175 ml) of 4-O-acetyl-2-azetidinone (5.42 g, 42.0 mmoles). The pH of the reaction mixture was adjusted to 7.4–7.6. The reaction mixture was stirred at 23° C. for 2 h and extracted with dichloromethane (1×200 ml, 4×100 ml). The organic extracts were combined, dried over anhydrous sodium sulfate and evaporated in vacuo leaving a slightly yellow oil; 9.7 g, 94% which crystallized on standing. Recrystallization from ether gave analytical sample (mixture of isomers); M.P. 93°–6° C. Analysis calc'd for C$_{10}$H$_{15}$NO$_4$S: C 48.96, H 6.16, N 5.71, S 13.07. Found: C 48.87, H 6.15, N 5.62, S 13.08. NMR (CDCl$_3$) δ: 6.8 (1H, b.s., NH), 5.21 (1H, dd, J$_{4,3}$ $_{cis}$=5.0 Hz, J$_{4,3}$ $_{trans}$=2.6 Hz, H-4), 4.73 (1H, m, H-1 of tetrahydropyranyl), 4.28 (2H, s, α-methylene of thioester), 3.8 (m, Hs-5 of tetrahydropyranyl), 3.36 (ddd, J$_{3\text{-}NH}$=2.0 Hz, J$_{3,4}$ $_{cis}$=5.0 Hz, H-3 cis), 2.97 (1H, ddd, J$_{3\text{-}NH}$=1.3 Hz, J$_{3,4}$ $_{trans}$=2.7 Hz, J$_{gem}$=15.5 Hz, H-3 trans) and 2.3–1.0 (6H, Hs-3, Hs-4, Hs-5 of tetrahydropyranyl). IR (CHCl$_3$) cm$^{-1}$: 1775 (C=O of β-lactam) and 1687 (C=O of thioester).

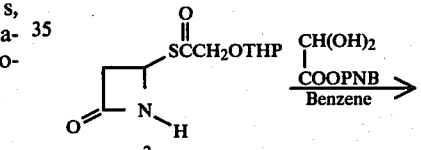

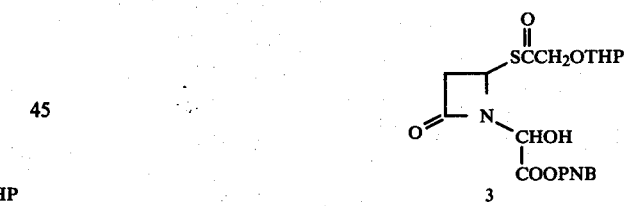

A suspension of p-nitrobenzyl glyoxylate hydrate (2.85 g, 12.5 mmoles) in benzene (170 ml) was refluxed for 0.5 h through a Dean-Stark trap filled with molecular sieves (4Å) and a solution of compound 2 (2.8 g, 11.4 mmoles) in tetrahydrofuran (10–15 ml) was added. The reaction mixture was refluxed for 6 h and the solvent was removed in vacuo leaving a yellow syrup; 5.2 g, 100%. NMR (CDCl$_3$) δ: 8.28 and 8.25 (2H, 2d, J$_{Hm,Ho}$=8.8 Hz, Hm of p-nitrobenzyl), 7.62 and 7.59 (2H, 2d, J$_{Ho,Hm}$=8.8 Hz, Ho of p-nitrobenzyl). 5.7–5.1 (4H, H-4, CH of glyoxylate and CH$_2$ of p-nitrobenzyl), 4.9–4.4 (2H, OH and H-2 of tetrahydropyranyl), 4.29 and 4.26 (2H, 2s, α-methylene of thioester), 4.0–3.3 (3H, m, Hs-6 of tetrahydropyranyl and dd partially resolved J$_{3,4}$ $_{cis}$=5.5 Hz, H-3 cis), 3.1 (1H, H-3 trans) and 2.2–1.1 (6H, Hs-3, Hs-4, Hs-5 of tetrahydropyranyl).

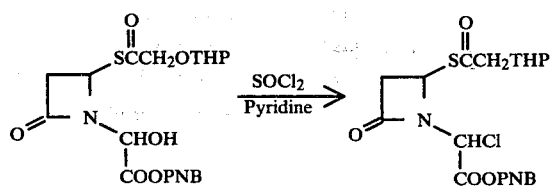 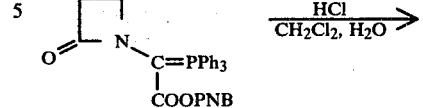

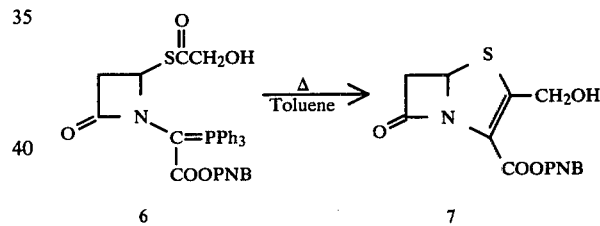

A solution of compound 3 (4.82 g, 0.0106 mole) in dry tetrahydrofuran (50 ml) protected from moisture by a stream of nitrogen was cooled at 0° C. in ice-water bath and successively treated with pyridine (0.94 ml, 0.0117 mole) and thionyl chloride (0.841 ml, 0.0117 mole) at such a rate that the temperature was kept between 2°–3° C. The reaction mixture was stirred at 2°–3° C. for 0.75 h and filtered. The solids were washed with benzene and, the filtrate and washings were combined and concentrated in vacuo to a dark syrup which was absorbed on a silica gel (50 g of silica gel 60 for dry column) pad. Elution with chloroform and evaporation of the appropriate fractions gave 3.5 g, 70% of a yellow syrup which is a mixture of isomers. This compound (purity ≧ 70% by NMR) was used for the next step without any further purification. NMR (CDCl$_3$) δ: 8.24 (2H, d, J$_{Hm,Ho}$=8.8 Hz, Hm of p-nitrobenzyl), 7.63 (2H, d, J$_{Ho,Hm}$=8.8 Hz, Ho of p-nitrobenzyl) 6.22 and 6.14 (2s, of glyoxylate), 5.7 (1H, M, H-4) 5.44 and 5.37 (2H, 2s, CH$_2$ of p-nitrobenzyl), 4.9–4.5 (1H, m, H-2 of tetrahydropyranyl), 4.28 (2H, bs, α-methylene of thioester), 4.1–2.9 (m, H-3 trans, H-3 cis and Hs-6 of tetrahydropyranyl) and 2.0–1.2 (m, Hs-3, Hs-4 and Hs-5 of tetrahydropyranyl)

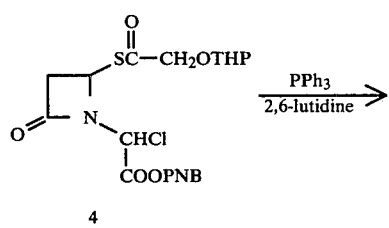

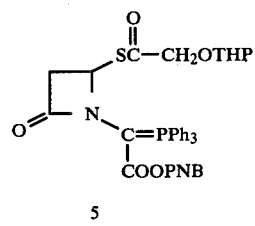

A solution of compound 4 (3.5 g, 7.4 mmoles), triphenylphosphine (2.7 g, 10.3 mmoles) and 2,6-lutidine (1.20 ml, 10.3 mmoles) in benzene (70 ml) was stirred for 22 h at 40° C. and then filtered after cooling at 23° C. The solids were washed with some benzene and the filtrate and washings were combined and concentrated in vacuo leaving a yellow syrup which was chromatographed (120 g of silica gel 60 for dry column, eluate: benzeneether, 1:1). Combination and evaporation of appropriate fractions gave a yellow syrup; 1.4 g, 27%.

A solution of hydrochloric acid (0.65 g, 17.8 mmoles) in dichloromethane (50 ml) was added to the crude phosphorane 5 (6.18 g, 8.8 mmoles) and the latter solution was stirred 5 min before adding water (50 ml). The reaction mixture was vigorously stirred for 6 h and neutralized by the addition of sodium bicarbonate. The aqueous phase was separated and the organic phase was washed with water (2×10 ml), dried over anhydrous magnesium sulfate and concentrated in vacuo to a yellow syrup; 5.6 g, >100%. A part of this amount was purified by preparation TLC (ethyl acetate).

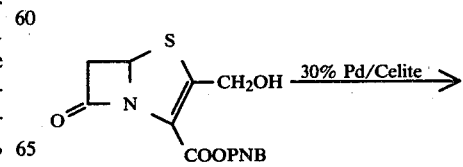

A solution of phosphorane 6 (0.365 g, 0.59 mmole) in toluene (10 ml) was refluxed for 3.5 h, cooled to 23° C. and concentrated in vacuo to a yellow semi-crystalline substance which was purified by preparative TLC (ether); 88 mg, M.P.: 115°–7° C., 44%. NMR (CDCl$_3$) δ: 8.29 (2H, d, J$_{Hm,Ho}$=8.9 Hz, Hm of p-nitrobenzyl), 7.65 (2H, d, J$_{Ho,Hm}$=8.9 Hz, Ho of p-nitrobenzyl), 5.71 (1H, dd, J$_{5,6\ cis}$=3.5 Hz, J$_{5,6\ trans}$=2.1 Hz, H-5), 5.36 (2H, center of ABq, J$_{a,b}$=14.0 Hz, CH$_2$ of p-nitrobenzyl), 4.70 (2H, bs, α-methylene on C-2), 3.90 (1H, dd, J$_{6,5\ cis}$=3.5 Hz, J$_{gem}$=16.8 Hz, H-6 cis), 3.52 (dd, J$_{6,5\ trans}$=2.1 Hz, J$_{gem}$=16.8 Hz, H-6 trans) and 3.4 (bs, OH).

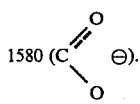

8

To a solution of ester 7 (0.529 g, 1.57 mmole) in tetrahydrofuran (54 ml) was added ether (108 ml), aqueous solution of sodium biarbonate (0.126 g, 1.5 mmole, 42 ml) and 30% palladium on celite (0.53 g). The reaction mixture was hydrogenated in a Parr apparatus under 30 p.s.i. for 5 h at 23°–25° C., filtered over celite pad and diluted with ether (15 ml). The aqueous phase was separated and washed with ether (2×5 ml). Lyophilization of the aqueous solution gave a colorless powder, 0.319 g, 91%. NMR (DMSO d-6) δ: 5.50 (1H, dd, $J_{5-6}=3.6$ Hz, $J_{5,6\ trans}=1.7$ Hz, H-5), 4.17 (2H, center of ABq, $J_{a,b}=15.5$ Hz, methylene on C-2), 3.63 (dd, $J_{6,5\ cis}=3.6$ Hz, $J_{gem}=16.1$ Hz, H-6 cis) and 3.27 (dd, $J_{6,5\ trans}=1.7$ Hz, $J_{gem}=16.1$ Hz, H-6 trans). IR (KBr) cm$^{-1}$: 3400 (OH), 1765 (C=O of β-lactam) 1610 and

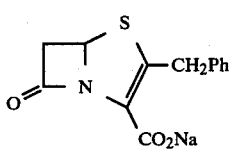

U.V. $\lambda_{max}^{H29}$ mμ: 253 (ε 3290) and 304 (ε 4610).

Preparation 21

Sodium 2-Benzylpenem-3-carboxylate

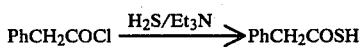

1.

A solution of triethylamine (34 ml, 0.25 mole) in 340 ml of dichloromethane was cooled to 0° and hydrogen sulfide was passed in for ½ h. A solution of phenylacetyl chloride (13.2 ml, 0.10 mole) in 130 ml of dichloromethane was added dropwise with stirring. The solution was stirred at 0° for one h then nitrogen was blown in to remove the excess hydrogen sulfide while the temperature was allowed to rise to 23°. The solvent was evaporated in vacuo and the residue was dissolved in 200 ml each of dichloromethane and water. Dilute hydrochloric acid (3M) was added until the aqueous phase was acidic. The organic phase was separated and extracted with 210 ml of 0.5 M sodium hydroxide. The aqueous extract was washed with dichloromethane (100 ml), acidified with 3 M hydrochloric acid and extracted with dichloromethane (150 ml+50 ml). The organic extract was dried (Na₂SO₄) and the solvent was evaporated in vacuo to give thioacid 1 as a violet liquid, 13.9 g (92% yield).

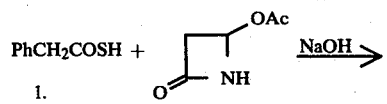

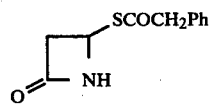

2.

To a stirred mixture of thioacid 1 (13.9 g, 91.5 mmoles) in 140 ml of water was added enough 1M sodium hydroxide to bring the solution to pH 8. A solution of 4-acetoxy-azetidinone (11.8 g, 9.15 mmoles) in 120 ml of water was added followed by several mls of 10% sodium bicarbonate to give a final pH of 7.5 to 8.0 for the solution. The mixture was stirred for 5 h at 23°, then extracted with ethyl acetate (400 ml+150 ml). The combined organic phases were washed with 1% sodium bicarbonate and saturated sodium chloride solutions (400 ml each). The solvent was evaporated in vacuo to give compound 2, 16.6 g (82% yield), as a pink solid.

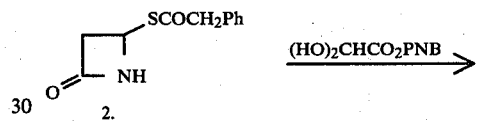

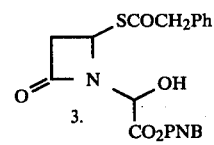

A mixture of 2 (16.25 g, 73.5 mmoles) and p-nitrobenzylglyoxylate (18.3 g, 81 mmoles) in 350 ml of benzene was stirred and heated under reflux for 6 h under a Dean-Stark trap. The cooled solution was mixed with 100 ml of benzene and washed with 300 ml of dil. sodium chloride. The aqueous phase was extracted with 100 ml of ethyl acetate. The combined organic phases were dried (Na₂SO₄) and the solvent was evaporatged in vacuo to give crude 2, 34.8 g, in 80–90% purity.

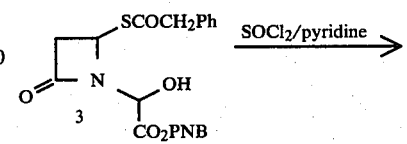

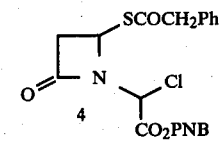

A solution of thionyl chloride (6.4 ml, 88 mmoles) in 60 ml of tetrahydrofuran was added dropwise with stirring to a solution of compound 3 (34.8 g, ≦73 mmoles), pyridine (7.1 ml, 88 mmoles) and tetrahydrofuran (420 ml) at 0°. The mixture was stirred at 0° for 4 h. The precipitate was removed by filtration and the solvent was evaporated in vacuo at 30°. The residue was dissolved in dichloromethane (400 ml), treated with charcoal and filtered. The solvent was evaporated in vacuo at 30° to give compound 4 as a brown tar, 36 g, with 75-80% purity.

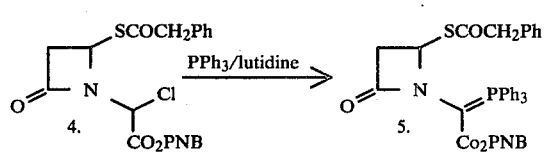

A mixture of compound 4 (36 g, 80 mmoles), triphenylphosphine (26 g, 0.10 mole), 2,6-lutidine (11.6 ml, 0.10 mole) and tetrahydrofuran (360 ml) was stirred at 23° for 17 h. The precipitate was removed by filtration and the solvent was evaporated in vacuo. The residue (65 g) was dissolved in 650 ml of dichloromethane and absorbed onto 300 g of silica gel which was placed (dry) on a 600 g silica gel column. The column was eluted with dichloromethane (3 l), dichloromethane/ethylacetate 3:1 (3 l) and ethylacetate (2 l). The ethyl acetate fractions were combined and the solvent was evaporated in vacuo to give compound 5, 22 g, in about 50% purity.

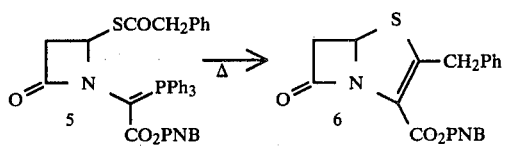

A solution of compound 5 (22 g) in toluene (660 ml) was stirred and heated under reflux for 4 h. On cooling, 110 g of silica gel was added, the solvent was evaporated in vacuo and the silica gel was placed (dry) on a 440 g silica gel column. The column was eluted with diethyl ether/cyclohexane 1:1; 500 ml fractions were collected. Fractions 3 to 10 were combined and the solvent was evaporated in vacuo to give a yellow solid. The solid was further purified by trituration with ether to give compound 6, 6.50 g with greater than 95% purity. The overall yield from 2 to 6 was 22%. A portion was recrystallized from benzene/cyclohexane 1:1, m.p. 110°–111°. Anal. calc'd for $C_{20}H_{16}N_2O_5S$: C, 60.60; H, 4.07; N, 7.07; S, 8.09. Found: C, 60.87; H, 4.14; N, 7.07; S, 8.11.

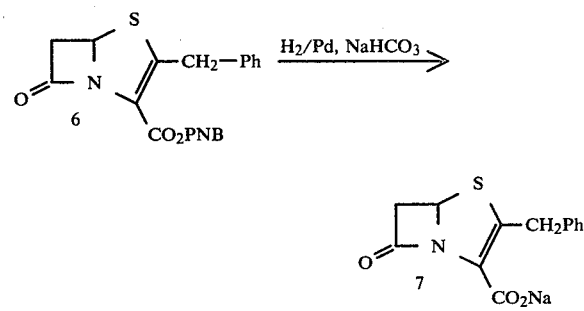

A mixture of compound 6 (396 mg, 1.00 mmole), sodium bicarbonate (84 mg, 1.00 mmole), 30% palladium on diatomaceous earth (400 mg) and tetrahydrofuran, ether, water (25 ml each) was hydrogenated on a Parr apparatus at 50 p.s.i. and 23° for 4 h. The catalyst was removed by filtration and the liquid phases were separated. The aqueous layer was washed with ethyl acetate, filtered and freeze-dried to give compound 7 as a colourless powder, 102 mg (36% yield), in about 90% purity. $\lambda_{max}^{H2O}$ 258 ($\ominus$=4220), 302 ($\epsilon$=5220).

Preparation 22

2-(Acetonyl-ethylene-ketal)penem-3-carboxylic Acid

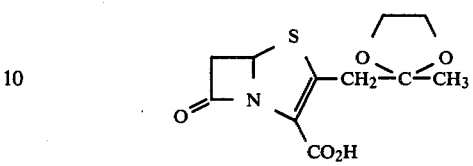

A methylene chloride (180 cc) solution of acid 1 (8.56 g 58.5 mmoles) was treated with triethyl amine (8.9 cc, 6.42 g, 63.9 mmoles, 1.09 eq.) and stirred for 15 min at room temperature. The resulting solution was cooled down at $-20°$ to $-25°$ C. It was treated dropwise with i-butyl chloroformate (8.36 cc, 8.80 g, 64.4 mmoles, 1.1 eq) keeping the reaction mixture temperature lower than $-20°$. The resulting mixed anhydride solution was stirred for a further 15 min at $-20°$. A previously prepared cold ($-78°$) methylene chloride (160 cc) solution of triethyl amine (16.0 cc, 11.6 g, 0.115 mole, 1.96 eq) $H_2S$ was poured into the anhydride mixture. It was then stirred for 15 min at $-15°$ C. or lower, acidified with diluted aqueous HCl to pH 2–3, washed 3 times with $H_2O$-brine and brine. The methylene chloride solution was dried over $Na_2SO_4$ and evaporated. (9.4 g, 98.9%). $\delta$(ppm CDCl$_3$) 4.72 (1H, b.s., S-H), 4.02 (4H, s, OCH$_2$C-H$_2$O), 2.95 (2H, s, CH$_2$), 1.43 (3H, s, CH$_3$). $\nu_{C=O}$ (KBr film) 1690, 1710, $\nu_{SH}$ 2560.

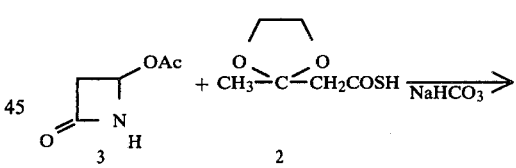

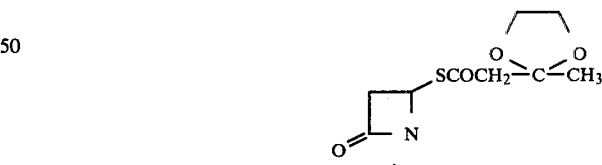

Thioacid 2 (9.4 g, 58 mmoles) was treated with an aqueous solution (75 cc) of NaHCO$_3$ (4.87 g, 58 mmoles) for 5 min. To the resulting solution was added an aqueous (20 cc) solution of 4-acetoxyazetidinone (5.82 g, 45 mmoles) at room temperature. The pH of the solution was adjusted to 7.4–7.5 and then it was stirred for 2 h. The aqueous mixture was extracted with methylene chloride (5×80 cc). The methylene chloride extracts were combined, washed with brine —H$_2$O (3×50 cc), brine and dried over MgSO$_4$ (11.24 g, 100%). Anal. calc'd for $C_9H_{13}NO_4S$: C, 46.74; H, 5.66; N, 6.06; S, 13.86. Found: C, 46.77; H, 5.69; N, 6.09; S, 13.64. δ(ppm, CDCl$_3$) 6.72 (1H, b.s., N—H), 5.23 (1H, dd, J$_{4-3}$ $_{trans}$=2.8, J$_{4-3}$ $_{cis}$=5, H-4), 3.90 (4H, s, O—(CH$_2$)$_2$—O), 3.47 (1H, ddd, J$_{gem}$=15, J$_{3-4}$ $_{cis}$=5, J$_{3-NH}$=1.5, H-3), 2.93 (2H, s, CH$_2$), 2.93 (1H, ddd, J$_{gem}$=15, J$_{3-4}$ $_{trans}$ 2.5, H-3), 1.45 (3H, s, CH$_3$). ν$_{c=o}$ (CHCl$_3$) 1780, 1695, ν$_{NH}$ 3430.

benzene, and treated with charcoal (3.63 g, 82%). δ(ppm, CDCl$_3$) 8.30 (2H, d, Hm aromatic), 7.63 (2H, d, Ho aromatic), 6.20 (1H, s, CHCl), 5.75 (1H, m, H-4), 5.40-5.45 (2H, 2d, CH$_2$—PNB), 4.03 (4H, s, O(CH$_2$)$_2$O), 3.88-3.10 (m, H-3), 2.93 (2H, bs, CH$_2$) 1.42 (3H, s, CH$_3$). ν$_{c=o}$ (CHCl$_3$) 1790, 1765 (shoulder), 1700 ν$_{NO_2}$ 1530.

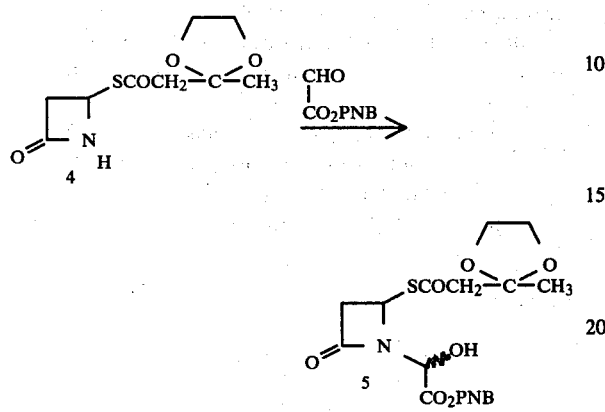

Hydrated p-nitrobenzyl glyoxylate (2.17 g, 9.56 mmoles) was refluxed in benzene (50 cc) through a Dean Stark condenser filled with 3Å molecular sieves for 2 h. Azetidinone 4 (2 g, 8.65 mmoles) was added to the benzene solution. The mixture was refluxed for 4 h and then it was checked by NMR. Further p-nitrobenzyl glyoxylate (217 mg, 0.956 mmole) was added in. The resulting solution was refluxed for 18 h and solvent flushed down to give 5 as an oil (4.28 g, >100%). δ(ppm CDCl$_3$) 8.17 (2H, d, J=9, Hm aromatic), 7.52, 7.47 (2H, 2d, J=9, Ho aromatic), 5.55-5.15 (5H, m, H-4, H—C—OH, CH$_2$—PNB) 3.96, 3.94 (4H, 2S, OCH$_2$CH$_2$O), 3.45 (1H, dd, J$_{gem}$=15, J$_{3-4}$ $_{cis}$=5, H-3), 3.07 (part of dd, J$_{3-4}$ $_{trans}$=3, H-3), 2.91-2.89 (2H, 2d, CH$_2$), 1.45 (3H, s, CH$_3$). ν$_{c=o}$ (CHCl$_3$) 1780, 1760, 1695 ν$_{NO_2}$ 1530. Anal. Calc'd for C$_{18}$H$_{20}$N$_2$O$_9$S: C, 49.09; H, 4.58; N, 6.36; S, 7.28. Found: C, 49.06; H, 4.60; N, 6.52; S, 6.55.

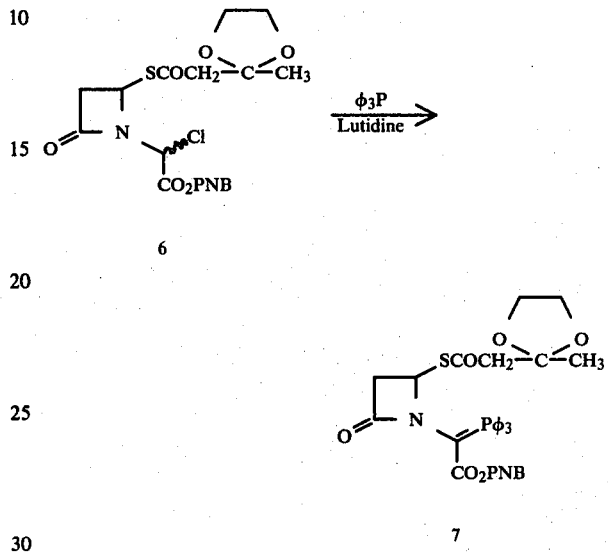

A THF (30 cc, distilled over LAH) solution of chloroazetidinone 6 (3.63 g, 7.92 mmoles) was treated with triphenyl phosphine (3.11 g, 11.9 mmoles, 1.5 eq) and 2,6-lutidine (920 mg, 1.00 ml, 8.60 mmoles, 1.1 eq). The mixture was stirred at room temperature for 72 h. The solid was filtered off and washed with benzene. The organic phase was washed with dilute HCl, water, dilute aqueous sodium bicarbonate, water and brine. The residue was passed through a silica gel (100 g) column (ethyl acetate) and gave pure 7 (3.0 g, 55%). ν$_{c=o}$ (CHCl$_3$) 1750, 1690 ν$_{phosphorane}$ 1620.

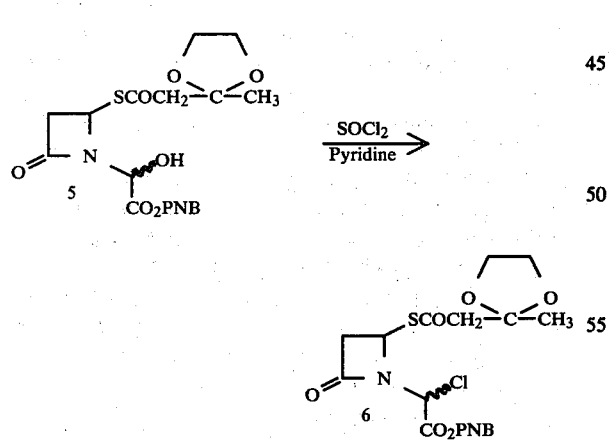

A cold (−15° C.) THF (40 cc, freshly distilled over LAH) solution of azetidinone 5 (4.09 g, 9.29 mmoles) was treated under nitrogen atmosphere with pyridine (845 mg, 0.864 ml, 10.7 mmoles, 1.15 eq) and thionyl chloride (1.27 g, 0.779 cc, 10.68 mmoles, 1.15 eq). The mixture was stirred for 20 min at −15° C. The solid was filtered off and washed with benzene. Evaporation of benzene gave a residue which was taken up again in

Phosphorane 7 (1 g, 1.46 mmole) was refluxed in toluene for 11 h. Toluene evaporation afforded a residue which was purified through a silica gel (20 g) column. (5% ether-benzene). It yielded 8 as a gum (266 mg, 49%). Anal. calc'd for $C_{18}H_{18}N_2O_7S$: C, 53.19; H, 4.46; N, 6.89; S, 7.89. Found: C, 52.48; H, 4.58; N, 6.67; S, 7.70. δ(ppm CDCl$_3$) 8.16 (2H, d, Hm aromatic), 7.55 (2H, d, Ho aromatic), 5.57 (1H, dd, $J_{5-6\ trans}$=2, $J_{5-6\ cis}$=3.5, H-5), 5.28 (2H, center of ABq, J=13.5, CH$_2$PNB), 3.95 (4H, s, O—(CH$_2$)$_2$—O), 3.67 (d, part of dd, $J_{6-5\ cis}$=3.6, H-6), 3.42 (d, part of dd, $J_{6-5\ trans}$=2, H-6), 3.28 (2H, center of ABq, J=14, CH$_2$), 1.37 (3H, s, CH$_3$). $\nu_{c=o}$ (CHCl$_3$) 1795, 1715, $\nu_{NO_2}$ 1528. U.V. (EtOH) $\lambda_{max}$ 320 (ε=5995), 262.5 (ε=8125).

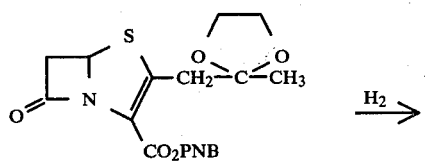

8

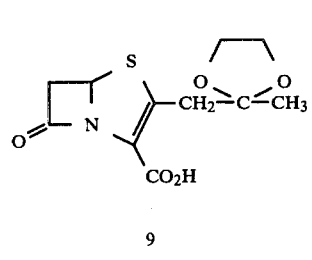

9

A mixture of ester 8 (95 mg, 0.234 mmoles) in THF (15 cc) ether (15 cc) and aqueous (15 cc) sodium bicarbonate (19 mg, 0.226 mmole) was shaken on a Parr hydrogenator for 3.25 h at 30 psi, using 30% Pd on celite (130 mg) as catalyst. The latter was filtered off and washed with water and ether. The aqueous phase was carefully washed with ether (3×50 cc) and freeze-dried to give 9 as the sodiun salt. The acid salt was taken up in 5 cc of water, carefully acidified to pH 3 and extracted with ethyl acetate (4×20 cc). The aqueous solution was further acidified to pH 1-2 and extracted again with ethyl acetate (4×20 cc). The organic phases were combined, washed with brine and dried over Na$_2$SO$_4$ (30 mg, 62%, dec. 104°-110°). δ(ppm C$_2$D$_6$CO) 5.78 (1H, dd, $J_{5-6\ trans}$=2, $J_{5-6\ cis}$=5, H-5), 4.06 (4H, s, O—(CH$_2$)$_2$—O), 3.86 (d, part of a dd, J=5, H-6), 3.61 (d, part of a dd, J=2, H-6), 1.46 (3H, s, CH$_3$) $\nu_{c=o}$ (nujol mull) 1780, 1670. U.V. (EtOH) $\nu_{max}$ 312.5 (ε=7257).

Preparation 23

2-(2',2'-Dimethylpropyl)penem-3-carboxylate

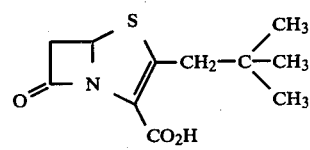

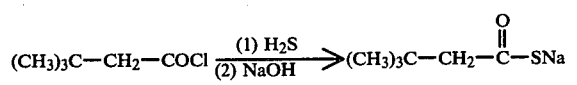

A solution of t-butylacetylchloride (12.5 ml, 90 mmoles) in dichloromethane (120 ml) was added dropwise to a cooled saturated solution of H$_2$S.Et$_3$N in dichloromethane [prepared by bubbling H$_2$S for 30 min through a solution of triethylamine (31.3 ml, 225 mmoles) in dichloromethane (310 ml) cooled to 0°].

After one hour the cooling bath was removed and nitrogen was bubbled through the reaction mixture for one hour. Concentration left a colorless residue which was redissolved in dichloromethane (200 ml) and water (200 ml). The aqueous phase was made acidic with hydrochloric acid and decanted from the organic phase which was extracted with a solution of sodium hydroxide (0.5 N, 185 ml). The basic aqueous phase was washed with dichloromethane (100 ml) and used as such for the next reaction.

A sample of the aqueous phase, acidified with hydrochloric acid and extracted with ether gave the thio t-butyl-acetic acid as a yellow oil: δ(ppm, CDCl$_3$): 4.10 (1H, S-H), 2.45 (2H, s, CH$_2$), 1.05 (9H, s, CH$_3$); $\nu_{c=o}$=1700 cm$^{-1}$.

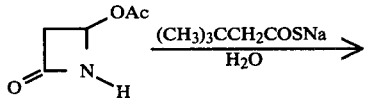

1

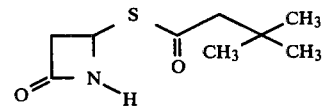

2

The pH of the crude solution of the sodium salt of thio-t-butylacetic acid described above was adjusted to 8. It was treated in one portion with a solution of 4-acetoxy azetidinone (11.5 g, 89 mmoles) in water (125 ml) and the pH of the resulting solution was immediately adjusted to 7.5 with sodium bicarbonate. After stirring 4 h at 20° the solution was extracted with ethyl acetate (3×150 ml), the combined organic extracts washed with a bicarbonate solution and with brine, dried over sodium sulfate and concentrated to leave a yellow oil. The oil was dissolved in benzene (60 ml), mixed with silica gel (8 g), stirred and filtered. The silica gel was washed with benzene-ether (1:3, 100 ml) and the combined filtrates concentrated to leave a solid. The solid was triturated with hexane to give the title compound (13.3 g, 74%) m.p. 49.5-50.5. Calc'd for $C_9H_{15}O_2NS$: C, 53.70; H, 7.51; N, 6.95%. Found: C, 53.79; H, 7.54; N, 6.90%. $\nu_{c=o}$=1780, 1690. δ(ppm, CDCl$_3$): 5.23 (1H, dd, $J_{cis}$=2.9, $J_{trans}$=5.0, H-4), 3.46 (1H, ddd, $J_{trans}$=5, $J_{gem}$=15, H-3 β), 2.88 (1H, ddd, $J_{cis}$=1, $J_{cis}$=2.5, $J_{gem}$=15, H-3 α), 2.45 (2H, s, CH$_2$COS), 1.03 (9H, s, CH$_3$).

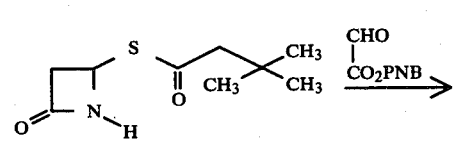

2

-continued

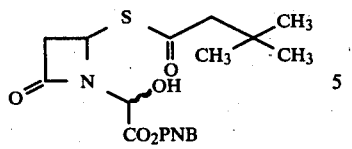

3

A benzene (15 ml) solution of the azetidinone 2 (603 mg, 3 mmoles) and of p-nitrobenzyl glyoxylate (750 mg, 3.3 mmoles) was refluxed through a Dean-Stark trap filled with 3Å molecular sieves for 12 h. The cooled reaction solution was diluted with benzene (25 ml) and washed with brine; the brine wash was extracted with ethyl acetate. The combined organic phases were dried and concentrated to leave the title compound as a colorless oil. 1.4 g. $\nu_{c=o}=1770, 1690$. δ(ppm, CDCl$_3$): 8.25 (2H, d, J=8, aromatic H-meta), 7.58 (2H, d, J=8, H-ortho), 5.40 (1H, dd, J$_{cis}$=3.0, J$_{trans}$=5.5, H-4), 5.36 (3H, m, CH$_2$ benzylic and CH-OH), 4.30 (1H, OH), 3.51 (1H, dd, J$_{trans}$=5.5, J$_{gem}$=15, H-3 β), 3.0 (1H, dd, J$_{cis}$=3, J$_{gem}$=15, H-3 α), 2.46 and 2.40 (2H, s, CH$_2$C), 1.03 (9H, s, CH$_3$).

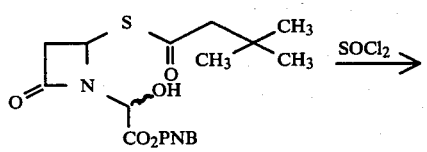

3

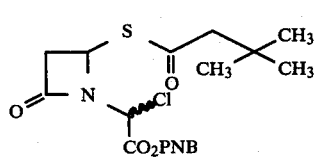

4

To a cooled (0° C.) and stirred solution of 3 (1.3 g, 3 mmoles) in THF (20 ml) was added pyridine (0.29 ml, 3.6 mmoles) followed by thionyl chloride (0.263 ml, 3.6 mmoles). The mixture was stirred 4 h at 0°, the precipitate filtered off and washed with benzene, and the filtrates concentrated on the rotary evaporator. The residual oil was dissolved in benzene, stirred with charcoal, filtered and concentrated to leave 4 as a yellow oil, 1.43 g. δ(ppm, CDCl$_3$): 8.26 (2H, d, J=8, aromatic H), 7.60 (2H, d, J=8, aromatic H), 6.11 and 6.08 (1H, 2s, CHCl), 5.65 (1H, m, H-4), 5.40 (2H, m, benzylic CH$_2$), 3.85 to 2.80 (2H, m, H-3), 2.48 and 2.45 (2H, 2s, CH$_2$C), 1.05 (9H, s, CH$_3$).

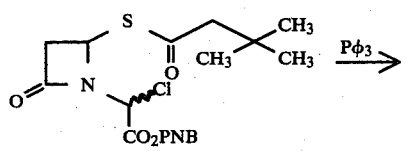

4

-continued

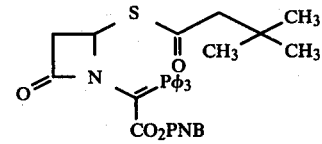

5

A mixture of 4 (1.43 g, 3 mmoles), 2,6-lutidine (0.42 ml, 3.6 mmoles), triphenylphosphine (0.94 g, 3.6 mmoles) and THF (14 ml) was stirred at room temperature under a nitrogen atmosphere for 65 h. The mixture was filtered and the solids washed with THF. The filtrates were concentrated and the residual oil purified by chromatography on silica gel (50 g, 4.4×7 cm, CH$_2$Cl$_2$:EtOAc). The pertinent fractions were concentrated to leave 5 as a solid which was recrystallized form chloroform-ether. 1.0 g, 51%, m.p. 209°–210°. Calc'd for C$_{36}$H$_{35}$N$_2$O$_6$PS: C, 66.04, H, 5.38; N, 4.27%. Found: C, 65.49; H, 5.53; N, 4.13%.

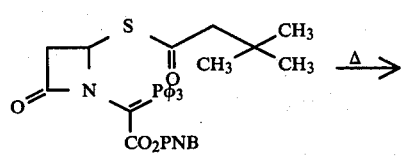

5

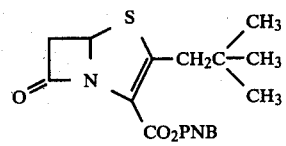

6

The phosphorane 5 (1.1 g, 1.68 mmole) was heated under reflux in o-xylene (15 ml) for 6 h under a nitrogen atmosphere. Concentration left an oil which was triturated with benzene to give a solid and a solution. The solid was found to be unreacted 5. The solution was concentrated and the residual oil was purified by chromatography over silica gel (55 g, 2.4×20.5 cm, ether:-benzene). The title compound 6 was isolated from the pertinent fractions 0.1 g, 20%. Crystallization from ether afforded 6 as a colorless solid m.p. 108°–190°. Calc'd for C$_{18}$H$_{20}$N$_2$O$_5$S: C, 57.43; H, 5.35%. Found: C, 57.46; H, 5.16%. $\nu_{c=o}=1795, 1715$. δ(ppm, CDCl$_3$): 8.25 and 7.61, 5.58 (1H, dd, J$_{cis}$=2, J$_{trans}$=3.5, H-4), 5.31 (2H, ABq, J$_{gem}$=14, benzylic CH$_2$), 3.80 (1H, dd, J$_{trans}$=3.5, J$_{gem}$=16, H-3 β), 3.43 (1H, dd, J$_{cis}$=2, J$_{gem}$=16, H-3 β), 2.85 (2H, ABq, J$_{gem}$=13, CH$_2$—C), 1.01 (9H, s, CH$_3$).

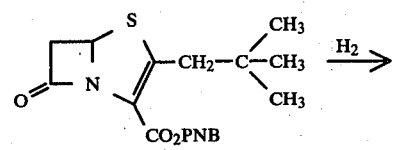

6

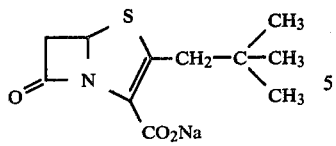

7

A mixture of the ester 6 (95 mg, 0.25 mmole), sodium bicarbonate (21 mg, 0.25 mole), water (6 ml), THF (6 ml), ether (6 ml) and palladium on Celite (30%, 100 mg) was hydrogenated in a Parr shaker at an initial pressure of 48 psi. After 6 h the catalyst was removed by filtration over Celite. The aqueous phase was decanted, washed with ethylacetate ether (30 ml; 20 ml) and lyophilized to give 7 as a white powder 50 mg, 76%.

Preparation 24

Sodium 2-Butylpenem-3-carboxylate

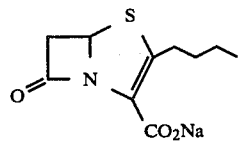

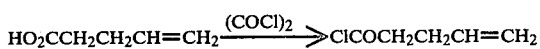

1.

A solution of 4-pentenoic acid (10 g, 0.10 mole) in oxalyl chloride (25 ml) was stirred at 23° for 4 h. The excess oxalyl chloride was distilled off in vacuo at 23°. The product was distilled at 15°-20°/20-30 mmHg and obtained as a colorless liquid, 1, 13.76 g, contaminated with about 15% oxalyl chloride.

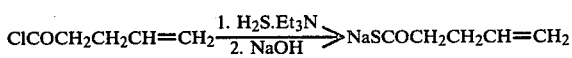

1.          2.

A solution of triethylamine (40 ml, 0.29 mole) in 400 ml of dichloromethane was cooled to 0° and hydrogen sulfide was passed in for ½ h. A solution of 1 (13.7 g, containing ~0.1 mole) in 140 ml of dichloromethane was added dropwise with stirring. The solution was stirred at 0° for one h, then nitrogen was blown in to remove the excess hydrogen sulfide while the temperature was allowed to rise to 23°. The solvent was evaporated in vacuo and the residue was dissolved in 300 ml of dichloromethane. This solution was washed with 400 ml of 1.5% hydrochloric acid then extracted with 700 ml of 1/7 M sodium hydroxide (100 ml of 1 M NaOH diluted to 700 ml). The basic extract was washed with 100 ml of dichloromethane and the pH was adjusted to about 8. This aqueous solution of 2 was then used directly in the subsequent experiment.

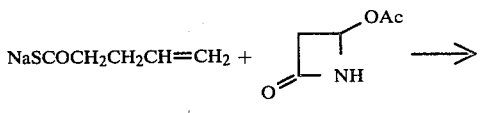

2.

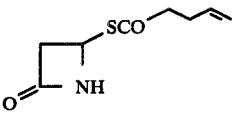

3.

4-Acetoxyazetidinone (12.9 g, 0.10 mole) was added to the aqueous solution of 2 (700 ml, containing about 0.1 mole) and the mixture was stirred at 23° for 5 h. The mixture was extracted with 400+200 ml of ethyl acetate and the extracts were washed with 200 ml each of 1% sodium bicarbonate and saturated sodium chloride. The combined organic extract was dried and the solvent was evaporated in vacuo to give a yellow-brown liquid. An ether solution of the liquid was passed through a column of silica gel (100 g). The column was extracted with 1 l of ether. The ether was evaporated in vacuo to give compound 3 as a pale yellow liquid, 8.96 g, in about 90% purity. The overall yield from 4-pentenoic acid was 48.5%.

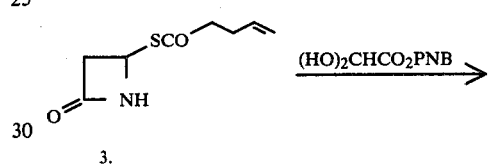

3.

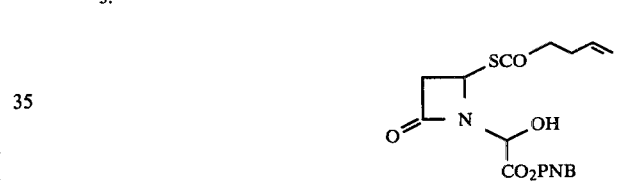

4.

A mixture of 3 (8.9 g, 48 mmoles) and p-nitrobenzyl-glyoxylate (10.7 g, 48 mmoles) in 200 ml of benzene was stirred and heated under reflux for 6 h under a Dean-Stark trap. The solvent was evaporated in vacuo to give the product 4 as a yellow oil, 19.48 g.

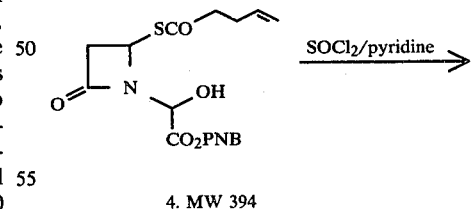

4. MW 394

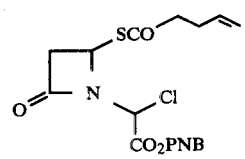

5 MW 413

A solution of thionyl chloride (4.3 ml, 60 mmoles) in 40 ml of tetrahydrofuran was added dropwise with stirring to a solution of compound 4 (19.4 g, ≦49 mmoles), pyridine (4.8 ml, 60 mmoles) and tetrahydrofuran (250 ml). The mixture was stirred at 0° for 4 h. The precipitate was removed by filtration and the solvent was evaporated in vacuo at 30°. The residue was re-dissolved in tetrahydrofuran, treated with charcoal and filtered. The solvent was evaporated in vacuo at 30° to give compound 5 as a brown tar, 19.95 g, in about 80% purity.

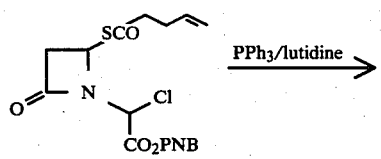

5.

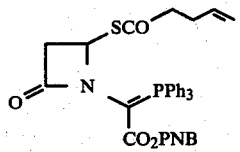

6.

A mixture of compound 5 (19.9 g, ≦48 mmoles), triphenylphosphine (15 g, 58 mmoles), 2,6-lutidine (6.8 ml, 58 mmoles) and tetrahydrofuran (200 ml) was stirred at 23° for 17 h. The precipitate was removed by filtration and the solvent was evaporated in vacuo. The residue (37.5 g) was dissolved in dichloromethane (375 ml) and absorbed onto 190 g of silica gel which was placed (dry) on a 375 g silica gel column. The column was eluted with dichloromethane (1.5 l), dichloromethane/ethylacetate 2:1 (750 ml) and ethyl acetate (1.5 l). The initial ethyl acetate fractions (1 l) were combined and the solvent was evaporated in vacuo to give a brown solid, compound 6, 15.2 g, in about 60% purity.

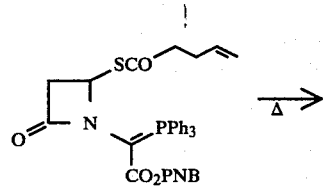

6.

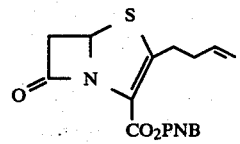

7.

A mixture of compound 6 (16 g) in toluene (480 ml) was stirred and heated under reflux for 7 h. On cooling, 80 g of silica gel was added, the solvent was evaporated in vacuo and the silica gel was placed (dry) on a 320 g silica gel column. The column was eluted with diethyl ether; 200 ml fractions were collected. Fractions 1 to 3 were combined and the solvent was evaporated in vacuo to give compound 7 as a yellow solid, 4.88 g in about 90% purity. The overall yield from 3 to 7 was 27%. A portion was recrystallized from cyclohexane/benzene 10:1, m.p. 95°–96°. Anal. calc'd for $C_{17}H_{16}N_2O_5S$: C, 56.66; H, 4.48; N, 7.77; S, 8.90. Found: C, 56.53; H, 4.34; N, 7.77; S, 8.94.

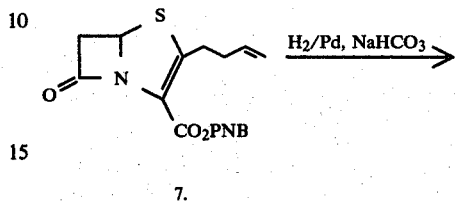

7.

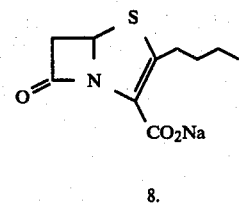

8.

A mixture of compound 7 (360 mg, 1.0 mmole), sodium bicarbonate (84 mg, 1.0 mmole), 30% palladium on diatomaceous earth (360 mg) and tetrahydrofuran, ether, water (25 ml each) was hydrogenated on a Parr apparatus at 40 p.s.i. and 23° for 6.5 h. The catalyst was removed by filtration and the liquid phases were separated. The aqueous layer was washed with ethyl acetate, filtered and freeze-dried to give compound 8 as a colorless powder, 250 mg (100% yield), in about 80% purity. $\nu_{c=o}$ 1780, ~1600.

Preparation 25

2'-(2'-Diethylphosphono-1'-ethyl)penem-3-carboxylic Acid

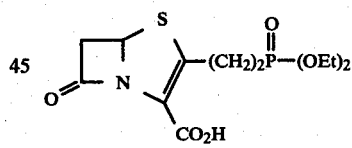

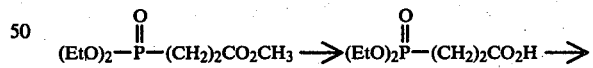

A mixture of 1 (11.2 g, 50 mmoles) and 5 N NaOH (10 ml) was stirred and cooled (ice-bath) for 15 min and at room temperature for 15 min. The mixture was extracted with ether and the extract discarded. The aqueous solution was acidified with 5 N HCl and extracted with $CH_2Cl_2$ to give after drying and evaporation of solvent 10.0 g (95%) of oil 2, nmr δ (CDCl$_3$), 4.1 (4H, m), 1.8–2.9 (4H, m) 1.2 (6H, t).

To a cooled (ice-bath) solution of 2 (2.26 g, 10.76 mmoles) was added dropwise oxalyl chloride (2.74 g, 1.88 ml, 21.5 mmoles). The mixture was kept at room temperature for 6 h and then it was evaporated to dryness. The traces of (COCl)₂ were removed azeotropically with benzene to give 2.4 g (quantitative yield) of crude 3. IR

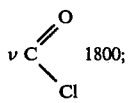

1735 cm⁻¹.nmr δ 4.3 (4H, m), 3.0-3.7 (2H, m) 2.0-3.0 (2H, m), 1.4 (6H, m). This was treated with H₂S/TEA in a standard procedure to give 1.9 g (80%) of oil 4 estimated to be 80% pure. Nmr: δ 4.1 (4H, q), 2.7-3.5 (2H, m), 1.7-2.5 (2H, m) 1.33 (6H, t).

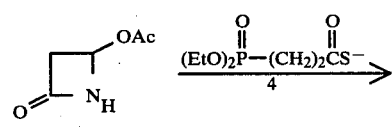

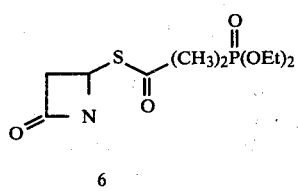

To 4 (1.9 g, 8.4 mmoles) was added under N₂ 1 M solution of NaHCO₃ (10 ml), followed by addition of 5 (0.813 g, 6.3 mmoles) in H₂O (3 ml). The pH of the mixture was adjusted to 7-8 by adding more NaHCO₃. After standing for 4 h the mixture was extracted with CHCl₃ to give after drying and concentration 1.05 g (56.4% based on 5) of solid 6, m.p. 64°-67°, nmr δ 7.7 (NH), 5.3 (1H q), 4.2 (4H,) 3.8 (1H q) 3.5 (1H, q), 2.6-3.2 (2H, m) 1.7-2.4 (2H, m), 1.3 (6H,)

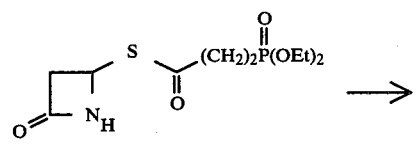

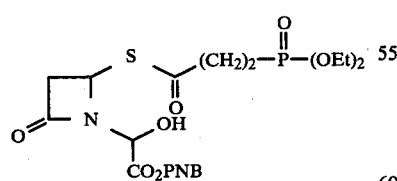

A mixture of 6 (260 mg, 0.88 mmole) and p-nitrobenzyl glyoxalate (198 mg, 0.88 mmole) was refluxed in benzene (6 ml) under a Dean Stark apparatus for 16 h to give after evaporation of benzene 453 mg of heavy oil 7, nmr δ 8.3 (2H, d) 7.6 (2H, d) 5.3-5.7 (4H,) 4.9 (OH), 4.2 (4H,) 3.55 (1H, g), 3.4 (1H, g), 2.5-3.2 (2H, m) 1.7-2.5 (2H, m) 1.3 (6H)

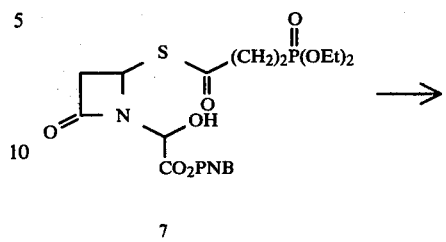

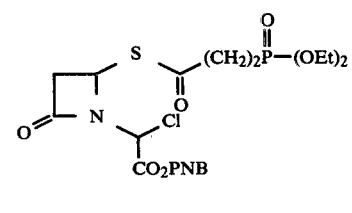

A crude 7 (504 mg, 0.88 mmole) was dissolved in 1 M solution of pyridine in THF (0.9 ml). To this was added dropwise with stirring and cooling (ice-bath)( 1 M solution of SOCl₂ in THF (0.9 ml) and the mixture was stirred in the cold for 15 min and at room temperature for 40 min. To it was added benzene (10 ml), and the solid was filtered off. The filtrate was concentrated in vacuo to give 463 mg (quantitative yield) of crude 8, nmr δ 8.3 (2H, d), 7.6 (2H, d), 6.1 (1H, s), 5.7 (1H, m), 5.3 (2H, d), 4.2 (4H), 1.8-3.6 (6H, m) 1.3 (6H).

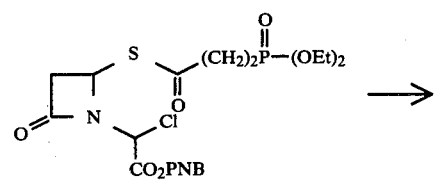

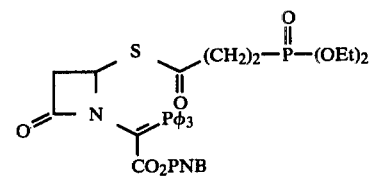

To a solution of crude 8 (463 mg, 0.88 mmole) in THF (4 ml) was added triphenylphosphine (236 mg, 0.9 mmole) and 2,6 lutidine (96 mg, 0.9 mmole) and the mixture was allowed to stand at room temperature for 65 h. Then it was filtered, the filtrate concentrated and the residual oil chromatographed on a silica gel column with ethyl acetate-2% EtOH as eluent, to give 203 mg (30.6%) of oil 9, which solidified on standing, m.p. 126°-128° C.

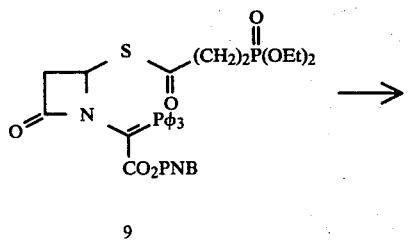

9

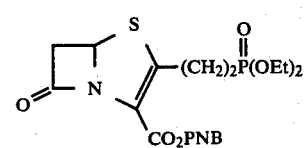

10

A solution of 9 (470 mg, 0.635 mmole) in toluene (30 ml) was refluxed for 5 h followed by concentration and chromatography on silica gel-ethyl acetate to give 167 mg (56%) of 10 as oil, IR 1795, 1710 cm$^{-1}$. nmr δ8,3 (2H, d) 7.7 (2H, d) 5.7 (1H, m), 5.38 (2H, d) 4.1 (4H) 1.8-3.8 (6H, 1.35 (6H).

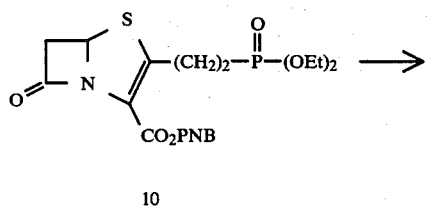

10

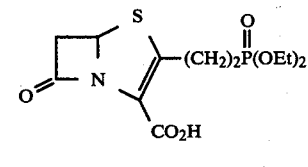

11

To a solution of 10 (59 mg, 0.126 mmole) in THF (3 ml) and ether (1 ml) was added NaHCO$_3$ (9 mg, 0.107 mmole), water (1 ml) and 10% Pd/celite (60 mg) and the mixture hydrogenated at 30 psi for 2 h. The product was isolated as usual to give 36 mg (86%) of 11 as oil, IR (CHCl$_3$) 1798, 1730, 1710 cm$^{-1}$, nmr δ9.0 (CO$_2$H), 5.6 (1H, m) 4.4 (4H), 3.6 (1H, g), 3.15 (1H, q) 1.7-3.0 (4H, m), 1.3 (6H).

Preparation 26

Sodium 2-(Dimethyldithiomethyl)penem-3-carboxylate

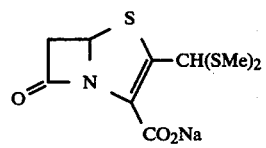

-continued

A mixture of 1 (1.52 g, 10 mmoles) and thionyl chloride (5.0 ml) was gently heated up until gas evolution ceased. The mixture was evaporated in vacuo and the residue was diluted with benzene and evaporated to give 2 1.55 g (91%) as a yellow oil. It was used in the next step without further purification. IR (CHCl$_3$) 1780 cm$^{-1}$. NMR (CDCl$_3$) δ4.6 (1H, s), 2.23 (6H, s).

A solution of triethylamine (1.9 ml, 13.65 mmoles) in methylene chloride (40 ml) was cooled in an ice-bath and hydrogen sulfide was bubbled through for 30 min., keeping the temperature between 5°-10° C. A solution of 2 (1.55 g 9.1 mmoles) in methylene chloride (20 ml) was added dropwise to the preceding cooled solution, then it was stirred at room temperature for 2 h. The reaction mixture was diluted with methylene chloride (20 ml), washed with 1N hydrochloric acid (2×5 ml) and water (2×5 ml), dried (MgSO$_4$) and evaporated in vacuo to give 3 1.5 g (98%) as an oil. The product was used in the next step without further purification. IR (CHCl$_3$) 1690 cm$^{-1}$. NMR (CDCl$_3$) δ4,9 (1H, bs), 4.48 (1H, s), 2.20 (6H, s).

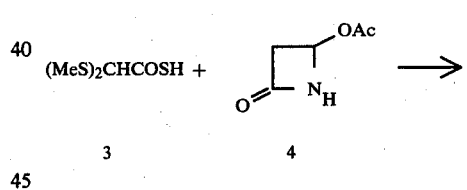

A solution of 3 (3.0 g, 17.9 mmoles) in 1 M solution of sodium bicarbonate (18 ml, 18 mmoles) was stirred at room temperature for 15 min and was then treated with 4 (2.3 g, 17.9 mmoles). The new solution was stirred at room temperature for 2 h. The reaction mixture was diluted with water (5 ml) and extracted with benzene/ether 1:1. Organic extracts were washed with brine, dried (MgSO$_4$) and evaporated in vacuo to give 5 3.1 g (73%) as an oil. It was used in the next step without further purification. IR (CHCl$_3$) 1780, 1680 cm$^{-1}$. NMR (CDCl$_3$) δ7.20 (1H, s), 5.22 (1H, dd, J$_{cis}$=5 Hz, J$_{trans}$=3 Hz), 4.5 (1H, s), 3.5 (1H, ddd, J$_{gem}$=15 Hz, J$_{cis}$=5 Hz, J$_{NH}$=2 Hz) 2.95 (1H, ddd, J$_{gem}$=15 Hz, J$_{trans}$=3 Hz), 2.18 (6H, s).

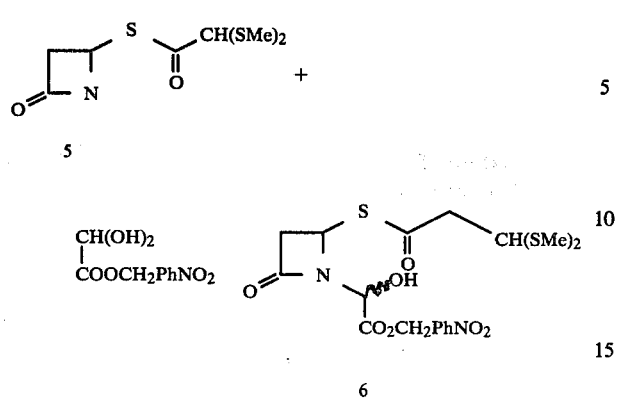
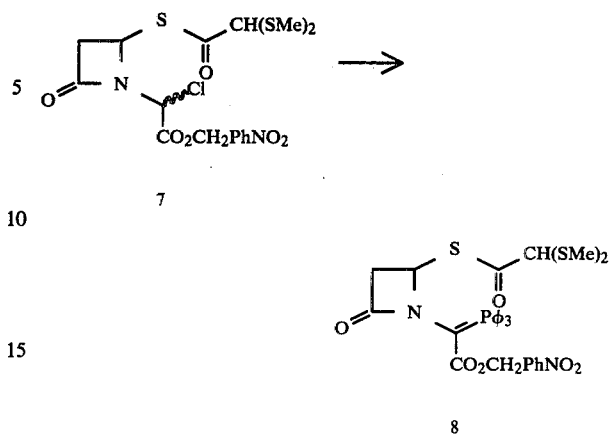

A suspension of 5 (3.1 g, 13.1 mmoles) and p-nitrobenzylglyoxalate hydrate (3.4 g, 15.1 mmoles) in benzene (50 ml) was refluxed for 9 h with a Dean-Stark condenser filled with 3Å molecular sieves.

The reaction mixture was cooled to room temperature, treated with pet. ether and then filtered over a Celite/charcoal bed. Filtrate was evaporated in vacuo to give 6, 6.0 g (quantitative), as an oil. It was used in the next step without further purification. NMR (CDCl$_3$) δ8.25(2H, d J=9 Hz), 7.55 (2H, J=9 Hz), 5.40 (4H, m), 4.42 (1H, 2s), 4.15 (1H, m), 3.52 (1H, dd, J$_{gem}$=15 Hz, J$_{cis}$=5 Hz), 3.0 (1H, dd, J$_{gem}$=15 Hz, J$_{trans}$=3 Hz), 2.15 (6H, s).

A mixture of 7 (5.0 g, 11 mmoles), triphenylphosphine (2.9 g, 11 mmoles) and 2,6-lutidine (1.5 ml) in dry tetrahydrofuran (25 ml, distilled over L.A.H.) was stirred for ½ h, then left at room temperature for 3 days. The reaction mixture was diluted with benzene/ether 1:1 (25 ml) and washed successively with water (10 ml), 1N hydrochloric acid (10 ml), 1M sodium bicarbonate (10 ml) and brine (10 ml). Organic layer was dried (MgSO$_4$) and evaporated in vacuo to give a crude oil. The residue was chromatographed on silica gel column. Elution with benzene to ether gave 8 1.0 g (13%) as an oil. IR (CHCl$_3$) 1760, 1680 cm$^{-1}$. NMR (CDCl$_3$) δ8.2 (2H, d J=9 Hz), 7.6 (15 H, bs), 6.78 (2H, d, J=9 Hz), 5.7 (1H, m), 5.2 (2H, bs), 4.42 (1H, bs), 2.8–3.8 (2H, m), 2.15 (6H, s).

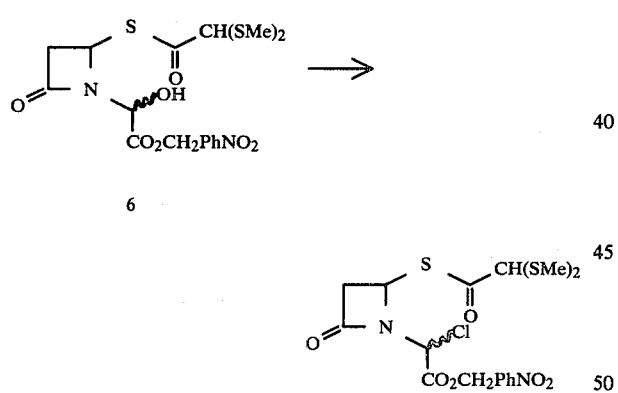

To a cooled (ice-bath) solution of 6 (5.8 g, 13 mmoles) in a 1 M solutin of pyridine/THF (13.5 ml, 13.5 mmoles) was added dropwise thionyl chloride 1M solution in tetrahydrofuran (13.5 ml, 13.5 mmoles). The reaction mixture was kept at 0° C. for 10 min, then at room temperature for 10 min, followed by dilution with methylene chloride and washing with water. Organic layer was dried (MgSO$_4$) and evaporated in vacuo to give 7 5.5 g (88%) as an oil. The product was used in the next step without further purification. NMR (CDCl$_3$) δ8.22 (2H, d J=9 Ha), 7.55 (2H, d, J=9 Hz), 6.2 (1H, bs), 5.6 (1H, m), 5.4 (3H, bs), 3.2 (2H, m), 2.2 (6H, s).

A solution of 8 (400 mg, 0.58 mmole) in toluene (20 ml) was heated under reflux for 4 h. The solvent was evaporated in vacuo and the residual oil was chromatographed on preparative plates (silica gel). Elution with ether gave 9 100 mg (42%) as an oil. IR (NEAT) 1790, 1710 cm$^{-1}$.

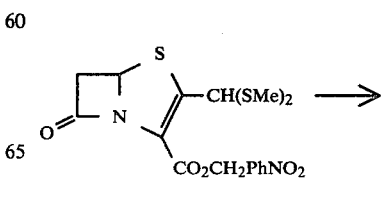

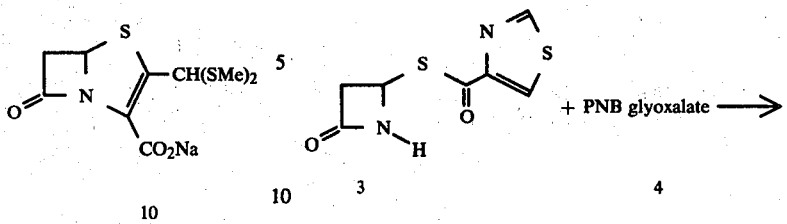

To a solution of 9 (56.1 mg, 0.142 mmole) in tetrahydrofuran (4 ml) and ether (2 ml) was added sodium bicarbonate (12 mg, 0.142 mmole), water (2 ml) and 30% Pd/Celite (60 mg) and this was hydrogenated 2 h at 45 p.s.i. The mixture was filtered and layers separated. The aqueous layer was washed with methylene chloride and lyophilized over 18 h to give 10 28 mg (66%) as an amorphous solid. IR (KBr) 1760, 1625 cm$^{-1}$.

Preparation 27

2-(4'-Thiazolyl)penem-3-carboxylic Acid

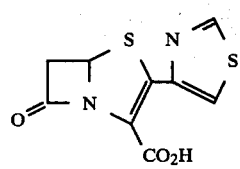

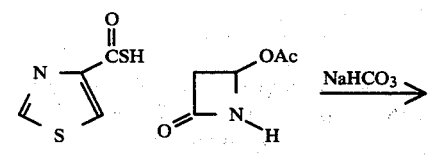

To a suspension of 1 (1.45 g, 10 mmoles) in H$_2$O (20 ml) was added dropwise at room temperature NaHCO$_3$ solution (10 ml of 1 M aqueous solution, 10 mmoles). After 15 min of vigorous stirring, 2 (1.032 g, 9 mmoles) was added as solids and the resulting mixture was stirred under N$_2$ for 8 h. It was filtered to give 1.50 g of solid and the filtrate was extracted with CHCl$_3$ to give after evaporation to dryness another 0.3 g of solid. The combined solid, 1.8 g, was recrystallized from Abs. EtOH to give 1.7 g of pure 34 m.p. 179°–182°. (79%) NMR δ (ppm, CDCl$_3$) 8.8 (H, d) 8.2 (H, d) 6.4 (H, NH), 5.4 (H, q), 2.9–3.8 (2H, m).

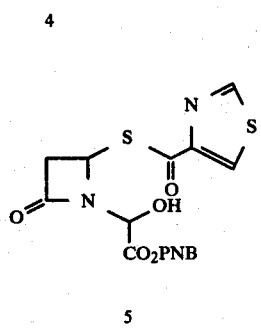

A mixture of 3 (1.07 g, 5 mmoles) and 4 (1.135 g, 5 mmoles) in benzene (120 ml) was refluxed under a Dean-Stark water separator (packed with molecular sieve 3 Å) for 18 h. It was cooled and evaporated to give 2.1 g of 5 as a thick oil. Quantitative yield). The oil crystallized on standing, M.P. (ether) 121°–124°. NMR δ (ppm, CDCl$_3$) 7.5–9.0 (6H, m), 5.15–5.8 (4H, m), 2.9–3.8 (2H, m).

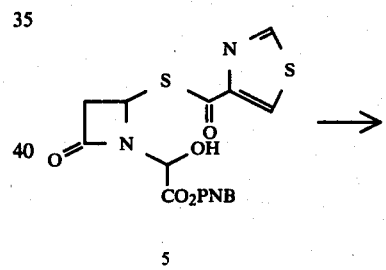

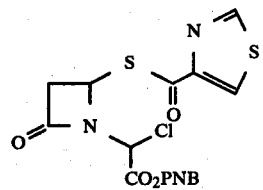

To a cooled (ice bath) mixture of 5 (1.0 g, 2.364 mmoles) and 1 M pyridine/THF (2.5 ml, 2.5 mmoles) was added dropwise under N$_2$ 1 M SOCl$_2$/THF (2.5 ml, 2.5 mmoles). The mixture was stirred in the cold for 20 min and at room temperature 1 h. It was diluted with benzene (10 ml), filtered and evaporated to dryness to give 1.0 g of 6 as an oil (96%). NMR δ (ppm, CDCl$_3$) 7.4–9.0 (6H, m), 6.2 (H, d), 5.85 (H, m) 5.2–5.5 (2H, d), 3.0–4.0 (2H, m).

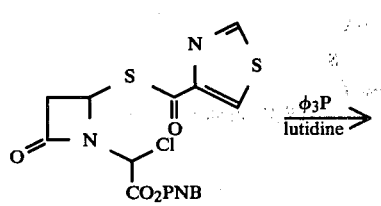

6

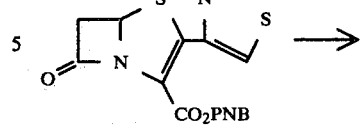

8

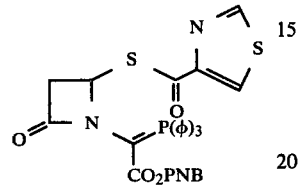

7

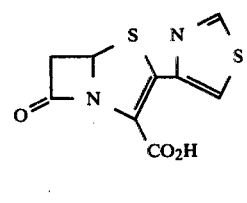

9

A mixture of 6 (0.9 g, 2.04 mmoles), lutidine (0.33 ml. 2.7 mmoles) and φ₃P (0.74 g, 2.7 mmoles) in dry THF (15 ml) was kept under N₂ for 5.5 days at room temperature. It was filtered and evaporated to dryness. The residue was taken up in CH₂Cl₂ and washed with 1 N HCl and brine. It was dried (MgSO₄) and evaporated to give 1.80 g of crude 7. The crude product was chromatographed on SiO₂ and eluted with ether and EtOAc to give 1.0 g of 7. (73.5%).

A mixture of 8 (0.2 g, 0.5 mmole, contained trace of (φ)₃P=O); NaHCO₃ (41.2 mg); Pd/celite (150 mg); THF (10 ml); H₂O (5 ml) and H₂O (5 ml) was hydrogenated at an initial pressure Et₂O (5 ml) and H₂O (5 ml) was hydrogenated at an initial pressure. The basic aqueous layer was acidified and extracted with CHCl₃. CHCl₃ solution was dried (MgSO₄) and evaporated to give 40 mg of 9 as a yellow solid (amorphous). 1R (KBr)

$$1670 \text{ cm}^{-1} (-\overset{\overset{\displaystyle O}{\|}}{C}-OH),$$

1765 cm⁻¹ (β-lactam) (31%).

Preparation 28

Alternate Preparation of (4-R and 4S) 4-Acetylthio-1-(paranitrobenzyl-2'-hydroxy-2'-acetate)-2-azetidinone

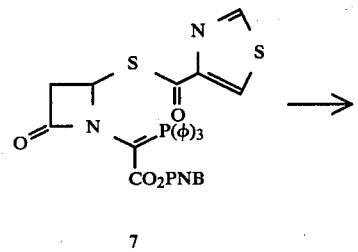

7

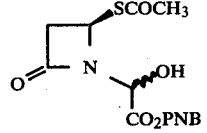

8

7 (0.5 g) in toluene (35 ml) was heated to reflux. 10 ml of solvent was distilled off to remove moisture and other solvent and the resulting solution was refluxed for 5 h. It was evaporated and chromatographed on SiO₂. The column was eluted with ether to give 0.2 g of 8 as a yellow (amorphous) solid. NMR δ (ppm, CDCl₃) 8.9 (2H, q), 8.3 (2H, d), 7.68 (2H, d) 5.7 (H, q), 5.3 (2H, d), 3.72 (2H, q) (69%).

(4R and 4S) 4-acetylthio-1-(paranitrobenzyl-2'-hydroxy-2'-acetate)-2-azetidinone

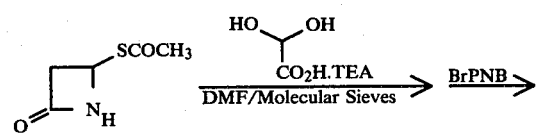

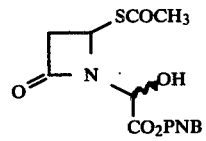

A cold (ice bath) DMF (2 ml) solution of (4R and 4S) 4-acetylthio-2-azetidinone (290 mg, 2 mmol) was treated successively with triethyl amine (0.28 ml, 2 mmol), glyoxylic acid (200 mg, 2.0 mmol) and 3 A molecular sieves (2 ml). The mixture was stirred for 18 h at room temperature (no remaining starting material as shown by tlc), treated with paranitrobenzyl bromide (432.1 mg, 2 mmol) and stirred again for an 18 h period at room temperature. The solid was removed by filtration. The solution was diluted with water (20 cc) and extracted with ethyl acetate (5+5 cc). The extracts were combined, washed successively with 2% aqueous HCl, water (twice), 5% aqueous NaHCO$_3$, water and brine, dried (MgSO$_4$) and filtered over a Celite-activated charcoal pad. Evaporation of the solvent gave the title compound (580 mg, 82%) which was found to be identical to an authentic sample prepared as described previously.

EXAMPLE 1

Sodium 6-Ethyl-2-methylpenem-3-carboxylate

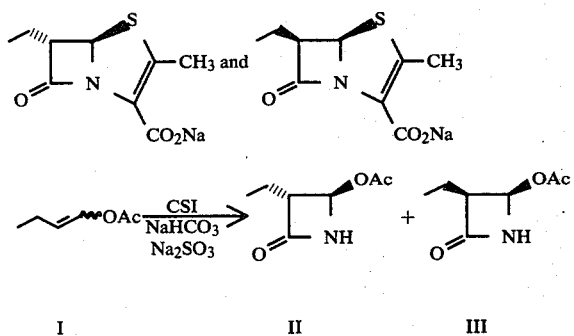

I   II   III

The 1-butenylacetate (about 1:1 mixture of cis and trans isomers) was prepared according to P. Z. Bedoukian, J. Am. Chem. Soc. 66 1325 (1944).

To cooled (−15° C.) I (50 ml) was added dropwise 10 ml (11 g, 78 mmoles) of CSI. The mixture was allowed to warm up gradually during 30 min. to 0° C. It was cooled to −20° C. and poured carefully onto a mixture of water (8 ml) ice (35 g), NaHCO$_3$ (18.4 g) and Na$_2$SO$_3$ (6.4 g). This was stirred vigorously at 0° C. for 30 min., treated with pet. ether (250 ml) and cooled to −40° C. The solvent was decanted and the residue was treated with another 100 ml of pet. ether in the same way. The combined pet. ether extracts were washed with water (30 ml) and dried (Na$_2$SO$_4$) for recycling of I.

The aqueous phases were combined and extracted with ethylacetate (5×40 ml). The extract was dried (Na$_2$SO$_4$) and concentrated in vacuo to give 7.0 g (57%) of a mixture of 28% II and b 72III, b.p. 82°–85° C. (0.01 mm); n.m.r. δ (ppm, CDCl$_3$) 7.3 (1H, NH) 5.92 (0.72 H, d, J=4.4, II-H-3), 3.3 (0.28 H, d, J=1.4, III-H-4), 3.3 (1H, m, H-3), 2.24 (3H, s), 2.72 (2H, two q, J=7), 1.1 (3H, two t, J=7). $v_{c=o}$ 1775, 1755 cm$^{-1}$ Anal. calcd. for C$_7$H$_{11}$NO$_3$ C 53.49, H 7.05, N 8.91. Found C 53.12, H 6.93, H 8.85.

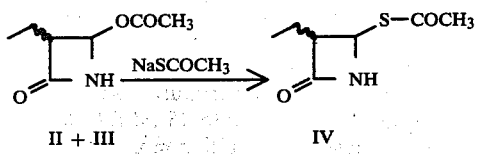

II + III   IV

Sodium thioacetate was prepared by addition of thioacetic acid (0.8 ml, 850 mg, 11.2 mmoles) to a cooled (ice-bath) IN sodium hydroxide solution (11.2 ml) under nitrogen. This was added to a cooled solution of II and III (1.57 g 10 mmoles) in water (5 ml) under N$_2$. The mixture was stirred for 1 h at room temperature. Since an oil was separating, acetone (9 ml) was added and stirring continued for 1.5 h. The mixture was concentrated in vacuo to remove acetone and then extracted with methylene chloride. The extract was dried and concentrated in vacuo to give 1.65 g (95%) of crude mixture of 85% trans IV and 15% cis IV bp 105°–110° (0.02 mm), 7.1 (1H, NH) 5.53 (0.24H, d, J=4.5, cis-H-4), 5.12 (0.8H, d, J=2.4 trans-H-4) 3.34 (1H, two t, J=7) 2.48 (3H) 1.9 (1H, two q, J=7) 1.15 (3H, two t, J=7. $v_{c=o}$ 1700, 1765 cm$^{-1}$. Anal. calcd for C$_7$H$_{11}$N C 48.53, H 6.40, N 8.07. Found C 48.18, H 6.47, N 7.77.

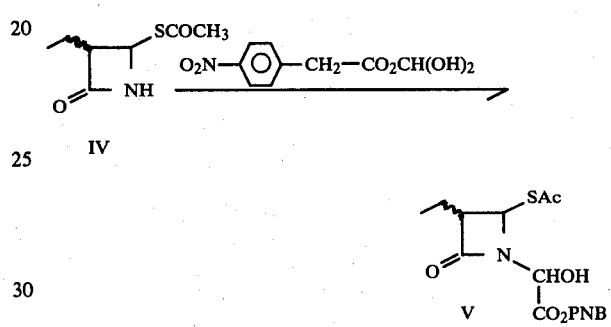

IV

V

A mixture of IV (1.25 g, 7.2 mmole) and p-nitrobenzyl glyoxylate (1.6 g, 7.5 mmole) in benzene (80 ml) was refluxed 20 h under a Dean Stark water collector followed by concentration in vacuo to give 3.01 g of crude product. This was filtered over a small amount of silica in chloroform to give 2.8 g (quantitative yield) of slightly yellow oil V containing some solvent, δ7.9 (4H, m) 5.3 (4H, m) 4.8 (1H, OH) 3.2 (1H, m) 3.37 and 3.33 (3H, two s) 1.8 (2H, m) 1.05 (3H, m) $v_{c=o}$. 1765, 1700 cm$^{-1}$. This product was used in the next step without further purification.

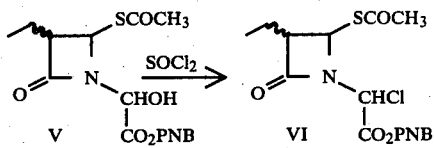

V   VI

To a cooled (ice-bath) stirred solution of V (2.1 g, 5.5 mmole) in dry benzene (10 ml) was added thionyl chloride (3 ml) and the mixture kept at 5° C. for 2 h followed by evaporation in vacuo at room temperature. The excess thionyl chloride was removed by repeated addition and evaporation of benzene and the product was purified by filtration of the benzene solution over a small amount of silica gel, to give after concentration in vacuo 1.7 g (77%) of crude slightly yellow oil VI, δ7.9 (4H, m) 6.0 (1H, s) 5.3 (3H, m) 3.3 (1H, m) 2.7 and 2.3 (3H, two s) 1.75 (3H, m) 1.0 (3H, m) $v_{c=o}$ 1700, 1775 cm$^{-1}$. The product was used in the next step without further purification.

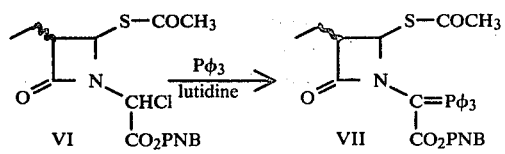

A mixture of VI (1.7 g, 4.2 mmoles), triphenylphosphine (1.57 g 6.0 mmoles) and 2,6-lutidine (5.35 mg, 5 mmoles) in dry dioxane (20 ml) was heated at 55° for 19 h, followed by concentration in vacuo. The dark-red residue was chromatographed on a silica gel column (35 g). Elution with benzene-ether gave 2.3 g (87%) of crude VII as light red oil, which was used in the next step without further purification.

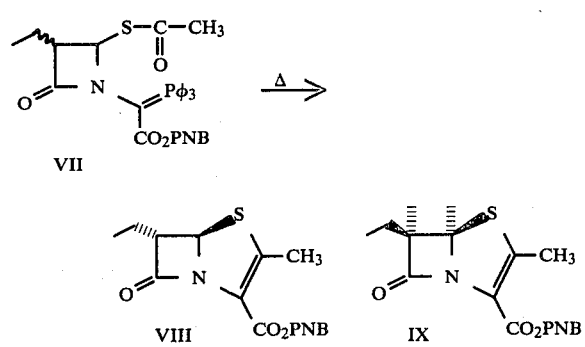

A solution of crude VII (2.3 g 3.67 mmoles) in toluene (40 ml) was heated under reflux for 4.5 h followed by evaporation of the solvent in vacuo. The residual oil was chromatographed on a silica gel column (30 g). Elution with benzene removed first 0.2 g of an unidentified impurity, followed by 750 mg of slightly red oil, which crystallized from ether-pet. ether to give 503 mg (39.3% of solid VIII, m.p. 88°-90°, δ8.25 (2H, d J=10), 7.6 (24, d, J=14) 5.2 (1H, d J=14) 5.33 (1H, d J=1.7 H-5) 3.66 (1H, two t, $J_1$=7, $J_2$=1.7 H-7) 2.35 (3H, s) 1.85 (2H, m) 1.1 (3H, t J=7) $\nu_{c=o}$ 1712, 1788 cm$^{-1}$. Anal. calc'd for $C_{16}H_{16}N_2O_5S$, C 55.16, H 4.63, H 8.04. Found C 55.21 H 4.65 N 8.09.

The cis isomer has been lost either in the course of formation of chloro compound VI, phosphorane VII or cyclization of VII to VIII.

In another experiment where chloro-intermediate was prepared by using puridine as base, the end product VIII was accompanied with 12-15% of the cis isomer IX. It was obtained in a partially hydrated form by recrystallization of the mixture from methylene chloride-ether, m.p. 151°-153° C, δ8.25 (2H, d, J=10) 7.62 (2H, d, J=10) 5.75 (1H, d, J=4.7) 5.5 (1H, d, J=14) 5.25 (5.25 (1H, d, J=14) 3.85 (1H, m) 2.45 (3H, s) 2.0 (2H, m) 1.1 (3H t, J=7). Anal. Calc'd. for $C_{16}H_{16}N_2O_5S$. $\frac{1}{4}H_2O$, C 54.46, H 4.71, N, 7.94. Found C 54.68, H 4.56, N 8.02.

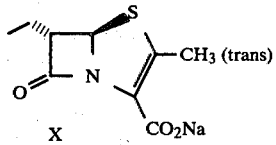

To a solution of VIII (1111 mg 0.32 mmole) in THF (9 ml) and ether (18 ml) was added sodium bicarbonate (27 mg 0.32 mmoles), water (7 ml) and 30% Pd/celite (110 mg) and this was hydrogenated 3 h at 30 P.S.I. The mixture was filtered and layers were separated. The aqueous layer was washed with ether and then lyophilized to give 60 mg (80%) of crude X, δ5.2 (d J=2) 3.6 (1H, m), 2.1 (3H, s) 1.65 (2H, m) 0.9 (3H t J=7). This sample contained 2-5% cis isomer XI and about 25% water (δ3.3).

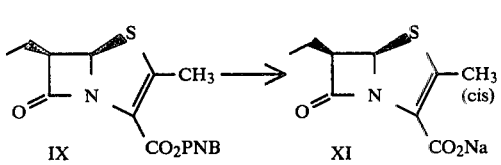

The sodium salt XI was obtained in 80% yield from IX (65 mg) in the same procedure as given for the preparation of X. δ (H, d, J=4) 3.6 (1H, m) 2.2 (3H, s) 1.6 (2H, m) 0.85 (3H, t J=7).

EXAMPLE 2

6-Acetoxymethyl-2-methylpenem-3-carboxylic Acid

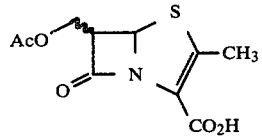

Preparation of 1,3-diacetoxypropene 1 (Ref. L. W. McTeer U.S. Pat. No. 2,866,813. CA 53 9063)

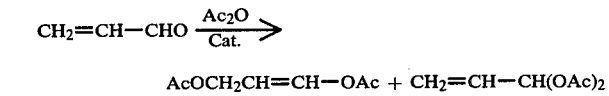

PREPARATION OF CATALYST:

A solution of boric acid (6.2 g) and oxalic acid (12.6 g) in water (44 ml) was evaporated to dryness to give the solid catalyst.

PROCEDURE:

Acrolein (140 g; 2.5 mol) was mixed with acetic anhydride (256 g, 2.5 mol) at r.t. A 5 ml portion of this mixture was transferred to a one-liter Erlenmeyer flask and treated with a few drops of catalyst, prepared by dissolving 1.0 g of solid catalyst in 5 ml acetic anhydride. A vigorous exothermic reaction set in and the reaction mixture was kept at a temperature of 40°-60° (controlled by cooling with ice-bath), and the rest of the acrolein-acetic anhydride mixture was introduced into the flask in portions of 10 to 15 ml followed by a few drops of catalyst. The resulting mixture was distilled to remove unreacted starting materials followed by 1,1-diacetoxy-propene. The product 51.6 g (13.06%) was obtained next, b.p. 54°-57° C./1.2 mm. NMR: δ (ppm, CDCl₃), 7.4 (H, d, J=12), 5.3-5.8 (H, m), 4.5 (2H, d, J=7), 2.16 (3H, s), 2.05 (3H, s). IR: $\nu_{c=o}$ 1770, 1750, $\nu_{c=o}$ 1680.

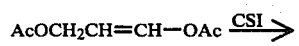

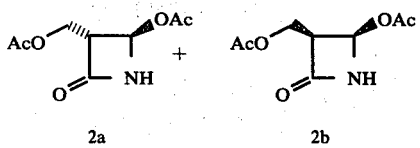

PROCEDURE:

CSI (16.92 g; 0.12 mol) was added dropwise to cooled (ice salt bath, −15° C.) 1 (18.96 g; 0.12 mol). The pale yellow mixture was kept at 5° for 5 h whereby it changed to deep yellow. This was diluted with ethyl acetate (20 ml), cooled to −30° C., and added in portions to a cooled (ice salt bath) mixture of water (3.4 ml); ice (17.0 g) NaHCO₃ (0.3 g) and Na₂SO₃ (3.4 g). After addition, the resulting mixture was stirred vigorously for 20 min and some additional NaHCO₃ was added to keep pH at 7-8. The layers were separated, and aqueous layer was extracted with ethyl acetate (2×50 ml). The combined organic phase was dried (Na₂SO₄; NaHCO₃; 1:1). It was filtered and evaporated to give 17.4 g of an oil. This was distilled under high vacuum (0.01-0.05 mm) in a hot air bath. (temp. 55°-85°) to remove 1. The undistilled light brown oil was cooled, taken up in ether and filtered over celite-charcoal to give, after evaporation to dryness 5.28 g (22%) of 4:1 mixture of 2a and 2b (determined by nmr) as colourless oil. NMR: 7.25 (H, NH), 6.0 (0.25H, d, J=4.3), 5.8 (0.75H, d, J=15.), 4.5 (0.5H, d, J=6.5), 4.4 (1.5H, d, J=4.5), 3.8 (0.25H, m), 3.5 (0.75H, m), 2.13 (3H, s), 2.1 (3H, s). IR: $\nu_{c=o}$ 1780, 1740.

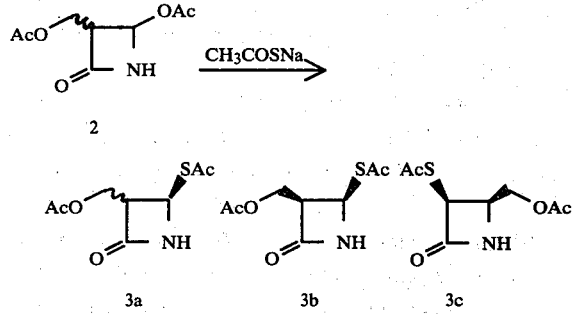

PROCEDURE:

Sodium thioacetate was prepared by addition of thioacetic acid (2.22 ml, 2.363 g) to a solution of 1M NaHCO₃ (31.0 ml) under nitrogen. This was added to a cooled (ice bath) solution of 2 (5.2 g; 25.9 mmoles) in water (20 ml) and stirred for 4 h at room temperature. Some acetone (20 ml) was added to render the reaction mixture homogeneous. The mixture was concentrated in vacuo to remove acetone and then extracted with methylene chloride. The extract was dried and evaporated to give 5.6 g of a mixture of isomers (83.14%) of 3a and 3b. The NMR spectrum of the crude oil showed that there were one trans and two cis compounds present in the mixture. A sample (550 mg) was chromatographed on silica gel (30 g, 10% H₂O) and eluted with benzene-ether-methanol to give 200 mg of a mixture of 3a and 3b in the ratio of 7:1, followed by 150 mg of an unknown cis compound (δ5.55, d, J=4.3) to which structure 3c was tentatively assigned. NMR: 6.78 (H, NH), 5.52 (0.17H, d, J=4.3), 5.18 (0.83H, d, J=1.5), 4.37 (2H, d, J=4.5), 3.45 (H, m), 2.35 (3H, s), 2.05 (3H, s). IR: $\nu_{c=o}$ 1765, 1740, 1600 cm⁻¹.

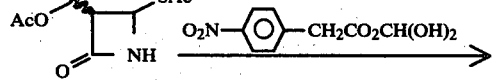

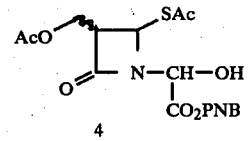

PROCEDURE:

A mixture of crude 3 (2.17 g; 10 mmoles) and p-nitrobenzyl glyoxylate (2.5 g; 11 mmoles) in benzene (200 ml) was refluxed 20 h under a Dean Stark water collector followed by concentration in vacuo to give 3.4 g of crude 4 as oil. This was used as such without further purification. NMR: δ 7.5-8.5 (4H), 5.2-5.8 (4H), 3.4-5.1 (4H), 2-2.4 (6H). IR: $\nu_{c=o}$ 1665, 1740, 1740, 1730, 1700.

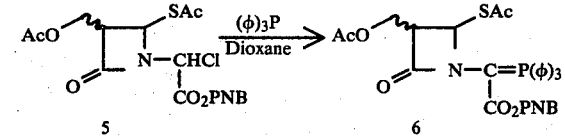

PROCEDURE:

To a cooled (ice-bath) solution of crude 5 (3.3 g; 7.75 mmoles) and pyridine (0.67 g; 8.5 mmoles) in benzene (20 ml) was added dropwise thionyl chloride (1.01 g; 8.5 mmoles) in benzene (10 ml) and the mixture stirred at the above temperature for 15 min and at r.t. for 15 min. The benzene solution was decanted, and the residual semi solid washed three times with 15 ml portions of benzene. The combined benzene solution was evaporated to give 1.90 g of crude 5 (55%). NMR: δ 7.5-8.5 (4H), 6.12 and 6.2 (1H), 5.66 (1H, m), 5.4 (2H, d, J=6), 4.3-4.7 (2H, m), 3.63 (H, m) 2.4 (3H, d), 2.1 (3H, s). IR: $\nu_{c=o}$ 1765, 1740, 1730, 1700.

PROCEDURE:

A mixture of crude 5 (1.90 g; 4.27 mmoles) triphenylphosphine (1.572 g; 6 mmoles) and 2,6-lutidine (0.642 g; 6 mmoles) in dioxane (20 ml) was heated at 55° for 18 h. It was cooled, filtered and evaporated to give 3.8 g of a crude dark oil. This was chromatographed on silica gel to give 1.2 g (42%) of 6.

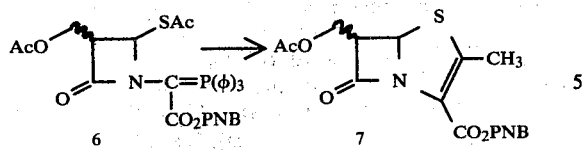

PROCEDURE:

A solution of crude 6 (1.20 g; 1.79 mmoles) in toluene (15 ml) was refluxed for 5 h. It was cooled and evaporated to give an oil which was chromatographed on $SiO_2$ (30 g) and eluted with benzene to give 0.4 g of 7 (57%). Anal. Calc'd for $C_{17}H_{16}N_2O_7S$. C 52.04; H 4.11; N 7.14. Found: C 51.77; H 4.08; N 7.30.

Separation of the cis and trans isomers was achieved through careful chromatography on silica gel (60 g) eluting with benzene. cis-isomer: δ (ppm, $CDCl_3$): 7.5–8.5 (4H, aromatics), 5.67 (1H, d, J=5, H-5), 5.28 (2H, AB quartet, benzyl), 4.33 (2H, d, AcO$CH_2$), 4.20 (1H, dt, H-6), 2.31 (3H, s, $CH_3$), 2.0 (3H, s, $CH_3CO$). $\nu_{c=o}$ 1770, 1740, 1730 cm$^{-1}$. trans isomer: δ (ppm, $CDCl_3$): 7.5–8.5 (4H, aromatics), 5.53 (1H, d, J=2, H-5), 5.30 (2H, AB quartet, benzyl), 4.32 (2H, d, AcO$CH_2$), 4.27 (1H, dt, J=5, J-2, H-6), 2.31 (3H, s, $CH_3$), 2.0 (3H, s, $CH_3CO$). $\nu_{c=o}$ 1770, 1740, 1730 cm$^{-1}$.

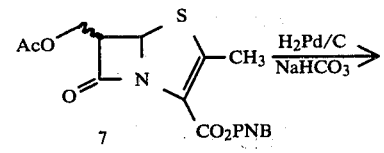

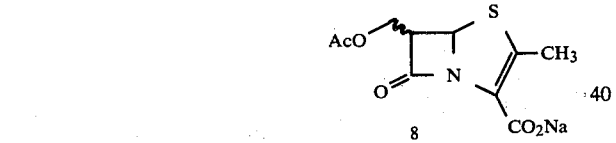

PROCEDURE:

To a solution of trans 7 (119 mg; 0.3 mmole) in ethyl acetate (15 ml) and water (7 ml) was added $NaHCO_3$ (25.2 mg, 0.3 mmole) and Pd/C (110 mg) and this was hydrogenated 4.5 h at 30 psi. The mixture was filtered and layers separated. The aqueous layer was washed with ether and then lyophilized to give 40 mg of solid 8 (48%). $\nu_{c=o}$ 1765, 1740, 1600 cm$^{-1}$. δ (ppm, $D_2O$): 5.52 (1H, H-5), 4.85 (2H, AcO$CH_2$), 4.0 (1H, H-6), 2.65 (3H, $CH_3$), 2.40 (3H, $CH_3CO$).

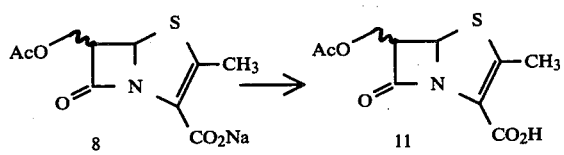

PROCEDURE:

To a solution of crude trans 8 (100 mg) in cold water (2 ml) was acidified with cold 1 N HCl and extracted with $CHCl_3$. The extract was dried ($Na_2SO_4$) and evaporated to give 30 mg of a pale yellow solid. M.P. 111°–113° with decomposition. IR: $\nu_{c=o}$ 1780, 1750, 1680. (Neat). IR: (KBr): $\nu_{c=o}$ 1775 (Strong), 1745, 1670.

Treatment of cis paranitrobenzyl 6-acetoxymethyl-2-methyl-penem-3-carboxylate according to the above procedure gives the cis sodium salt and free acid.

EXAMPLE 3

Potassium 6-(2'-Hydroxyisopropyl)-2-methylpenem-3-carboxylate (anion process)

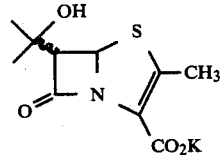

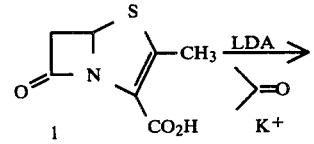

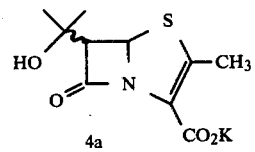

A solution of acid 1 (116 mg, 0.627 mmoles) in anhydrous THF (4 cc, freshly distilled over LAH) was added dropwise at −78° C. to a THF (2 cc) solution of LDA (from diisopropylamine, 70.7 mg, 98 μl, 0.699 mmoles, and n BuLi 1.6 M, 0.440 cc, 0.704 mmole stirred at −78° C. for 30 min). The mixture was stirred for 5 min. followed by successive addition of diisopropylamine (70.7 mg, 98 μl, 0.699 mmole) and 1.6 M n BuLi (0.440 cc, 0.704 mmole) at −78°. It was then stirred for 10 min. at −78° and treated rapidly with acetone (5 cc). The mixture was allowed to react with acetone for 10 min. It was acidified (pH=2) with 1% HCl, diluted with ethyl acetate (40 cc) and washed with brine (3×20 cc). It was dried over $Na_2SO_4$. Solvent evaporation gave a crude residue (3a) which was taken up in $CH_2Cl_2$ (crude yield 90 mg). The crude acid was dissolved in cold MIBK (2 cc) and treated dropwise with potassium 2-ethyl hexanoate. It gave two batches of potassium salt (36.4 mg, 26%) as a cis and trans mixture, the trans isomer being predominant. δ (ppm, $DMSOd_6$) 5.60 (1H, d, $J_{5-6\,cis}$=4, H-5), 5.55 (1H, d, $J_{5-6\,trans}$=2, H-5), 3.93 (1H, d, $J_{6-5\,cis}$=4, H-6), 3.62 (1H, d, $J_{6-5\,trans}$=2, H-6), 3.50 (b.s., OH), 2.34 (3H, s, $CH_3$), 1.47, 1.40 (6H, 2s, 2$CH_3$), 1.35, 1.32 (6H, 2s, 2$CH_3$) $\nu_{c=o}$ (nujol mull) 1765, 1582, $\nu_{OH}$ 3600–3100 UV (EtOH) $\lambda_{max}$ 257 (ε=3920), 300 (ε=4020).

EXAMPLE 4

Potassium 6-Hydroxybenzyl-2-methylpenem-3-carboxylate (anion process)

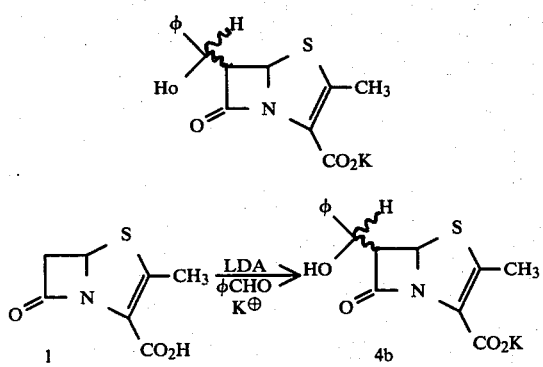

A solution of acid 1 (100 mg, 0.540 mmole) in anhydrous THF (6 cc, distilled over LAH) was added dropwise to a cold (−78°) THF (2 cc) solution of LDA made from diisopropylamine (84 μl, 60.6 mg, 0.599 mmole) and 1.6 M n-BuLi (0.380 cc, 0.608 mmole). The mixture was stirred for 5 min, followed by successive addition of diisopropyl amine (84 μl, 60.6 mg, 0.599 mmole) and 1.6 M n-BuLi (0.380 cc, 0.608 mmole). It was then stirred for 7 min at −78° and treated rapidly with benzaldehyde (300 μl). The mixture was allowed to react at −78° for 20 min. It was acidified with 1% HCl (pH≈2), diluted with ethyl acetate (40 cc), washed with 1:1 H₂O-brine (3×20 cc) and brine (1×20 cc) It was dried over Na₂SO₄. Solvent evaporation gave a residue which was dissolved in MIBK (2 cc). It was treated dropwise with potassium 2-ethyl hexanoate. It gave 4b (35 mg) in 20% yield as a diastereoisomeric mixture. δ: (ppm, DMSOd₆) 7.95 (5H, s, H-aromatic) 5.57 (d, $J_{5\text{-}6\ trans}=1.5$, H-5), 5.45 (d, $J_{5\text{-}6\ trans}=1.5$, H-5) 5.35 (d, $J_{5\text{-}6\ cis}=4$, H-5), 5.0 (m, C-H hydroxybenzyl), 4.25 (dd, $J_{6\text{-}5\ cis}=4$, $J_{6\text{-}C\text{-}H\ hydroxy\ benzyl}=10$, H-6), 3.90 (m, H-6), 3.65 (b.s., OH), 2.35 (3H, 2s, CH₃) $\nu_{c=o}$ (nujol mull) 1760, 1590, $\nu_{OH}$ 3600–3100. UV (H₂O) $\lambda_{max}$ 252 (ε=5,100), 296 (ε=3,300).

EXAMPLE 5

Potassium 6-Thiomethyl-2-methylpenem-3-carboxylate (anion process)

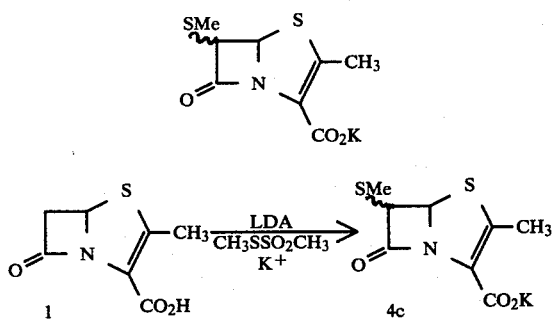

A solution of acid 1 (100 mg, 0.540 mmole) in anhydrous THF (5 cc, distilled over LAH) was added dropwise to a cold (−78°) THF (2 cc) solution of LDA made from diisopropylamine (84 μl, 60.6 mg, 0.599 mmole) and 1.6 M n-Butyl lithium (0.380 cc, 0.608 mmole). The mixture was stirred for 7–8 min, followed by successive addition of diisopropylamine (84 μl, 60.6 mg, 0.599 mmole) and 1.6 M n-Butyl lithium (0.380 cc, 0.608 mmole). It was then stirred for 7 min at −78° and treated rapidly with methyl thiomethylsulfonate (300 μl, excess). The mixture was allowed to react at −78° for 5 min. It was acidified with 1% HCl (ph≈2), diluted with ethyl acetate (40 cc), washed with 1:1 H₂O-brine (3×20 cc) and brine (20 cc). The organic solution was dried over Na₂SO₄. Solvent evaporation gave a residue which was dissolved in cold MIBK (2 cc). The cold solution was treated dropwise with potassium 2-ethylhexanoate. It gave 4c (40 mg) in 28% yield as a 8:3 mixture of cis and trans isomers (decomp.) 115°–120°) δ (ppm, DMSOd₆) 5.85 (1H, d, $J_{5\text{-}6\ cis}=4$, H-5), 5.57 (1H, d, $J_{5\text{-}6\ trans}=1.5$, H-5), 4.87 (1H, d, $J_{6\text{-}5\ cis}=4$, H-6), 4.72 (1H, d, $J_{6\text{-}5\ trans}=1.5$, H-6), 3.42 (b.s., OH), 2.37 (s, SCH₃), 2.33 (s, CH₃), 2.25 (s, SCH₃). $\nu_{c=o}$ (nujol mull) 1770, 1600, UV (H₂O) $\lambda_{max}$ 252 (ε=4200), 297 (ε=3700).

EXAMPLE 6

1-(p-Nitrobenzyloxycarbonylmethyltriphenylphosphoranyl)-4-(silver mercaptidyl)-2-azetidinone

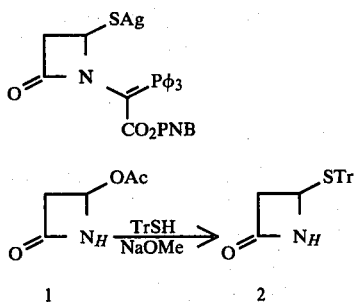

A methanol (90 cc) suspension of triphenylmethyl mercaptan (13.8 g, 0.05 mmole) was degassed for 0.5 hour with a nitrogen stream. The mixture was cooled down at 0° and sodium hydride (2.4 g, 0.05 mole, 50% oil dispersion) was added portionwise. The resulting solution was stirred for 5 min and 4-acetoxyazetidinone (7.7 g, 0.059 mole) in water (55 cc) was added rapidly. Precipitation of 4-triphenyl methyl mercaptoazetidinone (2) occurred immediately. The mixture was stirred for 4 h at room temperature. The solid was filtered off, washed with water and dissolved in methylene chloride. The methylene chloride solution was washed with diluted HCl, water, aqueous sodium bicarbonate water and brine and dried over MgSO₄ (89.8%, m.p.: 146.5°–147.5° C.). Anal. Calc'd for C₂₂H₁₉NOS: C, 76.49; H, 5.54; N, 4.05; S, 9.28 Found: C, 7.54; H, 5.60; N, 4.00; S, 9.36. δ (ppm, CDCl₃) 7.60–7.10 (15H, m, H-trityl), 4.62 (1H, bs, NH), 4.40 (1H, dd, $J_{4\text{-}3\ trans}=3.0$, $J_{4\text{-}3\ cis}=5$, H-4), 3.24 (1H, ddd, $J_{gem}=15$, $J_{3\text{-}4\ cis}=5$, $J_{3\text{-}NH}=1.8$, H-3), 2.81 (1H, ddd, $J_{gem}=15$, $J_{3\text{-}4\ trans}=3.0$, $J_{3\text{-}NH}=1.2$, H-3). $\nu_{c=o}$ (CHCl₃) 1760, $\nu_{NH}$ 3340.

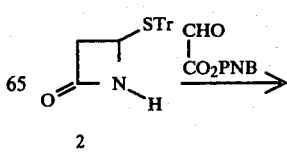

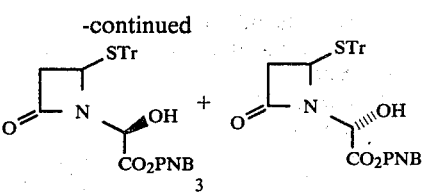

Hydrated p-nitrobenzyl glyoxylate (4.54 g, 0.02 mole) and azetidinone 2 (6.90, 0.02 mole) were refluxed in benzene through a Dean Stark condenser filled with 3 Å molecular sieves for 24 h. Further glyoxylate (2×454 mg, 2 mmoles) was added with reflux period (18 h) after each addition. The mixture was diluted with ether, washed with 5% aqueous HCl, water, aqueous 5% NaHCO$_3$ water and brine. It was dried over MgSO$_4$ (12 g, quantitative). A small fraction of the epimeric mixture was separated on a silica gel plate (CH$_2$Cl$_2$-ether 6:4)

Isomer A:

Rf=0.87, m.p.=170.5°–171.5°. δ (ppm, CDCl$_3$) 8.07 (2H, d, J=9, Hm aromatic), 7.45 (part of d, Ho aromatic), 7.40–7.00 (15H, m, Trityl), 5.25 (2H, s, CH$_2$—PNB), 4.75 (1H, s, H—C—O), 4.37 (1H, dd, J$_{3-4}$ trans=3, J$_{3-4}$ cis=4, H-3), 2.83 (1H, dd, J$_{gem}$=16, J$_{4-3}$ cis=4, H-4), 2.10 (1H, dd, J$_{gem}$=16, J$_{4-3}$ trans=3, H-4), 1.42 (b.s., OH). ν$_{c=o}$ (CHCl$_3$) 1770, 1760 (shoulder), ν$_{NO2}$ 1525, ν$_{OH}$ 3475.

Isomer B:

Rf=0.75, m.p.=152°–153°. δ (ppm, CDCl$_3$), 8.13 (2H, d, J=9, Hm aromatic), 7.47 (2H, d, J=9, Ho aromatic), 7.40–7.00 (15H, m, trityl), 5.30 (3H, s, CH$_2$—PNB, H—C—O), 4.45 (1H, t, J=3.5, H-4), 2.90–2.70 (2H, AB part of ABX, H-4), 1.55 (b.s., OH). ν$_{c=o}$ (CHCl$_3$) 1767, 1755 (shoulder), ν$_{NO2}$ 1525, ν$_{OH}$ 3500.

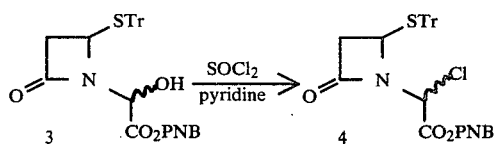

A cold (−15°) THF (150 cc, dried over molecular sieves) solution of azetidinone 3 (12 g, 21.7 mmoles) was treated with pyridine (1.9 g, 24.1 mmoles, 1.94 cc) and dropwise with thionyl chloride (2.86 g, 24 mmoles, 1.88 cc) under a nitrogen atmosphere. The mixture was stirred for 45 min at −15°. The precipitate was filtered off and washed with benzene. Evaporation of solvent gave a residue which was taken up in benzene and treated with activated charcoal (11.7 g, 94%, crystallized out from chloroform). δ (ppm, CDCl$_3$) 8.17 (2H, d, J=8, Hm aromatic), 7.67–7.00 (17H, m, Ho aromatic, Tr—H), 5.80 (s, H—C—Cl), 5.37, 5.33 (2s, H—C—Cl, CH$_2$—PNB), 4.81 (1H, m, H-4), 3.27–2.40 (2H, m, H-3) ν$_{c=o}$ (KBr film) 1785, 1770 ν$_{NO2}$ 1525.

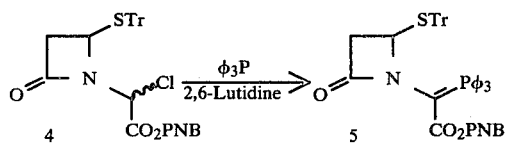

A THF (100 cc, distilled over LAH) solution of chloroazetidinone 4 (11.6 g, 20.2 mmoles) was treated with triphenyl phosphine (7.86 g, 30.0 mmoles) and 2,6-lutidine (2.36 g, 2.56 cc, 22.0 mmoles). The mixture was refluxed for 72 h. The precipitate was filtered off and washed with ether. The organic solution was washed with 2% aqueous HCl and 5% aqueous bicarbonate and dried over MgSO$_4$. Evaporation of solvent gave a residue which was purified through silica gel pad (200 g). The desired phosphorane was eluted with 30,40 and 50% ether-benzene (11.4 g, 70.4%, m.p.: 201°–202°). Anal. Calc'd for C$_{49}$H$_{40}$N$_2$O$_5$SP: C, 73.57; H, 5.04; N, 3.50; S, 4.01. Found: C, 73.58; H, 4.91; N, 3.44; S, 3.87. ν$_{c=o}$ (CHCl$_3$) 1740, ν phosphorane (1620, 1610), ν$_{NO2}$ 1525.

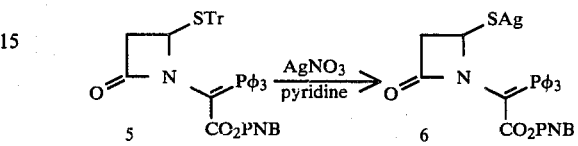

4-Tritylmercapto azetidinone 5 (1.6 g, 2 mmoles) was dissolved in CH$_2$Cl$_2$ (20 cc) and the solvent was flushed down at 55°–60°. Phosphorane 5 at 55°–60° was dissolved in preheated (55°–60°) methanol (32 cc). Immediately after the obtention of a methanolic solution of 6 it was treated with a preheated (55°–60°) mixture of methanolic 0.15 M silver nitrate solution (16 cc, 1.2 eq) and pyridine (174 mg, 178 μl, 2.2 mmoles, 1.1 eq). The warming bath was then immediately removed. The mixture was stirred at room temperature for 2 h and at 0° C. for 1 h. The silver mercaptide 6 was filtered off, washed twice with cold (0°) methanol and three times with ether. (1.12 g, 84.5%, m.p.: 130–135 dec.). ν$_{c=o}$ (CHCl$_3$) 1795, 1725 (shoulder), ν phosphorane (1620, 1605), ν$_{NO2}$ 1530.

EXAMPLE 7

1-(p-Nitrobenzyloxycarbonylmethyltriphenylphosphoranyl)-4-(silver mercaptidyl)-2-azetidinone

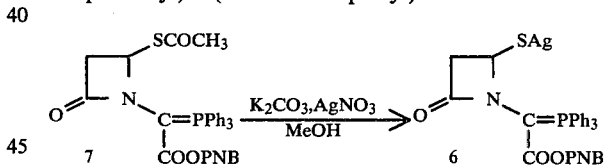

A solution of phosphorane 7 (1.796 g, 3.0 mmoles) in chloroform (3 ml) was diluted with methanol (90 ml), cooled at 0° C. under nitrogen atmosphere and treated successively with silver nitrate (0.51 g, 3.0 mmoles) and potassium carbonate (0.33 g, 2.4 mmoles). The reaction mixture (protected from light) was stirred at 0° C. for 15 min., then the cooling bath was removed and stirring was continued for 3 h. The reaction mixture was cooled down to −10° C., stirred for 1 h and filtered; the silver mercaptide was successively washed with cold methanol and ether; 1.91 g, M.P.: 138°–145° C. dec, 96%. I.R. (nujol) cm$^{-1}$: 1748, 1620 and 1605. An analytical sample was obtained by preparative TLC (ethyl acetate); M.P.: 140°–5° C. dec, calc'd for C$_{30}$H$_{24}$N$_2$O$_5$SPAg: C, 54.31; H, 3.65; N, 4.22; S, 4.83. Found: C, 54.11; H, 3.48; N, 3.92; S, 4.62.

EXAMPLE 8

1-(p-Nitrobenzyloxycarbonylmethyltriphenylphosphoranyl)-4-(silver mercaptidyl)-2-azetidinone A. Use of aniline as base

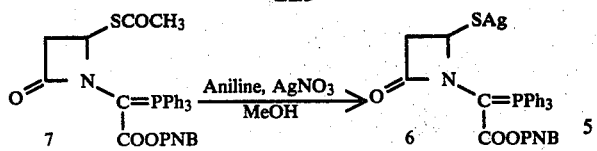

A solution of phosphorane 7 (1.8 g, 3.0 mmoles) in chloroform (4 ml) was diluted with methanol (90 ml), cooled to −15° C. under nitrogen atmosphere and treated successively with silver nitrate (0.56 g, 3.3 mmoles) and aniline (1.5 ml, 16.5 mmoles). The reaction mixture (protected from light) was stirred at −15° C. for 0.5 h and then the cooling bath was removed and stirring was continued for 24 h. The reaction mixture was cooled to −10° C. and stirred for 1 h before being filtered; the silver mercaptide was successively washed with cold methanol and ether; 1.55 g, M.P. 114°–5° C. dec. 77.9%. IR (nujol) cm−1; identical to compound of Example 7.

Silver-1-(paranitrobenzyl 2′-triphenylphosphoranylidene-2′-acetate)-2-azetidinone-4-thiolate B. Use of 4-dimethylaminopyridine (DMAP) as base

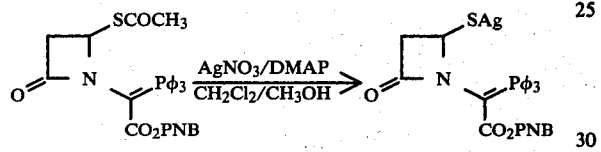

A solution of the above S-acetyl phosphorane (17.96 g, 30 mmol) in methanol and dichloromethane (1:2, 450 ml) was purged with nitrogen (5–10 min), cooled to 5° C. and treated successively with silver nitrate (5.35 g, 31.5 mmol) and 4-dimethylaminopyridine (3.85 g, 31.5 mmol). The ice-bath was removed and the solution refluxed vigorously for 2 h and then stirred at room temperature for 1 h. The colored reaction mixture was treated with charcoal, filtered and evaporated. The residue was redissolved in the minimum amount of dichloromethane and added dropwise, with stirring to cold methanol (300 ml). The precipitated silver salt was collected by filtration, washed with ether and dried; 18.1 g (91%); ir (CHCl3) $\nu_{max}$:1745 (C=O of β-lactam) and 1607 cm−1 (C=O of ester).

Silver-1-(paranitrobenzyl 2′-triphenylphosphoranylidene-2″-acetate)-2-2-azetidinone-4-thiolate C. Use of diazabicycloundecene (DBU) as base

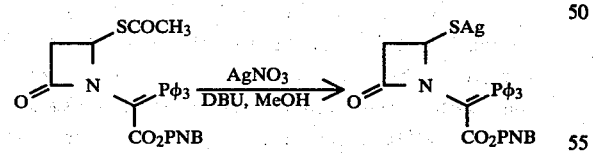

The above S-acetylphosphorane (36.0 g, 0.060 mol) was dissolved in methylene chloride 120 ml. The solvent was evaporated in order to obtain an oil. The resulting oily residue was dissolved in warm (35° C.) methanol (240 ml) and treated rapidly with a methanolic (420 ml) solution of silver nitrate (10.68 g, 0.0628 mol). The resulting solution (or suspension) was stirred at room temperature for 5 min, cooled down (ice bath) and a DBU (8.96 ml, 0.060 mol) solution in methanol (20 ml) was added over a 5 min period. The mixture was stirred for 5 min. The solid was filtered, washed once with cold (0° C.) methanol and ether and dried under vacuum; 37.0 g (93%); ir (nujol mull $\nu_{max}$ (c=O) and 1600 cm−1 (phosphorane)

D. Use of pyrrolidine as base

Silver 1-(paranitrobenzyl 2′-triphenylphosphoranylidene-2″-acetate)-2-azetidinone-4-thiolate

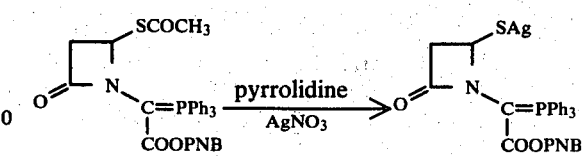

To a cold (0° C.) solution of 4-acetylthio-1-(paranitrobenzyl 2″-triphenylphosphoranylidene-2″-acetate)-2-azetidinone (0.60 g, 1.0 mmol) in Ch2Cl2 (2 ml) was added MeOH (4 ml), a solution of AgNO3 in MeOH (0.14 N, 7.86 ml, 1.1 mmol) and a solution of pyrrolidine (0.92 ml, 1.1 mmol) in MeOH (2 ml). The cooling bath was removed and the reaction mixture was stirred for 1.75 h, cooled to −10° C., stirred for 0.25 h and filtered. The solid was washed with cold MeOH and dried in vacuo; 0.548 g, m.p. 115° C., 82.4%. ir (nujol) $\nu_{max}$:1755 (C=O) and 1600 cm−1 (aromatics).

EXAMPLE 9

Mercuric (II)-[2′-Triphenylphosphoranylidene-2′-acetate]-2-azetidinone-4-thiolate

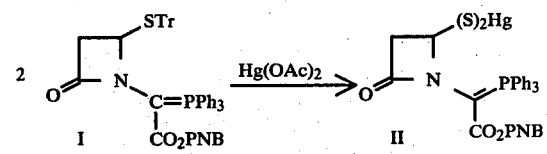

A solution of I (2.4 g, 3 mmoles) in dichloromethane (15 ml) was cooled to 5° C. and treated with a solution of mercuric acetate (0.525 g, 1.65 mmole) dissolved in methanol (15 ml). After stirring at 5° C. for 2 h, the solvent was evaporated and the residue redissolved in dichloromethane and washed with cold water. The organic solution after being dried (MgSO4) and treated with charcoal, was evaporated to give a foam which crystallized when triturated in ether. Yield: 1.73 g (91%) M.P. 123°–127° C., I.R. (CHCl3) 1745 cm−1 ($\nu_{c=1}$ β-lactam) 1608 cm[31 1] (phenyl).

EXAMPLE 10

2-Methylpenem-3-p-nitrobenzyl-carboxylate (from mercaptide intermediate)

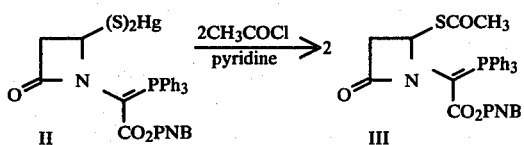

A solution of II (262 mg, 0.2 mmole), acetyl chloride (35 mg, 0.44 mmole) and 2 drops of pyridine in 10 ml of dichloromethane was stirred at 5° C. for 1 h. The precipitated mercuric chloride was then filtered off and the filtrate washed successively with cold dilute hydrochloric acid, sodium hydroxide and finally brine. The organic solution was submitted to a stream of hydrogen sulfide for 2 minutes at 5° C. and stirred at that temperature for an additional 10 minutes in order to precipitate the last traces of mercuric salts. Some charcoal was added to the black mixture which was then filtered through a pad of celite. Evaporation of the clear filtrate left 193 mg (80.7%) of III as a foamy material. I.R. (CHCl₃) 1755 ($v_{c=o}$ β-lactam) 1692 ($v_{SCOCH_3}$) 1620 (phenyl).

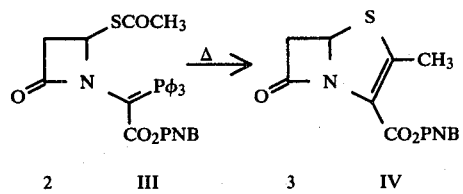

Phosphorane III (75 mg, 0.126 mmole) in toluene (10 cc) was refluxed over a 2.5 h period under nitrogen atmosphere. Solvent evaporation and purification of the residue afforded a crystalline derivative (25 mg, 63%) whose physical and spectral data were in complete agreement with those of the title product.

Product IV may if desired be subjected to catalytic hydrogenation (30% Pd on celite) to produce the corresponding 3-carboxylic acid product.

EXAMPLE 11

2-Phenoxymethylpenem-3-carboxylic Acid (from mercaptide intermediate)

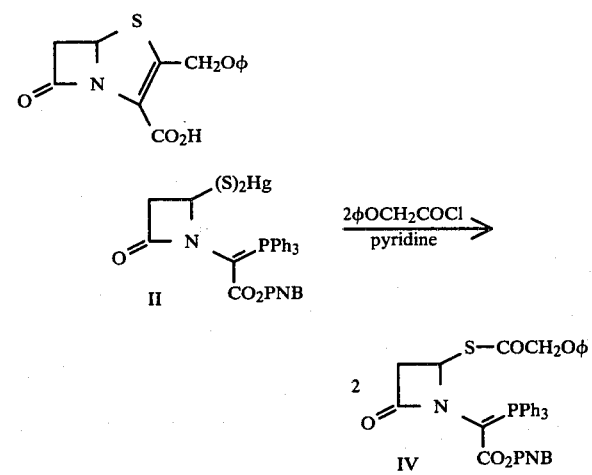

If the procedure of Example 10 is repeated with the acetyl chloride replaced with an equimolar weight of phenoxyacetyl chloride, intermediate IV is obtained in high yield. IR(CHCl₃): 1753 ($v_{c=o}$ β-lactam), 1689 ($v$—S—$\overset{|}{C}$=O).

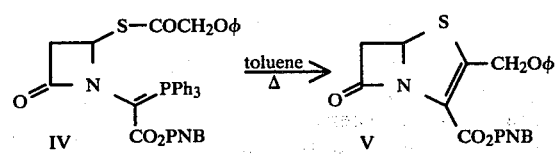

Intermediate V is obtained from IV by following the procedure of Preparation 12.

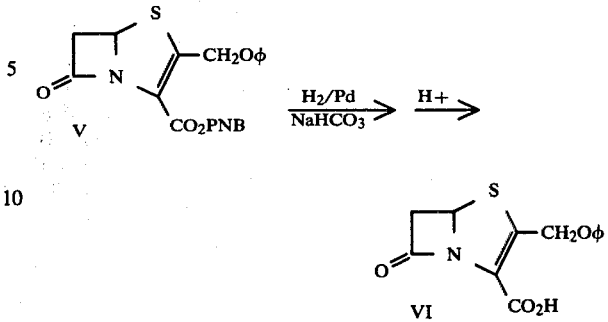

The title 3-carboxylic acid product is obtained from intermediate V by the procedure of Preparation 12.

EXAMPLE 12

2-Methylpenem-3-p-nitrobenzyl-carboxylate (from mercaptide intermediate)

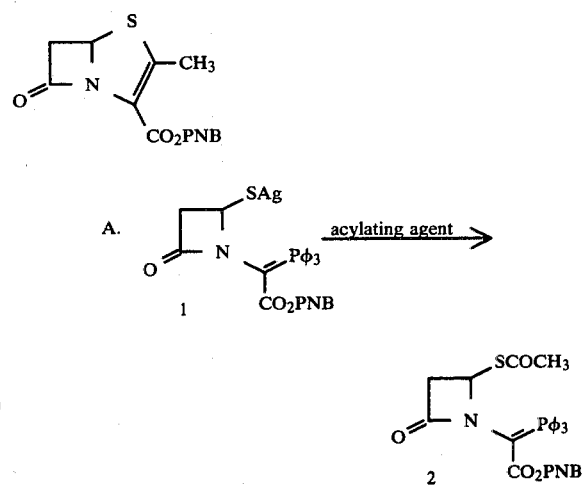

(A1) Use of acid chloride acylating agent (CH₃COCl)

A cold (0°) methylene chloride (7 cc) solution of silver salt 1 (105 mg, 0.158 mmole) was treated under nitrogen atmosphere with acetyl chloride (37 mg, 33.9 μl, 0.465 mmole, 3 eq) and pyridine (50 mg, 51 μl, 0.632 mmole, 4 eq). The mixture was stirred for 15 min. The solid was filtered off and washed with ether. The organic solution was diluted with ether and washed with 2% aqueous HCl, water, 2% sodium bicarbonate, water and brine. Solvent evaporation afforded a residue (75 mg, 79%) having physical and spectral characteristics in agreement with those of compound 2 obtained previously.

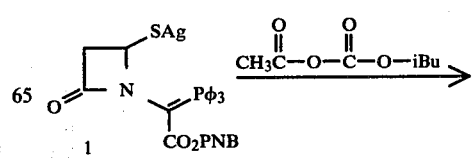

-continued

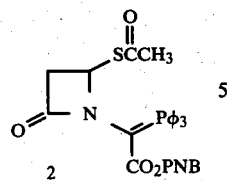

(A2) Use of mixed anhydride acylating agent

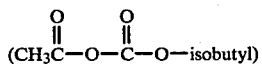

Triethyl amine (0.83 ml, 5.9 mmoles) was added to a solution of acetic acid (0.34 ml, 5.9 mmoles) in methylene chloride (10 ml). The resulting solution was cooled to −15° C., stirred, and treated dropwise (10 min) with isobutyl chloroformate (0.78 ml, 5.9 mmoles). The reaction mixture (precipitate of Et3N.HCl) was diluted with methylene chloride (10 ml) and stirred at −15° for 15 min. The silver mercaptide 1 (0.33 g, 0.5 mmole) was added in one portion and the resulting mixture was stirred at −15° for 30 min and allowed to come to room temperature overnight. The precipitate was removed by filtration and washed with ether. The combined filtrates were washed successively with water, aqueous hydrochloric acid, aqueous sodium bicarbonate solution and water. Drying and concentration left an oil which solidified upon trituration with ether. The yield of crystalline 2, m.p. 158°–161° was 0.219 g (73.5%)

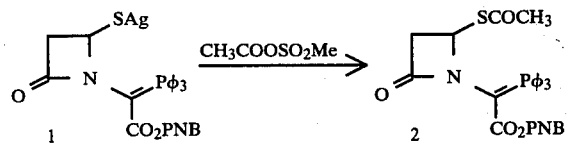

(A3) Use of mixed sulfonate anhydride (CH3COOSO2CH3)

Triethylamine (0.241 ml, 1.74 mmole) was added to a solution of acetic acid (100 μl, 1.74 mmole) in methylene chloride (4 cc). The solution was stirred for 1 h at room temperature, then cooled at 0° and treated dropwise (10 min) with methanesulphonyl chloride (134 μl, 1.74 mmole). The reaction mixture was stirred for 1 h at 0° and a solution of mercaptide 1 (330 mg, 0.50 mmole) in methylene chloride (4 ml) was added in one portion. The mixture was stirred at 0° for 3 h, then filtered, diluted with ether and filtered again over a celite pad. The filtrates were washed with water, dilute aqueous hydrochloric acid, water, dilute sodium bicarbonate, water and brine, dried and concentrated. The residual oil crystallized out from ether to give a yellowish solid 2 (115 mg, 38.6%).

B. 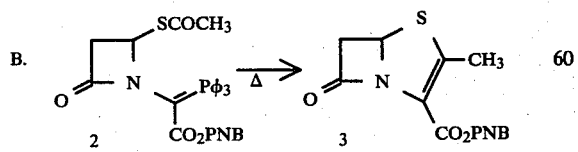

Phosphorane 2 (75 mg., 0.126 mmole) in toluene (10 cc) was refluxed over a 2.5 hour period under a nitrogen atmosphere. Solvent evaporation and purification of the residue afforded a crystalline derivative (25 mg., 63%) having physical and spectral characteristics consistent for structure 3.

EXAMPLE 13

Sodium 2-Benzylpenem-3-carboxylate (from mercaptide intermediate)

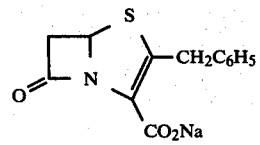

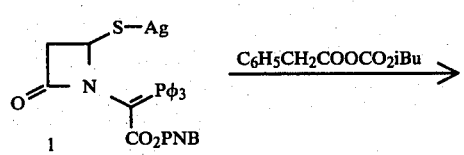

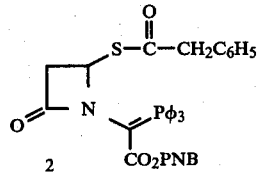

Triethylamine (0.208 ml, 1.49 mmole) was added to a solution of phenylacetic acid (203 mg, 1.49 mmole) in methylene chloride (7 ml). The solution was cooled to −15° and treated in 15 min with isobutyl chloroformate (0.194 ml, 1.49 mmole). The reaction mixture was stirred one hour at −15° and the mercaptide 1 (200 mg, 0.3 mmole) was added in one portion. The mixture was then stirred one hour at −15°, allowed to come to room temperature over 1 hour, filtered and the solids washed with ether. The combined filtrates were washed with water, aqueous hydrochloric acid, water, aqueous sodium bicarbonate and water, dried and then concentrated. The residual oil was crystallized in ether-petroleum ether to give a white solid. (115 mg, 57%), m.p. 168°–170°.

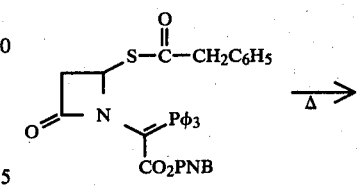

Compound 3 may be prepared from intermediate 2 by the procedure of Preparation 21.

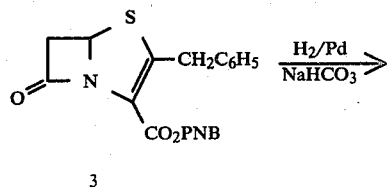

3

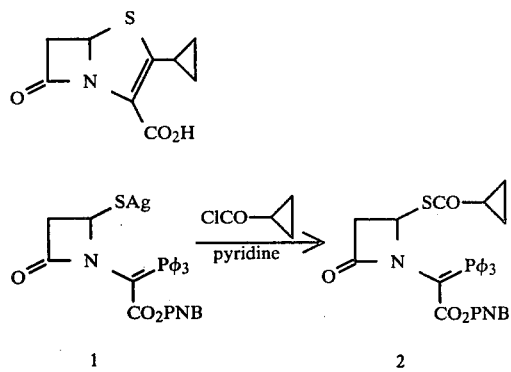

4

Title product 4 may be prepared by catalytic hydrogenation of 3 according to the procedure of Preparation 21.

EXAMPLE 14

2-Cyclopropylpenem-3-carboxylic Acid (from mercaptide intermediate)

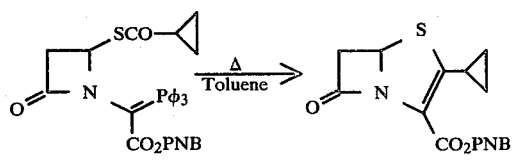

A cold (0°) methylene chloride (44 cc) solution of silver mercaptide 1 (1.12 g, 1.7 mmole) was treated with pyridine (178 mg, 182 μl, 2.25 mmoles, 1.3 eq) and dropwise with cyclopropane carboxylic acid chloride (212 mg, 184 μl, 2.03 mmoles, 1.2 eq). The mixture was stirred at 0° under nitrogen atmosphere for 15 min. The solid was filtered off and washed with ether. The organic solution was washed with 1% aqueous HCl, water, 1% aqueous sodium bicarbonate, water and brine. It was dried over $Na_2SO_4$. The residue obtained upon solvent evaporation crystallized out from $CH_2Cl_2$-ether (667 mg, 64%, m.p. 169°-170 °). Anal. calc'd for $C_{34}H_{29}N_2O_6SP$: C, 65.38; H, 4.68; N, 4.49; S, 5.13. Found: C, 64.39; H, 4.63; N, 4.39; S, 5.44. $\nu_{c=o}$(CHCl₃) 1750, 1685, 1620 $\nu_{NO_2}$ 1530.

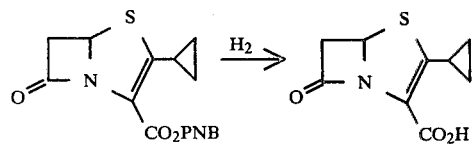

Phosphorane 2 (271 mg, 0.434 mmole) was refluxed in toluene for 24 h. Toluene evaporation afforded a residue which was passed through a silica gel (1:20 ratio) column (20% ether-benzene). It gave crystalline 3 (96 mg, 64%, m.p.: 154°-155°). Anal. calc'd for $C_{16}H_{14}N_2O_5S$: C, 55.48; H, 4.07; N, 8.09; S, 9.26. Found: C, 55.42; H, 4.10; N, 8.04; S, 9.22. δ (ppm, CDCl₃), 8.18 (2H, d, Hm aromatic), 7.57 (2H, d,Ho aromatic), 5.55 (1H, dd, $J_{5\text{-}6\ trans}=1.7$, $J_{5\text{-}6\ cis}=3.5$, H-5), 5.33 (2H, center of ABq, J=14, CH₂-PNB), 3.77 (1H, dd, $J_{gem}=16$, $J_{6\text{-}5\ cis}=5$, H-6), 3.40 (1H, dd, $J_{gem}=16$, $J_{6\text{-}5\ trans}=1.7$, H-6), 3.15-2.74 (1H, m, H-1' cyclopropyl), 1.20-0.30 (4H, m, H-2' and H-3' cyclopropyl). $\nu_{c=o}$(CHCl₃) 1788, 1700 $\nu_{NO_2}$ 1520. U.V. (EtOH) $\lambda_{max}$ 317 (ε=10,500), 264 (ε=11,750).

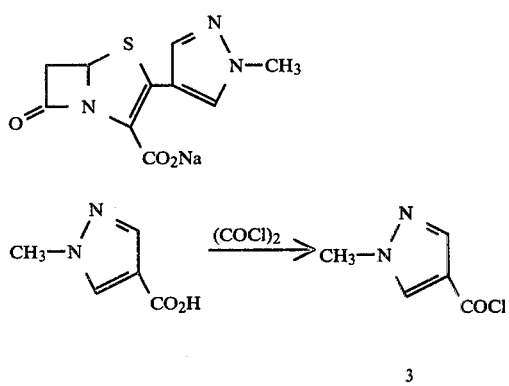

A mixture of ester 3 (96 mg, 0.277 mmole) in THF (10 cc)-ether (25 cc) and NaHCO₃ (23.3 mg, 0.277 mmole) in water (10 cc) was shaken on a Parr hydrogenator for 5 h at 40 p.s.i. H₂, using 30% Pd on celite (100 mg) as catalyst. The catalyst was filtered off and washed with ether and water. The aqueous phase was washed with ether (3×30 cc) and acidified gradually to pH=2 with 1% aqueous HCl (the aqueous phase was extracted with ethyl acetate (6×25 cc) between each HCl addition). The ethyl acetate extracts were combined and washed with brine (3×30 cc). The resulting crystalline residue was triturated with ether (17 mg, 29%, decomp. 140°). δ (ppm, CDCl₃), 5.53 (1H, dd, $J_{5\text{-}6\ trans}=1.8$, $J_{5\text{-}6\ cis}=3.8$, H-5), 4.53 (center of a b.s., OH), 3.78 (1H, dd, $J_{gem}=16$, $J_{6\text{-}5\ cis}=3.8$, H-6), 3.38 (1H, dd, $J_{gem}=16$, $J_{6\text{-}5\ trans}=1.8$, H-6), 3.10-2.75 (1H, m, H-1' cyclopropyl), 1.40-0.50 (4H, m, H-2', H-3' cyclopropyl). $\nu_{c=o}$(nujol mull) 1775, 1670. U.V. (EtOH) $\lambda_{max}$ 260 (ε=4,230), 312.5 (ε=8,870).

EXAMPLE 15

Sodium 3-(1-Methylpyrazol-4-yl)penem-3-carboxylate (from mercaptide intermediate)

To a cold (0° C.) solution of oxalyl chloride (10 ml) containing one drop of DMF was added 1-methylpyrazole-4-carboxylic acid (1.96 g, 15.6 mmoles) under nitrogen atmosphere. The mixture was allowed to warm up slowly to room temperature and stirred for 1 h at reflux. Complete evaporation of oxalyl chloride gave the desired acid chloride (2.20 g, 98%). δ(ppm CDCl₃) 8.00 and 7.95 (2H, 2s, H-3 and H-5), 4.00 (3H, s, N-CH₃). $v_{c=o}$ 1760 cm⁻¹.

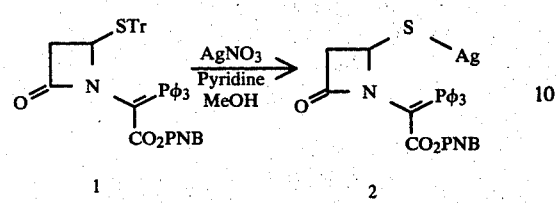

The solution of phosphorane 1(4.0 g, 5.0 mmoles) in methanol (60 ml), at 50°-60°, was treated with a hot (50°-60°) solution of silver nitrate in methanol (0.2 N, 27.5 ml, 5.5 mmoles) containing pyridine (0.42 ml, 5.2 mmoles), under nitrogen atmosphere, for 15 minutes. The reaction mixture, protected from light, was cooled down to 0° C., stirred for 1 h and filtered. The silver mercaptide was washed with cold methanol and ether; 2.79 g, 8.7%. IR (CH₂Cl₂) cm⁻¹ 1750 and 1610.

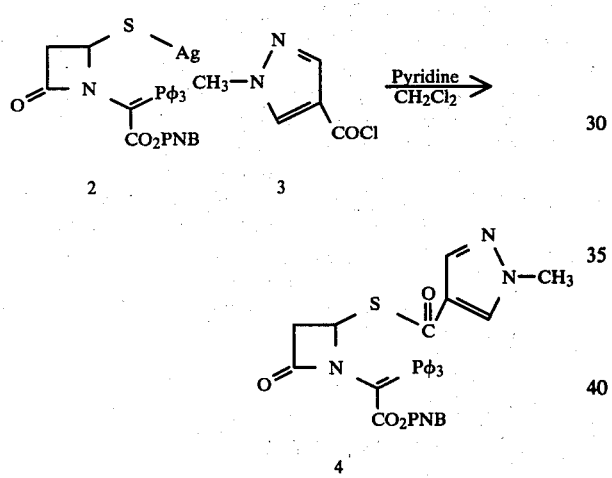

To a cold (0° C.) solution of acid chloride 3 (0.072 g, 5 mmoles) in methylene chloride (20 ml) was added a solution of silver mercaptide 3(2.79 g, 4.4 mmoles) in methylene chloride (40 ml) containing pyridine (0.35 ml, 4.4 mmoles). The reaction mixture was stirred at 0° for 15 min, then allowed to warm up to room temperature and stirred for 2.5 h. The solid was filtered, washed with 10% HCl and brine. It was dried over Na₂SO₄ and the solvent evaporated and the residue dry column chromatographed on silica gel (50 g) eluting with methylene chloride, methylene chloride; ethyl acetate 4:1. Evaporation of fractions gave 1.00 g (35%).

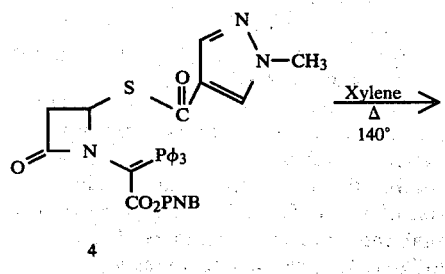

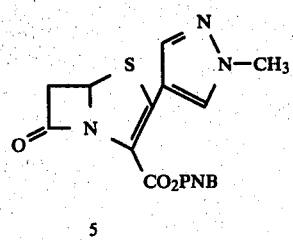

A solution of 4 (850 mg, 1.30 mmole) in xylene (20 ml) was reffluxed for 4 h. Evaporation of solvent gave a residue which was purified through silica gel (20 g) and eluted with methylene chloride; ethyl acetate 9:1. Evaporation of fractions gave 145 mg (30%). δ(ppm CDCl₃) 8.30 (1H, s, H-3'), 8.23 (2H, d, J=9, Hm aromatic), 7.83 (1H, s, H-5'), 7.63 (2H, d, J=9, Ho aromatic), 5.65 (1H, dd, J₅₋₆ trans=2, J₅₋₆ cis=4, H-5), 5.4 and 5.3 (2H , 2s, CO₂—CH₂ PNB), 3.94 (3H, s, N—CH₃), 3.85 (1H, dd, J_gem=15, J₅₋₆ cis =4, H-6cis) 3.47 (1H, dd, J_gem=15, J₆₋₅ trans=2, H-6 trans). ν(CH₂Cl₂) 1785, 1710.

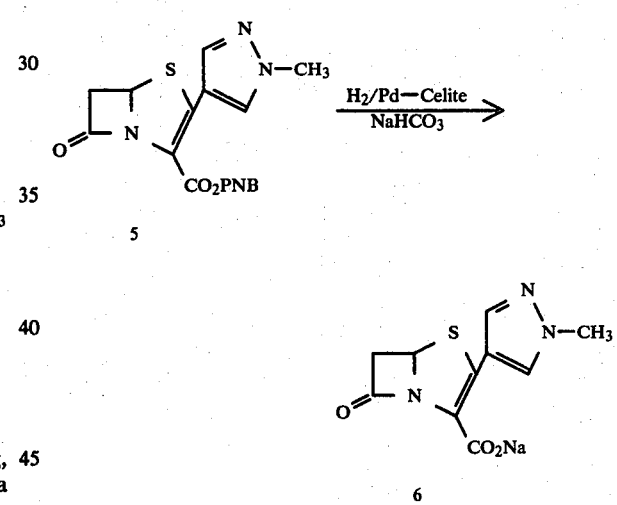

A mixture of ester 5 (117 mg, 0.31 mmole) in THF (10 ml), ether (20 ml) and NaHCO₃ (26 mg, 0.31 mmole) in water (10 ml) was shaken on a Parr hydrogenator for 3 h at 30 p.s.i. H₂ using 30% Pd on celite (110 mg) as catalyst. The catalyst was removed and washed with ether and water. The aqueous phase was shaken with ether (3×40 ml) and lyophilized to yield the sodium salt 6 73 mg (90%). δ(ppm CDCl₃) 8.28 (1H, s, H-3', 7.75 (1H, s, H-'), 5.50 (1H, m, H-5), 3.80 (3H-b 5's, N—CH₃) 3.55-3.15 (2H, m, H-6 cis and trans). ν(KBr) 1765 (β-lactam),

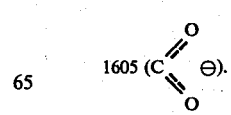

1605 (C⟋O ⟍O⁻ ⊖).

λ_max 252 (ε 7,332), 320 (ε 7,027).

EXAMPLE 16

2-Aminomethylpenem-3-carboxylic Acid (from mercaptide intermediate)

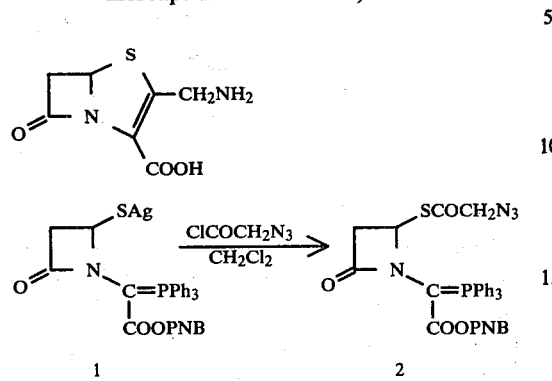

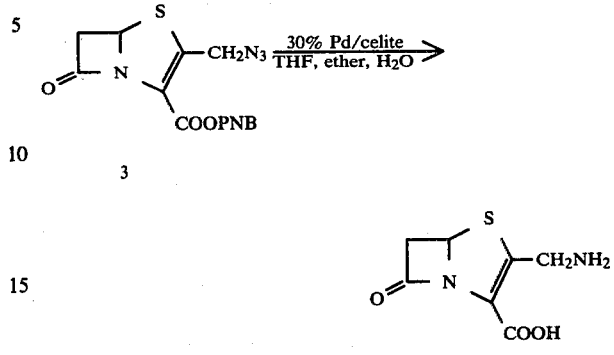

A solution of silver mercaptide 1 (1.25 g, 1.99 mmole) in dichloromethane (15 ml) kept under nitrogen atmosphere was cooled at 0° C. and treated dropwise with a 2M solution of azidoacetyl chloride in dichloromethane (1.13 ml, 2.26 mmoles). The reaction mixture was stirred at 0° C. for 1 h; the cooling bath was removed and stirring was continued for 5 h. The reaction mixture was filtered over a celite pad and the solids were washed with dichloromethane (35 ml). The filtrate and washings were combined, washed with sodium bicarbonate solution and water, dried over anhydrous sodium sulfate and concentrated in vacuo to an orange syrup which was purified by column chromatography (30 g of silica gel 60, eluate; ether-2% ethyl acetate (200 ml), ether-6% ethyl acetate (200 ml) and ether-20% ethyl acetate (500 ml), fraction size: 10 ml). The combination and evaporation of fractions 49–80 gave a yellow powder; 0.73 g, M.P. 61°–70°, 60.8%.

To a solution of penem 3(0.18 g, 0.5 mmole) in tetrahydrofuran (6 ml) was successively added ether (6 ml), water (6 ml) and 30% palladium on celite (0.18 g). The reaction mixture was hydrogenated under 30 p.s.i. at 23° C. for 2.5 h and filtered over celite pad; the pad was washed with water and the filtrate and washings were combined, washed with ether-THF mixture and lyophilized to give 30 mg, 30%, of compound 4. [Water and ether insoluble compound were dissolved in chloroform and the organic solution was washed with water and dried over anhydrous sodium sulfate. The evaporation of solvent under reduced pressure gave 77 mg (42.8%) of starting material 3]. NMR (DMSO d-6) $\delta$: 5.7 (dd, $J_{5\text{-}6\ cis}=3.5$ Hz, $J_{5\text{-}6\ trans}=1.5$ Hz, H-5). I.R. (nujol) cm$^{-1}$: 1775 (c=o of $\beta$-lactam) and 1615, 1585. U.V. $\lambda_{max}{}^{H2O}m\mu$: ($\epsilon=2320$) and 307 ($\epsilon=2685$).

Title product 4 was also obtained from intermediate 3 by the following route:

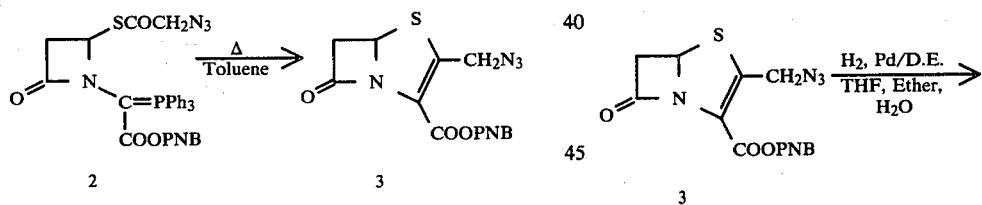

A solution of phosphorane 2(0.593 g, 0.93 mmole) in toluene (20 ml) was heated at 105° C. for 1 h, cooled to 23° C. and concentrated to a semi-crystalline compound which was purified by column chromatography (12 g of silica gel 60, Eluate: benzene (100 ml), benzene-2% ether (100 ml) and benzene-4% ether; fraction size: 10 ml). The combination and evaporation of fractions 18–26 gave a yellow syrup which crystallized on standing; 0.18 g, M.P.: 127°–8° C., 53.7% NMR (CDCl$_3$) $\delta$8.22 (2H, d, $J_{Ho,\ Hm}=8.8$ Hz, Ho of p-nitrobenzyl), 7.60 (2H, d, $J_{Hm,\ Ho}=8.8$ Hz, Hm of p-nitrobenzyl), 5.71 (1H, dd, $J_{5,6\ cis}=3.6$ Hz, $J_{5,6\ trans}=2.1$ Hz, H-5), 5.33 (2H, center of ABq, $J_{a,b}=14.0$ Hz, CH$_2$ of p-nitrobenzyl), 4.58 (2H, center of ABq, $J_{a,b}=15.0$ Hz, CH$_2$on C-2) 3.88 (1H, dd, $J_{6,5\ cis}=3.6$ Hz, $J_{gem}=16.5$ Hz, H-6 cis) and 3.55 (1H, dd, $J_{6,5\ trans}=2.1$ Hz, $J_{gem}=16.5$ Hz, H-6 trans). I.R. (Nujol) cm$^{-1}$: 2115 and 2090 (N$_3$), 1780 (c=o of $\beta$-lactam) and 1685 (c=o of p-nitrobenzyl ester).

An analytical sample was obtained by preparative T.L.C.; M.P. 127°–8° C., calc'd for C$_{14}$H$_{11}$N$_5$O$_5$S: C, 46.54; H, 3.07; N, 19.37; S, 8.87. Found: C, 46.43; H, 3.08; N, 19.37; S, 8.90.

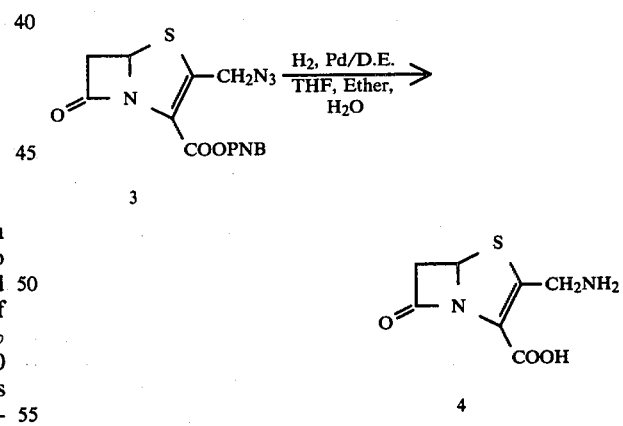

To a solution of penem 3 (2.4 g, 6.89 mmoles) in tetrahydrofuran-ether-water mixture (1:1:1, 165 ml) was added 30% palladium on diatomaceous earth (4.8 g). The reaction mixture was hydrogenated under 45 p.s.i. at 23° C. for 2.5 h and filtered over celite pad. The filtrate and washings were combined, washed twice with ether, centrifugated and filtered several times to give a clear solution which was lyophilized; 0.622 g, 45%. The crystallization of the compound was induced by the addition of water (0.8 ml); the suspension was centrifuged and the water was removed leaving an orange solid. This solid was washed twice with water and a slightly yellow solid was obtained after drying: 0.273 mg, 19.8%. UV $\lambda_{max}^{H2O}$: 307 ($\epsilon=4318$) and 257 ($\epsilon=2650$). Some crude starting material (1.2 g, 50%) was recovered. The compound (50 mg) can also be purified by column chromatography [Sephadex G10, column size: 1.6×100 cm, flow rate: 10 ml/h, eluent: distilled water, fraction volume: 1.5 ml, detector: refractive index]. UV $\lambda_{max}^{H2O}$: 307 ($\epsilon=3597$) and 255 ($\epsilon=2424$).

The stability of the compound in aqueous solution was checked by:
UV:
6 h 307 ($\epsilon=3545$) and 255 ($\epsilon=2773$)
21 h 307 ($\epsilon=3467$) and 255 ($\epsilon=2411$)
28 h 307 ($\epsilon=3337$) and 254 ($\epsilon=2398$)
46 h 307 ($\epsilon=3259$) and 254 ($\epsilon=2398$)
70 h 307 ($\epsilon=3076$)
94 h 307 ($\epsilon=2842$)
170 h 307 ($\epsilon=1900$)

A sample of compound 4 was kept at 23° C. for 3 days and the UV was taken: UV $\lambda_{max}^{H2O}$: 307 ($\epsilon=3055$) and 255 ($\epsilon=2008$).

Compound 4 was converted as described below to two additional 2-penem derivatives.

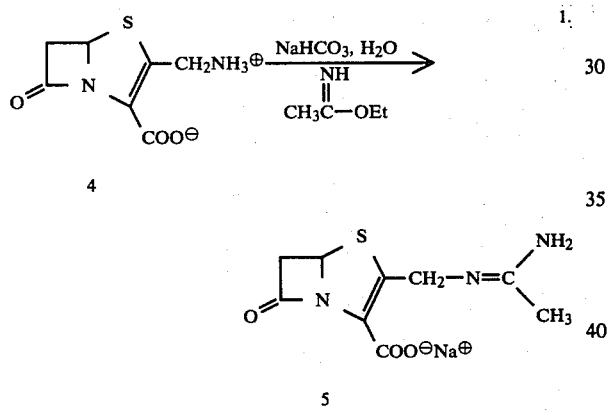

A suspension of compound 4 (50 mg, 0.25 mmole) in distilled water (0.5 ml) was treated with one equivalent of sodium bicarbonate (21 mg) followed by the addition of ethyl acetimidate (21.8mg, 0.024 ml). The reaction mixture was stirred at 23° C. for 20 min and lyophilized giving 52 mg of a yellow solid. NMR (D₂O) δ: 5.7 (m, H-5) and 2.23 (b.s., CH₃ of amidine). I.R. (KBr)cm⁻¹: 1772 (c=o of β-lactam). U.V. $\lambda_{max}^{D2O}$ mμ: 305 ($\epsilon=3116$) and 253 ($\epsilon=2525$). The compound 5 was applied on a column (Sephadex G10, column size: 1.6×100 cm⁻¹, Eluent: H₂O, detector: I.R. fraction size: 1.6 ml) and lyophilization of appropriate fractions gave 23 mg 45% of slightly yellow powder. U.V. $\lambda_{max}^{H2O}$. mμ: 303 ($\epsilon=2960$) and 248 ($\epsilon=2885$).

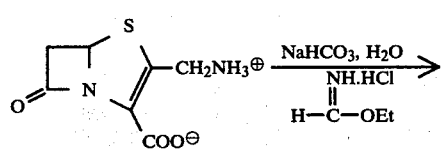

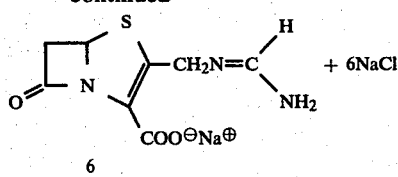

A suspension of compound 4 (50 mg, 0.25 mmole) in distilled water (0.5 ml) was treated with sodium bicarbonate (21 mg, 0.25 mmole) and stirred for 1.5 min before the addition (2 min) of a mixture of sodium bicarbonate (126 mg, 1.5 mmoles) and ethyl formimidate hydrochloride (164 mg, 1.5 mmole). The reaction mixture was stirred for 10 min at 23° C. and lyophilized giving an orange powder. U.V. $\lambda_{max}^{H2O}$ mμ: 304 ($\epsilon=2300$).

EXAMPLE 17

Sodium 2-Trifluoromethylpenem-3-carboxylate (from mercaptan intermediate)

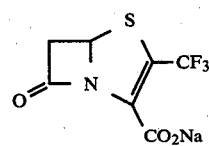

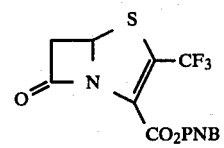

A cold (0°) methylene chloride (30 cc) solution of silver mercaptide 1 (663 mg, 1 mmole) was treated under nitrogen atmosphere with trifluoroacetic anhydride (0.3 cc, 446 mg, 2.12 mmoles) and trimethyl amine hydrochloride (191 mg, 2 mmoles). The mixture was stirred for 1 h at 0°. The solid was filtered off through a celite pad (The pad being washed with CH₂Cl₂ and ether). The organic solution was washed with water, 1% aqueous NaHCO₃, water and brine and dried over magnesium sulfate. IR spectrum (25315) of the residue, showed a mixture of phosphorane 2 and cyclic material 3. The mixture was stirred in methylene chloride (20 cc) at room temperature for 17 h. It was then passed through a silica gel (5 g) column (1% ether-benzene) and gave 3 (123 mg, 33% overall, m.p. 115°-116°).

Anal. calc'd for $C_{14}H_9N_2O_5F_3S$: C, 44.93; H, 2.42; N, 7.48; F, 15.23; S, 8.57. Found: C, 44,80; H, 2.35; N, 7.36; S, 8.86. δ (ppm, $CDCl_3$) 8.47 (2H, d, Hm aromatic), 7.56 (2H, d, Ho aromatic), 5.80 (1H, dd, $J_{5-6\ trans}=2.5$, $J_{5-6\ cis}=3.5$, H-5), 5.37 (2H, center of ABq, J=13.5, $CH_2$—PNB), 3.82 (1H, dd, $J_{gem}=16.5$, $J_{6-5\ cis}=3.5$, H-6), 3.68 (1H, dd, $J_{gem}=16.5$, $J_{6-5\ trans}=2,5$, H-6). $\nu_{c=o}(CHCl_3)$ 1805, 1730 $\nu_{NO_2}$ 1525. U.V. (EtOH) 333 (ε=7,010), 261 (ε=15,200).

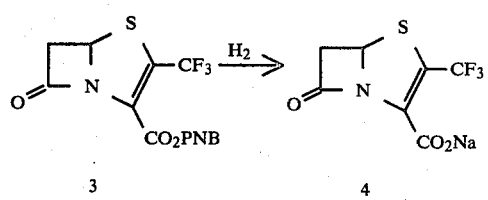

A mixture of ester 3 (84 mg, 0.225 mmoles) in dioxane (15 cc) water (10 cc), a 0.05 M pH7 buffer solution (5.45 cc, 0.273 mmoles) and 30% Pd on celite (200 mg) was shaken on a Parr hydrogenator for 3 h at 45 p.s.i. $H_2$. The catalyst was filtered off through a celite pad (The pad being washed with a small fraction of water and ether). The aqueous fraction was washed with ether (3×50 cc) and lyophilized (27 mg, 46%). δ (ppm, $DMSOd_6$) 5.78 (m, H-5), 4.0-3.0 (b.s. and m, OH and H-6). $\nu_{c=o}$(nujol mull) 1790, 1640. U.V. ($H_2O$) $\lambda_{max}$ 307 (ε=800, 293 (ε=1760).

EXAMPLE 18

2-(4'-Thiazolyl)methylpenem-3-carboxylic Acid (from mercaptide intermediate)

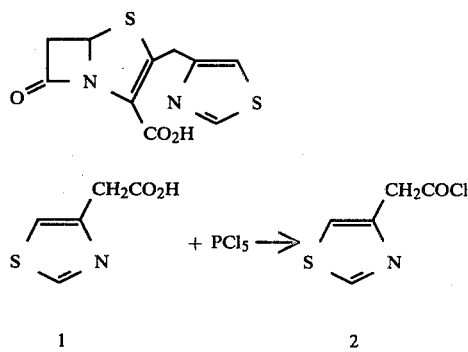

To a cooled (ice-bath) suspension of $PCl_5$ (4.1 g, 20 mmoles) in ethyl ether (20 ml) was added dropwise 1 (1.43 g, 10 mmoles) in tetrahydrofuran (20 ml). The reaction was stirred 15 min at room temperature, then refluxed for 2 h. After cooling at room temperature and filtration, the solid was washed with benzene and dried in vacuo to give 2 1.5 g (93%) as a light brown solid which decomposed at 162°-164° C. and which was used in the next step without further purification. IR(nujol 1780, cm$^{-1}$. NMR ($CDCl_3$): δ 10.18 (1H, d, J=2 Hz), 8.08 (1H, d, J=2 Hz), 4.10 (2H, s).

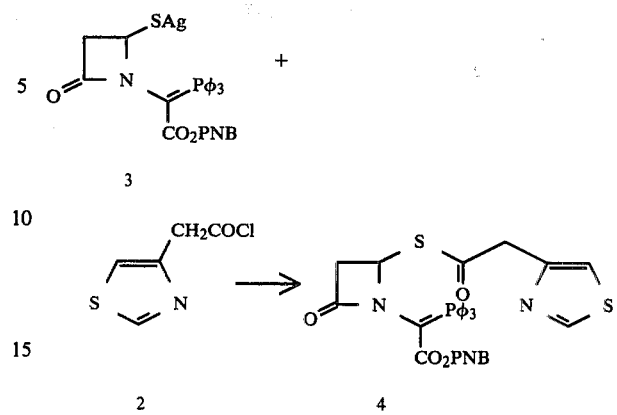

A solution of 3 (1.0 g, 1.51 mmole) and 2 (336 mg, 2.1 mmoles) in methylene chloride (50 ml) was cooled in an ice-bath and treated dropwise with a 1 M solution of pyridine in methylene chloride (2.5 ml, 2.5 mmoles). The resulting reaction mixture was stirred at room temperature for 2 h, and then filtered over Celite and washed with methylene chloride. Filtrate and washings were combined and washed successively with 1 N HCl (5 ml), water (5 ml), 1 M $NaHCO_3$ (5 ml), brine and then dried ($MgSO_4$) and evaporated under reduced pressure followed by high vacuum to afford 4 790 mg (77%) as an amorphous solid m.p.: 104°-6° C. It was used in the next step without further purification. IR (neat) 1755, 1690 cm$^{-1}$. NMR ($CDCl_3$): δ 8.85 (1H, bs), 8.15 (2H, d J=9 Hz), 7.5 (15 H, m), 6.72 (2H, d J=9 Hz), 5.1 (3H, m), 4.0 (2H, 2s), 2.3-3.1 (2H, m).

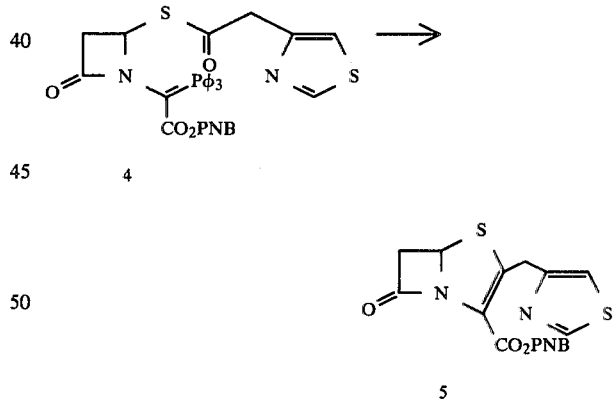

A solution of 4 (500 mg, 0.735 mmole) in toluene (50 ml) was heated under reflux for 5 h. The solvent was evaporated in vacuo and the residual oil was chromatographed on a silica gel column (10 g). Elution with benzene removed first the unpolar impurities and then ether to ethyl acetate gave 125 mg (42%) of 5 as an oil. IR ($CHCl_3$) 1785, 1710 cm$^{-1}$. NMR ($CDCl_3$): δ 8.80 (1H, d, J=2 Hz), 8.2 (2H, d J=9 Hz), 7.6 (2H, d, J=9 Hz), 7.2 (1H, d, J=2 Hz), 5.62 (1H, dd, $J_{cis}=5$ Hz, $J_{trans}=3$ Hz), 5.32 (2H, 2s), 4.4 (2H, 2s), 3.82 (1H, dd, $J_{gem}=15$ Hz, $J_{cis}=5$ Hz), 3.48 (1H, dd, $J_{gem}=15$ Hz, $J_{trans}=3$ Hz).

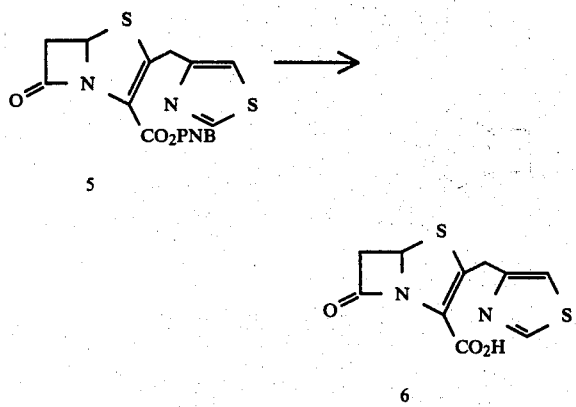

5

6

To a solution of 5 (100 mg, 0.25 mmole) in tetrahydrofuran (8 ml) and ether (4 ml) was added sodium bicarbonate (20.8 mg, 0.25 mmole), water (4 ml) and 30% Pd/Celite (100 mg). This mixture was hydrogenated 2 h at 45 p.s.i. The mixture was filtered and layers were separated. The aqueous layer, after washing with $CH_2Cl_2$ (2×5 ml), was cooled with ice, acidified with 1 N HCl (0.5 ml, 0.5 mmole) and then extracted with chloroform in a continuous extractor for 3 days. Solvent was evaporated in vacuo to give 6 43 mg (65%) as an oil. IR (neat) 1750 cm$^{-1}$. NMR (CDCl$_3$): δ 8.51 (1H, d J=2 Hz), 6.85 (1H, d, J=2 Hz), 5.30 (1H, dd, J$_{cis}$=5 Hz, J$_{trans}$=3 Hz), 4.15 (2H, 2s), 3.75–4.0 (1H, m), 3.45 (1H, dd, J$_{gem}$=15 Hz, J$_{cis}$=5 Hz), 3.15 (1H, dd, J$_{gem}$=15 Hz, J$_{trans}$=3 Hz).

EXAMPLE 19

Penem-3-carboxylic Acid (from mercaptide intermediate)

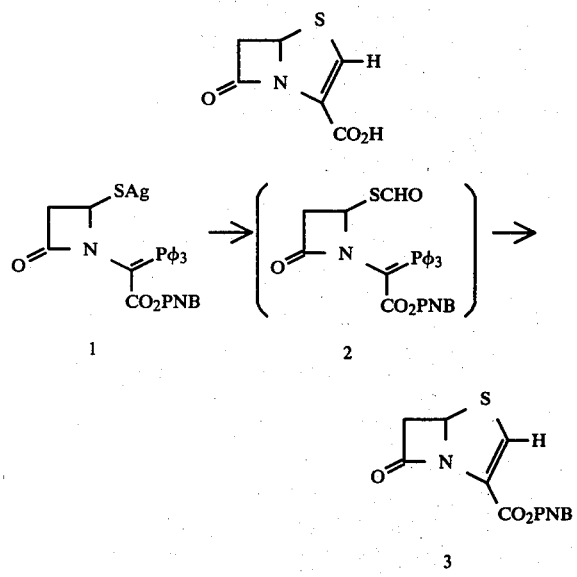

A methylene chloride (20 cc) solution of silver mercaptide 1 (1.185 g, 1.79 mmole) was treated successively with formic acetic anhydride (2 cc, 10 eq) and trimethyl amine hydrochloride (341 mg, 3.57 mmoles, 2 eq) under nitrogen atmosphere. The mixture was stirred at room temperature for 15 min. The solid was filtered off on celite and washed with ether. The organic solution was again diluted with ether, washed with water, 1% dilute aqueous sodium bicarbonate, water and brine. It was dried over magnesium sulfate. The residue obtained upon solvent evaporation was refluxed in methylene chloride for 1 h. The residue was then passed on a silica gel column (1–20 ratio) and 3 was eluted with benzene (63 mg, 11.5%, m.p. 151°–3°, decomp.). Anal. calc'd for $C_{13}H_{10}N_2O_5S$: C, 50.98; H, 3.29; N, 9.15; S, 10.47. Found: C, 50.88; H, 3.31; N, 9.09; S, 10.29. δ (ppm, CDCl$_3$) 8.15 (2H, d, J=8.5, Hm aromatic). 7.50 (2H, d, J=8.5, Ho aromatic), 7.26 (1H, m, H-2), 5.76 (1H, dd, J$_{5-6\ trans}$=2, J$_{5-6\ cis}$=4, H-5), 5.27 (2H, center of ABq, J=13.5, CH$_2$—PNB), 3.85 (1H, ddd, J$_{gem}$=16.5, J$_{6-5\ cis}$=4, J$_{6\ cis-2}$=0.8, H-6), 3.50 (1H, ddd, J$_{gem}$=16.5, J$_{6-5\ trans}$=2, J$_{6\ trans-2}$=1.2, H-6). ν$_{c=o}$ (nujol mull) 1800, 1700, ν$_{NO_2}$ 1520. U.V. (EtOH) λ$_{max}$ 264 (ε=6,810), 3.16 (ε=4,600).

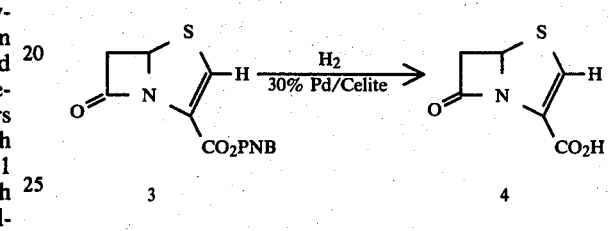

3

4

A mixture of ester 3 (110 mg, 0.36 mmole) in ether-THF (25 cc–10 cc), NaHCO$_3$ (30 mg, 0.36 mmole) in water (10 cc) and 30% Pd on celite (200 mg) was hydrogenated in a Parr shaker at 30 p.s.i. H$_2$ for 3.5 h. The catalyst was filtered off on a celite pad. The pad was then washed with water and ether. The aqueous phase was washed with ether (3×30 cc). It was then gradually acidified to pH 2 and extracted with ethyl acetate (10×20 cc) between every HCl (1 N) addition. The ethyl acetate extracts were combined, washed with brine (2×20 cc) and dried over MgSO$_4$ (28 mg, 45%, m.p. 160°–5° decomp.). δ (ppm, DMSOd$_6$) 8.47 (1H, m, H-2), 7.00 (b.s., O—H), 5.75 (1H, dd, J$_{5-6\ trans}$=2, J$_{5-6\ cis}$=4, H-5), 3.87 (dd, H-6), 3.57 (part of dd, H-6). ν$_{c=o}$ (nujol mull) 1790, 1780, 1670. U.V. (EtOH) λ$_{max}$ 308 (ε=2740), 255 (ε=2140).

EXAMPLE 20

2-(3'-Methyl-5'-isoxazolyl)penem-3-carboxylic Acid

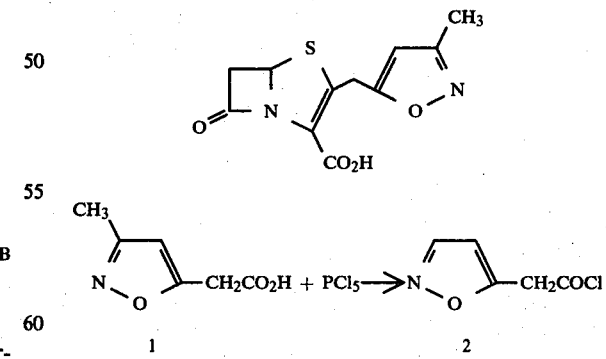

1

2

To a cooled (ice-bath) suspension of PCl$_5$ (4.1 g, 20 mmoles) in ethyl ether (20 ml) was added dropwise 1 (1.41 g, 10 mmoles) in a mixture of ethyl ether (10 ml) and tetrahydrofuran (10 ml). The reaction was stirred at room temperature for 1 h. Filtration over Celite and evaporation in vacuo gave 2 (1.6 g, quantitative) as a red oil. It was used in the next step without further purification. IR (CHCl$_3$) 1795 cm$^{-1}$. NMR (CDCl$_3$): δ 6.18 (1H, s), 4.32 (2H, s), 2.3 (3H, s).

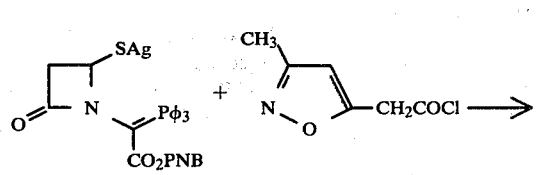

3          2

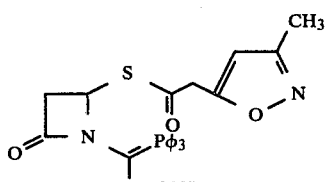

4

A solution of 3 (1.98 g, 3 mmoles) and 2 (668 mg, 4.2 mmoles) in methylene chloride (100 ml) was cooled in ice bath and treated dropwise with a 1 M solution of pyridine in methylene chloride (5 ml, 5 mmoles). The resulting reaction mixture was stirred at room temperature for 2 h and then filtered over Celite and washed with methylene chloride. Filtrate and washings were combined and washed successively with 1N HCl (10 ml), water (10 ml), 1M NaHCO$_3$ (10 ml) and brine and then dried (MgSO$_4$) and evaporated in vacuo to give 4 1.62 g (80%) as an amorphous solid. It was used in the next step without further purification. IR (CHCl$_3$) 1755, 1610 cm$^{-1}$. NMR (CDCl$_3$): δ 8.18 (2H, d, J=9Hz), 7.5 (15H, m), 6.75 (2H, d, J=9Hz), 6.0 (1H, bs), 5.7 (1H, m), 4.82 and 5.18 (2H, 2s), 3.70 (2H, s), 2.3–3.0 (2H, m), 2.28 (3H, s).

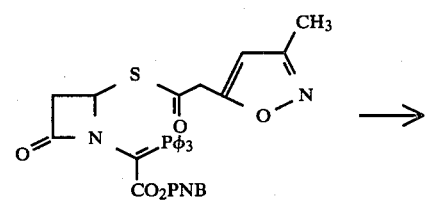

4

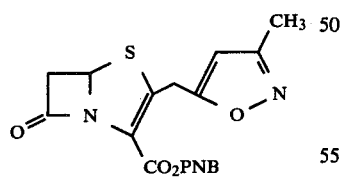

5

A solution of 4 (1.0 g, 1.47 mmole) in toluene (50 ml) was heated under reflux for 3 h. The solvent was evaporated in vacuo and the residual oil was chromatographed on a silica gel column (25 g). Elution with benzene removed the first unpolar material, then ether gave 5 450 mg (77%) as an oil. It was used in the next step without further purification. IR (CHCl$_3$) 1780, 1750 cm$^{-1}$. NMR (CDCl$_3$): δ (2H, d, J=9Hz), 7.55 (2H, d, J=9Hz), 6.12 (1H, s), 5.6 (1H, bs), 5.4 (2H, 2s), 3.75 (2H, d, J=3Hz), 3.80 (1H, dd, J$_{gem}$=15Hz, J$_{cis}$=5Hz), 3.30 (1H, dd, J$_{gem}$=15Hz, J$_{trans}$=3Hz), 2.3 (3H, d, J=2Hz).

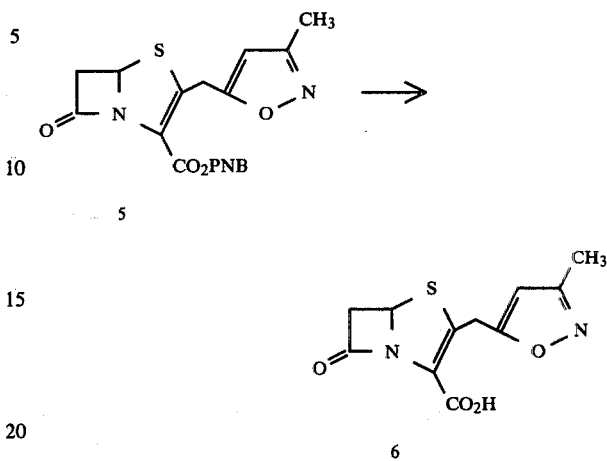

5

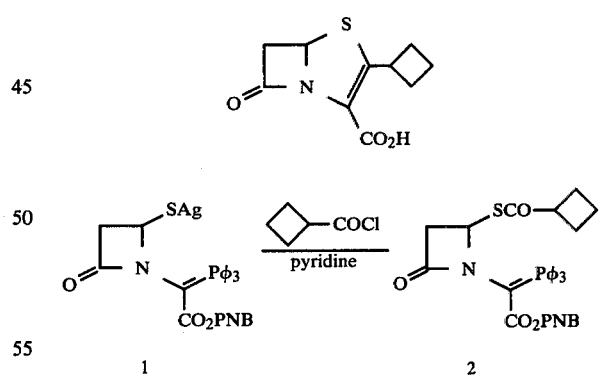

6

To a solution of 5 (250 mg, 0.625 mmole) in tetrahydrofuran (12 ml) and ether (6 ml) was added sodium bicarbonate (52.5 mg, 0.625 mmole), water, (6 ml) and 30% Pd/Celite (250 mg). This was hydrogenated 2 h at 45 p.s.i. The mixture was filtered and layers were separated. The aqueous phase, after washing with CH$_2$Cl$_2$ (2×5 ml), was cooled with ice, acidified with 1N HCl (1 ml), and then extracted with chloroform in a continuous extractor for 3 days. Solvent was evaporated in vacuo to give 6, 145 mg (87%) as an oil. IR (CHCl$_3$) 1790, 1735 cm$^{-1}$. NMR (CDCl$_3$): δ 8.50 (1H, m), 6.7 (1H, bs), 6.15 (1H, s), 5.52 (2H, bs), 3.78 (1H, dd J$_{gem}$=15Hz, J$_{cis}$=5 Hz), 3.2 (1H, dd, J$_{gem}$=15 Hz, J$_{trans}$=3Hz), 2.3 (3H, s).

EXAMPLE 21

2-Cyclobutylpenem-3-carboxylic Acid (from mercaptide intermediate)

A cold (0°) methylene chloride (80 cc) solution of silver mercaptide 1 (2.53 g, 3.82 mmoles) was treated with pyridine (0.393 g, 0.402 cc, 4.97 mmoles, 1.3 eq). Then cyclobutane carboxylic acid chloride (0.534 g, 4.6 mmoles, 1.2 eq) was added dropwise over a 5 min period. The resulting mixture was stirred for 15 min at 0°. The precipitate was filtered off through a celite pad and washed with methylene chloride (50 cc). The organic solution was washed with water, HCl (1N), water, dilute aqueous sodium bicarbonate, water and brine. The residue upon solvent evaporation was triturated with ether (1.54 g, 63%, m.p. 157°–158°). Anal. calc'd for C$_{35}$H$_{31}$N$_2$O$_6$SP: C, 65.82; H, 4.89; N, 4,38; S, 5.02. Found: C, 65.31; H, 4.77; N, 4.42; S, 5.08. $\nu_{c=o}$(CHCl$_3$) 1755, 1685, $\nu_{phosphorane}$ 1620, $\nu_{NO_2}$ 1520.

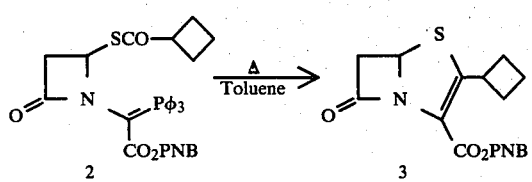

Phosphorane 2 (600 mg, 0.942 mmole) was refluxed in toluene (100 cc) for 16 h. Toluene was evaporated off. The residue was chromatographed on silica gel (1–20 ratio) and 3 was eluted with 1% ether-benzene (218 mg, 65%, m.p. 95°–96°). Anal. calc'd for C$_{17}$H$_{16}$N$_2$O$_5$S: C, 56.66; H, 4.48; N, 7.77; S, 8.90. Found: C, 56.46; H, 4.50; N, 7.70; S, 8.95. δ(ppm, CDCl$_2$) 8.16 (2H, d, Hm aromatic), 7.53 (2H, d, Ho aromatic), 5.55 (1H, dd, J$_{5-6}$ $_{trans}$=2, J$_{5-6}$ $_{cis}$=3.8, H-5), 5.25 (2H, center of ABq, J=13.5, CH$_2$—PNB), 4.45–3.95 (1H, m, H-1' cyclobutane), 2.77 (1H, dd, J$_{gem}$=16, J$_{6-5}$ $_{cis}$=3.8, H-6), 2.42 (1H, dd, J$_{gem}$=16, J$_{6-5}$ $_{trans}$=2, H-6), 2.50–1.65 (6H, m, H-cyclobutane). $\nu_{c=o}$ (CHCl$_3$) 1790, 1710, $\nu_{NO_2}$ 1525. U.V. (EtOH) λ$_{max}$ 320 (ε=11,640), 263 (ε=14,830).

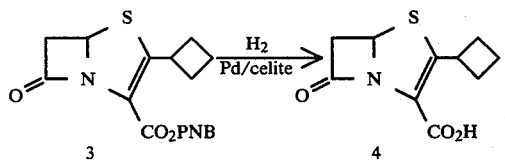

A mixture of ester 3 (146 mg, 0.42 mmole) in ether-THF (30 cc–15 cc), NaHCO$_3$ (45 mg, 0.53 mmoles in water (15 cc) and 30% Pd on Celite (300 mg) was shaken on a Parr hydrogenator for 5.5 h at 35 p.s.i. H$_2$. The catalyst was filtered off through a celite pad. The pad was washed with small volumes of ether and water. The aqueous phase was washed with ether (3×30 cc). It was then radually acidified to pH 2 with 1N HCl; the aqueous phase being extracted with ethyl acetate (6×30 cc) after such addition of aqueous HCl. The ethyl acetate extracts were combined, washed with brine (3×30 cc) and dried over MgSO$_4$. The residue upon solvent evaporation was triturated with ether (30 mg, 33%, m.p. 129°–133° dec.). δ(ppm, CDCl$_3$) 5.24 (1H, dd, J$_{5-6}$ $_{trans}$=2, J$_{5-6}$ $_{cis}$=3,5, H-5), 3.53 (1H, dd, J$_{gem}$=16, J$_{6-5}$ $_{cis}$=3.5, H-6), 3.45 (b.s., OH), 3.20 (1H, dd, J$_{gem}$=16, J$_{6-5}$ $_{trans}$=2, H-6), 2.50–1.40 (m, H-cyclobutane). $\nu_{c=o}$ (nujol mull) 1790, 1712. U.V. (EtOH) λ$_{max}$ 257 (ε=2,420), 314 (ε=5,750).

EXAMPLE 22

Sodium 2-Aminopropylpenem-3-carboxylate (from mercaptide intermediate)

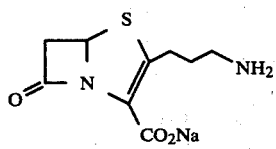

-continued

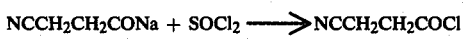

Sodium β-cyanopropionate monohydrate was dried in a drying pistol at 100° C. over phosphorous pentoxide (p≈0.1 torr) until the weight was constant. M.P. of anhydrous 1 was 148°–149° C.

A solution of thionyl chloride (18 ml, 0.25 mole) in dichloromethane (65 ml) was treated with anhydrous sodium β-cyanopropionate (15.3 g, 0.126 mole) and the temperature was kept below 30° C. After addition, the mixture was stirred for 30 min at 30° C. and filtered. The filtrate was concentrated and distilled (p=0.2 torr, t=57°–58° C.) to give 2; wt 11.6 g (78.4%). This compound was unstable and must be used freshly distilled.

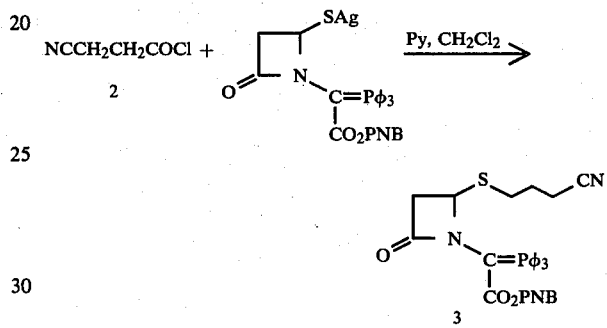

The β-cyanopropionyl chloride 2 (0.87 g, 7.4 mmoles) was added slowly to a cold solution (5° C.) of silver thiolate (4.0 g, 6.14 mmoles) is dichloromethane and pyridine and stirred for 2 h in an ice bath. A white precipitate of silver chloride was filtered after dilution with ether. The filtrate was washed by HCl 5%, saturated aqueous sodium bicarbonate and brine, dried by sodium sulfate and the solvent was evaporated. The oil was purified by column chromatography [silica gel, eluent: dichloromethane then an equal mixture of dichloromethane and ethyl acetate] and 3 was obtained as a foam by evaporation of fractions. Yield: 1.3 g, 32.5%.

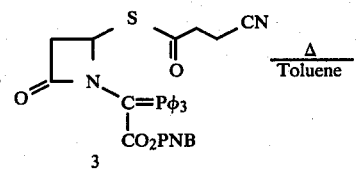

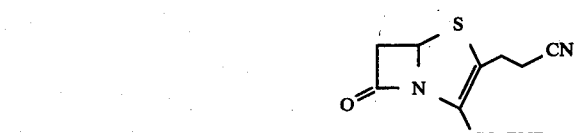

A solution of phosphorane 3 (1.3 g, 2 mmoles) in toluene (100 ml) was heated at reflux for 2 h 30 min. Evaporation of solvent and column chromatography [silica gel, eluent: CH$_2$Cl$_2$, then CH$_2$Cl$_2$—AcOEt (9:2)] gave after evaporation of good fractions of oil which solidified on standing. This solid was triturated in cold ether and dried. The compound 4 was obtained as an amorphous solid, slighly yellow (0.535 g, 74.4%); m.p. 149°–150° C.

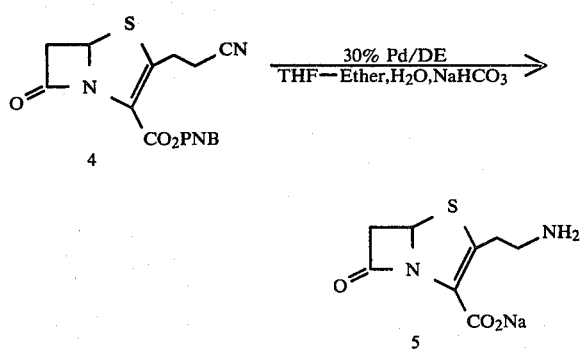

To a solution of ester 4 (50 mg, 0.133 mmole) in THF-ether mixture (1:1, 30 ml) was added water (10 ml), sodium bicarbonate (12 mg, 0.134 mmole) and 30% palladium on diatomaceous earth (50 mg). The reaction mixture was hydrogenated under 50 p.s.i. for 3 h at 25° C., filtered over a celite pad and washed twice with ether. The aqueous solution was lyophilized, yielding a yellow powder (35 mg) as the sodium salt. U.V. ($H_2O$) $\lambda_{max}$ 302 ($\epsilon = 3,733$), 257 ($\epsilon = 3,211$).

EXAMPLE 23

2-Carbethoxypenem-3-p-nitrobenzyl-carboxylate (from mercaptide intermediate)

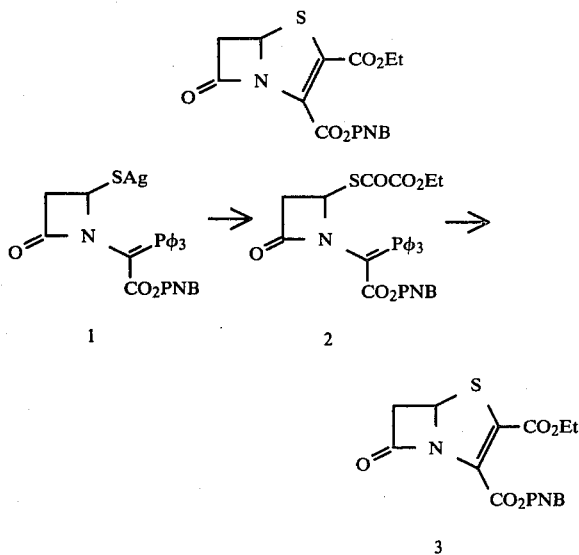

A cold (0°) methylene chloride (25 cc) solution of silver salt 1 (1.46 g, 2.20 mmoles) was treated under nitrogen atmosphere with pyridine (0.23 cc, 225 mg, 2.84 mmoles, 1.29 eq). Then ethyl oxalyl chloride (0.304 cc, 371 mg, 2.72 mmoles, 1.24 eq) was added dropwise over a 3 min period. The mixture was stirred for 10 more min. The solid was filtered off. The organic solution was diluted with ether and washed with 1% dilute HCl, water, diluted sodium bicarbonate, water and brine. Solvent evaporation afforded a residue which contained phosphorane 2 and cyclic penem 3 (920 mg). Pure 2 was isolated on small scale for characterization. The residue (920 mg) was allowed to stand in methylene chloride (20 cc) for 2 days. It was then chromatographed on silica gel (9 g, benzene and 1%, 2% ether-benzene). Penem 3 was isolated in 39.3% overall yield (327 mg, m.p. 98°–99°).

Phorphorane: $\nu_{c=o}$ ($CHCl_3$) 1760, 1690, $\nu_{phosphorane}$ 1630,1610, $\nu_{NO_2}$ 1520.

Penem:

Anal. calc'd for $C_{16}H_{14}N_2O_7S$: C, 50.79; H, 3.73; N, 7.40; S, 8.47 Found: C, 50.63; H, 3.71; N, 7.28; S, 8.53. δ(ppm, $CDCl_3$) 8.13 (2H, d, Hm aromatic), 7.48 (2H, d, Ho aromatic, 5.74 (1H, dd, $J_{5-6\ trans}=2.5$, $J_{5-6\ cis}=3.5$, H-5), 5.28 (2H, s, $CH_2$—PNB), 4.18 (2H, q, J=7, $CH_2$), 3.83 (1H, dd, $J_{gem}=16.5$, $J_{6-5\ cis}=3.5$, H-6), 3.55 (1H, dd, $J_{gem}=16.5$, $J_{6-5\ trans}=2.5$, H-6), 1.23 (3H, t, J=7, $CH_3$). $\nu_{c=o}$ ($CHCl_3$) 1805, 1725, $\nu_{NO_2}$ 1525. U.V. (EtOH) $\lambda_{max}$ 331 ($\epsilon=6,950$), 262 ($\epsilon=16,660$).

EXAMPLE 24

2-Aminoethylpenem-3-carboxylic Acid

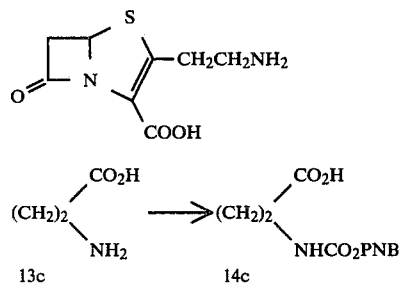

β-Alanine (4.45 g, 0.05 mole) was dissolved in 4N sodium hydroxide (15.6 ml, 0.0625 mole) and the solution was cooled in an ice-bath. p-Nitrobenzyl chloroformate (13.5 g, 0.0625 mole) (F. H. Carpenter and D. T. Gish, J. Am. Chem. Soc., 74, 3818, 1952) was dissolved in dioxane (32 ml). The cooled dioxane solution, along with a cold 4N sodium hydroxide solution (15.6 ml) was added to the β-alanine solution in five approximately equal portions, with at least five minutes being allowed between additions. The reaction mixture was stirred vigorously with cooling in an ice-bath. After the final addition the mixture was stirred an additional hour to ensure complete hydrolysis of the excess p-nitrobenzyl chloroformate. A crystalline by-product which had formed during the reaction was removed by filtration. The filtrate was then acidified with conc. hydrochloric acid. The carbo-p-nitrobenzyloxy derivative 14c which separated as a solid was removed by filtration and washed with cold water. The compound was recrystallized from boiling water to give 14c as a yellow solid m.p. 106°–107°. There was obtained 10.3 g, 77%. δ(ppm, DMSO-D₆): 8.33, 8.20, 7.70, 7.56, (4H, aromatic), 5.20 (2H,s benzylic H), 3.28 (2H,q,β-H), 2.40 (2H,tα-H), 12.25 (1H, $CO_2H$), 7.45 (1H,NH).$\nu_{c=o}=1730$, 1665 cm⁻¹. Anal. calc'd for CHNO: C, 49.26; H, 4.51; N, 10.44%. Found: C, 49.30; H, 4,51; N, 10.50%.

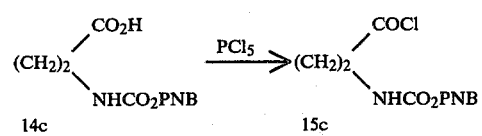

A mixture of carbo-p-nitrobenzyloxy-β-alanine 14c (2.8 g, 10 mmole) and dry ether (60 ml) was cooled in an ice-salt bath. Phosphorus pentachloride (2.3 g, 11 mmole) was added and the reaction was allowed to proceed with cooling and stirring for one hour. The mixture was then brought quickly to room temperature which caused most of the solids to pass into solution. The mixture was rapidly filtered through a sintered glass filter into a round bottom flask. When the ether was removed under vacuum the product crystallized and this crude 15c was used as such in the following experiment. Obtained: 3.8 g, δ(ppm, CDCl₃): 8.27, 8.12 7.58, 7.41, 7.30 (4H, aromatic), 5.5 (1H, N-H), 5.21 (2H, s, benzylic H), 3.50 (2H, m, β-H), 3.20 (2H, m, βH). $\nu_{c=o}$ 1795, 1735 cm⁻¹. The corresponding amide was prepared as a derivative from 15c and NH₃: m.p. 149–149.5 (EtOH—H₂O). Anal. Calc'd for $C_{11}H_{13}N_3O_5$: C, 49.44; H, 4.90; N, 15.72%. Found: C, 49.42; H, 4.93; N, 16.01%.

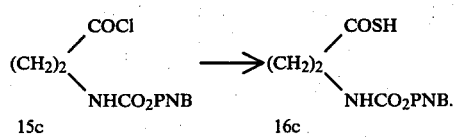

The acid chloride 15c (5.2 mmole) was added, portionwise, to a cooled (10°) and stirred solution of NaSH—3H₂O (1.15 g, 10.5 mmole) in ethanol (10 ml) and water (1.2 ml). The solution was stirred one hour at 5°–10° and the solvent was removed on the rotary evaporator. The residue was dissolved in boiling water (20 ml), filtered and the cooled filtrate acidified to pH 2.8 with 6N hydrochloric acid. The solid thioacid 16c was collected by filtration and dried in a stream of nitrogen. Obtained: 1,2 g, 81.5%. δ(ppm, CDCl₃.D₂O): 8.27, 8.10, 7.52, 7.40, CHCl₃ (4H, aromatic), 5.15 (2H, s, benzylic H), 3,47 (2H, t, J=6, β-H), 2.90 (2H, t, J=6, α-H).

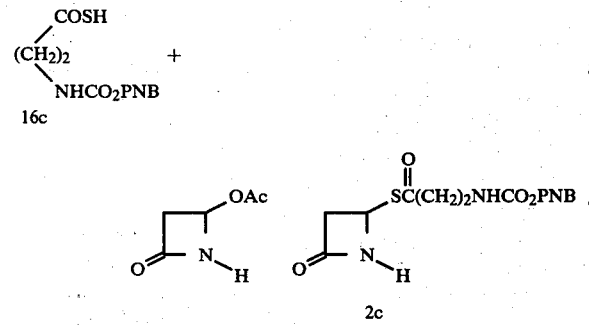

A solution of 16c (potassium salt) (3 mmole) and 4-acetoxy-2-azetidinone (0.2 g, 1.5 mmole) in ethanol (60 ml) was heated under reflux for 2 h. Concentration and chromatography over silica gel afforded pure 2c as a yellow oil. 0.16 g, 30%, Rf=0.3 (ether). δ(ppm, CDCl₃): 8.25, 8.10, 7.55, 7.40 (4H, aromatic), 7.28 and 5.88 (2H, exchange for D, N—H), 5.20 (3H, m, H-4 and benzylic H), 3.50 and 2.8 (6H, m, H-3,αand β-H). $\nu_{c=o}$=1770, 1690 cm⁻¹.

14c→[15c→16c→] 2c

[Preferentially the sequence 14c→2c is carried out as follows:

Thionyl chloride (0.7 g, 0.43 ml, 6 mmole) was added, dropwise, to an ice-bath cooled solution of 14c (1.34 g, 5 mmole) and triethylamine (0.5 g, 0.7 ml, 5 mmole) in methylene chloride (50 ml). The mixture was stirred at 0° for 30 min and concentrated on the rotary evaporator to leave crude 15c as an oil.

The oil was dissolved in methylene chloride (20 ml) and added to an ice-cold solution freshly prepared by bubbling hydrogen sulfide for 5 min. through a solution of triethylamine (1g, 1.4 ml, 10 mmole) in methylene chloride (20 ml). The mixture was stirred at 0° for 30 min. and concentrated on the rotary evaporator to leave crude 16c as an oil.

The oil was dissolved in water (40 ml) and acetone (30 ml) and cooled to 0°. Triethylamine (0.5 g, 0.7 ml, 5 mmole) was added followed by a solution of 4-acetoxy-2-azetidinone 1 (0.67 g, 5.2 mmole) in water (2 ml). The solution was stirred 2 h, the acetone removed in a vacuum and the aqueous solution extracted with methylene chloride. The combined organic extracts were washed with ice-cold 1N hydrochloric acid, dried cover magnesium sulfate and concentrated on the rotary evaporator to leave crude 2c as an oil. Purification by column chromatography afforded pure 2c, (1 g, 56%).]

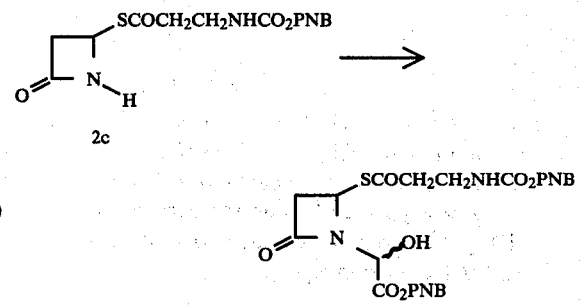

A solution of the lactam 2c (2.75 g, 7.8 mmole) and p-nitrobenzyl glyoxylate monohydrate (1.86 g, 8.2 mmole) in benzene (80 ml) was refluxed for 18 h in a Dean-Stark apparatus filled with molecular sieves. Concentration on the rotary evaporator left the crude 3c as an oil showing one major spot on TLC(Rf=0.5 CHCl₃:CH₃OH,9:1). 4.5 g, 100%, δ(ppm, CDCl₃): 8.25, 8.12, 7.55, 7.40 (8H, aromatic), 5.3 (8H,m), 3.5 and 2.8 (6H, m). $\nu_{c=o}$ =1760–1690 cm⁻¹.

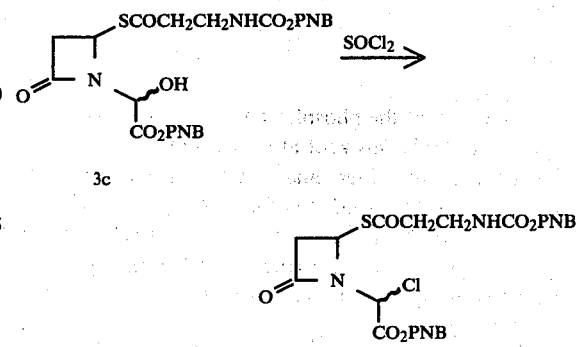

A solution of 3c (4.50 g, 7.8 mmole) and pyridine (0.656 g, 8.2 mmole) in anhydrous THF (70 ml) was cooled to −10°. Thionyl chloride (0.976 g, 8.2 mmole) in THF (3 ml) was added dropwise and the resulting mixture was stirred 0.5 h at 31 10°. The spearated pyridine hydrochloride was removed by filtration and washed with a little toluene. The combined filtrates were concentrated on the rotary evaporator and the residue (dissolved in a little chloroform) was filtered through a silica gel pad. Concentration of the filtrates left 4c as a yellow oil. 4.35 g δ(ppm, CDCl₃): 8.27, 8.10, 7.52, 7.40 (8H, aromatic), 6.17 (1H, δ, CHCl), 5.8 to 5.1 (6H, m) 3.9 to 2.5 (6H, m).

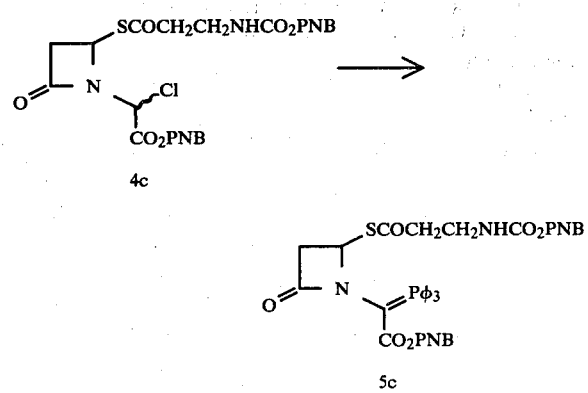

A solution of the chloro derivative 4c (4.35 g), triphenyl phosphine (2.62 g, 10 mmoles) in dioxane (50 ml) was kept at 50° for 18 h. Removal of the solvent left an oil which was purified by chromatography over silica gel (100 g) to give pure 5c as a yellow oil. 4.04 g, 64%, Rf=0.4 (CHCl₃:EtOAc, 1:1).

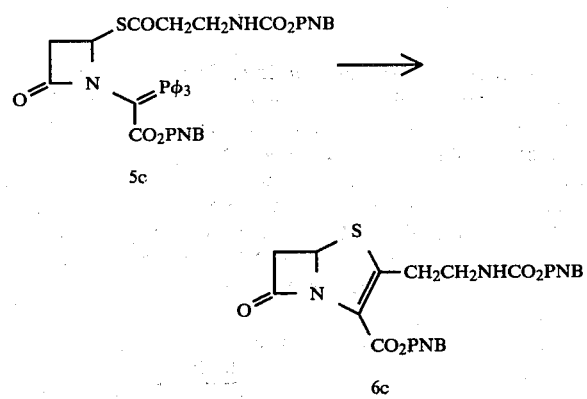

A solution of the phosphorane 5c (4.04 g, 5 mmole) in toluene (50 ml) was kept at reflux temperature for 3 h. Removal of the solvent and chromatography over silica gel afforded 0.85 g (32%) of pure 6c as a yellow solid, m.p. 128°–131°. δ(ppm, CDCl₃): 8.29, 8.16, 7.68, 7.56, 7.42, 7.38, 7.30 (9H, aromatic and N—H) 5.68 (1H, dd, H-5), 5.2 (6H, m), 4.1 to 2.7 (6H, m). $\nu_{C=O}$ 1800, 1775, 1695 cm⁻¹.

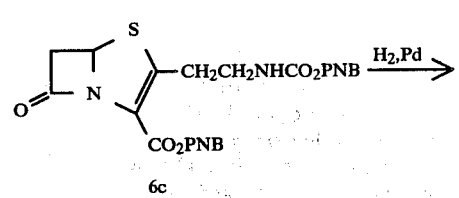

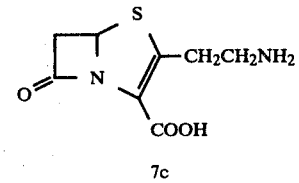

A mixture of the ester 6c (310 mg. 0.58 mmole), ethyl acetate (25 ml), water (12 ml) and palladium on charcoal (10%, 320 mg) was hydrogenated in the Parr shaker at an initial pressure of 30 psi of hydrogen. After 2.5 h, the catalyst was removed by filtration. The aqueous phase was decanted and lyophilized to give a white solid. Obtained: 25.5 mg, 21%. $\lambda_{max}$258 (ε1,330), 302 (ε1,682) (H₂O).

EXAMPLE 25

Sodium 2-(2′-Acetamido-1′-ethyl)penem-3-carboxylate

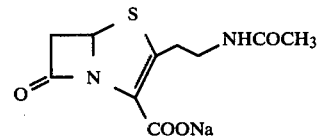

$$NH_2CH_2CH_2COOH \xrightarrow[100\%]{Ac_2O/AcOH}$$

8

CH₃CONHCH₂CH₂COOH

1

β-alanine (8) (44.5 g, 0.5 mole) is placed in a 1 l Erlenmeyer flask provided with calcium chloride drying tube. The amino acid is mixed with 450 ml of c.p. glacial acetic acid and brought to a boil, with gentle agitation on a hot plate. The mixture is removed from the hot plate to cool for two minutes and 75 ml (0.75 mole) of acetic anhydride is carefully added in portions so as to avoid superheating and explosive boiling. The resulting solution is returned to the hot plate, brought to the boiling point, held at this point for two minutes longer, and then allowed to cool to room temperature. The solution is then evaporated in vacuo at 40° to a syrup and the residue treated several times with water followed each time by evaporation in vacuo at 40°. After the final evaporation with the aid of benzene to remove the last traces of water, the syrup residue crystallizes. The crude solid was triturated with a mixture of acetone-benzene to obtian a white solid, m.p. 75°–79°. This compound is identical to the one described by E. J. King and G. H. King, J. Am. Chem. Soc., 78, 1089 (1958); m. p. 78.3°–80.3°.

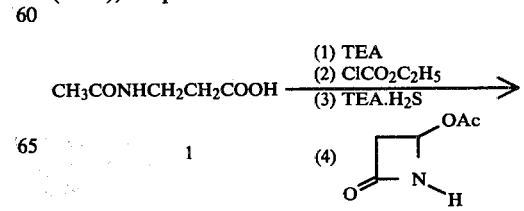

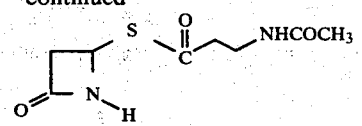

A solution of the acid 1 (3.93 g, 30 mmoles) in methylene chloride (80 ml) and triethylamine (6.07 g, 8.36 ml, 60 mmoles) was cooled to −10° and a solution of ethyl chloroformate (3.36 g, 2.96 ml, 31 mmoles) in methylene chloride (20 ml) was added. The resulting mixture was stirred at −10° for 1 h and then saturated with hydrogen sulfide during 20 min; the resulting reaction mixture was brought to 25° and stirred for 1 h under a nitrogen atmosphere. The methylene chloride was evaporated and the residue was dissolved with an aqueous solution (60 ml) of sodium bicarbonate (3.36 g, 40 mmoles), stirred at 25° until evolution of carbon dioxide was completed ($\simeq$10 min) and added (10–15 min) to an aqueous solution (60 ml) of 4-acetoxy-2-azetidinone (3.61 g, 29 mmoles). The reaction mixture was stirred for 2–3 h and extracted with ethyl acetate (8×100 ml). The organic extracts were combined, dried over anhydrous sodium sulfate and concentrated. The residue was purified by chromatography over silica gel (chloroform:methanol, 10:1), Rf - 0.4, 1.02 g, 17%. Recrystallization from EtOAc gave analytical sample: calc'd for $C_8H_{12}N_2O_3S$; C 44.43, H 5.59, N 12.95, S 14.83; found: C 44.46, H, 5.55, N 13.08, S 14.50. NMR (CDCl₃) δ: 7.40 (1H, NH, 6.80 (1H, NHCOCH₃), 5.20 (1H, m, H-4) 3.70–3.35, 3.10–2.78 (6H, m, SCH₂CH₂N and H-3 cis and trans), 2.00 (3H, s, CH₃CO). IR (CHCl₃) cm⁻¹:1515 (amide II), 1670 (C=O of thioester and amide, 1770 (C=O of β-lactam).

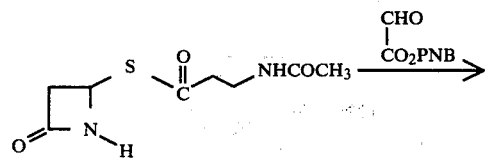

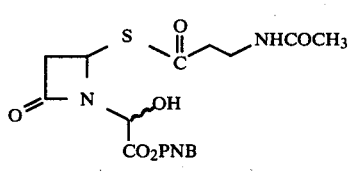

A mixture of azetidinone 2 (4.12 g, 19.1 mmoles), glycidic ester (4.40 g, 19.4 mmoles) in benzene (80 ml) and THF (50 ml) was refluxed through a Dean-Stark trap filled with 3A molecular sieves overnight. Evaporation of the solvents afforded an oily residue (8.6 g, 100%). NMR (CDCl₃) δ: 8.20 m, 7.55 (4H, aromatic), 5.9, 5.40, 5.30 (5H, m, two benzylic H, H-4, H of glyoxylate and OH), 2.55–3.90 (6H, m, SCH₂CH₂NH and H=3 cis and trans), 1.95 (3H, s, CH₃CO). IR (CHCl₃) cm⁻¹ 1520 (amide II), 1670 (C=O thioester and amide), 1760, 1770 (C=O ester and β-lactam). Mixture of two epimers.

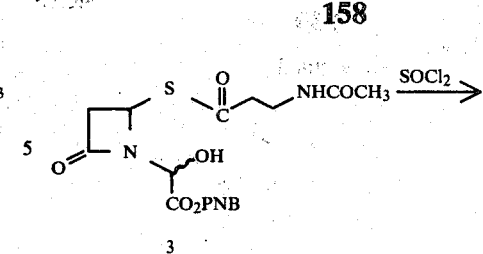

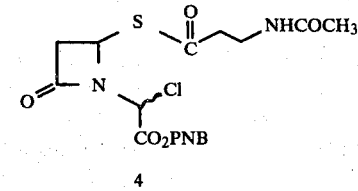

A cold (0°–5°) THF solution (100 ml freshly distilled over LAH) of azetidinone 3 (8.12 g, 19.1 mmoles) was treated with thionyl chloride (2.28 g, 19.4 mmoles) and pyridine (1.52 g, 19.9 mmoles). It was stirred for 1 h at 0°. The precipitate was filtered and THF was evaporated. NMR (CDCl₃) δ: 8.20, 7.55 (4H, aromatic), 6.20, 6.15 (1H, 2s, CHCl), 5.65 (1H, m, H-4), 5.40, 5.35 (3H, 2S, CH₂—PNB and NH), 3.90–2.65 (6H, m, SCH₂CH₂NH and H-3 cis and trans), 2.20, 2.15 (3H, 2s, CH₃CO). IR (CHCl₃) cm⁻¹ 1530 (amideII), 1670 (C=O amide), 1770, 1785 (C=O ester and β-lactam). Mixture of two epimers.

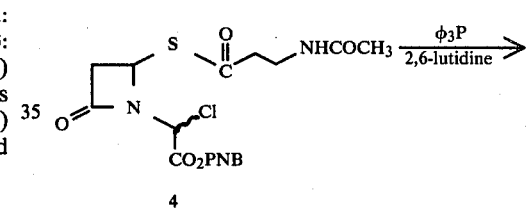

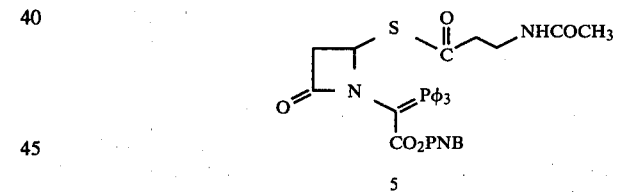

To a solution of chloro-azetidinone 4 (8.50 g, 9.1 mmole) in THF (100 ml) was added triphenyl phosphine (5.11 g, 19.5 mmoles) and 2,6-lutidine (2.04 g, 2.22 ml, 19.5 mmoles). The mixture was stirred for 16 h at room temperature under a nitrogen atmosphere. THF was evaporated and the residue was purified by chromatography over silica gel (150 g). The column was eluted with CHCl₃ (200 ml) CHCl₃: MeOH 50:1 (400 ml) which gave, after combination and evaporation of the appropriate fractions, a solid, 4.28 g, 34%. This compound was used in the next step without any further purification.

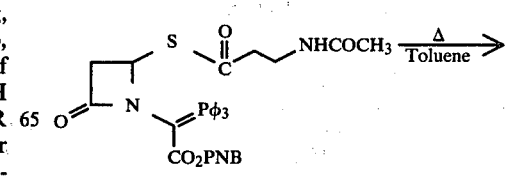

-continued

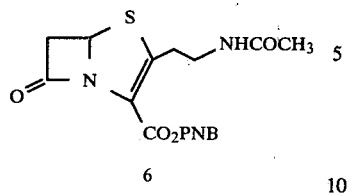

Phosphorane 5 (1.27 g, 1.90 mmole) in toluene was refluxed for 2 h. Toluene was evaporated. The cyclized material was purified through a silica gel (25 g) column and came out with ethyl acetate (430 mg, 60%, m.p. 120°–134°. Analysis calc'd for $C_{17}H_{17}N_3O_6S$: C 52.17, H 4.38, N 10.74, S 8.19. Found: C 51.99, H 4.22, N 10.73, S 8.40. NMR δ (CHCl₃): 8.25, 7.60 (4H, m, aromatic), 6.0 (1H, s, NH), 5.65 (1H, m, H-5), 5.35 (2H, AB type $J_{ab}=14$Hz, CH₂—PNB), 3.80-2.75 (6H, m, SCH₂CH₂NH and H-6 cis and trans), 1.90 (3H, s, CH₃CO). IR (CHCl₃) cm⁻¹. 1525 (amide II), 1670 (amide I), 1710 (C=O ester), 1795 (C=O β-lactam).

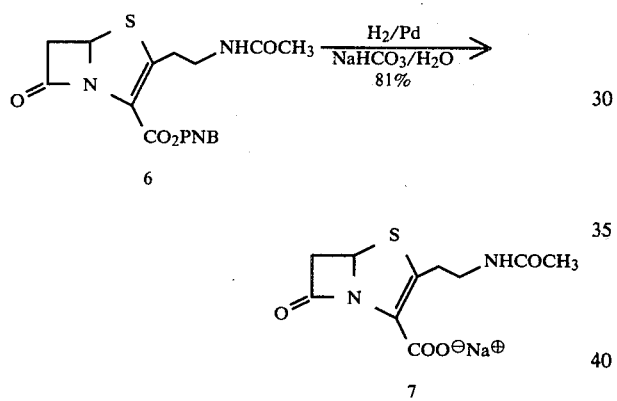

To a solution of the cyclic ester 6 (168 mg, 0.43 mmole) in ethyl acetate (25 ml) was added a solution of sodium bicarbonate (36.1 mg, 0.43 mmole) in water (12 ml) and then 30% palladium on celite (140 mg). The mixture was hydrogenated in the Parr shaker at room temperature and at an initial pressure of 30 p.s.i. of hydrogen. After 4 h the catalyst was removed by filtration. The aqueous layer (decanted) was washed once with diethyl ether and filtered again through a Millipore filter paper to obtain a yellowish solution which was lyophilized, yielding sodium 3-(acetyl-β-alamine)-7-oxo-4-thia-1-azabicyclo [3,2,0]. hept-2-ene-2-carboxylate (7) (96 mg; yield: 81%) as a yellow powder. NMR (DMSO+D₂O) δ: 5.60 (1H, m, H-5), 3.9-2.8 (6H, m, SCH₂CH₂NH, H-6 cis and trans), 1.90 (3H, s, CH₃CO). IR (KBr) cm⁻¹: 1765 (C=O β-lactam,

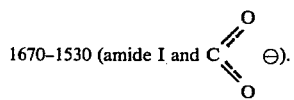

1670–1530 (amide I and C⊖).

UV $\lambda_{max}^{H2O}$ mμ: 258 (ε 3318) and 303 (ε 3991).

EXAMPLE 26

Sodium 2-Hydroxyaminopropylpenem-3-carboxylate

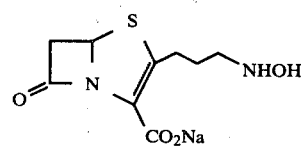

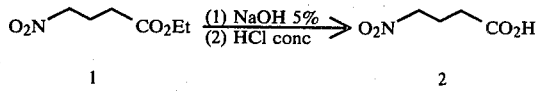

To a cold 5% aqueous solution of sodium hydroxide (320 ml) was added ester 1 (21.6 g, 0.134 mole). The resulting mixture was stirred at room temperature for 2 h and then concentrated to 250 ml and acidified with concentrated HCl. The mixture was extracted with ethyl acetate (4×200 ml) and the organic extracts were dried over sodium sulfate. Concentration on rotary evaporator left an oil. Yield 13.2 g (75%).

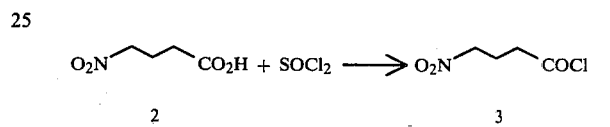

A solution of acid 2 (13.2 g, 0.1 mole) in SOCl₂ (25 ml) was stirred for 2 h at 30° C. After evaporation of thionyl chloride, the residue was distilled under vacuum T=76°–78° C. (P=0.2 mm Hg). Yield 8.8 g (58.3%) as a colourless liquid: n.m.r. (CDCl₃) δ ppm:240 (2H, m, β-CH₂); 3.15 (2H, t, α-CH₂); 4.50 (2H, t, γ-CH₂) i.r. (neat): 1550 cm⁻¹ ($v_{NO_2}$); 1790 cm⁻¹ ($v_{C=O}$, acid chloride).

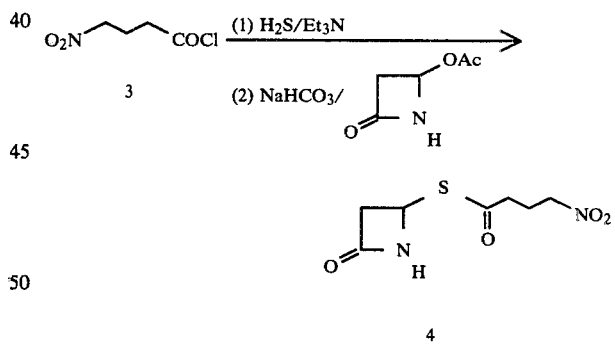

A solution of 3 (19.46 g, 0.128 mole) in methylene chloride (200 ml) was added rapidly to a cold (0°-10°) stirred solution of triethylamine (36 ml, 0.256 mole) in methylene chloride (500 ml) which had been saturated at 0°–5° with H₂S. The mixture was stirred at −10° for 1 h and then a stream of nitrogen was passed through the solution to eliminate the excess of H₂S. The mixture was washed with 10% HCl, the organic extract was concentrated to about 150 ml and then sodium bicarbonate (10.9 g) and water (500 ml) was added. The pH was adjusted to about 7.5 with NaHCO₃ or HCl. The resulting mixture was cooled to 0° C. and 4-acetoxy-2-azetidinone (16.8 g, 0.13 mole) in water (20 ml) was added with vigourous stirring. After 4 h the mixture was extracted with ethyl acetate. The extracts were washed with 10% HCl, sat. NaHCO₃, brine, dried (Na₂SO₄) and evaporated. The residue was purified by column chromatography (SiO₂; eluent: ether then ether-ethyl acetate 5%) giving an oil which crystallized in ethyl acetate-hexanes yielding 4 (3.5 g, 12.5%) as a white powder. (m.p. 45°–47° C.).

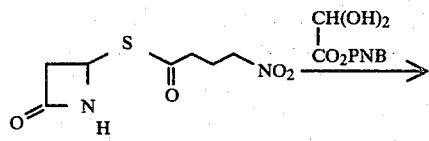

4

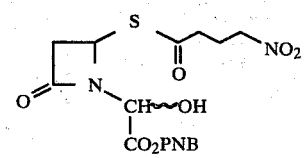

5

A mixture of azetidinone 4 (1.09 g, 5 mmoles) and p-nitrobenzyl glyoxylate hydrate (1.2 g, 5.25 mmoles) in benzene (100 ml) was heated at reflux with a Dean-Stark trap filled with 4A molecular sieves for 18 h. Evaporation of the solvent gave the glyoxylate adduct 5 (2.1 g) as an oil.

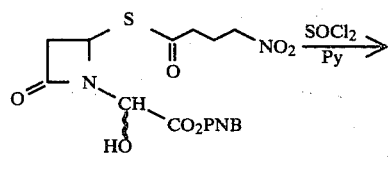

5

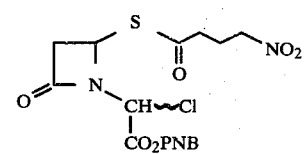

6

Azetidinone glyoxylate 5 (2.1 g) was dissolved in tetrahydrofuran (50 ml) and pyridine (0.57 ml, 7 mmoles) was added to the solution. The mixture was cooled to 0° C. and SOCl₂ (0.5 ml, 7 mmoles) was slowly added. The mixture was stirred 1 h at 0° C. and then filtered before evaporation to dryness. Filtration of this material over a pad of silica gel with CH₂Cl₂ gave a foam; yield 1.9 g (85%).

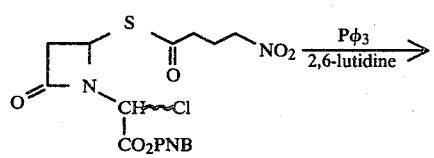

6

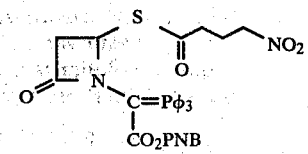

7

To a solution of chloroazetidinone (6.2 g, 14 mmoles) in THF (300 ml) was added triphenyl phosphine (5.5 g, 0.02 mole) and 2,6-lutidine (2.4 ml, 0.02 mole). The mixture was heated at 45° C. for 20 hours. Lutidine hydrochloride was filtered off and washed with ether. The filtrate was then evaporated. The residue was purified by chromatography through a silica gel column and eluted with dichloromethane and dichloromethane-ethylacetate (1:1). Evaporation of eluent gave a white solid (2.9 g, 30%).

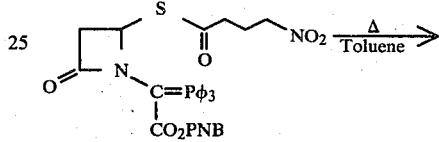

7

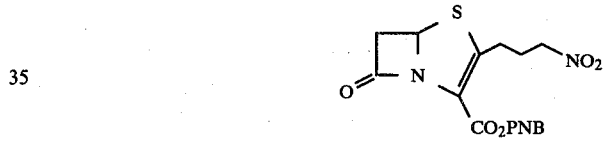

8

Phosphorane 7 (2.0 g, 3 mmoles) in toluene (150 ml) was refluxed for 2.5 h. Evaporation of solvent afforded an oil which was purified by chromatography through a silica gel column and eluted with dichloromethane and dichloromethane-ethylacetate (9:1). Evaporation of the solvent gave a syrup which crystallized in ethylacetate-hexanes as a white solid (0.82 g, 40.7%).

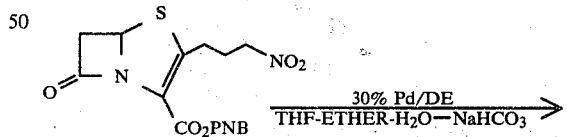

8

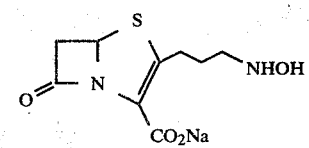

9

To a solution of ester 8 (50 mg, 0.127 mmole) in tetrahydrofuran-ether mixture (2:3, 25 ml) was added water (10 ml), sodium bicarbonate (10 mg, 0.127 mmole) and 30% palladium on diatomaceous earth (50 mg). The reaction mixture was hydrogenated under 50 p.s.i. for 3 h at 25° C., filtered over a celite pad and washed with ether. Aqueous solution was lyophilized yielding a yellow powder (30 mg) of hygroscopic compound.

EXAMPLE 27

The following compounds may be prepared according to the general procedures of Examples 1 and 2.

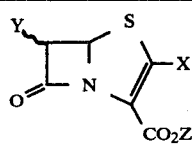

| Y | X | Z |
|---|---|---|
| —C₂H₅ | —C₂H₅ | PNB, H |
| —C₂H₅ | ◁ (cyclopropyl) | PNB, H |
| —C₂H₅ | —φ | PNB, H |
| —C₂H₅ | —CH₂φ | PNB, H |
| —C₂H₅ | —CH₂OCH₃ | PNB, H |
| —C₂H₅ | —CH₂OCH₂φ | PNB, H |
| —C₂H₅ | —CH₂O(CH₂)₂OCH₃ | PNB, H |
| —C₂H₅ | —(CH₂)₂NHAC | PNB, H |
| —C₂H₅ | —(CH₂)₄NPhTh | PNB, H |
| —C₂H₅ | 3-furyl | PNB, H |
| —C₂H₅ | —CH₂-(3-furyl) | PNB, H |
| —C₂H₅ | —CH₂-(3-tetrahydrothienyl) | PNB, H |
| —C₂H₅ | —CH₂SCH₃ | PNB, H |
| —C₃H₇ (iso) | —C₂H₅ | PNB, H |
| —C₃H₇ (iso) | ◁ (cyclopropyl) | PNB, H |
| —C₃H₇ (iso) | —CH₂OCH₃ | PNB, H |
| —C₃H₇ (iso) | —CH₂φ | PNB, H |
| —C₃H₇ (iso) | —CH₂-(2-thienyl) | PNB, H |
| —CH₂φ | —CH₃ | PNB, H |
| —CH₂φ | —CH₂OCH₃ | PNB, H |
| —CH₂φ | 3-furyl | PNB, H |
| —CH₂OAc | —C₂H₅ | PNB, H |
| —CH₂OAc | —CH₂φ | PNB, H |
| —CH₂OAc | —CH₂OCH₃ | PNB, H |
| —CH₂OAc | —CH₂-(3-thienyl) | PNB, H |
| —(CH₂)₂OAc | —CH₃ | PNB, H |
| —(CH₂)₂OAc | —CH₂OCH₃ | PNB, H |
| —(CH₂)₂OAc | —CH₂φ | PNB, H |
| —(CH₂)₂OAc | 3-furyl | PNB, H |
| —CH(CH₃)OAc | —CH₃ | PNB, H |
| —CH(CH₃)OAc | —CH₂OCH₃ | PNB, H |
| —CH(CH₃)OAc | ◁ (cyclopropyl) | PNB, H |
| phenyl | —CH₃ | PNB, H |
| 2-chlorophenyl | —CH₃ | PNB, H |
| 4-methylphenyl | —CH₃ | PNB, H |
| 2-methoxyphenyl | —CH₃ | PNB, H |
| (phenyl) | —CH₃ | PNB, H |
| 4-(trifluoromethyl)phenyl | —CH₃ | PNB, H |
| 2,3,5-trimethylphenyl | —CH₃ | PNB, H |

-continued

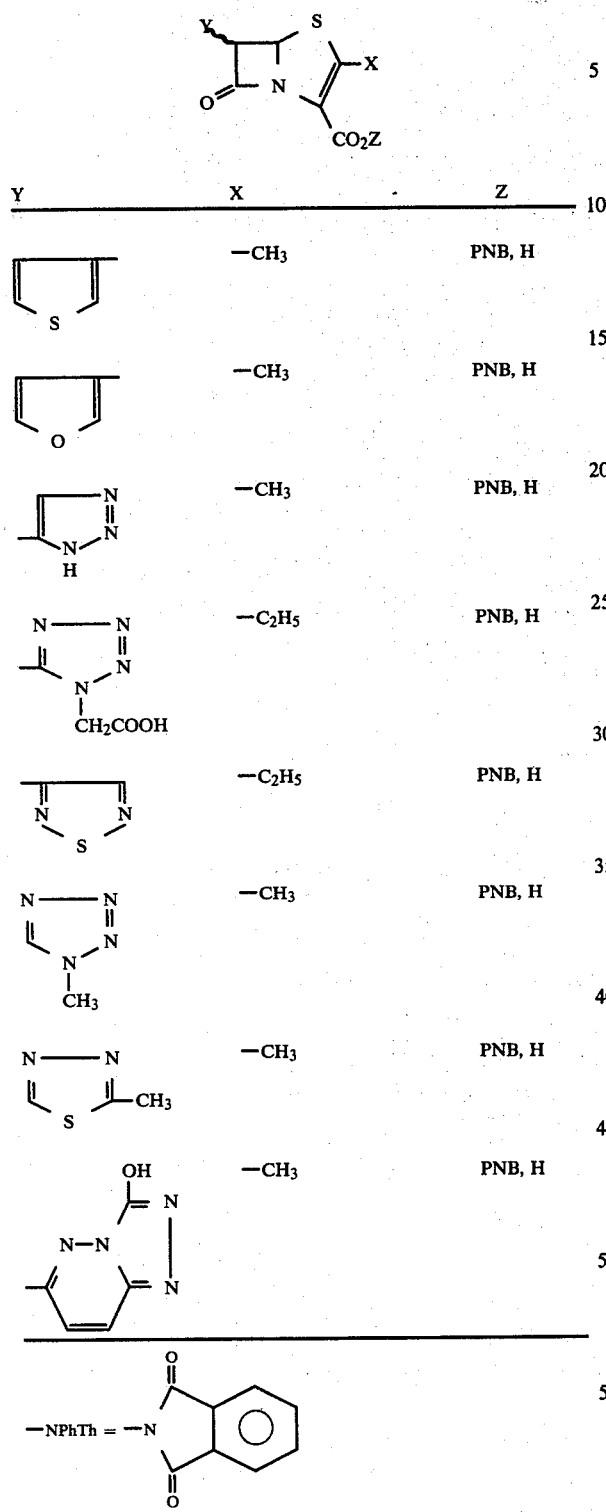

| Y | X | Z |
|---|---|---|
| (thiophene) | —CH₃ | PNB, H |
| (furan) | —CH₃ | PNB, H |
| (triazole-NH) | —CH₃ | PNB, H |
| (tetrazole-CH₂COOH) | —C₂H₅ | PNB, H |
| (thiadiazole) | —C₂H₅ | PNB, H |
| (N-methyl triazole) | —CH₃ | PNB, H |
| (methylthiazole) | —CH₃ | PNB, H |
| (hydroxy-pyridazine-azo) | —CH₃ | PNB, H |

—NPhTh = —N(phthalimido)

EXAMPLE 28

6-Ethyl-2-aminomethylpenem-3-carboxylate Acid (cis and trans isomers)

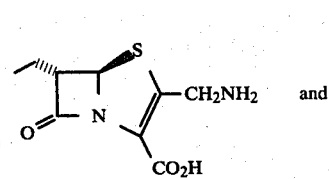 and

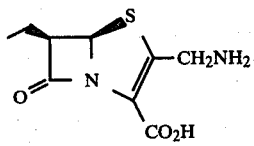

a. Silver cis and trans 3-ethyl-1-(p-nitrobenzyl-2'-triphenylphosphoranyli-dene-2'-acetate)-2-azetidinone-4-thiolates A solution of cis and trans 3-ethyl-1-(p-nitrobenzyl-2'-phosphoranylidene-2'-acetate)-4-acetylthio-2-azetidi-nones (1.88 g., 3.0 mmoles; Example 1, structure 7) in chloroform (4 ml.) was diluted with methanol (90 ml.), cooled to 0° and treated successively with finely powdered silver nitrate (0.51 g., 3.0 mmoles) and potassium carbonate (0.33 g., 2.4 mmoles). The mixture was stirred vigorously 15 min. at 0°, 3 h at room temperature and 1 h at −10° C. The precipitated silver mercaptide was collected by filtration, washed with methanol and with ether and dried in a vacuum. The title product was obtained as a greyish solid, m.p. 112°–135° d. $\nu_{C=O}$ 1750, 1620, 1605.

b. Cis and trans 3-ethyl-1-(p-nitrobenzyl-2'-phosphoranylidene-2'-acetate)-4-azidoacetylthio-2-azetidinones A solution of the above crude mercaptide (1.31 g, 2 mmoles) in dichloromethane (15 ml) was cooled to 0° and treated, under a nitrogen atmosphere, with a 2 M solution of azidoacetyl chloride in dichloromethane (1.13 ml, 2.26 mmoles). The mixture was stirred at 0° for 1 h and at room temperature for 5 h. The insoluble silver salts were removed by filtration over Celite and washed with dichloromethane. The combined filtrates were washed with dilute sodium bicarbonate solution and water, dried and concentrated. The oily residue was purified by chromatography over silica gel (35 g) eluting with ether-ethyl acetate. The pertinent fractions were concentrated to give a mixture of cis and trans acylated compounds as a semi-solid; 0.62 mg. $\nu$ (CDCl₃): 2105, 1760, 1690, 1621 cm⁻¹.

c. Cis and trans p-nitrobenzyl-2-azidomethyl-6-ethylpenem-3-carboxylates

A solution of the above crude phosphorane (0.60 g) in toluene (30 ml) was kept at 105° for 1 h, cooled and concentrated to leave an oily residue which was purified by column chromatography over silica gel (20 g) eluting with increasing proportions of ether in benzene. The pertinent fractions were concentrated to give both the cis and trans isomers.

cis isomer: δ (ppm, CDCl₃): 8.25 (2H, d, J=8.8, Ho of paranitrobenzyl), 7.65 (2H, d, Hm), 5.93 (1H, d, J=4.1, H-5), 5.38 (2H, AB quartet, J=14.0, benzyl), 4.68 (2H, AB quartet, J=15.0, C$H_2$—N$_3$), 3.4 (1H, m, H-6), 2.0 (2H, m, C$H_2$CH$_3$), 1.1 (3H, t, J=7.4, CH$_2$C$H_3$).

trans isomer: δ (ppm, CDCl$_3$): 8.18 (2H, d, J=8.8, Ho), 7.59 (2H, d, Hm), 5.52 (1H, d, J=1.4, H-5), 5.33 (2H, AB quartet, J=14.0, benzyl), 4.58 (2H, AB quartet, J=15.0, C$H_2$—N$_3$), 3.7 (1H, dt, J=1.4, J=7.4, H-6), 1.9 (2H, m, C$H_2$CH$_3$), 1.1 (3H, t, J=7.4, CH$_2$C$H_3$).

d. Trans 2-Aminomethyl-6-ethylpenem-3-carboxylic Acid

A mixture of the above trans p-nitro benzyl ester (0.20 g, 0.5 mmole), THF (6 ml), ether (6 ml), water (12 ml) and 30% palladium on celite (0.20 g) was reduced at 23° for 2.5 h at an initial hydrogen pressure of 30 psi. The catalyst was removed by filtration over celite and washed with water. The combined filtrates were washed with ether-THF and lyophilized to give the crude trans acid (12 mg). Chromatography over a column of Sephadex G-10 eluting with water gave the pure trans acid (6 mg) as a hygroscopic powder. $\nu_{C=O}$ 1775, 1615 cm$^{-1}$. $\lambda_{max}$=306 (ε=3465). δ (ppm, D$_2$O-DMSO): 5.40 (1H, d, J=2.0, H-5), 2.0 (2H, m, C$H_2$CH$_3$), 1.1 (3H, t, J=7.4, CH$_2$C$H_3$).

e. cis 2-Aminomethyl-6-ethylpenem-3-carboxylic Acid

Reduction of the cis-p-nitrobenzyl ester as described above for the trans-ester gave the cis-acid as a yellowish hygroscopic power (13%) $\nu_{C=O}$ 1775, 1615 cm$^{-1}$. $\lambda_{max}$ 304 (ε=3563). δ (ppm, D$_2$O-DMSO): 5.75 (1H, d, J=4.0, H-5), 2.0 (2H, m, C$H_2$CH$_3$), 1.1 (3H, t, J=7.4, CH$_2$C$H_3$).

EXAMPLE 29

The following compounds may be prepared according to the general procedure of Example 28.

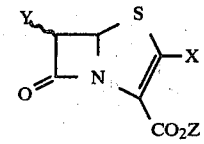

| Acylating Agent | Y | X | Z |
|---|---|---|---|
| CH$_3$COCl | —CH$_3$ | —CH$_3$ | Na, H |
| Ac$_2$O | —CH$_3$ | —CH$_3$ | Na, H |
| CH$_3$CO$_2$SO$_2$CH$_3$ | —CH$_3$ | —CH$_3$ | Na, H |
| C$_2$H$_5$COCl | —CH$_3$ | —C$_2$H$_5$ | Na, H |
| φCH$_2$COCl | —CH$_3$ | —CH$_2$φ | Na, H |
| φOCH$_2$COCl | —CH$_3$ | —CH$_2$Oφ | Na, H |
| ▷—COCl | —CH$_3$ | ◁ | Na, H |
| □—COCl | —CH$_3$ | □ | Na, H |
| (CF$_3$CO)$_2$O | —CH$_3$ | —CF$_3$ | Na |
| C$_2$H$_5$O$_2$C—COCl | —CH$_3$ | —CO$_2$Et | Na |
| pyrazolyl-COCl | —CH$_3$ | pyrazolyl | Na, H |
| thiazolyl-CH$_2$COCl | —CH$_3$ | —CH$_2$-thiazolyl | Na, H |
| N$_3$(CH$_2$)$_2$COCl | —CH$_3$ | —(CH$_2$)$_2$NH$_2$ | H |
| N$_3$(CH$_2$)$_3$COCl | —CH$_3$ | —(CH$_2$)$_3$NH$_2$ | H |
| NC(CH$_2$)$_2$COCl | —CH$_3$ | —(CH$_2$)$_3$NH$_2$ | H |
| O$_2$N(CH$_2$)$_3$COCl | —CH$_3$ | —(CH$_2$)$_3$NHOH | Na, H |
| N$_3$(CH$_2$)$_4$COCl | —CH$_3$ | —(CH$_2$)$_4$NH$_2$ | H |
| N$_3$(CH$_2$)$_2$OCH$_2$COCl | —CH$_3$ | —CH$_2$O(CH$_2$)$_2$NH$_2$ | H |
| N$_3$(CH$_2$)$_2$SCH$_2$COCl | —CH$_3$ | —CH$_2$S(CH$_2$)$_2$NH$_2$ | H |
| AcNH(CH$_2$)$_2$CO$_2$CO$_2$Et | —CH$_3$ | —(CH$_2$)$_2$NHAc | Na, H |
| CH$_3$COCl | —C$_2$H$_5$ | —CH$_3$ | Na, H |
| C$_2$H$_5$COCl | —C$_2$H$_5$ | —C$_2$H$_5$ | Na, H |
| φCH$_2$COCl | —C$_2$H$_5$ | —CH$_2$φ | Na, H |
| φOCH$_2$COCl | —C$_2$H$_5$ | —CH$_2$Oφ | Na, H |
| ▷—COCl | —C$_2$H$_5$ | ◁ | Na, H |
| N$_3$(CH$_2$)$_2$COCl | —C$_2$H$_5$ | —(CH$_2$)$_2$NH$_2$ | H |
| N$_3$(CH$_2$)$_3$COCl | —C$_2$H$_5$ | —(CH$_2$)$_3$NH$_2$ | H |
| O$_2$N(CH$_2$)$_3$COCl | —C$_2$H$_5$ | —(CH$_2$)$_3$NHOH | Na, H |
| N$_3$(CH$_2$)$_4$COCl | —C$_2$H$_5$ | —(CH$_2$)$_4$NH$_2$ | H |
| CH$_3$COCl | iso-C$_3$H$_7$ | —CH$_3$ | Na, H |
| C$_2$H$_5$COCl | iso-C$_3$H$_7$ | —C$_2$H$_5$ | Na, H |
| ▷—COCl | iso-C$_3$H$_7$ | ◁ | Na, H |
| furyl-COCl | iso-C$_3$H$_7$ | furyl | Na, H |
| thienyl-COCl | iso-C$_3$H$_7$ | thienyl | Na, H |
| φCH$_2$COCl | iso-C$_3$H$_7$ | —CH$_2$φ | Na, H |
| N$_3$CH$_2$COCl | iso-C$_3$H$_7$ | —CH$_2$NH$_2$ | H |
| N$_3$(CH$_2$)$_2$COCl | iso-C$_3$H$_7$ | —(CH$_2$)$_2$NH$_2$ | H |
| N$_3$(CH$_2$)$_3$COCl | iso-C$_3$H$_7$ | —(CH$_2$)$_3$NH$_2$ | H |
| O$_2$N(CH$_2$)$_3$COCl | iso-C$_3$H$_7$ | —(CH$_2$)$_3$NHOH | Na, H. |

EXAMPLE 30 cis- and trans-6-Acetoxymethyl-2-aminomethylpenem-3-carboxylic Acid

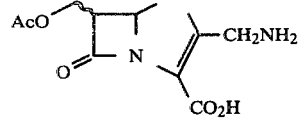

(a) 3-Acetoxymethyl-4-tritylthio-2-azetidinones (cis and trans isomers)

A solution of a mixture of cis and trans 4-acetoxy-3-acetoxymethyl-2-azetidinone (4.7 g, 25 mmoles) (Example 2, structure 26) in water (200 ml) was added rapidly to a vigorously stirred solution of sodium triphenylmethyl mercaptide (from triphenylmethyl mercaptan, 55.2 g; and sodium hydride, 9.6 g, in methanol, 300 ml). The mixture was stirred at room temperature for 4 h and the solids were collected by filtration, washed with water, and dissolved in dichloromethane. The solution was washed with dilute hydrochloric acid, water, aqueous sodium bicarbonate and water, dried and concentrated to leave 85% of a solid which was used as such in the next experiment.

(b) cis and trans 3-Acetoxymethyl-1-(p-nitrobenzyl-2'-hydroxy-2'-acetate)-4-tritylthio-2-azetidinones A solution of the above azetidinone (8.0 g, 20 mmoles) and p-nitrobenzyl glyoxylate (4.54 g, 20 mmoles) were refluxed in benzene (100 ml) through a Dean-Stark water separator filled with 3 Å molecular sieves. After 24 h a second quantity of p-nitrobenzyl glyoxylate (4.54 g) was added and the reflux continued for a further 24 h. The mixture was diluted with ether, washed with 5% aqueous hydrochloric acid, water, aqueous 5% sodium bicarbonate and water. Drying and concentration left 100% of the crude isomeric mixture as an oil.

(c) cis and trans 3-Acetoxymethyl-1-p-nitrobenzyl-2'-chloro-2'-acetate)-4-tritylthio-2-azetidinones A solution of azetidinones from part b (12.2 g, 20 mmoles) and pyridine (1.9 g, 24 mmoles) in dried THF (150 ml) was cooled to $-15°$ and treated dropwise with thionyl chloride (2.86 g, 24 mmoles) under a nitrogen atmosphere. The mixture was stirred 45 min at $-15°$, the precipitate was removed by filtration and washed with benzene, and the filtrates were concentrated to leave a semi-solid (95%).

(d) cis and trans 3-Acetoxymethyl-1-(p-nitrobenzyl-2'-triphenylphosphoranylidene-2'-acetate)-4-tritylthio-2-azetidinones A mixture of azetidinones from step c (12.6 g, 20 mmoles), triphenylphosphine (7.8 g, 30 mmoles) and 2,6-lutidine (2.6 cc, 22 mmoles) in THF (100 ml) was heated under reflux for 80 h. The insoluble material was removed by filtration and washed with ether. The filtrates were washed with 2% aqueous hydrochloric acid, 5% aqueous sodium bicarbonate and water, dried and concentrated. The residue was dissolved in benzene, filtered slowly through a pad of silica gel (250 g) and the pad was eluted with increasing proportions of ether in benzene. Concentration of the pertinent fractions gave a mixture of the title compounds (65%). $v_{c=o}$ 1740, $v_{c=P\phi_3}$ 1620, 1610, $v_{NO_2}$ 1525 cm$^{-1}$.

(e) Silver cis and trans 3-Acetoxymethyl-1-(p-nitrobenzyl-2'-triphenylphosphornaylidene-2'-acetate)-2-azetidinone-4-thiolates The crude azetidinones from step d (8.5 g, 10 mmoles) were dissolved in hot methanol (55°–60°). A hot solution (55°–60°) of silver nitrate (2.04 g; 12 mmoles) and pyridine (0.87 g, 11 mmoles) in methanol (80 ml) was added. The mixture was allowed to cool down to room temperature in 2 h and stirred a further 1 h at 0°. The silver mercaptide was collected by filtration, washed with ice-cold methanol and then with ether (5.7 g, 82%, melts with decomposition). $v_{c=o}$ 1745, 1740, 1625 cm$^{-1}$.

(f) cis and trans 3-Acetoxymethyl-4-azidoacetylthio-1-(p-nitrobenzyl-2'-triphenylphosphoranylidene-2'-acetate)-2-azetidinones The above silver mercaptide (from step e; 1.4 g, 2 mmoles) in dichloromethane (15 ml) treated as described in Example 28 with azidoacetylochloride (2.3 mmoles) gave 0.78 g of a yellow powder.

(g) cis and trans 6-Acetoxymethyl-2-azidomethylpenem-3-carboxylic Acid p-Nitrobenzyl Esters A solution of the above crude phosphorane (0.70 mg) in toluene (35 ml) was kept at 105° for 1 h, cooled and concentrated to leave an oil which was purified by chromatography over silica gel (25 g) eluting with increasing proportions of ether in benzene. The pertinent fractions were concentrated to give the cis and trans-isomers of the title compound.

cis isomer: δ (ppm, CDCl$_3$): 8.5–7.5 (4H, aromatics), 5.67 (1H, d, J=5, H-5), 5.31 (2H, AB quartet, CH$_2$-benzyl), 4.50 (2H, AB quartet, C$\underline{H}_2$N$_3$), 4.33 (2H, d, AcOC$\underline{H}_2$), 4.26 (1H, dt, H-6), 2.0 (3H, s, CH$_3$).

trans isomer: δ (ppm, CDCl$_3$): 8.5–7.5 (4H, aromatics), 5.62 (1H, d, J=2, H-5), 5.33 (2H, AB quartet, CH$_2$-benzyl), 4.40 (1H, dt, H-6), 4.50 (2H, AB quartet, C$\underline{H}_2$N$_3$), 4.27 (2H, d, AcOC$\underline{H}_2$), 2.0 (3H, s, CH$_3$).

(h) trans 6-Acetoxymethyl-2-aminomethylpenem-3-carboxylic Acid

Hydrogenation of the above trans isomer by the procedure described in Example 28 gave the title compound. $v_{c=o}$ 1775, 1740, 1616 cm$^{-1}$. $\lambda_{max}$ 304 ($\epsilon$=3192).

(i) cis 6-Acetoxymethyl-2-aminomethylpenem-3-carboxylic Acid

Hydrogenation of the corresponding cis isomer as described in Example 28 gave the title compound as an unstable hygroscopic semi-solid.

EXAMPLE 31

The following compounds may be prepared according to the general procedure of Example 30.

| Acylating Agent | Y | X | Z |
|---|---|---|---|
| CH$_3$COCl | —CH$_2$OAc | —CH$_3$ | H |
| C$_2$H$_5$COCl | —CH$_2$OAc | —C$_2$H$_5$ | H |
| ◁—COCl | —CH$_2$OAc | ◁ | H |
| (furyl)—COCl | —CH$_2$OAc | (furyl) | H |

-continued

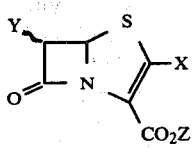

| Acylating Agent | Y | X | Z |
|---|---|---|---|
| 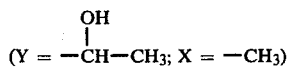 | —CH₂OAc | 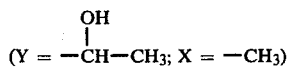 | H |
| N₃(CH₂)₂COCl | —CH₂OAc | —(CH₂)₂NH₂ | H |
| N₃(CH₂)₃COCl | —CH₂OAc | —(CH₂)₃NH₂ | H |
| N₃(CH₂)₄COCl | —CH₂OAc | —(CH₂)₄NH₂ | H |
| O₂N(CH₂)₃COCl | —CH₂OAc | —(CH₂)₃NHOH | H |
| CH₃COCl | —(CH₂)₂OAc | —CH₃ | H |
| 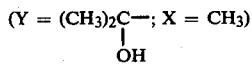—COCl | —(CH₂)₂OAc | —◁ | H |
| N₃CH₂COCl | —(CH₂)₂OAc | —CH₂NH₂ | H |
| N₃(CH₂)₂COCl | —(CH₂)₂OAc | —(CH₂)₂NH₂ | H |
| N₃(CH₂)₃COCl | —(CH₂)₂OAc | —(CH₂)₃NH₂ | H |
| CH₃COCl | CH₃<br>\|<br>—CH—OAc | —CH₃ | H |
| N₃CH₂COCl | CH₃<br>\|<br>—CH—OAc | —CH₂NH₂ | H |

EXAMPLE 32 trans
6-(2'-Hydroxy-2'-propyl)-2-methylpenem-3-carboxylic Acid (Y = (CH₃)₂C—; X = CH₃)
        |
        OH To a solution of 2-methylpenem-3-carboxylic acid (100 mg, 0.54 mmoles) in THF (8 ml) was added at 0°-5° diisopropylamine (0.16 ml, 1.14 mmoles). The solution was cooled to −78° and n-butyl lithium (0.75 ml, 1.20 mmoles) was added. The mixture was stirred at −78° for 5 min. Acetone (1 ml) was added and the solution was stirred for 10 min at −78°. The solution was neutralized with 0.1 N hydrochloric acid (12 ml) and extracted with ethyl acetate (3×20 ml). Concentration of the washed (brine) and dried ethyl acetate phase gave a yellow oil (59 mg). Trituration of this oil with ether, with chloroform and again with ether gave the title compound as a white solid (8 mg, 23%). m.p. 117°-121°, $v_{C=O}$ 1765, 1660 cm⁻¹; $v_{O-H}$ 3500 (broad cm⁻¹). $\lambda_{max}$ 265 ($\epsilon$=3400), 309 ($\epsilon$=5700) δ (ppm, acetone d₆): 5.63 (1H, d, J=1.8, H-5), 3.77 (1H, d, J=1.8, H-6), 2.35 (3H, s, CH₃), 1.35 (3H, s, CH₃), 1.30 (3H, s, CH₃).

EXAMPLE 33 cis and trans
6-(1'-Hydroxy-1'-ethyl)-2-methylpenem-3-carboxylic Acid, Sodium Salts

OH
      |
(Y = —CH—CH₃; X = —CH₃)

To a solution of 2-methylpenem-3-carboxylic acid (100 mg, 0.54 mmoles) in THF (8 ml) was added diisopropylamine (0.08 ml, 0.57 mmoles) at 0° and n-butyl lithium (0.75 ml, 1.20 mmoles) at −78°. After stirring 2 min at −78°, freshly distilled acetylaldehyde (0.5 ml) was added and stirring was continued for 10 min. The reaction mixture was quenched with a saturated ammonium chloride solution (10 ml) and washed with ethyl acetate. The aqueous layer was acidified with 0.1 N hydrochloric acid (18 ml) and extracted with ethyl acetate (3×20 ml). Concentration of the dried ethyl acetate phases left an oil (49 mg). The oil was dissolved in methylisobutyl ketone and treated with an excess of sodium methylhexanoate in the same solvent. Addition of ether precipitated the title compounds as a white amorphous solid (25 mg). δ (ppm, D₂O): 5.6–5.83 (1H, m, H-5, cis and trans), 2.27 (3H, s, CH₃), 1.22 and 0.90 (3H, 2d, CH₃).

EXAMPLE 34 cis
6-(1'-Hydroxy-1'-ethyl)-2-methylpenem-3-carboxylic Acid, Sodium Salt (isomer "D")

2-Methylpenem-3-carboxylic acid (100 mg) was treated with LDCA and acetaldehyde as described in Example 33. The residue (58 mg), obtained after concentration of the dried ethyl acetate phases, was extracted with ether and the ether solution concentrated to an oil (48 mg). This oil was converted to a sodium salt with sodium methyl hexanoate as described in Example 33. This yielded 29 mg of a white solid which was identified as cis-6-(1'-hydroxy-1'-ethyl)-2-methylpenem-3-carboxylic acid, sodium salt, contaminated with a little sodium 5-methyl-1,3-thiazole-4-carboxylate. δ (ppm, DMSO-d₆): 5.5 (1H, d, J=4.1, H-5), 2.22 (3H, s, CH₃), 1.02 (3H, d, J=5.5, CH₃).

EXAMPLE 35 cis and trans
6-(2'-Hydroxy-2'-propyl)-2-ethylpenem-3-carboxylic Acids, Potassium Salts (Y = (CH₃)₂C—; X = —C₂H₅)
        |
        OH Substitution in the general procedure of Example 3 for the 2-methylpenem-3-carboxylic acid used therein of an equimolar amount of 2-ethylpenem-3-carboxylic acid gave a mixture of potassium salts. δ (ppm, DMSOd₆): 5.60 and 5.56 (1H, 2d, J=4 and J=2, H-5), 3.92 and 3.60 (1H, 2d, J=4 and J=2, H-6), 2.88 and 2.86 (2H, 2q, CH₂—CH₃), 1.47, 1.41, 1.36 and 1.32 (6H, 4s, CH₃), 1.2 and 1.4 (3H, 2t, CH₂CH₃). $\lambda_{max}$ 257 ($\epsilon$=3705) and 302 ($\epsilon$=3815).

The 2-ethylpenem-3-carboxylic acid used above was prepared according to the method of Preparation 10.

EXAMPLE 36 cis and trans 6-(1'-Hydroxy-1'-ethyl)-2-methoxymethylpenem-3-carboxylic Acid, Sodium Salts To a solution of 2-methoxymethylpenem-3-carboxylic acid (see Preparation 6; 116 mg, 0.55 mmoles) in THF (10 ml) was added diisopropylamine (0.08 ml, 0.57 mmoles) at 0° and n-butyl lithium (0.72 ml, 1.20 mmoles) at −78°. After stirring 2 min at −78° freshly distilled acetaldehyde (0.5 ml) was added and stirring was continued for 10 min. The reaction mixture was quenched with a saturated ammonium chloride solution (10 ml) and washed with ethyl acetate. The aqueous layer was acidified with hydrochloric acid (0.1 N, 18 ml) and extracted with ethyl acetate (3×20 ml). Concentration of the dried ethyl acetate phases left an oil (53 mg) which was converted to a mixture of the sodium salts of the title compounds as described in Example 33. White amorphous hygroscopic powder (21 mg). δ (ppm, $D_2O$): 5.7–5.85 (1H, m, H-5, cis and trans) 3.38 (3H, 2s, $OCH_3$), 1.22 and 0.92 (3H, 2d, $CH_3$). $\nu_{c=o}$ 1770, 1600 cm$^{-1}$.

The 2-methoxymethylpenem-3-carboxylic acid used above was prepared according to the method of Preparation 6.

EXAMPLE 37 cis and trans 6-Acetyl-2-methylpenem-3-carboxylic Acid, Sodium Salts

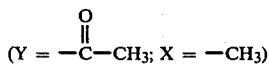

To a solution of 2-methylpenem-3-carboxylic acid (100 mg, 0.54 mmoles) in THF (10 ml) was added diisopropylamine (0.08 ml, 0.57 mmoles) at 0° and n-butyl lithium (0.75 ml, 1.20 mmoles) at −78°. After stirring for 2 min at −78°, ethyl acetate (1 ml) was added and stirring was continued for 10 min. The reaction mixture was quenched with a saturated ammonium chloride solution (10 ml) and washed with ethyl acetate. The aqueous layer was carefully acidified at 0° with 0.1 N hydrochloric acid and extracted rapidly with ethyl acetate (3×20 ml). Concentration of the dried extracts left an oil (36 mg) which was converted to the title compounds as described in Example 33. δ (ppm, $D_2O$): 5.90–6.10 (1H, 2d, J=4, J=2, H-5), 3.8 (1H, m, H-6 cis and trans), 2.34 and 2.27 (3H, 2s, $CH_3$), 2.12 and 2.0 (3H, 2s, $CH_3$).

EXAMPLE 38

The following compounds may be prepared according to the general procedures of Examples 3–5 and 32–37.

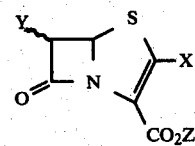

| X | Y | Z |
|---|---|---|
| $-CH_3$ | OH<br>\|<br>$-CH-C_6H_4-OCH_3$ | K |
| $-CH_3$ | OH<br>\|<br>$-CH-nBu$ | Na |
| $-CH_3$ | O<br>‖<br>$-C-\phi$ | Na |
| $-CH_3$ | $-CH_2OH$ | Na |
| $-CH_3$ | OH<br>\|<br>$-CHCF_3$ | Na |
| $-C_2H_5$ | $-SCH_3$ | K |
| $-C_2H_5$ | $-SOCH_3$ | K |
| $-C_2H_5$ | OH<br>\|<br>$-C-CH_3$ | Na |
| $-C_2H_5$ | O<br>‖<br>$-C-CH_3$ | Na |
| $-C_6H_5$ | OH<br>\|<br>$-CH-CH_3$ | Na |
| $-C_6H_5$ | OH<br>\|<br>$-C(CH_3)_2$ | K |
| $-C_6H_5$ | O<br>‖<br>$-C-CH_3$ | Na |
| furyl | OH<br>\|<br>$-CH.CH_3$ | Na |
| $-CH_2OCH_3$ | OH<br>\|<br>$-C(CH_3)_2$ | K |
| $-CH_2OCH_3$ | OH<br>\|<br>$-C-\phi$ | K |
| $-CH_2OCH_3$ | O<br>‖<br>$-C-CH_3$ | Na |
| $-CH_2OCH_3$ | O<br>‖<br>$-C-\phi$ | Na |
| $-CH_2SCH_3$ | OH<br>\|<br>$-CHCH_3$ | Na |
| $-CH_2-C(CH_3)(O-CH_2-CH_2-O)$ | OH<br>\|<br>$-C-(CH_3)_2$ | K |

EXAMPLE 39 cis and trans 2-Cyclopropyl-6-(2'-hydroxy-2'-propyl)penem-3-carboxylic Acids, Potassium Salts

(a) Silver 1-(p-nitrobenzyl-2'-triphenylphosphoranylidene-2'-acetate)-2-azetidinone-4-thiolate This was prepared according to the method of Example 7.

(b) 2-Cyclopropylpenem-3-carboxylic Acid

This was prepared from the silver mercaptide intermediate of step (a) according to the method of Example 14.

(c) cis and trans 2-Cyclopropyl-6-(2'-hydroxy-2'-propyl)penem-3-carboxylic Acid, Potassium Salts Following the procedure of Example 3, the title compounds were obtained as a white hygroscopic powder from the acid of step b. δ (ppm, $D_2O$): 5.51 and 5.46 (1H, 2d, J=4, J=2, H-5), 3.90 and 3.61 (1H, 2d, H-6), 3.2–2.75 (1H, m), 1.5–0.6 (10H, m). $\nu_{c=o}$ 1775, 1670 cm$^{-1}$.

EXAMPLE 40 cis and trans 6-(2'-Hydroxy-2'-propyl)penem-3-carboxylic Acids, Potassium Salts

(a) 2-H-Penem-3-carboxylic Acid

This was prepared from the silver mercaptide intermediate by the method of Example 19.

(b) cis and trans 6-(2'-Hydroxy-2'-propyl)penem-3-carboxylic Acid, Potassium Salts Following the general procedure of Example 3, the title compounds were obtained as a white hygroscopic powder from the acid of step (a). δ (ppm, $D_2O$): 8.54 (1H, H-2), 5.69 and 5.64 (1H, 2d, J=2, J=4, H-5), 4.13 and 3.82 (1H, 2d, H-6), 1.47–1.30 (6H, 2CH$_3$).

EXAMPLE 41

The following compounds may be prepared according to the general procedure of Example 39.

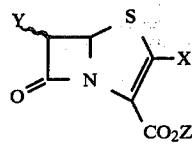

| X | Y | Z |
|---|---|---|
| —H | OH<br>\|<br>—CHCH$_3$ | Na |
| —H | OH<br>\|<br>—CH—φ | K |
| —H | OH<br>\|<br>—CH—C$_6$H$_4$OCH$_3$ | Na |

-continued

| X | Y | Z |
|---|---|---|
| —H | OH<br>\|<br>—CH—n-C$_3$H$_7$ | Na |
| —H | OH<br>\|<br>—CH—CF$_3$ | Na |
| —H | —CH$_2$OH | Na |
| —H | O<br>\|\|<br>—C—CH$_3$ | Na |
| —H | O<br>\|\|<br>—C—φ | Na |
| —H | —SCH$_3$ | K |
| ◁ | OH<br>\|<br>—CHCH$_3$ | Na |
| ◁ | OH<br>\|<br>—CH—φ | K |
| ◁ | O<br>\|\|<br>—C—CH$_3$ | Na |
| □ | OH<br>\|<br>—CH—CH$_3$ | Na |
| —CH$_2$Oφ | OH<br>\|<br>—CH—CH$_3$ | Na |
| —CH$_2$Oφ | OH<br>\|<br>—CH—φ | K |
| —CH$_2$Oφ | OH<br>\|<br>—CH(CH$_3$)$_2$ | K |

EXAMPLE 42 cis and trans 6-(2'-Hydroxy-2'-propyl)-2-methylpenem-3-carboxylic Acids, Potassium Salts The products of Example 3 may be prepared by the alternative procedure indicated below.

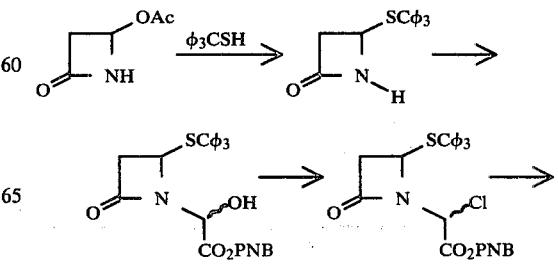

-continued

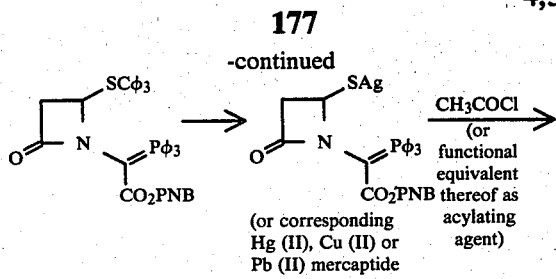

(or corresponding Hg (II), Cu (II) or Pb (II) mercaptide)

(or functional equivalent thereof as acylating agent)

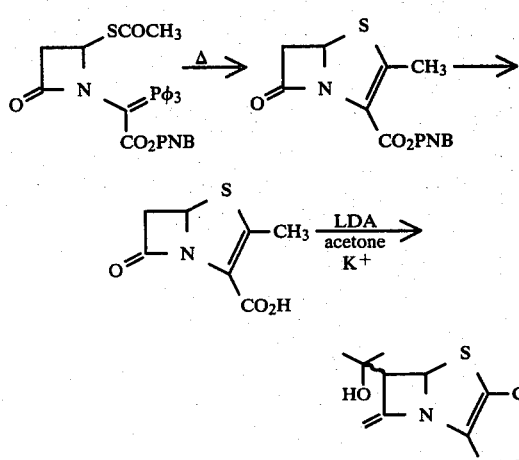

All of the compounds prepared by the procedures of Examples 3-5 and 32-41 may also be prepared by the procedure of Example 42.

EXAMPLE 43

2-(4'-Phthalimido-1'-butyl)penem-3-carboxylic Acid

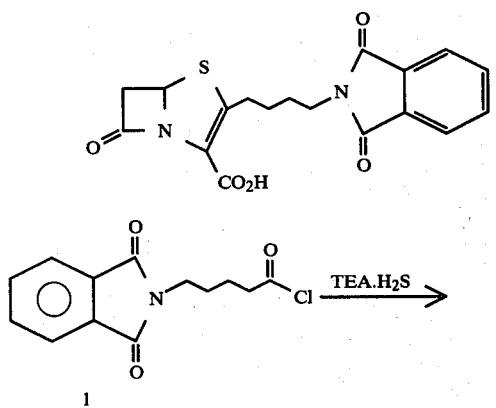

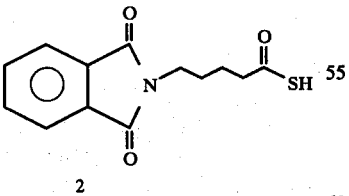

To a solution of triethylamine hydrosulfide, previously prepared by bubbling H$_2$S gas through a methylene chloride (200 ml) solution of triethylamine (8.8 ml, 63.7 mmoles), was added dropwise a methylene chloride (75 ml) solution of 1 (Gabriel Ber. 41, 2010) (10.65 g, 40.2 mmoles), at 0° C. over a 30 min period. The mixture was stirred at 0° C. for 15 min and 2 h at room temperature. The Organic solution was diluted with methylene chloride (125 ml) and washed with 1 N HCl (2×15 ml), water (2×15 ml) and brine. It was dried over MgSO$_4$ and the solvent was flashed down to give 10.5 g (100%) of 2 as a white solid. m.p.: 93°-94° C. n.m.r. (CDCl$_3$) δ 7.5-8 (4H, m), 4.47 (1H, broad s), 3.5-3.9 (2H, m), 2.5-2.9 (2H, m), 1.4-1.9 (4H, m). Anal. Calc'd for C$_{13}$H$_{13}$NO$_3$S: C, 59.29; H, 4.97; N, 5.32; S, 1217. Found: C, 58.92; H, 4.91, N, 5.42; S, 12.31.

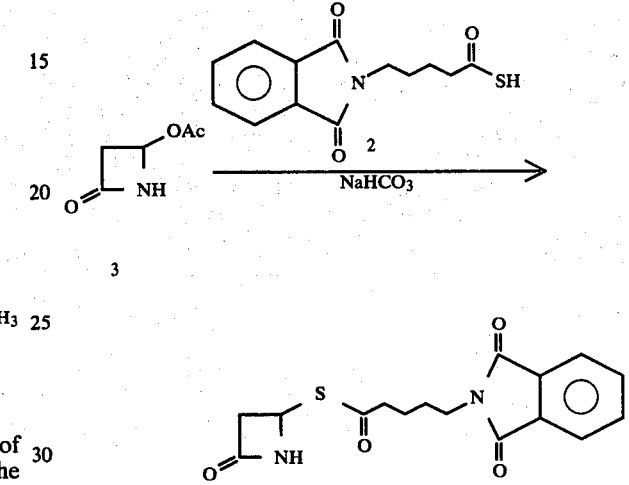

A suspension of 2 (3.04 g, 11.6 mmoles) in a solution of IM sodium bicarbonate (11.6 ml) was stirred at room temperature under nitrogen for 15 min. To it was added 3 (1.5 g, 11.6 mmoles) and the resulting mixture was stirred at room temperature for 1.5 h. The reaction mixture was diluted with water and extracted with methylene chloride. The organic phase was dried and evaporated in vacuo to give 3.82 g of solid 4; m.p.: 95°-96° C.; i.r. (CHCl$_3$) 1775, 1710 cm$^{-1}$. n.m.r. δ 7.8 (4H, d, J=2 Hz), 7.05 (1H broad s), 5.25 (1H, dd, J$_{cis}$=5 Hz, J$_{trans}$=3 Hz), 3.5-3.0 (2H, m), 1.5-2.0 (4H, m) Anal. calc'd for: C$_{16}$H$_{16}$N$_2$O$_4$S: C, 57.62; H, 4.85; N, 8.43; S, 9.64. Found C, 57.43; H, 4.82; N, 8.44; S, 9.71.

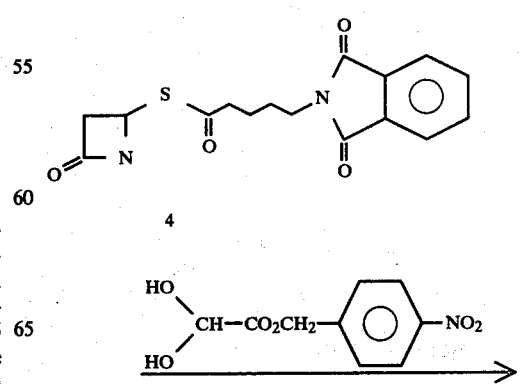

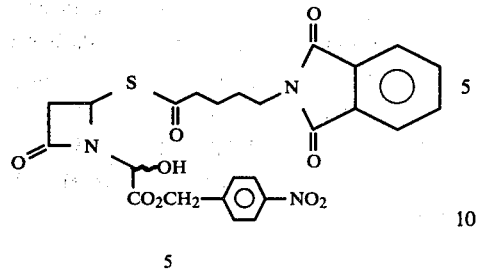

5

A benzene solution (30 ml) of 4 (3.0 g, 9.04 mmoles) and p-nitrobenzyl glyoxalate (2.22 g, 9.8 mmoles) was refluxed under a Dean-Stark condenser filled with 3 Å molecular sieves for 21 h. Evaporation of the solvent afforded 5.4 g of 5 as an oil (100%). i.r. (neat) 3200–3600, 1770, 1710, 1525 cm$^{-1}$ n.m.r. (CDCl$_3$) δ 8.21 (2H, d J=9 Hz), 7.75 (4H, d, J=2 Hz), 7.52 (2H, d, J=9 Hz, 5.52 (1H, broad s), 5.32 (3H, 2s), 4.55 (1H, broad s), 3.5–3.7 (2H, m), 3.45 (1H, dd J$_{gem}$=15 Hz, J$_{cis}$=5 Hz) 3.02 (1H, dd, J$_{gem}$=15 Hz, J$_{trans}$=3 Hz), 2.4–2.9 (2H, m), 1.4–2.0 (4H, m)

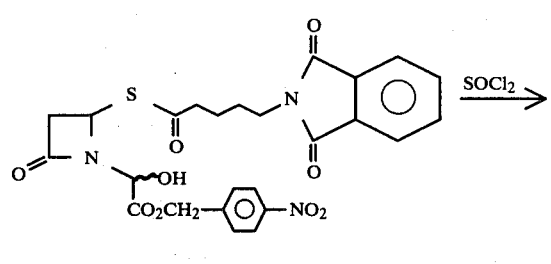

5

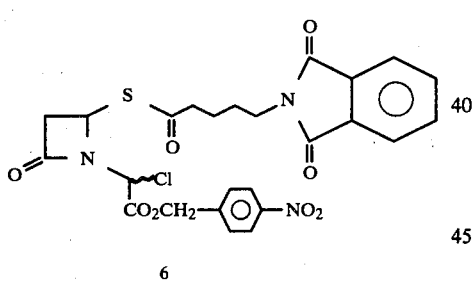

6

Azetidinone glyoxalate 5 (4.9 g, 9.05 mmoles) was treated at 0° C. with thionyl chloride (15 ml) at 0° C. for 0.5 h and at room temperature for 1 h. The excess of thionyl chloride was codistilled with benzene in vacuo to afford 6 as a yellow syrup (5.0 g, 100%) n.m.r. (CDCL$_3$) δ 8.2 (2H, J=9 Hz), 7.72 (4H, broad s), 7.60 (2H, d, J=9 Hz), 6.1 (1H, broad s), 5.50–5.85 (1H, m), 5.32 (2H, 2s), 3.4–4.0 (2H, m), 3.1–3.3 (1H, m), 2.8–3.05 (1H, m), 2.50–2.85 (2H, m), 1.5–1.9 (4H, m).

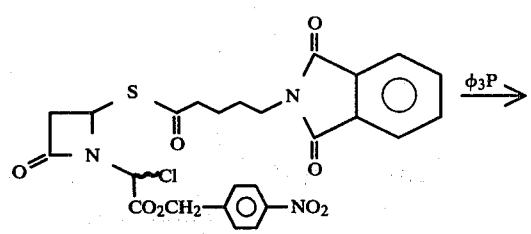

6

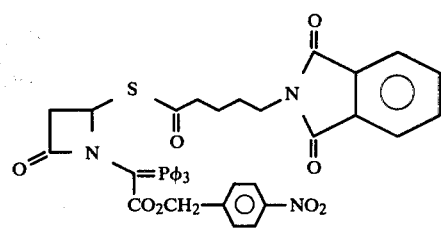

7

A solution of 6 (21.6 g, 38.8 mmoles) in tetrahydrofuran (85 ml, distilled over LAH) was treated with triphenyl phosphine (10.2 g, 38.8 mmoles) and 2.6-lutidine (5.0 ml, 42.9 mmoles) for 18 h at 40° C. The mixture was diluted with benzene-ether 1:1 (30 ml), washed with water, 1 N HCl, saturated NaHCO$_3$, brine and dried over MgSO$_4$. Evaporation of the solvent afforded a dark brown oil. It was passed through a silica gel (700 g) column (benzene-ether) to give 16.0 g (53%) of 7 as a thick oil. NMR (CDCl$_3$) δ 8.2 (2H, d, J=9 Hz), 7.8 (8H, d, J=2 Hz), 7.52 (16H, broad s), 5.2 (1H, broad s), 4.78 (1H, 2 s), 4.30–4.52 (1H, m), 3.5–3.8 (2H, m), 2.8–3.5 (2H, m), 2.1–2.9 (4H, m), 1.5–1.9 (4H, m)

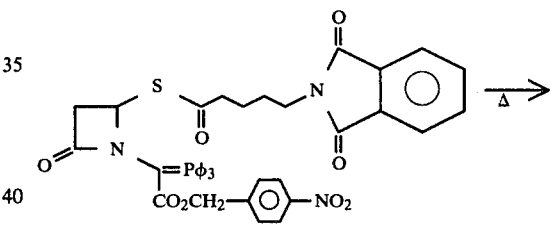

7

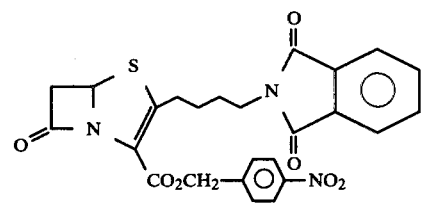

8

A solution of phosphorane 7 (5.0 g, 6.4 mmoles) in toluene (35 ml) was refluxed for 3 h. Evaporation of the solvent gave a residue which was passed through a silica gel (100 g) column. Elution with benzene followed by ether gave 600 mg of the ester 8 as oil i.r. (neat 1790, 1710, 1520 cm$^{-1}$) n.m.r. (CDCl$_3$) δ 8.22 (2H, d, J=9 Hz), 7.82 (4H, d, J=2 Hz), 7.65 (2H, d, J=9 Hz), 5.69 (1H, dd, J$_{cis}$=4 Hz, J$_{trans}$=2 Hz), 5.35 (2H, 2s), 4.12 (1H, dd, J$_{gem}$=16 Hz, J$_{cis}$=4 Hz), 3.50 (1H, dd, J$_{gem}$=16 Hz, J$_{trans}$=2 Hz), 3.1–3. 8 (2H, m), 2.5–3.0 (2H, m), 1.4–2.0 (4H, m).

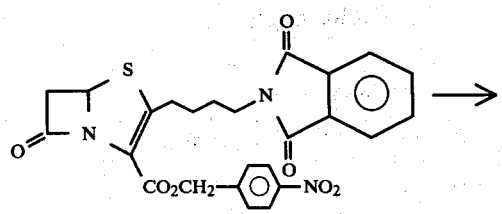

8

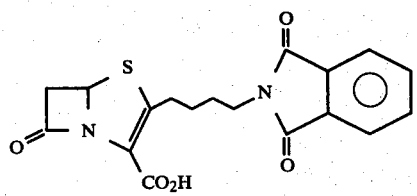

9

A two phase mixture made of ester 8 (196 mg, 0.39 mmole) in ether (2 ml), tetrahydrofuran (4 ml) and sodium bicarbonate (32 mg, 0.39 mmoles) in water (2 ml) was hydrogenated on 30% Palladium on Diatomaceous earth (190 mg) in a Parr shaker at 40 p.s.i. H$_2$. After 4.5 h it was filtered over celite pad and the pad was washed with water and tetrahydrofuran. The filtrate and washings were combined and the organic phase was separated. The aqueous solution was washed with ether, acidified with 1 N hydrochloric acid (3×0.4 ml) and extracted (after each acid portion added) with ethyl acetate (4×2 ml). The organic extracts were washed with brine, dried over MgSO$_4$ and the solvent was removed by evaporation to afford the acid 9, 67 mg (47%), as a yellow solid. i.r. (nujol) 1775, 1705, 1690 cm$^{-1}$. n.m.r. (DMSO) δ 7.92 (4H, s), 5.71 (1H, dd, J$_{cis}$=4 Hz, J$_{trans}$=2 Hz), 3.90 (1H, dd, J$_{gem}$=16 Hz, J$_{cis}$=4 Hz), 3.47 (1H, dd, J$_{gem}$=16 Hz, J$_{trans}$=2 Hz), 3.3–4.3 (3H, m), 2.7–3.05 2H, m), 1.5–2.0 (4H, m).

EXAMPLE 44

Sodium 2-(Acetonylmethyl oxime)-penem-3-carboxylate

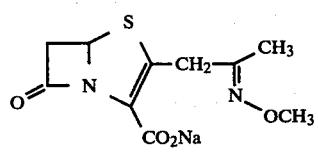

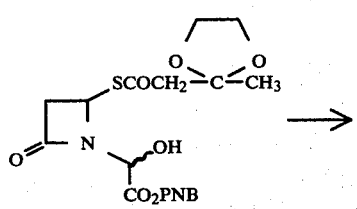

1

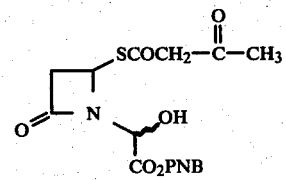

2

Ketal 1 (2.0 g, 4.54 mmoles) was treated at 0° with 95% TFA (20 cc) for 15 min. The mixture was diluted with brine and extracted with methylene chloride (4×30 cc). The methylene chloride extracts were washed with water-brine (3 times) and brine, and dried over MgSO$_4$ (1.44 g, 80%). δ(ppm, CDCl$_3$) 8.27 (2H, d, J=9, Hm aromatic), 8.60 (2H, d, J=9, Ho aromatic), 5.70–5.25

(m, CH$_2$—PNB, H—C—O, H—4, 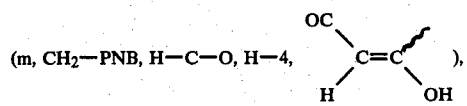 ), 4.75 (1H, bs, OH), 3.76 (center of ABq, CH$_2$—CO), 3.47 (part of a dd, J$_{3-4\ cis}$=5, H-3), 3.05 (2H, 2dd, J$_{gem}$=15, J$_{3-4\ trans}$=3, H-3), 2.30, 2.28 (1.67H, 2s, CH$_3$), 1.98 (1.33H, s, CH$_3$) ν$_{c=o}$(CHCl$_3$) 1780, 1755, ν$_{NO_2}$1525.

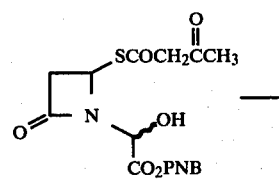

2

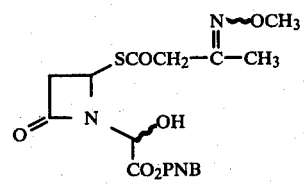

3

A methylene chloride (50 cc) solution of ketone 2 (1.44 g, 3.63 mmoles) was treated at 0° under nitrogen atmosphere with methoxyl amine hydrochloride (334 mg, 1.1 eq).

Triethyl amine (367 mg, 0.51 cc, 1 eq) was then added dropwise to the mixture. It was then stirred at room temperature for 18 h. The reaction mixture was diluted with methylene chloride, washed with water-brine (2 times), brine and dried over MgSO$_4$ (1.52 g, 98%). δ(ppm, CDCl$_3$) 8.12 (2H, d, J=8, Hm aromatic), 8.40 (2H, d, J=8 Ho aromatic), 5.50–5.05 (4H, m, CH$_2$—PNB, H-4, H—C—O), 3.80–3.60 (m, OCH$_3$, part of H-3 cis, part of OH), 3.55–270 (m, part of H-3 cis, H-3 trans, CH$_2$CO, part of OH), 1.97, 1.90, 1.88 (3H, 3s, CH$_3$) ν$_{c=o}$ (CHCl$_3$) 1770, 1750, 1690.

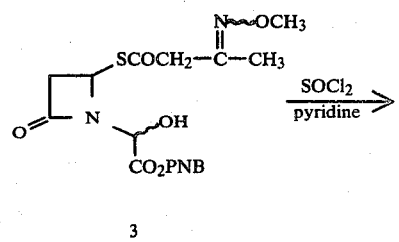

3

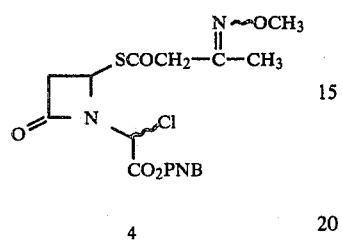

4

A cold (−15° C.) THF (20 cc, distilled over LAH) solution of azetidinone 3 (1.52 g, 3.57 mmoles) was treated dropwise with pyridine (325 mg, 0.332 cc, 4.10 mmoles, 1.15 eq) and thionyl chloride (488 mg, 0.299 cc, 4.10 mmoles, 1.15 eq) under nitrogen atmosphere. The mixture was stirred for 15 min at −15°. The solid was filtered off and washed with benzene. The resulting solution was evaporated down. The residue was taken upon benzene and treated with charcoal (1.2 g, 76%). δ(ppm, CDCl$_3$) 8.23 (2H, d, Hm aromatic), 7.80 (2H, d, Ho aromatic), 6.12, 6.08 (1H, 2s, H—C—Cl), 5.75–5.55 (1H, m, H-4), 5.40, 5.30 (2H, 2s, CH$_2$—PNB), 3.95–3.80 (3H, 3s, OCH$_3$), 3.80–2.95 (4H, m, 2H-3, CH$_2$—CO), 2.00–1.85 (3H, 4s, CH$_3$). $\nu_{c=o}$ (CHCl$_3$) 1790, 1765 (shoulder), 1700, $\nu_{NO_2}$ 1530.

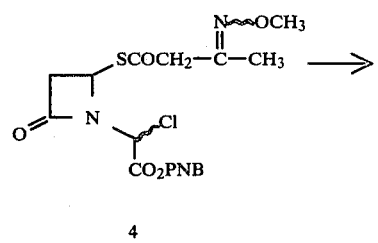

4

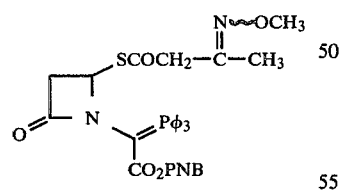

5

A THF (20 cc, distilled over LAH) solution of chloroazetidinone 4 (1.2 g, 2.70 mmoles) was treated with triphenyl phosphine (1.06 g, 4.05 mmoles 1.5 eq) and 2,6-lutidine (318 mg, 0.346 cc, 2.97 mmoles, 1.1 eq). The mixture was stirred for 4 days at room temperature under nitrogen atmosphere. It was diluted with ethyl acetate, washed with 2% aqueous HCl, H$_2$O, 2% aqueous NaHCO$_3$, water and brine. The solution was then dried over MgSO$_4$ and the solvent was evaporated. Crude 5 was purified on silica gel (10 times by weight) column (ethyl acetate, 770 mg, 45%). $\nu_{C=O}$ (CHCl$_3$) 1755, 1695, $\nu$ 1630–1610, $\nu_{NO_2}$ 1525.

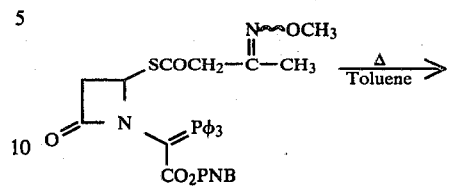

5

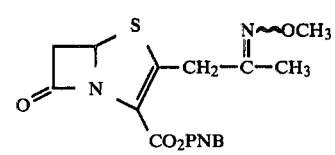

6

Phosphorane 5 (700 mg, 1.05 mmole) was refluxed in toluene for 4.5 h. Toluene evaporation afforded a residue which was passed through a silica gel (1:15 ratio) column (4% ether-benzene). It gave 6 as a crystalline material (251 mg, 62%, m.p. 116–125). Anal. calc'd for C$_{17}$H$_{17}$N$_3$O$_6$S: C, 52.17; H, 4.38; N, 10.74. Found: C, 51.15; H, 4.18; N, 10.33. δ(ppm, CDCl$_3$) 7.70 (2H, d, Hm aromatic), 7.12 (2H, d, Ho aromatic), 5.00 (2H, s, CH$_2$PNB), 4.85 (1H, m, H-5), 3.75–2.70 (7H, m, CH$_3$O, CH$_2$, H-6), 1.77, 1.72, 1.65 (3H, s, CH$_3$). $\nu_{c=o}$ (CHCl$_3$) 1787, 1742, 1705, $\nu_{NO_2}$ 1530. U.V. (EtOH) $\epsilon_{max}$ 318 (ε=8420), 262 (ε=12,539).

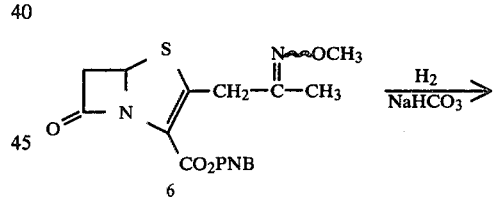

6

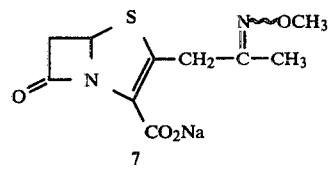

7

A mixture of ester 6 (151 mg, 0.386 mmole) in THF (20 cc), ether (40 cc) and NaHCO$_3$ (32 mg, 0.381 mmole) in water (20 cc) was shaken in a Parr hydrogenator for 3 h at 35 p.s.i. H$_2$, using 30% Pd on celite (200 mg) as catalyst. The catalyst was filtered off and washed with water and ether. The resulting aqueous mixture was washed with ether (3×60 cc) and lyophilized (32 mg, 30%). δ(ppm, DMSO) 5.50 (m, H-5), 3.75 (s, OCH$_3$), 0.77 (s, CH$_3$). $\nu_{c=o}$ (nujol mull) 1770, 1600, 1400. U.V. (H$_2$O) $\epsilon_{max}$ 300 (ε=2,800), 255 (ε=2,400).

EXAMPLE 45

Sodium 2-(2'-Aminophenyl)methylpenem-3-carboxylate

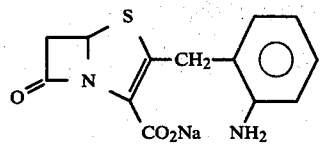

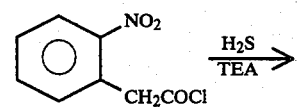

A cold (dry ice-acetone bath) methylene chloride (40 cc) solution of $H_2S$·triethyl amine (from 1.45 g, 2 cc 14.4 mmoles of triethylamine) was treated (fast) with a methylene chloride (20 cc) solution of acid chloride 1 (from 2 g, 11.0 mmoles of o-nitrophenylacetic acid) for 45 min under nitrogen atmosphere. The mixture was then diluted with ether and washed with 10% HCl, water and brine. It was dried over $MgSO_4$ (1.69 1 g, 77.5%). δ (ppm, $CDCl_3$) 8.27–8.08, 7.87–7.30 (m, 4H, aromatic-H), 4.90 (1H, b.s., SH), 4.33 (2H, s, $CH_2$). $\nu_{CO}$ (neat) 1705, $\nu_{SH}$ 2565, $\nu_{NO_2}$ 1525.

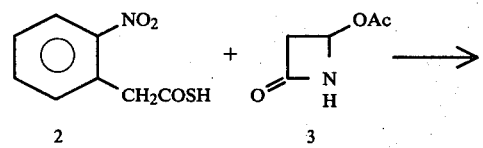

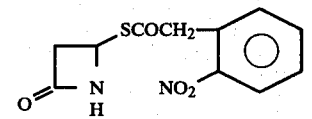

A cold (0° C.) THF-water (25 cc–200 cc) solution of thioacid 2 (7.92 g, 40.2 mmoles) was treated with $NaHCO_3$ (3.38 g, 40.2 mmoles) for 5 min under nitrogen atmosphere. The resulting solution was treated with an aqueous (50 cc) solution of azetidinone 3 (5.18 g, 40.1 mmoles). The mixture was stirred for 15 min at 0° and then allowed to react 4 h at room temperature. The solution was extracted with $CH_2Cl_2$ (4×50 cc). The methylene chloride extracts were combined, washed with 10% aqueous HCl, water and brine and dried over $MgSO_4$. The residue obtained upon solvent evaporation was passed through a silica gel (45 g) column (benzene-ether). Thioacetate 4 was obtained in 57% yield. (4.00 g, m.p.: 72°–72.5°). Anal. calc'd for $C_{11}H_{10}N_2O_4S$: C, 49.62; H, 3.78; N, 10.52; S, 12.04. Found: C, 49.55; H, 3.42; N, 10.74; S, 12.29. δ (ppm, $CDCl_3$) 8.28–8.07, 7.85–7.32 (4H, m, aromatic-H), 6.93 (1H, bs, N—H), 5.22 (1H, dd, $J_{3-4\ trans}$=2.8, $J_{3-4\ cis}$=5, H-3), 4.28 (2H, s, $CH_2CO$), 3.45 (1H, ddd, $J_{4-3\ gem}$=15.2, $J_{4-3\ cis}$=5, $J_{4-NH}$=2.2, H-4), 2.88 (1H, $J_{4-3\ gem}$=15.2, $J_{4-3\ trans}$=2.8, $J_{4-NH}$=1.2, H-4). $\nu_{c=o}$ ($CHCl_3$), 1777, 1695, $\nu_{NO_2}$ 1530, $\nu_{NH}$ 3420.

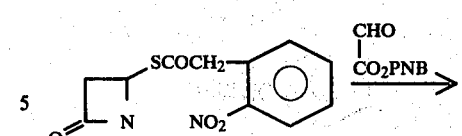

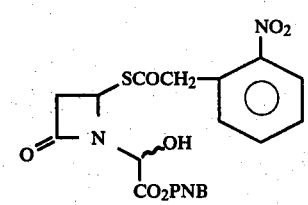

Hydrated p-nitrobenzyl glyoxylate (2.10 g, 9.24 mmoles) was refluxed in benzene (125 cc) through a Dean-Stark condenser filled with 3Å molecular sieves for 1 h. Azetidinone 4 (2.468, 9.27 mmoles) was added. The resulting mixture was refluxed for 24 h. (NMR spectrum of an aliquot showed minor traces of coupled product). It was then treated with DMF (5 drops) and refluxed for 72 h. (Reaction progression was followed by NMR). Benzene was evaporated off to yield 5 in quantitative yield. (4.57 g). δ (ppm, $CDCl_3$) 8.32–7.32 (8H, m, aromatic-H), 5.50 (m and s, H-4 and part of H—C—O), 5.32 (center of 2 s, $CH_2$—PNB, part of H—C—O), 4.70 (1H, b.s., OH), 4.25 (2H, 1 s+shoulder, $CH_2CO$), 3.49 (1H, dd, $J_{3-4\ gem}$=16, $J_{3-4\ cis}$=5, H-3), 3.10 (m, part of dd, H-3). $\nu_{c=o}$ ($CHCl_3$), 1780, 1760, 1700 $\nu_{NO_2}$ 1530.

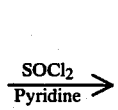

A cold (0° C.) THF (50 cc, distilled over LAH) solution of azetidinone 5 (4.42 g, 9.28 mmoles) was treated under nitrogen atmosphere with pyridine (0.782 g, 0.8 cc, 9.89 mmoles, 1.07 eq) and thionyl chloride (1.30 g, 0.8 cc, 10.97 mmoles, 1.18 eq). The mixture was stirred over a 1.5 h period and the temperature was allowed to rise gradually up to ambiant temperature. It was then filtered on a silica gel (75 g) column using $CH_2Cl_2$ as eluant (4.32 g, 94%). δ(ppm, $CDCl_3$), 8.32–7.30 (8H, m, aromatic-H), 6.07 (1H, s, H—C—Cl), 5.67 (1H, m, H-4), 5.37, 5.32 (2H, 2s, $CH_2$—PNB), 4.28 (2H, s, $CH_2$—ONB), 3.50 (part of dd, H-3), 3.07, 3.11 (1H, 2dd, $J_{3-4\ gem}$=15, $J_{3-4\ trans}$=3, H-3). $\nu_{c=o}$ ($CHCl_3$) 1785, 1760 (shoulder), 1700.

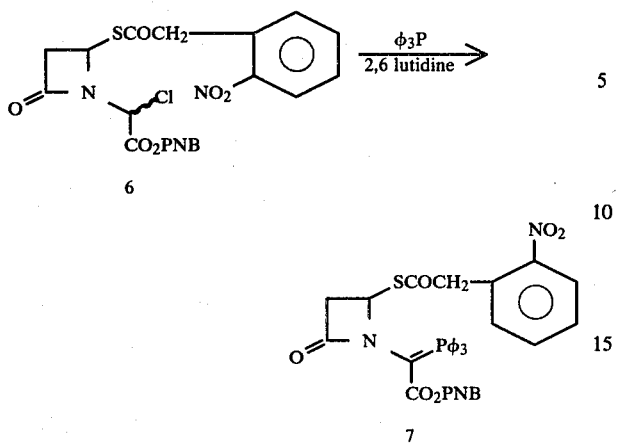

6

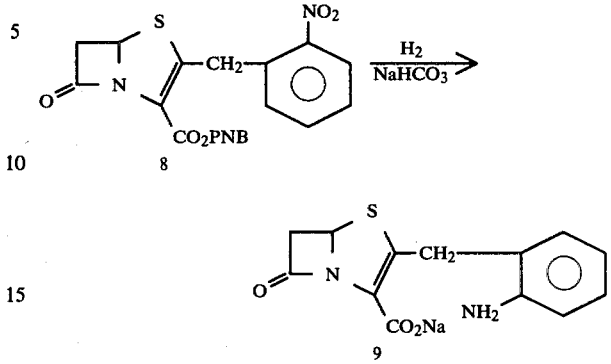

8

$\nu_{c=o}$(CHCl$_3$) 1792, 1710, $\nu$ 1530. U.V. (EtOH), $\nu_{max}$262 ($\epsilon$=12,000), 315 ($\epsilon$=6150).

9

To a THF (50 cc, distilled over LAH) solution of azetidinone 6 (4.32 g, 8.75 mmoles) was added triphenyl phosphine (3.48 g, 13.3 mmoles, 1.5 eq) and 2,6-lutidine (975 mg, 1.06 ml, 9.10 mmoles, 1.04 eq). This mixture was stirred for 3 days at room temperature. It was diluted with ether and washed with 10% aqueous HCl, water and brine and dried over MgSO$_4$. The residue upon solvent evaporation was purified through a silica gel column (30% ether-benzene and ether). Pure 7 crystallized out from ether (3.8 g, 60%, m.p.: 187 decomp.). Anal. calc'd for C$_{38}$H$_{30}$N$_3$O$_8$SP: C, 63.41; H, 4.20; N, 5.87; S, 4.45. Found: C, 64.03; H, 4.23; H, 5.91; S, 5.04. $\nu_{c=o}$ (CHCl$_3$) 1765, 1750, 1695 $\nu$ 1625, $\nu_{NO_2}$ 1530.

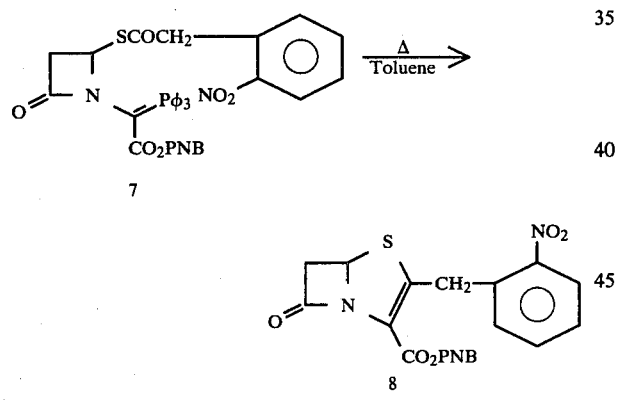

7

8

A toluene (300 cc) solution of phosphorane 7 (3.75 g, 5.20 mmoles) was refluxed for 4.5 h. Toluene evaporation afforded crude 8 which was purified through a silica gel (50 g) column (benzene, 913 mg, 40%). Anal. cald'd for C$_{20}$H$_{15}$N$_3$O$_7$S: C, 54.42; H, 3.43; N, 9.52, S, 7.26. Found: C, 54.97; H, 3.49; N, 9.35; S, 7.36. δ(ppm, CDCl$_3$) 8.28–7.30 (8H, m, aromatic-H), 5.65 (1H, dd, J$_{5-6}$ trans-2, J$_{5-6}$ cis=3.6, H-5), 5.35 (2H, center of ABq) J=14, CH$_2$—PNB), 4.55 (2H, center of ABq, J=16, CH$_2$—ONB), 3.87 (1H, dd, J$_{6-5}$ gem=16.6, J$_{6-5}$ cis=3.6, H-6), 3.43 (1H, dd, J$_{6-5}$ gem=16.6, J$_{6-5}$ trans=2, H-6).

A mixture of ester 8 (162 mg, 0.394 mmole) in THF (15 cc), ether (30 cc) and aqueous (15 cc) NaHCO$_3$ (31 mg, 0.369 mmole) was shaken on a Parr hydrogenator for 3 h at 30 p.s.i. H$_2$ using 30% Pd on celite (201 mg) as catalyst. The mixture was diluted with ether. The aqueous layer was separated, washed with ether (3 times) and filtered on celite. It was then frozen and lyophilized (60 mg, 55%). δ(ppm, DMSO) 7.25–6.25 (m, H aromatic), 5.55 (m, H-5), 4.05 (center of ABq, CH$_2$—), 3.75–3.0 (b.s, OH etc). $\nu_{c=o}$ (nujol mull) 1760, 1600. UV (H$_2$O) $\epsilon_{max}$290 ($\epsilon$=3080).

EXAMPLE 46

The following 2-penem compounds may be prepared by acylation of 1-(p-nitrobenzyloxycarbonylmethyltriphenylphosphoranyl)-4-(silver mercaptidyl)-2-azetidinone with the appropriate acylating agent followed by cyclization and deblocking steps. The general reaction scheme is shown below:

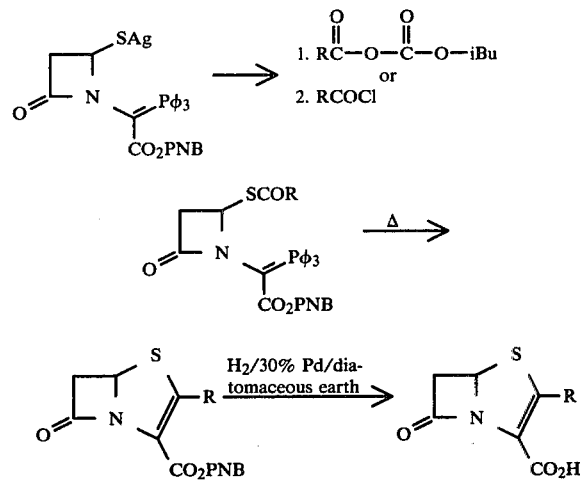

for variation 1: use RCO$_2$H + iBuCOCl
for variation 2: use HCl + PCl$_5$ + RCO$_2$H

| Acrylating Agent | Method | Product |
|---|---|---|
| φCH$_2$OCONH—(CH$_2$)$_4$—CO$_2$H | 1 | 2-(4-Aminobutyl)penem-3-carboxylic acid |

-continued

| Acrylating Agent | Method | Product |
|---|---|---|
| φCH$_2$OCONH—CH(CH$_3$)—CO$_2$H (both D and L) | 1 | 2-(1-Aminoethyl)penem-3-carboxylic acid |
| φCH$_2$OCONH—CH(CH$_2$CH$_3$)—CO$_2$H (both D and L) | 1 | 2-(1-Aminopropyl)penem-3-carboxylic acid |
| φCH$_2$OCONH—CH(CH(CH$_3$)$_2$)—CO$_2$H (both D and L) | 1 | 2-(1-Amino-2-methylpropyl)-penem-3-carboxylic acid |
| φCH$_2$OCONH—CH(φ)—CO$_2$H (both D and L) | 1 | 2-(1-Aminobenzyl)penem-3-carboxylic acid |
| φCH$_2$OCONH—CH(CH$_2$φ)—CO$_2$H (both D and L) | 1 | 2-(1-Amino-2-phenylethyl)-penem-3-carboxylic acid |
| φCH$_2$OCONH—CH(CH$_2$OCH$_2$φ—NO$_2$—p)—CO$_2$H (both D and L) | 1 | 2-(1-Amino-2-hydroxyethyl)-penem-3-carboxylic acid |
| φCH$_2$OCONH—CH(CH$_2$CO$_2$CH$_2$φ—NO$_2$—p)—CO$_2$H (both D and L) | 1 | 2-(1-Amino-2-carboxyethyl)-penem-3-carboxylic acid |
| φCH$_2$OCONH—CH(CH$_2$CONH$_2$)—CO$_2$H (both D and L) | 1 | 2-(1-Amino-2-carbamoylethyl)-penem-3-carboxylic acid |
| φCH$_2$OCONH—CH(CH$_2$CH$_2$SCH$_3$)—CO$_2$H (both D and L) | 1 | 2-(1-Amino-3-methylthiopropyl)-penem-3-carboxylic acid |
| φCH$_2$OCONH—CH((CH$_2$)$_4$NHCO$_2$CH$_2$φ)—CO$_2$H (both D and L) | 1 | 2-(1,5-Diaminopentyl)penem-3-carboxylic acid |
| φCH$_2$OCON(CH$_3$)CH$_2$CO$_2$H | 1 | 2-[(Methylamino)methyl]penem-3-carboxylic acid |
| φCH$_2$OCON(CH$_3$)CH$_2$CH$_2$CO$_2$H | 1 | 2-[2-(Methylamino)ethyl]-penem-3-carboxylic acid |
| φCH$_2$OCON(CH$_3$)CH$_2$CH$_2$CH$_2$CO$_2$H | 1 | 2-[3-(Methylamino)propyl]-penem-3-carboxylic acid |
| φCH$_2$OCON(CH$_3$)CH$_2$CH$_2$CH$_2$CH$_2$CO$_2$H | 1 | 2-[4-(methylamino)butyl]-penem-3-carboxylic acid |
| φCH$_2$OCON(C$_2$H$_5$)CH$_2$CO$_2$H | 1 | 2-[(Ethylamino)methyl]penem-3-carboxylic acid |
| φCH$_2$OCON(C$_2$H$_5$)CH$_2$CH$_2$CO$_2$H | 1 | 2-[2-(Ethylamino)ethyl]penem-3-carboxylic acid |
| φCH$_2$OCON(C$_2$H$_5$)CH$_2$CH$_2$CH$_2$CO$_2$H | 1 | 2-[3-(ethylamino)propyl]-penem-3-carboxylic acid |
| φCH$_2$OCON(C$_2$H$_5$)CH$_2$CH$_2$CH$_2$CH$_2$CO$_2$H | 1 | 2-[4-(Ethylamino)butyl]-penem-3-carboxylic acid |

-continued

| Acrylating Agent | Method | Product |
|---|---|---|
| φCH$_2$OCON(φ)CH$_2$CO$_2$H | 1 | 2-[(Phenylamino)methyl]-penem-3-carboxylic acid |
| φCH$_2$OCON(φ)CH$_2$CH$_2$CO$_2$H | 1 | 2-[2-(Phenylamino)ethyl]-penem-3-carboxylic acid |
| φCH$_2$OCON(φ)CH$_2$CH$_2$CH$_2$CO$_2$H | 1 | 2-[3-(Phenylamino)propyl]-penem-3-carboxylic acid |
| φCH$_2$OCON(φ)CH$_2$CH$_2$CH$_2$CH$_2$CO$_2$H | 1 | 2-[4-(Phenylamino)butyl]-penem-3-carboxylic acid |
| CH$_3$CONHCH$_2$CO$_2$H | 1 | 2-[(Acetylamino)methyl]-penem-3-carboxylic acid |
| CH$_3$CONHCH$_2$CH$_2$CO$_2$H | 1 | 2-[2-(Acetylamino)ethyl]-penem-3-carboxylic acid |
| CH$_3$CONHCH$_2$CH$_2$CH$_2$CO$_2$H | 1 | 2-[3-(Acetylamino)propyl]-penem-3-carboxylic acid |
| CH$_3$CONHCH$_2$CH$_2$CH$_2$CH$_2$CO$_2$H | 1 | 2-[4-(Acetylamino)butyl]-penem-3-carboxylic acid |
| C$_6$H$_5$CONHCH$_2$CO$_2$H | 1 | 2-[(Benzoylamino)methyl]-penem-3-carboxylic acid |
| C$_6$H$_5$CONHCH$_2$CH$_2$CO$_2$H | 1 | 2-[2-(Benzoylamino)ethyl]-penem-3-carboxylic acid |
| C$_6$H$_5$CONHCH$_2$CH$_2$CH$_2$CO$_2$H | 1 | 2-[3-(Benzoylamino)propyl]-penem-3-carboxylic acid |
| C$_6$H$_5$CONHCH$_2$CH$_2$CH$_2$CH$_2$CO$_2$H | 1 | 2-[4-(Benzoylamino)butyl]-penem-3-carboxylic acid |
| φCH$_2$OCONHCH$_2$CONHCH$_2$CO$_2$H | 1 | 2-[(Glycinamido)methyl]-penem-3-carboxylic acid |
| φCH$_2$OCONHCH$_2$CONHCH$_2$CH$_2$CO$_2$H | 1 | 2-[2-(Glycinamido)ethyl]-penem-3-carboxylic acid |
| φCH$_2$OCONHCH$_2$CONHCH$_2$CH$_2$CH$_2$CO$_2$H | 1 | 2-[3-(Glycinamido)propyl]-penem-3-carboxylic acid |
| φCH$_2$OCONHCH$_2$CONHCH$_2$CH$_2$CH$_2$—CH$_2$CO$_2$H | 1 | 2-[4-(Glycinamido)butyl]-penem-3-carboxylic acid |
| H$_2$NCONHCH$_2$CO$_2$H | 1 | 2-(Ureidomethyl)penem-3-carboxylic acid |
| H$_2$NCONHCH$_2$CH$_2$CO$_2$H | 1 | 2-(2-Ureidoethyl)penem-3-carboxylic acid |
| H$_2$NCONHCH$_2$CH$_2$CH$_2$CO$_2$H | 1 | 2-(3-Ureidopropyl)penem-3-carboxylic acid |
| H$_2$NCONHCH$_2$CH$_2$CH$_2$CH$_2$CO$_2$H | 1 | 2-(4-Ureidobutyl)penem-3-carboxylic acid |
| CH$_3$NHCONHCH$_2$CO$_2$H | 1 | 2-[(Methylcarbamoylamino)-methyl]penem-3-carboxylic acid |
| CH$_3$NHCONHCH$_2$CH$_2$CO$_2$H | 1 | 2-[2-(Methylcarbamoylamino)-methyl]penem-3-carboxylic acid |
| CH$_3$NHCONHCH$_2$CH$_2$CH$_2$CO$_2$H | 1 | 2-[3-(Methylcarbamoylamino)-propyl]penem-3-carboxylic acid |
| CH$_3$NHCONHCH$_2$CH$_2$CH$_2$CH$_2$CO$_2$H | 1 | 2-[4-(Methylcarbamoylamino)-butyl]penem-3-carboxylic acid |
| φNHCONHCH$_2$CO$_2$H | 1 | 2-[(Phenylcarbamoylamino)-methyl]penem-3-carboxylic acid |
| φNHCONHCH$_2$CH$_2$CO$_2$H | 1 | 2-[2-(Phenylcarbamoylamino)-ethyl]penem-3-carboxylic acid |
| φNHCONHCH$_2$CH$_2$CH$_2$CO$_2$H | 1 | 2-[3-(Phenylcarbamoylamino)-propyl]penem-3-carboxylic acid |
| φNHCONHCH$_2$CH$_2$CH$_2$CH$_2$CO$_2$H | 1 | 2-[4-(Phenylcarbamoylamino)-butyl]penem-3-carboxylic acid |
| CH$_3$CONHCONHCH$_2$CO$_2$H | 1 | 2-[(Acetylcarbamoylamino)-methyl]penem-3-carboxylic acid |
| CH$_3$CONHCONHCH$_2$CH$_2$CO$_2$H | 1 | 2-[2-(Acetylcarbamoylamino)-ethyl]penem-3-carboxylic acid |
| CH$_3$CONHCONHCH$_2$CH$_2$CH$_2$CO$_2$H | 1 | 2-[3-(Acetylcarbamoylamino)-propyl]penem-3-carboxylic acid |
| CH$_3$CONHCONHCH$_2$CH$_2$CH$_2$CH$_2$CO$_2$H | 1 | 2-[4-(Acetylcarbamoylamino)-butyl]penem-3-carboxylic acid |
| φCONHCONHCH$_2$CO$_2$H | 1 | 2-[(Benzoylcarbamoylamino)-methyl]penem-3-carboxylic acid |
| φCONHCONHCH$_2$CH$_2$CO$_2$H | 1 | 2-[2-(Benzoylcarbamoylamino)-ethyl]penem-3-carboxylic acid |
| φCONHCONHCH$_2$CH$_2$CH$_2$CO$_2$H | 1 | 2-[3-(Benzoylcarbamoylamino)-propyl]penem-3-carboxylic acid |
| φCONHCONHCH$_2$CH$_2$CH$_2$CH$_2$CO$_2$H | 1 | 2-[4-(Benzoylcarbamoylamino)-butyl]-penem-3-carboxylic acid |

-continued

| Acrylating Agent | Method | Product |
|---|---|---|
| $CH_3OCONHCONHCH_2CO_2H$ | 1 | 2-[(Carbomethoxycarbamoyl-amino)methyl]penem-3-carboxylic acid |
| $CH_3OCONHCONHCH_2CH_2CO_2H$ | 1 | 2-[2-(Carbomethoxycarbamoyl-amino)ethyl]penem-3-carboxylic acid |
| $CH_3OCONHCONHCH_2CH_2CH_2CO_2H$ | 1 | 2-[3-(Carbomethoxycarbamoyl-amino)propyl]penem-3-carboxylic acid |
| $CH_3OCONHCONHCH_2CH_2CH_2CH_2CO_2H$ | 1 | 2-[4-(Carbomethoxycarbamoyl-amino)butyl]penem-3-carboxylic acid |
| $(CH_3)_3Si(CH_2)_2OCONHCONHCH_2CO_2H$ | 1 | 2-[(2-trimethylsilylethyloxy-carbonylcarbamoylamino)-methyl]penem-3-carboxylic acid |
| $(CH_3)_3Si(CH_2)_2OCONHCONHCH_2-CH_2CO_2H$ | 1 | 2-[2-(2-trimethylsilylethyl-oxycarbonylcarbamoylamino)-ethyl]penem-3-carboxylic acid |
| $(CH_3)_3Si(CH_2)_2OCONHCONHCH_2-CH_2CH_2CO_2H$ | 1 | 2-[3-(2-trimethylsilylethyl-oxycarbonylcarbamoylamino)-propyl]penem-3-carboxylic acid |
| $(CH_3)_3Si(CH_2)_2OCONHCONHCH_2-CH_2CH_2CH_2CO_2H$ | 1 | 2-[4-(2-Trimethylsilylethyl-oxycarbonylcarbamoylamino)-butyl]penem-3-carboxylic acid |
| $CH_3S_2CNHCH_2CO_2H$ | 1 | 2-[(Methylthiothiocarbonyl-amino)methyl]penem-3-carboxylic acid |
| $CH_3S_2CNHCH_2CH_2CO_2H$ | 1 | 2-[2-(Methylthiothiocarbonyl-amino)ethyl]penem-3-carboxylic acid |
| $CH_3S_2CNHCH_2CH_2CH_2CO_2H$ | 1 | 2-[3-(Methylthiothiocarbonyl-amino)propyl]penem-3-carboxylic acid |
| $CH_3S_2CNHCH_2CH_2CH_2CH_2CO_2H$ | 1 | 2-[4-(Methylthiothiocarbonyl-amino)butyl]penem-3-carboxylic acid |
| $CH_3SO_2NHCH_2CO_2H$ | 1 | 2-[(Methanesulfonylamino)-methyl]penem-3-carboxylic acid |
| $CH_3SO_2NHCH_2CH_2CO_2H$ | 1 | 2-[2-(Methanesulfonylamino)-ethyl]penem-3-carboxylic acid |
| $CH_3SO_2NHCH_2CH_2CH_2CO_2H$ | 1 | 2-[3-(Methanesulfonylamino)-propyl]penem-3-carboxylic acid |
| $CH_3SO_2NHCH_2CH_2CH_2CH_2CO_2H$ | 1 | 2-[4-(Methanesulfonylamino)-butyl]penem-3-carboxylic acid |
| $\phi SO_2NHCH_2CO_2H$ | 1 | 2-[(Benzenesulfonylamino)-methyl]penem-3-carboxylic acid |
| $H_3CNHC(S)NHCH_2CH_2CO_2H$ | 1 | 2-[2-(N—Methylthiocarbamoyl-amino)ethyl]penem-3-carboxylic acid |
| $H_3CNHC(S)NHCH_2CH_2CH_2CO_2H$ | 1 | 2-[3-(N—Methylthiocarbamoyl-amino)propyl]penem-3-carboxylic acid |
| $H_3CNHC(S)NHCH_2CH_2CH_2CH_2CO_2H$ | 1 | 2-[4-(N—Methylthiocarbamoyl-amino)butyl]penem-3-carboxylic acid |
| $\phi NHC(S)NHCH_2CO_2H$ | 1 | 2-[(N—Phenylthiocarbamoyl-amino)methyl]penem-3-carboxylic acid |
| $\phi NHC(S)NHCH_2CH_2CO_2H$ | 1 | 2-[(2-(N—Phenylthiocarbamoyl-amino)ethyl]penem-3-carboxylic acid |
| $\phi NHC(S)NHCH_2CH_2CH_2CO_2H$ | 1 | 2-[3-(N—Phenylthiocarbamoyl-amino)propyl]penem-3-carboxylic acid |
| $\phi NHC(S)NHCH_2CH_2CH_2CH_2CO_2H$ | 1 | 2-[4-(N—Phenylthiocarbamoyl-amino)butyl]penem-3-carboxylic acid |

-continued

| Acrylating Agent | Method | Product |
|---|---|---|
| [structure: N=C(OH)–O–N=C–NHCH₂CO₂H cyclic] | 1 | 2-[(Guanylamino)methyl]-penem-3-carboxylic acid |
| [structure: N=C(OH)–O–N=C–NHCH₂CH₂CO₂H cyclic] | 1 | 2-[2-(Guanylamino)ethyl]-penem-3-carboxylic acid |
| [structure: N=C(OH)–O–N=C–NHCH₂CH₂CH₂CO₂H cyclic] | 1 | 2-[3-(Guanylamino)propyl]-penem-3-carboxylic acid |
| [structure: N=C(OH)–O–N=C–NHCH₂CH₂CH₂CH₂CO₂H cyclic] | 1 | 2-[4-(Guanylamino)butyl]-penem-3-carboxylic acid |
| [structure: H₃C–C(=N–O–)–C(=O)–N–CH₂CO₂H cyclic] | 1 | 2-[(Acetimidoylamino)methyl]-penem-3-carboxylic acid |
| [structure: H₃C–C(=N–O–)–C(=O)–N–CH₂CH₂CO₂H cyclic] | 1 | 2-[2-(Acetimidoylamino)ethyl]-penem-3-carboxylic acid |
| [structure: H₃C–C(=N–O–)–C(=O)–N–CH₂CH₂CH₂CO₂H cyclic] | 1 | 2-[3-(Acetimidoylamino)propyl]-penem-3-carboxylic acid |
| [structure: H₃C–C(=N–O–)–C(=O)–N–CH₂CH₂CH₂CH₂CO₂H cyclic] | 1 | 2-[4-(Acetimidoylamino)butyl]-penem-3-carboxylic acid |
| [structure: HC(=N–O–)–C(=O)–N–CH₂CO₂H cyclic] | 1 | 2-[(Formimidoylamino)methyl]-penem-3-carboxylic acid |
| [structure: HC(=N–O–)–C(=O)–N–CH₂CH₂CO₂H cyclic] | 1 | 2-[2-(Formimidoylamino)ethyl]-penem-3-carboxylic acid |
| [structure: HC(=N–O–)–C(=O)–N–CH₂CH₂CH₂CO₂H cyclic] | 1 | 2-[3-(Formimidoylamino)propyl]-penem-3-carboxylic acid |
| [structure: HC(=N–O–)–C(=O)–N–CH₂CH₂CH₂CH₂CO₂H cyclic] | 1 | 2-[4-(Formimidoylamino)butyl]-penem-3-carboxylic acid |
| $O_2NCH_2CO_2H$ | 1 | 2-[(Hydroxyamino)methyl]-penem-3-carboxylic acid |
| $O_2NCH_2CH_2CO_2H$ | 1 | 2-[2-(Hydroxyamino)ethyl]-penem-3-carboxylic acid |
| $O_2NCH_2CH_2CH_2CH_2CO_2H$ | 1 | 2-[4-(Hydroxyamino)butyl]-penem-3-carboxylic acid |
| $(CH_3)_3Si(CH_2)_2OCON(OCH_3)-CH_2CO_2H$ | *1 | 2-[(Methoxyamino)methyl]-penem-3-carboxylic acid |
| $(CH_3)_3Si(CH_2)_2OCON(OCH_3)-CH_2CH_2CO_2H$ | *1 | 2-[2-(Methoxyamino)ethyl]-penem-3-carboxylic acid |

-continued

| Acrylating Agent | Method | Product |
|---|---|---|
| (CH₃)₃Si(CH₂)₂OCONCH₂CH₂CH₂CO₂H with OCH₃ on N | *1 | 2-[3-(Methoxyamino)propyl]-penem-3-carboxylic acid |
| (CH₃)₃Si(CH₂)₂OCONCH₂CH₂CH₂CH₂CO₂H with OCH₃ on N | *1 | 2-[4-(methoxyamino)butyl]-penem-3-carboxylic acid |
| (CH₃)₃Si(CH₂)₂OCONCH₂CO₂H with NH₂ on N | *2 | 2-[(Hydrazino)methyl]penem-3-carboxylic acid |
| (CH₃)₃Si(CH₂)₂OCONCH₂CH₂CO₂H with NH₂ on N | *2 | 2-[2-(Hydrazino)ethyl]penem-3-carboxylic acid |
| (CH₃)₃Si(CH₂)₂OCONCH₂CH₂CH₂CO₂H with NH₂ on N | *2 | 2-[3-(Hydrazino)propyl]penem-3-carboxylic acid |
| (CH₃)₃Si(CH₂)₂OCONCH₂CH₂CH₂CH₂CO₂H with NH₂ on N | *2 | 2-[4-(Hydrazino)butyl]penem-3-carboxylic acid |
| (CH₃)₃Si(CH₂)₂OCONCH₂CO₂H with N(CH₃)₂ on N | *2 | 2-[(2,2-Dimethylhydrazino)methyl]penem-3-carboxylic acid |
| (CH₃)₃Si(CH₂)₂OCONCH₂CH₂CO₂H with N(CH₃)₂ on N | *2 | 2-[2-(2,2-Dimethylhydrazino)ethyl]penem-3-carboxylic acid |
| (CH₃)₃Si(CH₂)₂OCONCH₂CH₂CH₂CO₂H with N(CH₃)₂ on N | *2 | 2-[3-(2,2-Dimethylhydrazino)propyl]penem-3-carboxylic acid |
| (CH₃)₃Si(CH₂)₂OCONCH₂CH₂CH₂CH₂CO₂H with N(CH₃)₂ on N | *2 | 2-[4-(2,2-Dimethylhydrazino)butyl]penem-3-carboxylic acid |
| CH₃CONHNHCH₂CO₂H | *2 | 2-[(2-Acetylhydrazino)methyl]-penem-3-carboxylic acid |
| CH₃CONHNHCH₂CH₂CO₂H | *2 | 2-[2-(2-Acetylhydrazino)ethyl]penem-3-carboxylic acid |
| CH₃CONHNHCH₂CH₂CH₂CO₂H | *2 | 2-[3-(2-Acetylhydrazino)propyl]penem-3-carboxylic acid |
| CH₃CONHNHCH₂CH₂CH₂CH₂CO₂H | *2 | 2-[4-(2-Acetylhydrazino)butyl]penem-3-carboxylic acid |
| (CH₃)₂NCH₂CO₂H | 2 | 2-[(Dimethylamino)methyl]-penem-3-carboxylic acid |
| (CH₃)₂NCH₂CH₂CO₂H | 2 | 2-[2-(Dimethylamino)ethyl]-penem-3-carboxylic acid |
| (CH₃)₂NCH₂CH₂CH₂CO₂H | 2 | 2-[3-(Dimethylamino)propyl]-penem-3-carboxylic acid |
| (CH₃)₂NCH₂CH₂CH₂CH₂CO₂H | 2 | 2-[4-(Dimethylamino)butyl]-penem-3-carboxylic acid |
| CH₃CONCH₂CO₂H with CH₃ on N | 1 | 2-[(N—Methylacetamido)methyl]-penem-3-carboxylic acid |
| CH₃CONCH₂CH₂CO₂H with CH₃ on N | 1 | 2-[2-(N—Methylacetamido)ethyl]-penem-3-carboxylic acid |
| CH₃CONCH₂CH₂CH₂CO₂H with CH₃ on N | 1 | 2-[3-(n-Methylacetamido)propyl]-penem-3-carboxylic acid |
| CH₃CONCH₂CH₂CH₂CH₂CO₂H with CH₃ on N | 1 | 2-[4-(N—Methylacetamido)butyl]-penem-3-carboxylic acid |
| 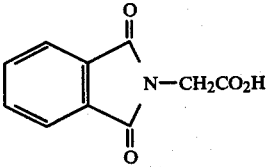 phthalimido-N—CH₂CO₂H | 1 | 2-[(Phthalimido)methyl]penem-3-carboxylic acid |

-continued

| Acrylating Agent | Method | Product |
|---|---|---|
| [phthalimide-N—CH₂CH₂CO₂H] | 1 | 2-[2-(Phthalimido)ethyl]-penem-3-carboxylic acid |
| [phthalimide-N—CH₂CH₂CH₂CO₂H] | 1 | 2-[3-(Phthalimido)propyl]-penem-3-carboxylic acid |
| [phthalimide-N—CH₂CH₂CH₂CH₂CO₂H] | 1 | 2-[4-(Phthalimido)butyl]-penem-3-carboxylic acid |
| φCH₂OCONHCH₂CH₂OCH₂CO₂H | 1 | 2-[(2-Aminoethoxy)methyl]-penem-3-carboxylic acid |
| φCH₂OCONHCH₂CH₂SCH₂CO₂H | 1 | 2-[(2-Aminoethylthio)methyl]-penem-3-carboxylic acid |
| φCH₂OCONHCH₂CH₂N(CO₂CH₂φ)CH₂CO₂H | 1 | 2-[(2-Aminoethylamino)methyl]-penem-3-carboxylic acid |
| φCH₂OCONHCH₂CH₂N(CH₃)CH₂CO₂H | 2 | 2-[N—(2-Aminoethyl)-N—methylamino]methylpenem-3-carboxylic acid |
| φCH₂OCONH—⟨phenyl⟩—CH₂CO₂H | 1 | 2-(p-Aminobenzyl)penem-3-carboxylic acid |
| φCH₂OCONH—⟨phenyl(o-CH₂CO₂H)⟩ | 1 | 2-(o-Aminobenzyl)penem-3-carboxylic acid |
| φCH₂OCONH—⟨phenyl⟩—CO₂H | 1 | 2-(p-Aminophenyl)penem-3-carboxylic acid |
| φCH₂OCONH—⟨phenyl(m-CO₂H)⟩ | 1 | 2-(m-Aminophenyl)penem-3-carboxylic acid |
| φCH₂OCONH—⟨phenyl(o-CO₂H)⟩ | 1 | 2-(o-Aminophenyl)penem-3-carboxylic acid |
| φCH₂OCONHCH₂—⟨phenyl⟩—CO₂H | 1 | 2-[p-(Aminomethyl)phenyl]-penem-3-carboxylic acid |
| φCH₂OCONHCH₂—⟨phenyl(m-CO₂H)⟩ | 1 | 2-[m-(Aminomethyl)phenyl]-penem-3-carboxylic acid |
| φCH₂OCONHCH₂—⟨phenyl(o-CO₂H)⟩ | 1 | 2-[o-(Aminomethyl)phenyl]-penem-3-carboxylic acid |

*use trimethylsilylethyl instead of PNB in azetidinone intermediate and deblock with F⁻.

EXAMPLE 47

The 2-penem products listed below as the triethylamine salts are treated with $(CH_3)_3N \cdot SO_3$ in $CH_2Cl_2$ solution at 0°. Addition of sodium 2-ethylhexanoate in 1-butanol to the reaction solution results in precipitation of the indicated products as disodium salts.

| Starting Material | Product |
|---|---|
| [penem]-$(CH_2)_n NH_2$, $CO_2N(C_2H_5)_3$ | [penem]-$(CH_2)_n$-$NHSO_3Na$, $CO_2Na$ |
| Exp. A  n = 1 | A. n = 1 |
| Exp. B  n = 2 | B. n = 2 |
| Exp. C  n = 3 | C. n = 3 |
| Exp. D  n = 4 | D. n = 4 |

EXAMPLE 48

The following 2-penem products may be prepared from the indicated starting materials by the procedure

[penem]-$(CH_2)_n N(CH_3)_2$, $CO_2PNB$ $\xrightarrow{CH_3I}$

-continued

[penem]-$(CH_2)_2 \overset{\oplus}{N}(CH_3)_3 \overset{\ominus}{I}$, $CO_2PNB$ $\xrightarrow{H_2/Pd}$

[penem]-$(CH_2)_n \overset{\oplus}{N}(CH_3)_3$, $CO_2^{\ominus}$

| Starting Material | Product |
|---|---|
| [penem]-$(CH_2)_n N(CH_3)_2$, $CO_2PNB$ | [penem]-$(CH_2)_n \overset{\oplus}{N}(CH_3)_3$, $CO_2^{\ominus}$ |
| Exp. A  n = 1 | A. n = 1 |
| Exp. B  n = 2 | B. n = 2 |
| Exp. C  n = 3 | C. n = 3 |
| Exp. D  n = 4 | D. n = 4 |

EXAMPLE 49

The following 2-penem products may be prepared from the indicated starting materials by the procedure

[penem]-SAg, $P\phi_3$, $CO_2PNB$ + $Cl(CH_2)_n COCl$ ⟶ [penem]-$SCO(CH_2)_n Cl$, $P\phi_3$, $CO_2PNB$ $\xrightarrow{\Delta}$

[penem]-$(CH_2)_n Cl$, $CO_2PNB$ $\xrightarrow{\text{pyridine}}$ [penem]-$(CH_2)_n$-$\overset{\oplus}{N}$(pyridinium), $CO_2PNB$ ↓ deblocking        ↓ deblocking

[penem]-$(CH_2)_n Cl$, $CO_2H$ $\xrightarrow{\text{pyridine}}$ [penem]-$(CH_2)_n$-$\overset{\oplus}{N}$(pyridinium), $CO_2^{\ominus}$

| Starting Material | Product |
|---|---|
| [penem]-$(CH_2)_n Cl$, $CO_2PNB$ | [penem]-$(CH_2)_n$-$\overset{\oplus}{N}$(pyridinium), $CO_2^{\ominus}$ |

| | | | |
|---|---|---|---|
| Exp. A | n = 1 | A. n = 1 | |
| Exp. B | n = 2 | B. n = 2 | |
| Exp. C | n = 3 | C. n = 3 | |
| Exp. D | n = 4 | D. n = 4 | |

EXAMPLE 50

The following 2-penem products may be prepared from the indicated starting materials by the procedure

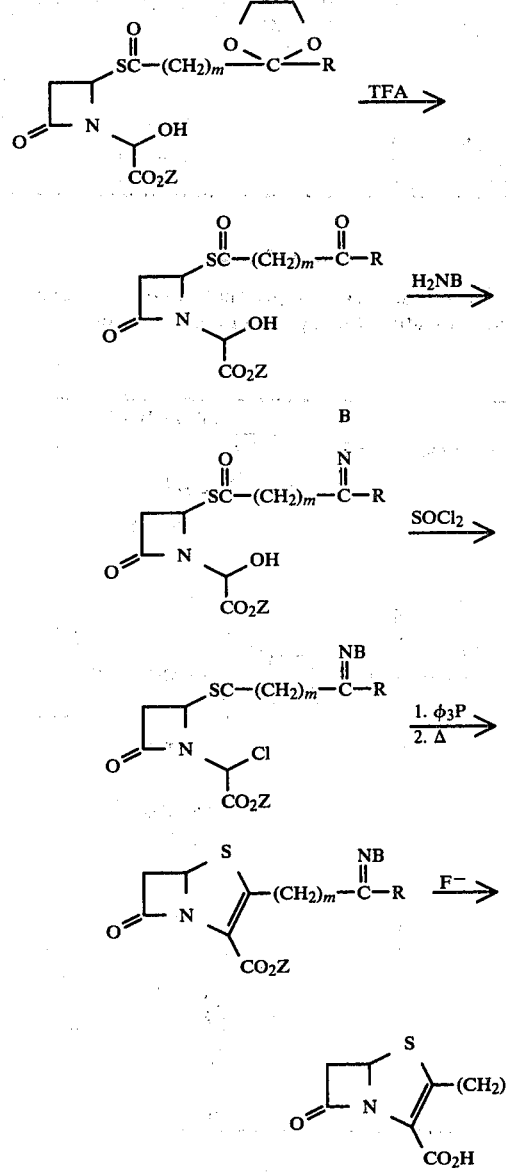

m = 0-2
R = H, CH₃
Z = —(CH₂)₂Si(CH₃)₃
B = —O(CH₂)₂Si(CH₃)₃

Starting Material    Product

| | |
|---|---|
| Exp. A R = H, m = 0 | A. R = H, m = 0 |
| Exp. B R = H, m = 1 | B. R = H, m = 1 |
| Exp. C R = H, m = 2 | C. R = H, m = 2 |
| Exp. D R = CH₃, m = 0 | D. R = CH₃, m = 0 |
| Exp. E R = CH₃, m = 1 | E. R = CH₃, m = 1 |
| Exp. F R = CH₃, m = 2 | F. R = CH₃, m = 2. |

Substitution in the above procedure of H₂NOCH₃ for the H₂NO(CH₂)₂Si(CH₃)₃ used therein results in formation of the following products.

| | |
|---|---|
| Exp. A | m = 0, R = H |
| Exp. B | m = 1, R = H |
| Exp. C | m = 2, R = H |
| Exp. D | m = 0, R = CH₃ |
| Exp. E | m = 1, R = CH₃ |
| Exp. F | m = 2, R = CH₃. |

Substitution in the above procedure of (CH₃)₃Si(CH₂)₂OCONHNH₂ for the H₂NO(CH₂)₂Si(CH₃)₃ used therein results in formation of the following products.

| | |
|---|---|
| Exp. A | m = 0, R = H |
| Exp. B | m = 1, R = H |
| Exp. C | m = 2, R = H |
| Exp. D | m = 0, R = CH₃ |
| Exp. E | m = 1, R = CH₃ |
| Exp. F | m = 2, R = CH₃. |

Substitution in the above procedure of (CH₃)₂NNH₂ for the H₂NO(CH₂)₂Si(CH₃)₃ used therein results in formation of the following products:

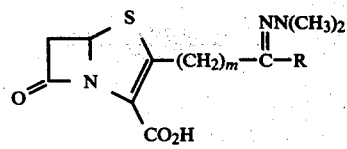

| | |
|---|---|
| Exp. A | m = 0, R = H |
| Exp. B | m = 1, R = H |
| Exp. C | m = 2, R = H |
| Exp. D | m = 0, R = CH₃ |
| Exp. E | m = 1, R = CH₃ |
| Exp. F | m = 2, R = CH₃ |

Substitution in the above procedure of

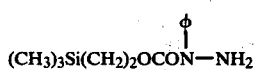

for the H₂NO(CH₂)₂Si(CH₃)₃ used therein results in formation of the following products:

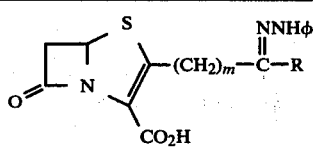

| | |
|---|---|
| Exp. A | m = 9, R = H |
| Exp. B | m = 1, R = H |
| Exp. C | m = 2, R = H |
| Exp. D | m = 0, R = CH₃ |
| Exp. E | m = 1, R = CH₃ |
| Exp. F | m = 2, R = CH₃ |

EXAMPLE 51

2-(γAminopropyl)penem-3-carboxylic Acid

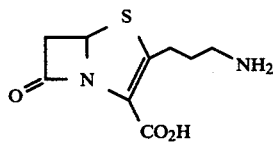

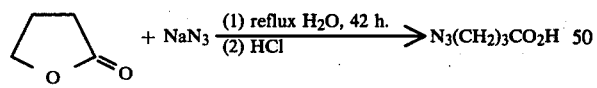

A solution of γ-butyrolactone 1 (86 g, 1 mole) and sodium azide (130 g, 2 moles) in water (200 ml) was heated under reflux for 42 h. The reaction mixture was cooled to 0° C. and acidified with concentrated hydrochloric acid (200 ml); the acid 2 was extracted with ether (3×400 ml). The organic phases were dried over sodium sulfate and concentrated to a pale yellow liquid. The acid 2 was purified by distillation giving a colourless liquid; Bp.$_{3.5}$93° C. (45.9 g, 35.5%). NMR (CDCl₃) δ:11.65 (1H, s, H of carboxylic acid), 3.38 (2H, t, J=6.6 Hz, γ-CH₂), 2.48 (2H, t, J=6.6 Hz, α-CH₂) and 1.92 (2H, m, β-CH₂). I.R. (neat) cm⁻¹:2100 (N₃) and 1705 (c=o of carboxylic acid).

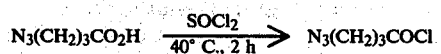

A solution of acid 2 (12.9 g, 0.1 mole) in thionyl chloride (10.8 ml, 0.15 mole) was heated at 40° C. for 2 h or until there was no more evolution of SO₂. The excess of thionyl chloride was evaporated to give a yellow liquid which was purified by distillation (Bp.$_{0.2}$:59°-60° C.) yielding the acid chloride 3 as a colourless liquid (12.7 g, 85.7%). NMR (CDCl₃) δ:3.41 (2H, t, J=6.4 Hz, γ-CH₂), 3.03 (2H, t, J=7.0 Hz, α-CH₂) and 1.9 (2H, m, β-CH₂). IR (neat) cm⁻¹:2100 (N₃) and 1795 (c=o of acylchloride).

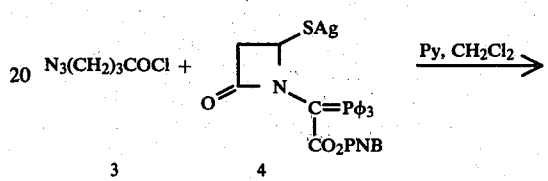

The γ-azidobutyryl chloride 3 (0.76 g, 5.14 mmoles) was slowly added to a cold solution (5° C.) of silver thiolate 4 (3.1 g, 4.67 mmoles) in CH₂Cl₂ (50 ml) containing pyridine (0.42 ml, 5.14 mmoles). The reaction mixture was stirred in an ice bath for 2 h and the white precipitate of silver chloride was filtered off after dilution with ether. The filtrate was washed by HCl 5%, saturated aqueous sodium bicarbonate and brine and dried over sodium sulfate. The solvent was evaporated to an oil which was purified by column chromatography (silica gel G, eluent: dichloromethane, then an equal mixture of dichloromethane and ethyl acetate]. Evaporation of appropriate fractions gave 5 as a foam which was triturated in ether and filtered [2.4 g, 77%, M.p.: 80°-90° C. (decomp.)] IR (KBr)cm⁻¹: 2090 (N₃) and 1750, 1685, 1655 and 1605 (c=o of β-lactam, thioester and ester).

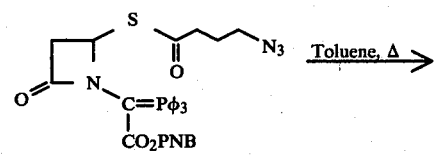

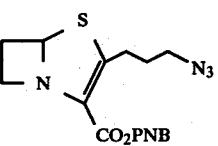

A solution of phosphorane 5 (2.1 g, 3.15 mmoles) in toluene (150 ml) was heated at reflux for 2 h 30 min. The evaporation of solvent gave an oil which was purified by column chromatography [silica gel G, eluent: $CH_2Cl_2$ and $CH_2Cl_2$—AcOEt (9:1)]. The evaporation of appropriate fractions gave 6 as an oil which solidified when triturated in ether; the filtration of the solid gave (0.5 g, 41%). NMR (CDCl$_3$) δ:8.23 (2H, d, $J_{Ho,Hm}=9.2$ Hz, Ho of p-nitrobenzyl), 7.60 (2H, d, $J_{Hm,Ho}=9.2$ Hz, Hm of p-nitrobenzyl), 5.66 (1H, dd, $J_{5,6\ cis}=3.8$ Hz, $J_{5,6\ trans}=1.6$ Hz, H-5), 5.32 (2H, center of Abq, $J_{a,b}=14.0$ Hz, CH$_2$ of p-nitrobenzyl), 3.85 (2H, dd, $J_{6.5\ cis}=3.8$ Hz, $J_{gem}=16.2$ Hz, H-6 cis), 3.43 (dd, $J_{6,5\ trans}=1.6$ Hz, $J_{gem}=16.2$ Hz, H-6trans), 3.34 (t, J=6.5 Hz, γ-CH$_2$ on C-2), 2.9 (2H, m, α-CH$_2$ on C-2) and 1.8 (2H, m, β-CH$_2$ on C-2). IR (KBr) cm$^{-1}$:2090 (N$_3$), 1780 (c=o of β-lactam) and 1700 (c=o of p-nitrobenzyl ester). UV $\lambda_{max}^{CHCl_3}$:315 (ε=10380) and 267 (ε=13760) An analytical sample was obtained after recrystallization from ethyl acetate-hexane mixture; m.p.:72°-73° C. Calc'd for $C_{16}H_{15}N_5O_5S$: C 49.35, H 3.88, N 17.99, S 8.23. Found: C 49.33, H 3.75, N 18.22, S 8.23.

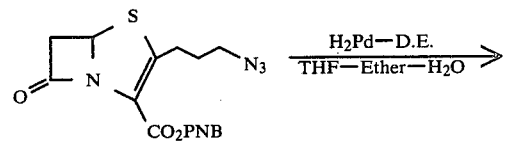

6

To a solution of ester 6 (200 mg, 0.5 mmole) in tetrahydrofuran (10 ml) was added ether (10 ml), water (10 ml) and 30% palladium on diatomaceous earth (200 mg). The reaction mixture was hydrogenated in a Parr apparatus under 35 p.s.i. at 25° C. for 2 h 30 min and filtered over a celite pad. The filtrate was washed twice with ether and the aqueous solution was lyophilized, giving a yellow powder which was purified by column chromatography [Sephadex G-10, bed dimensions: 100×1.6 cm, flow rate:12 ml/h, eluent: distilled water, fraction volume:1.5 ml detector: refractive index]. The right fractions were combined and lyophilized to give a white powder (10 mg, 8.8%). UV $\lambda_{max}^{H_2O}$ 301 (ε=4930), 258 (ε=3290). IR (KBr) cm$^{-1}$:1770 (c=o of β-lactam) and

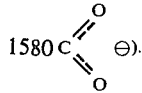

The stability of compound 7 in aqueous solution was followed by UV; after 6 h:301 (4795) and 258 (3105) and after 72 h:301 (4565) and 258 (3150).

EXAMPLE 52

2-(β-Aminoethyl)penem-3-carboxylic Acid

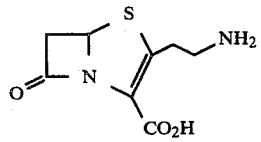

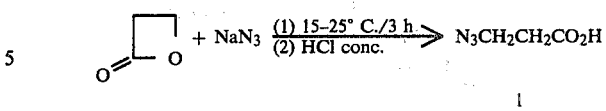

1

β-propiolactone (36 g, 0.5 mole) was added slowly to a solution of sodium azide (32.5 g, 0.5 mole) in water (100 ml). The reaction mixture was stirred and kept at 15°-25° C. with external cooling. After 3-3.5 h, the solution was cooled to 0° C., acidified slowly with concentrated HCl (50 ml) and extracted with ether. The ether phase was dried over sodium sulfate and concentrated to a yellow liquid, distillation of which gave a colourless liquid; 42.1 g, 73%, Bp.$_{0.35}$:71.2° C. NMR (CDCl$_3$) δ:11.94 (1H, s, hydrogen of carboxylic acid), 3.59 (2H, t, $J_{3,2}=6.1$ Hz, H-3) and 2.63 (2H, t, $J_{2,3}=6.1$ Hz, H-2). I.R. (neat) cm$^{-1}$: 2100 (N$_3$) and 1710 (c=o of carboxylic acid).

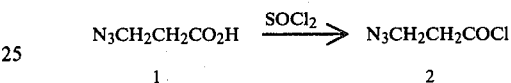

Thionyl chloride (35.6 g, 0.30 mole) was added to β-azido propionic acid 1 (23 g, 0.20 mole) and the resulting solution was stirred for 2 h at ca 50° C. The excess of thionyl chloride was evaporated and the acid chloride 2 was purified by distillation (72°-75° C., p=16 torr) yielding 21.4 g (80%) of colourless liquid. IR (neat) cm$^{-1}$:2090 (N$_3$) and 1780 (c=o of acylchloride).

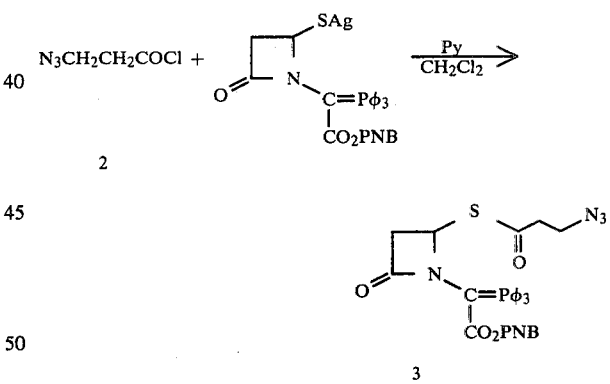

The β-azido propionyl chloride 2 (0.38 g, 2.85 mmoles) was added slowly to a cold solution (5° C.) of silver thiolate (1.72 g, 2.6 mmoles) in dichloromethane (25 ml) containing pyridine (0.24 ml). The reaction mixture was stirred in ice bath for 30 min, then for 2 h at room temperature. A white precipitate of silver chloride was filtered after dilution by ether. The filtrate was washed by HCl 5%, saturated aqueous sodium bicarbonate and brine, dried by sodium sulfate and concentrated under reduced pressure to a foam which was purified by column chromatography [silica gel, eluent: dichloromethane then an equal mixture of dichloromethane and ethyl acetate]. The evaporation of appropriate fractions gave 3 as an oil (1.4 g, 82.4%). I.R. (neat) cm$^{-1}$:2100 (N$_3$) and 1755, 1690, 1620 (c=o).

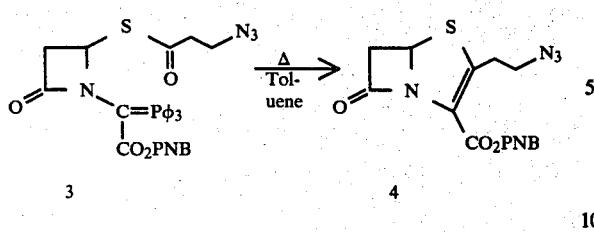

A solution of phosphorane 3 (1.4 g, 2.14 mmoles) in toluene (100 ml) was heated at reflux for 3 h 30 min. Evaporation of solvent and column chromatography [silica gel, eluent: $CH_2Cl_2$, then $CH_2Cl_2$—AcOEt (1:1)] gave after evaporation of good fractions an oil which solidified when triturated in ether. The compound 4 was obtained as a pale yellow solid (0.5 g, 62.3%, m.p.:62°-5° C. NMR ($CDCl_3$) δ:8.27 (2H, d, $J_{Hm,Ho}=8.8$ Hz, Hm of p-nitrobenzyl), 7.64 (2H, d, $J_{Ho,Hm}=8.8$ Hz, Ho of p-nitrobenzyl), 5.70 (1H, dd, $J_{5,6}$ cis=3.8 Hz, $J_{5,6\ trans}=2.0$ Hz, H-5), 5.37 (2H, center of ABq, $J_{a,b}=13.2$ Hz, $CH_2$ of p-nitrobenzyl), 3.87 (1H, dd, $J_{6,5\ cis}=3.8$ Hz, $J_{gem}=16.0$ Hz, H-6 cis) and 3.7–2.7 (5H, H-6 trans, α and β $CH_2$ on C-2). IR (KBr) $cm^{-1}$:2095 and 2125 ($N_3$), 1795 (c=o of β-lactam) and 1695 (c=o of β-nitrobenzyl ester). UV $\lambda_{max}^{CHCl_3}$: 267 (ε 11,700) and 319 (ε 8,750). An analytical sample was obtained by preparative TLC; m.p.:62°-65° C., calc'd for $C_{15}H_{13}N_5P_5S$: C 48.00, H 3.49, N 18.66, S 8.54. Found: C 47.84, H 3.36, N 18.69, S 8.62.

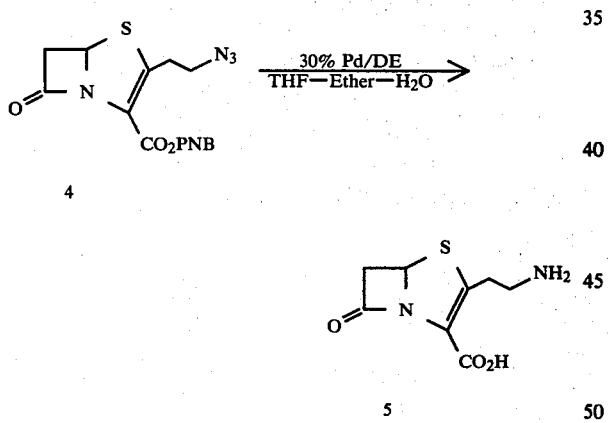

To a solution of ester 4 (260 mg, 0.6 mmole) in THF (10 ml) was added ether (10 ml), water (10 ml) and 30% palladium on diatomaceous earth (260 mg). The reaction mixture was hydrogenated in a Parr apparatus under 35 p.s.i. for 2 h 30 min at 25° C., and filtered over a celite pad. The filtrate was washed twice with ether and the aqueous solution was lyophilized, yielding a yellow powder (115 mg) from which 40 mg was purified by column chromatography [Sephadex G-10, bed dimensions: 100×1.6 cm, flow rate:12 ml/h, eluent: distilled water, fraction volume:1.5 ml, detector: refractive index]. The fractions 58 to 65 were combined and lyophilized to give a white powder (9 mg, 20%). U.V. ($H_2O$) $\lambda_{max}$ 302 (ε=5106), 258 (ε=3678). IR (KBr) $cm^{-1}$:1755 (c=o of β-lactam), 1660, 1605,

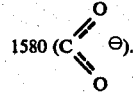

EXAMPLE 53

Sodium 2-(3-Pyridyl)penem-3-carboxylate

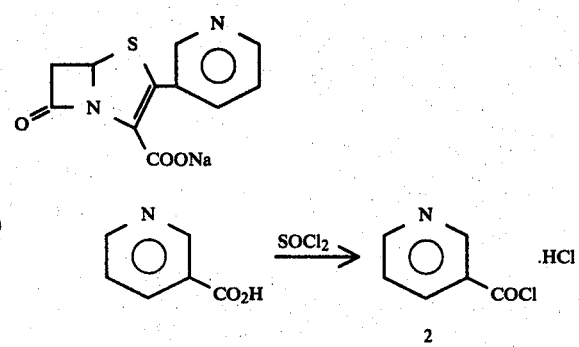

A mixture of nicotinic acid (2.46 g, 20 mmoles) and thionyl chloride was stirred for 2 h at 25°. The excess of thionyl chloride was distilled off at 30° and at 10–20 torr to give acid chloride 2 as a solid 3.56 g (100%). δ(ppm $CDCl_3$=DMSO) 8.8–9.3 and 8.2 (two m).

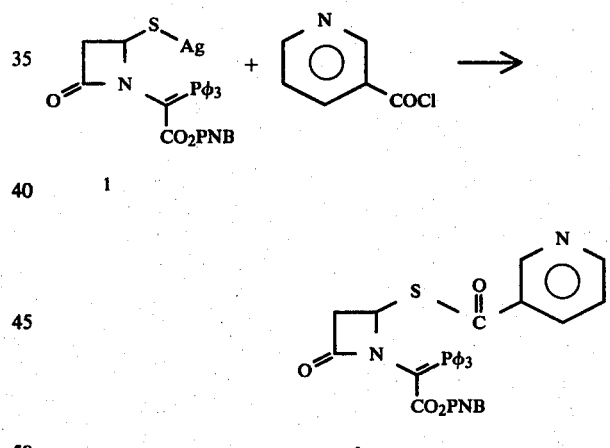

To a cold (0° C.) solution of acid chloride 2 (0.75 g, 4.2 mmoles) in methylene chloride (10 ml) was added a solution of silver mercaptide 1 (2.65 g, 4.0 mmoles) in methylene chloride (40 ml) containing the pyridine (0.80 ml, 10 mmoles). The reaction mixture was stirred at 0° for 10 min, then allowed to warm up to room temperature and stirred for 2 h. The precipitate was filtered off through a celite pad and washed with methylene chloride. The organic solution was washed with water, HCl (5%), diluted aqueous sodium bicarbonate, water and brine. The solvent was evaporated and the residue dry column chromatographed on silica gel (20 g) eluting with methylene chloride, methylene chloride: ethyl acetate 3:1. Evaporation of appropriate fractions gave 3, 820 mg (31%)

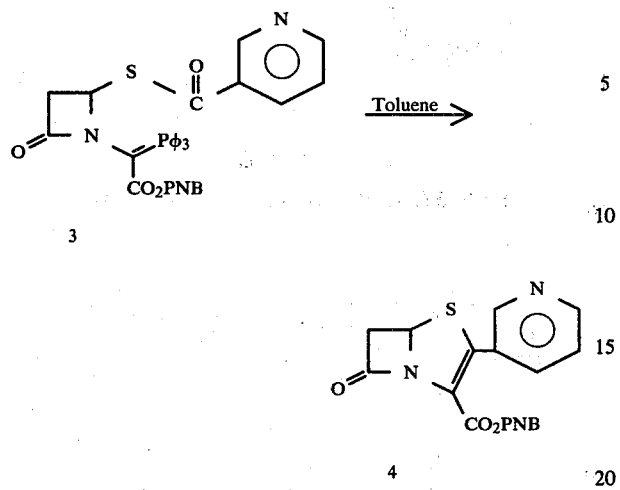

3

4

A solution of 3 (502 mg, 0.77 mmole) in toluene was refluxed for 1.5 h. Evaporation of solvent gave a residue which was purified through silica gel (20 g) and eluted with methylene chloride: ethyl acetate 9:1. Evaporation of appropriate fractions gave 4, 135 mg (46%). 138°–142°. δ(ppm CDCl$_3$) 8.62 (2H, m, H-2'–H-6'), 8.15 (2H, d, J=9, Hm), 7.92 (1H, m, H-4'), 7.40 (3H, d+m, Ho–ho5'), 5.82 (1H, m, H-5), 5.22 (2H, center of ABq, J=14, CH$_2$-PNB), 3.92 (1H, dd, J$_{gem}$=15, J$_{5-6\ cis}$=4, H-6 cis), 3.60 (1H, dd, J$_{gem}$=15, J$_{5-6\ trans}$=2, H-6trans). V$_{c=o}$ (cm$^{-1}$) 1790 (β-lactam), 1720 (ester).

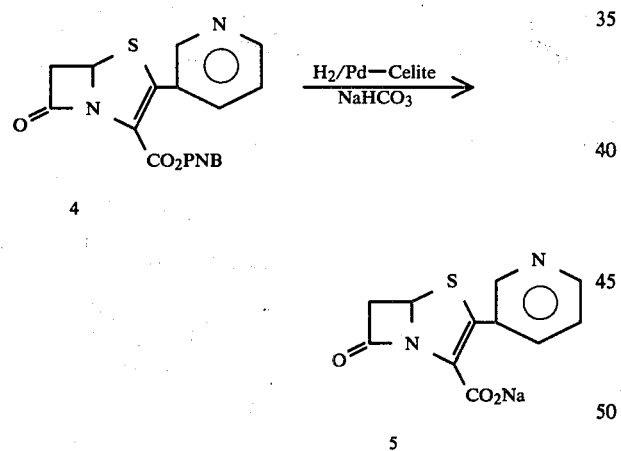

4

5

A mixture of ester 4 (53 mg, 0.14 mmole) in THF (10 ml), ether (15 ml) and NaHCO$_3$ (12 mg, 0.14 mmole) in water (10 ml) was shaken on a Parr hydrogenator for 3 h at 30 p.s.i. H$_2$ using 30% Pd on celite (50 mg) as catalyst. The catalyst was removed and washed with ether and water. The aqueous phase was shaken with ether (3×30 ml) and lyophilized to yield the sodium salt 5, 37 mg (98%). ν(KBr) (cm$^{-1}$) 1760 (β-lactam), 1595 (C$\overset{O}{\underset{O}{\lessgtr}}$ ⊖).

λ$_{max}$ 263 ($\frac{1}{3}$≃10,800), 320 (ε=6,757).

EXAMPLE 54

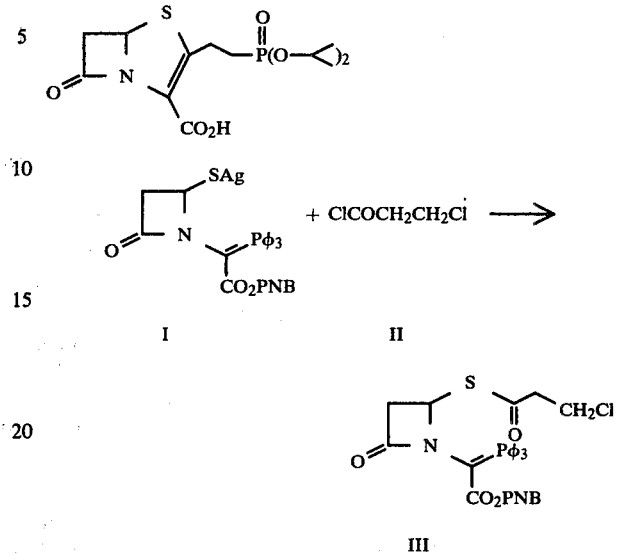

I  II

III

A solution of I (1.1 g., 1.6 mmole) and II (0.16 ml, 1.6 mmole) in methylene chloride (30 ml) was cooled in an ice bath and treated dropwise with 1 M solution of pyridine in methylene chloride (1.7 ml, 1.7 mmole). The resulting reaction mixture was stirred at room temperature for 1 h and then filtered over celite and washed with methylene chloride. The filtrate and washings were combined and washed successively with 1 N HCl (5 ml), water (5 ml), 1 M NaHCO$_3$ (5 ml) and brine, and then dried (MgSO$_4$) and evaporated in vacuo to give III 900 mg (87%) as an amorphous solid. It was used in the next step without further purification. IR (CHCl$_3$) 1755, 1690 cm$^{-1}$. NMR (CDCl$_3$) δ 8.22 (2H, d, J=9 Hz), 7.55 (15H, m), 6.72 (2H, d, J=9 Hz), 5.7 (1H, m), 5.0 (2H, 2s), 3.55 (2H, 2s), 2.8 (4H, m).

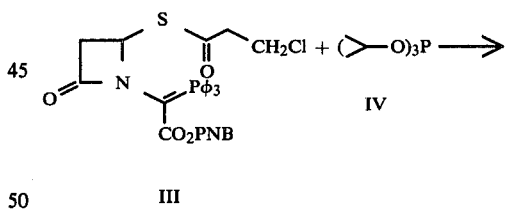

III  IV

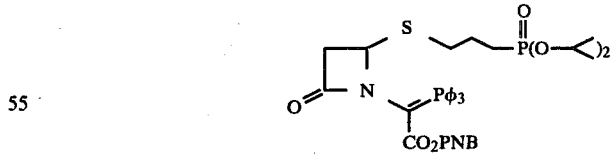

V

A mixture of III (1.3 g, 2 mmoles) and IV (0.65 ml, 3 mmoles) was heated at 80° C. for 4 h. The reaction mixture was diluted with methylene chloride (10 ml) and washed with water (2×5 ml). Organic layer was dried (MgSO$_4$) and evaporated in vacuo to give V, 1.4 g (90%), as an amorphous solid. It was used in the next step without further purification. IR (CHCl$_3$) 1755, 1690 cm$^{-1}$ NMR (CDCl$_3$) δ 8.25 (2H, d, J=9 Hz), 7.55

(15 H, m), 6.8 (2H, d, J=9 Hz), 5.7 (1H, m), 5.1 (2H, 2s), 4.72 (2H, dq J=12 Hz, J=6 Hz), 2.6 (4H, m), 1.4 (6H, s), 1.28 (6H, s).

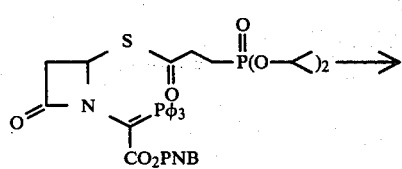

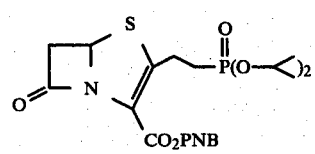

A solution of V (1.6 g, 2.06 mmoles) in toluene (60 ml) was heated under reflux for 5 h.

The solvent was evaporated in vacuo and the residual oil was chromatographed on silica gel column (30 g). Elution with benzene followed by ether removed first unpolar material and then ethyl acetate gave VI, 620 mg (62%) as a white solid, m.p.: 83°-4° C. from ether. IR (CHCl$_3$) 1790, 1710 cm$^{-1}$ NRM: (CDCl$_3$) δ 8.2 (2H, d, J=9 Hz), 7.6 (2H, d, J=9 Hz) 7.5 (2H, s) 5.65 (1H, dd, J$_{trans}$=4 Hz, J$_{cis}$=2 Hz), 5.22 (2H, 2s), 4.75 (2H, dq J=12 Hz, J=6 Hz), 3.85 (1H, dd, J$_{gem}$=15 Hz, J$_{trans}$=4 Hz), 3.5 (1H, dd, J$_{gem}$=15 Hz, J$_{cis}$=2 Hz), 2.8-3.3 (2H, m), 1.4 (6H, s), 1.28 (6H, s).

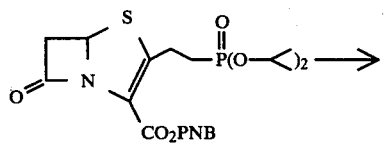

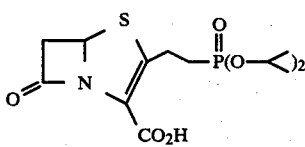

To a solution of VI (200 mg, 0.4 mmole) in tetrahydrofuran (8 ml) and ether (4 ml) was added sodium bicarbonate (34 mg, 0.4 mmole), water (4 ml) and 30% Pd/Celite (200 mg) followed by hydrogenation 2 h at 40 p.s.i. The mixture was filtered and layers were separated. The aqueous phase, after washing with methylene chloride (2×5 ml), was cooled with ice, acidified with 1 N HCl (1 ml), and extracted with chloroform (5×5 ml). Organic extracts were dried (MgSO$_4$) and evaporated in vacuo to give VII, 76 mg (52%), as an oil. IR (CHCl$_3$) 1790, 1710 cm$^{-1}$. NMR (CDCl$_3$) δ 9.5 (1H, ws), 5.65 (1H, dd, J$_{trans}$=4 Hz, J$_{cis}$=2 Hz), 4.72 (2H, dq J=12 Hz, J=6 Hz), 4.2-5.1 (2H, m), 3.4-4.1 (2H, m), 2.7-3.4 (2H, m), 1.35 (6H, s), 1.25 (6H, s).

EXAMPLE 55

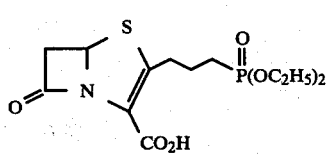

-continued

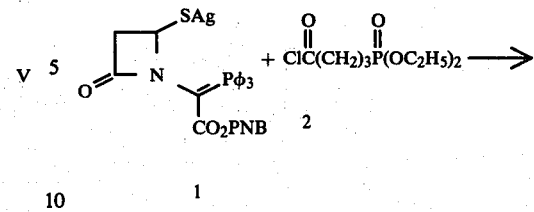

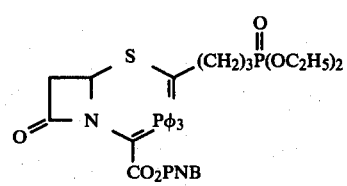

To a cooled (ice bath) mixture of 1 (1.324 g, 2 mmoles) and 2 (0,54 g, 2.2 mmoles, crude) in CH$_2$Cl$_2$ (15 ml) was added dropwise 1 M solution pyridine/CH$_2$Cl$_2$ (2.2 ml, 2.2 mmoles). The mixture was stirred at r.t. for 1 h and filtered over celite. The filtrate was washed successively with 0.5 N HCl, H$_2$O, 0.5 M NaHCO$_3$ and brine. It was dried (MgSO$_4$) and filtered over celite charcoal to give after evaporation to dryness 0.9 g of an oil. The oil was chromatographed on SiO$_2$ (10% H$_2$O) and eluted with ethylacetate to give 0.5 g of 3. (32.8%). NMR δ (ppm, CDCl$_3$) 7.0-8.4 (m, 19H), 4.8-5.8 (3H, m), 4.1 (4H, q), 3.3-4.2, (2H, m) 2.7 (2H, m), 1.9 (2H, m), 1.3 (6H, t).

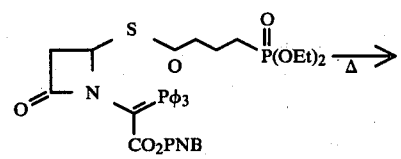

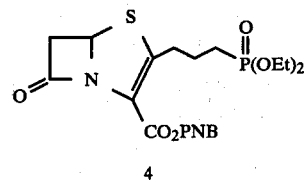

3 (0.4 g, 0.52 mmole) in toluene (35 ml) was refluxed for 4 h and evaporated to dryness to give an oil which contained 3, 4 and φ$_3$P=O. This was chromatographed on SiO$_2$ (10% H$_2$O) and eluted with EtOAc to give 0.1 g of pure 4, followed by 0.15 g of 3 and 4. NMR δ (ppm, CDCl$_3$). 8.3 (2H, d), 7.67 (2H, d), 5.7 (H, q), 5.33 (2H, d), 4.2 (4H, q), 3.83 (H, q), 3.4 (H, q), 2.9 (2H, m), 1.9 (2H, m), 1.3 (6H, t). IR (neat) 1790 cm$^{-1}$ (β-lactam) 1710 cm$^{-1}$ (ester).

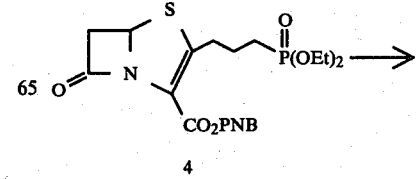

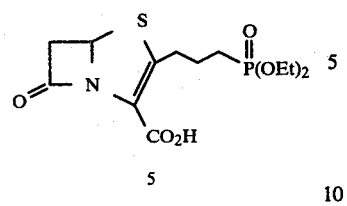

A mixture of 4 (0.1 g, 0.207 mmole), 30% Pd/celite (0.1 g) and NaHCO$_3$ (17 mg, 0.207 mmole) in THF (10 ml), ether (5 ml) and water (5 ml) was hydrogenated at an initial pressure of 40 psi for 2 h. It was filtered over celite and the layers separated. Basic aqueous layer was washed well with ethylacetate and acidified with 1NHCl. It was extracted with CH$_2$Cl$_2$ and dried (MgSO$_4$). The CH$_2$Cl$_2$ solution was evaporated to give 48 mg of 5 (66.5%). IR spectrum δ 1790 (β-lactam)

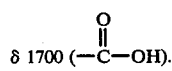

EXAMPLE 56

Sodium 3-(5-Methylthio-1,3,4-oxadiazol-2-yl)penem-3-carboxylate

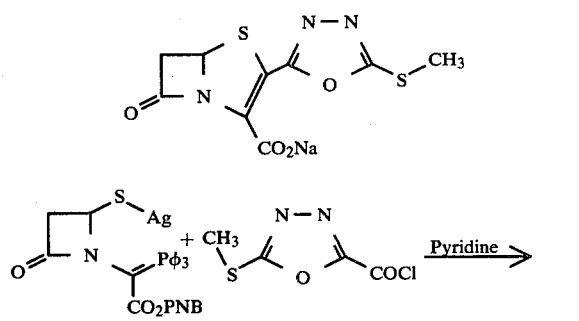

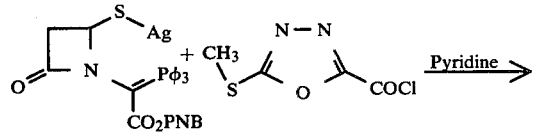

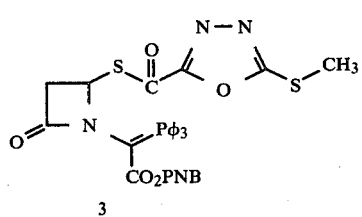

To a cold (0° C.) solution of acid chloride 2 (0.66 g, 3.7 mmoles) in methylene chloride (10 ml) was added a solution of silver mercaptide 1 (2.45 g, 3.7 mmoles) in methylene chloride (50 ml) containing pyridine (0.293 mg, 3.7 mmoles). The reaction mixture was stirred at 0° for 10 min and then allowed to warm up to room temperature and stirred for 2 h. The precipitate was filtered off through a Celite pad and washed with methylene chloride. The organic solution was washed with water, HCl (5%), diluted aqueous sodium bicarbonate, water and brine. The solvent was evaporated and the residue dry column chromatographed on silica gel (30 g) eluting with methylene chloride and methylene chloride:ether 4:1. Evaporation of appropriate fractions gave 3, 900 mg (35%).

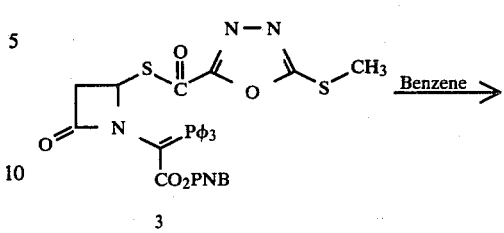

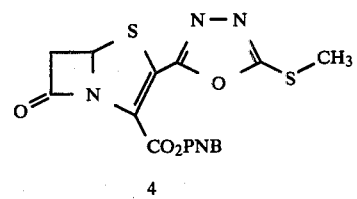

A solution of 3 (600 mg, 0.87 mmole) in benzene was refluxed for 15 min. Evaporation of solvent gave a residue which was purified through a silica gel (10 g) column eluting with methylene chloride, methylene chloride: ether 4:1. Evaporation of appropriate fractions gave 4, 273 mg (76%)) as a foam. δ (ppm CDCl$_3$) 8.20 (2H, d, J=9, Hm), 7.55 (2H, d, J=9, Ho), 5.88 (1H, dd, J$_{5-6\ trans}$=2, J$_{5-6\ cis}$ =4, H-5), 5.34 (2H, s, CH$_2$—CO$_2$PNB), 3.88 (1H, dd, J$_{gem}$=15, J$_{5-6\ trans}$=2, H-6 trans), 2.70 (3H, s, S—CH$_3$). This compound decomposes partially on T.L.C. $\nu_{c=o}$ (cm$^{-1}$) 1805 (β-lactam), 1725 (ester).

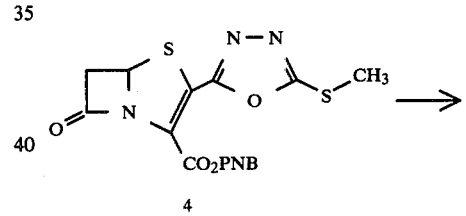

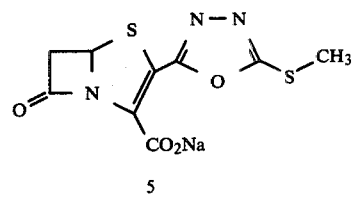

A mixture of ester 4 (82 mg, 0.195 mmole) in THF (10 ml), ether (15 ml) and NaHCO$_3$ (16 mg, 0.195 mmole) in water (10 ml) was shaken on a Parr hydrogenator for 3 h at 30 p.s.i. H$_2$ using 30% Pd on celite (80 mg) as catalyst. The catalyst was removed and washed with ether and water. The aqueous phase was shaken with ether (3×30 ml) and lyophilized to yield the sodium salt 5, 52.7 mg (88%). In NMR, it is a mixture of two or more compounds. $\nu$ (KBr) (cm$^{-1}$) 1785 (β-lactam),

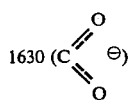

$\lambda_{max}$ 243 ($\epsilon$ 6,770), 280 ($\epsilon$ 4,770) 346 ($\epsilon$ 3,538).

EXAMPLE 57

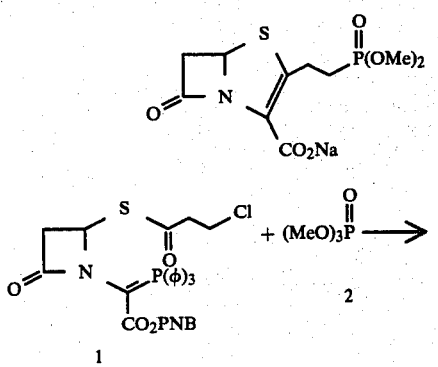

A mixture of 1 (1.07 g, 1.66 mmole) and 2 (0.42 g, 3 mmoles) in CH$_2$Cl$_2$ (3 ml) was heated at 80° for 5 h. The crude ol was chromatographed on SiO$_2$ (3% H$_2$O) and eluted with ether, ether-ethylacetate (1:1) and ethyl acetate: 5% EtOH to give 1.0 g of 3 (82%). The oil crystallized on standing, M.P. (ether) 138°–40°. NMR δ (ppm, CDCl$_3$) 8.2 (2H, d) 7.0–8.0 (17H, m), 4.6–5.5 (3H, m), 3.8 (3H, s), 3.6 (3H, s), 1.5–3.5 (6H, m).

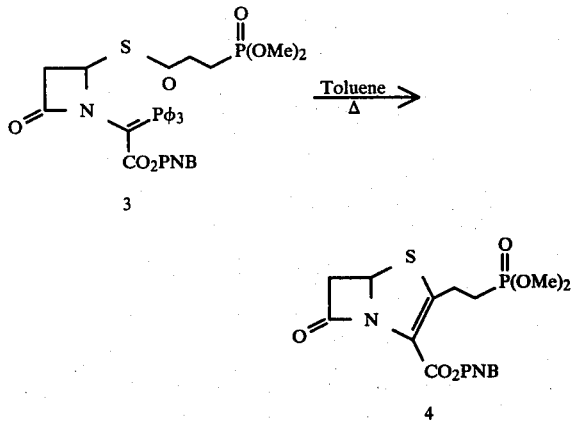

3 (0.5 g, 0.69 mmole) in toluene (30 ml) was refluxed for 4 h. It was evaporated to dryness, chromatographed on SiO$_2$ (3% H$_2$O) and eluted with Et$_2$O: EtOAc (1:1) followed by EtOAc: 10% EtOH to give 0.18 g of 4 (58%). NMR δ (ppm, CDCl$_3$), 8.25 (2H, d), 7.6 (2H, d), 5.65 (H, q), 5.3 (2H, d), 3.8 (3H, s) 3.6 (3H, s), 2.7–3.6 (2H, m), 1.5–2.5 (4H, m).

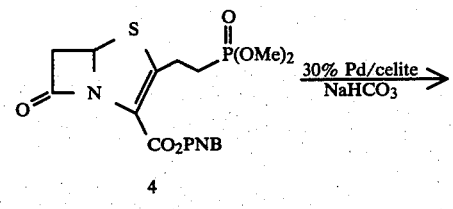

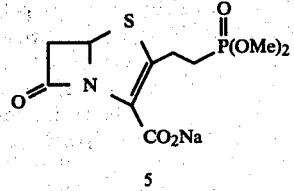

A mixture of 4 (50 mg, 0.112 mmole), NaHCO$_3$ (9.125 mg) and 30% Pd/celite (50 mg) in THF (5 ml), Et$_2$O (2.5 ml) and water (2.5 ml) was hydrogenated at an initial pressure of 40 psi (for 2 h). It was filtered over celite, and the layers separated. The basic aqueous layer was washed well with EtOAc and lyophilized under high vacuum to give 28 mg of 5. (75.9%) (hygroscopic). IR (KBr) 1770 cm$^{-1}$ (β-lactam), 1610 cm$^{-1}$ (—COO$^-$).

EXAMPLE 58

(1'R,5R,6R) and (1'S,5S,6S) 6-(1'-Hydroxy-1'-ethyl)-2-methylpenem-3-carboxylic Acid (isomer D) (illustrates most preferred process of introducing 6-substituent in mid-synthesis

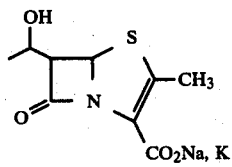

A. Preparation of 4-Tritylthio-2-azetidinone Intermediates 1. 1-(Trimethylsilyl)-4-tritylthio-2-azetidinone

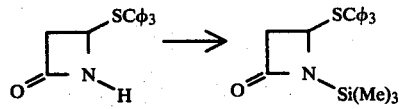

A solution of 4-tritylthio-2-azetidinone (345 mg, 1 mmole), 1,1,1,3,3,3,-hexamethyldisilazane (80 mg, 0.5 mmole) and chlorotrimethylsilane (55 mg, 0.5 mmole) in dichloromethane (20 ml) was heated under reflux for 18 h. Concentration of the reaction mixture left virtually pure title compound. δ (ppm, CDCl$_3$): 7.32 (15H, m, aromatics), 4.22 (1H, dd, H-4), 2.67 (1H, dd, J=4.1, J=16, H-3), 2.22 (1H, dd, J=2.2, J=16, H-3), 0.3 (9H, s, CH$_3$).

2. 1-(t-Butyldimethylsilyl)-4-tritylthio-2-azetidinone

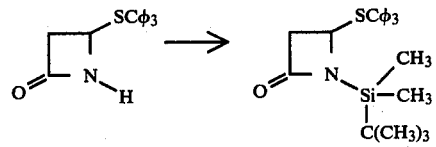

Triethylamine (1.62 ml, 11.6 mmoles) was added dropwise in 5 min to a cooled (0°) and stirred solution of 4-tritylthio-2-azetidinone (3.5 g, 10.1 mmoles) and chloro-t-butyldimethylsilane (1.68 g, 12.7 mmoles) in DMF (35 ml). The reaction mixture was stirred at room temperature for 18 h, diluted with water (250 ml) and ether (200 ml). The organic phase was washed with water

3. 1-Methoxymethyl-4-tritylthio-2-azetidinone

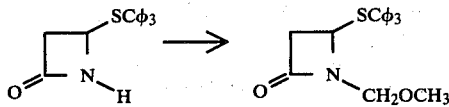

A solution of 4-tritylthio-2-azetidinone (1.38 g, 4.0 mmoles) in THF (10 ml) was added to a well stirred suspension of sodium hydride (200 mg of commercial 50%, 4.1 mmoles, washed with pentane) in THF (10 ml) maintained at −15°. Methanol (12 drops) was added and the mixture was stirred at −15° for 0.5 h. Methoxymethyl bromide (0.58 g, 4.6 mmoles) was added and the mixture was stirred for 2 h, diluted with ether, washed with water and brine, dried and concentrated to leave an oil (1.72 g). Crystallization from pentane gave a white solid (1.41 g) m.p. 72–76 δ (ppm, CDCl$_3$): 7.3 (15H, m, aromatics), 4.4 (3H, m, NCH$_2$O and H-4), 3.22 (3H, s, CH$_3$), 2.76 (2H, m, H-3).

4. 1-(Methoxyethoxymethyl)-4-tritylthio-2-azetidinone

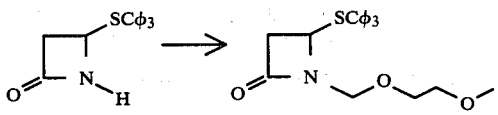

To a suspension of tetrabutylammonium bromide (322 mg, 1 mmole) and potassium hydroxide (85%, 70 mg, 1.1 mmole) in dichloromethane (10 ml) cooled to 5° was added with vigorous stirring 4-tritylthio-2-azetidinone (345 mg, 1 mmole) and methoxyethoxymethyl chloride (187 mg, 1.5 mmole). The mixture was stirred at room temperature for 2 h, the solvent was evaporated and the residue partitioned between water and ethyl acetate. The dried organic phase was concentrated to leave a viscous oil (415 mg). Purification by column chromatography on silica gel eluting with ether (5%)-dichloromethane gave the title compound (206 mg, 48%) as an oil. δ (ppm, CDCl$_3$): 7.30 (15H, m, aromatics), 4.57 (2H, AB quartet, N—CH$_2$O), 4.46 (1H, dd, H-4), 3.50 (4H, s, OCH$_2$CH$_2$O), 3.30 (3H, s, CH$_3$), 2.75 (2H, m, H-3).

5. 1-(2'-Tetrahydropyranyl)-4-tritylthio-2-azetidinone

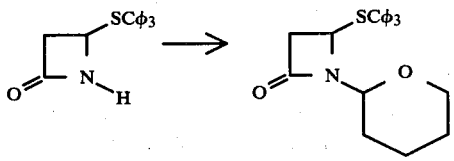

n-Butyl lithium (1.6 M, 1.6 ml, 2.56 mmoles) was added dropwise to a solution of 4-tritylthio-2-azetidinone (863 mg, 2.5 mmoles) in THF maintained at −78°. After stirring for 15 min, 2-chlorotetrahydropyran (560 mg, 4.7 mmoles) was added and the reaction mixture was allowed to come to room temperature in 1.5 h. The reaction solution was diluted with ethylacetate, washed with brine, dried and concentrated to leave an oil (635 mg). Column chromatography on silica gel eluting with dichloromethane-ether gave a mixture of the isomeric title compounds contaminated with a little starting material. δ (ppm, CDCl$_3$): 7.28 (15H, m, aromatics), 4.4 (H, dd, H-4), 2.9–2.2 (2H, m, H-3), 4.1–3.2 and 2.2–0.7 (tetrahydropyranyl).

B. Preparation of 3-(1'-Hydroxy-1'-ethyl)-1-methoxymethyl-4-tritylthio-2-azetidinones

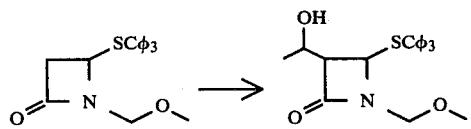

(a) (1'S,3S,4R and 1'R,3R,4S)isomer (isomer C)

A solution of lithium diisopropyl amide was prepared in THF (5 ml) at −78° C. from n-butyl lithium (1.6 M, 1.0 ml, 1.6 mmol) and diisopropylamine (0.25 ml, 1.84 mmol). After 30 min a solution of 1-methoxymethyl-4-tritylthio-2-azetidinone (491 mg, 1.42 mmol) in THF (6 ml) was added dropwise and the solution was stirred for 15 min. Acetaldehyde (3.0 ml) was added dropwise, followed, after 20 min, by water (30 ml). The mixture was acidified to pH 3 with 2% HCl and extracted with ethyl acetate (5×20 ml). The combined organic phases were washed with brine, dried and concentrated to leave an oil which crystallized upon trituration with ether: 440 mg, 80%, mp 188.5°–9° C.; $^1$Hmr (CDCl$_3$) δ: 7.1–7.5 (15H, m, aromatics), 4.37 (2H, ABq, N—CH$_2$O), 4.32 (1H, d, J=2, H-4), 3.17 (3H, s, OCH$_3$), 3.32–2.70 (2H, m, H-3 and H-5), and 1.12 ppm (3H, d, J=7, CH$_3$); Anal. calcd for C$_{26}$H$_{27}$NO$_3$S: C 72.02, H 6.28, N 3.23, S 7.39; found: C 71.99, H 6.02, N 3.21, S 7.40%.

(b) (1'S,3S,4R and 1'R,3R,4S) and (1'R,3S,4R and 1'S,3R,4S) (isomers C and B)

A solution of lithium diisopropyl amide (0.482 mmol) is prepared at −78° C. in dry ether (3 ml) from butyl lithium 0.191 ml of 2.52 M solution in hexane, 0.482 mmol) and diisopropyl amine (0.067 ml, 0.482 mmol). After 20 min, a solution of (4R and 4S) 1-methoxymethyl-4-tritylthio-2-azetidinone (0.171 g, 0.439 mmol) in a mixture of dry ether (1 ml) and dry THF (1 ml) was added dropwise and the resulting clear solution was stirred at −78° C. for 15 min. A solution of tetrabutyl ammonium fluoride (0.96 ml of a 0.5 M solution in THF, 0.48 mmol) was then added. A precipitate was formed with the generation of a slight pink colour. After 5 min at −78° C., the reaction mixture was quenched with freshly distilled acetaldehyde (0.2 ml, excess), and the stirring continued for 15 more min. The work-up was done by adding to a saturated solution of ammonium chloride and extracting with ethyl acetate (2×25 ml). The combined organic phases were washed with brine and dried over anhydrous magnesium sulfate. Evaporation of the solvent under vacuum gave an oil (0.228 g) which was chromatographed on 10 g of silica gel. A mixture of benzene and ethyl acetate (6:4) gave 0.106 g (62% recovery) of substrate and a mixture of the two isomer alcohols which were separated by chromatogra- (3×50 ml), dried and concentrated to leave an oil (4.33 g). Crystallization from pentane gave a total of 4.1 g (89%) of the title compound as a white solid, m.p. 113°–4°. δ (ppm, CDCl$_3$): 7.45 (15H, m, aromatics), 4.2 (1H, dd, H-4), 2.63 (1H, dd, J=4, J=16, H-3), 2.13 (1H, dd, J=2, J=16, H-3), 1.0 (9H, s, t-Bu), 0.35 (6H, s, Me). $v_{c=o}$ 1735 cm$^{-1}$. Anal. calc'd for C$_{28}$H$_{33}$NOSSi: C, 73.15; H, 7.24; N, 3.05; S, 6.97%. Found: C, 73.27; H, 7.32; N, 2.97; S 6.94%.

phy on thick layer plates (same solvent-system). The alcohol with the high Rf (0.033 g, 17%) was identical to the above isomer (isomer C): mp 188.5°-189° C. (Ether-dichloromethane); The alcohol with low Rf (0.030 g, 16%) (isomer B), was obtained as an oil which crystallized with difficulty from hexanes: mp 94°-95° C. ir (CH$_2$Cl$_2$) $\nu_{max}$: 3600 (OH), 1760 cm$^{-1}$ (C=O); $^1$Hmr (CDCl$_3$) δ: 6.9-7.5 (15H, m, aromatics), 4.2 (2H, center of ABq, J=11.5, CH$_2$—O—CH$_3$), 4.28 (1H, d, J=2.0, 4-H), 3.65 (1H, center of a broad sextet, H-1'), 3.3 (1H, dd, J$_{3,4\ trans}$=2.5, J$_{3,1'}$=5.5, H$_3$), 3.15 (3H, s, O—CH$_3$), 1.55 (1H, broad s, OH-1'), 1.05 (3H, d, J=6.5, H-2'); Anal. calcd for C$_{26}$H$_{27}$NO$_3$S: C 72.02, H 6.28, N 3.23, S 7.39; found: C 71.77, H 6.36, N 3.15, S 7.43%.

C. Preparation of trans 3-Acetyl-1-methoxymethyl-4-tritylthio-2-azetidinone

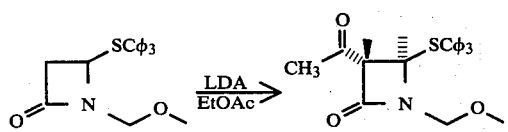

Lithium diisopropylamide was prepared under a nitrogen atmosphere at −78° C. in the usual manner from diisopropylamine (0.34 ml, 2.4 mmol) and n-butyl lithium (1.1 ml of a 2.2 M solution in hexane, 2.4 mmol) in THF (3 ml). A solution of 1-methoxymethyl-4-tritylthio-2-azetidinone (0.78 g, 2 mmol) in THF (3 ml) was added dropwise and, after stirring at −78° C. for 20 min, ethylacetate (0.53 g, 6 mmol) was added in one portion and stirring continued for 0.75 h at −78° C. The reaction mixture was diluted with ether and washed with an ammonium chloride solution, water and brine, dried and concentrated to give an oil (0.7 g). Purification was achieved by chromatography over silica gel (20 g) eluting with increasing amounts of ether in benzene. The pertinent fractions were concentrated to give the title material as a colorless oil (0.32 g, 37%); $^1$Hmr (CDCl$_3$) δ: 7.7-6.8 (15H, aromatics), 4.85 (1H, d, J=2, H-4), 4.5 (2H, s, N—CH$_2$—O), 3.9 (1H, d, J=2, H-3), 3.22 (3H, s, CH$_3$) and 2.0 ppm (3H, s, CH$_3$); ir $\nu_{max}$: 1770, 1710 cm$^{-1}$.

D. Preparation of trans 3-Acetyl-1-(t-butyldimethylsilyl)-4-tritylthio-2-azetidinone

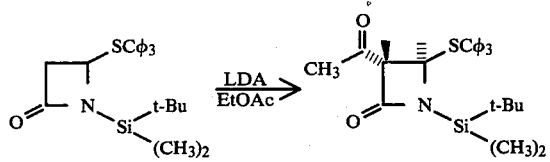

Diisopropyl lithium amide was prepared in the usual manner from diisopropylamine (0.18 ml, 1.24 mmol) and n-butyl-lithium (0.78 ml of a 1.6 M solution in hexane, 1.24 mmol) in THF (8 ml). A solution of 1-(t-butyldimethylsilyl)-4-tritylthio-2-azetidinone (0.46 g, 1 mmol) in THF (8 ml) was added dropwise at −78° C. After a 5 min stirring period, ethyl acetate (1 ml) was added in one portion and the mixture was stirred 3 h at −78° C. The mixture was acidified with cold hydrochloric acid (0.5 N) to pH 6 and extracted with ethyl acetate (2×20 ml). The combined organic phases were dried and concentrated to give an oil (0.5 g) which crystallized from pentane: 200 mg total, 40%; mp 122°-4° C.; ir $\nu_{max}$: 1750, 1710 cm$^{-1}$; $^1$Hmr (CDCl$_3$) δ: 8-7.1 (15H, m, aromatics), 4.83 (1H, d, J=2, H-4), 3.38 (1H, d, J=2, H=3), 1.80 (3H, s, CH$_3$), 0.92 (9H, s, Bu and 0.3 ppm (6H, s, CH$_3$).

E. Preparation of trans-1-(t-Butyldimethylsilyl)-3-formyl-4-tritylthio-2-azetidinone

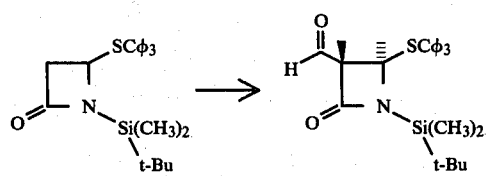

To a cooled (−78° C.) solution of diisopropylamine (0.34 ml, 2.4 mmol) in tetrahydrofuran (5 ml) was added dropwise, under N$_2$, a solution of 1.5 M n-BuLi (1.6 ml, 2.4 mmol). After stirring for 30 min, a solution of 1-(t-butyldimethylsilyl)-4-tritylthio-2-azetidinone (1.0 g, 2.18 mmol) in tetrahydrofuran (5 ml) was added dropwise and stirring was maintained for 30 min. Ethyl formate (0.8 ml, 9.9 mmol) was added and the cooled solution was stirred for 10 min. The reaction mixture was washed successively with cold 1 N hydrochloric acid (5 ml), 1 M sodium bicarbonate (6 ml), water (10 ml) and brine. The organic layer was dried (MgSO$_4$), evaporated and crystallized from pentane to give 810 mg (76%) of formate as a white solid mp 132°-3° C.; ir (CHCl$_3$) $\nu_{max}$: 1760, 1715 cm$^{-1}$; $^1$Hmr (CDCl$_3$) δ: 9.0 (1H, d, J=1.25 Hz), 7.30 (15H, m), 4.7 (1H, d, J=1.5 Hz) and 3.5 ppm (1H, t, J=1.5 Hz).

NOTE:
(a) diisopropyl amine was distilled over CaH and stored on KOH
(b) tetrahydrofuran was distilled over L.A.H. and stored on molecular sieves 3Å
(c) ethyl formate was stirred at room temperature with K$_2$CO$_3$, then distilled over P$_2$O$_5$
(d) n-BuLi was titrated with 1 N hydrochloric acid

F. Preparation of 1-(t-Butyldimethylsilyl)-3-(1'-hydroxy-1'-ethyl)-4-tritylthio-2-azetidinones. (4 isomers)

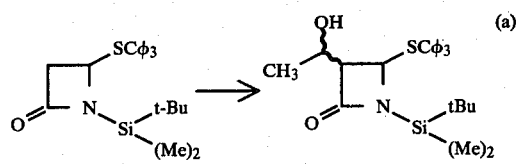

n-Butyllithium (1.6 M, 3.4 ml, 5.44 mmol) was added in 5 min to a solution of diisopropylamine (0.847 ml, 6.23 mmol) in THF (30 ml) maintained at −78° C. After 0.5 h a solution of 1-(t-butyldimethylsilyl)-4-tritylthio-2-azetidinone (2.0 g, 4.4 mmol) in THF (20 ml) was added; after 15 min acetaldehyde (10 ml) was added in one portion; after another 15 min water (100 ml) was added. The mixture was acidified (pH 5-6) with dilute hydrochloric acid and extracted with ethyl acetate (3×30 ml). The organic phases were washed with brine, dried and concentrated to leave an oil which was found to consist of a mixture of four isomers by tlc (labelled isomers A,B,C,D by decreasing order of polarity).

Crystallization of the oily residue in ethyl acetate-pentane gave isomers B and C as a white solid and left A and D in the mother-liquors. The four pure compounds were obtained by preparative chromatography (Waters, 500) of the above solid and mother-liquors. The relative proportions were: A, 17%; B, 32%; C, 39%; D, 12%. In the above reaction, when ether was substituted for THF and the reaction quenched after 1 min at −78° C., the relative proportions of A,B,C, and D were: 12.9, 30.5, 38.2 and 18.4%. In ether, when the reaction was allowed to come to 20° C. in 2 h before quenching, the proportions were: 13.4, 24.6, 44, and 18%. When one molar equivalent of anhydrous magnesium bromide was added to the reaction mixture, the proportions changed to: 19.2, 19.7, 30.1 and 31%.

Isomer A: This isomer possesses a cis-stereochemistry at $C_3$-$C_4$. It is a racemic mixture composed of the (1'S, 3R, 4R) and the (1'R, 3S, 4S) enantiomers. Compounds later derived from compound A are referred to as "Isomer A". They consist of an enantiomeric mixture and possess the same configuration at $C_{1'}$, $C_3$ and $C_4$. Compounds derived from compound A, through a reaction that proceeds with inversion of configuration, will be referred to as "Isomer D" if the inversion takes place at $C_1$, and as "Isomer C" for the inversion, at $C_3$ mp 152°–3° C.; $^1$Hmr (CDCl$_3$) δ: 8.0–6.8 (15H, m, aromatics), 4.30 (1H, d, J=5.5, H-4), 3.78 (1H, m, H-1'), 3.10 (1H, dd, J=5.5, J=10, H-3), 1.22 (3H, d, J=6.5, CH$_3$), 0.95 (9H, s, Bu), 0.27 (6H, 2s, CH$_3$). Anal. calcd for: $C_{30}H_{37}NO_2Si$: C 71.52, H 7.40, N 2.78, S 6.36%. found: C 71.28, H 7.41, N 2.48, S 6.19%.

Isomer B: This isomer possesses a trans-stereochemistry at $C_3$-$C_4$. It is a racemic mixture composed of the (1'R,3S,4R) and the (1'S,3R,4S) enantiomers. Compounds with the same configuration at $C_{1'}$, $C_3$ and $C_4$ are referred to as "Isomer B"; ir (CHCl$_3$) $\nu_{max}$: 1745 cm$^{-1}$ (C=O); mp 158°–9° C.; $^1$Hmr (CDCl$_3$) δ: 7.60–7.10 (15H, m, aromatics), 4.02 (1H, d, J=0.8 H-4), 3.32 (1H, dd, J=3.0, J=0.8, H-3), 3.55–3.15 (1H, m, H-1'), 0.88 (12H, CH$_3$, and t-Bu), 0.16 (6H, s, CH$_3$);

Isomer C: This isomer possesses a trans-stereochemistry at $C_3$-$C_4$. It is a racemate formed of the (1'S,3S,4R) and the (1'R,3R,4S) enantiomers. Compounds with the same configuration at $C_{1'}$, $C_3$ and $C_4$ are referred to as "Isomer C". mp 134°–6° C.; $^1$Hmr (CDCl$_3$) δ: 7.60–7.10 (15H, m, aromatics), 4.32 (1H, d, J=1.8, H-4), 3.02 (1H, dd, J=2.7, J=1.8, H-3), 3.0–2.5 (1H, dq, J=2.7, J=6, H-1'), 1.02 (3H, d, J=6, CH$_3$), 0.95 (9H, s, t-Bu), 0.27 (6H, s, CH$_3$); ir (CHCl$_3$) $\nu_{max}$: 1735 cm$^{-1}$ (C=O).

Isomer D: This isomer possesses a cis-stereochemistry at $C_3$-$C_4$. It is a racemate composed of the (1'R,3R,4R) and the (1'S,3S,4S) enantiomers. Compounds with the same configuration at $C_{1'}$, $C_3$ and $C_4$ are referred to as "Isomer D". mp 171°–2° C.; Hmr (CDCl$_3$): 7.80–6.90 (15H, m, aromatics), 4.70 (1H, d, J=4.5, H-4), 3.02 (1H, dd, J=4.5, J=0.5, H-3), 2.39 (1H, dq, J=0.5, J=6.5, H-1'), 1.0 (3H, d, J=6.5, CH$_3$), 0.97 (9H, s, t-Bu), 0.32 (6H, s, CH$_3$). Anal. calcd for $C_{30}H_{37}NO_2SSi$: C 71.52, H 7.40, N 2.78, S 6.36%. found: C 71.27, H 7.43, N 2.51, S 6.31%.

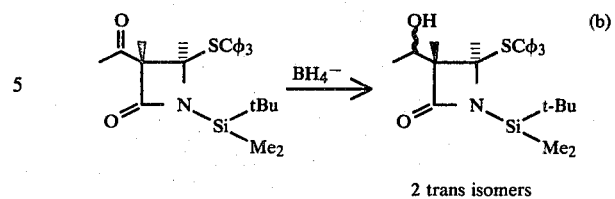

2 trans isomers

A solution of trans 3-acetyl-1-(t-butyldimethylsilyl)-4-tritylthio-2-azetidinone (1.0 g, 2 mmol) in THF (30 ml) was added dropwise, under a nitrogen atmosphere, to a cooled (0°) and stirred suspension of sodium borohydride (0.38 g, 10 mmol) in THF (120 ml). The ice bath was removed and the mixture was stirred at room temperature for 4 h. It was poured into ice-cold hydrochloric acid (1 N, pH 6), stirred for 15 min and extracted with ether (3×). The combined ether extracts were dried and concentrated to give an oil (1.04 g) which was crystallized in pentane to give the title compounds as a 70:30 mixture of the C and B isomers. mp 119°–121° C.; 84%.

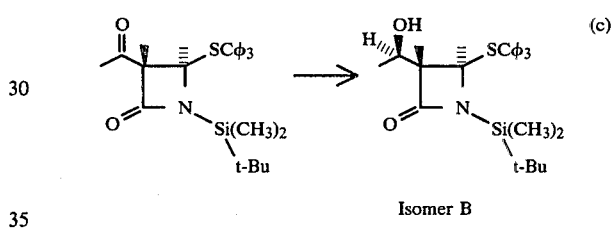

Isomer B

A suspension of cuprous iodide (4.78 g, 15 mmol) in ether (50 ml) was cooled to 0° C. and treated under N$_2$, with a 1.9 M solution of methyl lithium (26 ml, 50 mmol). The brown solution was stirred at 0° C. for 10 min and then cooled to −60° C. and treated dropwise with the trans 1-1(t-butyl dimethylsilyl)-3-formyl-4-tritylthio-2-azetidinone (2.43 g, 5.0 mmol) in a mixture of tetrahydrofuran (10 ml)/ether (40 ml). Stirring was continued for 3 h. The solution was warmed up to −40° C. and treated carefully with a 1 M solution of ammonium chloride. The mixture was filtered over Celite and the organic phase was washed with a 1 M solution of ammonium chloride (3×5 ml) and then brine and dried over sodium sulfate. Filtration and evaporation gave alcohol, isomer B, which crystallized from warm pentane to yield 1.6 g (65%), mp 160°–1° C.; ir (CHCl$_3$) $\nu_{max}$: 1730 cm$^{-1}$. $^1$Hmr (CDCl$_3$) δ: 7.32 (15H, m), 4.05 (1H, s), 3.4 (1H, d, J=3 Hz, 3.25–3.55 (1H, m), 1.6 (1H, s), 0.9 (12H, s) and 0.1 ppm (6H, s).

NOTE:
(a) tetrahydrofuran and ether were distilled over L.A.H.
(b) methyl lithium was titrated with 1N hydrochloric acid
(c) copper (I) iodide was purified by continuous extraction with anhydrous tetrahydrofuran in a Soxhlet extractor for 18 h, then dried under vacuum in a dessicator (P$_2$O$_5$) for 18 h.

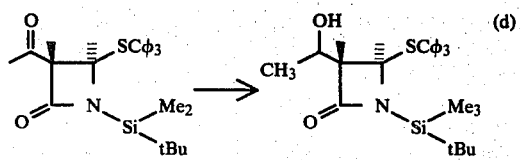

Methylmagnesium iodide (0.1 ml, 0.1 mmol) was added dropwise to a cooled (0° C.) and stirred solution of trans 1-(t-butyldimethylsilyl)-3-formyl-4-tritylthio-2-azetidinone (25 mg, 0.05 mmol) in THF (2 ml). The solution was stirred 1.5 h at 0° C., poured onto an ammonium chloride solution, acidified with a hydrochloric acid solution (1 N) and extracted with ether. Drying and concentration of the organic extracts left an oil consisting of starting material and a small amount of a mixture of the two trans title compounds with isomer B predominating.

F. Preparation of (1′S,3S,4R and 1′R,3R,4S) 1-(t-Butyldimethylsilyl)-3-(1′-trimethylsilyloxy-1′-ethyl)-4-tritylthio-2-azetidinone (isomer C)

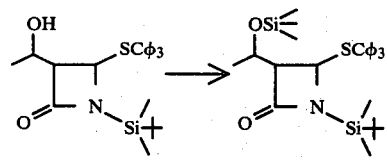

A solution of (1′S,3S,4R and 1′R,3R,4S) 1-(t-butyldimethylsilyl)-3-(1′-hydroxy-1′-ethyl)-4-tritylthio-2-azetidinone (15 mg, 0.3 mmol) and azidotrimethylsilane (35 mg, 0.30 mmol) in dry THF (6 ml) was stirred at room temperature until disappearance of the starting material (15 min). Purification of the reaction mixture by column chromatography (silica gel, $CH_2Cl_2$) gave the desired compound as a white solid (128 mg, 74%) mp 144°–46° C. $^1$Hmr ($CDCl_3$) δ: 7.10–7.60 (15H, m, aromatics), 4.30 (1H, d, J=1.5, H-4), 2.25–2.89 (2H, m, H-3, H-1′), 0.82–1.07 (12H, m, t-Bu, H-2′), 0.27 (6H, s, $CH_3$), −0.10 (9H, s, —O—Si($CH_3$)$_3$); ir ($CHCl_3$) $\nu_{max}$: 1736 cm$^{-1}$ (C=O).

G. Preparation of (1′S, 3R,4R and 1′R, 3S, 4S) 1′(t-Butyldimethylisilyl)-3-(1′-methoxymethoxy ether-1′-ethyl)-4-tritylthio-2-azetidinone (isomer A).

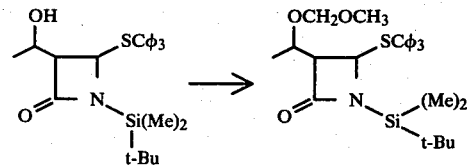

n-Butyllithium (ca 12.5 ml of 1.6M solution in hexane, 20 mmol; just enough to obtain a permanent pink coloration) was added dropwise to a solution of (1′S,3R,4R and 1′R,3S,4S) 1-(t-Butyldimethylsilyl)-3-(1′-hydroxyl-1′-ethyl)-4-tritylthio-2-azetidinone (isomer A) (10.1 g, 20 mmol) in THF (100 ml) maintained at −78°. After a 15 min stirring period a solution of bromomethoxymethyl ether (2 ml, 24 mmol) in THF (30 ml) was added dropwise. The mixture was stirred 1 h at −78° and 2 h at room temperature and poured into an ammonium chloride solution (200 ml). Extraction with ethyl acetate (3×200 ml), washing with brine, drying with sodium sulfate and concentration gave the crude title compound which was purified by chromatography on silica gel eluting with increasing amounts of ether in benzene (10.4 g 95%). $^1$Hmr (CDCl$_3$) δ: 7.1–7.5 (15H, m, aromatics), 4.47 (1H, d, H-4), 4.23 (2H, ABq, J-=7, O—CH$_2$—O), 3.1–3.4 (2H, m, H-3 and H-1′), 3.23 (3H, s, 0—CH$_3$), 1.37 (3H, d, J=6.5, ; CH$_3$) 0.97 (9H, s, BU) and 0.25 ppm (6H, 2s, CH$_3$).

H. Preparation of (1′S,3S,4R and 1′R, 3R,4S) 1-(t-Butyldimethylsilyl)-3-(1′-formyloxy-1′-ethyl)-4-tritylthio-2-azetidinone (isomer C)

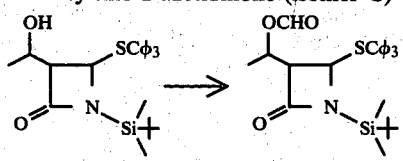

A solution of (1′S,3S,4R and 1′R,3R,4S) 1-(t-butyldimethylsilyl)-3-(1′-hydroxy-1′-ethyl)-4-tritylthio-2-azetidinone (isomer c) (50 mg, 0.1 mmol), p-bromobenzenesulfonylchloride (100 mg, 0.4 mmol) and dimethylaminopyridine (24 mg, 0.2 mmol) in DMF (3 ml) was stirred at room temperature until disappearance of starting material (0.5 h). Then the reaction mixture was diluted with water and extracted with ether. The organic extracts were washed with brine, dried (MgSO$_4$) and evaporated. The title compound was purified by column chromatography. $^1$Hmr (CDCl$_3$) δ: 7.80 (1H, s, CHO), 7.20–7.66 (15H, m, aromatics), 3.90–4.36 (1H, m, H-1′), 4.07 (1H, d, J=2, H-4), 3.22 (1H, broad s, H-3), 1.18 (3H, d, J=6.5, H-2′), 1.0 (9H, s, t-Bu), 0.31 (6H, s, di—CH$_3$).

I. Preparation of (1′R,3S,4R and 1′S,3R,4S) 1′(t-Butyldimenthylsilyl)-3-1′-acetoxy-1′-ethyl)-4-tritylthio-2-azetidinone (Isomer B)

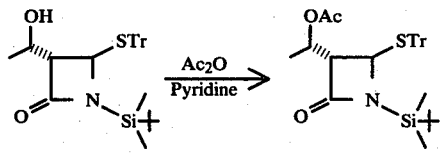

A solution of (1′R,3S,4S and 1′S 3R 4S) 1-t-butyldimethylsilyl)-3-(1′-hydroxy-1′-ethyl)-4-tritylthio-2-azetidinone (13.85 g, 27.5 mmol) in pyridine (75 ml) acetic anhydride (50 ml) (prepared at 0°) was stirred at room temperature for 40 h. The reagents were evaporated off (the last traces being removed azeotropically with toluene 3 times) leaving a nearly white solid. Crude derivative was crystallized from an ether-petroleum ether mixture to give pure title compound (97.5%). $^1$Hmr (CDCL$_3$ δ: 7.64–7.03 (15H, m, H aromatic), 4.60 (1H, m, J=6, H-1′), 3.92 (1H, d, J=2, H-4), 3.55 (1H, dd, J=2, J=6, H-3), 1.79 (3H, s, CH$_3$CO), 0.98 (3H, d, J=6, CH$_3$), 0.88 (9H, s, t-butyl), 0.12 (6H, s, CH$_3$); ir (CHCl$_3$) $\nu_{max}$: 1775, 1740 cm$^{-1}$(C=O).

J. Preparation of 1-(t-Butyldimethylsilyl)-3-(1′-paranitrobenzyldioxycarbonyl)-1′-ethyl)-4-tritylthio-2-azetidinone. (4 isomers)

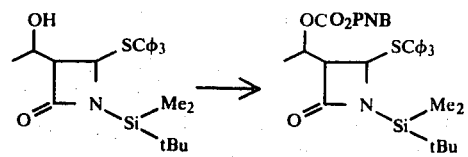

"Isomer C": n-Butyllithium (8.8 ml of 1.6 M solution in hexane, 14 mmol; just enough to obtain a permanent pink coloration) was added dropwise to a solution of "Isomer C" of 1-(t-butyldimethylsilyl)-3-(1'-hydroxy-1'-ethyl)-4-tritylthio-2-azetidinone (6.55 g, 13 mmol) in THF (70 ml) maintained at −78° C. After a 15 min stirring period a solution of paranitrobenzyl chloroformate (3.2 g, 14.8 mmol) in THF (30 ml) was added dropwise. The mixture was stirred 1 h at −78° C. and poured into an ammonium chloride solution (100 ml). Extraction with ethyl acetate (3×100 ml) washing with brine, drying and concentration left 11 g of crude material. The pure title compound was obtained by chromatography on silica gel (220 g) eluting with increasing amounts of ether in benzene. 93%, mp 118°-9° C. (ether); $^1$Hmr (CDCl$_3$) δ: 8.35-7 (19H, m, aromatics), 5.12 (2H, s, benzyl), 4.08 (1H, d, J=1.8, H-4), 4-3.5 (1H, dq, J=6.5, J=2, H-1'), 3.10 (1H, dd, J=2, J=1.8, H-3), 1.2 (3H, d, J=6.5, CH$_3$), 1.0 (9H, s, Bu) and 0.3 ppm (6H, 2s, CH$_3$); ir (CHCl$_3$) ν$_{max}$: 1745 cm$^{-1}$ (C=O); Anal. calcd for C$_{38}$H$_{42}$N$_2$O$_6$SiS: C 66.83, H 6.20, N 4.10, S 4.69; found: C 66.90, H 6.26, N 4.11, S 4.59.

"Isomer B": The "Isomer B" of 1-(t-butyldimethylsilyl)-3-(1'-hydroxy-1'-ethyl(-4-tritylthio-2-azetidinone, treated as described above gave pure "Isomer B" of 1-(t-butyldimethylsilyl-3-(1'-paranitrobenzyldioxycarbonyl-1'-ethyl)-4-tritylthio-2-azetidinone as a foam, 95%, $^1$Hmr (CDCl$_3$) δ: 8.32-6.90 (19H, m, aromatics), 5.1 (2H, s, benzyl), 4.65-4.20 (1H, m, H-1'), 3.97 (1H, d, J=1.5, H-4), 3.58 (1H, dd, J=1.5, J=5.8, H-3), 1.1 (3H, d, CH$_3$), 0.7 (9H, s, Bu and 0.2 ppm (6H, s, Ch$_3$); ir (film) ν$_{max}$: 1775, 1740 cm$^{-1}$ C=O.

"Isomer A": The "Isomer A" of 1-(t-butyldimethylsilyl-3-(1'-hydroxy-1'-ethyl)-4-tritylthio-2-azetidinone, treated as described above gave pure "Isomer A" of 1-(t-butyldimethylsilyl)-3-(1'-paranitrobenzyldioxycarbonyl-1'-ethyl)-4-tritylthio-2-azetidinone as an oil. 95% $^1$Hmr (CDCl$_3$) δ: 8.3-6.7 (19H, m, aromatics), 4.95 (2H, ABq, benzyl), 4.53 (1H, p, J=7.5, J=7.5, H-1'), 4.31 (1H, d, J=6, H-4), 3.32 (1H, dd, J=6, J=7.5, H-3), 1.44 (3H, d, J=6.5), 0.95 (9H, s, tBu) and 0.2 ppm (6H, 2s, CH$_3$).

"Isomer D": Likewise "Isomer D" of 1-(t-butyldimethylsilyl-3-(1'-hydroxy-1'-ethyl)-4-tritylthio-2-azetidinone, gave pure "Isomer D" of1-(t-butyldimethylsilyl)-3-(1'-paranitrobenzyldioxycarbonyl-1'-ethyl)-4-tritylthio-2-azetidinone, 90%. $^1$Hmr (CDCl$_3$) δ: 8.3-6.7 (19H, m, aromatics), 5.20 (2H, ABq, benzyl), 4.72 (1H, d, J=5, H-4), 3.50 (1H, dq, J=6.5, J=0.5, H-1'), 2.85 (1H, dd, J=0.5, J=5, H-3), 1.03 (3H, d, J=6.5, CH$_3$), 1.0 (9H, s, t-Bu) and 0.35 ppm (6H, s, CH$_3$); mp 130°-2° C. Anal. calcd for C 66.83, H 6.20, N 4.10, S 4.70; found: C 66.56, H6.28, N 3.96, S 4.89.

K. Preparation of (1'S, 3S, 4R and 1'R,3R,4S) 1-(t-Butyldimethylsilyl)-3-(1'-methanesulfonyloxy-1'-ethyl)-4-tritylthio-2-azetidinone (Isomer C)

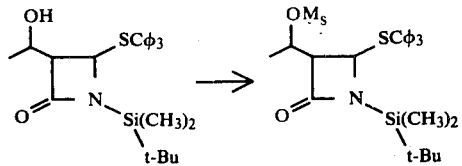

A solution of (1'S,3S,4R and 1'R,3R,4S)-1-(t-butyl-dimethylsilyl)-3-(1'-hydroxy-1'-ethyl)-4-tritylthio-2-azetidinone (Isomer C) (2.0 g, 4 mmol) in dichloromethane (80 ml) was treated at 5° C., with methanesulfonyl chloride (0.99 g, 8.6 mmol) and triethylamine (0.87 g, 8.6 mmol). After stirring at that temperature for 1 h under N$_2$, the solution was washed with brine, dried (MgSO$_4$) and evaporated to dryness. After crystallization from ether-pet-ether, 1.9 g (81.9%) of mesylate was obtained. mp 120°-22° C.; $^1$Hmr (CDCl$_3$) δ: 7.13-7.61 (15H, m, aromatics), 4.50 (1H, d, J=2, H-4), 3.62 (1H, dq, J=6.5, 2, H-1'), 2.96 (1H, dd, J=2, 2, H-3), 2.84 (3H, s, methanesulfonyl), 1.22 (3H, d, J=6.5, H-2'), 0.99 (9H, s, Si-t-Bu) and 0.30 ppm (6H, s, Si—(CH$_3$)$_2$); ir ν$_{max}$ (CHCl$_3$): 1746 (C=O), 1343 and 1180 cm$^{-1}$ (SO$_2$).

L. Preparation of (1'R,3S,4R and 1'S,3R,4S) 1-(t-Butyldimethylsilyl)-3-(1'-methanesulfonyloxy-1'-ethyl)-4-tritylthio-2-azetidinone (Isomer B)

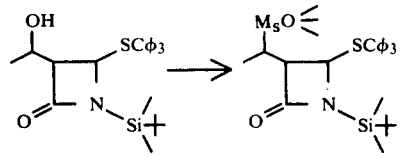

A solution of (1'R,3S,4R and 1'S,3R,4S) 1-(t-butyl-dimethylsilyl)-3-(1'-hydroxy-1'-ethyl)-4-tritylthio-2-azetidinone (Isomer B) (5.03 g, 10 mmol), methanesulfonylchloride (2.52 g, 22.0 mmol) and triethylamine (2.23 g, 22.0 mmol) in CH$_2$Cl$_2$ (200 ml) was stirred at 5° C. for 1 h. Then the solution was washed with brine, dried (MgSO$_4$) and evaporated to leave a residue which crystallized as a white solid when triturated in ether (5.40 g, 93%) mp 127°-31° C. $^1$Hmr (CDCl$_3$) δ: 7.20-7.63 (15H, m, aromatics), 4.51 (1H, dq, J=5.0-6.2, H-1'), 4.10 (1H, d, J=2.0, H-4), 3.60 (1H, dd, J=5.0-2.0, H-3), 2.03 (3H, s, —CH$_3$), 1.01 (3H, d, J=6.2, H-2'), 0.90 (9H, s, t-Bu), 0.12 (6H, s, —CH$_3$); ir (CHCl$_3$) ν$_{max}$: 1745 cm$^{-1}$(C=O).

M. Preparation of (1'S,3S,4R and 1'R,3R,4S) 3-(1'-p-Bromobenzenesulfonyloxy-1'-ethyl)-1-(t-butyl-dimethylsilyl)-4-tritylthio-2-azetidinone (Isomer C)

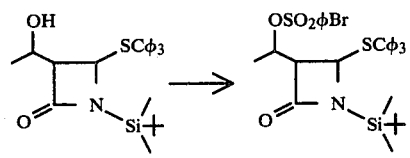

A solution of (1'S,3S,4R and 1'R,3R,4S)1-(t-butyl-dimethylsilyl)-3-(1'-hydroxyl-1'-ethyl)4-tritylthio-2-azetidinone (Isomer C) (2.5 g, 5 mmol) in dry THF (100 ml) was cooled to −78° C. and treated with 2.53M butyllithium/hexane (2.38 ml, 6 mmol). After 3-4 min p-bromobenzenesulfonylchloride (1.53 g, 6 mmol) dissolved in THF was added dropwise. The solution was stirred at −78° C. for 3 h and then allowed to come to room temperature. Then the solvent was evaporated and the desired product purified by column chromatography (silica gel, Ch$_2$Cl$_2$) (3.36 g, 94.6%) mp 142°-44° C.; $^1$Hmr (CDCl$_3$) δ: 7.68 (4H, s, benzenefulsonyl), 7.28-7.60 (15H, m, aromatics), 4.59 (1H, d, J=1.8, H-4), 3.68 (1H, dq, J=6.2, H-1'), 2.99 (1H, dd, J=1.8, 2.0, H-3), 1.18 (3H, d, J=6.2, H-2'), 1.08 (9H, s, t-Bu), 0.04 and 0.38 (6H, 2S, —CH$_3$); ir (CHCl$_3$) ν$_{max}$: 1749 cm$^{-1}$ (C=O).

N. Preparation of (1'S,3R,4R and 1'R,3S,4S) 3-(1'-Methoxymethyl-1'-ethyl)-4-tritylthio-2-azetidinone (isomer A).

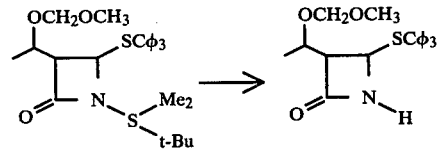

A cold (0° C.) HMPA—H₂O (116 ml–13 ml) solution of Isomer A of 1-(t-butyldimethylsilyl)-3-(1′-methoxymethyl-1′-ethyl)-4-tritylthio-2-azetidinone (11 g, 20 mmol) was treated with sodium azide (2.7 g, 42 mmol). The cold bath was removed and the mixture was stirred for 30 min. It was then poured into cold water (1.3 l) and dried. The title compound recrystallized from ethyl acetate-hexanes (7.2 g, 83%) as a white solid mp 173°–174° C. ¹Hmr (CDCl₃) δ: 7.10–7. (15H, m, aromatics), 4.85 (2H, ABq, J=7.4, O—CH₂—O), 4.53 (1H, d, J=5.2, H-4), 4.42 (1H, s, N—H), 4.15 (1H, m, H-1′), 3.5 (1H, m, H-3), (3H, s, O—CH₃), 1.5 (3H, d, J=6, CH₃). ir (KBr) $\nu_{max}$: 3400–3500 (N—H) and 1760 cm$^{-1}$ (C=O).

O. Preparation of (1′S,3S,4R and 1′R,3R,4S) 3-(1′-Methoxymethyloxy-1′-ethyl)-4-tritylthio-2-azetidinone (Isomer C)

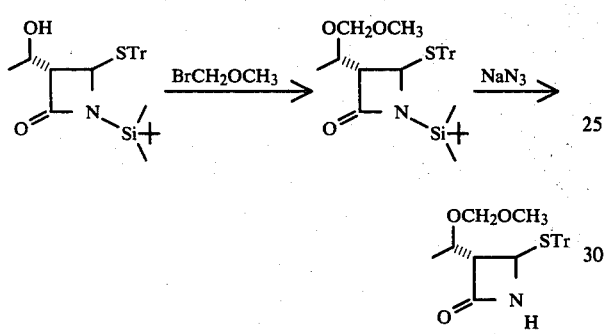

A cold (dry ice-acetone bath) solution of (1′S,3S,4R and 1′R,3R,4S) 1-(t-butyldimethylsilyl)-3-(1′-hydroxy-1′-ethyl)-4-tritylthio-2-azetidinone (5.03 g, 10 mmol) in THF (50 ml, distilled over LAH) was treated dropwise with a 1.6M solution of n-butyl lithium in hexane (13.0 ml) until a pink coloration persisted. A THF (20 ml) solution of bromomethyl methylether (1.49 g, 0.97 ml, 1.19 mmol) was added dropwise. The mixture was stirred at −78° C. for 30 min and for a 3 h period at 0° C. It was poured in an ice cold ammonium chloride solution and extracted with ether. The ether extracts were combined, washed with water, dried (MgSO₄) and concentrated to give crude (1′S,3S,4R and 1′R,3R,4S) 1-(t-butyldimethylsilyl)-3-(1′-methoxy-methyloxy-1′-ethyl)-4-tritylthio-2-azetidinone (5.83 g, 100%) which was deprotected as described below:

A cold (ice bath) solution of the above derivative (5.83 g, 10 mmol) in HMPA-H₂O (90 ml–10 ml) was treated with sodium azide (1.365 g, 21 mmol). The cooling bath was removed and the mixture was stirred at room temperature for a 2 h period. It was then poured slowly into ice cold water (900 ml) and stirred for 30 min. The precipitate was collected by filtration and redissolved in methylene chloride. The solution was washed with water and brine and dried (MgSO₄) to give the title compound (3.0 g, 69.3%), mp 172-2.5 (ethyl acetate-hexane); ir (CHCl₃) $\nu_{max}$: 3400 (N—H) and 1760 cm$^{-1}$ (C=O); ¹Hmr (CDCl₃) δ: 7.67–7.12 (15H, m, H aromatics), 4.63 (2H, center of ABq, J=6, O—CH₂—O), 4.49 (1H, s, N—H), 4.40 (1H, d, J=3, H-4), 4.25–3.80 (1H, m, H-1′), 3.35–3.15 and 3.26 (4H, s+m, CH₃ and H-3) and 1.30 ppm (3H, d, J=6, CH₃).

P. Preparation of (1′R,3S,4R and 1′S,3R,4S) 3-(1′-Formyloxy-1′-ethyl)-4-tritylthio-2-azetidinone (Isomer B)

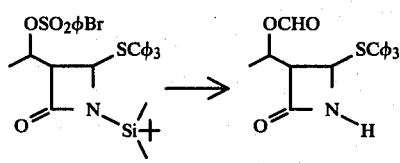

A solution of (1′S,3S,4R and 1′R,3R,4S) 3-(1′-p-bromobenzenesulfonyloxy-1′-ethyl)-1-(t-butyldimethylsilyl)-4-tritylthio-2-azetidinone (Isomer C) in DMF (3 ml) was heated at 50° C. for 48 h and then at 100° C. for 4 h. The reaction mixture was then diluted with H₂O and extracted with ether. The ethereal extracts were washed with brine, dried (MgSO₄) and evaporated. The title compound was obtained as white crystals after purification by column chromatography (silica gel, 5% CH₃CN—CH₂Cl₂) (2 mg, 4.8%) mp 131°–32° C; ¹Hmr (CDCl₃) δ: 8.07 (1H, s, CHO), 7.24–7.56 (15H, m, aromatics), 5.23 (1H, dq, J=6.4, 7, H-1′), 4.38 (1H, dm J=2.4, H-4), 4.25 (1H, s, NH), 3.20 (1H, dd, J=7, 2.4, H-3), 1.43 (3H, d, J=6.4, H-2′); ir (CHCl₃) $\nu_{max}$: 3400 (NH), 1765 (C=O), 1725 cm$^{-1}$ (C=O).

Q. Preparation of (1′R,3S,4R and 1′S,3R,4S) 3-(1′-Acetoxy-1′-ethyl)-4-tritylthio-2-azetidinone (isomer B)

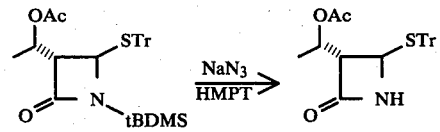

Pure derivative (1′R,3S,4R and 1′S,3R,4S) 1-(t-butyldimethylsilyl)-3-(1′-acetoxy-1′-ethyl)-4-tritylthio-2-azetidinone (5.77 g, 10.57 mmol) was dissolved in warm HMPT-water (60 ml, 10 ml). The solution was cooled down at room temperature and NaN₃ (1.2 g was added in. It was stirred for 45 min (reaction progression was followed by tlc) and poured slowly in stirred cold water (800 ml). The mixture was stirred for 20 more min. The crystalline material was collected and washed with water. It was redissolved in CH₂Cl₂, washed with water (twice) and brine and dried over MgSO₄. Solvent evaporation left a foam which crystallized out from ether-petroleum ether (4.90 g, 96.5%, mp 143°–44.5° C.). ir (CH₂Cl₂)$\nu_{max}$: 3395 (N—H), 1772, 1738 cm$^{-1}$ (C=O). ¹Hmr (CDCl₃) δ: 7.9–6.8 (15H, m, H aromatic), 5.12 (1H, center of dq, J=6.5, 7.5, H-1′), 4.33 (1H, d, J=2.8, H-4), 4.20 (1H, bs, N—H), 3.17 (1H, ddd, J₃₋₁′=7.5, J₃₋₄=2.8, J₃₋NH=1, H-3), 2.1 (3H, s, CH₃CO), 1.35 (3H, d, J-6.5, CH₃).

Preparation of 3-(1′-Hydroxy-1′-ethyl)-4-tritylthio-2-azetidinone. Mixture of four isomers)

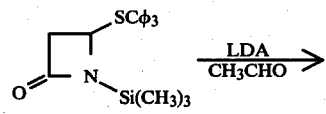

-continued

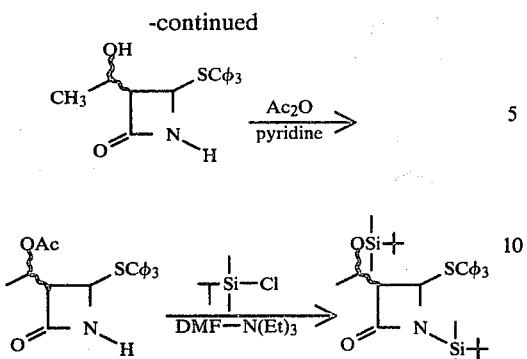

A solution of lithium diisopropyl amide[1] (0.74 mmol) was prepared at −78° C. in dry tetrahydrofuran (5 ml) from diisopropyl amine (0.103 ml, 0.74 mmol) and BuLi (0.29 ml of a 2.52 M in hexane). After 30 min at −78° C., a solution of the (R and S) 1-trimethylsilyl-4-tritylthio-2-azetidinone (0.292 g, 6.99 mmol) in dry tetrahydrofurane (2 ml) was added dropwise. After 5 min, excess of freshly distilled acetaldehyde (0.2 ml) was added all at once. After 20 min at −78° C., tlc indicated complete disappearance of starting materials and the reaction mixture was quenched by adding to a saturated solution of ammonium chloride. Extraction with ethyl acetate (2×25 ml) followed by washing of the combined organic phases with saturated $NH_4Cl$, brine and drying on anhydrous magnesium sulfate gave, after evaporation of the solvent, a yellow oil. Filtration of this oil on silica gel (10 g, elution $C_6H_6$:EtOAc, 6:4) gave a mixture of alcohols (0.215 g, 80%). This mixture ($^1$Hmr) cannot be separated either by hplc or by tlc.

a: Acetylation

Acetylation of an aliquot of the mixture (0.065 g) with excess acetic anhydride (1.0 ml) and pyridine (1.4 ml) gave a mixture of acetates. hplc Analysis indicated four components[2]: (a) 34:6%; (b) 17.4%; (c) 30.1%; (d) 17.9%. Compound (a) was identical to the isomer B by direct comparison (hplc)[3]

b: t-Butyldimethyl silyl derivatives

The mixture of alcohols (0.121 g, 0.34 mmol) was treated with t-butyl dimethylchlorosilane (0.117 g, 0.776 mmol) and triethyl amine (0.10 ml, 7.14 mmol) in dry dimethylformamide (1 ml) for 36 h at room temperature. After dilution with ethyl acetate, the solution was washed with saturated ammonium chloride and dried over anhydrous magnesium sulfate. Evaporation gave an oil (0.716 g) which contains 4 components by HPLC. a=3.7%; b=60.6%; c=31.1%; d=4.6% (the identity of each one has not been established[4]

NOTE:
[1]Butyl lithium and lithium hexamethyl disilazane were ineffective
[2]Order of increasing polarity
[3]Acetylation of the product derived from 1-t-butyldimethylsilyl-4-tritylthio-2-azetidinone gave the following ratio: d=29.5%; c=24.1%; b=33.8%; a=12.6%
[4]Reaction of a mixture of alcohols derived from (R and S) 1-(t-butyl-dimethylsilyl)-4-tritylthio-2-azetidinone gave the following proportions: a=5.2%; b=41.3%; c=48%; d=4.6%

S. Preparation of (1′R,3S,4R and 1′S,3R,4S) 3-(1′-Benzoxy-1′-ethyl)-4-tritylthio-2-azetidinone (Isomer B)

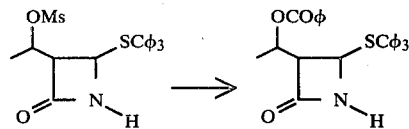

A solution of (1′S,3S,4R and 1′R,3R,4S) 3-(1′-methanesulfonyloxy-1′-ethyl)-4-tritylthio-2-azetidinone (Isomer C) (035 mg, 2 mmol) and sodium benzoate (432 mg, 3 mmol) in 10% $H_2O$—DMF (10 ml) was heated at 90° C. for 7.5 h. Then the reaction mixture was diluted with $H_2O$ and extracted with ethyl acetate. The organic extracts were washed with brine, dried ($MgSO_4$) and evaporated. The residue, purified by column chromatography (silica gel, 5% $CH_3CN$—$CH_2Cl_2$) gave the title compound as a white solid (108 mg, 23.2%) mp 158° C. $^1$Hmr (CDCl$_3$) δ: 7.03–8.25 (20H, m, aromatics), 5.32 (1H, dq, J=6.1, 9, H-1′), 4.40 (1H, d, J=2.5, H-4), 4.30 (1H, s, N—H), 3.40 (1H, dd, J=9, 2.5, H-3), 1.50 (3H, d, J=6.1, H-2′); ir (CHCl$_3$) $ν_{max}$: 3400 (N—H), 1765 (C—O), 1715 cm$^{-1}$ (C=O).

T. Preparation of 3-(1′-Paranitrobenzyldioxycarbonyl-1′-ethyl)-4-tritylthio-2-azetidinone (4 isomers).

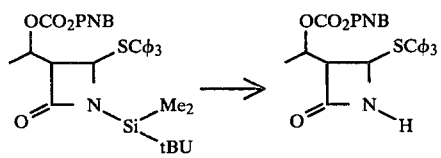

"Isomer C"

(a) A solution of "Isomer C" of 1-(t-butyldimethylsilyl)-3-(1′-paranitrobenzyldioxycarbonyl-1′-ethyl)-4-tritylthio-2-azetidinone (1.3 g) in a mixture of TFA (5 ml), water (5 ml), dichloromethane (20 ml) and methanol (30 ml) was stirred for 2 days at room temperature. The solution was diluted with water and the aqueous phase extracted with dichloromethane. The combined organic phases were washed with sodium bicarbonate and water, dried and concentrated to leave an oil. Crystallization from ether gave the pure title compound (902 mg), mp 78°–80° C.; $^1$Hmr (CDCl$_3$) δ: 8.25–6.75 (19H, m, aromatics), 5.21 (2H, s, benzyl), 5.05 (1H, m, H-1′), 4.40 (1H, s, N—H), 4.27 (1H, d, J=2.8, H-4), 3.37 (1H, dd, J=5.3, 2.8, H-3) and 1.37 ppm (3H, d, J=6.5, CH$_3$); ir (CHCl$_3$) $ν_{max}$: 3390 (N—H), 1765 and 1745 (shoulder) (C=O), and 1525 cm$^{-1}$ (NO$_2$).

(b) A cold (0° C.) HMPT-$H_2O$ (90 ml–19 ml) solution of "Isomer C" of 1-(t-butyldimethylsilyl)-3-(1′-paranitrobenzyldioxycarboxyl-1′-ethyl)-4-tritylthio-2-azetidinone (9.11 g, 13.3 mmol) was treated with sodium azide (1.82 g, 27.9 mmol). The cold bath was removed and the mixure was stirred for 30 min. It was then poured into water (1 l) and extracted with ether (5×200 ml). The ether fractions were combined and washed with water (5×200 ml), brine and dried over $MgSO_4$. Alternatively since the title compound precipitated out on water dilution, it was filtered off and recrystallized from ether; 7.22 g, 89%, mp 78°–80° C.

"Isomer B"

"Isomer B" of 3-(1'-paranitrobenzyldioxycarbonyl-1'-ethyl)-4-tritylthio-2-azetidinone was prepared as described above for the "Isomer C"; 92%; mp 155.5°–6° C. (ether); $^1$Hmr (CDCl$_3$) δ: 8.25–6.80 (19H, m, aromatics), 5.20 (2H, s, benzyl), 4.95 (1H, m, H-1'), 4.35 (1H, d, J=2.9, H-4), 4.17 (1H, s, N—H), 3.20 (1H, dd, J=10.8, J=2.9, H-3) and 1.40 ppm (3H, d, J=7.5, CH$_3$); ir (CHCl$_3$) ν$_{max}$: 3480, 3390 (N—H), 1772, 1750 (C═O), and 1525 cm$^{-1}$ (NO$_2$). Anal. calcd for C$_{32}$H$_{28}$N$_2$O$_6$S: C 67.59, H 4.96, N 4.93, S 5.64; found: C 67.48, H 4.98, N 4.92, S 5.67.

"Isomer A"

"Isomer A" of 3-(1'-paranitrobenzyldioxycarbonyl-1'-ethyl)-4-tritylthio-2-azetidinone was prepared as described above for the "Isomer C"; mp 205°–6° C. $^1$Hmr (CDCl$_3$) δ: 8.2–6.7 (19H, m, aromatics), 5.22 (2H, ABq, benzyl), 5.57–4.85 (1H, m, H-1'), 4.65 (1H, N—H), 4.50 (1H, d, J=6.5, H-4), 3.65 (1H, dd, J=6.5, 12, J$_{N-H}$=1, H-3) and 1.52 ppm (3H, d, J=7.5).

"Isomer D"

"Isomer D" of 3-(1'-paranitrobenzyldioxycarbonyl-1'-ethyl)-4-tritylthio-2-azetidinone was prepared as described above for "Isomer C"; $^1$Hmr (CDCl$_3$) δ: 8.15–6.70 (19H, m, aromatics), 5.23 (2H, ABq, benzyl), 5.20 (1H, m, H-1'), 4.75 (1H, NH), 4.52 (1H, d, J=5.5, H-4), 3.42 (1H, J=5.5, 3, H-3 and 1.5 ppm (3H, d, J=6.5, CH$_3$). (J value for H-3 taken after D$_2$O. exchange).

U. Preparation of (1'R,3S,4R and 1'S,3R,4S) 3-(1'-methanesulfonyloxy-1'-ethyl)-4-tritylthio-2-azetidinone (isomer B)

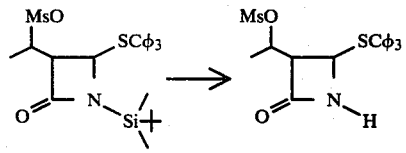

A solution of (1'R,3S,4R and 1'S,3R,4S) 1-(t-butyldimethylsilyl)-3-(1'-methanesulfonyloxy-1'-ethyl)-4-tritylthio-2-azetidinone. (Isomer B) (4.95 g, 8.5 mmol) and sodium azide (1.11 g, 17.0 mmol) in 10% H$_2$O-HMPA (50 ml) was stirred at room temperature for 30 min. Then the solution was diluted with water (250 ml) and extracted with ether. The organic extracts were washed with brine, dried (MgSO$_4$) and evaporated. Crystallization of the residue (ether-pet-ether) gave the title compound (3.33 g, 83.8%). mp 130°–31° C. $^1$Hmr (CDCl$_3$) δ: 7.20–7.62 (15H, m, aromatics), 4.97 (1H, dq, J=6.4, 6.1, H-1'), 4.56 (1H, d, J=2.8, H-4), 4.22 (1H, m, N—H), 3.27 (1H, dd, J=6.1, 2.8, H-3), 3.0 (3H, s, —CH$_3$), 1.63 (3H, d, J=6.4, H-2'); ir (nujol) ν$_{max}$: 3195 (n-H), 1768 cm$^{-1}$ (C═O).

V. Preparation of (1'S,3S,4R and 1'R,3R,4S)3-(1'-methanesulfonyloxy-1'-ethyl)-4-tritylthio-2-azetidinone (Isomer C)

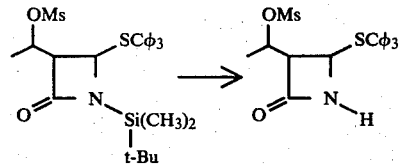

A solution of (1'S,3S,4R and 1'R,3R,4S)1-(t-butyldimethylsilyl)-3-(1'-methanesulfonyloxy-1'-ethyl)-4-tritylthio-2-azetidinone (isomer C) (2.85 g; 4.9 mmol) in 10% aqueous HMPA (25 ml) was treated with sodium azide (0.65 g, 10 mmol) and stirred at 25° C. for 0.5 h. By diluting the solution with water (250 ml), the reaction product was forced to crystallize out. The crude mesylate was redissolved in dichloromethane, washed with brine, dried (MgSO$_4$) and evaporated. Trituration in ether gave the title compound as white crystals mp 155°–60° C.; 1.80 g; 78.6%; $^1$Hmr (CDCl$_3$) δ: 7.43 (15H, m, aromatic), 5.02 (1H, dq, J=6.9, 4.9, H-1'), 4.55 (1H, s, N—H), 4.95 (1H, d, J=3, H-4), 3.33 (1H, dd, J=4.9, 3, H-3), 1.51 (3H, d, J=6.9, H-2'); ir ν$_{max}$: 3395 (N—H), 1768 cm$^{-1}$ (C═O); Anal. calcd for C$_{25}$H$_{25}$NO$_4$S. C 64.22, H 5.39, N 3.00; found: C 63.93, H 5.39, N 3.24%.

W. Preparation of (1'S,3S,4R and 1'R,3R,4S) 3-(1'-p-Bromobenzenesulfonyloxy-1'-ethyl)-4-tritylthio-2-azetidinone (Isomer C)

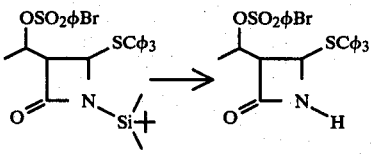

A solution of (1'S,3S,4R and 1'R,3R,4S) 3-(1'-p-bromobenzenesulfoxyloxy-1'-ethyl)-1-(t-butyldimethylsilyl)-4-tritylthio-2-azetidinone (Isomer C) (1.42 g, 2 mmol) and sodium benzoate (0.865 g, 6 mmol) in 10% H$_2$O-HMPA (40 ml) was stirred at room temperature for 1 h. Then the solution was diluted with H$_2$O (100 ml) and extracted with ether. The ether extracts were washed with brine, dried (MgSO$_4$) and evaporated. The crude crystalline title compound was triturated in a small volume of ether and collected by filtration (0.92 g, 77%) mp 125°–26° C. $^1$Hmr (CDCl$_3$) δ: 7.80 (4H, s, benzenesulfonyl), 7.30–7.65 (15H, m, aromatics), 5.13 (1H, dq, J=6.5, 4.0, H-1'), 4.50 (1H, d, J=2.9, H-4), 4.40 (1H, s, N—H), 3.40 (1H, dd, J=4.0, 2.9, H-3), 1.50 (3H, d, J=6.5, H-2'); ir (CHCl$_3$) ν$_{max}$: 3400 cm$^{-1}$ (N—H), 1770 cm$^{-1}$ (C═O).

X. Preparation of (1'R,3S,4R and 1'S,3R,4S) 3-(1'-Hydroxy-1'-ethyl)-4-tritylthio-2-azetidinone (Isomer B)

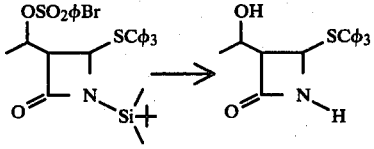

To a warm solution of (1'S,3S,4R and 1'R,3R,4S) 3-(1'-p-bromobenzenesulfonyloxy-1'-ethyl)-1-(t-butyldimethylsilyl)-4-tritylthio-2-azetidinone (Isomer C) in HMPA (5 ml) was added dropwise 1 ml of H$_2$O. The reaction mixture was kept at 90° C. for 20 h, then diluted with ether and washed 4 times with brine. The organic solution was dried (MgSO$_4$), evaporated and the crude title compound purified by column chromatography (silica gel, 15% CH$_3$CN—CH$_2$Cl$_2$). A white solid was obtained (122 mg, 44.5%) mp 187°–189° C. which was found to be identical to a sample of the title compound prepared by another method.

Y. Preparation 3(1'-Hydroxy-1'-ethyl)-4-tritylthio-2-azetidinone

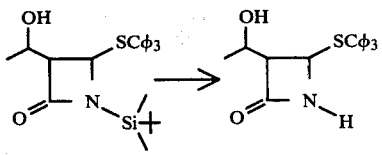

Both isomers, (1'S,3S,4R and 1'R,3R,4S) 3-(1'-hydroxy-1'-ethyl)-4-tritylthio-2-azetidinone (Isomer C) and (1'R,3S,4R and 1'S,3R,4S) 3-(1'-hydroxy-1'-ethyl)-4-tritylthio-2-azetidinone (Isomer B) were prepared by the same method. For example, a solution of (1'S,3S,4R and 1'R,3R,4S) 1-(t-butyldimethylsilyl)-3-(1'-hydroxy-1'-ethyl)-4-tritylthio-2-azetidinone (Isomer C) (1.0 g, 2 mmol) and sodium benzoate (0.865 g, 6 mmol) in 10% $H_2O$—DMF (40 ml) was stirred at room temperature for 18 h. Then the reaction mixture was diluted with $H_2O$ and extracted with ether. The organic extracts were washed with brine, dried ($MgSO_4$) and evaporated. The crude title compound was crystallized from cold ether (0.47 g, 61%) mp 134°–35° C. $^1$Hmr (CDCl$_3$) δ: 7.12–7.56 (15H, m, aromatics), 4.48 (1H, s, N—H), 4.28 (1H, d, J=2.8, H-4), 2.94 (1H, dq, J=6.5, 6.2, H-1'), 3.06 (1H, dd, J=6.2, 2.8, H-3), 2.18 (1H, s, —OH), 1.30 (3H, d, J=6.5, H-2'); ir (CHCl$_3$) $\nu_{max}$: 3400 (N—H), 1760 cm$^{-1}$ (C=O). Similarly (1'R,3S,4R and 1'S,3R,4S) 1-(t-butyldimethylsilyl)-3-(1'-hydroxy-1'-ethyl)-4-tritylthio-2-azetidinone (Isomer B) mp 190°–92° C. $^1$Hmr (CDCl$_3$) δ: 7.10–7.55 (15H, m, aromatics), 4.45 (1H, d, J=2.5, H-4), 4.28 (1H, s, NH), 4.10 (1H, dq, J=6.4, 5.3, H-1'), 3.08 (1H, dd, J=5.3, 2.5, H-3), 1.50 (1H, s, —OH), 1.30 (3H, d, J=6.4, H-2'); ir (CHCl$_3$) $\nu_{max}$: 3400 (N—H), 1760 cm$^{-1}$ (C=O)

Z. Preparation of (1'S,3R,4R and 1'R,3S,4S) 3-(1'-Methoxymethyl-1'-ethyl)-1-(paranitrobenzyl 2''-hydroxy-2''-acetate)-4-tritylthio-2-azetidinones (Isomer A)

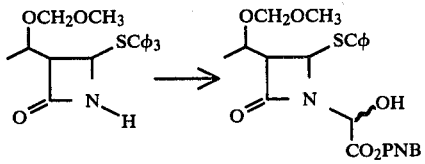

A mixture of Isomer A of 3-(1'-methoxymethyl-1'-ethyl-4-tritylthio-2-azetidinone (7.5 g, 17.3 mmol), paranitrobenzyl glyoxylate hydrate (4.7 g, 20.8 mmol) and toluene (300 ml) was heated under reflux for 1 h in a Dean and Stark apparatus filled with 3 Å molecular sieves. The solution was cooled in ice and triethylamine (0.24 ml, 1.7 mmol) was added dropwise. The mixture was stirred for 1 h, washed with diluted hydrochloric acid, sodium bicarbonate and brine, dried and concentrated to give the title compound as a foam (10.5 g, 94%). $^1$Hmr (CDCl$_3$) δ: 8.25–6.84 (19H, m, aromatics), 5.24 (2H, s, benzyls), 4.67–4.83 (3H, m, O—CH$_2$ and H-4), 4.34–4.55 (1H, m, H-2''), 4.02 (1H, m, H-1'), 3.54 (1H, m, H-3), 3.40 (3H, s, O—CH$_3$), 1.38 (3H, d, J=6.5, CH$_3$); ir (KBr) $\nu_{max}$: 3360 (OH), 1770 (C=O of β-lactam), 1735 (C=O of ester) and 1605 cm$^{-1}$ (aromatics).

AA. Preparation of (1'S,3S,4R and 1'R,3R,4S) 3-(1'-Methoxymethoxy-1'-ethyl)-1-(paranitrobenzyl 2''-hydroxy-2''-acetate)-4-tritylthio-2-azetidinone (Isomer C)

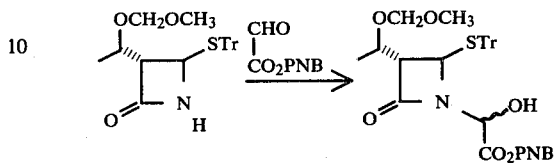

A solution of hydrated paranitrobenzyl glyoxylate (1.73 g, 7.11 mmol) was refluxed in toluene (90 ml) using a Dean Stark condenser filled with 3 Å molecular sieves for a 2 h period. To the boiling solution was added (1'S,3S,4R and 1'R,3R,4S) 3-(1'-methoxymethyloxy-1'-ethyl)-4-tritylthio-2-azetidinone (3.0 g, 6.93 mmol) and the mixture was refluxed for 2 h more. The mixture was cooled to room temperature, triethyl amine (70 mg, 97 μl, 0.69 mmol) was added and it was stirred for 2 h. The reaction mixture was diluted with ether, washed with 1% aqueous HCl, water, 1% aqueous NaHCOhd 3, water and brine, dried (MgSO$_4$) and concentrated to give the title compound (4.60 g, 100%); ir (CHCl$_3$) $\nu_{max}$:3530–3100 (O—H), 1765, 1750 (C=O) and 1525 cm$^{-1}$ (NO$_2$); $^1$Hmr (CDCl$_3$) δ: 8.22, 8.18 (2H, 2d, J=8, Hm aromatics), 7.67–7.0 (17H, m, H-aromatics), 5.3 (2H, bs, CH$_2$—PNB), 5.30–5.02 (m, H-2''), 4.89–4.52 (m, H-1' and O—H), 4.63, 4.59 (1H, 2d, J=2, H-4), 4.33, 4.30 (2H, 2 center of 2 ABq, J=7, J=7, O—CH$_2$—O), 4.1–3.67 (1H, m, H-1'), 3.2 (1H, H-3), 3.1, 3.6 (3H, 2s, CH$_3$—O), and 1.15 ppm (3H, d, J=6.5, CH$_3$).

BB. Preparation of (1'R,3S,4R and 1S,3R,4S) 3-(1'-Acetoxy-1'-ethyl)-1-(paranitrobenzyl-2''-hydroxy-2''-acetate)-4-tritylthio-2-azetidinone

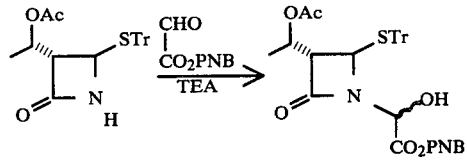

"Isomer B"

A solution of hydrated p-nitrobenzyl glyoxylate (triturated with ether) (1.82 g, 30 mol) was refluxed in benzene through a Dean Stark condenser filled with 3 Å molecular sieves for 2 h. To that was added azetidinone (1'R,3S,4R and 1'S,3R,4S) 3-(1'-acetoxy-1'-ethyl)-4-tritylthio-2-azetidinone (10.88 g, 25.2 mmol) and the mixture was refluxed for 1 h more. The solution was cooled at room temperature and triethyl amine (0.35 ml, 2.5 mmol was added. It was then stirred for 2 h; the reaction progression being followed by tlc. Solvent evaporation afforded a white foam in quantitative yield (100%, mixture of epimers) Alternatively the solution can be acid and base washed. ir (CH$_3$Cl$_2$) $\nu_{max}$: 3520 (OH), 1775, 1745 cm$^{-1}$ (C=O); $^1$Hmr (CDCl$_3$) δ: 8.2, 8.18 (2H, 2d, J=8, Ho aromatic), 7.80–6.90 (17H, m, H-aromatic), 5.28, 5.17 (2H, 24, CH$_2$—PNB, 4.89 (0.67H, d, J=7.2, CHO), 4.80 (center of m, H-1'), 4.38 (0.33H, 2d, J=8.8, CHO), 4.22 (D.33H, d, J$_{4-3}$=2.5, H-4), 4.09 (0.67H, d, $J_{4-3}=2.1$, H-4), 3.65 (D.67H, dd, $J_{3-1'}=5.8$, $J_{3-4}=2.1$, H-3), 3.47 (0.33H, dd, $J_{3-1'}=5.5$ $J_{3-4}=2.5$, H-3), 3.33 (0.33H, d, J=8.8, OH), 3.23 (0.67H, d, J=7.5, OH), 1.88, 1.86 (3H, 2s, $CH_3CD$), 1.10, 1.06 (3H, 2d, J=5.8, 6.3, $CH_3$)

CC. Preparation of 3-(1'-Paranitrobenzyldioxycarbonyl-1'-ethyl)-1-(paranitrobenzyl 2"-hydroxy-2"-acetate)4-tritylthio-2-azetidinone (4 isomers)

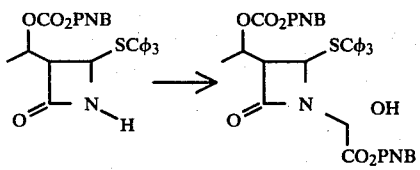

"Isomer C"

A mixture of "Isomer C" of 3-(1'-paranitrobenzyldioxycarbonyl-1'-ethyl)-4-tritylthio-2-azetidinone (1.70 g, 0.4 mmol), paranitrobenzyl glyoxylate hydrate (815 mg, 3.6 mmol) and toluene (50 ml) was heated under reflux 7 days in a Dean and Stark apparatus filled with 3 Å molecular sieves. The cooled solution was washed with dilute hydrochloric acid, sodium bicarbonate and brine, dried and concentrated to give the title compound (2.1 g) as an epimeric mixture at carbon-2". Purification was effected by chromatography over silica gel. Alternatively the title compound could be prepared by using a catalytic amount of triethyl amine. Less polar epimer at 2": $^1$Hmr (CDCl$_3$) δ: 8.25–6.80 (23H, m, aromatics), 5.30 and 3.12 (4H, 2s, benzyls), 4.65 (1H, d, J=9, H-2"), 4.45 (1H, d, J=2.5, H-4), 4.45–4.10 (1H, m, H-1'), 3.50 (1H, d, J=9, 2"-OH), 3.28 (1H, dd, J=2.5, J=2.5, H-3) and 1.23 ppm (3H, d, J=6.5, $CH_3$); ir (CHCl$_3$) $\nu_{max}$: 3530 to 3200 (D—H), 1765, 1750 (C=O) and 1525 cm$^{-1}$ (NO$_2$). More polar isomer at C-2": $^1$Hmr (CDCl$_3$) δ: 8.25–6.85 (23H, m, aromatics), 5.25 and 5.08 (4H, 2s, benzyls), 5.05 (1H, d, J=7, H-2"), 4.35 (1H, d, J=2.5, H-4), 4.40–4.05 (1H, m, H-1'), 3.42 (1H, J=7, 2"-OH), 3.33 (1H, dd, J=2.5, 2.5, H-3), 1.23 (3H, d, J=6.5, $CH_3$); ir (CHCl$_3$) $\nu_{max}$: 3520 to 3200 (O—H), 1755 (C=O) and 1525 cm$^1$ (NO$_2$).

"Isomer B"

A mixture of hydrated paranitrobenzylglyoxylate (1.74 g, 7.66 mmol) and (1'R,3S,4R and 1'S,3R,4S) 3-(1'-paranitrobenzyldioxycarbonyl-1'-ethyl)-4-tritylthio-2-azetidinone (3.63 g, 6.38 mmol) was refluxed in toluene (70 ml) on a Dean Stark condenser filled with 3 Å molecular sieves for 3 h. The solution was cooled down to room temperature and triethyl amine (64.5 mg, 89 ml, 0.639 mmol) was added. It was then stirred for 4 h, diluted with ether and washed with 2% aqueous HCl, water, 2% aqueous NaHCO$_3$, water and brine. It was dried and concentrated to give pure title compound (5.02 g, 100%). Separation of the 2 epimers was effected on preparative silica gel plate. Less polar epimer at 2": ir (CHCl$_3$) $\nu_{max}$: 3500 (O—H), 1772, 1750 (C=O) 1525 cm$^{-1}$ (NO$_2$); $^1$Hmr (CDCl$_3$) δ: 8.30–8.0 and 7.65–6.80, (23H, m, aromatics), 5.27 and 5.13 (4H, 2s, benzyls), 4.71 (1H, m, J=6.5, 6.5, H-1'), 4.28 (1H, d, J=2.2, H-4), 4.23 (1H, d, J=8.7, H-2"), 3.50 (1H, dd, J=2.2, 6.5, H-3), 3.28 (1H, d, J=8.7, O—H) and 1.18 ppm (3H, d, J=6.5, $CH_3$). More polar epimer: ir (CHCl$_3$) $\nu_{max}$: 3480 (O—H) 1772, 1750 (C=O) and 1525 cm$^{-1}$ (NO$_2$); $^1$Hmr (CDCl$_3$) δ: 8.35–6.90 (23H, m, aromatics), 5.15 (4H, benzyls), 4.72 (1H, d, J=7.5, H-2"O), 4.90–4.50 (1H, m, J=6.5, 6.5, H-1'), 4.10 (1H, d, J=2, H-4), 3.68 (1H, dd, J=2, 6.5, H-3), 3.28 (1H, d, J=6.5, O—H) and 1.15 ppm (3H, d, J=6.5, $CH_3$).

"Isomer A"

The "Isomer A" of 3-(1'-paranitrobenzyldioxycarbonyl-1'-ethyl)-4-tritylthio-2-azetidinone likewise gave a mixture of "Isomer A" of (3-(1'-paranitrobenzyldioxycarbonyl-1'-ethyl)-1-(paranitrobenzyl 2"-hydroxy-2"-acetate)-4-tritylthio-2-azetidinones. $^1$Hmr (CDCl$_3$) δ: 8.3–6.7 (23H, m, aromatics), 5.17 (2H, benzyls), 5.0 (1H, m, H-1'), 4.9 and 4.8 (1H, 2d, J=6, H-4, two epimers), 4.32 and 3.96 (1H, 2s, H-2", two epimers), 3.68 (1H, dd, J=6, 6, H-3) and 1.47 ppm (3H, 2d, J=6.5, $CH_3$, two epimers).

"Isomer D"

The "Isomer D" of 3-(1'-paranitrobenzyldioxycarbonyl-1'-ethyl)-4-tritylthio-2-azetidinone likewise gave a mixture of "Isomer D" of 3-(1'-paranitrobenzyldioxycarbonyl-1'-ethyl)-1-(paranitrobenzyl 2"-hydroxy-2"-acetate)-4-tritylthio-2-azetidinones. $^1$Hmr (CDCl$_3$) δ: 8.30–6.60 (23H, m, aromatics), 5.20 (4H, m, benzyls), 4.83 (1H, 2d, J=5, H=4), 5.50–4.30 (2H, m, H-1' and H-2"), 3.48 (1H, m, H-3), 3.15 (1H, m, O—H), 1.37 and 1.30 ppm (3H, 2d, $CH_3$).

DD. Preparation of (1'S,3S,4R and 1'R,3R,4S)3-(1'-Methanesulfonyloxy-1'-ethyl)-1-(paranitrobenzyl 2"-hydroxy-2"-acetate)-4-tritylthio-2-azetidinone (isomer C) (epimers of C$_2$")

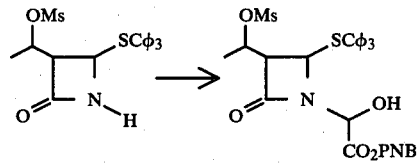

A solution of paranitrobenzylglyoxylate hydrate (9.72 g; 42.6 mmol) in benzene (350 ml) was refluxed for 2 h, removing the water azeotropically in a Dean-Stark trap. To that solution was added the (1'S,3S,4R and 1'R,3R,4S)3-(4'-methanesulfonyloxy-1'-ethyl)-4-tritylthio-2-azetidinone (16.62 g. 35.5 mmol) and the reflux maintained for an additional 0.5 h. Then the reaction mixture was cooled to room temperature, treated with triethylamine (0.5 ml; 3.5 mmol) and stirred for 3 h in order to complete the reaction. Evaporation of the solvent left a white foam which was used as such in the next step. $^1$Hmr (CDCl$_3$) δ: 812 (2H, d, J=9, Hm aromatic), 7.28 (17H, part of d,Ho aromatic, trityl), 5.28 (2H, s, —CH$_2$— PNB), 4.88 (0.5 H, s, H-1"), 4.62 (1.5H, m, H-2" and H-4), 4.00 (2H, m, H-1', —OH), 3.15 (1H, m, H-3), 2.73 (3H, s, mesylate and 1.30 ppm (3H, d, J=6 Hz, H-2'); ir $\nu_{max}$: 3520 (O—H), 1775 (C=O) and 1765 cm$^{-1}$ (C=O).

EE. Preparation of (1'S,3R,4R and 1'R,3S,4S) 3-(1-Methoxymethyl-1'-ethyl)-1-(paranitrobenzyl 2''-chloro-2''-acetate)-4-tritylthio-2-azetidinone (Isomer A)

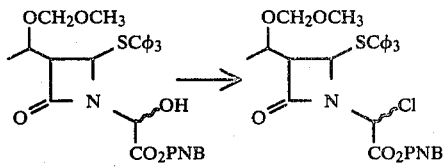

Pyridine (1.1 ml, 14.2 mmol) was added dropwise to a solution of Isomer A of 3-(1'-methoxymethyl-1'-ethyl)-1-(paranitrobenzyl-2''-hydroxy-2''-acetate)-4-tritylthio-2-azetidinone (7 g, 10.9 mmol) in THF (350 ml) cooled to −15° C. Immediately after thionyl chloride (1.0 ml, 14.0 mmol) was added dropwise and the mixture was stirred at −15° for 0.5 h. The precipitate was removed by filtration and washed with benzene. The combined filtrates were concentrated, the residue dissolved in fresh benzene and the solution treated with activated charcoal, filtered and concentrated to leave to title compound as an oil (6.5 g, 90%), $^1$Hmr (CDCl$_3$) δ: 6.65–8.35 (19H, m. aromatics), 5.24 (2H, s. benzyl), 3.43 (3H, s, OCH$_3$) and 1.42 ppm (3H, d, J=6, CH$_3$).

FF. Preparation of (1'S,3S,4R and 1'R,3R,4S) 3-(1'-ethoxymethyloxy-1'-ethyl)-1-(paranitrobenzyl 2''-chloro-2''-acetate)-4-tritylthio-2-azetidinone (Isomer C)

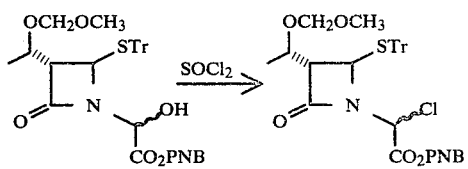

A cold (ice-MeOH bath) THF (60 ml, distilled over LAH) solution of (1'S,3S,4R and 1'R,3R,4S) 3-(1'-methoxymethyloxy-1'-ethyl)-1-paranitrobenzyl 2''-hydroxy-2''-acetate)-4-tritylthio-2-azetidinone (4.25 g, 6.62 mmol) was treated dropwise with pyridine (0.696 ml, 8.61 mmol) and thionyl chloride (0.530 ml, 8.61 mmol). The mixture was stirred for 30 min at −15° C. The precipitate was collected by filtration and washed with benzene. The THF-benzene solution was concentrated and the residue was dissolved again in benzene. The resulting solution was treated with charcoal. Removal of charcoal on a Celite pad and subsequent benzene evaporation afforded the title compound (4.86 g, 100%); ir (CHCl$_3$) $\nu_{max}$: 1770 (C=O) and 1525 cm$^{-1}$ (NO$_2$); $^1$Hmr (CDCl$_3$) δ: 8.15, 8.12 (2H, 2d, H-aromatics), 7.70–7.00 (17H, m, H-aromatics), 5.62, 5.02 (1H, 2s, H-2''), 5.27 (2H, s, CH$_2$—PNB), 4.7 (1H, d, H-4), 4.7–3.7 (m, O—CH$_2$—O, H-1'), 3.5–2.8 (m, H-3), 3.12, 3.08 (3H, 2s, O—CH$_3$), and 1.30–0.96 ppm (3H, m, CH$_3$).

GG. Preparation of (1'R,3S,4R and 1'S,3R,4S) 3-(1'-Acetoxy-1'-ethyl)-1-(paranitrobenzyl 2''-chloro-2''-acetate)-4-tritylthio-2-azetidinone

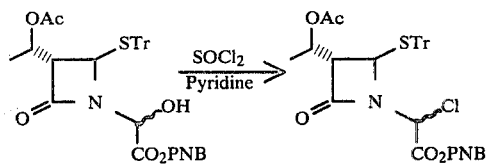

"Isomer B"

A THF (distilled over LAH) solution of (1'R,3S,4R and 1'S,3R,4S) 3-(1'-acetoxy-1'-ethyl)-1-(paranitrobenzyl-2''-hydroxy-2''-acetate)-4-tritylthio-2-azetidinone (from 10.88 g of N-H) was treated at −15° C. (ice-methanol bath) under nitrogen atmosphere with pyridine (2.19 g, 2.24 ml, 27.7 mmol) and thionyl chloride (3.3 g, 2.02 ml, 27.7 mmol) and thionyl chloride (3.3 g, 2.02 ml, 27.7 mmol). The mixture was stirred for 20 min at −15°. The salt was filtered off and washed with benzene. Solvent (THF+benzene) evaporation afforded a residue which was taken up in benzene (warm) and treated with charcoal. The suspension was filtered through a celite pad and solvent evaporation left a foam; ir (CH$_2$Cl$_2$) $\nu_{max}$: 1780, 1740 cm$^{-1}$ (C=O) $^1$Hmr (CDCl$_3$ δ: 8.17, 8.21 (2H, 2d, J=8, Ho aromatic) 7.76–6.88 (17H, m, H-aromatic), 5.31, 5.16, 5.12, 4.73 (3H, 4s, CH$_2$—PNB, CHCl), 5.12–4.55 (1H, m, H-1'), 4.35–4.25 (1H, m, H-4), 3.80–3.45 (1H, m, H-3) 1.90 (3H, s, CH$_3$CO), 1.12 1.07 (3H, J=6.5, CH$_3$).

HH. 3-(1'-Paranitrobenzylidoxycarbonyl-1'-ethyl)-1-(paranitrobenzyl 2''-chloro-2''-acetate)-4-tritylthio-2-azetidinones (mixture of epimers at C2'').

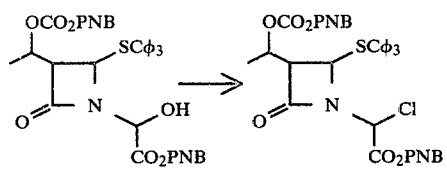

"Isomer C"

Pyridine (58 mg, 0.73 mmol) was added dropwise to a soluti of "Isomer C" of 3-(1'-paranitrobenzyldioxycarbonyl-1'-ethyl)-1-(paranitrobenzyl 2''-hydroxy-2''-acetate)-3-tritylthio-2-azetidinones (470 mg, 0.6 mmol; mixture of epimers at C-2'') in THF (15 ml) cooled to −15° C. Immediately after thionyl chloride (86.5 mg., 0.73 mmol) was added dropwise and the mixture was stirred at −15° C. for 0.5 h. The precipitate was removed by filtration and washed with benzene. The combined filtrates were concentrated, the residue dissolved in fresh benzene and the solution treated with activated charcoal, filtered and concentrated to leave the title compound as an oil. 530 mg; 100%. $^1$Hmr (CDCl$_3$) δ: 8.7–6.8 (23H, m, aromatic), 5.53 (1H, s, H-2''), 5.30 and 5.17 (4H, 2s, benzyls), 4.52 (1H, d, J=2, H-4), 4.20–3.70 (1H, m, H-1'), 3.31 (1H, dd, H-3), 1.27 and 1.21 ppm (3H, 2d, J=6.5); ir (CHCl$_3$) $\nu_{max}$: 1780, 1750 (C=O) and 1525 cm$^{-1}$ (NO$_2$).

"Isomer B"

"Isomer B" of 3-(1-paranitrobenzyldioxycarbonyl-1'-ethyl)-1-(paranitrobenzyl 2"-chloro-2"-acetate)-4-tritylthio-2-azetidinones (mixture of C-2" epimers) was prepared as described above for the "Isomer C" in quantitative yield. ¹Hmr (CDCl₃) δ: 8.25–6.90 (23H, m, aromatics), 5.40–5.0 (4H, m, benzyls), 5.40–4.45 (1H, m, H-1'), 4.82 and 4.57 (1H, 2s, H-2"), 4.36 and 4.31 (1H, 2d, J=2.5, H-4), 3.63 (1H, m, J=2.5, J=6.5, H-3), 1.25 and 1.18 ppm (3H, 2d, J=6.5, CH₃); ir (CHCl₃)ν$_{max}$: 1780, 1750 (C=O), and 1525 cm⁻¹ (NO₂).

"Isomer A"

"Isomer A" of 3-(1'-paranitrobenzyldioxycarbonyl-1'-ethyl)-1'(paranitrobenzyl 2"-chloro-2"-acetate)-4-tritylthio-2-azetidinones (mixture of C-2" epimers). ¹Hmr (CDCl₃) δ: 8.30–6.80 (23H, m, aromatics), 5.45–4.80 (1H, m, H-1'), 5.18 and 5.21 (4H, 2s, benzyls), 4.87 (1H, 2d, H-4), 4.22 and 3.87 (1H, 2s, H-2"), 4.05–3.40 (1H, m, H-3), 1.57 and 1.50 ppm (3H, 2d, CH₃).

"Isomer D"

"Isomer D" of 3-(1"-paranitrobenzyldioxycarbonyl-1'-ethyl-1'-(paranitrobenzyl 2"-chloro-2"-acetate)-4-tritylthio-2-azetidinones (mixture of C-2" epimers). ¹Hmr (CDCl₃) δ: 8.30–6.70 (23H, m, aromatics), 5.32–5.10 (4H, m, benzyls), 5.48 and 5.30 (1H, 2s, H-2"), 4.82 (1H, d, J=5, H-4), 5.30–5.20 (1H, m, H-1'), 3.15 (1H, m, H-3), 1.40 and 1.30 ppm (3H, 2d, J=6.5, CH₃); ir CHCl₃) ν$_{max}$: 1780, 1750 (C=O) and 1525 cm⁻¹ (NO₂)

II. Preparation of (1'S,3S,4R and 1'R,3R,4S)3-(1'-Methanesulfonyloxy-1'-ethyl)-1-(paranitrobenzyl 2"-chloro-2"-acetate(-4-tritylthio-2-acetidinone (isomer C) (epimers at C₂")

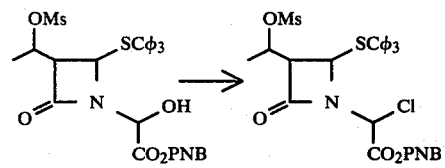

To a cold solution (5° C.) of (1'S,3S,4R and 1'R,3R,4S)3-(1'-methanesulfonyloxy-1'-ethyl)-1-(paranitrobenzyl 2"-hydroxy-2"-acetate)-4-tritylthio-2-azetidinone (24.0 g, 35.5 mmol) in dry tetrahydrofuran (350 ml) was added pyridine (3.65 g, 46.2 mmol) and thionyl chloride (5.5 g, 46.2 mmol) dropwise. After stirring for 45 min, ether (100 ml) was added to precipitate the hydrochloride salt which was filtered off. The filtrate was evaporated and the residue redissolved in benzene (200 ml) and treated with charcoal. Evaporation of the solvent left a nearly white foam which was used as such in the next step. ¹Hmr (CDCl₃) δ: 8.18 (2H, d, J=9, Hm aromatic), 7.72 (17H, m, part of d, Ho aromatic, trityl), 5.57 and 5.12 (1H, s, H-2") 5.28 (2H, s, —CH₂PNB), 4.73 (1H, 2d, H-4), 3.21 (1H, 2dq, H-3), 2.78 (3H, 2s, mesylate and 1.21 ppm (3H, 2d, H-6H₂; H-2'); ir ν$_{max}$ 1779 cm⁻¹ (C=O)

JJ. Preparation of (1'S,3R,4R and 1'R,3S,4S) 3-(1'-Methoxymethoxy-1'-ethyl)-1-(paranitrobenzyl 2"-triphenylphosphoranylidene-2"-acetate)-4-tritylthio-2-azetidinone (Isomer A)

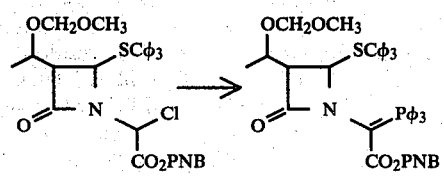

A mixture of Isomer A of 3-(1'-methoxymethoxy-1'-ethyl)-1-(paranitrobenzyl-2"-chloro-2"-acetate)-4-tritylthio-2-azetidinone (6.6 g, 10 mmol), triphenylphosphine (3.3 g, 12.5 mmol), 2,6-lutidine (1.3 ml, 11 mmol) and dioxane (140 ml) was heated under reflux for 2 days. The solution was diluted with ether, washed with dilute acid (5% HCl), water, dilute sodium bicarbonate solution and brine, dried and concentrated. The residue was purified by chromatography on silica gel eluting with 10% ether in benzene. Concentration of the pertinent fractions left the title compound as a foam (1.4 g, 13.7%) ir (KBr) ν$_{max}$: 1750 (C=O) and 1660–1650 cm⁻¹ (C=C, aromatics).

KK. Preparation of (1'S,3S,4R and 1'R,3R,4S) 3-(1'-Methoxymethyloxy-1'-ethyl)-1-(paranitrobenzyl 2"-triphenylphoshoranylidene-2"-acetate)-4-tritylthio-2-azetidinone (Isomer C).

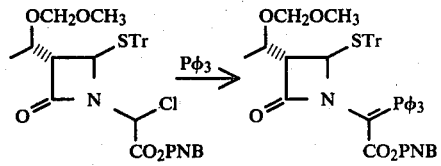

A dioxane (100 ml, distilled over LAH) solution of (1'S, 3S,4R and 1'R,3R,4S) 3-(1'-methoxymethyloxy-1'-ethyl)-1-(paranitrobenzyl-2"-chloro-2"-acetate)-4-tritylthio-2-azetidinone (4.86 g, 6.62 mmol), triphenylphosphine (2.60 g, 9.93 mmol) and 2,6-lutidine (770 mg, 0.837 ml, 7.20 mmol) was heated under reflux for 4 h and kept in a hot bath (100° C.) for 16 h. The mixture was diluted with ether, washed with 1% aqueous HCl, water, 10% aqueous NaHCO₃, water and brine and dried (MgSO₄). The solution was concentrated and the residue filtered through a silica gel (65 g) column (5%, 10% and 20% ether-benzene) to give the title compound (2.8 g, 48%). ir (CHCl₃) ν$_{max}$: 1795 (C=O), 1620 and 1605 (phosphorane) and 1515 cm⁻¹ (NO₂).

LL. (1'R,3S,4R and 1'S,3R,4S) 3-(1'-Acetoxy-1'-ethyl)-1-(paranitrobenzyl-2"-triphenylphosphoranylidene-2"-acetate)-4-tritylthio-2-azeditinone (Isomer B)

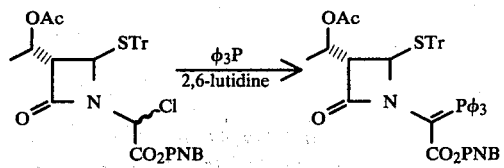

A dioxane (100 ml, freshly distilled over LAH) solution of crude (1'R,3S,4R and 1'S,3R,4S) 3-(1'-acetoxy-1'-ethyl)-1-(paranitrobenzyl 2"-chloro-2"-acetate)-4-tritylthio-2-azetidinone was treated with 2,6-lutidine (2.97 g, 3.23 ml, 27.72 mmol) and triphenyl phosphine (9.91 g, 37.8 mmol). The mixture was refluxed (oil bath 130°) for 18 h. The solvent was evaporated and the residue was redissolved in methylene chloride. The resulting solution was successively washed with diluted HCl, H$_2$O, diluted aqueous NaHCO$_3$, H$_2$O and brine. Drying and solvent evaporation left the title compound as a solid which was triturated with ether and collected by filtration (14.6 g, 65.9%); ir (CH$_2$Cl$_2$) $\nu_{max}$: 1750 (C=O) and 1620, 1610 cm$^{-1}$ (phosphorane).

MM. 3-(1'-Paranitrobenzyldioxycarbonyl-1'-ethyl)-1-(paranitrobenzyl-2"-triphenylphosphoranylidene-2"-acetate)-4-tritylthio-2-azetidinone

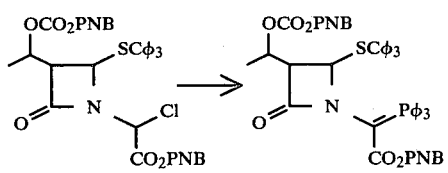

Isomer B

A mixture of (1'R,3S,4R and 1'S,3R,4S) 3-(1'-paranitrobenzyl-dioxycarbonyl-1'-ethyl)-1-(paranitrobenzyl-2"-chloro-2"-acetate)-4-tritylthioazetidinone (isomer B) (4.96 g, 6.22 mmol, mixture of epimers at C-2"), triphenyl phosphine (2.47 g, 9.42 mmol) and 2,6-lutidine (740 mg, 0.80 ml, 6.91 mmol) was refluxed in dioxane (freshly distilled over LAH) for 30 h. The solution was diluted with ether and ethyl acetate, washed with 5% aqueous HCl, water, 10% aqueous NaHCO$_3$, water and brine and dried (MgSO$_4$). Solvent evaporation afforded a residue which was passed through a silica gel (10 times its weight) column (10% ether-benzene, ether and ethyl acetate). The title compound was obtained as a crystalline solid (3.1 g, 49%), mp 189°-190° (ether); ir (CHCl$_3$) $\nu_{max}$: 1750 (C=O), 1620, 1605 (phosphorane) and 1522 cm$^{-1}$ (NO$_2$).

Isomer C

Isomer C of 3-(1'-paranitrobenzyldioxycarbonyl-1'-ethyl)-1-(paranitrobenzyl-2"-triphenylphosphoranylidene-2"-acetate)-4-tritylthio-2-azetidinone was prepared as described above for isomer B. ir (CHCl$_3$) $\nu_{max}$: 1750 (C=O), 1610, 1620 (phosphorane) and 1520 cm$^{-1}$ (NO$_2$); $^1$Hmr (CDCl$_3$) δ: 8.6–6.7 (H, aromatics), 5.22 and 4.95 (benzyls), 4.70 (H-4), 2.6 (H-3), 1.19 and 1.07 ppm (CH$_3$).

Isomer D

A mixture of Isomer D of 3-(1'-p-nitrobenzyldioxycarbonyl-1'-ethyl)-1-(p-nitrobenzyl 2"-chloro-2"-acetate)-4-tritylthio-2-azetidinone (4.598 g, 4.45 mmol; purity 77%, mixture of epimers at C-2"), triphenylphosphine (1.425 g, 5.44 mmol; Aldrich) and 2,6-lutidine (0.63 ml, 580 mg, 5.40 mmol; Anachemia) in dioxane (65 ml; distilled from LAH) was heated at gentle reflux under N$_2$ for 41 h, monitoring the reaction by tlc (benzene:ether=3:1). The dark reaction mixture was cooled, diluted with EtOAc and washed successively with 0.1 NHCl, water, 2% NaHCO$_3$ and then brine. Drying (Na$_2$SO$_4$) and evaporation of the solvents gave 4.18 g of a dark coloured oil which was purified by column chromatography (SiO$_2$, 88 g; eluent 10–25% ether in benzene), yielding 1.108 g (1.08 mmole, yield 24.3%) of the title compound as a yellowish foam; $^1$Hmr (CDCl$_3$) δ: 1.08 (d, J=6Hz, 1'-CH$_3$); ir (neat) $\nu_{max}$: 1745 cm$^{-1}$ (s, C=O).

NN. Preparation of (1'S,3S,4R and 1'R,3R,4S)3-(1'-Methanesulfonyloxy-1'-ethyl)-1-(pananitrobenzyl 2"-triphenylphosphoranylidene-2"-acetate)-4-tritylthio-2-azetidinone (isomer C)

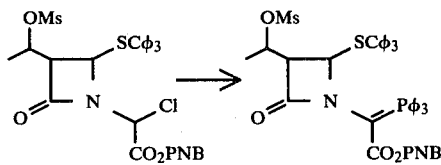

A solution of (1'S,3S,4R and 1'R,3R,4S)3-(1'-methanesulfonyloxy-1'-ethyl)-1-(paranitrobenzyl 2"-chloro-2"-acetate)-4-tritylthio-2-azetidinone (24.7 g, 35.5 mmol), triphenylphosphine (11.2 g, 42.7 mmol) and 2.6-lutidine (4.2 g, 39.1 mmol) in dry dioxane (350 ml) was refluxed under nitrogen for 19h. The solvent was evaporated and the crude product redissolved in ethyl acetate and washed successively with dilute HCl, NaHCO$_3$ and brine. Purification was completed by chromatography on a silica gel column (8.5×12 cm). Elution with 10% ether-dichloromethane (1.5l) and then ether (1.5l) gave the purified phosphorane; 12.36 g (40%). $^1$Hmr (CDCl$_3$) δ: 2.53 and 2.93 ppm (3H, 2s, mesylate); ir $\nu_{max}$: 1749 and 1620 cm$^{-1}$ (C=O)

OO. Preparation of (1'R,3S,4R and 1'S, 3R,4S) 3-(1'-Hydroxy-1'-ethyl)-1-(paranitrobenzyl-2"-triphenylphosphoranylidene-2"-acetate) 4-tritylthio-2-azetidinone (Isomer B)

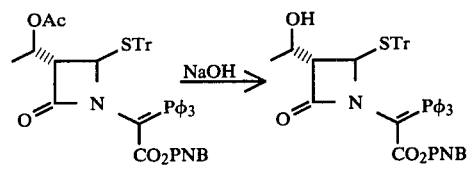

A solution of phoshorane (1'R,3S,4R and 1'S,3R4S) 3-(1'-acetoxy-1'-ethyl)-1-(paranitrobenzyl 2"-triphenylphosphoranylidene-2"-acetate)-4-tritylthio-2-azetidinone (4.43 g, 5.00 mmol) in methanol (10 ml) THF (60 ml ) was treated at room temperature with 1% aqueous NaOH (1 eq, 200 mg in 20 ml H$_2$O). The reaction progression was followed by tlc*. The mixture was diluted with ether-ethyl acetate and washed with HCl, H$_2$O, aqueous NaHCO$_3$, H$_2$O and brine. Solvent evaporation afforded a residue which was crystallized from benzene-ether (3.7 g, 87.7%) mp 169.5°-170.5° C. ir (CH$_2$Cl$_2$) $\nu_{max}$: 1745 (C=O) and 1620 cm$^{-1}$ (phosphorane).

*Heating the mixture increased the reaction rate.

PP. Preparation of (1'S,3R,4R and 1'R,3S,4S) Silver 3-(1'-methoxymethyl-1'-ethyl)-1-(paranitrobenzyl 2''-triphenylphosphoranylidene-2''-acetate)-2-azetidinone-4-thiolate (Isomer A)

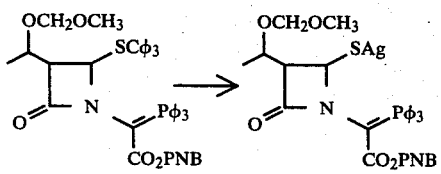

Silver 3-(1'-methoxymethyl-1'-ethyl)-1-(paranitrobenzyl-2''-triphenylphoshporanylidene-2''-acetate)-3-tritylthio-2-azetidinone (isomer A), was prepared as described elsewhere for the isomer C of the paranitrobenzyldioxy carbonyl derivative. Yield 50%. ir (neat $\nu_{max}$: 1745 cm$^{-1}$ (C=O).

QQ. Preparation of 1'S,3S,4R and 1'R,3R,4S) Silver 2-(1'-methoxymethyloxy-1'-ethyl)-1-(paranitrobenzyl 2''-triphenylphosphoranylidene-2''-acetate)-2-azetidinone-4-thiolate (Isomer C).

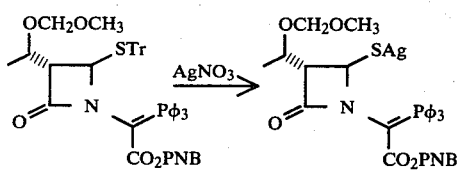

(1'S,3S,4R and 1'R,3R,4S) 3-(1'-methoxymethyloxy-1'-ethyl)-1-(paranitrobenzyl 2''-triphenylphosphoranylidene-2''-acetate)-4-tritylthio-2-azetidinone (887 mg, 1.0 mmol) was first dissolved in hot (40° C.) methanol (30 ml), treated with pyridine (103 mg, 0.105 ml, 1.3 mmol) and, after cooling, was treated with a 0.15 M methanol solution of silver nitrate (8.7 ml, 1.3 mmol). The mixture was stirred for 1 h at 23° C., cooled (ice bath) and stirred for 20 min. The salt was filtered and washed successively with cold methanol and ether (3 times, 671 mg, 87%). ir (CHCl$_3$) $\nu_{max}$: 1745 (C=O), 1605 (phosphorane) and 1520 cm$^{-1}$ (NO$_2$).

RR. Preparation of Silver 3-(1'-paranitrobenzyldioxycarbonyl-1'-ethyl)-1-(paranitrobenzyl 2''-triphenylphosphoranylidene-2''-acetate)-2-azetidinone-4-thiolate.

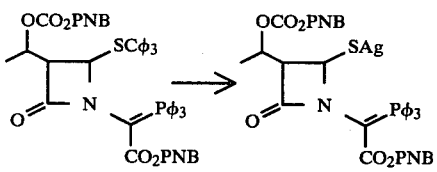

"Isomer B"

(1'R,3S,4R and 1'S,3R,4S) 3-(1'-paranitrobenzylcarbonyldioxy-1'-ethyl)-1-(paranitrobenzyl-2''-triphenylphosphoranylidene-2''-acetate)-4-trithio-2-azetidinone (1.02 g, 1 mmol) was first dissolved in CH$_2$Cl$_2$ (3 ml) and diluted with hot (55° C.) MeOH (20 ml). The hot solution was treated first with pyridine (120 ml, 117 mg, 1.48 mmol) and a hot (55° C.) 0.15 M methanolic solution of silver nitrate (8 ml, 1.2 mmol). The mixture was stirred at room temperature for 15 min, then at 0° C. for 2 h. It was then concentrated to a 10% solution on the rotary evaporator (no bath). The mercaptide was filtered and washed twice with cold (−15° C.) methanol and three times with ether. (917 mg, 100%). ir (nujol mull) $\nu_{max}$: 1745 (C=O), 1600 (phosphorane( and 1517 cm$^{-1}$ (NO$_2$).

"Isomer C"

Silver 3-(1'-paranitrobenzyldioxycarbonyl-1'-ethyl)-1-(paranitrobenzyl 2''-triphenylphosphoranylidene-2''-triphenylphosphoranylidene-2''-acetate)-2-azetidinone-4-thiolate, "Isomer C", was prepared as described above for the "Isomer B"; ir (nujol) $\nu_{max}$: 1745 (C=O) and 1600 cm$^{-1}$ (phosphorane).

"Isomer D"

A solution of Isomer D of 3-(1'-p-nitrobenzylcarbonyldioxy-1'-ethyl)-1-(p-nitrobenzyl 2''-triphenylphosphoranylidene-2''-acetate)-4-tritylthio-2-azetidinone (145 mg, 0.142 mmol) was prepared by first dissolving it in CH$_2$Cl$_2$ (5 ml), removing the CH$_2$Cl$_2$ at 55°–60° and adding hot MeOH (4 ml). To the above solution was added a hot solution of AgNO$_3$ in MeOH (0.15 M, 1.14 ml, 0.17 mmol, 1.2 eq), followed by pyridine (14 μl, 0.17 mmol, 1.2 eq). The silver mercaptide started to precipitate immediately. The mixture was stirred 2 h at room temperature and 1 h at 0°. The mercaptide was collected by filtration and washed with ice-cold MeOH and ether, yielding 99 mg (0.11 mmol, 78%) of the title compound as a brownish solid: ir (Nujol) $\nu_{max}$: 1750 cm$^{-1}$ (s, C=O).

SS. Preparation of (1'R,3S,4R and 1'S,3R,4S) Silver 3-(1'-hydroxy-1'-ethyl)-1-)paranitrobenzyl-2''-triphenylphosphoranylidene-2''-acetate)-2-azetidinone-4-thiolate (Isomer B)

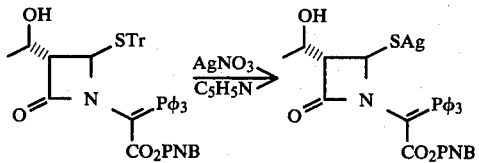

A solution* of (1'R,3S,4R and 1'S,3R,4S) 3-(1'-hydroxy-1'-ethyl)-1-(paranitrobenzyl-2''-triphenylphosphoranylidene-2''-acetate)-4-tritylthio-2-azetidinone (1 g, 1.19 mmol) in MeOH (10 ml), was treated with pyridine (124 μl, 121.3 mg, 1.53 mmol) and at 10° C. with a 0.15 M solution of silver nitrate in MeOH (15 ml, 2.25 mmol—or until no more precipitation of the silver mercaptide occurred). The mixture was stirred for 1 h and concentrated on the rotary evaporator (no bath) to approximatively 10% concentration. The solvent was filtered off. The cake was washed once with MeOH and 3 times with ether, and pumped under high vacuum (954 mg, 100%). ir (Nujol mull) $\nu_{max}$: 3500-3400 (O—H), 1752 (C=O) 1595 (phosphorane) and 1525 cm$^{-1}$ (NO$_2$).

*The crystalline material was first dissolved in CH$_2$Cl$_2$.

TT. Preparation of (1'R,3R,4R and 1'S,3S,4S) 4-Acetylthio-3-(1'-p-nitrobenzyldioxycarbonyl-1'-ethyl)-1-(p-nitrobenzyl 2''-triphenylphosphoranylidene-2''-acetate)-2-azetidinone (Isomer D)

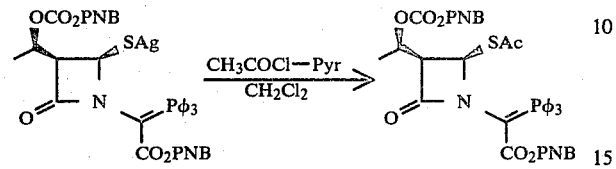

To a stirred solution of silver 3-(1'-paranitrobenzyl 2''-triphenylphosphoranylidene-2''-acetate)-2-azetidinone-4-thiolate (isomer D) (85 mg, 0.095 mmol) in $CH_2Cl_2$ (5 ml) containing pyridine (30 μl, ≈0.37 mmol; Fisher) was added at 0°–5° C. $CH_3COCl$ (20 μl, 0.28 mmol) and the mixture was stirred at 0°–5° C. for 30 min. The precipitate which formed was filtered and washed with $CH_2Cl_2$. The filtrate and washings were combined, washed successively with brine, diluted HCl, saturated $NaHCO_3$ and then brine ($Na_2SO_4$) and evaporated yielding 75 mg (0.091 mmol, crude yield 95%) of the title compound as a syrup: $^1$Hmr ($CDCl_3$) δ: 2.33 (s, —$SOCOCH_3$); ir (neat) $\nu_{max}$: 1750 (β-lactam, ester), 1695 (thioester), 1520 and 1350 cm$^{-1}$ (—$NO_2$).

UU. Preparation of (1'R,5R,6R and 1'S,5S,6S) cis p-Nitrobenzyl 2-methyl-6-(1'-p-nitrobenzyldioxycarbonylmethyl-penem-3-carboxylate (Isomer D)

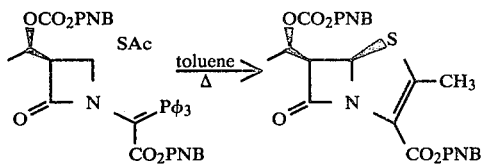

A solution of the above acetylthioazetidinone (74 mg, 0.09 mmol) in toluene (30 ml) was heated at reflux under $N_2$ atmosphere for 7 h. After evaporation of the solvent, the residue was purified by hplc ($SiO_2$; eluent, benzene:ether=3:1) yielding 24 mg (0.044 mmol, yield 49%) of the penem ester as a syrup. (Note: this oil could be crystallized from THF-ether or $CH_2Cl_2$-ether: $^1$Hmr ($CDCl_3$) δ: 1.40 (3H, d, J=6.5 Hz, 1'-$CH_3$), 2.38 (3H, s, 2-$CH_3$), 4.07 (1H, dd, $J_{5,6}$=4 Hz, $J_{6,1}$=9 Hz, 6-H), 5.05–5.30–5.34–5.59 (2H, AB type, 3-$CO_2\underline{CH_2}$—Ar), 5.30 (2H, s, 1'—$OCO_2$—$CH_2$—Ar), 5.1–5.6 (1H, m, 1'-H), 5.68 (1H, d, $J_{5,6}$=4 Hz, 5-H), 7.49–7.64–8.18–8.33 (4H, $A_2'B_2'$, 1'-aromatic Hs), 7.53–7.68–8.18–8.33 (4H, $A_2'B_2'$, 3-aromatic Hs); ir (neat) $\nu_{max}$: 1780 (β-lactam), 1750 (—$OCO_2$—), 1710 (ester), 1520 and 1350 cm$^{-1}$ (—$NO_2$).

VV. Preparation of (1'R,5R,6R and 1'S,5S,6S) Potassium and sodium 6-(1'-hydroxyethyl)-2-methylpenem-3-carboxylate (isomer D).

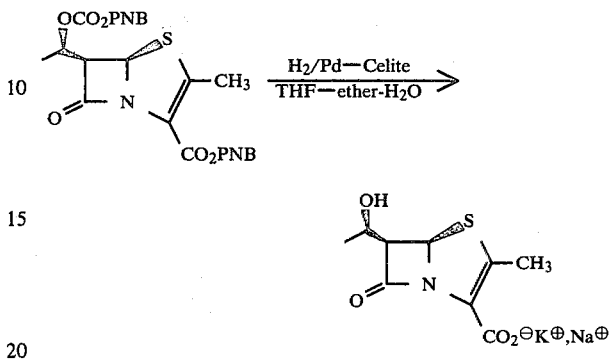

A solution of the above penem ester (24 mg, 0.044 mmol) in THF (5 ml) was mixed with ether (10 ml), $H_2O$ (5 ml), phosphate buffer (1.00 ml, 0.05 molar pH 7.00: Fisher) and 30% Pd-Celite (50 mg, Engelhard). This mixture was hydrogenated at 35 psi for 21.5 h at room temperature. After removal of the catalyst (over Celite), the aqueous layer was separated, washed with ether and lyophilized yielding 12 mg of the title mixture of sodium and potassium salts as a white powder: $^1$Hmr ($D_2O$) δ: 1.23 (3H, d, J=6 Hz, 1'-$CH_3$), 2.27 (3H, s, 2-$CH_3$), 3.85 (1H, dd, $J_{5,6}$=4 Hz, $J_{6,1}$=9 Hz, 6-H), 4.3 (1H, m, 1'-H) and 5.65 ppm (1H, d, $J_{5,6}$=4 Hz, 5-H); ir (Nujol) $\nu_{max}$: 1755 (β-lactam) and 1570 cm$^{-1}$ (—$CO_2^\ominus$); uv ($H_2O$)$\lambda_{max}$: 297 (ε 2300, calcd as K-salt), 258 (ε 1900, calcd as K-salt). This material was identical to a sample of title compound prepared by an aldol condensation of acetaldehyde with the dianion of 2-methylpenem-3-carboxylic acid. ($^1$Hmr, ir, uv)

EXAMPLE 59

(1'S,5R,6S and 1'R,5S,6R) 6-1;-Hydroxy-1'-ethyl)-2-methylpenem-3-carboxylic Acid (isomer C)

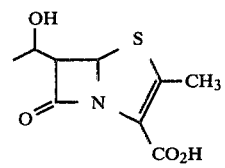

Method A:

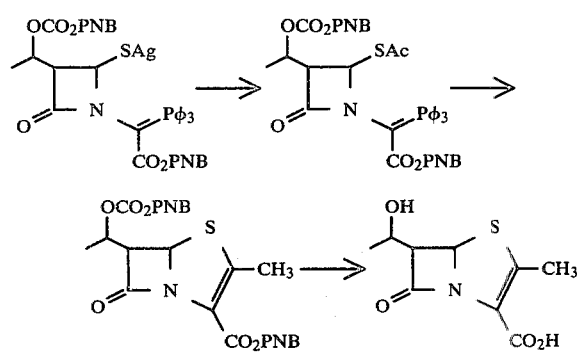

Method B:

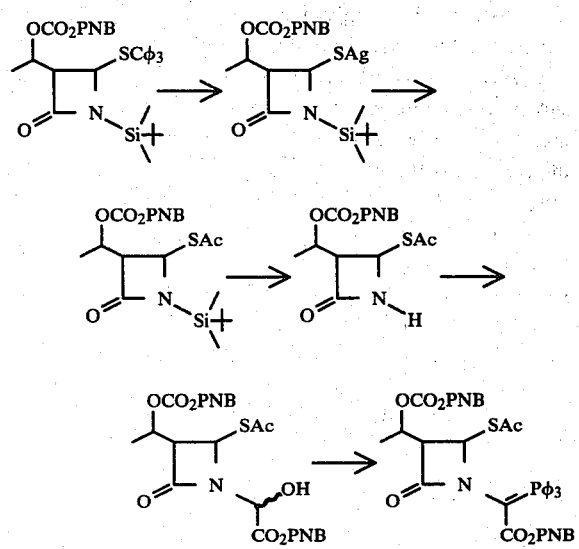

METHOD A

(1) (1'S,3S,4R and 1'R,3R,4S) 4-Acetylthio-3-(1'-paranitrobenzyldioxycarbonyl-1'-ethyl)-1-(paranitrobenzyl 2''-triphenylphosphoranylidene-2''-acetate)-2-azetidinone (isomer C).

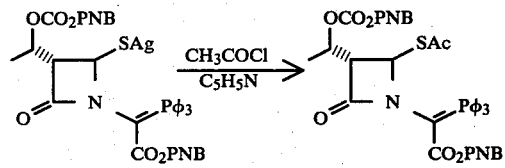

A cold (ice-MeOH bath) solution of 1'S,3S,4R and 1'R,3R,4S) silver 3-(1'-paranitrobenzyl-dioxycarbonyl-1'-ethyl)-1-(paranitrobenzyl 2''-triphenylphosphoranylidene-2''-acetate)-2-azetidinone-4-thiolate (isomer C) (1.14 g, 1.30 mmol) in CH$_2$Cl$_2$ (60 ml) was treated with pyridine (0.6 ml, 0.74 mmol) and dropwise with acetyl chloride (236 mg, 0.213 ml, 3.00 mmol). The reaction mixture was stirred for 1 h at −15° C. The precipitate was filtered and washed with ether. The filtrate was washed with 2% aqueous HCl, water, 2% aqueous NaHCO$_3$, water and brine and dried (MgSO$_4$). The residue upon solvent evaporation was triturated in ether (895 mg, 83.7%), mp 184°-5° C. dec); ir (CHCl$_3$) $\nu_{max}$: 1755, 1695 (C=O), 1620 and 1605 cm$^{-1}$ (phosphorane). Anal. calcd for C$_{42}$H$_{36}$N$_3$O$_{11}$SSi: C 61.38, H 4.42, N 5.11, S 3.90; found: C 61.26, H 4.49, N 4.88, S 4.26.

(2) (1'S,5R,6S and 1'R,5S,6R) Paranitrobenzyl 2-methyl-6-(1'-paranitrobenzyldioxycarbonyl-1'-ethyl)-penem-3-carboxylate (isomer C)

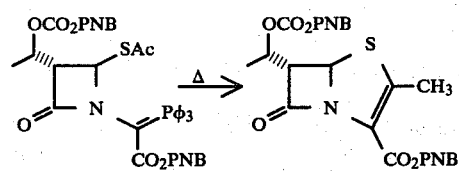

A solution of (1'S,3S,4R and 1'R,3R,4S) 4-acetylthio-3-(1'-paranitrobenzyldioxycarbonyl-1'-ethyl)-1-(paranitrobenzyl 2''-triphenylphosphoranylidene-2''-acetate)-2-azetidinone (isomer C) (855 mg, 1.04 mmol) in toluene (60 ml) was heated under reflux for 4.5 h. The residue upon concentration of the solution was passed through a silica gel (10 g) column (1% ether in benzene) to give the pure title compound (393 mg, 69.6%), mp 157°–158° C. (CHCl$_3$-ether); ir (CHCl$_3$) $\nu_{max}$: 1785, 1745, 1710 (C=O) and 1525 cm$^{-1}$ (NO$_2$); $^1$Hmr (CDCl$_3$) δ: 8.30–7.2 (8H, m, H-aromatics) 5.46 (1H, d, J=1.8, H-5), 5.40–5.0 (5H, m, z CH$_2$—PNB and H-1'), 3.95 (1H, dd, J=1.8, J=5.4, H-6), 2.35 (3H, s, CH$_3$) and 1.43 ppm (3H, d, J=5.4, CH$_3$); Anal. calcd for C$_{24}$H$_{21}$N$_3$O$_{10}$S: C 53.04, H 3.89, N 7.73; found C 52.76, H 3.86, N 7.69.

(3) (1'S,5R,6S and 1'R,5S,6R) 6-(1'-Hydroxy-1'-ethyl)-2-methyl penem-3-carboxylic acid (isomer C)

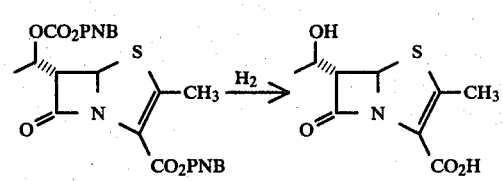

A mixture made of (1'S,5R,6S and 1'R,5S,6R) paranitrobenzyl 2-methyl-6-(1'-paranitrobenzyldioxycarbonyl-1'-ethyl)-penem-3-carboxylate (206 mg, 0.379 mmol), THF-ether-H$_2$O (30 ml, 40 ml, 20 ml), a 0.05 M pH 7 buffer solution (7.64 ml, 0.382 mmol) and 30% Pd on Celite (500 mg) was hydrogenated at 42 psi H$_2$ on a Parr shaker for 16 h. The catalyst was filtered and washed with water. The aqueous phase was washed with ether (3 times), acidified portionwise with cold 1% aqueous HCl to pH 2.5 and extracted with ethyl acetate (15×20 ml) between each HCl addition. The ethyl acetate extracts were combined and washed with brine (3×30 ml). Evaporation of the solvent and trituration of the residue with ether gave the title compound (57 mg, 65.6%), ir (KBr) $\nu_{max}$: 3580–3300 (O—H), 1755 and 1660 cm$^{-1}$ (C=O); uv (EtOH) λ$_{max}$ 311 (ε 6538), 262 (ε 3672); $^1$Hmr (DMSO-d$_6$) δ: 5.57 (1H, d, J=1.7, H-5), 4.02 (1H, m, H-1'), 3.75 (1H, dd, J=1.7, J=3.5, H-6), 2.23 (3H, s, CH$_3$) and 1.23 ppm (3H, d, CH$_3$).

METHOD B

(1) Silver (1'S,3S,4R and 1'R,3R,4S) 1-(t-Butyldimethylsilyl)-3-(1'-paranitrobenzyldioxycarbonyl-1'-ethyl)-2-azetidinone-4-thiolate (isomer C)

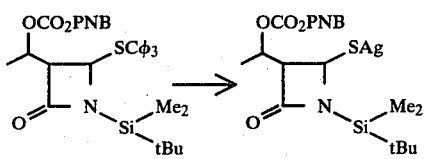

Isomer C of 1'-(t-butyldimethylsilyl)-3-(1'-paranitrobenzyldioxycarbonyl-1'-ethyl)-4-tritylthio-2-azetidinone (1 g, 143 mmol) was dissolved by stirring in hot (40° C.) methanol (12 ml). A solution of silver nitrate (0.59 g) in methanol (12 ml) was added followed by pyridine (0.13 ml). The mixture was stirred vigorously 1 h at room temperature and 2 h at 0°. The solid silver mercaptide was collected by filtration and washed with ether, 352 mg (46%). ir $v_{max}$: 1735 cm$^{-1}$ (C=O). (2) (1'S,3S,4R and 1'R,3R,4S) 4-Acetylthio-1-(t-butyldimethylsilyl)-3-(1'-paranitrobenzyldioxycarbonyl-1'-ethyl)-2-azetidinone (isomer C)

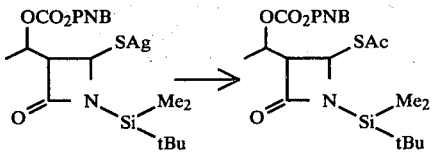

To a solution of isomer C of silver 1-(t-butyldimethylsilyl)-3-(1'-paranitrobenzyldioxycarbonyl-1'-ethyl)-2-azetidinone-4-thiolate (880 mg) in dichloromethane (40 ml) stirred at 0° C. was added pyridine (0.57 ml) followed, dropwise, by acetyl chloride (0.49 ml). The mixture was stirred 0.5 h at 0°, the solids removed by filtration and the filtrates diluted with ether, washed with aqueous hydrochloric acid (2%), water, sodium bicarbonate (2%) and brine, dried and concentrated to leave the title material as an oil. (610 mg). $^1$Hmr (CDCl$_3$) δ: 8.2 and 7.48 (4H, 2d, aromatics), 5.40 (1H, d, J=2.2, H-4), 5.2 (2H, s, benzyl), 5.3-4.9 (1H, m, H-1'), 3.42 (1H, dd, J=2, H-3), 2.32 (3H, s, CH$_3$), 1.40 (3H, d, J=6.5, CH$_3$), 0.95 (9H, s, t-Bu) and 0.2 ppm (6H, CH$_3$).

(3) (1'S,3S,4R and 1'R,3R,4S) 4-Acetylthio-3-(1'-paranitrobenzyldioxycarbonyl-1'-ethyl)-2-azetidinone. (isomer C)

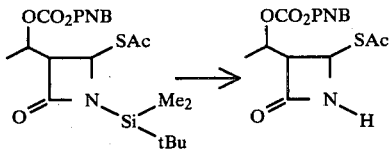

Isomer C of the above S-acetyl N-t-butylmethyl-silyl-azetidinone derivative (1.4 g) was dissolved in a mixture of TFA (0.5 ml), water (0.5 ml), methanol (3 ml) and dichloromethane (2 ml) and stirred at room temperature for 48 h. The solution was diluted with water (100 ml) and extracted with dichloromethane (4×20 ml). The combined organic extracts were washed with sodium bicarbonate (2%) and brine, dried and concentrated to leave the crude title compound as an oil. Purification was done by chromatography over silica gel (30 g) eluting with 5% ether in benzene; (650 mg). Crystallization from benzene gave a white solid. $^1$Hmr (CDCl$_3$) δ: 8.15 and 7.45 (4H, 2d, aromatics), 6.18 (1H, N—H), 5.19 (2H, s, benzyl), 5.05 (2H, m, H-4 and H-1'), 3.35 (1H, dd, J=2.5, 4.5, H-3), 2.34 (3H, s, CH$_3$) and 1.42 ppm (3H,d, J=6.5, CH$_3$); ir $v_{max}$: 1780, 1750, 1695 cm$^{-1}$ (C=O).

(4) (1'S,3S,4R and 1'R,3R,4S) 4-Acetylthio-3-(1'-paranitrobenzyldioxycarbonyl-1'-ethyl)-1-(paranitrobenzyl 2''-hydroxy-2''-acetate)-2-azetidinones (epimers at C-2'') (isomer C)

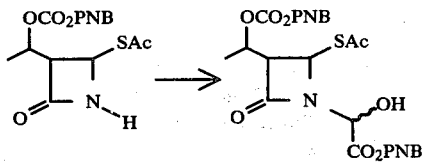

A mixture of isomer C of 4-acetylthio-3-(1'-paranitrobenzyldioxycarbonyl-1'-ethyl)-2-azetidinone (750 mg), paranitrobenzylglyoxylate hydrate (525 mg) and benzene (50 ml) was heated under reflux for 3 days over a Dean and Stark apparatus filled with 3 Å molecular sieves. A second portion of glyoxylate (52 mg) was added and reflux was continued for 2 more days. The mixture was diluted with ether, washed with hydrochloric acid (2%), water, sodium bicarbonate (2%) and water, dried and concentrated to leave an oily residue (975 mg). Chromatography on silica gel, eluting with benzene-ether (85-15) gave the pure title compounds. $^1$Hmr (CDCl$_3$) δ: 8.25-6.75 (8H, m, aromatics), 5.30 and 5.12 (4H, 2s, benzyls), 5.05-4.70 (1H, H-2''), 4.45-4.35 (1H, 2d, H-4), 4.50-4.10 (1H, m, H-1'), 3.30 (1H, m, H-2 and 1.25 ppm (3H, 2d, CH$_3$).

(5) (1'S,3S,4R and 1'R,3R,4S) 4-acetylthio-3-(1'-paranitrobenzyldioxycarbonyl-1'-ethyl)-1-(paranitrobenzyl 2''-triphenylphosphoranylidene-2''-acetate)2-azetidinone (isomer C)

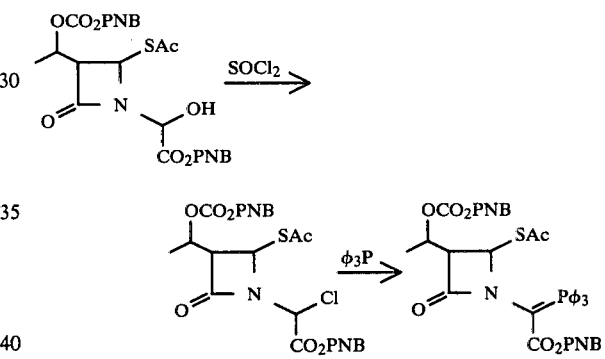

Isomer C of 4-acetylthio-3-(1'-paranitrobenzyldioxycarbonyl-1'-ethyl)-1-(paranitrobenzyl 2''-hydroxy-2''-acetate)-2-azetidinone (577 mg, 1 mmol) was dissolved in anhydrous THF (10 ml) and pyridine (95 mg, 1.2 mmol) was added to the solution. The solution was cooled to 0° and thionyl chloride (143 mg, 1.2 mmol) was added slowly. The mixture was stirred 30 min at 0°, diluted with a little ether and the insoluble salts removed by filtration and washed with ether. The combined filtrates were concentrated to give the crude mixture of epimers of the C-2'' chloro compound. It was dissolved in THF (20 ml), triphenylphosphine (314 mg, 1.2 mmol) and 2,6-lutidine (129 mg, 1.2 mmol) were added and the solution was stirred at 45° C. for 4 days. The solids were removed by filtration, washed with benzene and the combined filtrates were concentrated to leave an oil whose spectral characteristics and tlc behaviour were identical to a sample of the title compound prepared by acylation of the corresponding silver thiolate.

The desired penem product may be produced by reacting the title compound according to the method of steps 2 and 3 of Example 59 (Method A).

EXAMPLE 60

(1'R,5R,6S and 1'S,5S,6R)
6-(1'-Hydroxy-1'-ethyl)-2-methylpenem-3-carboxylic Acid (isomer B)

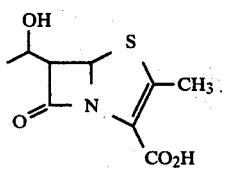

METHOD A

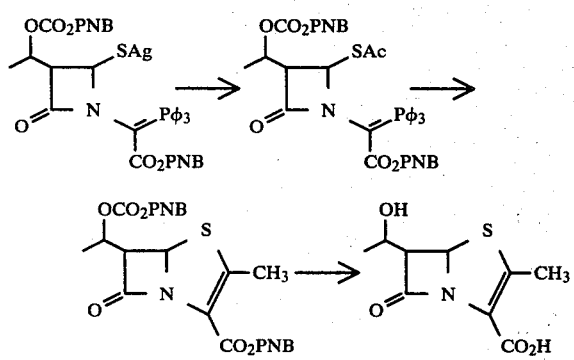

METHOD B

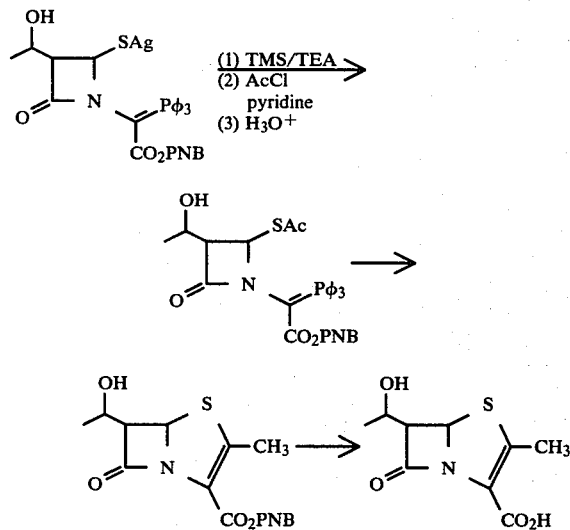

METHOD A (1) (1'R,3S,4R and 1'S,3R,4S)
4-Acethylthio-3-(1'-paranitrobenzyl-dioxycarbonyl-1'-ethyl)-1-(paranitrobenzyl 2''-triphenylphosphoranylidene-2''-acetate)-2-azetidinone, (isomer B)

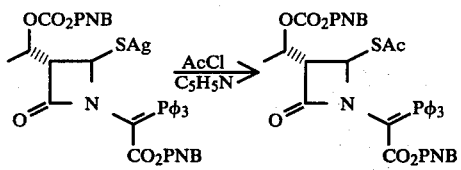

A solution of (1'R,3S,4R and 1'S,3R,4S) silver 3-(1'-paranitrobenzyldioxycarbonyl-1'-ethyl) 1'-paranitrobenzyl 2''-triphenylphosphoranylidene-2''-acetate)-2-azetidinone-4-thiolate (isomer B) (917 mg, 1.03 mmol) in $CH_2Cl_2$ (20 ml) was treated at $-15°$ C. (ice-MeOH bath) with pyridine (242 μl, 247 mg, 3.13 mmol) and dropwise with acetyl chloride (142 μl, 157 mg, 2.0 mmol). The mixture was stirred for 15 min at $-15°$ C. and the solid was filtered and washed with ether. The organic solution was washed with 2% aqueous HCl, water, 2% aqueous $NaHCO_3$, water and brine and dried over $MgSO_4$. The residue upon solvent evaporation crystallized from ether (710 mg, 80%, mp 183°-185° C.; ir ($CHCl_3$) $\nu_{max}$: 1755, 1695 (C=O), 1620, 1605 (phosphorane) and 1625 $cm^{-1}$ ($NO_2$).

(2) (1'R,5R,6S and 1'S,5R,6R) Paranitrobenzyl 2-methyl-6-(1'-paranitrobenzyldioxycarbonyl-1'-ethyl)-enem-3-carboxylate (isomer B)

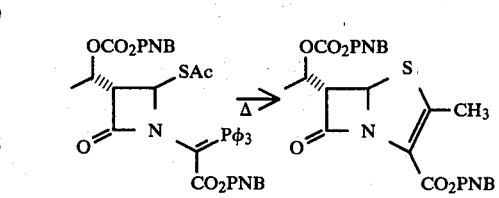

A solution of (1'R,3S,4R and 1'S,3R,4S) 4-acetylthio-3-(1'-paranitrobenzyldioxycarbonyl-1'-ethyl)-1-(paranitrobenzyl 2''-triphenylphosphoranylidene-2''-acetate)-2-azetidinone (650 mg, 0.791 mmol) was refluxed in toluene for 7 h. The concentrated solution upon solvent evaporation was passed through a silica gel column (10 times its weight) and the title compound (0.5% ether-benzene to 2% ether-benzene) was obtained as a white solid; 329 mg, 77%, mp 134°-135° C., ($CH_2Cl_2$-ether); ir ($CHCl_3$) $\nu_{max}$: 1785, 1745, 1705 (C=O) and 1525 $cm^{-1}$ ($NO_2$); $^1$Hmr ($CDCl_3$) δ: 8.20 (2H, d, Ho aromatic), 7.60 (2H, d, Hm aromatic), 5.55 (1H, d, J=1.5, H-s), 5.5-4.75 (5H, m, $2CH_2$-PNB, H-1'), 3.86 (1H, dd, J=7.8, J=1.5, H-6), 2.38 (3H, s, $CH_3$) and 1.50 ppm (3H, d, J=6.3, $CH_3$); Anal. calcd for $C_{24}H_{21}N_3O_{10}S$: C 53.04, H 3.89, N 7.73, S 5.90; found: C 53.05, H 3.98, N 7.63, S 6.02.

(3) (1'R,5R,6S and 1'S,5S,6R)
6-(1'-Hydroxy-1'-ethyl)-2-methyl penem-3-carboxylic acid (isomer B)

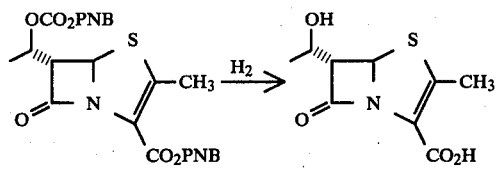

A mixture of (1'R,5R,6S and 1'S,5S,6R) paranitrobenzyl 2-methyl-6-(1'-paranitrobenzyldioxycarbonyl-1'-ethyl)-penem-3-carboxylate (isomer B) (65 mg, 0.12 mmol), 0.05 M pH 7 buffer solution (1.06 eq), $H_2O$-THF-ether (10 ml, 10 ml, 25 ml) was shaken on a Parr hydrogenator using 30% Pd on Celite (200 mg) for 16 h at 50 psi $H_2$. The catalyst was filtered and washed with small volumes of water. The aqueous layer was washed with ether (3 times), acidified portionwise with 1% cold aqueous HCl, extracted with ethyl acetate between each addition of HCl, and saturated with brine and extracted thoroughly with ethyl acetate. The ethyl acetate extracts were combined, washed with brine (5 times) and dried (MgSO4). Solvent evaporation afforded a solid residue which was triturated with methylene chloride (19.4 mg, 71%). ir (nujol) $\nu_{max}$: 3500 (O—H), 1785, 1672 cm$^{-1}$ (C=O); uv (EtOH) $\lambda_{max}$: 260 ($\epsilon$ 3450), 309 ($\epsilon$ 6400); $^1$Hmr (DMSO d$_6$) δ: 5.54 (1H, d, J=1.5, H-5), 3.88 (1H, m, H-1'), 4.2–3.5 (2H, bs, O—H), 3.65 (1H, dd, J=6.5, J=1.5, H-6), 2.28 (3H, s, CH$_3$) and 1.15 ppm (3H, d, J=6, CH$_3$).

METHOD B (1) (1'R,3S,4R and 1'S,3R,4S) 4-Acetylthio-3-(1'-trimethylsilyloxy-1'-ethyl)-1-(paranitrobenzyl 2''-triphenylphosphoranylidene-2''-acetate)-2-azetidinone (isomer B)

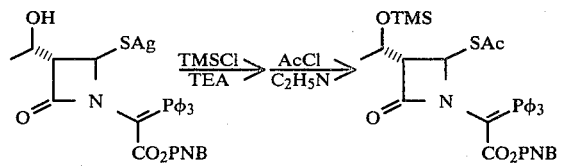

A suspension of (1'R,3S,4R and 1'S,3R,4S) silver 3-(1'-hydroxy-1'-ethyl)-1-(paranitrobenzyl 2''-triphenylphosphoranylidene-2''-acetate)-2-azetidinone-4-thiolate (505 mg, 0.715 mmol) in THF (25 ml) was cooled to −15° C. (ice-MeOH bath), treated dropwise with triethyl amine (289 mg, 398 μl, 2.86 mmol), trimethyl chlorosilane (310 mg, 362 μl, 2.85 mmol) and finally with imidazole (50 mg, 0.734 mmol), stirred for 3 h at −15° C. and at room temperature for 16 h. (ir of an aliquot showed absence of hydroxyl group). The mixture was cooled to −15° C., diluted with CH$_2$Cl$_2$ (20 ml), treated with pyridine (226 mg, 231 μl, 2.86 mmol) and acetylchloride (168 mg, 152 μl, 2.14 mmol), stirred for 0.5 h, diluted with ether, washed with dilute aqueous HCl, water 5% aqueous NaHCO$_3$ water and brine and dried. The solvent was removed on the rotary evaporator and the residue purified by filtration through a silica gel column (1:10 ratio, 3% to 10% ether in benzene) to give the title compound (360 mg, 84.2%) mixed with a little of the desilylated derivative (30 mg, 7.8%). ir (liquid film) $\nu_{max}$: 1750, 1790 (C=O), 1620 (phosphorane) and 1518 cm$^{-1}$ (NO$_2$).

(2) (1'R,3S,4R and 1'S,3R,4S) 4-Acetylthio-3-(1'-hydroxy-1'-ethyl)-1-(paranitrobenzyl 2''-triphenylphosphoranylidene-2''-acetate)-2-azetidinone (isomer B)

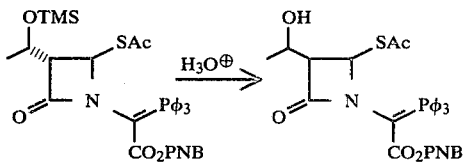

A solution of (1'R,3S,4R and 1'S,3R,4S) 4-acetylthio-3-1'-trimethylsilyloxy-1'-ethyl)-1(paranitrobenzyl 2''-triphenylphosphoranylidene-2''-acetate)-2-azetidinone (360 mg, 0.504 mmol) was treated with TFA (3 drops) and stirred at room temperature for 18 h. The mixture was diluted with ethyl acetate, washed with water, dilute aqueous NaHCO$_3$, water and brine and dried (MgSO$_4$). Solvent evaporation afforded the title compound (334 mg, 100%); ir (CHCl$_3$) $\nu_{max}$: 1755, 1690 (C=O), 1620, 1605 (phosphorane and 1520 cm$^{-1}$ (NO$_2$).

(3) (1'R,5R,6S and 1'S,5S,6R) Paranitrobenzyl 2-methyl-6-(1'-hydroxy-1'-ethyl)-penem-3-carboxylate (isomer B)

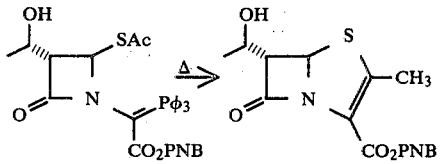

A solution of (1'R,3S,4R and 1'S,3R,4S) 4-acetylthio-3-(1'-hydroxy-1'-ethyl)-1(paranitrobenzyl 2''-triphenylphosphoranylidene-2''-acetate)-2-azetidinone (410 mg, 0.638 mmol) in toluene (40 ml) was refluxed for a 7 h period. Toluene was partially evaporated. The residue was passed through a silica gel (1 to 12 ratio) column (3%, 4% and 5% ether in benzene) to give the title compound (151 mg, 65%) as a white solid mp 161°–161.5° C.; ir (CDCl$_3$) $\nu_{max}$: 3600, 3500–3400 (OH), 1780, 1608 (C=O) and 1525 cm$^{-1}$ (NO$_2$); $^1$Hmr (CDCl$_3$) δ: 8.20 (2H, d, J=7, Ho aromatic), 7.60 (2H, d aromatic), 5.57 (1H, d, J=2, H-5), 5.29 (2H, center of ABq, J=15, CH$_2$—PNB), 4.2 (1H, dq, J=7, J=6, H-1'), 3.67 (1H, dd, J=7, J=2, H-6), 2.33 (3H, s, CH$_3$) and 1.33 ppm (3H, d, J=6, CH$_3$); Anal. calcd for C$_{16}$H$_{16}$N$_2$O$_6$S: C 52.74, H 4.43, N 7.69, S 8.80; found: C 52.67, H 4.41, N 7.71, s 8.96.

(4) (1'R,5R,6S and 1'S,5S,6R) 6-(1'-Hydroxy-1'-ethyl)-2-methyl penem-3-carboxylic acid (isomer B)

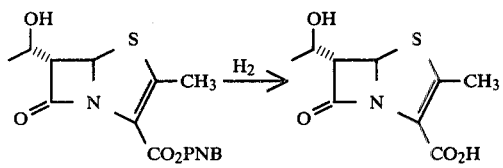

A mixture of (1', 5R, 6S and 1'S,5S,6R) paranitrobenzyl 6-(1'-hydroxy-1'-ethyl)-2-methylpenem-3-carboxylate (89 mg, 0.244 mmol), THF-H$_2$O-ether (15 ml, 10 ml, 30 ml), a 0.05 M pH 7 buffer solution (5.06 ml, 0.253 mmol) and 30% Pd on Celite (250 mg) was shaken on a Parr hydrogenator for 3.5 h at 45 psi H$_2$. A work-up identical to the one previously described gave title compound (32 mg, 57%).

EXAMPLE 61

(1'S,5R,6R and 1'R,5S,6S) 6-(1'-Hydroxy-1'-ethyl)-2-methylpenem-3-carboxylic Acid (isomer A)

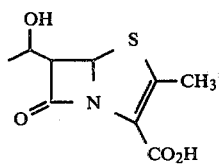

(1) (1'S,3R,4R and 1'R,3S,4S)
4-Acetylthio-3-(1'-methoxymethoxy-1'-ethyl)-1-(paranitrobenzyl 2"-triphenylphosphoranylidene-2"-acetate)-2-azetidinone (isomer A)

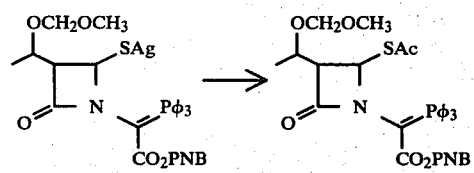

Isomer A of 4-acetylthio-3-(1'-methoxymethoxy-1'-ethyl)-1-(paranitrobenzyl-2"-triphenylphosphoranylidene-2"-acetate)-2-azetidinone was prepared as described elsewhere for isomer C of the paranitrobenzyl dioxycarbonyl derivative, yield 85%. ir (neat) $\nu_{max}$: 1750 and 1690 cm$^{-1}$ (C=O).

(2) (1'S,3R,4S and 1'R,3S,4S)
4-Acetylthio-3-(1'-hydroxy-1'-ethyl)-1-(paranitrobenzyl 2"-triphenylphosphoranylidene-2"-acetate)-2-azetidinone, (isomer A)

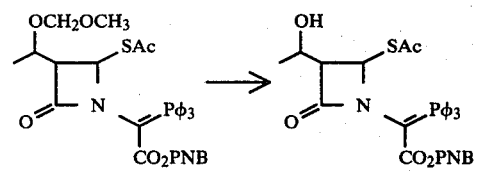

Isomer A of 4-acetylthio-3-(1'-methoxymethoxy-1'-ethyl)-1-(paranitrobenzyl-2"-triphenylphosphoranylidene-2"-acetate)- 2-azetidinone (500 mg, 0.68 mmol) was added to a cooled solution (0° C.) of trifluoroacetic acid (50 ml) and water (10 ml) and stirred for 15 min in ice and 3 h at room temperature. The reaction mixture was concentrated, dichloromethane was added and the solution was washed with sodium bicarbonate, water, and brine, dried and concentrated to give the title compound (450 mg, 96%); ir (neat) $\delta_{max}$: 3400 (OH), 1745 and 1690 cm$^{-1}$ (C=O).

(3) (1'S,5R,6R and 1'R,5S,6S) Paranitrobenzyl 6-(1'-hydroxy-1'-ethyl)-2-methyl penem-3-carboxylate (isomer A).

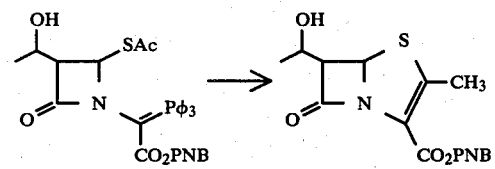

Prepared as described for isomer C of the paranitrobenzyl dioxycarbonyl derivative, yield 45%, $^1$Hmr (CDCl$_3$) δ: 7.93 (4H, ABq, aromatics), 5.68 (1H, d, J=4.0, H-5), 5.33 (2H, ABq, benzyl), 4.3 (1H, m, H-1'), 3.8 (1H, dd, J=4.0, H-6), 2.41 (3H, s, CH$_3$), 2.31 (1H, s, OH), and 1.42 ppm (3H, d, J=6, CH$_3$); ir (CHCl$_3$) $\nu_{max}$: 3100–3600 (OH), 1780 and 1710 cm$^{-1}$ (C=O).

(4) (1'S,5R,6R and 1'R,5S,6S)
6-(1'-Hydroxy-1'-ethyl)-2-methyl penem-3-carboxylic acid (isomer A)

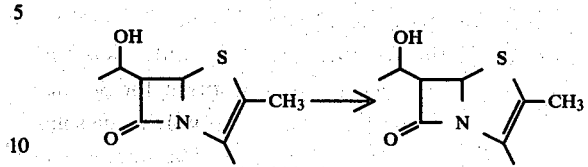

A mixture of isomer A of paranitrobenzyl 6-(1'-hydroxy-1'-ethyl)-2-methyl penem-3-carboxylate (82 mg, 0.2 mmol), palladium on Celite (30%, 400 mg), THF (10 ml), ether (25 ml), water (10 ml) and buffer (0.05 M, pH=7, Fisher #SO-B-108) (4 ml) was hydrogenated on a Parr shaker at an initial hydrogen pressure of 45 psi for 4 h. The catalyst was removed by filtration on Celite and washed with water. The filtrates were washed with ether and the aqueous layer was acidified with the cold hydrochloric acid (0.25 M) and extracted with ethyl acetate (5×10 ml.). The combined organic extracted were washed with brine, dried and concentrated. The foamy solid was triturated in ether to give a white solid (20 mg, 44%). ir (nujol) $\nu_{max}$: 3500 (OH), 1765 and 1665 cm$^{-1}$ (C=O); uv (EtOH) $\lambda_{max}$: 301 (ε 5922), 260 (ε4280).

EXAMPLE 62

(1'R,5R,6S and 1'S,5S,6R)
2-Aminomethyl-6-(1'-hydroxy-1'-ethyl)-penem-3-carboxylic Acid (isomer B)

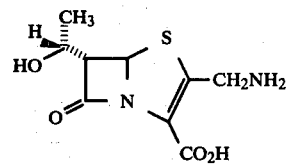

(1'R,3S,4R and 1'S,3R,4S)
4-azidoacetylthio-3-(1'-hydroxy-1'ethyl)-1-(paranitrobenzyl 2"-triphenylphosphoranylidene-2"-acetate)-2-azetidinone (isomer B)

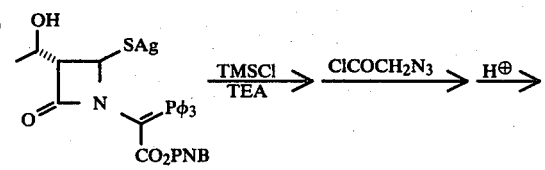

A cold (ice-MeOH bath) suspension of (1'R,3S,4R and 1'S,3R,4S) silver 3-(1'-hydroxy-1'-ethyl)-1-(paranitrobenzyl 2"-triphenyl phosphoranylidene-2"-acetate)-2-azetidinone-4-thiolate (970 mg, 1.37 mmol, from 1 g of the corresponding trityl) in THF (40 ml) was treated dropwise with trimethylchlorosilane (0.695 ml, 595 mg, 5.48 mmol), triethyl amine (0.765 ml, 555 mg, 5.49 mmol) and imidazole (50 mg, 0.734 mmol). The mixture was stirred under $N_2$ for 17 h, then cooled to $-15°$ C. (ice-MeOH bath) and azidoacetyl chloride (406 mg, 3.40 mmol) was added in. It was stirred for 30 min (reaction progression being followed by tlc). The solid was filtered and washed with ether. The filtrate was diluted with more ether, washed with 1% aqueous HCL, water, 1% aqueous $NaHCO_3$, water and brine and dried ($MgSO_4$). The residue upon solvent evaporation was taken up in moist $CH_2Cl_2$ (50 ml) and treated with TFA (3 drops, cleavage of TMS-ether being followed by tlc). The methylene chloride solution was then washed with 1% aqueous $NaHCO_3$, water and brine and dried ($MgSO_4$). The residue was passed through a silica gel (8 times its weight) column (benzene-ether 1:1, ether and ethylacetate-ether 1:1) to give the title compound (565 mg, 69.8%); ir (film) $v_{max}$: 3500–3200 (O—H), 2100 ($N_3$), 1755, 1609 (C=O), 1620–1605 (phosphorane) and 1518 cm$^{-1}$ ($NO_2$).

(1'R,5R,6S and 1'S,5S,6R) paranitrobenzyl 2-azidomethyl-6-(1'-hydroxy-1'-ethyl)-penem-3-carboxylate (isomer B)

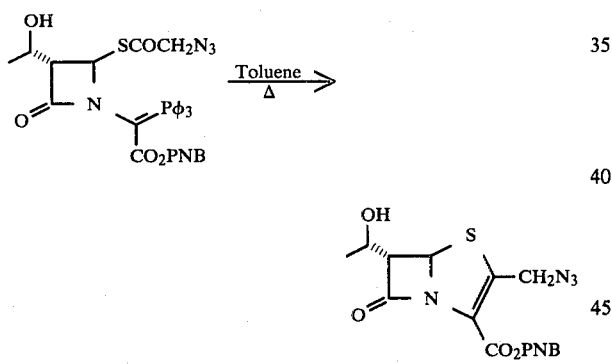

A solution of (1'R,3S,4R and 1'S,3R, 4S) 4-azidoacetylthio-3-(1'-hydroxy-1'-ethyl)-1-(paranitrobenzyl 2''-triphenylphosphoranylidene-2''-acetate)-2-azetidinone (500 mg, 0.731 mmol) in toluene 100 ml was refluxed under $N_2$ for 30 min. The solution was concentrated under vacuum and the residue was passed through a silica gel (5 g) column (3.5–4% ether-benzene) and yielded the title compound (193 mg, 65.1%) as a yellowish solid $^1$Hmr (CDCl$_3$) δ: 8.13 (2H, d, Ho aromatic), 7.52 (2H, d, Hm aromatic), 5.59 (1H, d, J=1.8, H-5), 5.27 (2H, center of ABq, J=13.5, $CH_2$-PNB), 4.50 (2H, center of ABq, J=16, $CH_2$—$N_3$), 4.15 (1H, m, H-1'), 3.73 (1H, dd, J=6.3, J=1.8, H-6), 1.92 (1H, d, J=4, O-H) and 1.33 ppm (3H, d, J=6.3 $CH_3$); ir (CHCl$_3$) $v_{max}$: 2110 ($N_3$), 1785, 1705 (C=O) and 1520 cm$^{-1}$ ($NO_2$).

(1'R,5R,6S and 1'S,5S,6R) 2-aminomethyl-6-(1'-hydroxy-1'-ethyl)-penem-3-carobxylic acid (isomer B)

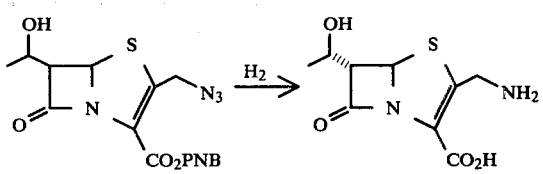

A solution of (1'R,5R,6S and 1'S,5S,6R) paranitrobenzyl 2-azidomethyl-6-(1'-hydroxy-1'-ethyl)-penem-3-carboxylate (25 mg, 0.062 mmol) in THF-ether-water (6 ml, 6 ml, 15 ml) was shaken on a Parr hydrogenator for 2.5 h at 40 psi $H_2$ using 10% Pd on carbon (100 mg). The catalyst was filtered and washed with small volumes of water. The aqueous layer was washed with ether (3 times) and lyophilized to give the title compound (11 mg, 73%). $^1$Hmr (D$_2$O) δ: 5.75 (1H, d, J=2, H-5), 4.30 (1H, center of m, J=6.5, H-1'), 4.02 (1H, dd, J=6.5, J=2, H-6) and 1.37 ppm (3H, d, J=6.5, $CH_3$); ir (nujol mull) $v_{max}$: 3550–2450 (O—H, N—H), 1765 (C=O) and 1600 cm$^{-1}$ ($CO_2^\ominus$); uv (H$_2$O), $\lambda_{max}$: 309 (ε 3650), 255 (ε 2815).

EXAMPLE 63

(1'S,5R,6S and 1'R,5S,6R) Paranitrobenzyl 2-azidomethyl-6-(1'-hydroxy-1'-ethyl)-penem-3-carboxylate (isomer C)

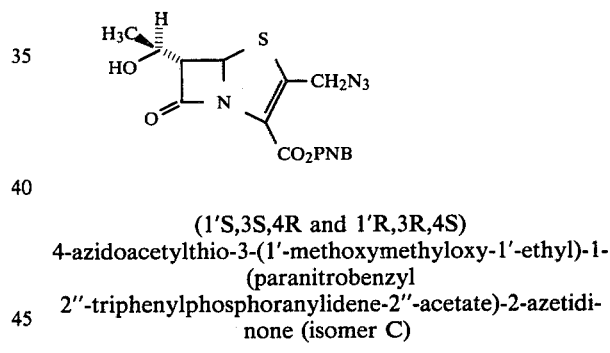

(1'S,3S,4R and 1'R,3R,4S) 4-azidoacetylthio-3-(1'-methoxymethyloxy-1'-ethyl)-1-(paranitrobenzyl 2''-triphenylphosphoranylidene-2''-acetate)-2-azetidinone (isomer C)

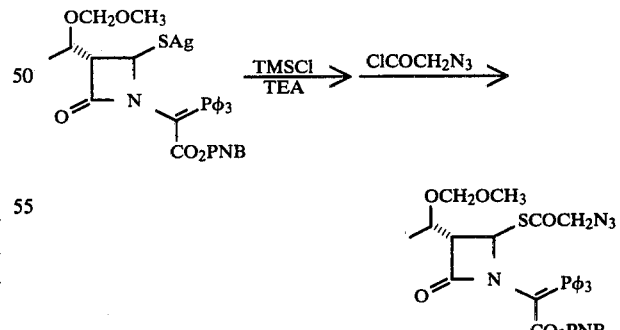

A cold (ice-MeOH bath) THF (10 ml, distilled over LAH) suspension of (1'S,3S,4R and 1'R,3R,4S) silver 3-(1'-methoxymethyloxy-1'-ethyl)-1-(paranitrobenzyl 2''-triphenylphosphoranylidene-2''-acetate)-2-azetidinone-4-thiolate (250 mg, 0.33 mmol) was treated successively with triethyl amine (83 mg, 0.115 ml, 0.825 mmol), trimethylchlorosilane (90 mg, 0.104 ml, 0.825 mmol) and imidazole 20 mg, 0.294 mmol). The mixture was stirred at room temperature for 17 h, cooled (ice-MeOH bath) and treated with azidoacetylchloride (70 mg, 0.59 mmol). The reaction mixture was stirred for 20 min, diluted with ether, washed with 2% aqueous HCl, water, 5% aqueous NaHCO₃, water and brine and dried (MgSO₄). The residue was concentrated on the rotary evaporator and filtered through a silica gel (1 to 10 ratio) column (103 mg, 44%); ir (nujol) $v_{max}$: 2100 (N₃), 1755, 1690 (C=O), 1620, 1605 (phosphorane) and 1515 cm⁻¹ (NO₂).

(1'S,3S,4R and 1'R,3R,4S)
4-azidoacetylthio-3-(1'-hydroxy-1'-ethyl)-1-(paranitrobenzyl
2''-triphenylphosphoranylidene-2''-acetate)-2-azetidinone (isomer C)

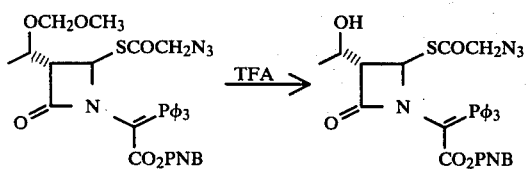

A cold (ice bath) mixture of (1'S,3S,4R and 1'R,3R,4S) 4-azidoacetylthio-3-(1'-methoxymethyloxy-1'-ethyl)-1-(paranitrobenzyl 2''-triphenylphosphoranylidene-2''-acetate)-2-azetidinone (293 mg, 0.416 mmol) and 15% H₂O in TFA (6 ml) was stirred for 20 min. The ice bath was removed and the solution was stirred for 2 h. TFA was removed under a vacuum and the residue was diluted with ether and ethyl acetate. It was washed with water, 10% aqueous NaHCO₃, water and brine and dried (MgSO₄) to afford pure title compound* (251 mg, 88.4%) ir (CHCl₃) 3600—3200 (O—H), 2105 (N₃), 1750-1690 (C=O), 1625, 1605 (phosphorane and 1520 cm⁻¹ (NO₂).

*Alternatively the title compound could be made from (1'S,3S,4R and 1'R,3R,4S) silver 3-(1'-hydroxy-1'-ethyl)-1-(paranitrobenzyl 2''-triphenylphosphoranylidene-2''-acetate)-2-azetidinone-4-thiolate according to the procedure described for the synthesis of the corresponding isomer B.

(1'S,5R,6S and 1'R,5S,6R) paranitrobenzyl
2-azidomethyl-6-(1'-hydroxy-1'-ethyl)
penem-3-carboxylate (Isomer C)

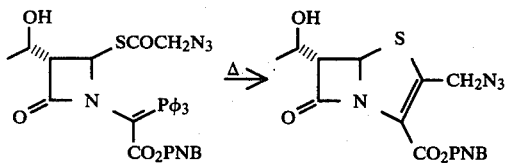

A solution of (1'S,3S,4R and 1'R,3R,4S) 4-azidoacetylthio-3-(1'-hydroxy-1'-ethyl)-1-(paranitrobenzyl 2''-triphenylphosphoranylidene-2''-acetate)-2-azetidinone (116 mg, 0.170 mmol) in toluene (30 ml) was heated under reflux for 30 min. The toluene was concentrated and the residue was filtered on silica gel (1 to 10 ratio) to give the title compound (23 mg, 34%); ir (CHCl₃) $v_{max}$: 3700-3200 (O—H), 2105 (N₃), 1785, 1710 (C=O) and 1525 cm⁻¹ (NO₂); ¹Hmr (CDCl₃) δ: 8.26 (2H, d, J=9, Hm aromatic), 7.62 (2H, d, J=9, Ho aromatic), 5.65 (1H, d, J=2, H-5), 5.35 (2H, center of ABq, J=14, CH₂—PNB, 4.59 (2H, center of ABq, J=16, CH₂—N₃), 4.4–4.1 (1H, m, H-1'), 3.92 (1H, dd, J=4, J=2, H-6), 2.17 (1H, 6s, O—H) and 1.42 ppm (3H, d, J=6, CH₃).

EXAMPLE 64

(1'R,5R,6S and
1'S,5S,6R)-2-(4-Aminobutyl)-6-(1'-hydroxy-ethyl)-penem-3-carboxylic Acid (isomer B)

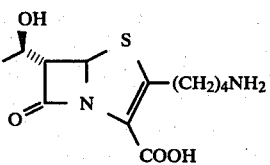

(1'R,3S,5R and 1'S,3R,4S)
4-(δ-azidobutanoylthio)-3-(1'-hydroxyethyl)-1-(paranitrobenzyl
2''-triphenylphosphoranylidene-2''-acetate)-2-azetidinone

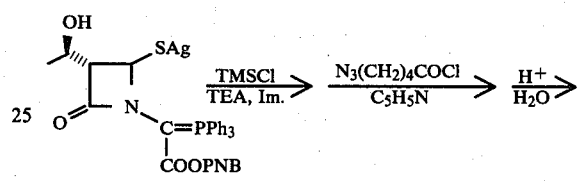

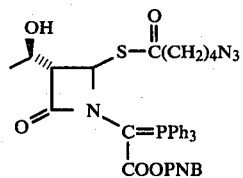

A solution of (1'R,3S,4R and 1'S,3R,4S) silver 3-(1'-hydroxyethyl)-1-(paranitrobenzyl 2''-triphenylphosphoranylidene-2''-acetate)-2-azetidinone-4-thiolate (3.03 g, 4.28 mmol) in dry THF (55 ml) kept under a nitrogen atmosphere was cooled to −25° C. and successively treated with triethylamine (2.39 ml, 17.12 mmol), trimethylchlorosilane (2.18 ml, 17.12 mmol) and imidazole (0.10 g, 1.47 mmol). The reaction mixture was stirred at −25° C. for 0.25 h, the cooling bath was removed, and the stirring was continued for 16 h. The reaction mixture was cooled to 0° C. and diluted with CH₂Cl₂ (55 ml); it was then treated succesively with pyridine (0.73 ml, 9.0 mmol) and with a solution of 4-aminobutanoyl chloride (1.36 g, 8.56 mmol) in CH₂Cl₂ (10 ml). The reaction mixture was stirred at 0° C. for 1 h and filtered through a Celite pad. The pad was washed with CH₂Cl₂ (25 ml); the filtrate and washings were combined and diluted with EtOAc (300 ml). The organic solution was washed with 1 N HCl solution, H₂O, saturated NaHCO₃ solution and H₂O, dried over anhydrous MgSO₄ and concentrated on a rotary evaporator to an orange syrup (3.83 g). The syrup was dissolved in CH₂Cl₂ (75 ml) and water (4 ml) and TFA (0.2 ml) were added; the reaction mixture was stirred at 23° C. for 1.5 h, washed with NaHCO₃ and H₂O, dried over anhydrous Na₂SO₄ and concentrated to an orange syrup (3.4 g). Purification of the syrup was achieved by a column chromatography (silica gel G 60, 80 g; eluent-:ETOAc in CH₂Cl₂ 10%→75%). Evaporation of the appropriate fractions gave an oil; 2.14 g, 67.7%. Anal. calcd for C₃₇H₃₆N₅O₇SP: C 61.23, H 5.00, N 9.65, S 4.42; found: C 61.17, H 5.10, N 10.02, S 3.71.

(1'R,5R,6S and 1'S,5S,6R) paranitrobenzyl 2-(δ-azidobutyl)-6-(1'-hydroxyethyl)-penem-3-carboxylate

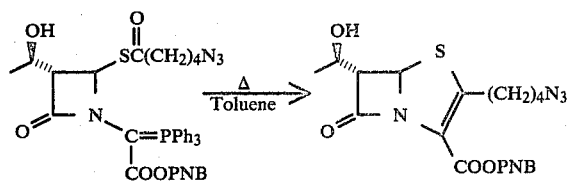

A solution of (1'R,3S,4R and 1'S,3R,4S) 4-(δ-azidobutanoylthio)-3-(1'-hydroxy-1'-ethyl)-1-(paranitrobenzyl-2''-triphenylphosphoranylidene-2''-acetate)-2-azetidinone (2.04 g, 2.81 mmol) in a toluene-CH$_2$Cl$_2$ mixture (30:1, 310 ml) was refluxed for 9 h under a nitrogen atmosphere (The CH$_2$Cl$_2$ was removed at the beginning of reflux). The reaction mixture was cooled to 23° C. and the toluene was removed in vacuo leaving an orange residue which was purified by column chromatography (silica gel 60, 45 g; eluent, ether in pet. ether, 1:1→9:1). The appropriate fractions were combined and concentrated to a syrup which was crystallized from an ether-pet.ether mixture, 0.443 g, mp 85° C., 35.2%. Anal. calcd for C$_{19}$H$_{21}$N$_5$O$_6$S: C 51.00, H 4.73, N 15.65, S 7.17; found: C 51.05, H 4.86, N 15.86, S 7.19. The fractions corresponding to unreacted starting material were cyclized as described above to give an additional quantity (0.276 mg, 21.9%) of title compound. $\nu_{max}$: 2100 (N$_3$), 1770 (C=O, β-lactam) and 1705 cm$^{-1}$ (C=O, PNB ester); uv (H$_2$O 23° C.) $\lambda_{max}$: 268 (ε 13757), 316 (ε 9826). $^1$Hmr (CDCl$_3$) δ: 1.36 (d, $J_{H-2''-H-1''}$=6.3 Hz, 3H, methyl), 1.52-1.77 (m, 4H, H-2', H-3'), 2.57-3.00 (m, 2H, H-4'), 3.00-3.42 (m, 2H, H-1'), 3.72 (dd, $J_{H-6-H-5}$=1.6 Hz, $J_{H-6-H-1''}$=6.4 Hz, H-6), 4.02-4.42 (m, 1H, H-1''), 5.32 (ABq, $J_{a-b}$=13.6 Hz, 2H, CH$_2$ of PNB ester), 5.60 (d, $J_{H-5-H-6}$=1.6 Hz, 1H,H-5), 7.61 (d, $J_{Hm-Ho}$=8.8 Hz, 2H, Hm of PNB ester) and 8.21 ppm (d, $J_{Ho-Hm}$=8.8 Hz, 2H, Ho of PNB ester).

(1'R,5R,6S and 1'S,5S,6R) 2-(4-aminobutyl)-6-(1'-hydroxyethyl)-penem-3-carboxylic acid

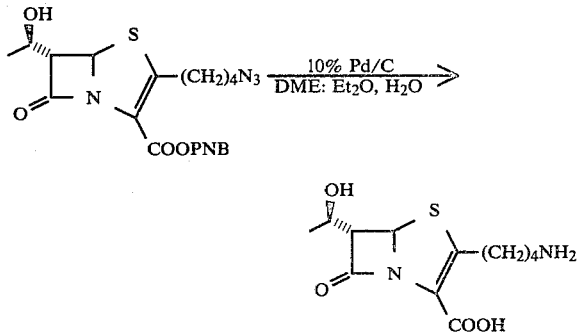

To a solution of (1'R,5R,6S and 1'S,5S,6R) paranitrobenzyl 2-(δ-azidobutyl)-6-(1'-hydroxyethyl)-penem-3-carboxylate (0.54 g, 1.21 mmol) in dimethoxyethane (50 ml) was added ether (50 ml), water (50 ml) and 10% Palladium on charcoal (0.54 g). The reaction mixture was hydrogenated under 45 psi of hydrogen at 23° C. for 3 h. The reaction mixture was filtered over a Celite pad and the filtrate was diluted with ether. The aqueous phase was separated, washed with ether and lyophylized. The crude title compound was purified by hplc. ir (KBr) $\nu_{max}$: 1760 (C=O, β-lactam) and 1565 cm$^{-1}$ (C—O, carboxylate); $^1$Hmr (D$_2$O) δ: 1.32 (d, $J_{CH_3-H-1''}$=6.4 Hz, 3H, CH$_3$), 1.45-1.85 (m, 4H, H-1',H-3'), 2.50-3.20 (m, 4H, H-1', H-4'), 3.84 (dd, $J_{H-6-H-1''}$=6.1 Hz, $J_{H-6-H-5}$=1.4 Hz, 1-H, H-b 6), 4.00-4.45 (m, 1H, H-1''- and 5.62 ppm (d, $J_{H-5-H-6}$=1.4 Hz, 1H, H-5); uv (H$_2$O) $\lambda_{max}$: 260 (ε 4240), 302 (ε 5480).

EXAMPLE 65

(1''R,5R,6S and 1'S,5S,6R)-2-(trans-3'-Amino-1'-cyclobutyl)-6-(1''-hydroxy-1''-ethyl)penem-3-carboxylic Acid (isomer B)

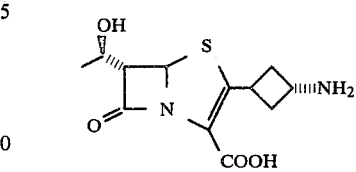

(1''R,3S,4R and 1''S,3R,4S) 4-(trans-3'-azidocyclobutanoylthio)-3-(1''-hydroxy-1''-ethyl)-1-(paranitrobenzyl 2'''-triphenylphosphoranylidene-2'''-acetate)-2-azetidinone

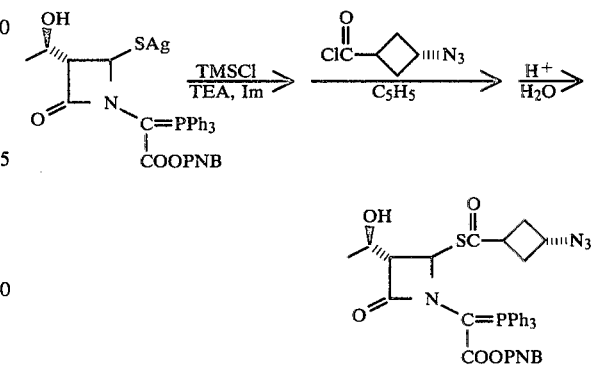

A solution of (1'R,3S,4R and 1'S,3R,4S) silver 3-(1'-hydroxyethyl)-1-(paranitrobenzyl 2''-triphenylphosphoranylidene-2''-acetate)-2-azetidinone-4-thiolate (1.01 g, 1.43 mmol) in dry THF (25 ml), kept under a nitrogen atmosphere, was cooled to −40° C. and successively treated with triethylamine (0.80 ml, 5.74 mmol) trimethylchlorosilane (0.726 ml, 5.72 mmol) and imidazole (0.10 g, 1.47 mmol). The reaction mixture was warmed to −15° C., stirred for 3 h, the cooling bath was removed and the stirring was continued for 18 h. The reaction mixture was cooled to −15° C. and diluted with CH$_2$Cl$_2$ (25 ml); it was then treated with pyridine (0.15 ml, 1.85 mmol) and trans-3-azidocyclobutanoylchloride (0.274 g, 1.72 mmol). The cooling bath was removed and the solution was stirred for 1 h and treated with pyridine (0.15 ml, 1.85 mmol) and trans-3-azidocyclobutanoylchloride (0.274 g, 1.72 mmol). The reaction mixture was stirred at 23° C. for 1 h and filtered through a Celite pad. The filtrate was diluted with EtOAc (100 ml) and washed with 1 N HCl,H$_2$O, saturated NaHCO$_3$ solution and H$_2$O, dried over anhydrous MgSO$_4$ and concentrated on a rotary evaporator to an orange syrup (1.47 g). To a solution of the syrup in CH$_2$Cl$_2$ (50 ml) was added H$_2$O (2 ml) and TFA (0.2 ml). The reaction mixture was stirred at 23° C. for 2 h, washed with saturated NaHCO₃ solution and H₂O, dried over anhydrous Na₂SO₄ and concentrated to an orange syrup (1.1 g). Purification of the syrup was achieved by column chromatography (silica gel 60, 20 g; eluent EtOAc-ether 35%→70%). Evaporation of the appropriate fractions gave the title compound as an oil; 0.77 g, 74.4% ir (neat) $\nu_{max}$: 3440 (OH), 2100 (N₃), 1755 (C=O β-lactam), 1735 (C=O), 1680 (C=O)and 1625 cm⁻¹ (aromatics).

(1″R,5R,6S and 1″S,5S,6R) paranitrobenzyl 2-(trans-3′-azidocyclobutyl)-6-(1″-hydroxy-1″-ethyl)-penem-3-carboxylate

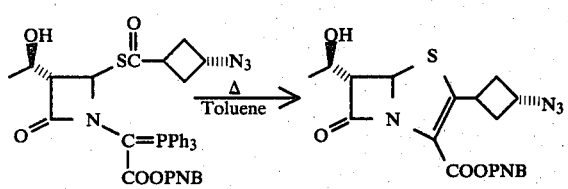

A solution of (1″R,3S,4R and 1″S,3R,4S) 4-trans-3′-azidocyclobutanoylthio)-3-(1″-hydroxy-1″-ethyl)-1-(paranitrobenzyl-2‴-triphenylphosphoranylidene-2‴-acetate)-2-axetidinone (2.27 g, 3.14 mmol) in CHCl₃ (40 ml) was diluted with toluene (300 ml) and refluxed under a nitrogen atmosphere for 6 h. The first 60 ml of solution (CHCl₃+toluene) were removed with a Dean-Stark trapp. The reaction mixture was cooled to 23° C. and the solvent was evaporated under a reduced pressure leaving an orange syrup which was purified by a silica gel column (silica gel 60, 35 g, eluent, ether-benzene, 0→6%). Evaporation of the appropriate fractions gave the title compound, 0.38 g, mp 134°-5° C., 27.3%. Anal calcd for C₁₉H₁₉N₅O₆S: C 51.24, H 4.30, N 15.73, S 7.20; found: C 50.98, H 4.20, N 15.83, S 7.10; ir (KBr) $\nu_{max}$: 2110 (N₃), 1765 C=O β-lactam), 1690 (C=O PNB ester), 1510 (NO₂) and 1355 cm⁻¹ (NO₂); ¹Hmr (CDCl₃) δ:1.36 (d, $J_{CH_3-H-1''}$=6.3 Hz, 3H, CH₃), 2.0-2.75 (m, 4H, H-2′, H-4′), 3.67 (dd, $J_{H-6-H-5}$=1.5 Hz, $J_{H-6-H-1''}$=6.5 Hz, 1H, H-6), 3.8-4.55 (m, 3H, H-1′, H-3′and H-1″-, 5.30 (ABq, $J_{a-b}$=13.6 Hz, 2H, C$\underline{H}_2$-Ph-NO₂), 5.60 (d, $J_{H-5-H-6}$=1.5 Hz, 1H, H-5), 7.59 (d, $J_{Ho-Hm}$=8.8 Hz, 2H, H-m of PNB) and 8.20 (d, $J_{Hm-Ho}$=8.8 Hz, 2H, H—O of PNB). uv (CHCl₃, 23° C.) $\lambda_{max}$: 266 (ε 13050) and 322 ppm (ε 10008). The unreacted phosphorane was recovered mixed with Ph₃P-O and cyclized as described before to give an additional quantity of title compound: 0.145 g, 10.4% for a total yield of 37.7%.

(1″R,5R,6S and 1″S,5S,6R)-2-(trans-3′-amino-1′-cyclobutyl(-6-(1″-hydroxyethyl)penem-3-carboxylic acid

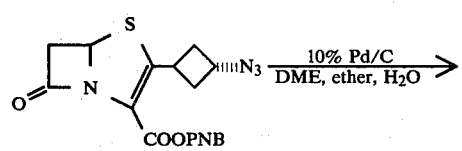

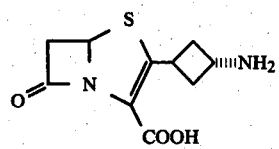

To a solution of (1″R,5R,6S and 1″S,5S,6R) paranitrobenzyl 2-(trans-3′-azidocyclobutyl)-6-(1″-hydroxyethyl)-penem-3-carboxylate (0.33 g, 0.74 mmol) in dimethoxyethane (40 ml) was added ether (40 ml) and 10% Palladium on charcoal (0.33 g). The reaction mixture was hydrogenated under 45 psi of H₂ for 3 h and filtered over a Celite pad. The pad was washed with water and the filtrate and washings were combined and diluted with ether. The aqueous phase was separated, washed with ether and lyophylized, 0.20 g, 95%, uv (H₂O, 23° C.) $\lambda_{max}$: 258 (ε 2725) and 306 (ε 3613). The crude material was triturated with water and the white solid was filtered and dried over P₂O₅ under high vacuum for 5 h, 84 mg, 40%; ¹Hmr (D₂O) δ: 1.34 (d, $J_{H-2''-H-1''}$=6.3 Hz, 3H, H-2″-, 2.3-2.7 (m, 4H, H-2′, H-4′), 3.90 (dd, $J_{H-6-H-5}$=1.5 Hz, $J_{H-6-H-1''}$=6.1 Hz, 1H, H-6) and 5.68 (d, $J_{H-5-H-6}$=1.5 Hz, 1H, H-5); uv (H₂O, 23° C.) $\lambda_{max}$: 258 (ε 4738) and 306 (ε 6318). The filtrate was purified by hplc, 58 mg; uv (H₂O, 23° C.) $\lambda_{max}$: 257 (ε 3580) and 306 (ε 5033).

EXAMPLE 66

(1′R,5R,6S and 1′S,5S,6R) 6-(1′-Hydroxyethyl)-2-(2-aminoethoxymethyl)penem-3-carboxylic Acid (isomer B)

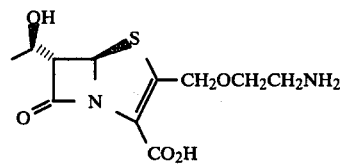

(1′R,3S,4R and 1′S,3R,4S) 4-(2-Azidoethoxy)acethylthio-3-(1′-hydroxyethyl)-1-(p-nitrobenzyl 2″-triphenylphosphoranylidene-2″-acetate)-2-azetidinone (Isomer B)

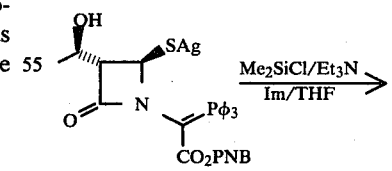

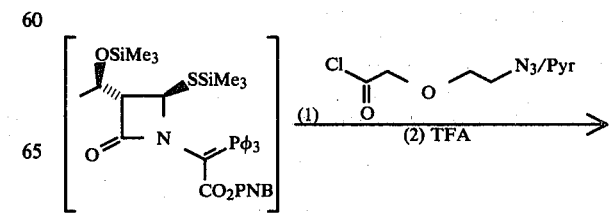

-continued

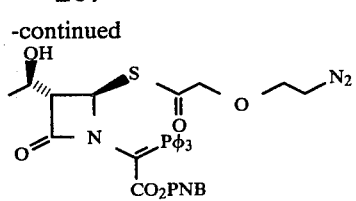

To a stirred solution of (1'R,3S,4R and 1'S,3R,4S) silver 3-(1'-hydroxyethyl)-1-(p-nitrobenzyl 2''-triphenylphosphoranylidene-2''-acetate)-2-azetidinone-4-thiolate (Isomer B) (820 mg, 1.16 mmol) in THF (20 ml) was added at −15° (MeOH-ice bath) under $N_2$ atmosphere successively triethylamine (01648 ml, 4.66 mmol, 4.02 eq), chlorotrimethyl silane (0.589 ml, 4.64 mmol, 4.00 eq) and imidazole (81.2 mg, 1.12 mmol). The mixture was stirred at room temperature for 18 h (overnight) and then cooled to −10∼−15°. To this was added pyridine (0.220 ml, 2.72 mmol) and then a solution of 2-azidoethoxyacetyl chloride (372 mg, 2.27 mmol, 1.96 eq) in $CH_2Cl_2$ (20 ml). It was stirred at room temperature for 1 h. After filtration of the precipitate, the filtrate, diluted with EtOAc, was washed successively with 1 N HCl, brine, saturated $NaHCO_3$ and brine, dried ($Na_2SO_4$) and evaporated yielding 748 mg an oil. This oil dissolved in wet $CH_2Cl_2$ (20 ml with 3 drops of water) was treated with trifluoroacetic acid (2 drops) at room temperature for 30 min. The mixture was washed with saturated $NaHCO_3$ and then brine, dried ($Na_2SO_4$) and evaporated yielding 695 mg of a crude oil. This oil was purified by column chromatography ($SiO_2$ 15 g, eluent EtOAc: $CH_2Cl_2$=1:1) collecting 538 mg (0.739 mmol, yield 63.7%) of the title compound as a yellowish oil: $^1$Hmr ($CDCl_3$) δ: 1.22 (d, J=6Hz, $CH_3$-1'), 5.6 (2d, H-4) and 7.3=8.4 ppm (aromatic Hs); ir (neat) $\nu_{max}$: 3420 (OH), 2100 (—$N_3$), 1750 (C=O) and 1690 cm$^{-1}$ (thioester); Rf 0.20 ($CH_2Cl_2$:EtOAc=1:1).

(1'R,5R,6S and 1'S,5S,6R) p-Nitrobenzyl 6-(1'-hydroxyethyl)-2-(2-azidoethoxymethyl)penem-3-carboxylate (Isomer B)

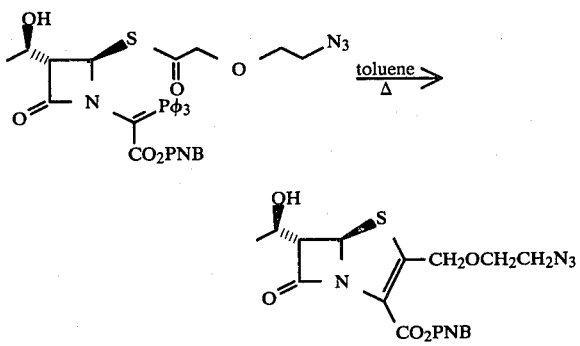

A solution of (1'R,3S,4R and 1'S,3R,4S) 4-(2-azidoethoxy) acetylthio-3-(1'-hydroxyethyl)-1-(p-nitrobenzyl 2''-triphenylphosphoranylidene-2''-acetate)-2-azetidinone, (Isomer B) (490 mg, 0.673 mmol) in toluene (80 ml) was heated at gentle reflux for 3 h. Evaporation of the solvent in vacuo gave an oily residue which was purified by column chromatography ($SiO_2$, 10 g; eluent 5–10% EtOAc in $CH_2Cl_2$) followed by crystallization from $CH_2Cl_2$-ether to obtain 202 mg (0.449 mmol, yield 66.8%) of the title compound as light yellow crystals: $^1$Hmr ($CDCl_3$) δ: 1.35 (3H, d, J=6.5Hz, $CH_3$-1'), 2.18 (1H, br, OH), 3.2–3.9 (5H, m, —$CH_2$—and H-6), 3.9–4.5 (1H, m, H-1'), 4.45–4.72–4.75–5.02 (2H, AB type, $CH_2$-2), 5.02–5.25–5.35–5.57 (2H, AB type, —$CH_2Ar$), 5.62 (1H, d, J=1Hz, H-5) and 7.42–7.65–8.13–8.28 ppm (4H, $A_2'B_2'$, aromatic Hs); ir (nujol) $\nu_{max}$: 3460 (—OH), 2110 (—$N_3$), 1765 (β-lactam) and 1680 cm$^{-1}$ (ester). An analytical sample was obtained by further crystallization: mp 107°–8° C. ($CH_2Cl_2$-ether uv (EtOH) $\lambda_{max}$: 264 (ε 12000) and 323 mμ(ε 9200); Rf 962 ($CH_2Cl_2$:EtOAc=1:1); Anal. calcd for $C_{18}H_{19}N_5O_7S$: C 48.10, H 4.26, N 15.88, S 7.13; found: C 47.81, H 4.18, N 15.00, S 7.16.

(1'R,5R,6S and 1'S,5S,6R) 6-1'-hydroxyethyl)-2-(2-azidoethoxymethyl)penem-3-carboxylic acid (Isomer B)

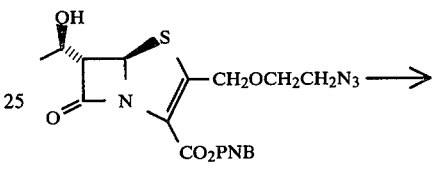

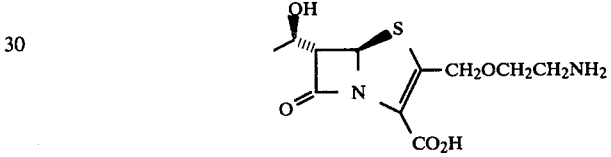

A solution of (1'R,5R,6S and 1'S,5S,6R) p-nitrobenzyl 6-(1'-hydroxyethyl)-2-(2-azidoethoxymethyl)-penem-3-carboxylate (Isomer B) (180 mg, 0.400 mmol) in THF (18 ml) was mixed with ether (19 ml), $H_2O$ (18 ml) and 10% Pd-C (180 mg). It was hydrogenated ($H_2$, 55 psi) at room temperature for 2.5 h. After filtering off the catalyst the aqueous filtrate was washed with EtOAc and lyophilized to yield 84.4 mg (0.293 mmol, crude yield 73.2%) of the title compound as a crude yellowish powder: uv ($H_2O$) $\lambda_{max}$: 305.5 (ε 4800) and 255 mμ(ε 3800). This powder was purified by hplc (Waters $C_{18}$ Micro Bondapack Reverse Phase 30 cm×10 mm; eluent 1% $CH_3CN$ in $H_2O$) to give 44.7 mg (0.155 mmol, yield 38.8%) of the title compound as white powder: $^1$Hmr ($D_2O$) δ: 1.34 (3H, d, J=6.4 Hz, $CH_3$-1'), 3.26 (2H, m, —$CH_2N$), 3.82 (2H, m, —O$\underline{CH_2}CH_2$—), 3.94 (1H, dd, $J_{6-1'}$=6.2 Hz, $J_{6-5}$=1.4 Hz, H-6), 4.2–4.4 (1H, m, H-1'), 4.52–4.70–4.84–5.02 (2H, AB type, $CH_2$-2) and 5.71 ppm (1H, d, J=1.3 Hz, H-5); ir (KBr disc) $\nu_{max}$: 3420 (OH), 3000–2600 (br, $CO_2H$), 1765 (β-lactam) and 1575 cm$^{-1}$ (—$CO_2H$); uv ($H_2O$) $\lambda_{max}$: 306 (ε 5300) and 258 mμ(ε 3600).

EXAMPLE 67

Following the general procedure of Example 58, the following 2,6-disubstituted penem compounds may be prepared using the indicated electrophiles.

| Product |
| --- |

-continued
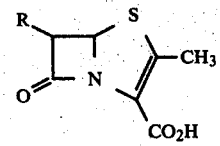
| Electrophile | R = |
|---|---|
| CH₃I | CH₃— |
|  | CH₃CH₂— |
| 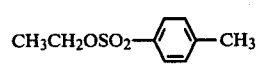 |  |
|  | CH₃CH₂CH₂— |
| 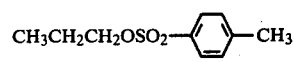 |  |
| CH₂=CH—CH₂—Br | CH₂=CHCH₂— |
| HC≡C—CH₂Br | HC≡CCH₂ |
|  |  |
| 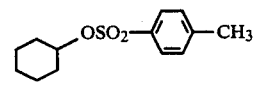 |  |
| φCH₂Br | φCH₂— |
| 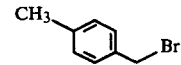 | 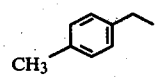 |
| φCH₂CH₂CH₂OSO₂—⟨⟩—CH₃ | 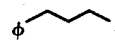 |
| φCH=CHCH₂Br |  |
| φC≡CCH₂Br | φC≡CCH₂— |
| 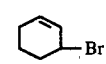 |  |
| Br<br>CH₃CH—CH₃ |  |
| CH₃OCH₂Cl | CH₃OCH₂— |
| CH₃SCH₂Cl | CH₃SCH₂—(a) |
| 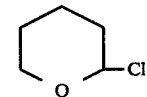 | 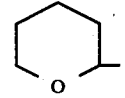 |
| CH₃OCH₂CH₂Cl | CH₃OCH₂CH₂— |
| CH₃SCH₂CH₂Cl | CH₃SCH₂CH₂—(b) |
| HCHO | HOCH₂—(c) |
| CH₃CH₂CHO | OH<br>CH₃CH₂CH—(c) |
|  | HOCH₂CH₂—(c) |
|  | OH<br>CH₃CH—CH₂—(c) |
|  | HSCH₂CH₂—(d)(e) |

-continued
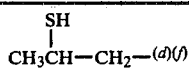
CH₃CH—CH₂—(d)(f)
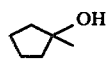
φOCH₂Cl
φCH₂OCH₂Cl
φOCH₂CH₂Cl
φCH₂OCH₂CH₂Cl
φSCH₂Cl
φCH₂SCH₂Cl
φSCH₂CH₂Cl
φCH₂SCH₂CH₂Cl
φOCH₂—
φCH₂OCH₂—
φOCH₂CH₂—
φCH₂OCH₂CH₂—
φSCH₂—(g)
φCH₂SCH₂—(h)
φSCH₂CH₂—(i)
φCH₂SCH₂CH₂—(j)
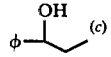
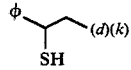
φCH₂CHO
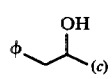
φCH=CH—CHO
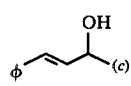
CH₃CH₂CO₂CH₃
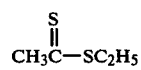
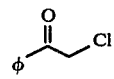
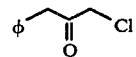
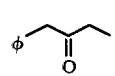
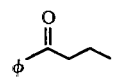
φCO₂CH₃
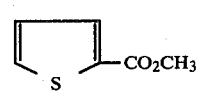
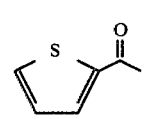
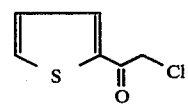
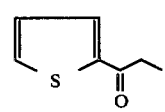
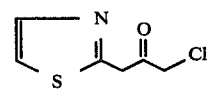
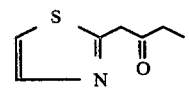

-continued
| | |
|---|---|
| φCH=CHCO$_2$CH$_3$ | 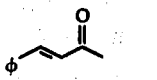 |
| φC≡C—CHO | 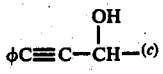 (c) |
| φC≡C—CO$_2$CH$_3$ | 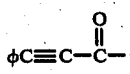 |
| φCHS |  (d) |
| 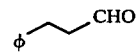 | 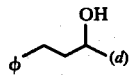 (d) |
| 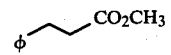 | 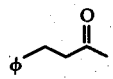 |
|  |  |
| 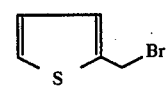 | 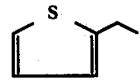 |
| 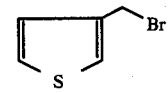 | 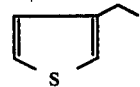 |
| 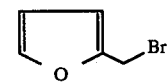 | 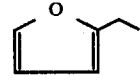 |
| 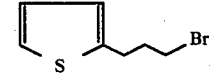 | 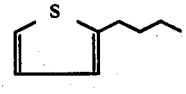 |
| 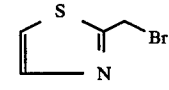 | 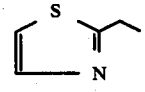 |
| 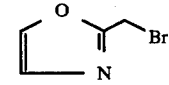 | 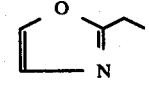 |
| 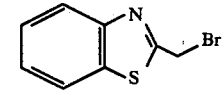 | 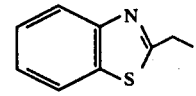 |
| 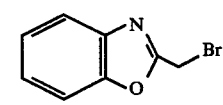 | 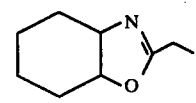 |
| 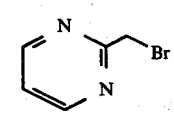 | 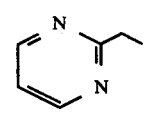 |

-continued

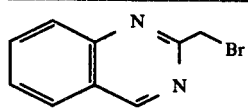    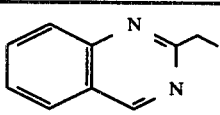

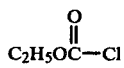    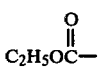

    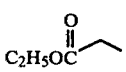

    

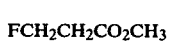

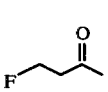

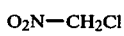    

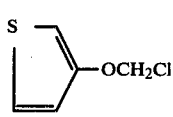    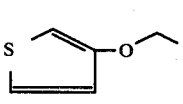

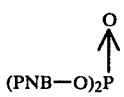

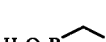

$CH_3CHO$

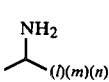

$\phi CH_2CHO$    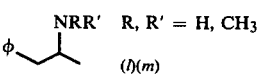  R, R' = H, $CH_3$   (l)(m)

    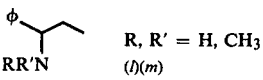  R, R' = H, $CH_3$   (l)(m)

$CH_3OCl$         $CH_3O-$

---

(a) may be oxidized to produce $CH_3\overset{\overset{O}{\uparrow}}{S}CH_2-$ and $CH_3\overset{\overset{O}{\uparrow}}{\underset{\downarrow}{S}}CH_2-$ (b) may be oxidized to produce $CH_3\overset{\overset{O}{\uparrow}}{S}CH_2CH_2-$ and $CH_3SO_2CH_2CH_2-$ (c) OH protected via $-\overset{\overset{O}{\|}}{C}-OPNB$ (d) SH protected $-\overset{\overset{O}{\|}}{C}-O-PNB$ (e) may be oxidized to produce $HO_3SCH_2CH_2-$ (f) may be oxidized to produce $CH_3CH-CH_2-$
$\qquad\qquad\qquad\qquad\qquad\qquad\quad |$
$\qquad\qquad\qquad\qquad\qquad\qquad SO_3H$ (g) may be oxidized to produce $\phi\overset{\overset{O}{\uparrow}}{S}CH_2$ and $\phi SO_2CH_2-$ -continued
(h) may be oxidized to produce φCH2SCH2— and φCH2SO2CH2—
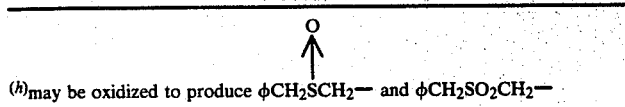
(i) may be oxidized to produce φSCH2CH— and φSO2CH2CH2—
(j) may be oxidized to produce φCH2SCH2CH2— and φCH2SO2CH2CH2—
(k) may be oxidized to produce
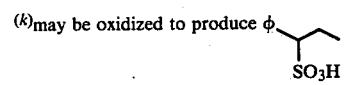
(l) via
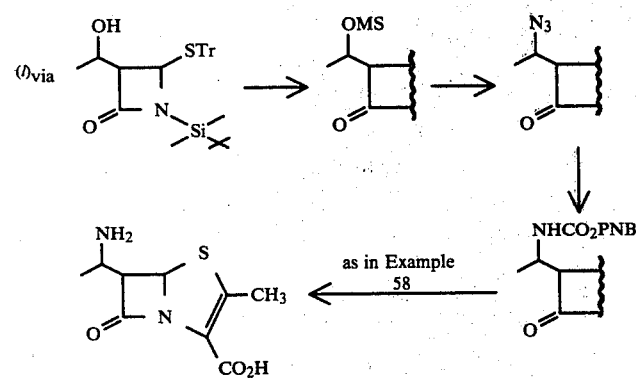
(m) Also,
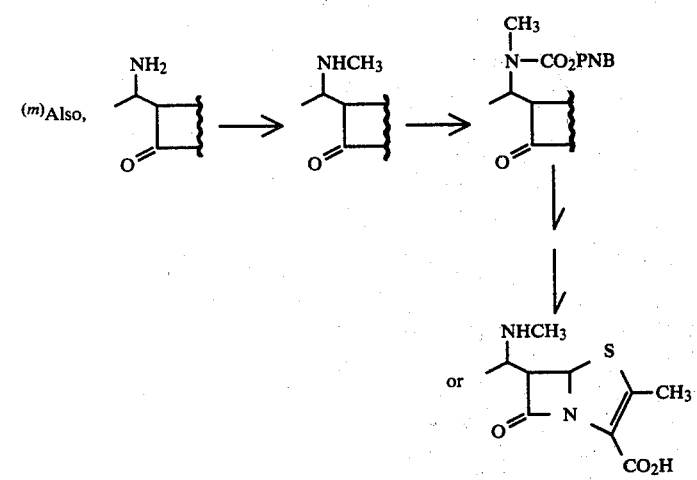
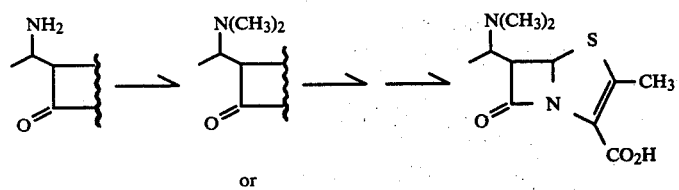
or
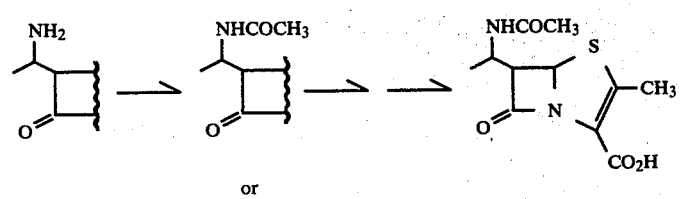
or -continued
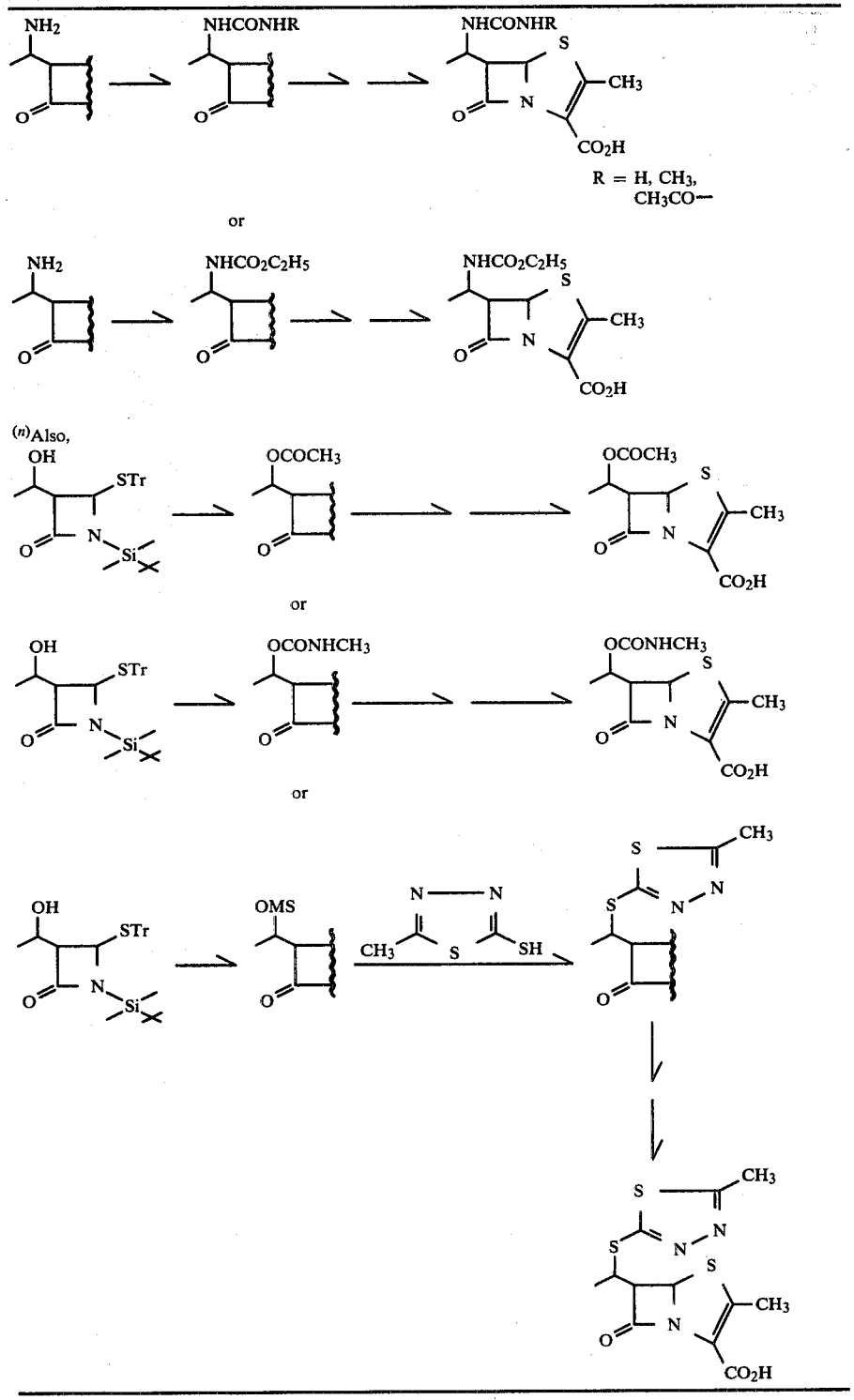

EXAMPLE 68 trans 6-Hydroxymethyl-2-methylpenem-3-carboxylic Acid

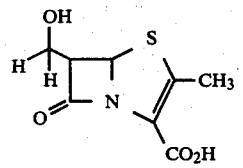

trans 1-(t-butyldimethylsilyl)-3-hydroxymethyl-4-tritylthio-2-azetidinone

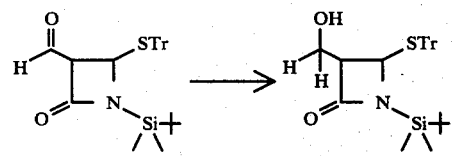

To a cold (ice bath) suspension of NaBH$_4$ (227 mg, 6 mmol) in tetrahydrofuran (20 ml) was added dropwise a solution of trans 1-(t-butyldimethylsilyl)-3-formyl-4-tritylthio-2-azetidinone (2.0 g, 4.1 mmol) in tetrahydrofuran (5 ml). The reaction mixture was stirred at room temperature for 30 min, then diluted with ethyl acetate and washed successively with cold 1N HCl and brine. The organic layer was dried (MgSO$_4$) and evaporated in vacuo to give the title compound (2.0 g) (quantitative) as an amorphous solid. It was used in the next step without further purification. ir $\nu_{max}$ (CDCl$_3$): 1740 cm$^{-1}$. $^1$Hmr (CDCl$_3$)$\delta$: 7.25 (15H, m), 4.30 (1H, d, J=2, H-4), 3.28 (1H, dd, J=11, J=3, H-1'), 3.0 (1H, m, H-3), 2.55 (1H, dd, J=11, J=3, H-1'), 2.2 (1H, m, O—H), 0.9 (9H, s, t-Bu and 0.22 ppm (6H, s, CH$_3$).

trans 3-hydroxymethyl-4-triphenylmethylthio-2-azetidinone

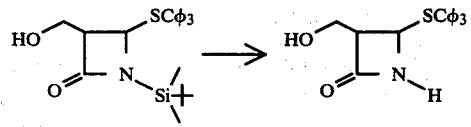

To a solution of trans 1-t-Butyldimethylsilyl-3-hydroxymethyl-4-triphenylmethylthio-2-azetidinone (9.3 g, 19 mmol) in HMPA-10% H$_2$O (40 ml) was added sodium azide (1.5 g, 23 mmol) and the mixture stirred at room temperature for 4.5 h, followed by partition between water and a mixture of ether (60 ml) and petroleum ether (40 ml). The organic phase was washed with water several times, dried and concentrated to give an oil which crystallized from CH$_2$Cl$_2$-ether to give the title compound as a solid, mp 160°-162° C., Hmr (CDCl$_3$) $\delta$: 7.4 (15H, m), 4.48 (1H, d, J=2.3, 4-H), 3.75 (2H, m) and 3.22 ppm (1H, m).

Trans 3-formyloxymethyl-4-triphenylmethylthio-2-azetidinone

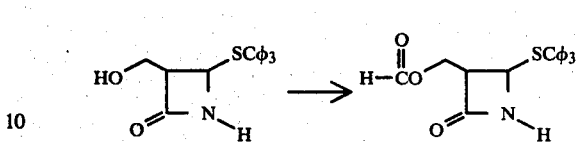

To a cooled (ice-salt) stirred solution of 3-hydroxymethyl-4-triphenylmethylthio-2-azetidinone (1.76 g 4.7 mmol) in CH$_2$Cl$_2$ (10 ml) and triethylamine (2.6 g, 25 mmol) was added dropwise formic-acetic acid anhydride (1.76 g, 20 mmol). The mixture was stirred 20 min at −10° C. and 20 min at room temperature, followed by partition between water and CH$_2$Cl$_2$. Drying and concentration of organic phase gave an oil which crystallized from ether to give 1.7 g (94.4%) of the title compound as white solid, mp 143°-144° C.; $^1$Hmr (CDCl$_3$) $\delta$: 7.98 (1H, formyl) 7.3 (15H, s), 4.82 (1H, 4-H), 4.25 (2H, d, J=9 Hz) and 3.37 ppm (1H, m); ir (nujol) $\nu_{max}$: 1723, 1763, 1776 cm$^{-1}$.

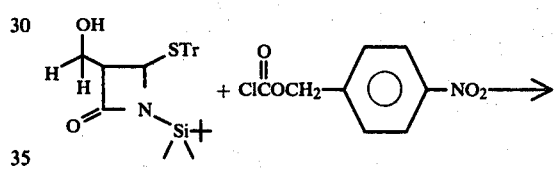

To a cold (dry ice-acetone bath, −78° C.) solution of trans 1-(t-butyldimethylsilyl)-3-hydroxymethyl-4-tritylthio-2-azetidinone (4.89 g, 10 mmol) in tetrahydrofuran (15 ml) was added dropwise 1.6 M n-BuLi (8.2 mmol). The red solution was stirred in a cold bath for 25 min and then treated dropwise with a solution of paranitrobenzylchloroformate (2.6 g, 12 mmol). Stirring was continued for 2 h. The reaction mixture was partitioned between ammonium chloride and ethyl acetate. The aqueous layer was separated and extracted with ethyl acetate (2×10 ml). The organic layers were combined and washed with brine, dried (MgSO$_4$), and evaporated in vacuo. The residual oil was chromatographed on a silica gel column (70 g). Elution with benzene gave the title compound 4.0 g (60%) as an amorphous solid. ir $\nu_{max}$ (CDCl$_3$) 1750, 1610 cm$^{-1}$ $^1$Hmr (CDCl$_3$) $\delta$: 8.40 (2H, d, J=9), 7.45 (17H, m), 5.22 (2H, s, benzyl), 4.4 (1H, d, J=1.5, H-4), 4.05 (1H, dd, J=14, J=4.5, H-1'), 3.28 (1H, m, H-3), 3.18 (1H, dd, J=14, J=4, H=1'), 0.95 (9H, s, t-Bu) and 0.32 ppm (6H, s, CH$_3$).

trans
3-paranitrobenzyldioxycarbonylmethyl-4-tritylthio-2-azetidinone

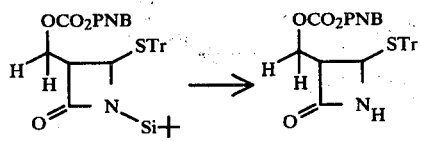

To a cold (ice bath) solution of trans 1-(t-butyldimethylsilyl)-3-paranitrobenzyldioxycarbonylmethyl-4-tritylthio-2-azetidinone (3.2 g, 4.8 mmol) in hexamethylphosphoramide (27 ml) and water (3 ml) was added sodium azide (624 mg, 9.6 mmol). The reaction mixture was stirred at room temperature for 30 min. It was then diluted with water and extracted with ether (2×10 ml). The ether extracts were washed with water (5×5 ml), dried (MgSO$_4$) and evaporated in vacuo to give the title compound 2.25 g, (85%) as a white solid. mp 163°–5° C. (ether). ir $\nu_{max}$ (CDCl$_3$): 1770, 1610 cm$^{-1}$. $^1$Hmr (CDCl$_3$) δ: 8.18 (2H, d, J=9), 7.3 (17H, m), 6.15 (1H, s, N—H), 5.20 (2H, s, benzyl), 4.25 (1H, d, J=2, H-4), 4.1 (2H, m, H-1′) and 3.35 ppm (1H, m, H-3).

trans
3-paranitrobenzyldioxycarbonylmethyl-1-(paranitrobenzyl
2″-hydroxy-2″-acetate)-4-tritylthio-2-azetidinone

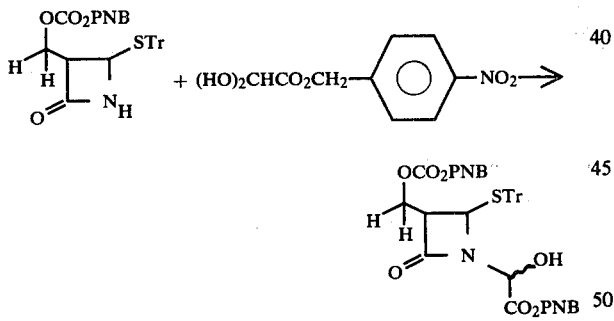

A solution of trans 3-paranitrobenzyldioxycarbonylmethyl-4-tritylthio-2-azetidinone (1.1 g, 2.0 mmol), paranitrobenzyl glyoxylate hydrate (590 mg, 2.63 mmol) and triethylamine (5 drops) in tetrahydrofuran (15 ml) was stirred at room temperature for 2 h. The reaction mixture was filtered over MgSO$_4$ and the solvent was evaporated under vacuo to give the title compound, (1.5 g) (quantitative) as an amorphous solid. It was used in the next step without further purification, ir $\nu_{max}$ (CDCl$_3$): 1765, 1610 cm$^{-1}$. $^1$Hmr (CDCl$_3$) δ: 8.15 (4H, d, J=0), 7.30 (19H, m), 5.28 (2H, s, benzyl), 5.10 (2H, s, benzyl), 4.92 (1H, m), 4.50 (1H, m), 3.90 (2H, m) and 3.45 ppm (2H, m).

trans
3-paranitrobenzyldioxycarbonylmethyl-1-(paranitrobenzyl 2″-chloro-2″-acetate)-4-tritylthio-2-azetidinone

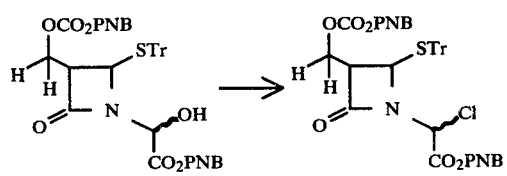

To a cooled (ice-salt bath, −15° C.) solution of the hydroxyglyoxylate (1.87 g, 2.45 mmol) in tetrahydrofuran (40 ml) was added dropwise 1M solution pyridine in tetrahydrofuran (3.7 ml, 3.7 mmol) followed by 1M solution thionyl chloride in tetrahydrofuran (3.7 ml, 3.6 mmol). The resulting mixture was stirred in a cold bath for 1 h and then filtered over Celite and evaporated. The residue was diluted with benzene and treated with charcoal; filtration and evaporation gave the title compound 2.0 g (quantitative) as an amorphous solid. It was used in the next step without further purification. ir $\nu_{max}$ (CHCl$_3$): 1775, 1610 cm$^{-1}$. $^1$Hmr (CDCl$_3$) δ: 8.20 (4H, d, J=9), 7.35 (19H, m), 5.32 (2H, s), 5.20 (2H, s), 5.3 (2H, m), 4.65 (1H, s) and 3.5 ppm (2H, m).

trans
3-paranitrobenzyldioxycarbonylmethyl-1-(paranitrobenzyl 2″-triphenylphosphoranyidene-2″-acetate)-4-tritylthio-2-azetidinone

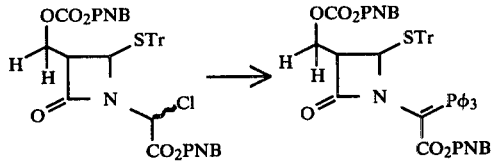

To a solution of the chloroglyoxylate (2.6 g, 3.33 mmol) in dioxane (30 ml) was added triphenylphosphine (872 mg, 3.33 mmol) and 2.6-lutidine (0.46 ml, 4.0 mmol). The reaction mixture was heated at 80° C. for 3 days and refluxed for 6 h. It was then diluted with benzene/ether (30 ml, 1:1) and washed successively with water (10 ml), 1N, HCl (5 ml), 1M NaHCO$_3$ (5 ml), brine (10 ml). The organic layer was dried (MgSO$_4$) and evaporated in vacuo. The residual oil was chromatographed on silica gel column (25 g). Elution with benzene to 30% ether in benzene gave the title compound 1.07 g (32%) as an amorphous solid. ir $\nu_{max}$ (CHCl$_3$): 1750, 1605 cm$^{-1}$. $^1$Hmr (CDCl$_3$) δ: 6.8–8.3 (38H, m), 4.5–5.3 (5H, m) and 2.5–3.8 ppm (3H, m).

trans silver 3-paranitrobenzyldioxycarbonylmethyl-1-(paranitrobenzyl 2″-triphenylphosphoranylidene-2″-acetate)-2-azetidinone-4-thiolate

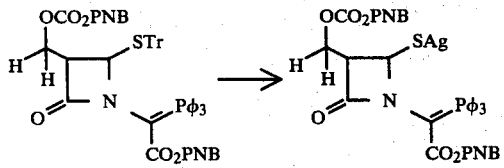

A solution of the phosphorane (1.07 g, 1.06 mmol) in dichloromethane (20 ml) was evaporated to dryness and diluted with hot methanol (40 ml). The solution was stirred at 60° C. and treated with a pre-heated (60° C.) solution of silver nitrate (221 mg, 1.3 mmol) in methanol (10 ml) followed by pyridine (0.105 ml). The creamy solution was stirred at room temperature for 30 min, then in ice bath for 2 h. The solid was filtered and washed with cold methanol and ether, then it was dried to give the title compound, 842 mg (91%), as a beige eolid mp 110°–111° C. dec. ir $\nu_{max}$(CHCl$_3$): 1755, 1605 cm$^{-1}$. $^1$Hmr (CDCl$_3$) δ: 6.5–8.3 (23H, m and 2.5–5.6 ppm (8H, m).

trans 4-acetylthio-3-paranitrobenzyldioxycarbonylmethyl-1-(paranitrobenzyl 2″-triphenylphosphoranylidene-2″-acetate)-2-azetidinone

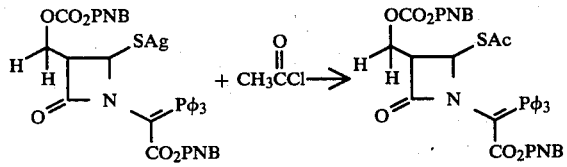

To a cooled (ice bath) mixture of thiolate (842 mg, 0.97 mmol) and acetylchloride (0.083 ml, 1.16 mmol) in dichloromethane (10 ml) was added dropwise 1M solution of pyridine in dichloromethane (1.15 ml, 1.16 mmol). The dark solution was stirred in a cold bath for 30 min. It was then filtered over Celite and washed with benzene. The filtrate and washing were combined and washed successively with 1N HCl (2 ml), water (5 ml), 1M NaHCO$_3$ (2 ml), brine. The organic layer was dried (MgSO$_4$) and evaporated in vacuo to give the title compound, 690 mg (88%) as an amorphous solid. It was used in the next step without further purification. ir $\nu_{max}$(CHCl$_3$): 1760, 1690, 1610 cm$^{-1}$; $^1$Hmr (CDCl$_3$) δ: 8.22 (4H, d, J=9), 7.5 (19H, m), 5.72 (1H, wm), 5.05 (4H, 2s), 4.5 (2H, m), 3.5 (1H, m) and 2.3 ppm (3H, 2s).

trans paranitrobenzyl 2-methyl-6-paranitrobenzyldioxycarbonylmethyl-penem-3-carboxylate

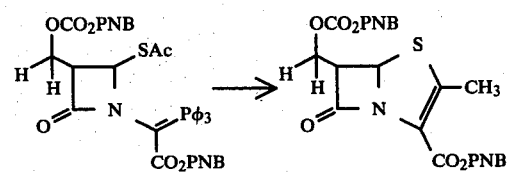

A solution of the phosphorane (690 mg, 0.86 mmol) in toluene (20 ml) was refluxed for 6 h. The solvent was evaporated and the residue was chromatographed on a silica gel column (5.0 g). Elution with benzene to 5% ether in benzene gave the title compound 340 mg (75%) as an amorphous solid. ir $\nu_{max}$ (CHCl$_3$): 1790, 1750, 1710, 1610 cm$^{-1}$. $^1$Hmr (CDCl$_3$) δ: 8.15 (4H, d, J=9), 7.5 (4H, dd, J=9, 5), 5.6 (1H, d, J=1.8, H-5), 5.25 (4H, 2s, benzyls), 4.52 (2H, d, J=5, H-1′), 4.10 (1H, dt, J=5, 1.8, H-6) and 2.35 ppm (3H, s, CH$_3$).

trans 6-hydroxymethyl-2-methyl penem-3-carboxylic acid

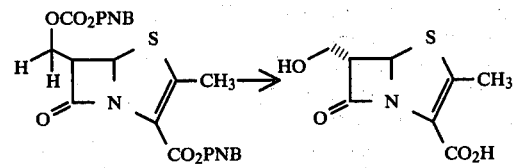

To a solution of the above ester (100 mg, 0.19 mmol) in tetrahydrofuran (4 ml) and ether (2 ml) was added sodium bicarbonate (32 mg, 0.38 mmol) in water (4 ml) and 30% Pd/Celite (250 mg). The two phase mixture was hydrogenated at 45 psi for 4 h at room temperature. Then it was filtered over a celite pad and the layers were separated. Th aqueous phase was washed with ether (2×5 ml), acidified with 1N HCl (1 ml, 1 mmol), and extracted with ethyl acetate (5×3 ml). The organic extracts were washed with brine, dried (MgSO$_4$) and evaporated in vacuo to give the title compound (11.5 mg, 28%) as a yellow solid. mp 154°–5° C. ir $\nu_{max}$: 3400–3500, 1775, 1690, 1585 cm$^{-1}$; $^1$Hmr (DMSO-d$_6$) δ: 5.5 (1H, d, J=1.3, H-4), 3.7 (4H, m), 3.30 (1H, ws) and 2.3 ppm (3H, s); uv $\lambda_{max}^{MeOH}$: 308 (ε 5079), 261 (ε 2798).

EXAMPLE 69

(1′S,5R,6S, and 1′R,5S,6R) β-Trimethylsilylethyl-6(1′-acetoxy-1′-ethyl)-2-methyl-penem-3-carboxylate (Isomer C)

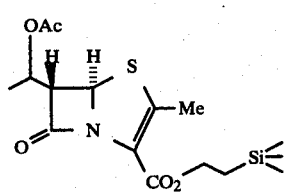

3-(1'-hydroxy-1'-ethyl)-1-(β-trimethylsilylethyl 2''-triphenylphosphoranylidene-2''-acetate)-4-tritylthio-2-azetidinone

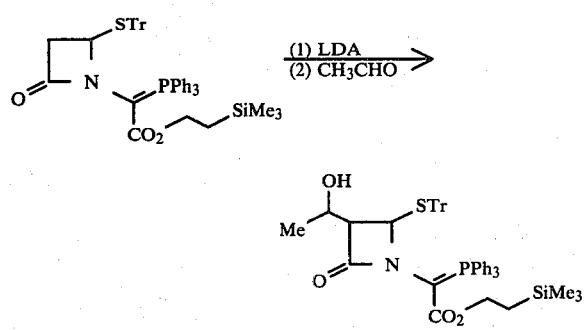

To a solution of diisopropylamine (185 mg, 1.84 mmol) in tetrahydrofuran (5 ml) at −78° C. was added n-butyl lithium (1.3 ml, 2.0 mmol) with stirring. After 5 min, a solution of 1-(β-trimethylsilylethyl 2'-triphenylphosphoranylidene-2'-acetate)-4-tritylthio-2-azetidinone (1.27 g, 1.67 mmol) in tetrahydrofuran (15 ml) was added dropwise over 20 min with stirring. After 2 min, freshly distilled acetaldehyde (1 ml) was added and the solution was stirred for 5 min. Hydrochloric acid (12.6 ml of 0.3M) was added and the mixture was allowed to warm to 23° C. Water and ethyl acetate (20 ml each) were added, shaken, and separated. The organic phase was washed with water and saturated sodium chloride (20 ml each), dried and the solvent was evaporated in vacuo to give crude product, 1.37 g. The product was absorbed from methylene chloride onto 7 g of silica gel and placed (dry) on a 28 g silica gel column. The column was eluted with ether (100 ml) and then with ether/ethyl acetate 1:1 (50 ml). The first 20 ml of column fractions were discarded. The rest were combined and the solvent was evaporated in vacuo to give a product, 1.03 g. This product was absorbed from ether onto a 50 g silica gel comumn (wet). The column was eluted with ether (680 ml) and then with ethyl acetate (200 ml). Later fractions were combined (major low Rf spot on tlc) and the solvent was evaporated in vacuo to give partially purified title compound, 440 mg (33%); ir $\nu_{max}$: 3400 (OH) and 1750 cm$^{-1}$ (β-lactam and ester); $^1$Hmr (CHCl$_3$) δ: too poorly resolved to make peak assignments other than aromatics and trimethylsilyl.

Silver 3-(1'-hydroxy-1'-ethyl)-1-(β-trimethylsilylethyl 2''-triphenylphosphoranylidene-2''-acetate)-2-azetidinone-4-thiolate.

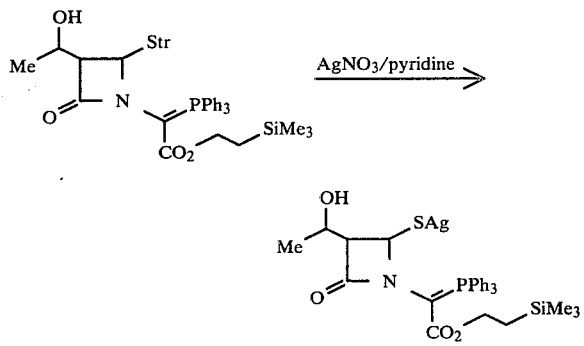

A solution of silver nitrate (425 mg, 2.5 mmol). pyridine (79 mg, 1.0 mmol) and water (10 ml) was added to a solution of the above compound (403 mg, 0.50 mmol) in ether (10 ml). The mixture was stirred vigorously for 1 h. The precipitate was collected by filtration and washed with water and ether to give the title mercaptide 267 mg (80%). ir $\nu_{max}$: 3400 (OH) and 1750 cm$^{-1}$ (β-lactam and ester).

4-Acetylthio-3-(1'-acetoxy-1'-ethyl)-1-(β-trimethylsilylethyl 2''-triphenylphosphoranylidene-2''-acetate)-2-azetidinone

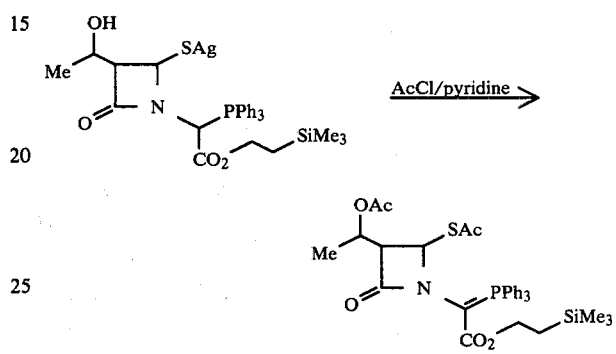

A solution of acetyl chloride (70 mg, 0.88 mmol) in methylene chloride (1 ml) was added dropwise to a solution of the above silver mercaptide (267 mg, 0.40 mmol) and pyridine (70 mg, 0.88 mmol) in methylene chloride (5 ml) at 0° C. The mixture was stirred at 0° C. for 1.5 h and then at 23° C. for 15 min. The precipitate was filtered off and the solution was washed with 0.1 M hydrochloric acid and 0.1 M sodium bicarbonate (10 ml each). The solvent was evaporated in vacuo to give the title compound, 153 mg (59%); ir $\nu_{max}$: 3450 (OH), 1750 (β-lactam and ester) and 1690 cm$^{-1}$ (thioester); $^1$Hmr (CDCl$_3$) δ: 7.5–8.2 (m, 15H, Ph), 5.85 (br, 1H, H-4), 3.0–5.0 (unresolved, 4H, OCH, OCH$_2$, H-3), 2.0–2.6 (3 singlets; 6H, OAc, SAc), 0.9–1.7 (m, 5H, CH$_3$, CH$_2$Si) and 0.20 ppm (s, 9H, SiMe$_3$).

(1'S,5R,6S and 1'R,5S,6R) β-trimethylsilylethyl 6-(1'-acetoxy-1'-ethyl)-2-methylpenem-3-carboxylate (isomer C)

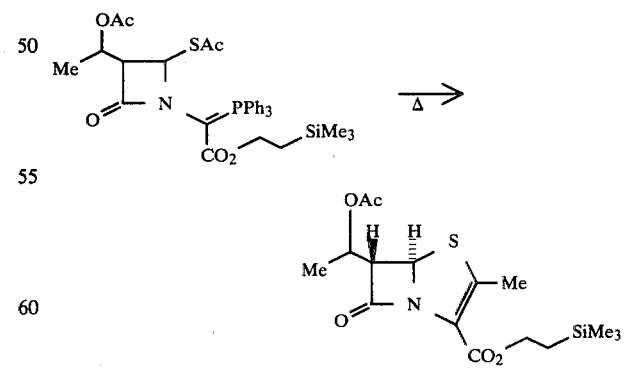

A solution of the above phosphorane (150 mg, 0.23 mmol) in toluene (15 ml) was heated under reflux for 2 h. The solution was mixed with 1 g of silica gel and the solvent was evaporated in vacuo. The silica was placed on a 4 g silica gel column (dry) and eluted with ether.

The first 5 ml fraction (single high Rf spot on tlc), on evaporation of the solvent, gave the title compound, 65 mg (76%) as a waxy solid. ir $\nu_{max}$: 1790 (β-lactam), 1740 (ester) and 1700 cm$^{-1}$ (OAc); $^1$Hmr (CDCl$_3$) δ: (d, J=2Hz, 1H, H-5), 5.4 (m, 1H, H-1'), 4.3 (m, 2H, OCH$_2$), 3.90 (q, J=2 Hz, 4 Hz, 1H, H-7), 2.37 (s, 3H, 2-CH$_3$), 2.11 (s, 3H, OAc), 1.42 (d, J=6.5, Hz, 3H, 2'-CH$_3$), 1.1 (m, 2H, CH$_2$Si) and 0.05 ppm (s, 9H, SiMe$_3$). The product was found to be a single isomer.

EXAMPLE 70

(1'R,5R,6S and 1'S,5S,6R) 6-1'-Amino-1'-ethyl)-2-methylpenem-3-carboxylic Acid

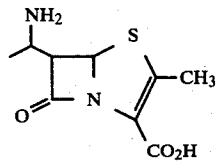

Procedure A (1'R,3S,4R and 1'S,3R,4S)3-(1'-azido-1'-ethyl)-1-(paranitrobenzyl 2''-triphonylphosphoranylidene-2''-acetate)-4-tritylthio-2-azetidinone (isomer B)

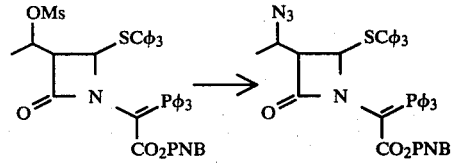

A solution of (1'1 S,3S,4R and 1'R,3R,4S)3-(1-methanesulfonyloxy-1'-ethyl)-b 1-(paranitrobenzyl 2''-triphenylphosphoranylidene-2''-acetate)-4-tritylthio-2-azetidinone (isomer C) (12.36 g, 13.4 mmol) in 10% H$_2$O-HMPA (135 ml) was heated at 85° C. for 7 h in the presence of sodium azide (1.75 g 27.0 mmol). The solution was then poured into cold water (1 l) and the reaction product which crystallized out was collected by filtration. Redissolution in dichloromethane, washing with brine and drying (MgSO$_4$) gave the azido phosphorane as a yellow foam after evaporation of the solvent; 11.5 g (98.9%). It was used as such for the next step. ir $\nu_{max}$ (CHCl$_3$): 2100 (N$_3$), 1740 and 1610 cm$^{-1}$ (C=O).

(1'R,3S,4R and 1'S,3R,4S)4-acetylthio-3-(1'-azido-1'-ethyl)-1-(paranitrobenzyl 2''-triphonylphosphoranylidene-2''-acetate)-2-azetidinone (isomer B)

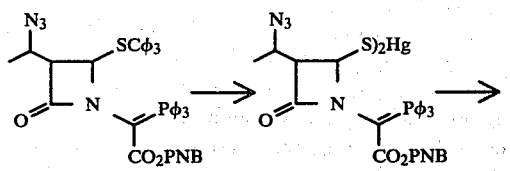

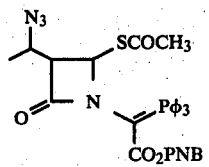

A cooled solution (5° C.) of (1'R,3S,4R and 1'S,3R,4S)3-(1'-azido-1'-ethyl)-1-(paranitrobenzyl 2''-triphonylphosphoranylidene-2''-acetate)-4-tritylthio-2-azetidinone (8.9 g, 10.25 mmol) in dichloromethane (30 ml) was treated with a solution of mercuric acetate (2.12 g, 6.66 mmol) in methanol (30 ml). After stirring at 5° C. for 0.5 h and room temperature for 1.5 h, the solvent was evaporated and the crude mercuric salt redissolved in dichloromethane and washed with dilute NaHCO$_3$ and brine. After drying (MgSO$_4$) the solution was cooled to 5° C. and treated directly with pyridine (1.66 g, 21 mmol) and dropwise with acetyl chloride (1.65 g, 21 mmol). The reaction mixture was stirred at 5° C. for 1 h. The precipitated mercuric chloride was filtered off and the filtrate washed successively with dilute HCl, NaHCO$_3$ and brine. Then the organic solution was saturated at 5° C. with hydrogen sulfide in order to precipitate the remaining mercuric impurities as mercuric sulfide. The crude thioester obtained after evaporation of the solvent was purified on a silica gel column (8.5×9 cm), eluting with dichloromethane (500 ml) and 15% acetonitrile-dichloromethane: 5.1 g (74.6%); $^1$Hmr (CDCl$_3$) δ: 3.70 (1H, m, H-1'), 2.98 (1H, m, H-3), 2.33 and 2.20 (3H, 2s, acetyl), 1.28 (3H, d, J=6.2 Ha, H-2'); ir $\nu_{max}$ (CHCl$_3$): 2115 (N$_3$), 1758, 1693 and 1620 cm$^{-1}$ (C=O).

(1'R,5R,6S and 1'S,5S,6R)paranitrobenzyl 6-(1'-azido-1'-ethyl)-2-methyl penem-3-carboxylate (isomer B)

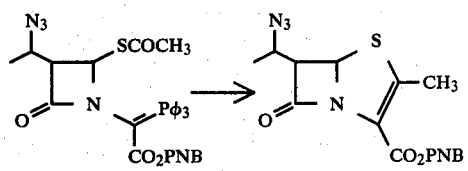

A solution of (1'R,5R,6S and 1'S,5S,6R)4-acetylthio-2-(1'-azido-1'-ethyl)-1-paranitrobenzyl 2''-triphenylphosphoranylidene-2''-acetate)-2-azetidinone (5.1 g, 13.1 mmol) in toluene (100 ml) was refluxed for 2 h under nitrogen. The solvent was evaporated and the reaction mixture purified by chromatography on a silica gel column (7×5 cm). The azido penem was eluted with dichloromethane (further elution with 10% ether-dichloromethane allowed to recover 1.82 g of unreacted phosphorane): 1.21 g (40.6%) mp 132°-34° C.; $^1$Hmr (CDCl$_3$) δ: 8.21 (2H, d, Hm aromatic), 7.60 (2H, d, Ho aromatic), 5.51 (1H, d, J=1.6 Hz, H-5), 5.33 (2H, ABq, H-benzyl), 3.92 (1H, dq, J=8, 6.4 Hz, H-1'), 3.67 (1H, dd, J=1.6, 8 Hz, H-6), 2.37 (3H, s, CH$_3$), 1.46 (3H, d, J=6.4 Hz, H-2'); ir $\nu_{max}$ (CDCl$_3$): 2123 (N$_3$), 1788 and 1712 cm$^{-1}$ (C=O).

(1'R,5R,6S and 1'S,5S, 6R)6-(1'amino-1'-ethyl)-2-methyl penem-3-carboxylic acid (isomer B)

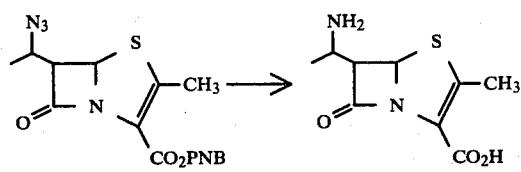

A solution of (1'R,5R,6S and 1'S,5S,6R) paranitrobenzyl 6-(1'-azido-1'-ethyl)-2-methyl penem-3-carboxylate (440 mg, 1.13 mmol) in THF-ether-water (1:1:1) (120 ml) was hydrogenated at 50 psi for 1 h in the presence of 10% Pd-C (440 mg). The catalyst was filtered off, the filtrate extracted with ether and the aqueous phase lyophilized. The crude amino acid (100 mg) was purified by hplc: 19.5 mg $^1$Hmr (D$_2$O) δ: 5.69 (1H, d, J=0.9 Hz, H-5), 3.94 (2H, m, H-6, H-1'), 2.28 (3H, s, CH$_3$), 1.50 (3H, d, J=6.4 Ha, H-2'); ir $\nu_{max}$ (Nujol): 1767, 1576 cm$^{-1}$ (C=O); uv (H$_2$O) $\lambda_{max}$: 300 mµ (ε5326).

Procedure B
(1'R,3S,4S and 1'S,3R,4S) 3-(1'-azido-1'-ethyl)-4-tritylthio-2-azetidinone (Isomer B)

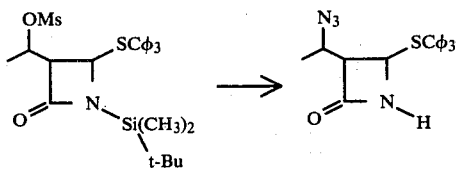

A solution of (1'S,3S,4R and 1'R,3R,4S) 1-(t-butyldimethylsilyl)-3-(1'-methanesulfonyloxy-1'-ethyl)-4-tritylthio-2-azetidinone (Isomer C) (1.75 g, 3 mmol) and sodium azide (0.39 g, 6 mmol) in 10% H$_2$O:HMPA (15 ml) was heated under N$_2$ at 75°-80° C. for 3 h. Then the reaction mixture was diluted with ethyl acetate and washed several times with brine. The organic phase was dried (MgSO$_4$) and evaporated to leave an oil which crystallized spontaneously. Trituration in ether and filtration gave 951 mg (76.5%) of the azido compound as a white solid mp 185°-90° C., dec. $^1$HMR (CDCl$_3$) δ: 7.23-7.78 (15H, m, aromatics), 4.43 (1H, d, J=3, H-4), 4.37 (1H, s, N—H), 3.89 (1H, dq, J=7, 6.5, H-1'), 3.16 (1H, dd, J=7, 3, H-3), 1.50 (3H, d, J=6.5, H-2'); ir $\nu_{max}$ (CHCl$_3$): 3410 (N—H), 2123 (N$_3$) and 1765 cm$^{-1}$ (C=O).

(1'R,3S,4R and 1'S,3R,4S) 3-(1'-amino-1'-ethyl)-4-tritylthio-2-azetidinone (Isomer B)

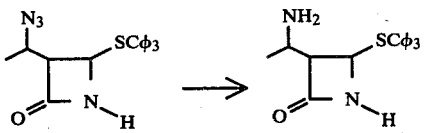

A suspension of (1'R,3S,4R and 1'S,3R,4S) 3-(1'-azido-1'-ethyl)-4-tritylthio-2-azetidinone (Isomer B) (1.0 g, 2.41 mmol) and platinum oxide (100 mg) in ethyl acetate (100 ml) was hydrogenated for 1 h at a pressure of 50 psi. Since the reaction was incomplete, 200 mg of platinum oxide was added and the mixture hydrogenated for one additional hour. Finally, 200 mg of platinum oxide was again added and the reaction continued for 2.5 h. Total catalyst: 500 mg. Total time: 4.5 h. Then the catalyst was filtered off and the solvent evaporated. The crude amine crystallized from ether: 700 mg (80%). mp 128°-30° C. $^1$Hmr (CDCl$_3$) δ: 7.13-7.63 (15H, m, aromatics), 4.40 (1H, d, J=2.5, H-4), 4.30 (1H, broad, H-1), 3.30 (1H, dq, J=5.1, 6.3, H-1'), 3.03 (1H, dd, J=5.1, 2.5, H-3), 1.20 (3H, d, J=6.3, H-2') and 1.0-1.80 ppm (2H, broad, NH$_2$).

(1'R,3S,4R and 1'S,3R,4S) 3-(1'-p-nitrobenzyloxycarbonylamino-1'-ethyl)-4-tritylthio-2-azetidinone (Isomer B)

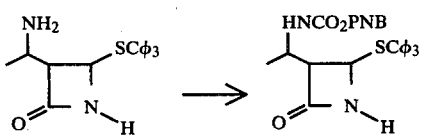

A solution of (1'R,3S,4R and 1'S,3R, 4S) 3-(1'-amino-1'-ethyl)-4-tritylthio-2-azetidinone (Isomer B) (1.00 g, 2.57 mmol) in dichloromethane (100 ml) was cooled to 5° C. and treated with p-nitrobenzylchloroformate (0.61 g, 2.83 mmol) and pyridine (0.22 g, 2.83 mmol). After stirring at 5° C. for 45 min and at room temperature for 2.25 h, the reaction mixture was washed with dilute HCl, brine, dried (MgSO$_4$) and finally evaporated to dryness. The crude carbamate was crystallized from ether: 1.03 g (70.5%). mp 147°-50° C. $^1$Hmr (CDCl$_3$) δ: 7.10-8.33 (19H, m, aromatics), 5.23 (2H, s, benzyl), 5.08 (1H, N—H), 4.40 (1H, s, N—H), 4.29 (1H, d, J=2.2, H-4), 4.10 (1H, dq, J=8, 6, H-1'), 3.18 (1H, dd, J=2.2, 8, H-3) and 1.23 ppm (3H, d, J=6, H-2'); ir $\nu_{max}$ (CHCl$_3$): 3395 (N—H), 1765 and 1724 cm$^{-1}$ (C=O).

(1'R,5R,6S and 1'S,5S,6R) p-nitrobenzyl 2-methyl 6-(1'-p-nitrobenzyloxycarbonylamino-1'-ethyl) penem-3-carboxylate (Isomer B)

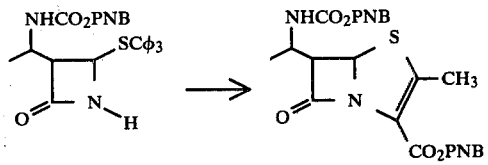

The title product was prepared from (1'R,5R,6S and 1'S,5S,6R) 3-(1'-p-nitrobenzyloxycarbonylamino-1'-ethyl)-4-tritylthio-2-azetidinone (isomer B) by the standard procedure; mp 108°-110° C. $^1$Hmr (CDCl$_3$) δ: 7.50-8.40 (8H, m, aromatics), 5.58 (1H, d, J=1.20, H-5), 5.35 (2H, ABq, benzyl ester), 5.20 (2IH, s, benzyl carbamate), 4.90 (1H, broad N—H), 4.20 (1H, dq, J=6, 8, H-1'), 3.80 (1H, dd, J=1.2, 8.0, H-6), 2.40 (3H, s, (CH$_3$), 1.40 (3H, d, J=6, CH$_3$); ir $\nu_{max}$: 3435 (N—H), 1777 and 1717 cm$^{-1}$ (C=O).

The p-nitrobenzyl ester may be subjected to catalytic hydrogenation as by the procedure of Example 70 (Procedure A) to provide the corresponding carboxylic acid.

EXAMPLE 71

6-Dimethylaminomethyl-2-methylpenem-3-carboxylic Acid

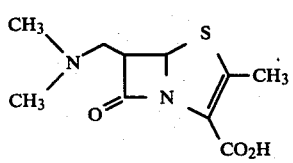

1-(t-butyldimethylsilyl)-3-dimethylaminomethyl-4-tritylthio-2-azetidinone (cis and trans)

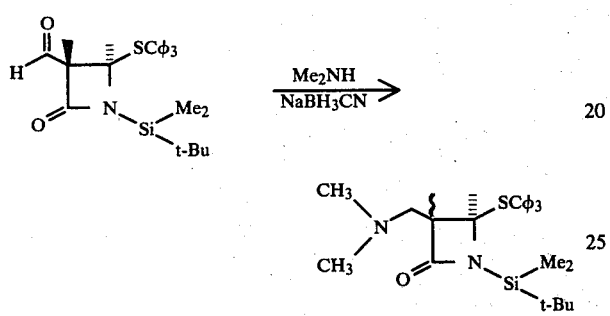

To a solution of dimethylamine (18.5 ml of a 2N solution in methanol, 36.9 mmoles) in methanol (80 ml) was added a solution of hydrochloric acid in methanol (2.5 ml of a 5N solution in methanol) followed by trans 1-(t-butyldimethylsilyl)-3-formyl-4-tritylthio-2-azetidinone (3.0 g, 6.16 mmoles) and by sodium cyanoborohydride (0.27 g, 4.31 mmoles). The mixture was stirred at room temperature for 3.5 h, poured onto ice-hydrochloric acid (pH=2) and made basic with sodium hydroxide (1N NaOH, pH=9). The mixture was extracted with ether and the ether phase was washed with brine, dried and evaporated to give the title compound as a crude oil (3.0 g).

cis and trans 3-dimethylaminomethyl-4-tritylthio-2-azetidinone

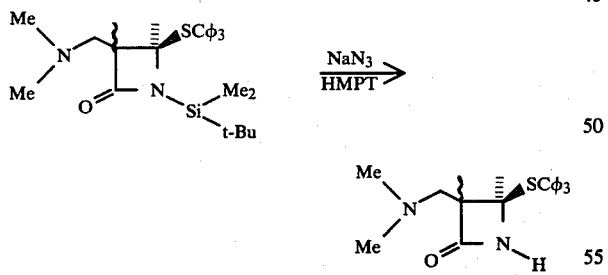

A solution of the above crude compound (3.0 g, 6 mmoles) in hexamethylphosphorous triamide (HMPT, 16 ml) containing water (10%) was cooled (5°) and treated with sodium azide (0.78 g, 12 mmol). The mixture was stirred 1.5 h at room temperature, poured onto ice-water and extracted with ether (5×30 ml). The organic phases were extracted with hydrochloric acid (1N) and the acidic extracts washed well with ether to remove the HMPT. The acidic phase was made basic (1N, NaOH) and extracted with dichloromethane. The organic layer was washed with brine, dried and concentrated to give the title compounds as an amorphous white solid (1.5 g, 62.5% overall). The mixture of isomers was separated on a Waters Prep 500, eluting with methanol (5%), ammonia (0.2%), ethyl acetate (95%). Trans isomer: 1.0 g, m.p. 129°–131° C. (pentane); δ (ppm, CDCl$_3$): 6.8–7.8 (15H, m, aromatics), 4.5 (1H, N—H), 4.28 (1H, d, J=2.5, H-4), 3.35 (1H, m, H-3), 2.75–2.1 (2H, m, H-1'), 2.3 (6H, s, CH$_3$).

Cis isomer: 0.5 g, m.p. 132°–3° C. (ether-pentane); δ (ppm, CDCl$_3$): 7.7–6.7 (15H, m, aromatics), 4.72 (1H, N—H), 4.5 (1H, d, J=5.3, H-4), 3.5 (1H, m, H-3), 2.85–2.35 (2H, m, H-1'), 2.31 (6H, s, CH$_3$). The cis to trans ratio can be varied by changes in conditions.

cis and trans 6-dimethylaminomethyl-2-methylpenem-3-carboxylic acid

The title compound was prepared from cis and trans 3-dimethylaminomethyl-4-tritylthio-2-azetidinone by the procedure of Example 58. δ(ppm, CDCl$_3$): 5.5 (1H, d, J=1.3), 3.7 (1H, dt, J=1.3, J=8), 2.8 (2H, d, J=8), 2.35 (6H, s), 2.3 (3H, s).

EXAMPLE 72 2-(1'-Aminoethyl)-penem-3-carboxylic Acid (via mercaptide intermediate)

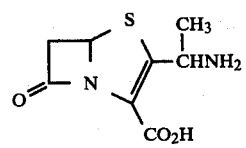

Ethyl α-azidopropionate

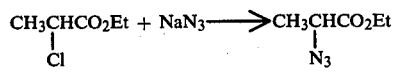

This product was prepared by the procedure described in the literature [J.A.C.S. 77, 112 (1955)] as follows:

A mixture of ethyl α-dichloropropionate (27.5 g, 0.2 mmol) and sodium azide (15 g, 0.23 mmol) in absolute ethanol (350 ml) was refluxed with stirring for 60 h. The reaction mixture was filtered to remove the sodium chloride and the filtrate evaporated to dryness. The residue was distilled to give 15 g (52%) of title material bp 58°–60° C./20 mm.

α-Azidopropionic acid

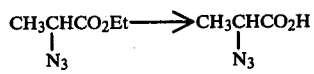

This compound was prepared by a literature procedure [J.A.C.S. 77, 112 (1955)] as follows:

To a solution of potassium hydroxide (5.6 g, 0.1 mol) in ethanol-water mixture (1:10, 25 ml) was added the ester (14.3 g, 0.1 mol) and the mixture was gradually warmed to reflux and then refluxed for 0.5 h. After cooling to room temperature, the reaction mixture was poured into ice, extracted with ether and the ether extract was discharged. The aqueous phase was acidified with concentrated sulfuric acid (4.5 ml) to pH 2 and extracted with ether (3×80 ml) and then with $CH_2Cl_2$ (2×30 ml). The combined extracts were washed first with water, then with brine and dried. Removal of the solvent by evaporation gave 10.5 g (91%) of the azido acid as an oil; $^1$Hmr (CDCl$_3$) δ: 8.80 (s, 1H, CO$_2$H), 4.05 (q, 1H, CHN$_3$, J=8 Hz) and 1.50 ppm (d, 3H, CH$_3$, J=8.0 Hz).

α-Azidopropionyl chloride

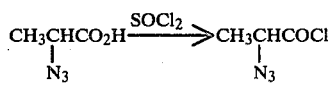

This compound was prepared by a literature procedure [J.A.C.S. 77, 112 (1955)] as follows:

To the acid (10.5 g, 91 mmol) was added slowly in a period of 10 min, 16.3 g (137 mmol) of thionyl chloride at 0° C. After the addition of thionyl chloride was completed, the reaction mixture was gradually heated to reflux and maintained at the refluxing temperature until the evolution of gas had ceased (1.5 h). The reaction mixture was evaporated and the residue distilled to give 6.5 g (53.5%) of title compound bp 50°-54° C./23-27 mm; $^1$Hmr (CDCl$_3$) δ: 4.23 (q, 1H, CHN$_3$, J=8.0 Hz and 1.63 ppm (d, 3H, CH$_3$, J=8.0 Hz).

4-(2'-azidopropionylthio)-1-(paranitrobenzyl 2''-triphenylphosphoranylidene-2''-acetate)-2-azetidinone

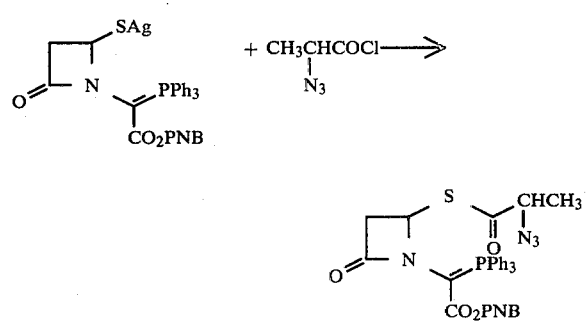

To a stirred solution of silver 1-(paranitrobenzyl 2'-triphenylphosphoranylidene-2'-acetate-2-azetidinone-4-thiolate (1.0 g, 1.67 mmol) in methylene chloride (15 ml) at 0° C. was added a solution of α-azidopropionyl chloride (270 mg, 2 mmol) in methylene chloride (4 ml) and the reaction mixture was stirred at 0° C. under nitrogen atmosphere for 1 h. The reaction mixture was filtered through a pad of Celite and the cake washed with methylene chloride. The combined filtrate and washings were washed successively with 5% NaHCO$_3$ (10 ml), brine and water and then dried and filtered. The filtrate was evaporated to give 1.0 g of syrup which was purified by chromatography on silica gel (10 g) using as eluent first CH$_2$Cl$_2$ (100 ml) and then 3% MeOH—CH$_2$Cl$_2$ (150 ml). The fraction of eluent containing the title compound (tlc on silica, 5% MeOH—CH$_2$Cl$_2$) were combined and evaporated to give 360 mg (33%) of title compound as a syrup.

paranitrobenzyl 2-(1'-azidoethyl)-penem-3-carboxylate

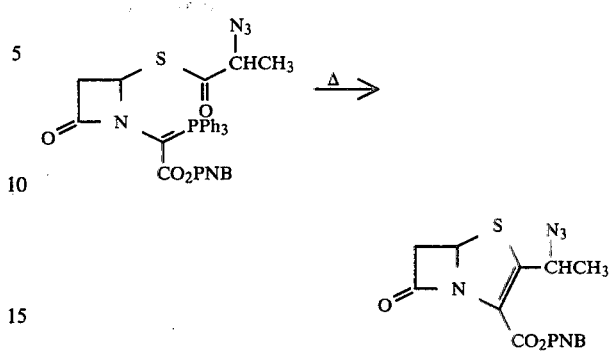

The above phosphorane (131 mg, 0.2 mmol) was dissolved in dry toluene (10 ml) and the resulting solution was refluxed for 3 h and then evaporated to dryness. The residue was dissolved in a small volume of CH$_2$Cl$_2$, filtered through a pad of silica gel (2 g) and the pad washed successively with CH$_2$Cl$_2$ (30 ml) and 1% MeOH in CH$_2$Cl$_2$. The filtrate was evaporated to dryness to provide 34 mg (45.5%) of title compound, mp 87°-89° C. as a mixture of two diastereoisomers in a ratio of about 60:40 as estimated by $^1$Hmr. On tlc (silica, 15% etherbenzene) this product showed a single spot of Rf 0.65; ir (Nujol) ν$_{max}$: 2100, 1790, 1700 cm$^{-1}$; $^1$Hmr (CDCl$_3$) δ: 8.23 (d, 2H, Hm aromatic), 7.60 (d, 2H, Ho aromatic), 5.6 (m, 2H, H-5 and CHN$_3$), 5.30 (d, 2H, CH$_2$PNB), 3.82 (dd, 1H, H-6, J$_{5,6\ trans}$=3.5 Hz, J$_{vic}$=16 Hz), 3.43 (dd, 1H, H-6, J$_{5,6\ cis}$=2 Hz, J$_{vic}$=16), 1.47 (d, 3H, CH$_3$, J=8.0 Hz) and 1.40 ppm (d, 3H, CH$_3$, J=13 Hz); Anal. calcd for C$_{15}$H$_{13}$N$_5$O$_5$S: C 47.99, H 3.49, N 18.66; found: C 48.16, H 3.47, N 17.91.

2-(1'-aminoethyl)-penem-3carboxylic acid

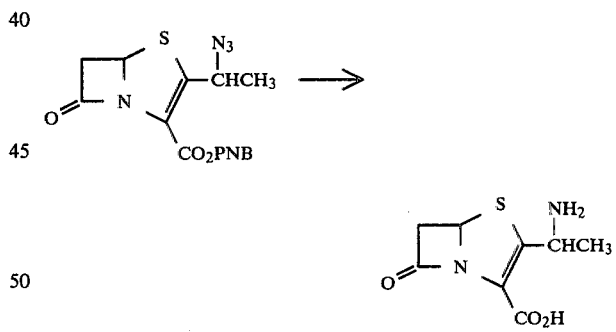

The above azide (232 mg, 0.618 mmol) was dissolved in THF (5 ml) which was freshly distilled over LAH. To this solution was added ether (5 ml), water (5 ml) and 50% Pd on diatomaceous earth (700 mg) and the mixture was hydrogenated at 40 psi for 1.15 h. The reaction mixture was filtered through a pad of Celite. The filtrate was extracted with ether-THF (10:1, 11 ml) and with ether-CH$_2$Cl$_2$ (10:1, 11 ml) to remove water insoluble material. The aqueous phase was lyophylized to give 34 mg of title compound as a powder of greenish color. This product was purified by hplc on a reverse phase column (90 g) using water as eluent. The appropriate fractions were combined and lyophylized to give 19 mg of title compound as a powder; Uv λ$_{max}$: 305 (ε=5430).

EXAMPLE 73

2-(4'-Aminobutyl)-penem-3-carboxylic Acid (via mercaptide intermediate)

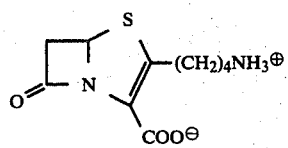

5-Azido valeronitrile

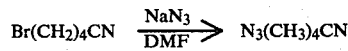

A solution of 5-bromovaleronitrile (48.6 g, 0.3 mol) in N, N-dimethylformamide (600 ml) was treated with sodium azide (23.4 g, 0.36 mol) and stirred at 100° C. for 4 h. The reaction mixture was cooled to 23° C. and diluted with water (500 ml); the resulting solution was extracted with ether (4×400 ml). The ether extracts were combined, washed with water (3×200 ml) and dried over anhydrous magnesium sulfate. The evaporation of ether under reduced pressure gave a yellow liquid which was distilled under high vacuum; bp 83°–4° C. (0.6 mm)[1]; $^1$Hmr (CDCl$_3$) δ: 3.37 (2H, m, δ-H), 2.4 (2H, m, α-H) and 2.0–1.3 ppm (4H, β-H and γ-H).

[1] F. M. D'Itri and A. I. Popov, J. Am. Chem. Soc., 90, 6476–81 (1968).

5-Azidovaleric acid

A solution of 5-azidovaleronitrile (12.4 g, 0.1 mol) in ethanol (50 ml) was diluted with water (12 ml) and treated with potassium hydroxide (8.4 g, 0.15 mol). The reaction mixture was refluxed for 18 h, cooled to 23° C. and washed with ether. The aqueous solution was acidified with concentrated hydrochloric acid, saturated with sodium chloride and extracted with ethyl acetate. The organic extracts were combined and dried over anhydrous sodium sulfate. The ethyl acetate was evaporated under reduced pressure and the resulting yellow liquid was distilled under high vacuum; bp 104°–6° C./(0.3 mm); 10.8 g; 87%; ir (neat) $v_{max}$: 2095 (N$_3$) and 1708 cm$^{-1}$ (C=O of carboxylic acid; $^1$Hmr (CDCl$_3$) δ: 11.63 (1H, s, H of carboxylic acid), 3.3 (2H, m, δ-H), 2.4 (2H, m, α-H) and 2.0–1.2 ppm (4H, β-H and γ-H).

5-Azidovaleryl chloride

In a one neck round bottom flask containing 5-azidopentanoic acid (0.88 g, 0.068 mol) was added thionyl chloride (7.35 ml, 0.102 mol). The reaction mixture was stirred at 60° C. for 2 h and the thionyl chloride was evaporated under reduced pressure to give crude 5-azidopentanoyl chloride. The distillation of crude acyl chloride gave a colorless liquid; 6.93 (62%), bp 111°–4° C. (1.2–1.4 mm); ir (neat) $v_{max}$: 2100 (N$_3$) and 1800 cm$^{-1}$ (C=O); $^1$Hmr (CDCl$_3$) δ: 3.37 (2H,δ-H), 3.00 (2H, α-H) and 2.1–1.2 ppm (4H, β-H and γ-H).

4-(5'-azidopentanoylthio)-1-(paranitrobenzyl 2''-triphenylphosphoranylidene-2''-acetate)-2-azetidinone

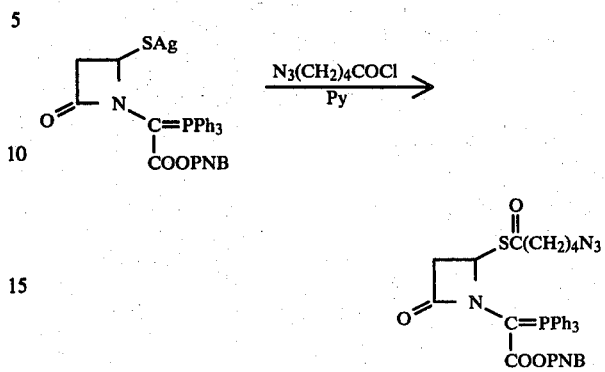

To a solution of the above silver thiolate (3.18 g, 4.79 mmol) in dichloromethane (50 ml), kept under a nitrogen atmosphere and cooled in ice-water bath, was added pyridine (0.43 ml, 5.31 mmol) followed by the dropwise addition (0.25 h) of a solution of 5-azidopentanoyl chloride (0.86 g, 5.27 mmol) in dichloromethane (4 ml). The reaction mixture was stirred at 0° C. for 2.5 h and 3 h at 23° C. The solids were filtered over a Celite pad and washed with some dichloromethane. The filtrate and washings were combined, washed successively with 10% hydrochloric acid solution, saturated sodium bicarbonate solution and water, dried over anhydrous sodium sulfate and concentrated to an orange syrup. Purification was achieved by a silica gel column (silica gel G, 45 g, fraction size: 50 ml, eluent: ethylacetatedichloromethane: 0%, 500 ml; 50%, 1000 ml). Combination and concentration of the appropriate fractions gave 1.51 g (46%) of yellow syrup; ir (CHCl$_3$) $v_{max}$: 2100 (N$_3$), 1750 (shoulder at 1765 (C=O of β-lactam and C=O of p-nitrobenzyl ester), 1695 (C=O of thioester), 1620 (phosphorane) and 1520 and 1350 cm$^{-1}$ (NO$_2$); Anal. calcd for C$_{35}$H$_{32}$N$_5$O$_6$SP: C 61.67, H 4.73, N 10.27, S 4.70; found: C 61.71, H 4.61, N 10.28, S 5.08.

Paranitrobenzyl 2-(4'-azidobutyl)-penem-3-carboxylate

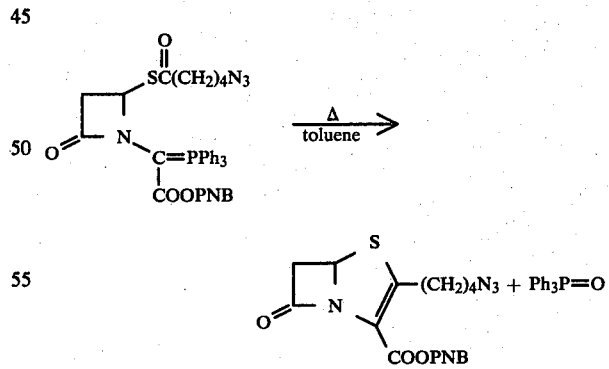

A solution of the above phosphorane (4.00 g, 5.87 mmol) in dichloromethane (25 ml) was diluted with toluene (600 ml) and then refluxed for 4–4.5 h under a nitrogen atmosphere after removal of dichloromethane (15 min, 100 ml of solvent was removed by a Dean-Stark trap). The reaction mixture was cooled to 23° C. and the toluene was evaporated in vacuo leaving a yellow oil which was purified by column chromatography [silica gel G 60 g, fraction size: 50 ml, eluent: etherbenzene, 0% (1000 ml), 2% (500 ml), 4% (1000 ml)]. Evaporation of the appropriate fractions gave a yellow syrup; 1.12 g, 47%; ir (CHCl₃) $\nu_{max}$: 2100 (N₃), 1785 (C=O of β-lactam), 1705 (C=O of p-nitrobenzyl ester), 1525 and 1350 cm⁻¹ (NO₂); ¹Hmr (CDCl₃) δ: 8.22 (2H, d, $J_{Hm,Ho}$=8.8 Hz, Hm of p-nitrobenzyl), 7.60 (2H, d, $J_{Ho,Hm}$=8.8 Hz, Ho of p-nitrobenzyl), 5.63 (1H, dd, $J_{5,6\ cis}$=3.8 Hz, $J_{5,6\ trans}$=2.0 Hz, H-5), 5.32 (center of ABq, $J_{a,b}$=14.2 Hz, CH₂ of p-nitrobenbyl), 3.83 (1H, dd, $J_{gem}$=16.3 Hz, $J_{6,5\ cis}$=3.8 Hz, H-6 cis, 3.40 (dd, $J_{6,5\ trans}$=2.0 Hz, H-6 trans), 3.28 (m, H'-4), 2.88 (2H, m, H'-1) and 1.0-1.3 ppm (4H, H'-2 and H'-3).

2-(4'-aminobutyl)-penem-3-carboxylic acid

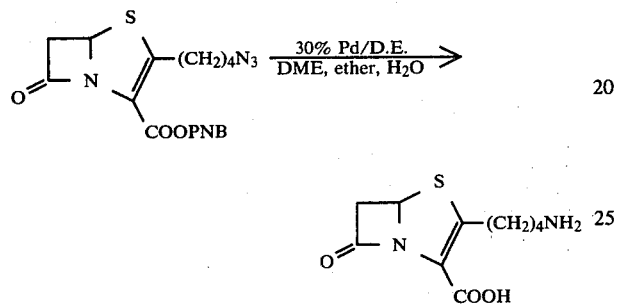

To a solution of the above penem (0.680 g, 1.69 mmol) in dimethoxyethane (50 ml) was successively added ether (50 ml), water (50 ml) and 30% palladium on diatomaceous earth (1.75 g). The reaction mixture was shaken at 23° C. for 2.5 h under 60 psi of hydrogen and filtered over a Celite pad. The pad was washed with water and the filtrate and washings were combined and washed with ether. The aqueous solution was stirred under high vacuum for 1.5 h, frozen at −78° C. and lyophylized; a yellow powder (0.283 g, 69.3%) was obtained; uv (H₂O) $\lambda_{max}$: 301 (ε=4052), 256 (ε=3470). The crude amino-acid was divided in two parts and purified by column chromatography (sephadex G 10, 90 g, column size: 1.6×100 cm, detector: R.I. Volume size: 1.5 ml, time: 10 min/fraction, chart speed: 0.05 cm/min, eluent: H₂O, attenuation: 40). The pure penem was obtained after lyophylization of the appropriate fractions: 98 mg, 24%, uv (H₂O) $\lambda_{max}$: 301 301 (ε=4966), 258 (ε=3800); ir (KBr) $\nu_{max}$: 1765 (C=O) of β-lactam) and 1575 cm⁻¹ (broad, carboxylate); ¹Hmr (D₂O) δ: 5.68 (1H, dd, $J_{5,6\ cis}$=3.5 Hz, $J_{5,6\ trans}$=1.7 Hz, H-5), 3.81 (1H, dd, $J_{gem}$=16.7 Hz, $J_{6,5\ cis}$=3.5 Hz, H-6 cis), 3.44 (dd, $J_{gem}$16.7 Hz, $J_{6,5\ trans}$=1.7 Hz, H-6 trans), 3.2-2.45 (4H, H'-1 and H'-4) and 2-1.1 ppm (4H, H'-2 and H'-3).

EXAMPLE 74

2-(p-Aminomethylphenyl)penem-3-carboxylic Acid
(via mercaptide intermediate)

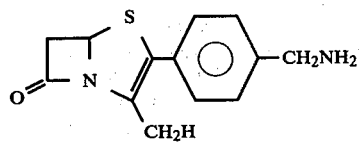

Parabromomethylbenzoic acid

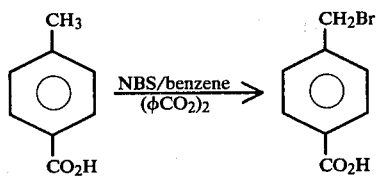

A mixture (suspension) of p-toluic acid (13.6 g, 98 mmol), N-bromosuccinimide (17.8 g, 99 mmol) and benzoylperoxide (0.2 g, 0.826 mmol) in dry benzene (100 ml) was heated at reflux for 21 h. After evaporation of the solvent in vacuo, the white residual solid was suspended in boiling water (100 ml), collected by filtration and washed with boiling water (4×100 ml). The crude dried product was crystallized from hot MeOH, yielding 15.0 g (69.7 mmol, 71.1%) of p-bromomethylbenzoic acid as white crystals mp 223°-225° C.; ¹Hmr (DMSO-d₆)δ: 4.75 (2H, s, —CH₂Br), 7.47-7.62-7.88-8.02 ppm (4H, A₂'B₂', aromatic Hs); ir (nujol) $\nu_{max}$: 2500-2600 (br.—CO₂H), and 1670 cm⁻¹(C=O—CO₂H). Procedure of D. H. Rich and S. K. Gurmura, J. Am. Chem. Soc., 97 1575 (1975).

Paraazidomethylbenzoic acid

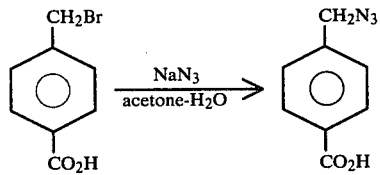

To a stirred solution of p-bromomethylbenzoic acid (13.607 g, 63.3 mmol) in acetone (300 ml) and H₂O (15 ml) was added dropwise at room temperature a solution of NaN₃ (4.123 g, 63.4 mmol) in H₂O (40 ml). The reaction mixture was stirred at room temperature overnight (ca 20 h). After evaporation of the acetone, the residual solid was suspended in water and filtered, yielding 10.13 g (57.2 mmol, 90.3%) of p-azidomethylbenzoic acid as a white powder: ¹Hmr (DMSO-d₆ 4.57 (2H, s, —CH₃N₃), 7.43-7.55-7.93-8.07 (4H, A₂'B₂', aromatic Hs) and 12.7 ppm (br, s, —CO₂H): ir (nujol) $\nu_{max}$: (—N₃) and 1670 cm⁻¹ (—CO₂H).

Paraazidomethylbenzoyl chloride

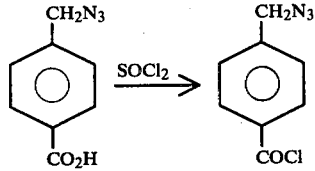

To a solution of p-azidomethylbenzoic acid (1.063 g, 6.00 mmol) in CH₂Cl₂ (60 ml) at room temperature were added dropwise thionyl chloride (1 ml, excess) and DMF (5 drops). The mixture was stirred at room temperature for 2.5 h and evaporated, yielding 1.13 g of title compound as a light yellow oil: ¹Hmr (CDCl₃) δ: 4.48 (2H, s, —CH₂N₃), 7.38-7.52-8.07-8.22 ppm (4H, A₂'B₂', aromatic Hs); ir (neat) $\nu_{max}$: 2090 (—N₃) and 1750 cm⁻¹ (br. —COCl). This material was used in the next step without further purification.

4-Paraazidomethylbenzoylthio-1-(paranitrobenzyl 2'-triphenylphosphoranylidene-2'-acetate)-2-azetidinone

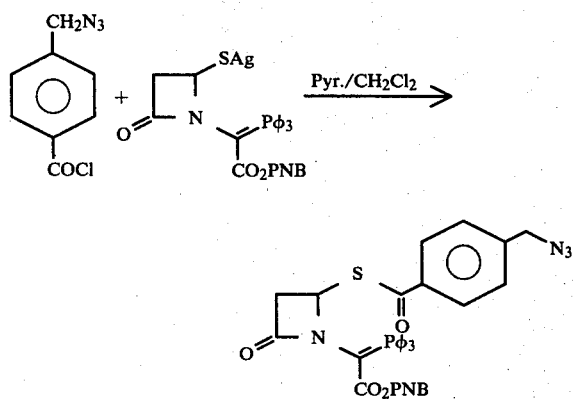

To a stirred solution of p-azidomethylbenzoyl chloride (1.112 g, 5.69 mmol) in CH₂Cl₂ (30 ml) was added at 0°–5° a solution of the above silver salt (3.32 g, 5.00 mmol) in CH₂Cl₂ (50 ml). After dropwise addition of pyridine (0.90 ml, 11.1 mmol), the mixture was stirred at room temperature for 5 h. The precipitate was removed and washed with EtOAc (100 ml). The filtrate and the washings were combined, washed successively with 0.1N HCl (130 ml), 2% NaHCO₃ (20 ml) and then brine and dried (Na₂SO₄). Evaporation of the solvents gave 2.66 g of coloured foam which was purified by column chromatography (SiO₂, 53 g; eluent; 50% benzene-ether) collecting 1.98 g (2.77 mmol, 55.3%) of the title phosphorane as yellowish foam; ¹Hmr (CDCl₃) δ: 4.43 ppm (s, —CH₂N₃): ir (neat) $\nu_{max}$: 2100 (—N₃) and 1750 cm⁻¹ (β-lactam and ester).

Paranitrobenzyl 2-paraazidomethylphenylpenem-3-carboxylate

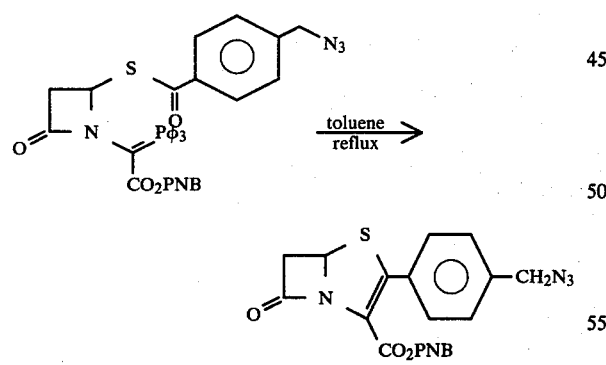

A solution of the above phosphorane (1.176 g, 1.65 mmol) in toluene (240 ml, dried over molecular sieves) and heated at reflux for 4.5 h. The solvent was evaporated and the crystals formed were collected, yielding 372 mg (0.850 mmol, 51.5%) of cyclic title compound. The mother liquor was purified by column chromatography (SiO₂, 15 g; eluent 20% ether in benzene) collecting 56 mg (0.128 mmol, 7.76%) of title compound. Total yield was 428 mg (0.979 mmol, 59.7%); mp 140°–5° C. (dec.); ¹Hmr (CDCl₃) δ: 3.57 (1H, dd, $J_{gem}$=16.5 Hz, $J_{trans}$=Hz, C₅—H), 3.93 (1H, dd, $J_{gem}$=16.5 Hz, $J_{cis}$=3.5 Hz, C₅—H), 4.37 (2H, s, —CH₂N₃), 5.22 (2H, ABq., J=14 Hz, benzylic protons), 5.80 (1H, dd, $J_{cis}$=3.5 Hz, $J_{trans}$=2 Hz, C₂—H), 7.2–7.6 (4H, m, aromatic Hs), 7.33–7.47-8.12–8.27 ppm (4H A₂' B₂', aromatic Hs); ir (CHCl₃ $\nu_{max}$: 2100 (—N₃), 1795 (C=O of β-lactam), 1720 (C=O of ester) and 1525 cm⁻¹ (—NO₂); uv (THF) $\lambda_{max}$: 290 (ε9×10³), 335 (ε8×10³); Anal. calcd for C₂₀H₁₅N₅O₅S: C 54.91, H 3.46, N 16.01; found: C 55.24, H 3.42, N 15.67%.

2-Paraaminomethylphenylpenem-3-carboxylic acid

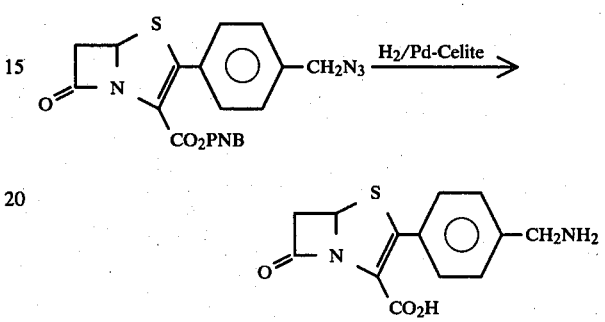

A mixture of the above cyclic ester (33 mg, 0.075 mmol), THF (4 ml), diethylether (3 ml) and H₂O (3 ml) was hydrogenated in the presence of 30% Pd-Celite (35 mg) at room temperature (2H: 30 psi, for 3.5 h. The catalyst was filtered and washed with ether and H₂O. The aqueous layer, washed with 50% ether/THF (3×9 ml) was lyophilized to give 15 mg (0.054 mmol, 72%) of the title amino-acid as a yellowish powder: ¹Hmr (D₂O) δ: 3.50 (1H, dd, $J_{gem}$=16 Hz, $J_{trans}$=2 Hz, C₆—H), 3.87 (1H, dd, $J_{gem}$=16 Hz, $J_{cis}$=4 Hz, C₆—H) and 7.42 ppm (4H, s, aromatic Hs); ir (nujol) $\nu_{max}$: 1770 (C=O of β-lactam) and 1585 cm⁻¹ (—CO₂H). A pure material was obtained by column chromatography on Sephadex G 10 (yield ca 30%): uv (H₂O $\lambda_{max}$: 323 (ε5.1×10³), 258 (shoulder ε8.9×10³).

EXAMPLE 75

2-(trans 3-Aminocyclobutyl)-penem-3-carboxylic Acid (via mercaptide intermediate)

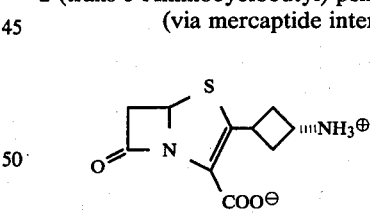

Methyl 3-azidocyclobutane carboxylate

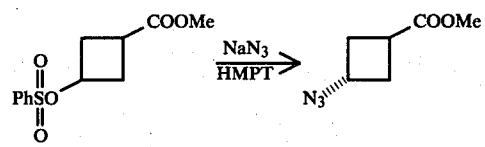

A solution of cis 3-carbomethoxycyclobutyl benzenesulfonate¹ (5.0 g, 18.5 mmol) in hexamethylphosphoramide (30 ml) was treated with sodium azide (2.41 g, 37.0 mmol) and stirred at 105° C. for 2.75 h. The reaction mixture was cooled to 23° C., diluted with water (300 ml) and extracted with ether (4×100 ml).

The organic extracts were combined, washed with water (2×10 ml), dried over anhydrous magnesium sulfate, and concentrated in vacuo to a slightly yellow liquid (2.53 g, 88%) which was distilled under reduced pressure; bp 72°-6° C./4.1 mm; 2.38 g; 83%; ir (neat) $\nu_{max}$: 2100 ($N_3$) and, 1730 and 1735 cm[1] (C=O of methyl ester; [1]Hmr (CDCl$_3$) δ: 4.2 (1H, m, H-1), 3.74 (3H, s, methyl) and 3.4–2.1 ppm (5H, H-2, H-3 and H-4).

[1]K. B. Wiberg, G. M. Lampman, R. P. Ciula, D. S. Connor, P. Schertler and J. Lavanish, Tetrahedron, 21, 2749–69 (1965).

Trans 3-azidocyclobutane carboxylic acid

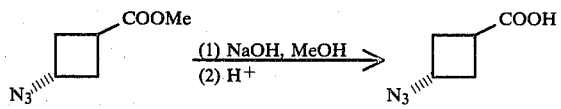

To a solution of trans methyl 3-azidocyclobutane carboxylate (2.38 g, 15.3 mmol) in methanol (5 ml) was added water (5 ml). The resulting cloudy mixture was stirred vigorously and treated dropwise (0.5 h) with an aqueous solution of sodium hydroxide (1N, 15.3 ml) at such a rate that the temperature was kept under 25° C. The reaction mixture was stirred at 23° C. for 2 h and the methanol was evaporated in vacuo to a slightly yellow residue which was diluted with water (10 ml). The aqueous solution was washed with ether (2×10 ml), acidified with 1N hydrochloric acid and extracted with dichloromethane (4×25 ml). The organic extracts were combined, washed with water, dried over anhydrous sodium sulfate and concentrated to a colorless oil which solidified on standing; 2.02 g, 93%; mp 39°–41° C. Anal. calcd for $C_5H_7N_3O_2$: C 42.55, H 5.00, N 29.78; found: C 42.41; H 5.02, N 29.59; ir (KBr) $\nu_{max}$: 2100 ($N_3$) and 1705 cm$^{-1}$ with shoulder at 1735 (C=O of carboxylic acid); [1]Hmr (CDCl$_3$) δ: 4.19 (1H, m, H-1) and 3.5–2.0 ppm (5H, H-2, H-3, H-4).

Trans 3-azidocyclobutanecarbonyl chloride

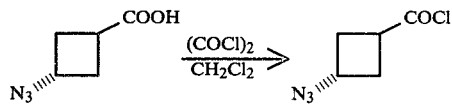

To a solution of trans 3-azidocyclobutanecarboxylic acid (0.58 g, 4.1 mmol) in dichloromethane (10 ml) was added oxalyl chloride (0.45 ml) followed by one drop of N,N-dimethylformamide. The reaction mixture was stirred at 23° C. until the evolution of gas ceased (∼2 h) and the solvent was evaporated in vacuo leaving a slightly yellow oil; 0.63 g, 95%; ir (neat) $\nu_{max}$: 2100 ($N_3$) and 1785 cm$^{-1}$ (C—O of acyl chloride); [1]Hmr (CDCl$_3$) δ: 4.12 (1H, m, H-1), 3.6 (1H, m, H-3) and 3.1–2.1 ppm (4H, H-2, H-4).

4-(3'-Azidocyclobutylcarbonylthio)-1-(paranitrobenzyl 2"-triphenylphosphoranylidene-2"-acetate)-2-azetidinone

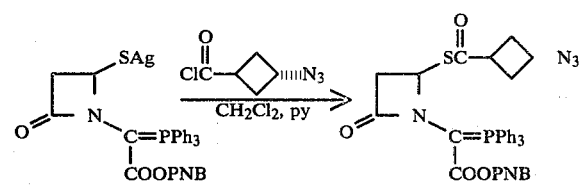

A solution of the above silver salt (2.62 g, 3.95 mmol) in dichloromethane (25 ml), kept under a nitrogen atmosphere, and containing one equivalent of pyridine (0.319 ml) was treated dropwise (0.5 h) with a solution of trans 3-azidocyclobutylcarbonyl chloride (0.61 g, 3.95 mmol) in dichloromethane (10 ml). The reaction mixture was stirred at 23° C. for 0.5 h; the precipitate was filtered off and washed with dichloromethane. The filtrate and washings were combined, washed with 1N hydrochloric acid, water, sodium bicarbonate and water, dried over anhydrous sodium sulfate and concentrated to an orange syrup which was chromatographed (silica gel G, 60 g, fraction size: 10 ml, eluent; ethyl acetate in dichloromethane with increasing polarity, 0%→50%). Evaporation of the appropriate fractions gave a yellow syrup; this syrup was dissolved in dichloromethane and the title compound crystallized out on standing; 1.30 g, 48.4%; mp 175°–180° C., dec. Anal. calcd for $C_{35}H_{30}N_5O_6SP$: C 61.85, H 4.45, N 10.30, S 4.72; found: C 61.64, H 4.62, N 10.15, S 4.89; ir (KBr) $\nu_{max}$: 2100 ($N_3$), 1758 (C=O of β-lactam and C=O of p-nitrobenzyl ester), 1680 (C=O of thioester), 1618 (phosphorane) and, 1515 and 1350 cm$^{-1}$ ($NO_2$).

Paranitrobenzyl 2-(trans 3'-azidocyclobutyl)-penem-3-carboxylate

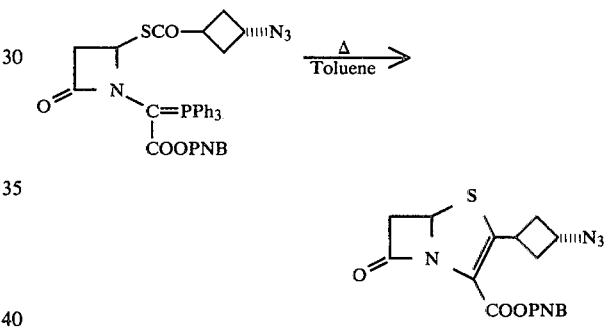

A suspension of the above phosphorane (0.998 g, 1.47 mmol) in toluene (90 ml) was heated at 110° C. for 12.5 h under a nitrogen atmosphere. The phosphorane went into solution as the suspension was warmed up. The reaction mixture was cooled to 23° C. and the toluene was evaporated under reduced pressure to an orange syrup which was chromatographed on a silica gel G column. Evaporation of the appropriate fractions gave a yellow syrup; 0.25 g, 42.4%, ir (neat) $\nu_{max}$: 2100 ($N_3$), 1785 (C=O of β-lactam), 1705 (C=O of p-nitrobenzyl ester), 1605 (C—O), 1580 (phenyl) and 1520 and 1350 cm$^{-1}$ ($NO_2$); [1]Hmr (CDCl$_3$) δ: 8.24 (2H, d, $J_{Hm,Ho}$=8.8 Hz, Hm of p-nitrobenzyl), 7.62 (2H, d, $J_{Ho,Hm}$=8.8 Hz, Ho of p-nitrobenzyl), 5.66 (1H, dd, $J_{5,6\ cis}$=3.6 Hz, $J_{5,6\ trans}$=1.9 Hz, H-5), 5.32 (2H, center of ABq, $J_{a,b}$=13.7 Hz, $CH_2$ of p-nitrobenzyl), 4.26 (1H, m, H'-3), 3.88 (1H, dd, $J_{6,5\ cis}$=3.6 Hz, $J_{gem}$=14.7 Hz, H-6 cis), 3.48 (1H, dd, $J_{6,5}$ trans=1.0 Hz, $J_{gem}$=14.7 Hz, H-6 trans) and 2.8–1.8 ppm (4H, 2H'-2,2H'-4).

2-(3'-aminocyclobutyl)-penem-3-carboxylic acid

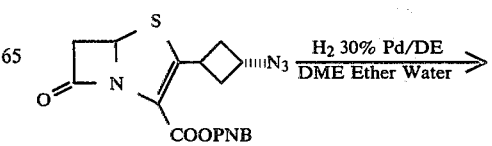

-continued

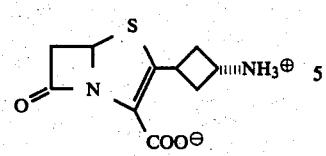

To a solution of the above penem (0.251 g, 0.63 mmol) in dimethoxyethane (14 ml) was successively added ether (14 ml), water (14 ml) and 30% Palladium on diatomaceous earth (0.5 g). The mixture was hydrogenated at 23° C. under 45 psi for 2.25 h and filtered over a Celite pad; the pad was washed with water. The filtrate and the washings were combined and diluted with ether. The aqueous phase was separated, washed with ether and lyophilized giving a yellow powder; 125 mg, 83%; uv (H$_2$O) λ$_{max}$: 303 (ε=3859), 255 (ε=2985). The yellow powder was triturated in water and the suspension was centrifuged; the supernatant was decanted and the solid was treated as before two more times. The white powder was cooled to −78° C. and dried under high vacuum; 24 mg, 16%; uv (H$_2$O) λ$_{max}$: 305 (ε=5064) 257 (ε=3822); ir (KBr) ν$_{max}$: 1775 (C=O of β-lactam),

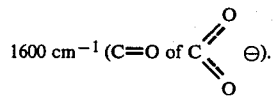

The title compound was found to be stable for more than 5 days in solution in water. This reaction was repeated using the conditions described above on a sample (900 mg) purified by preparative tlc; the crude sample [0.388 g, 71.7%; uv (H$_2$O) λ$_{max}$: 304 (ε=4422), 257 (ε=2962)] was triturated with water giving a white powder (0.250 g, 46%); uv (H$_2$O) λ$_{max}$: 304 (ε=5652) 257 (ε=3827); ir (KBr) ν$_{max}$: 1775 (C=O of δ-lactam), 1590 and 1565 cm$^{-1}$ (C=O of carboxylate); $^1$Hmr (D$_2$O) δ: 5.75 (1H, dd J$_{5,6\ trans}$=1.8 Hz, J$_{5,6\ cis}$=3.5 Hz, H-5), 3.85 (dd, J$_{6,5\ cis}$=3.5 Hz, J$_{gem}$=16.7 Hz, H-6 cis and 3.50 ppm (dd, J$_{6,5\ trans}$=1.8 Hz, J$_{gem}$=16.7 Hz, H-6 trans).

EXAMPLE 76

Sodium 2-(1H-Tetrazolemethyl)-penem-3-carboxylate
(via mercaptide intermediate)

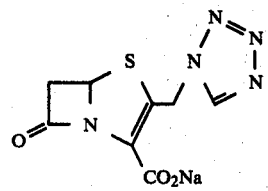

1H-Tetrazole-1-acetic acid

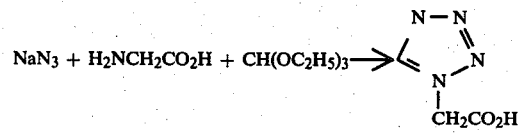

The title compound was prepared by a literature procedure* as follows: A mixture of sodium azide (10.5 g, 0.3 mol) and glacial acetic acid (125 ml) was blanketed with nitrogen and heated at 55° C. with stirring. After most of the solids had dissolved (15 min), glycine (18.75 g, 0.25 mol) and triethyl orthoformate (40 g, 0.27 mol) were added to the reaction mixture and heating at 55°-50° C. with stirring under nitrogen continued for 6 h. The reaction mixture was cooled to room temperature, acidified with concentrated hydrochloric acid (25 ml) and evaporated to dryers. The residue was extracted with ethyl acetate (4×100 ml) and the extracts evaporated to give 9.0 g (28%) of the title compound mp 121°-125° C. (lit. mp 125°-127° C.). $^1$Hmr (DMSO-d$_6$) δ: 5.35 (s, 2H,—CH$_2$—) and 9.25 ppm (s, 1H, C$_5$—H).
* CA 78, P111331 p-Nitrobenzyl
(4-[1H-tetrazole-1-acetyl]thio-2-azetidinone-1-yl)
triphenylphosphoranylideneacetate

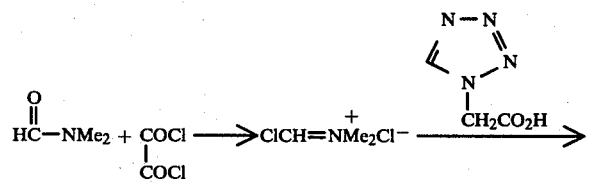

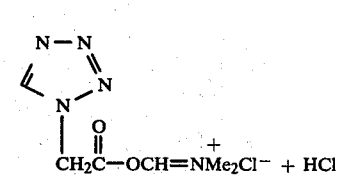

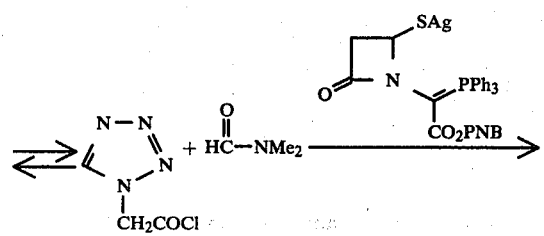

-continued

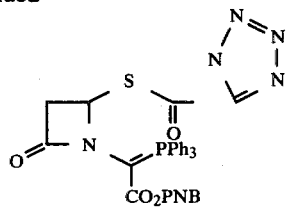

Preparation of the acylating mixture

Into a flame-dried and nitrogen purged 100 ml three-neck flask was added a solution of dry DMF (0.388 ml, 0.366 g, 5 mmol) dry and ethanol-free chloroform (20 ml); the solution was cooled to 0° C. under nitrogen with stirring. To this solution was added dropwise oxalyl chloride (0.42 ml, 0.634 g, 5 mmol) at such a rate as to keep the fast evolution of gas under control. After the addition was completed (5 min), the reaction mixture was stirred at room temperature for 15 min. Powdered 1H-tetrazole-1-acetic acid (0.64 g, 5 mmol) was added to the above solution and the mixture stirred at room temperature until all material had dissolved (5–10 min). A sample was examined by ir and showed carbonyl bands at 1805 and 1755 cm$^{-1}$.

Preparation of the title compound

To a solution of silver 1-(paranitrobenzyl 2'-triphenylphosphoranylidene-2'-acetate)-2-azetidinone-4-thiolate (3.3 g, 5 mmol) and pyridine (1 ml, 12 mmol) in dry methylene chloride (10 ml) at 0° C. was added portionwise the above acylating mixture and the resulting mixture was stirred at room temperature for 2 h. The reaction mixture was diluted with CH$_2$Cl$_2$ (100 ml) and filtered through a pad of Celite. The filtrate was washed successively with water (80 ml), 1% hydrochloric acid (80 ml), 1% sodium bicarbonate (100 ml) and water (100 ml) and dried. Removal of the solvent by evaporation left a residue which was purified by wet column chromatography on silica (8 cm×4 cm I.D), using an eluent first 2% MeOH in CHCl$_3$ (~300 ml) and then 5% MeOH in CHCl$_3$. The fractions containing the title compound (Rf 0.31, silica with 5% MeOH—CHCl$_3$) were combined and evaporated to give 1.5 g (45%).

p-Nitrobenzyl 2-(1H-tetrazolemethyl)-penem-3-carboxylate

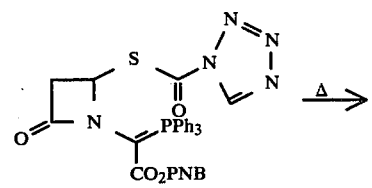

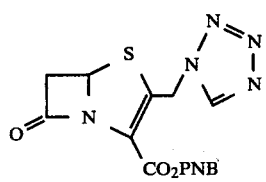

A solution of the above phosphorane (1.5 g) in toluene (200 ml) was heated under reflux for 2 h and then cooled to room temperature and filtered. Removal of the solvent by evaporation gave 880 mg of crude title compound as an oil which solidified. This product showed on tlc (silica, 5% MeOH—CH$_2$Cl$_2$) three spots of Rf 0.68, 0.43 and 1. The crude material was purified by wet column chromatography on a silica column (26 cm×1.8 cm I.D) using 2% MeOH—CHCl$_3$ mixture as eluent to give 265 mg (30%) of title compound, mp 145°–147° C. (CH$_2$Cl$_2$-ether); ir (nujol) $\nu_{max}$: 1790, 1750, 1710 cm$^{-1}$; $^1$Hmr (CDCl$_3$) δ: 3.56 (dd, J$_{gem}$=14, J$_{5,6\ trans}$=2 Hz, 1H, H-6$_b$), 3.93 (dd, J$_{gem}$=14, J$_{5,6\ cis}$=3.8 Hz, 1H, H-6$_a$), 5.37 (center of ABq, J=14 Hz, 2H, CH$_2$PNB), 5.7 (dd, J$_{5,6\ trans}$=2.0, J$_{5,6\ cis}$=3.8 Hz, 1H, H-5), 5.8 (center of ABq, J=16 Hz, 2H,—CH$_2$N—), 7.57 (d, J=8 Hz, 2H, Ho aromatic), 8.23 (d, J=8 Hz, 2H, Hm aromatic) and 8.86 ppm (s, 1H, N=CH—). Anal calcd for C$_{15}$H$_{12}$N$_6$O$_5$S: C 46.39, H 3.11, N 21.64; found: C 46.08, H 3.00, N 21.39.

Sodium 2-(1H-tetrazolemethyl)-penem-3-carboxylate

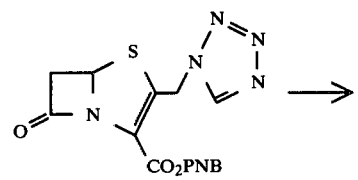

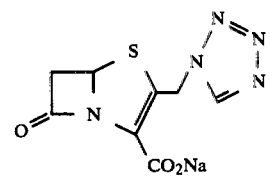

To a solution of the above ester (106 mg, 0.28 mmol) in freshly distilled THF (10 ml) was added ether (10 ml), a solution of sodium bicarbonate (23.4 mg) in water (10 ml) and Palladium on diatomaceous earth catalyst (110 mg) and the mixture was hydrogenated in a Parr apparatus at 50 psi for 5 h. The reaction mixture was filtered through a pad of Celite and the pad washed with water (5 ml). The combined filtrate and washings were extracted with ethyl acetate (2×20 ml) and the aqueous phase was lyophilized to give 63 mg (85%) of title compound as an amorphous powder; $^1$Hmr (D$_2$O) δ: 3.53 (dd, J$_{gem}$=14, J$_{5,6\ trans}$=2.0 Hz, 1H, H-6$_b$), 3.90 (dd, J$_{gem}$=14, J$_{5,6\ cis}$=3.8 Hz, 1H, H-6$_a$), 5.73 (dd, J$_{5,6\ trans}$=2.0, J$_{5,6\ cis}$=3.8 Hz, 1H, H-5), 6.07 (center of ABq, J=16 Hz, 2H,—CH$_2$N—) and 9.33 ppm (s, 1H, —NCH=N—); uv λ$_{max}$: 306 (3260).

EXAMPLE 77

Sodium 2-(3,5-Dimethyl-1H-pyrazolemethyl)-penem-3-carboxylate (via mercaptide intermediate)

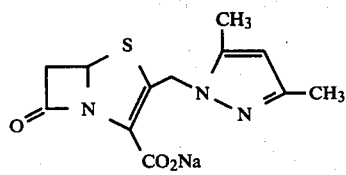

p-Nitrobenzyl (4-[3,5-dimethylpyrazole-1-acetyl)thio-2-azetidinone-1-yl]) triphenylphosphoranylideneacetate

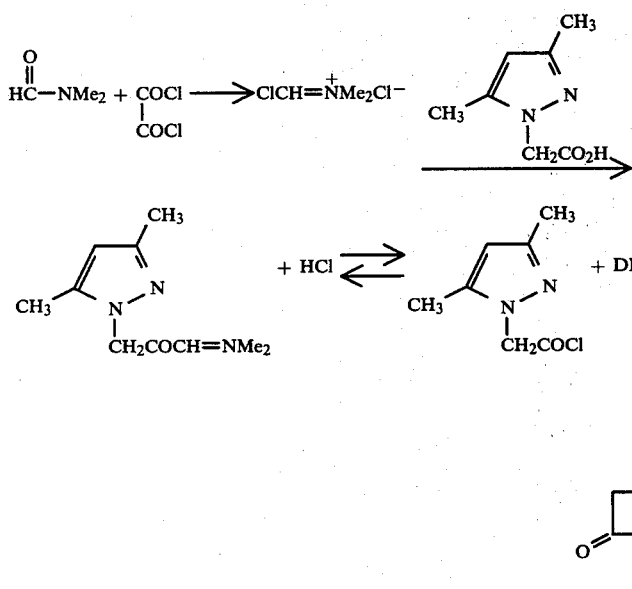

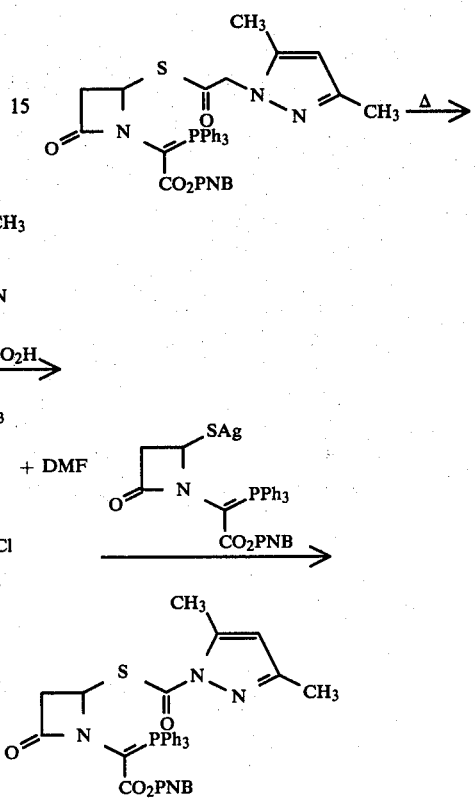

p-Nitrobenzyl 2-(3,5-dimethyl-1H-pyrazolemethyl)-penem-3-carboxylate

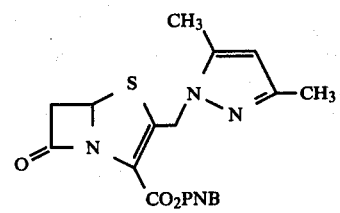

Preparation of the acrylating mixture.

Into a flame-dried and nitrogen purged 50 ml three-neck flask was added a solution of (0.365 g, 5 mmol) of dry DMF in (10 ml) dry and ethanol-free chloroform (10 ml); the solution was cooled to 0° C. under nitrogen with stirring. To this solution was added dropwise a solution of oxalyl chloride (0.635 g, 5 mmol) in chloroform (5 ml) at such a rate as to keep the fast evolution of gasses under control. After the addition was completed, the reaction mixture was stirred at room temperature for 10–15 min. The ir spectrum of this solution showed two carbonyl bands at 1715 and 1780 cm$^{-1}$.

Preparation of title compound

A solution of the silver 1-(paranitrobenzyl 2'-triphenylphosphoranylidene-2'-acetate)-2-azetidinone-4-thiolate (3.32 g, 5 mmol) and pyridine (0.80 g, 10 mmol) in dry methylene chloride (20 ml) was blanketed with nitrogen and cooled to 0° C. with stirring. To this solution was added the above acylating mixture. After stirring at 0° C. for 15 min and at room temperature for 3 h, the reaction mixture was filtered through a pad of Celite. The filtrate was washed successively with water (2×20 ml), 1% hydrochloric acid (25 ml), 2.5% NaHCO$_3$ (25 ml) and water (25 ml) and dried. Removal of the solvent in vacuo left a residue (3 g) which was purified by wet column chromatography on silica (140 g) using 2% MeOH in CHCl$_3$ as eluent to give 0.826 g (24%) of title compound as a syrup; Rf 0.35 (silica, 5% MeOH—CH$_2$Cl$_2$) $\nu_{max}$: 1760 (ester and lactam), 1685 (S—C=) cm$^{-1}$.

A solution of the above phosphorane (0.632 g, 0.95 mmol) in dry toluene (60 ml) was refluxed for 3.5 h. Removal of the solvent by evaporation left a syrup which was purified by wet column chromatography on a silica column (30 cm×1.5 cm I.D) using a 2% MeOH in CH$_2$Cl$_2$ solvent mixture as eluent. A yield of 0.252 g (66.5%) of crystalline title compound was obtained, mp 156°–158° C.; Rf 0.6 (silica, 5% MeOH—CH$_2$Cl$_2$); ir (CHCl$_3$) $\nu_{max}$: 1797, 1710 cm$^{-1}$; $^1$Hmr (CDCl$_3$) δ: 2.20 (s, 6H, 2CH$_3$), 3.43 (dd, J$_{gem}$=14, J$_{5,6\ trans}$=2 Hz, 1H, H-6$_b$), 3.83 (dd, J$_{gem}$=14, J$_{5,6\ cis}$=4 Hz, 1H, H-6$_a$), 5.07 (m, 4H, —CH$_2$PNB and —CH$_2$N—), 5.60 (dd, J$_{5,6\ trans}$=2, J$_{5,6\ cis}$=4 Hz), 5.80 (s, 1H, —CH=), 7.60 (d, J=8 Hz, 2H, Ho aromatic) and 8.23 ppm (d, J=8 Hz, Hm aromatic).

Sodium 2-(3,5-dimethyl-1H-pyrazolemethyl)-penem-3-carboxylate

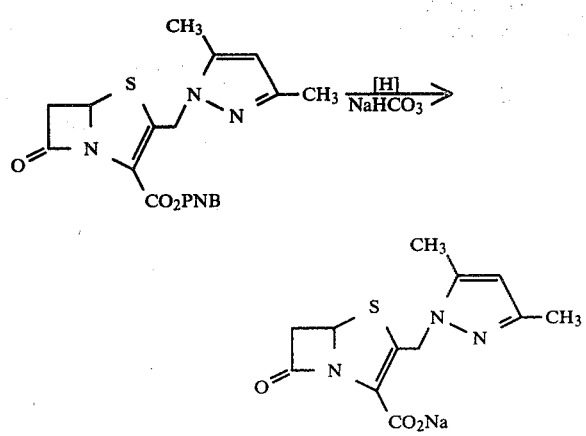

To a solution of the above ester (83 mg) in freshly distilled THF (10 ml) was added ether (10 ml), a solution of 16.8 mg of sodium bicarbonate in water (10 ml) and 20% palladium on Celite catalyst (110 mg) and the mixture was shaken under nitrogen in a Paar apparatus at 45 psi for 5 h. The reaction mixture was filtered through a pad of Celite and the cake on the funnel washed with water (5 ml). The combined filtrate and washings were extracted with benzene (10 ml) and ethyl acetate (10 ml) and the extracts were discharged. The aqueous phase was lyophilized to give 57 mg (94%) of the title compound as an amorphous powder; uv $\lambda_{max}$: 304 ($\epsilon$=4740); ir (nujol) $\nu_{max}$: 1775, 1590 cm$^{-1}$; $^1$Hmr (D$_2$O) δ: 2.23 (s, 6H, 2CH$_3$), 3.40 (dd, J$_{gem}$=14, J$_{5,6\ trans}$=2 Hz, 1H, H-6$_b$), 3.83 (dd, J$_{gem}$=14, J$_{5,6\ cis}$=4 Hz, 1H, H-6$_a$), 5.20 (center of ABq J=14 Hz, 2H, —CH$_2$N—), 5.63 (dd, J$_{5,6\ trans}$=2, J$_{5,6\ cis}$=4 Hz, 1H, H-5) and 6.0 ppm (s, 1H, C═C—H).

EXAMPLE 78

2-(cis-3'-Aminocyclobutyl)penem-3-carboxylic Acid (via mercaptide intermediate)

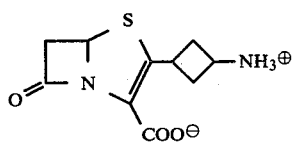

cis Methyl 3-azidocyclobutane carboxylate

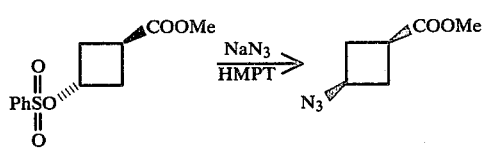

A solution of trans 3-carbomethoxycyclobutyl benzenesulfonate* (6.1 g, 22.6 mmol) in hexamethylphosphoramide (35 ml) was treated with sodium azide (289 g, 44.5 mmol) and stirred at 105° C. for 2.75 h. The reaction mixture was cooled to 23° C., diluted with water (350 ml) and extracted with ether (4×125 ml). The organic extracts were combined, washed with water (2×15 ml), dried over anhydrous magnesium sulfate and concentrated in vacuo to a slightly yellow liquid which was distilled under high vacuum; bp 66°-7° C. (0.6 mm); 2.8 g; 80%; ir (neat) $\nu_{max}$: 2100 (N$_3$) and 1735 cm$^{-1}$ (C═O); Hmr (CDCl$_3$) δ: 40.34 (m, H-1), 3.7 (s, methyl) and 2.9–2.1 ppm (5H, 2H-2, H-3 and 2H-4).

*K. B. Wiberg, G. M. Sampman, R. P. Ciula, D. S. Connor, P. Schertler and J. Savanish, Tetrahedron 21, 2749–69 (1965)

cis 3-Azidocyclobutane carboxylic acid

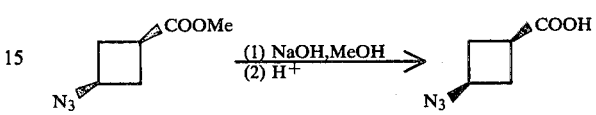

To a solution of cis-3-carbomethoxycyclobutylazide (2.8 g, 18.0 mmol) in methanol (8 ml) was added water (8 ml). The resulting cloudy solution was well stirred and treated dropwise (0.5 h) with an aqueous solution of sodium hydroxide (1N, 18.0 ml) at such a rate that the temperature was kept under 28° C. The reaction mixture was stirred at 23° C. for 2 h and the solvents were evaporated in vacuo to a yellow residue which was diluted with water (12 ml). The aqueous solution was washed with ether (2×15 ml), acidified with 1N hydrochloric acid and extracted with dichloromethane (4×30 ml). The organic extracts were combined, washed with water, dried over anhydrous sodium sulfate and concentrated to a colorless oil; 2.29 g, 90%; ir (neat) $\nu_{max}$:2100 (N$_3$) and 1705 cm$^{-1}$ (C═O of carboxylic acid); $^1$Hmr (CDCl$_3$) δ:11.88 (1H, s, H of carboxylic acid), 3.8 (1H, m, H-1) and 3.2–2.0 ppm (5H, 2H-2, H-3 and 2H-4).

cis 3-Azidocyclobutanecarbonyl chloride

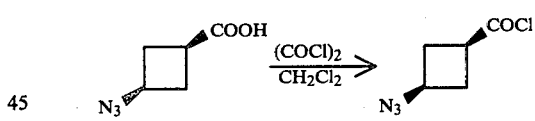

A solution of cis-3-carboxycyclobutyl azide (1.86 g, 13.2 mmol) in dichloromethane (30 ml) was treated with oxalyl chloride (1.5 ml, 17.2 mmol) followed by one drop of N,N-dimethylformamide. The reaction mixture was stirred at 23° C. until the evolution of gas ceased (0.5–1 h) and the solvent was evaporated in vacuo leaving a yellow oil; 2.0 g, 95% ir (neat) $\nu_{max}$:2100 (N$_3$) and 1785 cm$^{-1}$ (C═O of acylchloride).

4-(cis 3'-azidocyclobutanecarboxylthio)-1-(paranitrobenzyl 2''-triphenylphosphoranylide-2''-acetate)-2-azetidinone

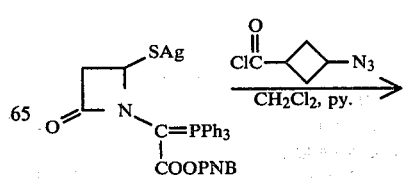

-continued

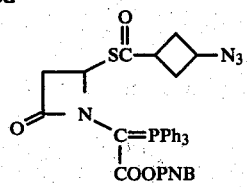

A solution of the silver mercaptide (8.90 g, 13.4 mmol) in dichloromethane (75 ml) kept under a nitrogen atmosphere and containing one equivalent of pyridine was treated dropwise (30 min) with a solution of cis-3-azidocyclobutylcarbonyl chloride (2.10 g, 13.2 mmol) in dichloromethane (30 ml). The reaction mixture was stirred at 23° C. for 1.5 h, and the solids were filtered off and washed with some dichloromethane. The filtrate and washings were combined, washed successively with 1N hydrochloric acid, water, saturated aqueous sodium bicarbonate solution and water, dried over anhydrous sodium sulfate and concentrated to an orange syrup. Purification was achieved by column chromatography (silica gel 60; 210 g; fraction size: 50 ml; eluent, EtOAc: CH$_2$Cl$_2$ with increasing polarity from 0% to 50%). The appropriate fractions were combined and the solvent was evaporated partially until the title compound crystallized out slowly; 2.5 g; mp 186°–189° C.; 27.9%. The filtrate was concentrated and filtration of the crystals gave 1.7 g of title compound for a total amount of 4.2 g, 46.8%. Anal. calcd for C$_{35}$H$_{30}$N$_5$O$_6$SP: C 61.85, H 4.45, N 10.30, S 4.75; found: C 61.13, H 4.48, N 10.09, S 4.59; ir (KBr) $\nu_{max}$:2100 (N$_3$), 1755 (C=O of β-lactam and C=O of p-nitrobenzyl ester), 1690 and 1675 (C=O of thioester), 1625 (phosphorane) and 1510 and 1345 cm$^{-1}$ (NO$_2$).

paranitrobenzyl 2-(cis 3'-azidocyclobutyl)penem-3-carboxylate

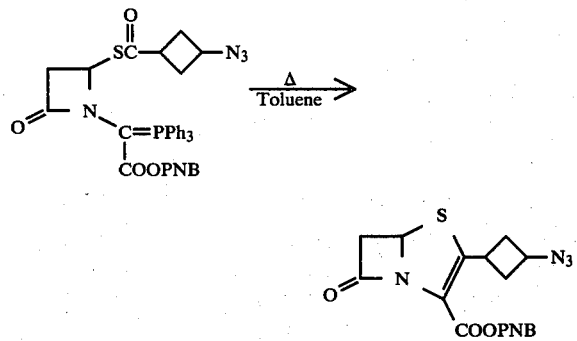

A suspension of the above phosphorane (2.20 g, 3.24 mmol) in toluene (220 ml) was stirred under a nitrogen atmosphere at 110° 1 C. for 5.5 h. The phosphorane went into solution as the temperature increased. The reaction mixture was cooled to 23° C. and the solvent was evaporated under reduced pressure to a yellow solid which was purified by column chromatography (silica gel 60: 65 g, fraction size: 20 ml; eluent: ether-benzene, 2%). Concentration of the appropriate fractions gave a colorless syrup which crystallized upon trituration with ether; 0.61 g mp 117°–118° C.; 47%. Anal. calcd for C$_{17}$H$_{15}$N$_5$O$_5$S: C 50.87, H 3.77, N 17.45, S 7.99; found: C 50.95, H 3.60, N 17.27, S 7.72; ir (KBr) $\nu_{max}$:2110 (N$_3$), 1795 (C=O of β-lactam), 1700 (C=O of p-nitrobenzyl ester), 1605 and 1570 (C=C and phenyl) and 1520 cm$^{-1}$ (NO$_2$); $^1$Hmr (CDCl$_3$) δ:8.34 (2H, d, J$_{Hm,Ho}$=8.8 Hz, Hm of p-nitrobenzyl), 7.58 (2H, d, J$_{Ho,Hm}$=8.8 Hz, Ho of p-nitrobenzyl), 5.63 (1H, dd, J$_{5,6}$ cis=4.0 Hz, J$_{5,6}$ trans=2.1 Hz, H-5), 5.29 (center of ABq, J$_{a,b}$=13.9 Hz, CH$_2$ of p-nitrobenzyl), 4.3–3.2 (4H, H-6 cis, H-6 trans, H'-1 and H'-3), 3.45 (dd, J$_{gem}$=16.5 Hz, J$_{6,5 trans}$=2.1 Hz, H-6 trans) and 3.0–1.7 ppm (4H, 2H'-2 and 2H'-4); uv (CHCl$_3$) λ$_{max}$:266 (ε=10950) and 321 (ε=8430).

2-(cis 3'-aminocyclobutyl)-penem-3-carboxylic acid

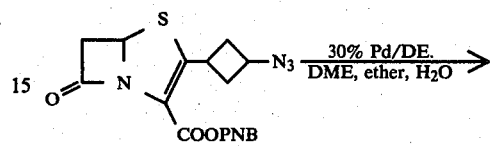

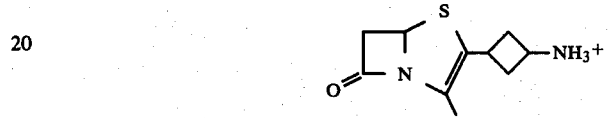

To a solution of the above ester compound (0.344 g, 0.86 mmol) in dimethoxyethane (30 ml) was successively added ether (25 ml), water (25 ml) and 30% palladium on Celite (0.70 g). The reaction mixture was hydrogenated at 23° C. for 2.5 h under 50 psi and filtered over a Celite pad. The filtrate was diluted with ether and the aqueous phase was separated, washed with ether and lyophylized: 0.172 g, 83%; uv (H$_2$O) λ$_{max}$: 305 (ε3416), 256 (ε2614). The crude material was triturated in water and the suspension was centrifuged. The supernatant was decanted and the white powder was freeze-dried 0.057 g, 27.7% uv (H$_2$O) λ$_{max}$: 305 (ε4644), 257 (68 3323); ir (KBr) $\nu_{max}$: 1765 (C=O of β-lactam) and

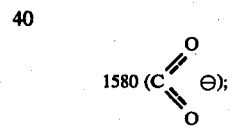

1580 (C $^1$Hmr (D$_2$O) δ: 5.70 (1H, dd, J$_{5,6}$ cis=3.5 Hz, J$_{5,6}$ trans=1.7 Hz, H-5), 4.3–3.3 (4H, 2H-6, H'-1 and H'-3) and 3.0–1.8 ppm (4H, 2H'-2 and 2H'-4).

EXAMPLE 79

2-(trans-2-Aminoethyl-1-cyclopropyl)-penem-3-carboxylic Acid (via mercaptide intermediate)

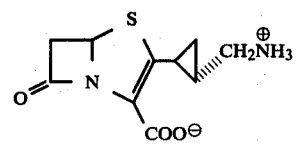

trans*-ethyl 2-hydroxymethyl-1-cyclopropanecarboxylate[1]

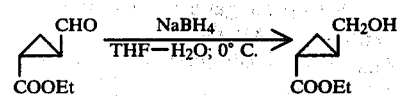

Sodium borohydride (0.798 g, 21.08 mmol) was dissolved in water (ml) and diluted with cold (0° C.) THF (150 ml). Then ethyl 2-formyl-1-cyclopropanecarboxylate (7.490 g, 52.70 mmol) in THF (20 ml) was added dropwise (10 min) to the cold (0° C.) solution. After one h at 0° C. tlc indicated no substrate left. The mixture was diluted with ether (500 ml) and washed with brine, dilute HCl (2%), saturated sodium bicarbonate and brine to neutral pH. After drying on anhydrous magnesium sulfate the organic phase was concentrated under reduced pressure and distilled under vacuum to give a clear oil: 6.022 g (79%); bp 86°–92° C./0.7 mm; ir (film) $\nu_{max}$: 3440 (OH), 1722 cm$^{-1}$ (C=O); $^1$Hmr (CDCl$_3$) δ: 4.10 (2H, q, J=8, CH$_2$—CH$_3$), 3.5 (2H, m which formed two doublets by addition of D$_2$O at 3.56 and 3.50, J=6, J=6, CH$_2$—OH), 2.65 (1H, m, exchanged by D$_2$O, OH), 1.8~0.6 (4H, m, cyclopropyl), 1.26 (3H, s, J7, CH$_3$—CH$_2$) [1] W. Ando, I. Imai and T. Migisa, J. Org. Chem., 37, 3596 (1972)

*Trans on the basis that the cis isomer forms a lactone.

trans-Ethyl 2-methanesulfonyloxymethyl-1-cyclopropanecarboxylate

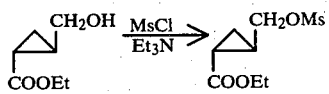

A solution of trans-ethyl 2-hydroxymethyl-1-cyclopropanecarboxylate (1.136 g, 7.88 mmol) in dry tetrahydrofuran (20 ml) was cooled to 0° C. (ice bath), treated dropwise with mesyl chloride (0.675 ml, 8.66 mmol) and then treated immediately with triethylamine (1.32 ml, 9.52 mmol). This solution was stirred at 0° C. for 1.5 h (tlc indicated no substrate left). After dilution with ether (200 ml), the solution was washed with water, saturated ammonium chloride (10 ml), brine and dried over anhydrous magnesium sulfate. Evaporation of the solvent under reduced pressure gave a clear oil, 1.690 g (97%) which was used as such for the next step without purification. ir (film) $\nu_{max}$: 1720 cm$^{-1}$ (C=O); $^1$Hmr (CDCl$_3$) δ: 4.13 (2H, q, J=7, CH$_2$—CH$_3$, 3.05 (2H, s, CH$_2$—OMs), 2.0~0.6 (4H, m, cyclopropyl), 1.27 ppm (3H, t, J=7, CH$_3$—CH$_2$).

trans-Ethyl 2-azidomethyl-1-cyclopropanecarboxylate

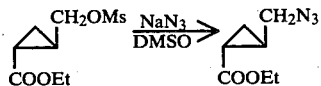

The trans-ethyl 2-methanesulfonyloxymethyl-1-cyclopropanecarboxylate from the previous step (1.655 g, 7.45 mmol) was dissolved in dry dimethyl sulfoxide (20 ml), treated with sodium azide (0.969 g, 14.89 mmol), and stirred at room temperature for 16 h. (tlc indicated no substrate left). After dilution with water, (50 ml), the reaction mixture was extracted with ether (3×50 ml) and the combined organic extracts washed several times (×6) with water and then brine (×3). After drying on anhydrous magnesium sulfate, evaporation of the solvent under reduced pressure gave an oil. Bulb to bulb gave a clear liquid; 1.178 g (93%); bp 86°–90° C./4.0 mm Hg (air bath temperature); ir (film) $\nu_{max}$: 2090 (N$_3$), 1725 cm$^{-1}$ (C=O); $^1$Hmr (CDCl$_3$) δ:4.13 (2H, q, J=7, CH$_2$—CH$_3$), 3.21 (2H, d, J=6, CH$_2$—OMs), 2.0–0.6 (4H, m, cyclopropyl), 1.23 (3H, t, 5.7, CH$_2$—CH$_3$). Anal. calcd for C$_7$H$_{11}$N$_3$O$_2$: C 49.69, H 6.55, N 24.83; found: C 49.81, H 6.71, N 24.29.

trans-2-azidomethyl-1-cyclopropanecarboxylic acid

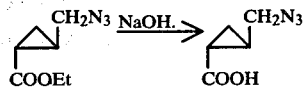

A solution of trans-ethyl-2-azidomethyl-1-cyclopropane carboxylate (7.282 g, 37.13 mmol) in a mixture of methanol (20 ml) and water (10 ml) was cooled to 0° C. and treated dropwise with 40.8 ml of 1M sodium hydroxide in water (40.8 mmol). After the addition was completed the bath was removed and the solution was stirred at room temperature for 3 h. The methanol was evaporated under reduced pressure and the aqueous solution was extracted with ether (2×10 ml). After acidification with dilute hydrochloric acid (3N), the aqueous phase was extracted with dichloromethane (4×25 ml) and the combined organic extracts washed with water (10 ml), brine (10 ml) and dried over anhydrous sodium sulfate. Evaporation of the solvent and distillation (bulb to bulb) of the residue under vacuum gave 4.830 g (92%) of a clear oil; bp 100°–108° C./0.6 mm Hg (air bath temperature); ir (film) $\nu_{max}$: 2095 (N$_3$), 1695 cm$^{-1}$ (C=O); $^1$Hmr (CDCl$_3$) δ: 3.25 (2H, d, J=6, CH$_2$N$_3$), 2.0~0.6 (4H, m, cyclopropyl), 12.3 (1H, s, COOH). Anal. calcd for C$_5$H$_7$N$_3$O$_2$: C 42.55, H 5.00, N 29.77; Found: C 42.55, H 4.89, N 29.75.

trans 2-azidomethyl-1-cyclopropanecarboxylic acid chloride

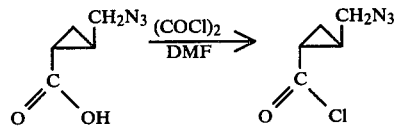

A solution of trans-2-azidomethyl-1-cyclopropane carboxylic acid (2.188 g, 15.50 mmol) in dry dichloromethane (25 ml) was treated at room temperature with oxalyl chloride (1.57 ml, 18.60 mmol) and a drop of N,N-dimethylformamide. After the evolution of gas has ceased (2.5 h), the solvent was evaporated under reduced pressure and the residue was distilled under vacuum (bulb to bulb distillation) to give 2.411 g (98%) of a clear oil: bp 70°–75° C./0.8 mm Hg (air bath temperature; ir (film) $\nu_{max}$: 2100 (N$_3$), 1775 cm$^{-1}$ (C=O); $^1$Hmr (CDCl$_3$) δ: 3.33 (2H, d, J=6, CH$_2$N$_3$) ~2.2–1.0 ppm (4H, m, cyclopropyl).

(1'S,2'R,4R and 1'R,2'S,4S; 1'S,2'R,4S and 1'R,2'S,4R) (trans-2-azidomethyl-1-cyclopropanecarboxylthio)-1-(paranitrobenzyl 2''-triphenylphosphoranylidene-2''acetate)-2-azetidinone

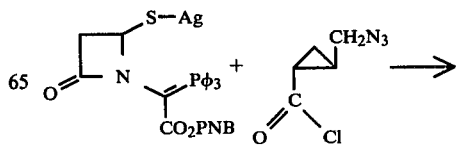

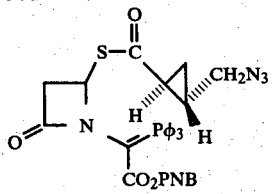

A solution of (4R and 4S) silver 1-(paranitrobenzyl 2'-triphenylphosphoranylidene-2'acetate)-2-azetidinone-4-thiolate (2.736 g, 4.125 mmol) in dry dichloromethane (28 ml) was cooled at 0° C. (ice bath) and then treated dropwise with pyridine (0.48 ml) and then with the trans-2-azidomethyl-1-cyclopropanecarboxylic acid chloride (0.855 g, 5.36 mmol) in dry dichloromethane (2 ml). After 10 minutes at 0° C., a heavy precipitate was formed and tlc indicated no substrate left. The reaction mixture was filtered on Celite and the combined filtrate and washings were washed with dilute hydrochloric acid (0.6 N, 20 ml), brine, saturated sodium bicarbonate (X2), brine and dried over anhydrous sodium sulfate. Evaporation of the solvent left an oil which upon crystallization from dichloromethane benzene gave 1.731 g (62%) of a white powder. The mother liquors were chromatographed on silica gel (20 g, elution dichloromethane-ethyl acetate; 0–40%) and gave 0.862 g (30%) of product. (total yield: 92%): mp 179°–183° C. (benzene-dichloro methane); ir (CH$_2$Cl$_2$) $\nu_{max}$: 2100 (N$_3$) 1755 (C=O β-lactam), 1675 (C=O of thioester) 1620, 1540 cm$^{-1}$ (NO$_2$). Anal. calcd for C$_{35}$H$_{30}$N$_5$O$_6$PS: C 61.84, H 4.45, N 10.30, S 4.72; found: C 61.32, H 4.40, N 9.92, S 4.67.

(1'R,2'S,5R and 1'S,2'R,5S; 1'S,2'R,5R and 1'R,2'S,5S) Paranitrobenzyl 2-(trans-2-azidomethyl-1-cyclopropyl)-penem-3-carboxylate

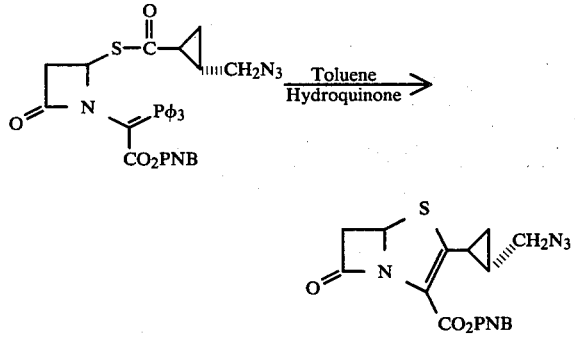

A suspension of the (1'S,2'R,4R and 1'R,2'S,4S; 1'S,2'R,4S and 1'R,2'S,4R) 4-(trans-2-azidomethyl-1-cyclopropane carbonylthio)-1-(paranitrobenzyl 2''-triphenylphosphoranylidene-2''-acetate)-2-azedidinone (0.556 g, 0.82 mmol) in dry tolune (50 ml) was heated under reflux for 10 h in the presence of a trace of hydroquinone. The solvent was evaporated under reduced pressure and the residual oil was immediately chromatographed on 20 g of silica gel. A mixture of benzene and ethyl acetate (8:2) eluted 0.241 g (73%) of the penem as a light yellow oil which crystallized on standing: mp 113°–118° C. (dichloromethane-ether); ir (KBr) $\nu_{max}$: 2085 (N$_3$), 1792 (C=O β-lactam), 1695 (C=O of ester), 1515 cm$^{-1}$ (NO$_2$); $^1$Hmr (CDCl$_3$) δ:(mixture of diastereoisomers) 8.23 (2H, d, J$_{HmHo}$=8.8, Hm of p-nitrobenzyl), 7.61 (2H, d, J$_{Ho,Hm}$=8.8, Ho of p-nitrobenzyl), 5.59 (1H, dd, J$_{5-6\ cis}$=3.6, J$_{5-6\ trans}$=2.2, H-5), 5.34 (2H, cenipro/ABq, J$_{AB}$=13.8, CH$_2$ of p-nitrobenzyl), 3.80 (1H, dd, J$_{6-5\ cis}$=3.6, J$_{gem}$=16.3, H-6 cis), 3.42 (1H, dd, J$_{6-5\ trans}$2.2, J$_{gem}$=16.3, H=6 trans), ~3.2 (2H, m, CH$_2$N$_3$), 2.9 (1H, m, CH cyclopropyl) and ~1.5–0.8 ppm (3H, m, cyclopropyl). Anal. calcd for C$_{17}$H$_{15}$N$_5$O$_5$S: C 50.86, H 3.77, N 17.45, S 7.99; found: C 50.63, H 3.65, N 17.17, S 8.06.

(1'R,2'S,5S and 1'S,2'R,5S; 1'S,2'R,5R and 1'R,2'S,5S) 2-(trans-2-aminomethyl-1-cyclopropyl)-penem-3-carboxylic acid

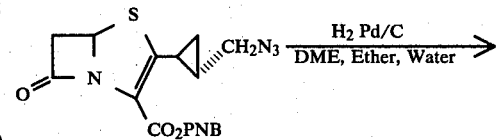

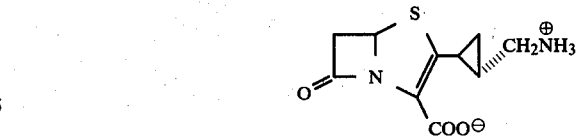

A solution of (1'R,2'S,5R and 1'S,2'R,5S; 1'S,2'R,5R and 1'R,2'S,5S paranitrobenzyl 2-(trans-2-azidomethyl-1-cyclopropyl)-penem-3-carboxylate (0.352 g, 0.88 mmol) in a mixture of THF (30 ml), ether (40 ml) and distilled water (40 ml) was hydrogenated over Pd/C (10%) (0.300 g) at 45 psi for 2.5. The catalyst was filtered and washed with ether and water. The filtrate and the washings were combined and the aqueous phase was washed with ether and lyophilized to give 0.156 g (74%) of a light yellow powder: uv (H$_2$O) λ$_{max}$: 306 nm (ε4355), 255 mµ (ε3200). hplc (reverse phase) of this material indicated two diastereoisomers. Separation of 200 mg of this crude material (reverse phase u-Bondapak C 18) gave two products. The first eluted component (minor isomer:B) was obtained as a white powder: 0.021 g; uv (H$_2$O) λ$_{max}$: 306 nm (ε5381), 250 mµ (ε3500); ir (KBr) $\nu_{max}$: 1768 cm$^{-1}$ (C=O); $^1$Hmr (D$_2$O) δ: 5.69 (1H, dd, J$_{5,6\ cis}$=3.8, J$_{5,6\ trans}$=1.7, H-5), 3.83 (1H, dd, J$_{6-5\ cis}$=3.6, J$_{gem}$ 16.7, H-6 cis), 3.44 (1H, dd, J$_{6,5\ trans}$=1.7, J$_{gem}$=16.7, H-6 trans) and 3.2~0.9 ppm (4H, m, cyclopropyl).

The second component eluted (Main isomer A) was obtained as a white powder: 0.061 g, uv (H$_2$O: 306 (ε6056), 260 (ε3614); ir (KBr) $\nu_{max}$: 1772 (C=O); $^1$Hmr (D$_2$O) δ: 5.63 (1H, dd, J$_{5,6\ cis}$=3.6, J$_{5,6\ trans}$=1.7, H-5), 3.81 (1H, dd, J$_{5,6\ cis}$=3.6, J$_{gem}$=16.8, H$_6$-cis), 3.44 (1H, dd, J$_{6,5\ trans}$=1.7, J$_{gem}$=16.8, H$_6$-trans), 3.2 0.9 ppm (14 H, m, cyclopropyl). The identity of each isomer has not been established.

EXAMPLE 80

2-(3'-Aminobutyl)-penem-3-carboxylic Acid (via mercaptide intermediate)

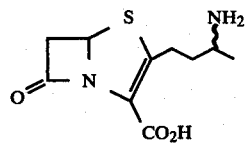

4-Hydroxypentanonitrile

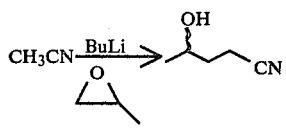

To a stirred, cooled (−78° C.), solution of butyl lithium (135 ml of 1.6 M, 0.216 mol) was added dry THF (120 ml) followed by dropwise addition of dry acetonitrile (8.8 g, 0.215 mol) in THF (20 ml). The resulting mixture was stirred at −78° C. for 15 min. To this was added dropwise propylene oxide (15 ml, 12 g, 0.215 mol) and stirring was continued while the cooling bath was removed. After about 20 min an exothermic reaction set in raising the temperature of the reaction mixture to 30°–35° C. After stirring for 1 h the mixture was treated with cold 5 N HCl (30 ml). The layers were separated and the aqueous layer extracted with ether (8×50 ml). The combined organic phase was dried over $K_2CO_3$ and concentrated in vacuo to give 18.8 g (88.3%) of the title compound as colourless oil: $^1$Hmr ($CDCl_3$) δ: 3.88 (1H, q, J=13 Hz); 2.5 (2H, t, J=13 Hz), 1.88 (2H, d, J=13 Hz) and 1.22 ppm (3H, d, J=13 Hz) ir, (neat) $\nu_{max}$: 2244 cm$^{-1}$.

4-Methanesulphonyloxypentanonitrile

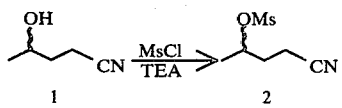

To a cooled (ice bath) stirred solution of 4-hydroxypentanonitrile (18.8 g, 0.19 mol) in benzene (100 ml) and triethyl amine (20 g, 0.198 mol) was added dropwise a solution of methanesulphonyl chloride (22.34 g, 0.195 mol) in benzene (20 ml) over a period of 40 min. After addition was complete the stirring was continued for 20 min at room temperature. The solid (TEA.HCl) was filtered off and washed with benzene. The filtrate and washings were combined and concentrated in vacuo to give 37.7 g of the title compond containing approximately 12% of benzene: $^1$Hmr ($CDCl_3$) δ: 7.38 (3H, benzene), 4.82 (1H, q, J=13 Hz), 3.1 (3H, s), 2.48 (2H, dt), 2.0 (2H, dt) and 1.46 ppm (3H, t, J=13 Hz); ir (neat) $\nu_{max}$: 2243 cm$^{-1}$.

4-Azidopentanonitrile

To a stirring solution of $NaN_3$ (15 g) in boiling water (20 ml) was added a solution of crude 4-methanesulphonyloxypentanonitrile (37.7 g, ≈0.189 mol) in ethanol (240 ml) and the mixture refluxed for 1.5 h. After cooling the mixture was partitioned between $H_2O$ and $CH_2Cl_2$. The organic phase was dried and concentrated in vacuo to give 21.4 g of the title material as a light brown oil, (91.6): $^1$Hmr ($CDCl_3$) δ: 4.05 (1H, q, J=13 Hz), 2.46 (2H, t, J=13 Hz), 1.8 (2H, t, J=13 Hz) and 1.35 ppm (3H, d, J=13 Hz); ir (neat) $\nu_{max}$: 2242, 2100 cm$^{-1}$.

4-Azidopentanoic acid

A solution of 4-azidopentanonitrile (21.4 g, 0.174 mol) in ethanol (80 ml) and 2N NaOH (87 ml) was refluxed for 1 h, followed by concentration in vacuo to a volume of ca 60 ml. This was shaken with ether (60 ml) and the ether was then discarded. The aqueous phase was acidified with cold concentrated HCl (20 ml) and extracted with $CH_2Cl_2$ (2×50 ml) to give after drying and evaporation of solvent 17.85 g (71.7%) of crude title compound as an oil: $^1$Hmr ($CDCl_3$) δ: 3.53 (H, q, J=13 Hz), 2.48 (2H, t, J=13 Hz), 1.82 (2H, t, J=13 Hz) and 1.3 ppm (3H, t, J=13 Hz); ir (neat) $\nu_{max}$: 2100, 1710 cm$^{-1}$.

4-Azidopentanoyl chloride

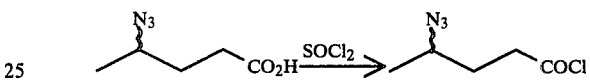

A mixture of crude 4-azidopentanoic acid (8.0 g, 56 mmol) and thionyl chloride (10 g, 84 mmol) was heated at 40°–45° C. for 1.5 h, followed by evaporation of excess thionylchloride in vacuo. The residual oil was distilled to give 6.8 g (75%) of the title compound, bp 60°–65° C./0.3 mm: $^1$Hmr ($CDCl_3$) δ: 3.55 (1H, q, J=13 Hz), 3.03 (2H, t, J=13 Hz), 1.9 (2H, t, J=13 Hz and 1.3 ppm (3H, d, J=13 Hz); ir (neat $\nu_{max}$: 2100, 1792 cm$^{-1}$.

4-(4′-Azidopentanoylthio)-1-(paranitrobenzyl 2′′-triphenylphophoranylidene-2′′-acetate)-2-azetidinone

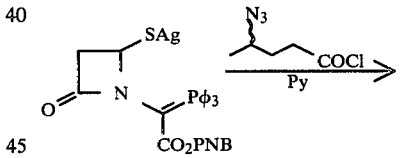

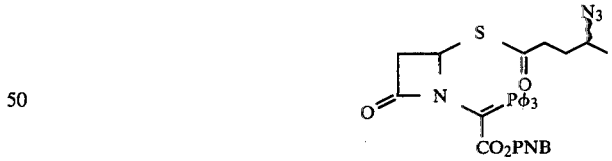

To a cooled (ice bath) stirred solution of silver-1-(paranitrobenzyl 2′-triphenylphosphoranylidene-2′-acetate)-2-azetidinone-4-thiolate (8.66 g, 13.36 mmol) in $CH_2Cl_2$ (80 ml was added a 1M solution of pyridine in THF (14 ml) followed by a solution of 4-azidopentanoyl chloride (2.16 g, 13.36 mmol) in $CH_2Cl_2$ (5 ml). The mixture was stirred in the cold for 30 min followed by 1 h at room temperature. Then it was diluted with ether (100 ml), filtered, and the filtrate washed with dilute HCl followed by dilute $NaHCO_3$, dried and concentrated in vacuo. The residual solid was covered with ether (60 ml) and MeOH (8 ml) and after standing for 1 h filtered to give 5.7 g of the crude title compound. This was chromatographed on silica gel column using ethyl acetate-benzene 4:1 as eluent to give after evaporation of the appropriate fractions and washing with ethylacetate 3.6 g (38.4%) of almost white solid title compound, mp 149°–152° C.; ir (nujol) $v_{max}$: 2110, 1700, 1688 cm$^{-1}$.

paranitrobenzyl 2-(3'-azidobutyl)-penem-3-carboxylate

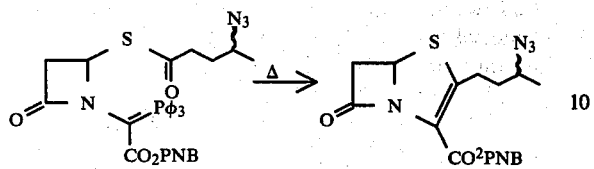

A solution of 4-(4'-azidopentanoylthio)-1-(paranitrobenzyl 2''-triphenylphosphoranylidene-2''-acetate)-2-azetidinone (4.6 g, 6.75 mmol) in dry toluene (600 ml) was refluxed for 2.5 h followed by evaporation of solvent and chromatography of the residual oil on silica gel column. Elution of the column with benzene —3% ether gave 710 mg (20%) of the title compound as an oil: $^1$Hmr (CDCl$_3$) δ:8.22 (2H, dd, J=8.8 Hz), 7.60 (2H, dd, J=8.8 Hz), 5.55 (1H, dd, J=3.7, 2.0 Hz, 5-H), 5.33 (2H, ABq benzylic Hz), 3.87 (1H, ABXq, J=16.4, 3.7 Hz, trans 6-H), 3.47 (1H, BAXq, J=16.4, z:OHz, cis 6-H), 2.9 (2H, m), 1.8 (2H, m) and 1.29 ppm (3H, d, J=7.5 Hz); ir (neat) $v_{max}$: 2100, 1785, 1605 cm$^{-1}$.

2-(3'-aminobutyl)-penem-3-carboxylic acid

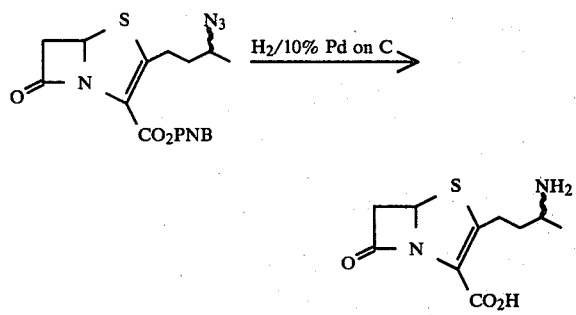

To a solution of paranitrobenzyl 2(3'-azido butyl)-penem-3-carboxylate (200 mg 0.826 mmol) in THF (912 ml) and ether (16 ml) was added water (12 ml) and 10% palladium on carbon (300 mg). The mixture was hydrogenated at 35 psi and room temperature for 2.5 h. The catalyst was filtered off over Celite and washed twice with water (5 ml). The filtrate and washings were combined and washed with ether (2×30 ml), followed by lyophylization to give 66 mg of the crude title compound as a white solid. The product was chromatographed on a reverse phase column. Elution with H$_2$0-4% CH$_3$CN gave two fractions: (1) 17.7 mg, uv (H$_2$O) λ$_{max}$: 301.5 (ε7562), 258 (ε4930), ir (nujol) $v_{max}$: 1770 cm$^{-1}$; $^1$Hmr (D$_2$O) δ:5.77 (0.5 H, dd, J=1.7, 3.6, 5-H), 5.68 (0.5H, dd, J=1.7, 3.6, Hz, 5-H), 3.85 (1H, dd, J=3.6, 16.8 Hz, trans 6-H), 3.45 (1H, dd, J=1.7, 16.8 Hz cis-6-H), 2.5–3.6 (3H, m), 1.8 (2H, m), 1.35 and 1.33 ppm (3H, two d, J=6.6, 4'-CH$_3$, ratio 1:1). The spectrum corresponds to a mixture of approximately 1:1 of the two possible diastereoisomers. (2) 8 mg, uv (H$_2$0) λ$_{max}$: 301.5 (ε5808) 258 (ε3872); ir (nujol) $v_{max}$: 1770 cm$^{31}$ $^1$; $^1$Hmr (D$_2$O) δ: 5.77 (0.39H, dd, J=1.7, 3.6 Hz, 5-H), 5.68 (0.61 H, dd, J=1.7, 3.6 Hz, 5-H), 3.85 (1H, dd, J=3.6, 16.8 Hz, trans 6-H), 3.45 (1H, dd, J=1.7, 16.8 Hz, cis 5-H), 2.5–3.6 (3H, m) 1.9 (2H, m), 1.35 and 133 ppm (3H, two d, J=6.6 Hz 4'—CH$_3$, ratio 8:5).

EXAMPLE 81

2-Aminoacetoxymethyl-penem-3-carboxylic Acid (via mercaptide intermediate)

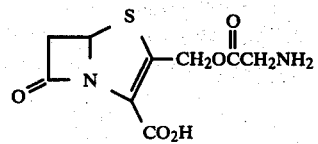

4-Azidoacetoxyacetylthio-1-(paranitrobenzyl 2'-triphenylphosphoranylidene-2'-acetate)-2-azetidinone

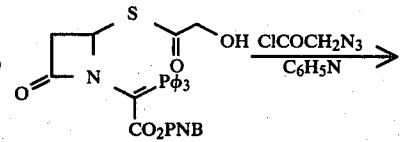

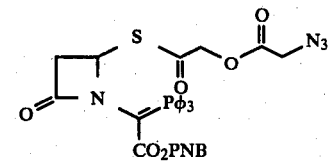

A cold (ice-MeOH bath) solution of 4-hydroxyacetylthio-1-(paranitrobenzyl 2'-triphenylphosphoranylidene-2'-acetate)-2-azetidinone (586 mg, 0.954 mmol) in methylene chloride (15 ml) was treated successively with azido acetyl chloride (240 mg, 2.01 mmol) and dropwise with pyridine (226 mg, 231 ml, 3.0 mmol) in methylene chloride (10 ml): At the end of the addition tlc showed disappearance of starting material. The mixture was diliuted with ether, washed successively with dilute HCl, water, dilute aqueous sodium bicarbonate, water and brine. It was dried over sodium sulfate. Purification of the residue was performed on a silica gel (10 g) column, eluting with 20% ether in benzene, ether, and 30% ethyl acetate in ether. Concentration of the pertinent fraction gave the title compound as a foam; 533 mg, 80.1%; ir $v_{max}$: (CHCl$_3$): 1763, 1702 (C=O), 1625 (C=Pφ$_3$), 1522 (NO$_2$) and 2110 cm$^{-1}$ (N$_3$).

paranitrobenzyl 2-azidoacetoxymethylpenem-3-carboxylate

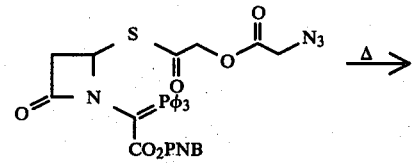

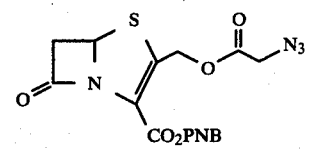

A solution of phosphorane (533 mg, 0.764 mmol) was heated under reflux in toluene (90 ml) for 0.5 h using a catalytic amount of hydroquinone. The solvent was concentrated on the evaporator and the concentrated solution was passed through a silica gel (10 g) column. (benzene: ether, 48:2). It gave the title compound (236 mg, 73.7%) as an oil. This oil was found to be unstable at room temperature. It was kept at −78° C. until needed. ¹Hmr (CDCl₃) δ: 8.21 (2H, d, Hm aromatic), 7.57 (2H, d, Ho aromatic), 5.68 (1H, dd, $J_{5-6\ cis}=4$, $J_{5-6\ trans}=2$, H-5), 5.43 (2H, center of ABq, J=16, CH₂-PNB), 5.39 (2H, CH₂), 3.93 (2H, s, CH₂—N₃), 3.72 (part of dd, $J_{6-5\ cis}=4$, H-6), and 3.50 ppm (1H, dd, $J_{gem}=17$, $J_{6-5\ trans}=2$, H-6); ir $\nu_{max}$ (CHCl₃): 1795, 1755, 1710 (C=O), 1525 (NO₂), 2110 cm⁻¹ (N₃).

2-Aminoacetoxymethylpenem-3-carboxylic acid

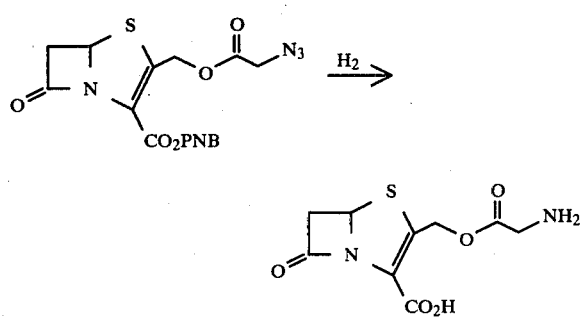

A mixture of above ester (219 mg, 0.522 mmol) in THF (16 ml)-ether (30 ml) and water (16 ml) was shaken on a Parr hydrogenator for 2.25 h at 50 psi of H₂ using 10% Pd/C (240 mg) as catalyst. The catalyst was filtered off and washed with water and ether. The aqueous phase was washed with ether (3×30 ml) and lyophilized. The crude powder was purified on a reversed phase hplc column and gave the title compound (8 mg, 6.7%) as a white powder. ¹Hmr (D₂O) δ: 5.72 (1H, dd, $J_{5-6\ cis}=3.5$, $J_{5-6\ trans}=2$, H-5), 5.37 (2H center of ABq, J=13.5 CH₂—O), 3.96 (2H, s, CH₂—NH₂), 3.87 (1H, dd, $J_{gem}=16.5$, $J_{6-5\ cis}=3.5$, H-6) and 3.49 Nmr (1H, dd, $J_{gem}=16.5$, $J_{6-5\ trans}=2$, H-6); ir $\nu_{max}$ (nujol): 1775, 1755 and 1600 cm⁻¹ (C=O); uv (H₂O) $\lambda_{max}$ 306 (ε4900), 256 (ε3000).

EXAMPLE 82

(1′R,5R and 1′S,5S) and (1′R,5S and 1′S,5R) 2-(1′-Aminobutyl)-penem-3-carboxylic Acid (via mercaptide intermediate)

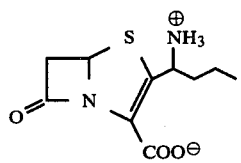

(2R and 2S) Ethyl 2-azido pentanoate

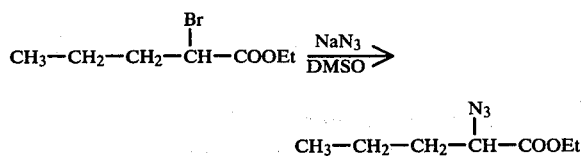

A solution of ethyl 2-bromopentanoate (4.18 g, 20.0 mmol) in dry dimethyl sulfoxide (50 ml), was treated with sodium azide (2.60 g, 40.0 mmol) at room temperature for 5 h. The reaction mixture was diluted with ether (300 ml), washed several times with water and dried over anhydrous magnesium sulfate. Evaporation of the solvent gave an oil which was distilled (bulb to bulb distillation) to give a clear liquid: 3.359 g (98%); bp 70°–75° C./3.5 torr (air bath temperature); ir (film) $\nu_{max}$: 2100 (N₃), 1738 (C=O); ¹Hmr (CDCl₃) δ: 4.23 (2H, q, J=7, C$\underline{H}_2$—CH₃), 3.76 (1H, dd, J=7, J=6, H-2), 2.01.0 (4H, m, H-3 and H-4), 1.30 (3H, t, J=7.0, CH₂C$\underline{H}_3$) and 0.96 ppm (3H, distorted t, J=6, H-5); Anal. calcd. for C₇H₁₃N₃O₂: C 49.11, H 7.65, N 24.55; found: C 49.12, H, 7.69, N 24.40.

(R and S) 2-Azidopentanoic acid

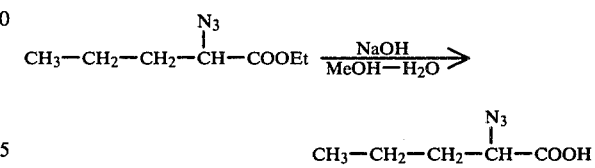

A solution of ethyl 2-azidopentanoate (3.082 g, 18.0 mmol) in a mixture of methanol (10 ml) and water (5 ml) was treated dropwise with 20 ml of 1M sodium hydroxide (20 mmol, 1.1 equiv). After 1.5 h at room temperature, the methanol was evaporated under reduced pressure and the remaining aqueous phase was washed with ether (2×10 ml) and acidified with dilute HCl (3N) at 0° C. The aqueous phase was extracted with dichloromethane (3×25 ml). The combined organic phases were washed with water and dried over anhydrous sodium sulfate. Evaporation of the solvent gave an oil which was distilled (bulb to bulb) to give 2.393 g (93%) of a clear liquid: 80°–85° C./0.5 toor (air bath temperature; ir (firm) $\nu_{max}$: 2110 (N₃), 1720 cm⁻¹ (C=O); ¹Hmr (CDCl₃) δ: 3.90 (1H, dd, J=6, J=7, H-2), 2.0-1.0 (4H, m, H-3, H-4) and 1.00 ppm (3H, distorted t, J=6, H-5); Anal. calcd for C₅H₉N₃O₂: C 41.95, H 6.34, N 29.36; found: C 42.06, H 6.49, N 29.26.

(2R and 2S) 2-Azidopentanoic acid chloride

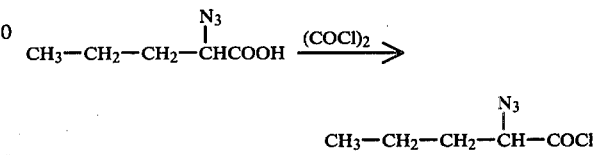

A solution of (2R and 2S) 2-azidopentanoic acid (2.213 g, 15.46 mmol) in dry dichloromethane (20 ml) was treated with oxalyl chloride (1.57 ml, 18.55 mmol) and a drop of N,N-dimethyl formamide. After the evolution of gas had ceased (2 h), the solvent was evaporated under reduced pressure and the residual liquid was distilled off (bulb to bulb) under vacuum to give 2.224 g (89%) of a clear oil: bp 50°–55° C./5 torr (air bath temperature); ir (film) $\nu_{max}$: 2105 (N₃), 1785 cm⁻¹ (C=O), ¹Hmr (CDCl₃) δ: 4.1 (1H, dd, J=7, J=6, H-2), 2.2-1.2 (4H, m, H-3 and H-4) and 0.98 ppm (3H, distorted t, J=6, H-5).

(2'S,4R and 2'S,4S) and (2'S,4R and 2'R,4S) 4-(2-azidopentanoylthio)-1-(paranitrobenzyl 2''-triphenylphosphoranylidene-2''-acetate)-2-azetidinone

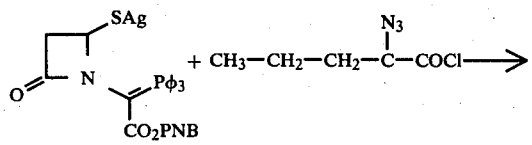

A solution of 4R and 4S) silver 1-(paranitrobenzyl 2'-triphenylphosphoranylidene-2'-acetate)-2-azetidinone-4-thiolate (1.415 g, 2.13 mmol) in dry dichloromethane (15 ml) was cooled to 0° C. and then treated with pyridine (0.241 ml, 2.99 mmol) and 2R and 2S) 2-azidopentanoic acid chloride (0.448 g, 2.77 mmol) in dry dichloromethane (2 ml). The solution was stirred at room temperature for 15 min and the precipitate was filtered and washed with dichloromethane. The combined filtrate and the washings were washed with dilute HCl (0.3M, 2×20 ml), brine, saturated sodium bicarbonate (2×20 ml) and brine. After drying on anhydrous sodium sulfate, evaporation of the solvent under vacuum gave an oil (1.424 g) which was chromatographed on 25 g of silica gel. Elution with a mixture of dichloromethane and ethyl acetate (6:4) gave 1.114 g (77%) of a slight yellow oil. (all attempts of crystallization failed): ir (CH$_2$Cl$_2$$\nu$max: 2110 (N$_3$) 1758 (C=O) $\beta$-lactam), 1565 (C=O of thioester), 1520 cm$^{-1}$ (NO$_2$). (This product was unstable and an analysis could not be obtained).

(1'R, 5R and 1'S, 5S) and (1'R, 5S and 1'S, 5R) paranitrobenzyl 2-(1'-azidobutyl)-penem--carboxylate

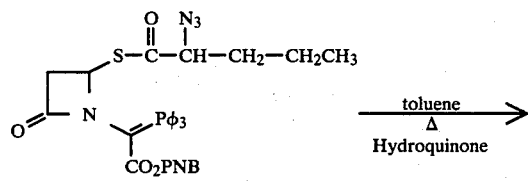

A solution of (2'R, 4R and 2'S, 4S) and (2'R, 4S and 2'S, 4R) 4-(2'-azidopentanoylthio)-1-(paranitrobenzyl 2''-triphenyl phosphoranylidene-2''-acetate)-2-azetidinone (0.900 g, 1.32 mmol) in dry toluene (100 ml) was heated under reflux for 15 h in the presence of traces of hydroquinone. After evaporation of the solvent under vacuum, rapid chromatography of the residual oil on 20 g of silica gel (elution benzene-ethyl acetate 85:15) gave 0.412 g (77%) of a light yellow oil: ir (CH$_2$Cl$_2$) $\nu$max:2100 (N$_3$), 1782 (C=O of $\beta$-lactam), 1710 (C=O of ester), 1525 cm$^{-1}$ (NO$_2$); $^1$Hmr (CDCl$_3$) $\delta$: 8.20 (2H, d, J$_{Hm, Ho}$=8.8, Hm of p-nitrobenzyl), 7.60 (1H, d, J$_{Ho, Hm}$=8.8, Ho of p-nitrobenzyl), 5.66 (1H, m, H-5), 5.4 (1H, under CH$_2$ of p-nitrobenzyl, H-1'), 5.33 (2H, center of ABq, J$_{AB}$=14, CH$_2$ of p-nitrobenzyl), 3.90 (1H, dd, J$_{6,5\,cis}$=4, J$_{gem}$=16, H-6 cis), 3.53 (1H, dd, J$_{6,5\,trans}$=2.0, J$_{gem}$=16, H-6 trans), 2.0-1.0 (4H, n, H-2' and H-3'), and 0.95 ppm (3H, distorted t, J=6 Hz, H-4'). (This product is unstable and analysis could not be obtained).

(1'R,5R and 1'S,5S) and (1'R,5S and 1'S,5R) 2-(1'-aminobutyl)-penum-3-carboxylic acid

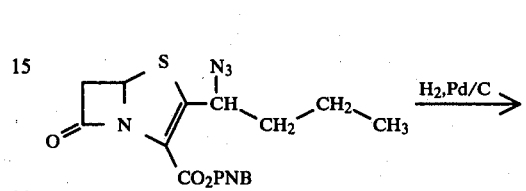

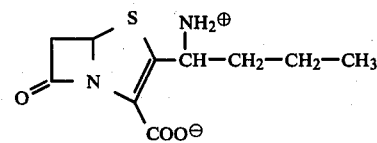

A solution of (1'R,5R and 1'S,5S) and (1'R,5S and 1'S,5R) paranitrobenzyl 2-(1'-azidobutyl)-penem-3-carboxylate (1.100 g, 2.73 mmol) in a mixture of dimethoxy ethane (40 ml), ether (40 ml) and water (40 ml) was hydrogenated over 1.1 g of 10% Pd/C under 45 psi of H$_2$ for 2 h. The catalyst was filtered on a celite pad and washed with water and ether. The aqueous phase was washed with ether (×2) and lyophylized to give 0.271 g (41%) of a slight yellow solid: uv (H$_2$O) $\lambda_{max}$: 305 ($\epsilon$3647), 250 m$\mu$ ($\epsilon$2735). A chromatography was done on 0.336 g of this material (hplc reverse phase u-Bondapak C 18) and gave 0.115 g of a white powder (mixture of the two diastereoisomers): uv (H$_2$O) $\lambda_{max}$: 307 (5678), 255 m$\mu$ ($\epsilon$3400); ir (KBr) $\nu_{max}$: 1778 cm$^{-1}$ (C=O); $^1$Hmr (D$_2$O) $\delta$: 5.77 (1H, two overlapping q, H-5), 4.82 (1H, m, H-1'), 3.91 (1H, dd, J$_{5,6\,cis}$=3.6, J$_{gem}$=16.9, H-6 cis), 3.55 (1H, dd, J$_{5,6\,trans}$=1.8, J$_{gem}$=16.9, H-6 trans), 2.1-1.1 (4H, m, H-2' and H-3') and 0.96 ppm (3H, distorted t, J=6.7, H-4').

EXAMPLE 83

2-(1'-Amino-3'-cyanopropyl)-penem-3-carboxylic Acid (via mercaptide intermediate)

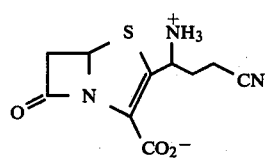

Methyl 2-azido-4-iodobutyrate

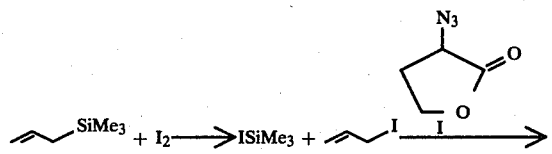

-continued

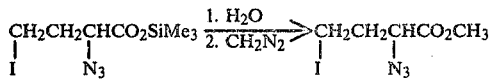

A. Preparation of trimethylsilyl iodide

This product was prepared in situ by a literature procedure as follows: To a stirred suspension of iodine (24 g, 95 mmol) in dry carbon tetrachloride was added a solution of allyltrimethylsilane (11.4 g, 100 mmol) and the mixture stirred at room temperature until all the iodine has dissolved (45 min).

B. Preparation of methyl 2-azido 4-iodobutyrate

To the above solution was added a solution of the α-azidobutyrolactone (10.2 g, 80 mmol) in carbon tetrachloride (20 ml) and the reaction mixture heated at 55° C. while stirring for 2 hr. Removal of the solvent by evaporation left a syrup which was dissolved in benzene and evaporated to remove residual trimethylsilyliodide and allyl iodide. The residue was dissolved in chloroform (200 ml), washed with a solution of sodium thiosulfate to remove free iodine, dried and evaporated to give the silylester as a syrup. The trimethylsilyl 2-azido-4-iododobutyrate was dissolved in 95% acetone-water mixture and the solution left at room temperature for 10–15 min to effect complete hydrolysis and then evaporated to yield the acid as a liquid. This product was dissolved in ether and treated with an ethereal solution of diazomethane at 0° C. The ether solution was washed with water and 8% sodium bicarbonate, dried and evaporated to give 17 g (79%) of the corresponding methyl ester which on tlc (silica, benzene) showed a major spot of Rf 0.53 and a trace of a spot of Rf 0. A sample was purified by chromatography on silica using benzene as eluent; ir (neat) $\nu_{max}$: 2100, 1740 cm$^{-1}$; $^1$Hmr (CDCl$_3$) δ: 2.23 (m, 2H, —CH$_2$—), 3.27 (t, J=7.0 Hz, 2H, —CH$_2$I), 3.80 (s, 3H, OCH$_3$) and 3.77 ppm (q, J$_2$=6.0 Hz, 1H, —CHN$_3$). Anal. calcd for C$_5$H$_8$N$_3$IO$_2$: C 22.32, H 2.99, I 47.17; found: C 22.35, H 2.98 I 47.48.

Methyl 2-azido-4-cyanobutyrate

To a cold (10°) suspension of potassium cyanide (1.5 g, 23 mmol) in dry DMSO (25 ml) was added methyl 2-azido-4-iodobutyrate (4.0 g, 15 mmol) and the mixture stirred at 10° C. for 10 min and at room temperature for 45 min. The reaction mixture was poured into cold water (200 ml) and the solution was extracted with chloroform (4×80 ml). The chloroform extract was washed with water (4×50 ml), dried and evaporated to give a syrup (2.0 g) which on tlc (silica, 10% ether-benzene) showed a major spot of Rf 0.4 and some impurities (Rf 0, 0.67, and 1.0). The product was purified by chromatography on a silica column (20 cm×2.9 cm 1-D) using 10% ether in benzene as eluent to give 1.1 g (44%) of title compound as a syrup; ir (neat) $\nu_{max}$: 2100, 1745 cm$^{-1}$; $^1$Hmr (CDCl$_3$) δ:2.17 (m, 2H, —CH$_2$—), 2.5 (m, 2H, CH$_2$CN), 3.83 (s, 3H, OCH$_3$) and 4.13 ppm (q, J=9, 6 Hz, 1H, CHN$_3$). Anal. calcl for C$_6$H$_8$N$_4$O$_2$: C 42.84, H 4.89, N 33.31; found: C 42.76, H 4.72, N 33.16.

2-Azido-4-cyanobutyric acid

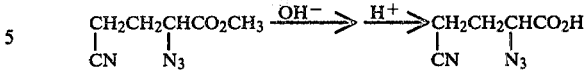

Methyl 2-azido-4-cyanobutyrate (1.1 g, 6.55 mmol) was dissolved into a solution of sodium hydroxide in 90% ethanol (7 ml of 1N) and the resultant solution let stand at room temperature for 45 min. Thin layer chromatography (silica, 10% ether-benzene) indicated the reaction was completed. The reaction mixture was diluted with water (7 ml) and stirred (5 min) with Dowex 50W-X8 (acidic, H$^+$ form) resin and then filtered. The filtrate was concentrated under reduced pressure to half the volume (to remove EtOH) and the remaining solution extracted with chloroform (5×10 ml). The chloroform solution, after drying, was evaporated to give 0.89 g (89%) of the title acid as a liquid; ir (neat) $\nu_{max}$: 3200, 2250, 2110, 1740 cm$^{-1}$; $^1$Hmr (CDCl$_3$) δ: 2.23 (m, 2H, CH$_2$), 2.57 (m 2H, CH$_2$CN) and 4.27 ppm (q, J$_1$=9, J$_2$=6 Hz, 1H, CHN$_3$). Anal. calcd for C$_5$H$_6$N$_4$O$_2$: C 39.62, H 3.92, N 36.36; found: C 39.00, H 3.85, N 36.10.

2-Azido-4-cyanobutanoyl chloride

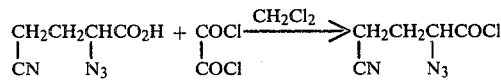

To a solution of 2-azido-4-cyanobutyric acid (0.76 g, 4.94 mmol) in dry methylene chloride (20 ml) was added oxalyl chloride (0.65 g, 5.1 mmol) and a drop (~15 mg) of DMF. The reaction mixture was stirred at room temperature until the evolution of gas ceased (15 min) and then refluxed for 10 min. Removal of the solvent in vacuo gave 0.84 g (99%) of the title compound as a syrup; ir (neat) $\nu_{max}$: 2250, 2110, 1780 cm$^{-1}$.

p-Nitrobenzyl [4-(2-azido-4-cyaanbutanoylthio)-2-azetidinon-1-yl]triphenylphosphoranylideneacetate

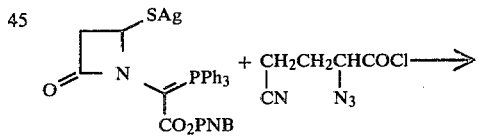

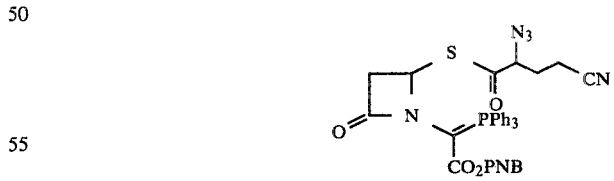

Silver 1-(paranitrobenzyl-2'-triphenylphosphoranylidene-2'-acetate)-2-azetidinone-4-thiolate (6 g, 9 mmol) was dissolved in dry methylene chloride (30 ml) and the solution was placed under a slow stream of nitrogen and cooled to 0° C. with stirring. To this solution was added a solution of 2-azido-4-cyanobutyroylchloride (1.55 g, 9 mmol) in methylene chloride (20 ml). The reaction mixture was stirred at room temperature for 2 h and then filtered through a pad of Celite. The filtrate was washed first with a 2% sodium bicarbonate solution (60 ml) and then with water (60 ml) and dried. Removal of the solvent by evaporation left a residue (6.3 g) which on tlc (silica, 5% MeOH—CH$_2$Cl$_2$) showed a major spot of Rf 0.67 and some impurities with lower Rf values. This material was purified by wet column chromatography on a column of silica (20 cm × 3.8 cm 1.D) using 2% MeOH—CHCl$_3$ mixture as eluent to yield 5.2 g (84%) of title compound.

p-Nitrobenzyl 2-(1'-azido-3'-cyanopropyl)-penem-3-carboxylate

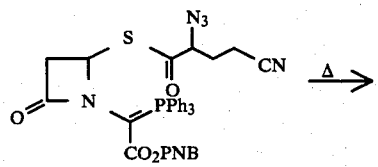

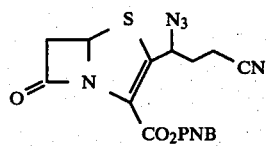

A solution of the above phosphorane (3.6 g) in dry toluene (200 ml) was heated under reflux for 3 h and then evaporated to dryness. The residue showed on tlc (silica, ether-benzene, 1:1) two spots for the two isomers of the title compound with Rf values of 0.43 and 0.53 and a spot at the origin. The crude product was dissolved in ether-benzene mixture (1:1, 50 ml) and the solution was fast filtered* through a pad of silica (25 g). The silica pad was washed with the same solvent mixture (100 ml) and the washing was combined with the filtrate. Removal of the solvent by evaporation yielded 1.46 g (68%) of the title compound as a mixture of the two diastereoisomers; ir (CHCl$_3$) $\nu_{max}$: 2110, 1795, 1715 cm$^{-1}$; $^1$Hmr (CDCl$_3$) $\delta$: 2.0 (m, 2H, CH$_2$), 2.43 (m, 2H, CH$_2$CN), 3.53 (dd, J$_{gem}$=16, J$_{5,6\ trans}$=2 Hz, 1H, H-6$_b$), 3.90 (dd, J$_{gem}$=16, J$_{5,6\ cis}$=4Hm, 1H, H-6a), 5.33 (center of ABq, J=14 Hz, 2H, CH$_2$PNB), 5.6 (m, 2H, H-5 and CHN$_3$), 7.6 (d, J=8 Hz, 2H, Ho aromatic) and 8.2 ppm (d, J=8 Hz, 2H, Hm aromatic). Anal. calcd for C$_{17}$H$_{14}$N$_6$O$_5$S: C 49.27, H 3.40, N 20.28; found: C 48.38, H 3.30, N 17.72.

\* Chromatography on silica gel resulted in decomposition of the product.

2-(1'-Amino-3-cyanopropyl)-penem-3-carboxylic acid

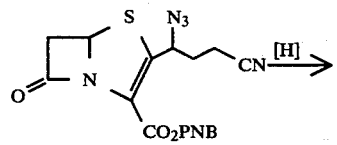

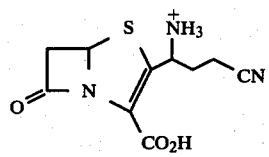

To a solution of the above ester (0.37 g) in freshly distilled THF (15 ml) was added ether (15 ml), water (15 ml) and 30% Palladium on Celite catalyst (1.0 g) mixture was shaken with hydrogen in a Parr apparatus at 55 psi for 2.5 h. The reaction mixture was filtered through a pad of Celite, the cake washed with water (5 ml) and the washing and filtrate were combined. The solution was extracted first with benzene (2×25 ml) and then with ethyl acetate (2×25 ml). The aqueous phase was concentrated by evaporation (30° C., 0.1 mm) to a small volume and lyophilized. The product was purified by hplc to give 50 mg of title compound; ir (nujol) $\nu_{max}$: 3300, 2250 (CN), 1780 cm$^{-1}$; $^1$Hmr (D$_2$O) $\delta$: 3.55 (dd, J$_{gem}$=14, J$_{5,6\ trans}$=2 Hz, 1H, H-6$_b$), 3.90 (dd, J$_{gem}$=14, J$_{5,6\ cis}$=4 Hz, 1H, H-6a) and 5.75 ppm (dd, J$_{5,6\ trans}$=2, J$_{5,6\ cis}$=4 hz, 1H, 1H, H-5). Anal. calcd for C$_{10}$H$_{11}$N$_3$O$_3$S: C 47.42, H 4.38, N 16.59; found: C 44.92, H 4.43, H 16.06.

EXAMPLE 84

(1'R,2'R,5R and 1'S,2',5S), (1'R,2'R,5S and 1'S,2'S,5R), (1'R,2'S,5S and 1'S,2'R,5R), (1'R,2'S,5R and 1'S,2'R,5S) 2-(1'-Amino-2,3-dihydroxy-2,3-acetonyl propyl)-penem-3-carboxylic Acid (via mercaptide intermediate)

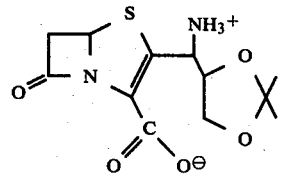

(2R,3R, and 2S,3R) and (2R,3S and 2S,3R) 2-azido-3,4-dihydroxy-3,4-acetonyl butyric acid

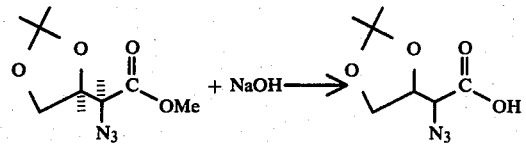

A solution of (2R,3R and 2S,3R; 2R,3S and 2S,3R) methyl 2-azido-3,4-dihydroxy-3,4-acetonyl butyrate (3.324 g, 15.44 mmol) in a mixture of methanol (10 ml and water (10 ml) was cooled to 0° C. and treated with a 1.0M sodium hydroxyde solution in water (15.5 ml) for 30 min. After evaporation of the methanol under reduced pressure, the solution was diluted with water (20 ml) and extracted with ether (2×10 ml). The aqueous phase was then treated at 0° C. with oxalic acid (1.112 g, 12.35 mmol) and extracted with dichloromethane (5×10 ml). The combined organic fractions were washed with water (10 ml) and dried over anhydrous magnesium sulfate. Evaporation of the solvent gave 1.883 (61%) of a clear oil which was immediately used in the next step without further purification; ir (film) $\nu_{max}$: 2120 (N$_3$) and 1740 cm$^{-1}$ (C=O of an acid); $^1$Hmr (CDCl$_3$) $\delta$: 10.55 (1H, s, CO) and 4.7–3.7 ppm (4H, m, H-2, H-3 and H-4).

(2′R,3′R,4R and 2′S,3′S,4S), (2′R,3′R,4S and 2′S,3′S,4R), (2′R,3′S,4S and 2′S,3′R,4R), (2′S,3′R,4S and 2′R,3′S,4R) 4-(2-azido-3,4-dihydroxy-3,4-acetonyl butyrylthio)-1-(paranitrobenzyl 2″-triphenylphosphoranyliodene-2″-acetate)-2-azetidinone

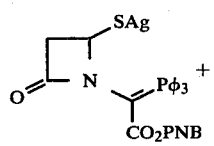

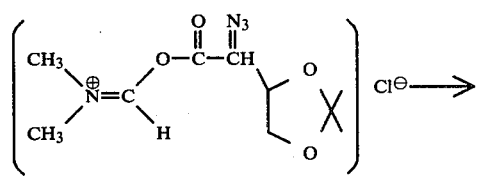

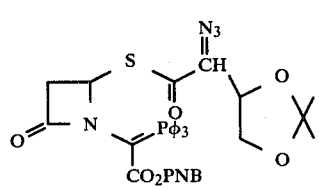

A solution of dry N,N-dimethylformamide (2.47 ml, 32.0 mmol) in dry acetonitrile (10 ml) was cooled to −20° C. and treated with oxalylchloride (0.94 ml, 10.75 mmol). After 15 min at −20° C., the mixture containing a white precipitate was treated with a solution of (2R,3R and 2S,3R) and 2R,3S and 2S,3R) 2-azido-3,4-dihydroxy-3,4-acetonylbutyric acid (1.883 g, 9.35 mmol) in dry acetonitrile (3 ml). The resulting clear solution was stirred at −20° C. for 15 min. To this complex was then added pyridine (2.50 ml, 31.0 mmol) immediately followed by a solution of (4R and 4S) silver 1-(paranitrobenzyl-2′-triphenylphosphoranylidene-2′-acetate)-2-azetidinone-4-thiolate in dry dichloromethane (25 ml). After 15 min at −20° C. a heavy precipitate was formed and tlc indicated no silver salt left. The solid was filtered and washed with dichloromethane. The combined filtrate and the washings were washed with acetic acid (5%), brine, saturated sodium bicarbonate and brine. After drying over anhydrous sodium sulfate, evaporation of the solvent left a brown oil (5.117 g) which was chromatographed on silica gel (50 g). A mixture of benzene and ethyl acetate (6:4) gave 3.886 g (59%) of the thioester as a yellow foam: ir (CH$_2$Cl$_2$) $\nu_{max}$: 2115 (N$_3$), 1760 (C=O of ester), 1680 (C=O of thioester) and 1522 cm$^{-1}$ (NO$_2$). (N.B. this product is unstable).

(1′R,2′R,5R and 1′S,2′S,5S), (1′R,2′R,5S and 1′S,2′S,5R), (1′R,2′S,5S and 1′S,2′R,5R), (1′R,2′S,5R and 1′S,2′R,5S) paranitrobenzyl 2-(1′-azido-2′,3′dihydroxy-2′,3′-acetonyl-propyl)-penem-3-carboxylate.

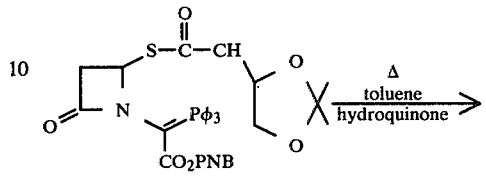

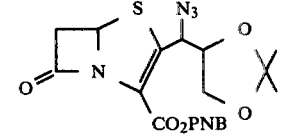

A solution of (2′R,3′R,4R and 2′S,3′S,4S), (2′R,3′R,4s and 2′S,3′S,4R), (2′R,3′S,4S and 2′S,3′R,4R), (2′S,3′R,4R and 2′R,3′S 4S), (2′R,3′S,4R and 2′S,3′R,3S) 4-(2-azido-3,4-dihydroxy-3,4-acetonyl butyrylthio)-1-paranitrobenzyl 2″-triphenylphosphoranylidene-2″-acetate)-2-azetidinone (3.800 g, 5.13 mmol) in dry toluene (350 ml) was maintained at 105° C. for 15h in the presence of traces of hydroquinone. Evaporation of the solvent under reduced pressure, followed by chromatography of the solvent under reduced pressure, followed by chromatography of the residue on silica gel (50 g, elution benzene-ethylacetate, 6:4) gave 1.011 g (42%) of the mixture of penems as an oil: ir (CH$_2$Cl$_2$) $\nu_{max}$: 2110 (N$_3$), 1796 (C=O of β-lactam), 1710 (C-O of ester) and 1525 cm$^{-1}$ (NO$_2$); $^1$Hmr (CDCl$_3$) δ: (mixture of diastereoisomers: complex) 8.22 (2H, d, J$_{Hm,Ho}$=8.6, Hm of p-nitrobenzyl), 7.60 (2H, d, J$_{Ho,Hm}$=8.6, Ho of p-nitrobenzyl), 5.9–5.4 (2H, m, H-5 and H-1′), 5.34 (2H, center of ABq, JAB=14, CH$_2$ of p-nitrobenzyl), 4.4–3.8 (3H, m, H-2′and H-3′), 3.9 (1H, dd, J$_{6,5}$ $_{cis}$=3.7, J$_{gem}$=16, H-6 cis), 3.53 (1H, dd, J$_{6,5 trans}$=1.9, J$_{gem}$=16, H-6 trans), 1.47, 1.40 and 1.33 ppm (3H, s, H-acetonide).(N.B. This product is unstable).

(1′R,2′R,5R and 1′S,2′S,5S), (1′R,2′R,5S and 1′S,2′S,5R), (1′R,2′S,5S and 1′S,2′R,5R), (1′R,2′S,5R and 1′S,2′R,5S) 20(1′-amino-2,3-dihydroxy-2,3-acetonyl propyl)-penem-3-carboxylic acid

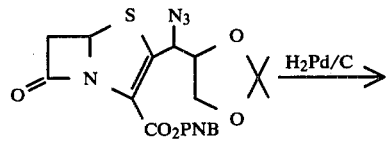

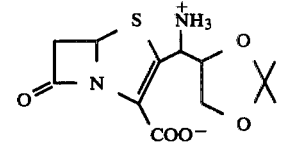

A solution of (1′R,2′R,5R and 1′S,2′S,5S), (1′R,2′R,5S and 1′S,2′S,5R), (1′R,2′S,5S and 1′S,2′R,5R), (1′R,2′S,5R and 1′S,2′R, 5S) paranitrobenzyl 2-(1′-azido-2,3-dihydroxy-2,3-acetonyl-propyl)-penem-3-carboxylate (0.975 g, 2.11 mmol) in a mixture of dimethoxyethane (35 ml), ether (70 ml) and water (50 ml) was hydrogenated over 10% Pd/C (1.00 g) under 45 psi of $H_2$ for 3 h. The catalyst was then filtered and washed with water and ether. The aqueous phase was then washed with ether and lyophylized to give ~0.350 g (55%) of a yellow powder: uv ($H_2O$) $\lambda_{max}$: 307 nm (3360). Chromatography of this material (hplc reversed phase μ-Bondapak-C-18) gave two fractions. The first fraction contained a mixture of diastereoisomers: 0.111 g (18%); uv ($H_2O$) $\lambda_{max}$: 307.5 (ε3062); ir (KBr) $\nu_{max}$: 1778 (C=O of β-lactam) and 1600 cm$^{-1}$ (C=O of acid); $^1$Hmr ($D_2O$) δ: complex.

A second fraction was obtained as a white powder; 0.036 g (6%); uv ($H_2O$) $\lambda_{max}$: 310.5 (ε4136); ir (KBr) $\nu_{max}$: 1782 cm$^{-1}$ (C=O); $^1$Hmr ($D_2O$) δ: 5.85 (1H, m, H-5), 5.0~3.8 (4H, m, H-1', H-2' and H-3'), 3.90 (1H, dd, $J_{6,5\ cis}$=3.9, $J_{gem}$=17.5, H-6 cis), 3.58 (1H, dd, $J_{6,5\ trans}$=1.9, $J_{gem}$=17.5, H-6 trans), 1.53 and 1.44 (6H, 2s, H-acetonyl).

The residue on the millipore filter (used for hplc) was taken in water (20 ml) and placed in an ultrasonic bath. After filtration on a small celite pad and lyophilization 0.028 g (4%) of a white powder was obtained: uv ($H_2O$) $\lambda_{max}$ 309 nm (ε4925); ir (KBr) $\nu_{max}$: 1778 cm$^{-1}$ (C=O); $^1$Hmr ($D_2O$) δ: 5.81 (1H, dd, $J_{5,6\ trans}$ 3.4, $J_{5,6\ cis}$=1.8, H=5), 5.08 (1H, d, J3.2, H-1'), 3.9~4.5 (3H, m, H-2' and H-3'), 3.89 (1H, dd, $J_{6,5\ cis}$=3.5, $J_{gem}$=16.8, H-6 cis), 3.59 (1H, dd, $J_{6,5\ trans}$=1.0, $J_{gem}$=16.8, H-6 trans), 1.53 and 1.41 ppm (6H, 2s, 11-acetonyl).

EXAMPLE 85

2-(p-Aminomethylbenzyl)penem-3-carboxylic Acid (via mercaptide intermediate)

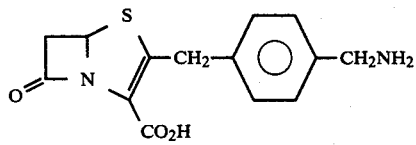

p-Bromomethylphenylacetic acid

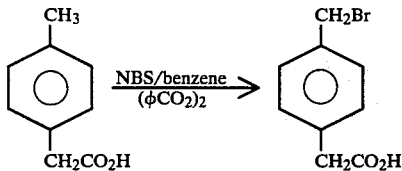

A mixture (suspension) of p-tolylacetic acid (5.00 g, 33.3 mmol), N-bromosuccinimide (5.93 g, 33.3 mmol) and benzoylperoxide (65 mg, 0.27 mmol) in dry benzene (30 ml) was heated at reflux for 5 h. After cooling it in an ice-bath (ca 10° C.), a white precipitate formed. It was collected and dried yielding 7 g of a white powder. This was triturated with warm water (1×5 ml), filtered and dried to obtain 3.75 g (16.4 mmol, 49.2%) of p-bromomethylphenylacetic acid as a white powder. This material contained a small amount of succinimide but was used as such in the next step. An analytical sample was obtained by further trituration with warm water: mp 170°-173° C.; $^1$Hmr (DMSO-$d_6$) δ: 3.57 (2H, s, —$CH_2CO_2$), 4.69 (2H, s, —$CH_2Br$) and 7.13-3.95-7.33-7.47 ppm (4H, $A_2'B_2'$, aromatic Hs); ir (nujol) $\nu_{max}$: 1690 cm$^{-1}$ (s,C=O).

p-Azidomethylphenylacetic acid

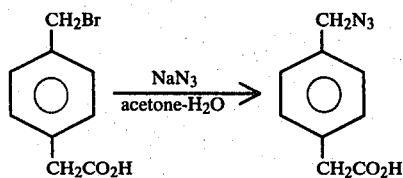

A solution of p-bromomethylphenylacetic acid (3.64 g, 15.9 mmol) in acetone (100 ml) was treated with a solution of sodium azide (1.04 g, 16.0 mmol) in $H_2O$ (15 ml). The mixture was stirred at room temperature overnight (ca. 20 h). After evaporation of the acetone, the residual solution was cooled in an ice-bath. The white gelatinous precipitate that formed was collected, washed with cold water and dried yielding 2.175 g (11.4 mmol, 71.5%) of p-azidomethylphenylacetic acid as a white solid: $^1$Hmr (DMSO-$d_6$) δ: 3.59 (2H, s, —$CH_2CO_2$), 4.42 (2H, s, —$CH_2N_3$) and 7.32 ppm (4H, s, aromatic Hs); ir (nujol) $\nu_{max}$: 2500-3400 (b, —$CO_2H$), 2070 (s, —$N_3$) and 1690 cm$^{-1}$ (s, C=O).

p-Azidomethylphenylacetyl chloride

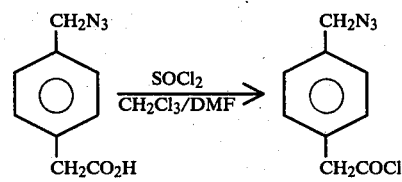

A solution of p-azidomethylphenylacetic acid (1.147 g, 6.0 mmol) in $CH_2Cl_2$ (60 ml) was treated with thionyl chloride (1 ml) and DMF (5 drops). The mixture was stirred at room temperature for 3 h and then it was heated at reflux for another 3 h. Evaporation of the solvent and the excess thionyl chloride gave 1.27 g of crude p-azidomethylphenylacetyl chloride as a yellowish oil: $^1$Hmr (CDCl$_3$) δ: 4.17 (2h, s, —$CH_2COCl$), 4.33 (2H, s, —$CH_2N_3$) and 7.33 ppm (4H, s, aromatic Hs); ir (neat $\nu_{max}$: 2100 (s,$N_3$) and 1795 cm$^{-1}$ (s, —COCl). This material was used in the next step without any purification.

4-(p-Azidomethylphenyl)acetylthio-1-(p-nitrobenzyl 2″-triphenylphosphoranylidene-2″-acetate)-2-azetidinone

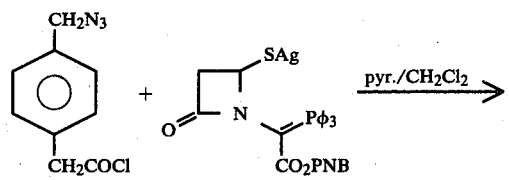

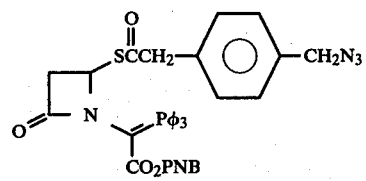

To a stirred solution of silver 1-(p-nitrobenzyl 2'-triphenylphosphoranylidene 2'-acetate)-2-azetidinone-4-thiolate (3.32 g, 5.00 mmol) in CH$_2$Cl$_2$ (30 ml) was added at 0.5° C. a solution of p-azidomethylphenylacetyl chloride (1.27 g, <6.0 mmol) in CH$_2$Cl$_2$ (45 ml). The mixture was stirred at room temperature for 5 min and then pyridine (0.90 ml, 11 mmol) added. The reaction mixture was stirred at room temperature overnight (ca 16 h) and then diluted with EtOAc (50 ml). The precipitate was removed and washed with EtOAc (50 ml). The filtrate and the washings were combined, washed successively with 1N HCl (14 ml), 2% NaHCO$_3$ (25 ml) and then brine, and dried (Na$_2$SO$_4$). Evaporation of the solvents gave 3.07 g of a foam which was purified by column chromatography (SiO$_2$, 60 g, eluent 30%–50% ether in EtOAc) collecting 1.41 g (1.93 mmol, 38.6%) of the title compound as a yellowish foam: $^1$Hmr (CDCl$_3$) δ: 4.32 ppm (s, —CH$_2$N$_3$); ir (neat) $\nu_{max}$: 2100 (s, N$_3$), 1755 (s, β-lactam), 1735 (sh, ester) and 1685 cm$^{-1}$ (n, thioester).

p-Nitrobenzyl
2-(p-azidomethyl)benzylpenem-3-carboxylate

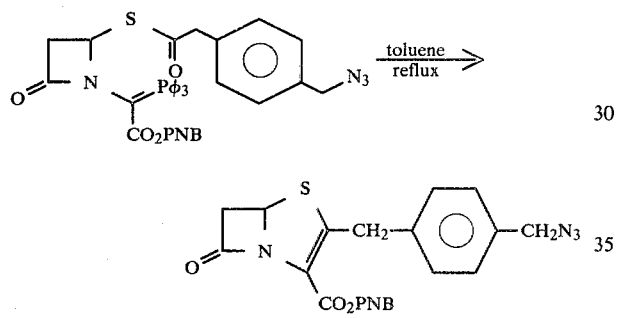

A solution of the above phosphorane (1.008 g, 1.38 mmol) in toluene (200 ml, dried over molecular sieves) was heated at reflux for 4.5 h. The solvent was evaporated in vacuo and the residue was purified by column chromatography (SiO$_2$, 20 g; eluent 20% ether in benzene) collecting 408 mg (0.904 mmol, 65.5%) of the title compound as a yellowish oil: $^1$Hmr (CDCl$_3$) δ: 3.38 (2H, dd, J$_{6,5\ trans}$=2 Hz, J$_{gem}$=16.5 Hz, H-6), 3.80 (2H, dd, J$_{6-5\ cis}$=3.5 Hz, J$_{gem}$=16.5 Hz, H-6), 3.88–4.14–4.18–4.43 (2H, ABq, 2-CH$_2$—) 4.30 (2H, s, —CH$_2$N$_3$), 5.07–5.30–5.37–5.61 (2H, ABq, 3-CO$_2$CH$_2$Ar), 5.61 (1H, dd, J$_{5-6\ cis}$=3.5 Hz, J$_{5-6\ trans}$=2 Hz, H-5), 7.25 (4H, s, 2-aromatic Hs), 7.50–7.66–8.13–8.28 ppm (4H, A$_2'$B$_2'$, 2-aromatic Hs); ir (neat) $\nu_{max}$: 2100 (s, N$_3$), 1785 (s, β-lactam) and 1705 cm$^{-1}$ (s, ester). This oil was crystallized by trituration with ether: mp 63°–65° C.; uv (CHCl$_3$) λ$_{max}$: 266 (ε13,200) and 318 mμ (ε9170); Anal. calcd for C$_{21}$H$_{17}$N$_5$O$_5$S: C 55.87, H 3.80, N 15.51, S 7.10; found: C 55.66, H 3.84, N 15.40, S 6.98.

2-(p-Aminomethylbenzyl)penem-3-carboxylic acid

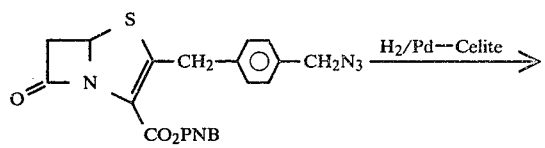

-continued

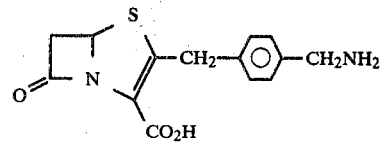

A solution of the above ester (40 mg, 0.088 mmol) in THF (25 ml) was mixed with ether (25 ml), H$_2$O (20 ml) and 30% Pd-Celite (80 mg). The mixture was hydrogenated (H$_2$:40 psi) at room temperature for 7 h. The catalyst was filtered (over Celite) and washed with H$_2$O and ether. The aqueous layer of the filtrate was washed with ether-THF (1:1) and lyophilized to give 22 mg (0.076 mmol, 84%) of crude title compound as a white powder: $^1$Hmr (D$_2$O) δ: 3.38 (1H, dd, J$_{gem}$=17 Hz, J$_{6-5\ trans}$=2 Hz, H-6), 3.78 (1H, dd, J$_{gem}$=17 Hz, J$_{6-5\ cis}$=4 Hz, H-6), 4.19 (4H, s, —CH$_2$NH$_2$ and 2-CH$_2$—Ar), 5.63 (1H, dd, J$_{5-6\ cis}$=4 Hz, J$_{5-6\ trans}$=2 Hz, H-5) and 7.41 ppm (4 H, s, aromatic Hs); ir (nujol) $\nu_{max}$: 1770 (s, β-lactam) and 1585 cm$^{-1}$ (s —CO$_2$H). A pure material was obtained in hplc (Waters C$_{18}$ Micro Bondapack Reverse Phase 30 cm×10 mm; eluent 10% CH$_3$CN in H$_2$O; ca 5%); uv (H$_2$O) λ$_{max}$: 302 (ε4780) and 260 mμ (ε4200).

EXAMPLE 86

2-(2-Aminoethoxymethyl)penem-3-carboxylic Acid
(via mercaptide intermediate)

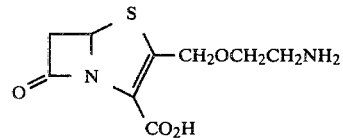

Ethyl 2-chloroethoxyacetate

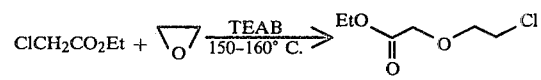

A mixture of ethyl chloroacetate (24.5 g, 0.200 mol), ethyleneoxide (8.80 g, 0.300 mol) and tetraethylammonium bromide (0.40 g, 1.9 mmol; dried in vacuo) was heated in a bomb at 150°–160° C. for 6 h. After cooling, the reaction mixture was distilled under reduced pressure collecting 6.66 g (54.4 mmol, 27.2%) of ethyl chloroacetate, bp 22°–24° C. (0.5 mmHg) and 8.39 g (50.4 mmol, 25.2%) of ethyl 2-chloroethoxyacetate as a colourless oil; bp 49°–53° C. (0.1 mmhg); $^1$Hmr (CDCl$_3$) δ: 1.28 (3H, t, J=7 Hz,—CH$_3$), 3.5–4.0 (4H, m, A$_2$B$_2$,—CH$_2$CH$_2$—Cl), 4.15 (2H, s, —COCH$_2$O—), 4.25 ppm (2H, q, J=7 Hz, —OCH$_2$CH$_3$); ir (neat) $\nu_{max}$: 1740 cm$^{-1}$ (C═O ester). Procedure of D. Klamann et al, Jastus Liebig Ann., 710, 59 (1967) (Reported: yield 42%, bp 55.5°/0.35 mmHg).

Ethyl 2-azidoethoxyacetate

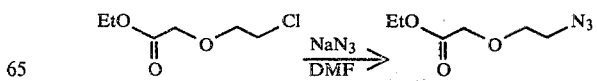

A mixture of ethyl 2-chloroethoxyacetate (7.71 g, 36.3 mmol) and sodium azide (3.31 g, 50.9 mmol) in DMF (100 ml) was heated at 80°–90° C. for 3.5 h by which time tlc (hexane; ether 1:1) indicated that the reaction was complete. The cooled mixture was poured into H$_2$O (1 l) and extracted with ether (250 ml×3). The extracts washed with H$_2$O (×2) and brine (×1) were dried (MgSO$_4$) and evaporated yielding 7.16 g (41.4 mmol 89.4%) of ethyl 2-azidoethoxyacetate as a yellowish oil: $^1$Hmr (CDCl$_3$) δ: 1.30 (3H, t, J=7 Hz, —OCH$_2$CH$_3$), 3.3–4.0 (4H, m, —OCH$_2$ CH$_2$N$_3$), 4.13 (2H, s, —COCH$_2$O—), 4.23 ppm (2H, q, J=7 Hz, —OCH$_2$CH$_3$); ir (neat) ν$_{max}$: 2100 (N$_3$) and 1750 cm$^{-1}$ (C=O ester). This material was used in the next step without further purification.

2-Azidoethoxyacetic acid

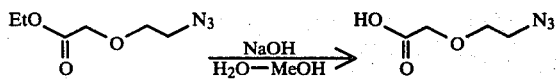

To a solution of ethyl 2-azidoethoxyacetate (6.56 g, 37.9 mmol) in MeOH (80 ml) was added 1N aq. NaOH (80 ml) and the mixture was stirred at room temperature overnight (17 h). After removing the insoluble material, the methanol was evaporated in vacuo and this was saturated with sodium chloride and washed with ether (30 ml×3). The aqueous layer acidified with 3N HCl (30 ml) was extracted with ether (40 ml×4). The ether extracts were washed with brine, dried (MgSO$_4$) and evaporated to yield 4.25 g (29.3 mmol, 77.3%) of 2-azidoethoxyacetic acid as a colourless oil: $^1$Hmr (CDCl$_3$) δ: 3.3–4.0 (4H, m, —OCH$_2$CH$_2$N$_3$), 4.22 (2H, s, —COCH$_2$O—), 9.52 ppm (1H, s, —CO$_2$H, exchanged with D$_2$O); ir (neat) ν$_{max}$: 2600–3300 (br,—CO$_2$H) 2100 (azide) and 1740 cm$^{-1}$ C=O—CO$_2$H). This material was used in the next step without further purification.

2-Azidoethoxyacetyl chloride

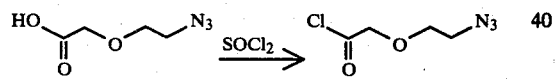

A solution of 2-azidoethoxyacetic acid (2.09 g, 14.4 mmol) in thionyl chloride (5 ml) was stirred at room temperature for 4 h. The excess thionyl chloride was removed under the vacuum of the water aspirator and the residue dissolved in benzene (10 ml, dried over molecular sieves) was evaporated in vacuo. The oil so obtained was dried in vacuo (water pump) over NaOH for 1 h yielding 2.23 g (13.6 mmol, 94.4%) of 2-azidoethoxyacetyl chloride as a colourless oil: $^1$Hmr (CDCl$_3$) δ: 3.43 (2H, br. t, J=5 Hz, —CH$_2$O—) 3.78 (2H, br. t, J=5 Hz, —CH$_2$N$_3$) and 4.50 ppm (2H, s, —COCH$_2$O—); ir (neat) ν$_{max}$: 2100 (azide) and 1800 cm$^{-1}$ (—COCl). This material was used in the next reaction without any purification.

4-(2'-azidoethoxyacetylthio)-1-(paranitrobenzyl 2''-triphenylphosphoranylidene-2''-acetate)-2-azetidinone

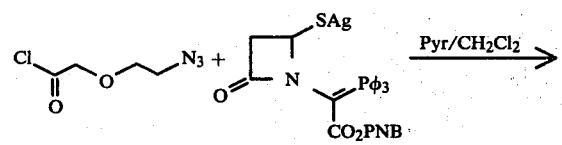

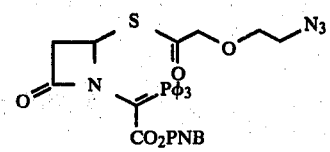

To a stirred solution of silver 1(paranitrobenzyl-2'-triphenylphosphoranylide-2'-acetate)-2-azetidinone-4-thiolate (7.96 g, 12.0 mmol) in CH$_2$Cl$_2$ (100 ml) containing pyridine (1.94 ml, 24.0 mmol) was added at 0°–5° C. under a nitrogen atmosphere a solution of 2-azidoethoxyacetyl chloride (2.23 g, 13.6 mmol) in CH$_2$Cl$_2$ (20 ml) and the mixture was stirred at room temperature for 2 h. After filtration of the precipitate, the filtrate was evaporated and the residual oil was purified by column chromatography (SiO$_2$, 160 g; eluent, EtOAc: CH$_2$Cl$_2$=1:1) collecting 4.216 g (6.17 mmol, 51.4%) of the title phosphorane as a yellowish foam. This foam was used in the next step. An analytical sample was obtained by crystallization from CH$_2$Cl$_2$-ether (1:9): mp 128°–129° C. (dec.); ir (nujol) ν$_{max}$: 2090 (—N$_3$), 1755 (β-lactam) and 1690 cm$^{-1}$ (thioester); Anal. calcd for C$_{34}$H$_{30}$N$_5$O$_7$PS: C 59.74, H 4.42, N 10.26, S 4.69; found: C 59.33, H 4.49, N 9.69, S 5.19; tlc (EtOAc) Rf=0.55.

p-Nitrobenzyl 2-(2-azidoethoxy)methyl-penem-3-carboxylate

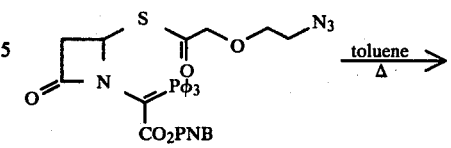

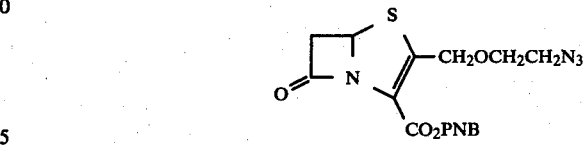

A solution (cloudy) of the above phosphorane (4.13 g, 6.04 mmol) in toluene (200 ml) was heated under reflux under a nitrogen atmosphere for 1.5 h. After removal of the insoluble material, the solvent was evaporated in vacuo and the residual oil was purified by column chromatography (SiO$_2$, 80 g, eluent 5% ether in benzene) collecting 2.44 g (6.02 mmol, 99.6%) of title compound as a yellowish oil. This oil was used in the next step. Crystallization from CH$_2$Cl$_2$-ether (1:9) gave an analytical sample: mp 88°–89.5° C.; $^1$Hmr (CDCl$_3$) δ: 3.35 (2H, t, J=5 Hz, —OCH$_2$—), 3.47 (1H, dd, J$_{gem}$=16 Hz, J$_{trans}$=2 Hz, C$_6$—H), 3.67 (2H, t, J=5 Hz, —CH$_2$N$_3$), 3.85 (1H, dd, J$_{gem}$=16 Hz, J$_{cis}$=3.5 Hz, C$_6$-H), 4.73 (2H, ABq, J=16, 19 C$_2$—CH$_2$), 5.30 (2H, ABq, J=13.5, 9, —OCH$_2$Ar), 5.63 (1H, dd, J$_{trans}$=2 Hz, J$_{cis}$=3.5 Hz, C$_5$-H), 7.50–7.63–8.12–8.27 ppm (4H, A$_2$'B$_2$', aromatic Hs); ir (nujol) ν$_{max}$: 2100 (—N$_3$), 1785 (β-lactam) and 1695 cm$^{-1}$ (ester) uv (EtOH) λ$_{max}$: 263 mμ (ε12000), 320.5 mμ (ε9600) tlc (benzene: ether=1:1) Rf=0.60.

2-(2-Aminoethoxy)methyl-penem-3-carboxylic acid

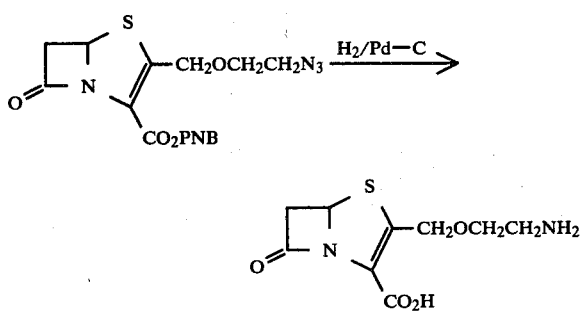

A solution of the above azido ester (1.62 g, 4.00 mmol) in dimethoxyethane (50 ml) was mixed with ether (50 ml), H$_2$O (50 ml) and 10% Pd-C (1.62 g; Engelhard) and hydrogenated at room temperature (H$_2$: 55 psi) for 2.5 h. After filtration of the catalyst, the aqueous layer was washed with ether (50 ml×2) and then EtOAc (50 ml×1). The aqueous solution was lyophilized to give 817 mg (3.34 mmol, 83.6%) of the title amino-acid as a yellowish powder: uv (H$_2$O) $\lambda_{max}$: 304 m$\mu$ ($\epsilon$5000). This material was purified by hplc (Waters, C$_{18}$ Micro Bondapak Reverse Phase 30 cm×10 mm; eluent 1% CH$_3$CN in H$_2$O) to give 432 mg (1.77 mmol, 44.2%) of the title amino-acid as a white powder: $^1$Hmr (D$_2$O) $\delta$: 3.19–3.9 (4H, m, —OCH$_2$CH$_2$NH$_2$), 3.54 (1H, dd, J$_{gem}$=16.9 Hz, J$_{trans}$=1.9 Hz, C$_6$—H), 3.88 (1H, dd, J$_{gem}$=16.8 Hz, J$_{cis}$=3.7 Hz, C$_6$—H), 4.52-4.70-4.83–5.01 (2H, AB type, C$_2$—CH$_2$O—) and 5.77 ppm (1H, dd, J$_{cis}$=3.6 Hz, J$_{trans}$=1.9 C$_5$—H); ir (KBr disc) $\nu_{max}$: 1770 ($\beta$-lactam) and 1580 cm$^{-1}$ (—CO$_2$H); uv (H$_2$O) $\lambda_{max}$: 304 m$\mu$ ($\epsilon$5400), 256 m$\mu$ ($\epsilon$3100).

EXAMPLE 87

2-(5'-Aminopentyl)-penem-3-carboxylate (via mercaptide intermediate)

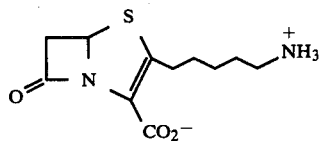

6-Azidohexanoic acid

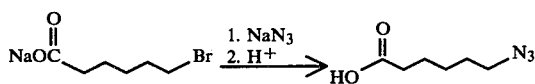

The above compound was prepared by a literature procedure [W. M. Rothe and K. Gehrke, Makromol Chem. 83, 1 (1965)] as follows: To a solution of 6-bromohexanoic acid (21.6 g, 0.11 mol) in 3.3N sodium hydroxide (33.3 ml) was added sodium azide (8.33 g, 1.27 mol) and the mixture stirred at room temperature for 5 min. Ether (5 ml) was then added and the reaction mixture was refluxed for 6 h, cooled to room temperature and acidified with 2N H$_2$SO$_4$ to pH 2. The oily layer which formed was separated and the aqueous layer extracted with ether (25 ml). The organic extract was combined with the oily layer and the resulting solution dried (Na$_2$SO$_4$) and evaporated to yield 14.5 g (83.6%) of title compound as an oil; ir (neat) $\nu_{max}$: 2097 (N$_3$), 1708 cm$^{-1}$ (C=O); $^1$Hmr (CDCl$_3$) $\delta$: 1.2–2.0 (m, 6H, 3CH$_2$), 2.4 (m, 2H,—CH$_2$CO—), 3.3 (m, 2H, CH$_2$N$_3$), 11.5 (s, 1H, CO$_2$H).

6-Azidohexanoyl chloride

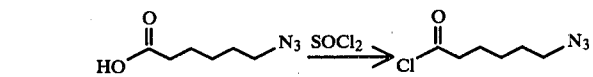

The above compound was prepared by a literature procedure [V. M. Rothe and K. Gehrke, Makromol Chem. 83, 1 (1965)] as follows: To 6-azidohexanoic acid (7.5 g, 47.7 mmol) previously cooled to 0° C. was added 10 ml (16.3 g, 137 mmol) of thionyl chloride and the solution was stirred in cold until the evolution of gas had subsided (5–10 min) and then refluxed for 1 h. The reaction mixture was evaporated and the residue distilled to give 5.5 g (65.6%) of title compound bp 110°–111° C./12 Tor (lit. bp 73°–75° C./0.1 torr); ir (neat) $\nu_{max}$: 2097 (N$_3$), 1795 cm$^{-1}$ (C=O); $^1$Hmr (CDCl$_3$) $\delta$: 1.1–2.0 (m, 6H, 3CH$_2$), 2.9 (m, 2H, CH$_2$CO), 3.27 (m, 2H, CH$_2$N$_3$).

p-Nitrobenzyl 4-(6-azidohexanoylthio)-2-azetidinon-1-yl)triphenyl-phosphoranylideneacetate

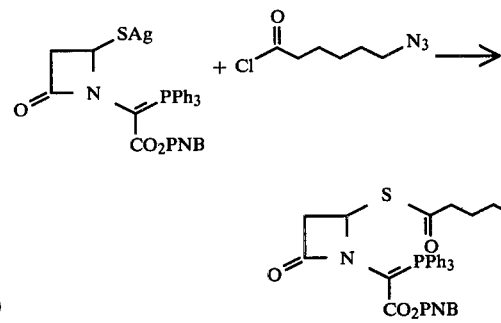

To a ice-cooled solution of silver thiolate (6.63 g, 10 mmol) in dry CH$_2$Cl$_2$ (40 ml) was added a solution of 6-azidohexanoyl chloride (1.76 g, 10 mmol) in dry CH$_2$Cl$_2$ (10 ml). The reaction mixture was stirred at 0° C. for 5 min and then at 23° C. for 1.5 h. The mixture was filtered through a pad of celite and the cake washed with CH$_2$Cl$_2$ (20 ml). The filtrate and washings were combined and washed successively with 2% sodium hydrogen carbonate (400 ml) and water (500 ml), dried and evaporated. The residue was chromatographed on a wet column of silica gel (90 g) using CH$_2$Cl$_2$ and CH$_2$Cl$_2$—MeOH mixtures as eluent (CH$_2$Cl$_2$, 200 ml; 1% MeOH—CH$_2$Cl$_2$, 300 ml; 1.5% MeOH—CH$_2$Cl$_2$, 300 ml). The fractions containing the product were combined and evaporated to provide 2.59 g (37.2%) of title compound. Rf 0.59 (silica, 5% MeOH—CH$_2$Cl$_2$); ir (neat) $\nu_{max}$: 2095 (N$_3$), 1752 (ester and lactam) cm$^{-1}$.

p-Nitrobenzyl 2-(5'-azidopentyl)-penem-3-carboxylate

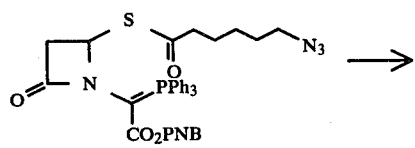

-continued

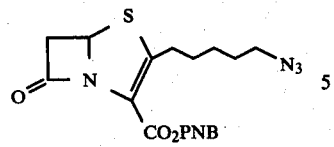

The phosphorane (1.36, 1.96 mmol) was suspended in dry toluene (50 ml) and the mixture refluxed for 9 h. After cooling to room temperature, the reaction mixture was filtered and the filtrate evaporated. The residue was chromatographed on a small silica gel column (7.0 cm×3.5 cm I.D) using benzene-ether mixture (1:1) as eluent. The fractions containing the product were combined and evaporated to give 0.58 g (71%) of title compound as a syrup; Rf 0.41 (silica, 20% ether in benzene); ir (neat) $\nu_{max}$: 2096 ($N_3$), 1790 (lactam), 1710 cm$^{-1}$ (ester) $^1$Hmr (CDCl$_3$) δ: 1.46–2.0 (m, 6H, 3CH$_2$),

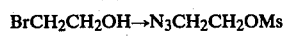

2.83–3.23 (m, 4H, CH$_2$N$_3$ and CH$_2$—), 3.43 (dd, J$_{gem}$=14, J$_{5,6\ trans}$=2 Hz, 1H, H-6$_b$), 3.80 (dd, J$_{gem}$=14, J$_{5,6\ cis}$=3.8 Hz, 1H, H-6a), 5.27 (center of ABq, J=14, 2H, CH$_2$PNB), 5.57 (dd, 1H, H-5), 7.57 (d, J=8, 2H, Ho aromatic), 8.17 (d, J=8, 2H, Hm aromatic).

2-(5-Aminopentyl)-penem-3-carboxylic acid

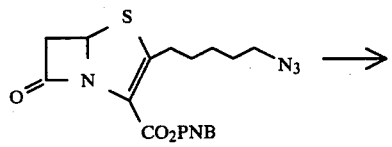

To a solution of the ester (0.48 g, 1.15 mmol) in freshly distilled THF was successively added ether (20 ml), water (20 ml) and Palladium on diatomaceous earth catalyst (30%, 1.2 g). The mixture was shaken at room temperature under hydrogen at 55 psi for 2 h. The catalyst was removed by filtration through a pad of Celite and washed on the funnel with water (20 ml). The combined filtrate and washing was extracted with benzene and with ethyl acetate. The aqueous phase was lyophylized to give 130 mg of an amorphous powder. In another separate experiment, 450 mg of the ester were hydrogenated by the above procedure to yield 136 mg of product. The samples from the two experiments were combined and purified by hplc to provide, after lyophylization, 103 mg (17.2%) of title compound, mp 168° C. (dec.); ir (nujol) $\nu_{max}$: 3200–2600 (N$^+$H$_3$), 1765 (lactam, 1570 cm$^{-1}$ (C=O); uv (H$_2$O) λ$_{max}$: 301 (ε5516) and 261 (ε4026); $^1$Hmr (D$_2$O ε: 1.4–1.9 (m, 6H, 3CH$_2$), 2.71–3.35 (m, 4H, and —CH$_2$N—), 3.54 (dd, J$_{gem}$=16, J$_{5,6\ trans}$=1.7 Hz, 1H, H-6$_b$), 3.74 (dd, J$_{gem}$=16, J$_{5,6}$ cis=3.5 Hz, 1H, H-6$_a$), 5.70 (dd, 1H, H-5). Anal. calcd for C$_{11}$H$_{16}$N$_2$O$_3$S: C 51.55; H 6.29; N 10.93. found: C 48.67; H 6.17; N 10.33.

EXAMPLE 88

2-(2-Aminoethylthiomethyl)penem-3-carboxylic Acid (via mercaptide intermediate)

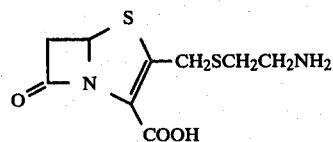

2-Azidoethyl methanesulfonate

BrCH$_2$CH$_2$OH→N$_3$CH$_2$CH$_2$OMs

A solution of bromoethanol (7.5 g, 60.0 mmol) and sodium azide (5.0 g, 76.9 mmol) in HMPT (30 ml) was heated at 115° C. for 2.5 h. The reaction mixture was cooled to 23° C. and diluted with CH$_2$Cl$_2$ (100 ml). The solids were removed by filtration and the CH$_2$Cl$_2$ was evaporated on the rotary evaporator leaving a yellow liquid which was cooled to 0° C. and successively treated with mesylchloride (5.57 ml, 72.0 mmol) and triethylamine (10.0 ml, 72.0 mmol). The reaction mixture was stirred at 0° C. for 1 h, then at 23° C. for 6 h, and poured into H$_2$O (300 ml). The aqueous solution was extracted with ether (1×200 ml, 4×100 ml); the ether extracts were combined, washed with 1N HCl solution, H$_2$O saturated NaHCO$_3$ solution and H$_2$O, dried over anhydrous MgSO$_4$ and concentrated on a rotary evaporator to an orange liquid which was distilled under high vacuum bp 95°–100° C. 0.3 torr, 5.8 g, 58.5%; ir (neat) $\nu_{max}$: 2005 (s, N$_3$), 1345 (s, SO$_2$—O), 1175 (m, SO$_2$—O) cm$^{-1}$. $^1$Hmr (CDCl$_3$) δ: 3.03 (s, 3H, OCH$_3$), 3.43–3.76 (m, 2H, H-2) and 4.2–4.46 ppm (m, 2H, H-1).

2'-Azidoethylthioglycolic acid

N$_3$CH$_2$CH$_2$SCH$_2$COOH

Thioglycolic acid (3.14 g, 34.1 mmol) was treated with 1N NaOH solution (68 ml, 68.0 mmol) and the resulting solution was stirred at 23° C. for 0.5 h and treated with a solution of 2'-azidoethyl methanesulfonate (5.3 g, 32.1 mmol) in dimethoxy ethane (15 ml). The reaction mixture was stirred at 45° C. for 22 h, cooled to 23° C., washed with CH$_2$Cl$_2$ (3×20 ml), acidified with 6 N HCl solution and extracted with CH$_2$Cl$_2$ (7×40 ml). The CH$_2$Cl$_2$ extracts were combined, dried over anhydrous Na$_2$SO$_4$ and concentrated on a rotary evaporator to an oil which was distilled under high vacuum bp 117°–22° C./0.27 torr, 4.2 g, 81.2% ir (neat) $\nu_{max}$: 2100 (s, N$_3$), 1708 (s, C=O) cm$^{-1}$. $^1$Hmr (CDCl$_3$) δ: 2.7–3.07 (m, 2H, H-1'), 3.35 (s, 2H, H-1), 3.30–3.73 (m, 2H, H-2') and 11.81 ppm (s, 1H, COOH).

2'-Azidoethylthioacetyl chloride

To a solution of 2-azidoethylthio glycolic acid (3.33 g, 20.7 mmol) in CH$_2$Cl$_2$ (50 ml) was added oxalyl chloride (3.9 ml) and DMF (one drop). The reaction mixture was stirred at 23° C. for 1.5 h and the solvent was removed on a rotary evaporator leaving a yellow liquid. ir(neat) $\nu_{max}$: 2100 (s, $N_3$), 1785 (bs, C=O). $^1$Hmr (CDCl$_3$) δ: 2.6–3.0 (m, 2H, H-1'), 3.37–3.73 (m, 2H, H-2'), and 3.82 ppm (s, 2H, H-1).

4-(2'-azidoethylthioacetylthio)-1-(paranitrobenzyl 2''-triphenylphosphoranylidene-2''-acetate)-2-azetidinone

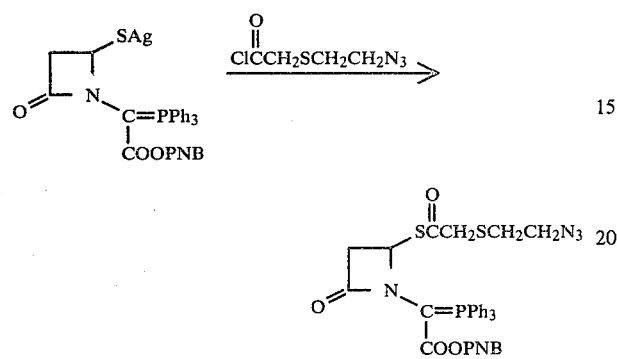

A solution of silver 1-(paranitrobenzyl 1'-triphenyl-phosphoranylidene-1'-acetate)-2-azetidinone-4-thiolate (15.7 mmol) and pyridine (1.6 ml, 19.8 mmol) in CH$_2$Cl$_2$ (200 ml) was treated dropwise (0.25 h) with a solution of 2'-azidoethylthioacetyl chloride (3.64 g, 20.3 mmol) in CH$_2$Cl$_2$ (50 ml). The reaction mixture was stirred at 23° C. for 1.5 h and filtered; the solids were washed with CH$_2$Cl$_2$. The filtrate and washings were combined and washed with 0.1N HCl solution, H$_2$O, saturated NaHCO$_3$ solution and H$_2$O, dried over anhydrous Na$_2$SO$_4$ and concentrated on a rotary evaporator to an orange syrup. A column chromatography (300 g of silica gel G-60, eluent; EtOAc in CH$_2$Cl$_2$, 0–40% of crude compound gave after evaporation of solvent a white powder, 7.7 g, 70%. An analytical sample was obtained after a recrystallization from CH$_2$Cl$_2$-ether-pet. ether, mp 150°–1° C. dec. Anal. calcd for C$_{34}$H$_{30}$N$_5$O$_6$S$_2$P: C 58.36, H 4.32, N 10.01, S 9.17; found: C 58.64, H 4.36, N 10.03, S 9.25. ir (KBr) $\nu_{max}$: 2100 (s, N$_3$), 1750 (s, C=O of β-lactam), 1675 (s, C=O), 1655 (s, C=O), 1610 (s, aromatics), and 1440 cm$^{-1}$ (s, P—Ph).

paraNitrobenzyl 2-aminoethylthiomethylpenem-3-carboxylate

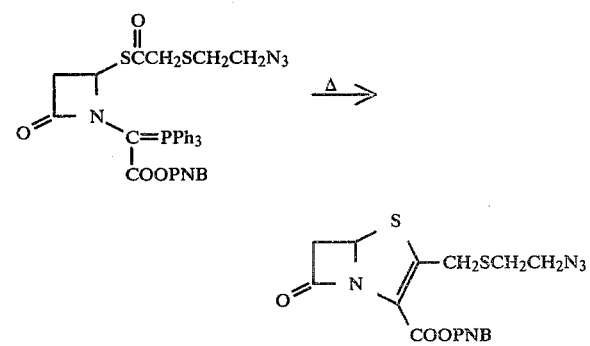

A suspension of 4-(2'-azidoethylthioacetylthio)-1-(paranitrobenzyl 2''-triphenylphosphoranylidenylacetate)-2-azetidinone (4.5 g, 6.43 mmol) in toluene (375 ml) was stirred at 110° C. for 2.25 h under a nitrogen atmosphere. The reaction mixture was cooled to 23° C. and the evaporation of solvent on a rotary evaporator gave an orange syrup. The purification of crude material was done on a silica gel column (90 g of silica gel G-60, eluent: ether-pet-ether, 1:1–3:2); the pure material was obtained as a yellow syrup, 2.2 g, 81%). ir (neat) $\nu_{max}$: 2100 (s, N$_3$), 1785 (s, C=O of β-lactam), 1705 cm$^{-1}$ (s, C=O of PNB); $^1$Hmr (CDCl$_3$) δ: 2.53–2.90 (m, 2H, H-1''), 3.30–3.67 (m, 3H, HO2'', H-6 trans), 3.98 (ABq, J$_{a-b}$=14.8 Hz, 2H, H-1'), 5.32 (ABq, J$_{a-b}$=13.0 Hz, 2H, CH$_2$—PhNO$_2$), 5.66 (dd, J$_{H-5,H-6\,cis}$=3.6 Hz, J$_{H-5,H-6\,trans}$=1.9 Hz, 1-H, H-5), 7.58 (d, J$_{Ho-Hm}$=8.8 Hz, 2H, Ho PNB) and 8.19 ppm (d, J$_{Hm-Ho}$=8.8 Hz, 2H, Hm PNB).

2-Aminoethylthiomethylpenem-3-carboxylic acid

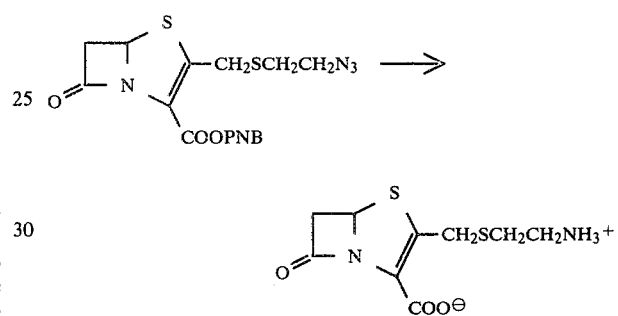

To a solution of p-nitrobenzyl 2-azidoethylthiomethylpenem-3-carboxylate (45 mg, 0.11 mmol) in dimethoxyethane (5 ml) were added ether (5 ml), water (5 ml) and 10% Pd/C (45 mg, 0.11 mmol). The reaction mixture was hydrogenated at 23° C. under 45 psi of hydrogen for 3.0 h and filtered over a Celite pad. The pad was washed with water and the filtrate and washings were combined and diluted with ether. The water phase was separated and washed with ether and lyophylized. The crude compound (20 mg) was purified by hplc: 5 mg, 18%; ir (KBr) $\nu_{max}$: 1765 (C=O), 1600 cm$^{-1}$ (b, COO$^-$); $^1$Hmr (D$_2$O) δ: 2.70–3.00 (m, 2H, H-1''), 3.15–3.45 (m, 2H, H-2''), 3.49 (dd, J$_{gem}$=16.8 Hz, J$_{6,5\,trans}$=1.7 Hz, H-6 trans), 3.85 (dd, J$_{gem}$=16.8Hz, J$_{6-5cis}$=3.4 Hz, H-6 cis), 4.05 (ABq, J$_{a-b}$=14.6 Hz, 2H, H-1) and 5.74 ppm (dd, J$_{5-6\,cis}$=3.4 Hz, J$_{5-6\,trans}$=1.7 Hz, 1H, H-5); uv λ$_{max}$: 307 (ε4330), 250 (ε3282).

EXAMPLE 89

Silver 1-(β-Trimethylsilylethyl-2'-triphenylphosphoranylidene-2'-acetate)-2-azetidinone-4-thiolate

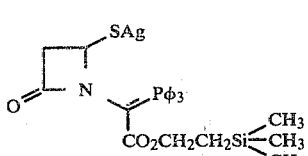

di-β-trimethylsilylethyl fumarate

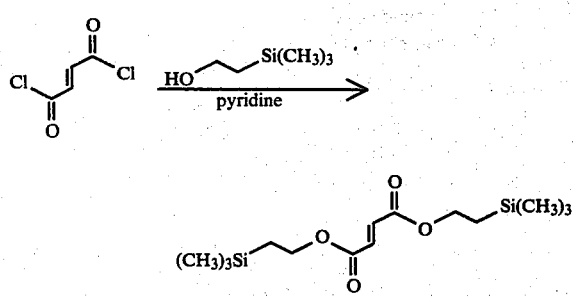

To a cold (−10° C.) ether (20 ml) solution of 2-trimethylsilyl ethanol (4.73 g, 0.04 mmol) [H. Gerlach Helv. Chim. Acta 60, 3039 (1977)] and pyridine (5.66 ml, 0.07 mol), under nitrogen, was added dropwise (15 min) fumaryl chloride (3.78 ml, 0.035 mol) dissolved in ether (10 ml). The black mixture was stirred five minutes at −10° C. and ten at room temperature. Charcoal was added and the reaction mixture filtered on a Celite pad. The filtrate was washed with sodium bicarbonate 1% - brine (1:1, 150 ml). The aqueous phase was back extracted with ether (30 ml). The ether solutions were combined, washed with brine, dried over sodium sulfate, filtered and concentrated under reduced pressure to give a brown solid. This compound was purified on a silica gel pad (30 g, 4×5 cm) with benzene (300 ml) as eluent to give an oil (4.855 g, 77%) which solidified on standing: mp 33°-34° C. Anal. calcd for $C_{14}H_{28}O_4Si_2$: C 53.12, H 8.91; found: C 53.35, H 8.91. $^1$Hmr (CDCl$_3$) δ: 6.78 (2H, s, C═CH), 4.26 (4H, m, CH$_2$—O), 1.03 (4H, m, CH$_2$—Si) and 0.06 ppm (18H, s, (CH$_3$)$_3$Si); ir (CHCl$_3$) $\nu_{max}$: 1710 (C═O of ester), 1643 (C═C), 1267, 1258, 862 and 840 cm$^{-1}$ (Si—C).

Trimethylsilylethyl glyoxylate hydrate

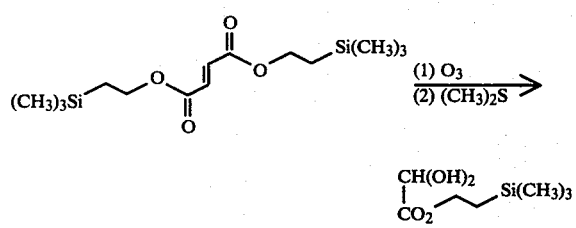

A solution of di-β-trimethylsilylethyl fumarate (37 g, 0.117 mmol) in methylene chloride (1.1l) was ozonized at −78° C. until a blue color persisted. The excess ozone was purged with nitrogen and dimethyl sulfide (2.57 ml, 0.351 mol) was added. The solution was allowed to gradually warm to 23° C. The reaction mixture was diluted with carbon tetrachloride to 2 liters and washed with 1% aqueous solution of sodium carbonate (500 ml). The organic phase was dried over sodium sulfate, filtered on Celite and evaporated (∼25° C.) to dryness to give 43.9 g of the title compound (97%); ir (neat) $\nu_{max}$: 3450 (—OH), 1740 (ester, 1255, 860 and 840 cm$^{-1}$ (Si—C).

1-(β-trimethylsilylethyl 2'-hydroxy-2'-acetate)-4-tritylthio-2-azetidinone

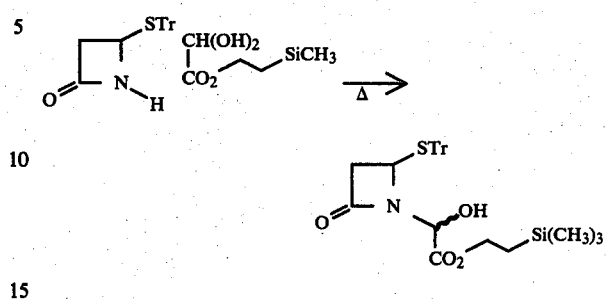

Trimethylsilylethyl glyoxylate hydrate (4.000 g, 11.6 mmol) and the 4-tritylthio-2-azetidinone (4.8 g, 24.96 mmol) were refluxed in benzene (25 ml) through a Dean Stark condenser, under nitrogen for 24 h. The solvent was evaporated under a vacuum. The product was chromatographed on a silica gel column (450 g, 8.5×14.5 cm) and eluted with ethyl acetate:methylene chloride (1:19) until the title compound started to come out (∼1.5 l) and then with ethylacetate:methylene chloride (1:9, 2 l). The fractions containing the title compound were combined and evaporated to dryness to give 5.415 g (89%) of the title compound. $^1$Hmr (CDCl$_3$) δ: 7.80 to 6.70 (15H, m, trityl), 5.23 and 4.90 (1H, 2s, H—C—O), 4.50 to 4.10 (3H, m, H-3 and O—CH$_2$), 2.60 (2H, m, H-2), 0.95 (2H, m, CH$_2$—Si and 0.1 ppm (9H, s, Si—CH$_3$); ir (CHCl$_3$) $\nu_{max}$: 3520 (—OH), 1765 (C═O of β-lactam), 1740 (C═O of ester), 1595 (C—H, aromatic), 1257, 860 and 840 cm$^{-1}$ (C—Si)

1-(β-trimethylsilylethyl 2'-chloro-2'-acetate)-4-tritylthio-2-azetidinone

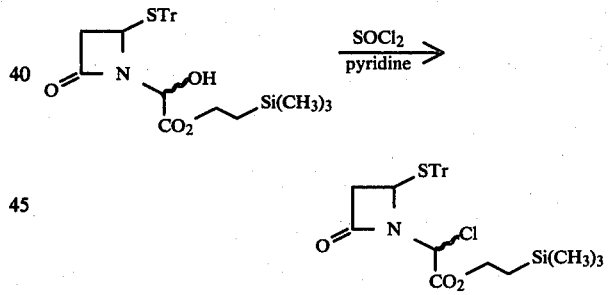

A solution of thionyl chloride (0.74 ml, 10.37 mmol) in dry THF (9 ml) was added dropwise with stirring to a solution of 1-(β-trimethylsilylethyl 2'-hydroxy-2'-acetate)-4-tritylthio-2-azetidinone (4.9 g, 9.37 mmol), pyridine (0.84 ml, 10.38 mmol) and dry THF (40 ml) at −15° C. under a nitrogen atmosphere. The mixture was stirred at −15° C. for 2 h. The precipitate was removed by filtration on a Celite pad and washed with benzene (50 ml). The filtrate was evaporated in vacuo at 30° C. The residue was dissolved in benzene (100 ml), treated with charcoal and filtered through a Celite pad. Evaporation of the solvent gave a residue which was purified through a silica gel pad (100 g, 4.7×11 cm): hexane-benzene (1:1, 400 ml), ether-benzene (1:19, 1 l). Evaporation of the pertinent fractions gave 4.64 g of the title compound (92%). $^1$Hmr (CDCl$_3$) δ: 7.30 (15H, m, aromatic H), 5.77 and 5.43 (1H, 2s, CH—Cl), 4.7 to 4.2 (3H, m, H-4 and CH$_2$—O), 2.85 to 2.50 (2H, m, H-3), 1.15 (2H, m, CH$_2$—Si) and 0.06 ppm (9H, s, Si—CH$_3$); ir (neat) $v_{max}$: 1760 (C=O), 860 and 840 cm$^{-1}$ (C—Si).

1-(β-trimethylsilylethyl-2'-triphenylphosphoranylidene-2'-acetate)-4-tritylthio-2-azetidinone

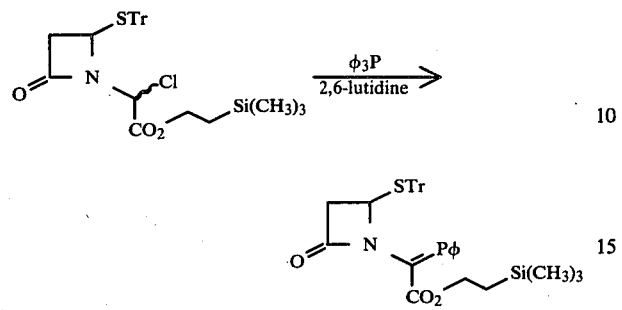

A dioxane (20 ml) solution of the above chloroazetidinone (4.12 g, 7.568) was treated with triphenylphosphine (2.209 g, 8,424 mmol) and 2,6-lutidine (0.98 ml, 8.424 mmol). The mixture was refluxed for 3.5 h. The cooled solution was filtered and the white solid washed with THF. The filtrate was evaporated to dryness. The residue was purified on a silica gel column (200 g, 4×31 cm) using ethylacetate-hexane (3:7, 1 l; 7:3, 1 l) to give the title phosphorane (4.836 g, 83%). ir (film) $v_{max}$: 1755 (C=O), 1615 (phosphorane), 850 and 830 cm$^{-1}$ (Si—C). Anal. calcd for C$_{47}$H$_{46}$NO$_3$PSSi: C 73.89, H 6.07, N 1.81; found: C 72.18, H 6.08, N 1.83

Silver 1-(β-trimethylsilylethyl 2'-triphenylphosphoranylidene-2'-acetate)-2-azetidinone-4-thiolate

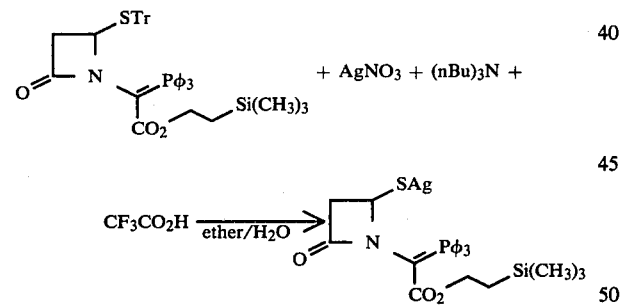

1-(β-trimethylsilylethyl 2'-triphenyl phosphoranylidene-2'-azetate)-2-azetidinone (7.64 g, 10 mmol) was dissolved in ether (60 ml). An aqueous solution of silver nitrate (0.5M, 80 ml, 40 mmol) was added followed by a rapid addition (1 min) of a solution of tributylamine (3 ml, 12.58 mmol) and trifluoroacetic acid (0.154 ml, 0.2 mmol) in ether (20 ml). The mixture was mechanically stirred for 19 min. The precipitate was filtered, rinsed with ether (200 ml), triturated in water (70 ml), filtered again and rinsed with ether (100 ml). The light brown solid was dried under vacuum (water aspirator 10 min and pump 65 min) to give the title compound (6.42 g). ir (CHCl$_3$) $v_{max}$: 1862 (C=O, 1630 (phosphorane), 860 and 840 cm$^{-1}$ (Si—C).

EXAMPLE 90

2-Methylpenem-3-carboxylic Acid, Sodium Salt (via mercaptide intermediate using β-trimethylsilylethanol as the carboxylic acid protecting group)

4-Acetylthio-1-(β-trimethylsilylethyl 2'-triphenylphosphoranylidene-2'-acetate)-2-azetidinone

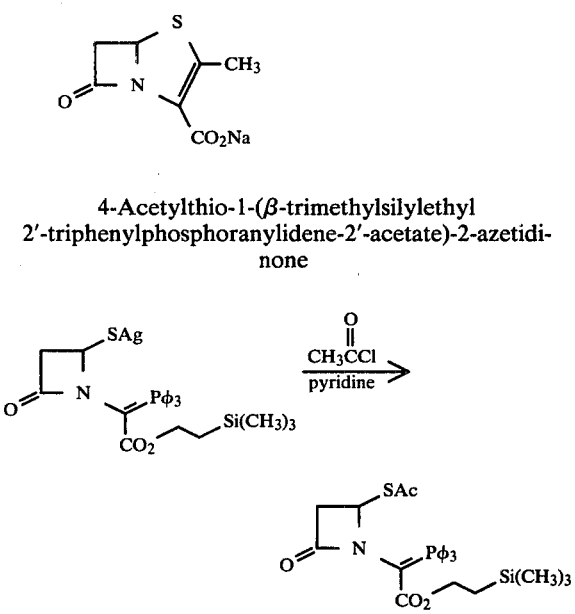

To a cold (0° C.) methylene chloride (2 ml) solution of silver 1-(β-trimethylsilylethyl-2'-triphenylphosphoranylidene-2'-acetate-2-azetidinone-4-thiolate (154 mg, 0.22 mmol) and pyridine (0.026 ml, 0.33 mmol) was added acetylchloride (0.023 ml, 0.33 mmol). The reaction mixture was protected from light and stirred vigorously for 15 min. The precipitate was filtered and washed with chloroform (10 ml). The filtrate was evaporated and the residue purified on a silica gel plate (ethyl acetate-ether 35:65) to give the title phosphorane (85 mg, 66%) as a foam. Anal. calcd for C$_{30}$H$_{34}$NO$_4$PSSi: C 63.91, H 6.07, N 2.48; found: C 64.20, H 6.13, N 2.42. ir (film) $v_{max}$: 1760 (C=O of β-lactam), 1695 (C=O of ester), 1645 (C=O of thioester), 1615 (phosphorane), 842 and 865 cm$^{-1}$ (Si—C).

β-trimethylsilylethyl 2-methylpenem-3-carboxylate

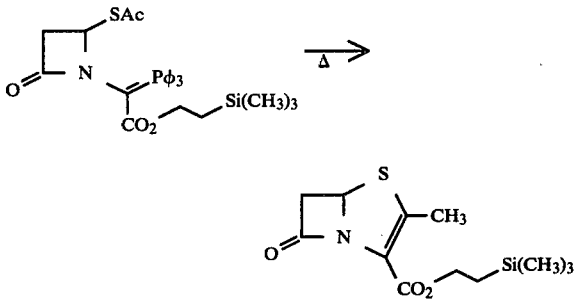

The above phosphorane (39 mg, 0.069 mmol) was refluxed in toluene (5 ml) for one hour. The solvent was evaporated. The crystalline residue was triturated in ether and filtered. The filtrate was evaporated and the residue purified on a silica gel column (1 g, 0.8×4 cm) with ether as eluent to give a product (16 mg, 81%), for which spectral data were in agreement with an authentic sample of β-trimethylsilylethyl 2-methylpenem-3-carboxylate prepared by esterification of the corresponding acid.

Sodium 2-methylpenem-3-carboxylate

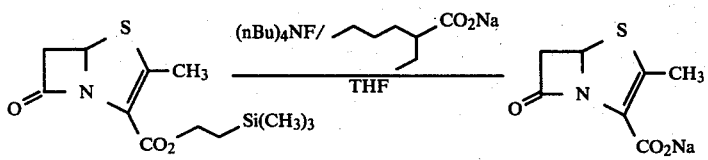

The above ester (260 mg, 0.811 mmol) was dissolved in a molar solution of tetrabutylammonium fluoride in THF (3.64 ml, 3.64 mmol) under a nitrogen atmosphere. Sodium 2-ethyl-hexanoate (151 mg, 0.911 mmol) and ether (3.5 ml) were added. The reaction mixture was stirred at room temperature for 30 min. The solvents were evaporated. The residue was triturated with ether (10 ml) and filtered. The solid was dissolved in water (5 ml), treated with charcoal and filtered on Celite. The filtrate was filtered on Millipore and lyophilized to afford a residue (123 mg, 66%). Spectral data were in agreement with a sample of sodium 2-methylpenem-3-carboxylate prepared previously by another method.

EXAMPLE 91

2-(3'-Nitropropyl)-penem-3-carboxylic Acid (via mercaptide intermediate)

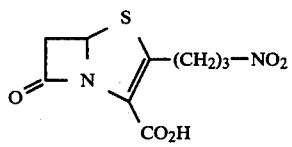

4-(4'-Nitrobutyrylthio)-1-(β-trimethylsilylethyl-2''-triphenylphosphoranylidene-2''-acetate)-2-azetidinone

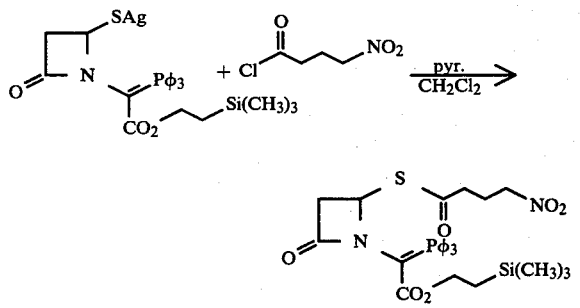

A three-neck flask (100 ml) equipped with a mechanical stirrer and two dropping funnels was charged with silver 1-(β-trimethylsilylethyl-2'-triphenylphosphoranylidene-2'-acetate)-2-azetidinone-4-thiolate. The dropping funnels were filled with methylene chloride (15 ml) solutions of pyridine (1.25 ml, 15.45 mmol) and 4-nitrobutyryl chloride (2.27 g, 15 mmol). The flask was cooled in an ice-water bath. The silver salt was dissolved in cold methylene chloride (30 ml). The pryidine and acylchloride solutions were successively added. The reaction mixture was stirred for three min and directly poured on a silica gel column (250 g, 5×28 cm; topped with 2 cm of Celite). The column was eluted with ethyl acetate methylene chloride (1:1, 1.8 l). The pertinent portions were collected and evaporated to give the title compound as an oil (4.13 g, 65%)* ir (CHCl₃) ν$_{max}$: 1753 (C=O of β-lactam), 1690, 1610, 1553 (NO₂), 865 and 840 cm⁻¹ (Si-C).

*The product is stored in the refrigerator dissolved in toluene with a trace of hydroquinone.

8-trimethylsilylethyl 2-(3'-nitropropyl)penem-3-carboxylate

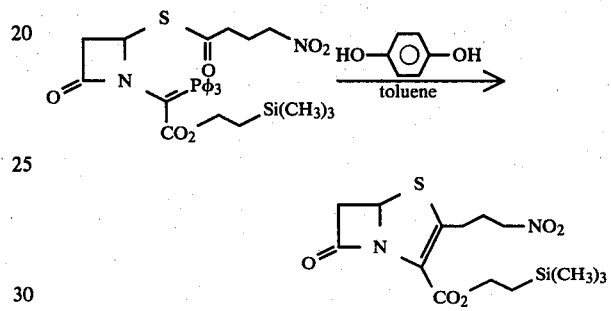

A toluene (200 ml) solution of the above phosphorane and a trace of hydroquinone was refluxed for 55 min. The solvent was evaporated and the residue purified by column chromatography on silica gel (125 g, 4×24.5 cm); eluent ethyl acetate-methylene chloride (2:98). The pertinent fractions were collected and evaporated to give the title compound (1.046 g). This oil was crystallized in ether hexane (mp 75°-6° C., 0.89 g, 25%); Anal. calcd for C₁₄H₂₂N₂O₅SSi: C 46.90, H 6.18, N 7.81; found: C 47.17, H 6.22, N 7.75; ir (CHCl₃) νmax: 1890 (C=O of β-lactam), 1695 (C=O of ester), 1582 (C=C), 1552 (NO₂), 862, 840 cm⁻¹ (Si—C); ¹Hmr (CDCl₃) δ: 5.61 (1H, dd, J$_{5-6\ trans}$=1.7 Hz, J$_{5,6\ cis}$=4 Hz, H-5), 4.6 to 4.1 (4H, m, CO₂—CH₂ and CH₂NO₂), 3.85 (1H, dd, J$_{gem}$=15 Hz, J$_{6-5\ cis}$=4 Hz, H-6), 3.45 (1H, dd, J$_{gem}$=15 Hz, J$_{6-5\ trans}$=1.7 Hz, H-6), 2.90 (2H, m, CH₂—CH₂—CH₂NO₂), 2.30 (2H, m, CH₂CH₂CH₂NO₂), 1.10 (2H, m, CH₂—Si) and 0.06 ppm (9H, s, Si—CH₃).

2-(3'-Nitropropyl)-penem-3-carboxylic acid

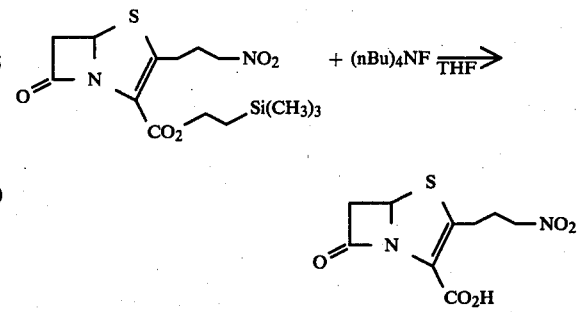

A solution of the above ester (0.107 g, 0.3 mmol) in THF (1 ml), under nitrogen, was treated with two portions of tetrabutylammonium fluoride dissolved in THF (0.5M, 0.62 and 0.60 ml) at two min interval. After 8 min, the reaction mixture was poured on a pH 8 buffer (100 ml) and extracted with ether (3×25 ml). The aqueous phase was then acidified to pH 3.5 with 1N HCl and extracted with ethyl acetate (3×50 ml). The organic phase was dried over sodium sulfate, filtered and evaporated to dryness to give the title acid (76 mg). ir (CHCl$_3$) $\nu_{max}$: 1790 (C=O of β-lactam), 1715 (C=O of acid), 1585 (C=C), 1555 cm$^{-1}$ (NO$_2$); $^1$Hmr (CDCl$_3$) δ: 7.0 (1H, b, CO$_2$H), 5.63 (1H, dd, J$_{5\text{-}6\ trans}$=1.6 Hz, J$_{5\text{-}6\ cis}$=3.5 Hz, H-5), 4.45 (2H, m, CH$_2$NO$_2$), 3.58 (2H, AB dedouble, J$_{AB}$=16 Hz, J$_{6\text{-}5\ trans}$=1.6 Hz, J$_{6\text{-}5\ cis}$=3.5 Hz, H-6), 3.58 (2H, m, CH$_2$CH$_2$CH$_2$NO$_2$) and 2.20 ppm (2H, m, CH$_2$CH$_2$CH$_2$NO$_2$); uv (EtOH) $\lambda_{max}$: 308 nm (ε5808), 259 nm (ε3115). A sample of the acid was crystallized in methylene chloride-hexane.

EXAMPLE 92

6-Formamidomethyl-2-methylpenem-3-carboxylic acid, sodium and postassium salts

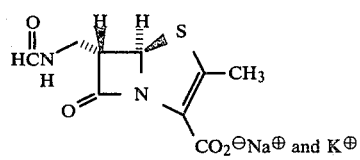

trans 1-(t-butyldimethylsilyl)-3-methanesulfonyloxymethyl-4-tritylthio-2-azetidinone

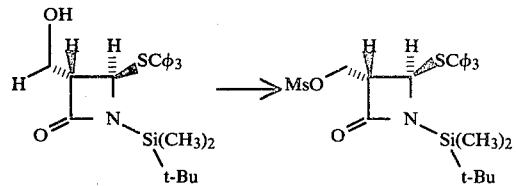

A solution of trans-1-(t-butyldimethylsilyl)-3-hydroxymethyl-4-tritylthio-2-azetidinone (8.0 g, 16.36 mmol) in dichloromethane (50 ml) was treated at 5° C. with methanesulfonyl chloride (1.4 ml, 18 mmol) in dichloromethane (10 ml) and triethylamine (2.5 ml, 18 mmol). Stirring was maintained for 1 h under N$_2$. Then the solution was washed successively with cold 1N hydrochloric acid, 1M sodium bicarbonate and brine, dried (MgSO$_4$) and evaporated in vacuo. The residue (mixture of hydroxy and mesylate cpd) was treated a second time as before, to give the mesylate (90 g, 97%) as an amorphous solid. It was used as such in the next step without further purification. The analytical sample was recrystallized from methylene chloride mp 167°-168° C.; ir (neat) $\nu_{max}$: 1755 cm$^{-1}$; $^1$Hmr (CDCl$_3$) δ: 7.3 (15H, m), 4.4 (1H, d, J=2 Hz), 3.9 (1H, dd, J=8 Hz, 4 Hz), 3.2 (2H, bs), 2.8 (3H, s), 0.95 (9H, s) and 0.3 ppm (6H, s).

trans 3-methanesulfonyloxymethyl-4-tritylthio-2-azetidinone and trans-3-azidomethyl)-4-tritylthio-2-azetidinone

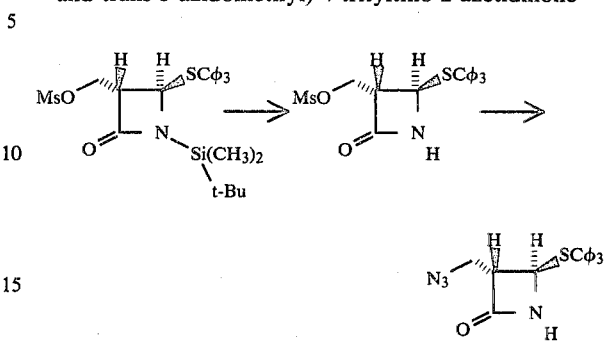

A solution of trans -1-(t-butyldimethylsilyl)-3-methane-sulfonylmethyl-4-tritylthio-2-azetidinone (21.0 g, 37.0 mmol) in HMPA (90 ml) was cooled in an ice bath and treated with sodium azide (2.7 g, 41.2 mmol) in H$_2$O (10 ml). The reaction mixture was stirred at room temperature for 1 h, diluted with ethyl acetate, washed with H$_2$O (5×100 ml), dried (MgSO$_4$) and evaporated in vacuo. The trans-3-methanesulfonyloxymethyl-4-tritylthio-2-azetidinone was diluted with HMPA (90 ml), treated at room temperature with sodium azide (2.7 g, 41.2 mmol) in H$_2$O (10 ml), heated at 60° C. for 2 h and triturated with cold water. The crude azide was diluted with benzene-ether (5:1) and washed with water (5×20 ml). Evaporation of the solvent followed by crystallization from ether gave 18.0 g (77%) of azide as a white solid. The analytical sample was recrystallized from CH$_2$Cl$_2$/ether mp 174°-5° C.; Anal. calcd for C$_{23}$H$_{20}$N$_4$OS: C 68.97, H 5.03, N 13.99; found C 68.78, H 5.00, N 14.16; ir (nujol) $\nu_{max}$: 2100, 1765 cm$^{-1}$; $^1$Hmr (CDCl$_3$) δ: 7.35 (15H, m), 4.75 (1H, bs), 4.4 (1H, d J=2 Hz), and 3.1-3.7 ppm (3H, m).

trans-3-aminomethyl-4-tritylthio-2-azetidinone

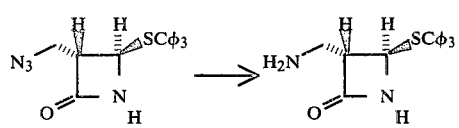

To a solution of trans 3-azidomethyl-4-tritylthio-2-azetidinone (10.0 g, 47.5 mmol) in dry methanol (500 ml) was added ammonium chloride (19.0 g) and zinc powder (1.0 g) and the suspension was stirred at room temperature for 5 h. The reaction mixture was filtered and evaporated. The residue was partitioned between 1N hydrochloric acid and benzene. The aqueous layer was basified with 1M sodium bicarbonate and extracted with methylene chloride. The extracts were washed with brine, dried (MgSO$_4$) and evaporated in vacuo. The crude amine crystallized from ether, 14.05 g (79%); mp 139°-139.5° C.; Anal. calcd for C$_{23}$H$_{22}$N$_2$OCl.¼ CH$_2$Cl$_2$: C 70.56, H 5.73, N 7.08; Found: C 70.68, H 5.94, N 7.27; ir (CHCl$_3$) $\nu_{max}$: 3400 and 1760 cm$^{-1}$; $^1$Hmr (CDCl$_3$) δ: 7.35 (15H, m), 5.15 (1H, m), 4.3 (1H, bs), 2.7-3.5 (3H, m) and 1.3 ppm (2H, m).

trans 3-phthalimidomethyl-4-tritylthio-2-azetidinone

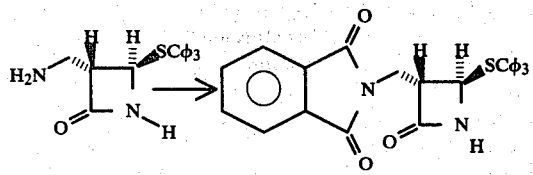

A solution of trans 3-aminomethyl-4-tritylthio-2-azetidinone (13.9 g, 37.2 mmol) and N-carbethoxyphthalimide (8.3 g, 37.9 mmol) in benzene (200 ml) was heated under reflux for 15 h. The solvent was evaporated in vacuo and the residue crystallized from ether to give (17.4 g (93%) of the title compound; mp 172°–3° C.; Anal. calcd for $C_{31}H_{24}N_2O_3S$: C 73.78, H 4.79, N 5.55, found: C 73.92, H 4.87, N 5.49; ir (CHCl₃) $\nu_{max}$: 1770 and 1715 cm$^{-1}$; ¹Hmr (CDCl₃) δ: 7.8 (4H, m), 7.3 (15H, m), 4.45 (1H, d, J=2 Hz), 3.3–4.1 (3H, m) and 3.3–4.6 ppm (1H, m).

trans 3-phthalimidomethyl-1-(paranitrobenzyl 2'-hydroxy-2'-acetate)-4:tritylthio-2-azetidinone

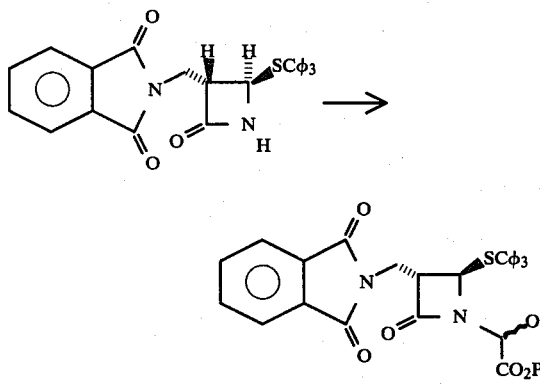

A mixture of trans-3-phthalimidomethyl-4-tritylthio-2-azetidinone (17.4 g, 34.52 mmol), paranitrobenzylglyoxylate hydrate (9.4 g, 41.4 mmol) and triethylamine (4.8 ml, 34.5 mmol) in tetrahydrofuran (250 ml) was stirred at room temperature for 20 h. The reaction mixture was evaporated in vacuo and the residue was treated with charcoal in benzene. Evaporation of the solvent yielded the crude hydroxyglyoxylate (25 g, quantitative) as an amorphous solid. It was used in the next step without further purification. ir (CHCl₃) $\nu_{max}$: 1770 and 1715 cm$^{-1}$; ¹Hmr (CDCl₃) δ: 8.1 (2H, d, J=9Hz), 7.55 (3H, d, J=9Hz), 7.3 (19H, m), 5.0–5.4 (2H, bs), 4.3–5.0 (2H, m) and 2.8–3.8 ppm (4H, m).

trans-3-phthalimidomethyl-1-(paranitrobenzyl-2'-chloro-2'-acetate)-4-tritylthio-2-azetidinone

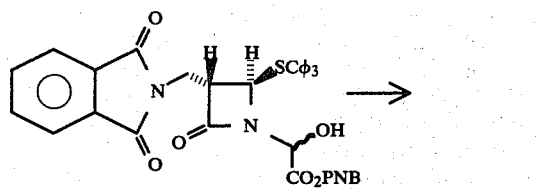

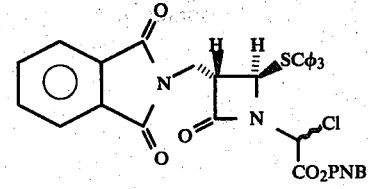

To a cooled (ice bath, 0° C.) solution of trans-3-phthalimidomethyl-1-(paranitrobenzyl-2'-hydroxy-2'-acetate)-4-tritylthio-2-azetidinone (25 g, 35 mmol) in tetrahydrofuran (150 ml) was added dropwise a 1 M solution of thionyl chloride in tetrahydrofuran (46 ml, 46 mmol) followed by a 1 M solution of pyridine in tetrahydrofuran (46 ml, 46 mmol). The reaction mixture was stirred at room temperature for 20 min, diluted with pet-ether (50 ml) and filtered over a Celite/charcoal bed. The solvent was evaporated in vacuo to give the chloro azetidinone (26 g, quantitative) as an amorphous solid. It was used in the next step without further purification. ir (CHCl₃) $\nu_{max}$: 1775 and 1720 cm$^{-1}$. ¹Hmr (CDCl₃) δ: 8.12 (2H, d, J=9 Hz), 7.60 (2H, d, J=9 Hz), 7.3 (19H, m), 5.25 (2H, m), 4.7–5.4 (1H, m), 4.55 (1H, bs) and 3.3–4.0 ppm (3H, m).

trans-3-phthalimidomethyl-1-(paranitrobenzyl-2'-triphenylphosphoranylidene-2'-acetate)-4-tritylthio-2-azetidinone

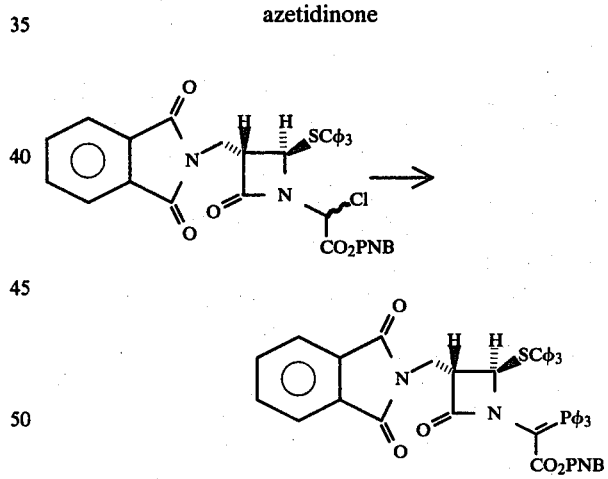

A mixture of trans-3-phthalimidomethyl-1-(paranitrobenzyl-2'-chloro-2'-acetate)-4-tritylthio-2-azetidinone (26 g, 35.5 mmol), triphenylphosphine (10.25 g, 39.1 mmol) and 2.6 lutidine (4.6 ml, 39.1 mmol) in dioxane (200 ml) was heated at 100° C. for 20 h. The reaction mixture was filtered over Celite and evaporated. The residue was chromatographed on a silica gel column (350 g) eluting with benzene to benzene/ether (1:1) to yield the phosphorane (21 g, 62%) as a white solid. ir (CHCl₃) $\nu_{max}$: 1750 and 1710 cm$^{-1}$. ¹Hmr (CDCl₃) δ: 7.4 (38H, m), 4.8–5.4 (3H, m), 4.6 (2H, m) and 3.7 ppm (1H bs).

trans-3-phthalimidomethyl-1-(paranitrobenzyl-2'-triphenylphosphoranylidene-2'-acetate)-4-tritylthio-2-azetidinone

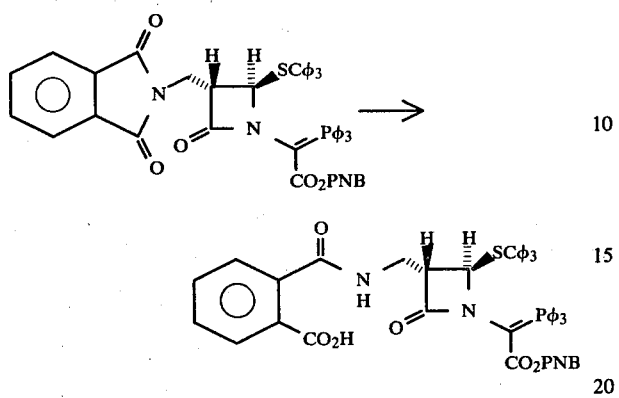

A cooled (ice bath) suspension of trans-3-phthalimidomethyl-1-(paranitrobenzyl-2'-triphenylphosphoranylidene-2'-acetate)-4-tritylthio-2-azetidinone (18.02 g, 18.83 mmol) in tetrahydrofuran (30 ml), water (30 ml) and acetone (30 ml) was treated dropwise with sodium sulfide (4.97 g, 20.7 mmol) in acetone/water 1:1 (30 ml) and heated to reflux for 8 h. The reaction mixture was diluted with water, acidified with 1N hydrochloric acid and extracted with dichloromethane. The organic extracts were washed with brine and evaporated in vacuo to give 17.1 g (88%) of the title compound as an amorphous light yellow solid. It was used in the next step without further purification. ir (neat) $\nu_{max}$: 3150–3600, 1750 and 1700 cm$^{-1}$; $^1$Hmr (CDCl$_3$) δ: 7.4 (38H, m) and 3.3–5.5 ppm (8H, m).

trans-3-phthalisoimidomethyl-1-(paranitrobenzyl-2'-triphenylphosphoranylidene-2'-acetate)-4-tritylthio-2-azetidinone

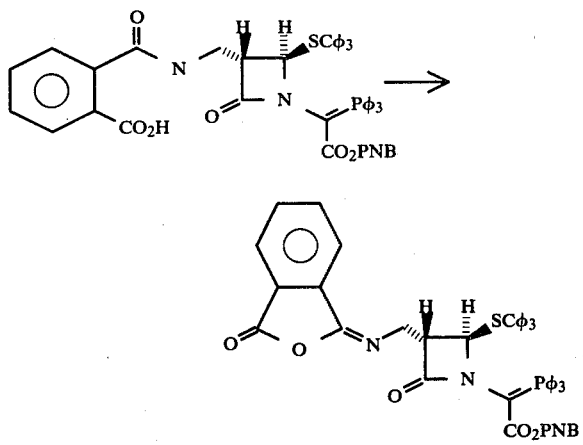

A solution of trans-3-phthalimidomethyl-1-(paranitrobenzyl-2'-triphenylphosphoranylidene-2'-acetate)-4-tritylthio-2-azetidinone (17.1 g, 17.54 mmol) in dichloromethane (125 ml) was treated dropwise at room temperature with N,N'-dicyclohexylcarbodiimide (3.62 g, 17.54 mmol) in dichloromethane (30 ml). The solution was filtered over Celite and evaporated to give the title compound (18.23 g, quantitative) as an oil. It was used in the next step without further purification. ir (neat) $\nu_{max}$: 2110, 1755 and 1710 cm$^{-1}$; $^1$Hmr (CDCl$_3$) δ: 7.5 (38H, m), 4.6–5.3 (4H, m) and 3.9 ppm (2H, bs).

trans-3-aminomethyl-1-(paranitrobenzyl-2'-triphenylphosphoranylidene-2'-acetate)-4-tritylthio-2-azetidinone

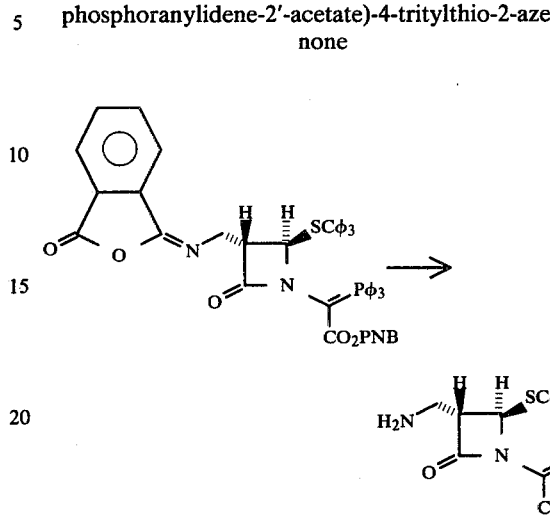

A solution of trans-3-phthalisoimidomethyl)-1-(paranitrobenzyl-2'-triphenylphosphoranylidene-2'-acetate)-4-tritylthio-2-azetidinone (5.9 g, 6.16 mmol) in tetrahydrofuran (40 ml), cooled to −20° C., was treated dropwise under N$_2$ with hydrazine (0.2 ml, 6.16 mmol) and stirring was maintained for 30 min. The reaction mixture was acidified with 1N hydrochloric acid and washed with ether; the aqueous phase was basified with 1M sodium bicarbonate and extracted with methylene chloride. The organic extracts were washed with brine, dried (MgSO$_4$) and evaporated. The residue was purified on a silica gel column (60 g) eluting with ether to ethyl acetate to give 3.38 g (66%) of the amino phosphorane as an amorphous solid. ir (CHCl$_3$) $\nu_{max}$: 1730, 1710 cm$^{-1}$; $^1$Hmr (CDCl$_3$) δ: 6.5–8.1 (34H, m), (3.8–5.3 (6H, m) and 0.9–1.9 ppm (2H, m).

trans 3-formamidomethyl-1-(paranitrobenzyl-2'-triphenylphosphoranylidene-2'-acetate)-4-tritylthio-2-azetidinone

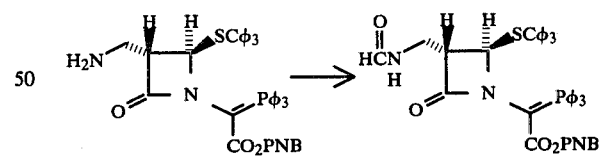

To a cooled (ice bath) solution of trans 3-(aminomethyl-1-(paranitrobenzyl-2'-triphenylphosphoranylidene-2'-acetate)-4-tritylthio-2-azetidinone (5.0 g, 6.04 mmol) in dichloromethane (50 ml) was added dropwise under N$_2$ a solution of acetic formic anhydride (600 mg, 6.8 mmol) in dichloromethane (5 ml) followed by a solution of triethylamine (1 ml, 7 mmol) in dichloromethane (2 ml). Stirring was continued for 30 min. The solution was washed successively with 1N hydrochloric acid, water, 1M sodium bicarbonate and brine. The organic layer was dried (MgSO$_4$), evaporated and the residue was chromatographed on a silica gel column (50 g). Elution with ether to ethyl acetate yielded 2.0 g (39%) of the formamide as an amorphous solid. ir (CHCl$_3$)

$v_{max}$: 1740, 1685 and 1620 cm$^{-1}$; $^1$Hmr (CDCl$_3$) δ: 6.6–8.2 (35H, m), and 2.5–5.3 ppm (7H, m).

trans silver 3-formamidomethyl-1-(paranitrobenzyl-2'-triphenylphosphoranylidene-2'-acetate)-2-azetidinone-4-thiolate

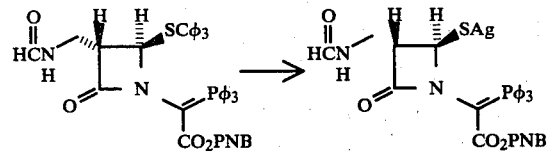

A solution of trans 3-formamidomethyl-1-(paranitrobenzyl-2'-triphenylphosphoranylidene-2'-acetate)-4-tritylthio-2-azetidinone (550 mg, 0.64 mmol) in dichloromethane (10 ml) was evaporated to dryness and diluted with hot methanol (20 ml). The solution was stirred at 60° C. and treated with a pre-heated (60° C.) solution of 0.15 M silver nitrate in methanol (5.7 ml, 0.86 mmol) followed by a solution of 1.5 M pyridine in methanol (0.57 ml, 0.86 mmol). The creamy solution was stirred at room temperature for 30 min, then in an ice bath for 2 h. The solid was filtered washed with cold methanol and ether, and dried to give 300 mg (65%) of the silver salt as a beige solid. It was used in the next step without further purification.

trans 4-acetylthio-3-formamidomethyl-1-(paranitrobenzyl-2'-triphenylphosphoranylidene-2'-acetate)-2-azetidinone

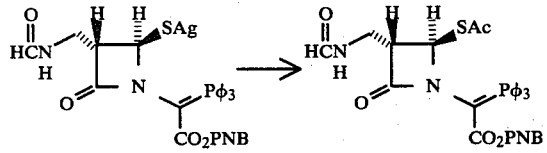

To a cooled (ice bath) solution of trans silver 3-formamidomethyl-1-(paranitrobenzyl-2'-triphenylphosphoranylidene-2'-acetate)-2-azetidinone-4-thiolate (800 mg, 1.11 mmol) in dichloromethane (10 ml) was added dropwise under N$_2$ a solution of 1M acetylchloride in dichloromethane (1.33 ml, 1.33 mmol) followed by a solution of 1M pyridine in dichloromethane (1.33 ml, 1.33 mmol). The solution was stirred in a cold bath for 1 h, and was then filtered over Celite. The filtrate was washed successively with 1N hydrochloric acid, water, 1M sodium bicarbonate and brine and the organic layer was dried (MgSO$_4$) and evaporated. The residue was purified on a silica gel column (5.0 g) and eluted with ethyl acetate to 10% methanol in ethyl acetate to give 450 mg (62%) of the title compound: ir (CHCl$_3$) $v_{max}$: 1755, 1685 and 1620 cm$^{-1}$; $^1$Hmr (CDCl$_3$) δ: 8.18 (2H, d, J=9 Hz), 7.0–8.0 (20H, m), 6.75 (2H, d, J=9 Hz), 6.3 (1H, m), 5.5 (1H, m), 5.2 (2H, bs), 4.9 (1H, bs), 3.6 (1H, m), 3.0 (1H, m) and 2.2 ppm (3H, two s).

paranitrobenzyl 6-formamidomethyl-2-methylpenem-3-carboxylate

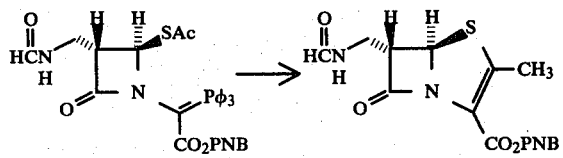

A solution of trans 4-acetylthio-3-formamidomethyl-1-(paranitrobenzyl-2'-triphenylphosphoranylidene-2'-acetate)-2-azetidinone (450 mg, 0.686 mmol) in toluene (10 ml) was heated under reflux for 12 h. Concentration and purification on a silica gel column eluting with ether to 10% methanol in ether gave 100 mg (39% of the penem as an amorphous solid. ir (CHCl$_3$) $v_{max}$: 1780 and 1690 cm$^{-1}$; $^1$Hmr (CDCl$_3$) δ: 8.2 (2H, d, J=9 Hz), 8.2 (1H, s), 7.6 (2H, d, J=9 Hz), 6.9 (1H, m), 5.55 (1H, s), 5.35 (2H, 2s), 3.3–4.1 (3H, m) and 2.33 ppm (3H, s).

6-formamidomethyl-2-methylpenem-3-carboxylic acid sodium and potassium salts

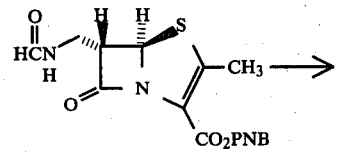

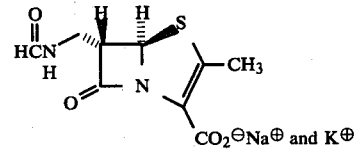

A mixture of paranitrobenzyl 6-formidomethyl-2-methylpenem-3-carboxylate (80 mg, 0.21 mmol), palladium on Celite (30%, 100 mg), tetrahydrofuran (10 ml), ether (25 ml) and 0.05 M buffer solution pH 7 (4.46 ml, 0.223 mmol) was hydrogenated on a Parr shaker at an initial hydrogen pressure of 45 psi for 3 h. The catalyst was removed by filtration on Celite and washed with water. The filtrate and washings were combined and the phases separated. The aqueous phase was washed with ether (3×15 ml) and lyophylized. The crude solid was purified by hplc to give 18 mg of a mixture of the sodium and potassium salts. uv (H$_2$O) $\lambda_{max}$: 299 (ε4933), 259 (ε4094); ir (nujol) $v_{max}$: 3100–3650 and 1755 cm$^{-1}$; $^1$Hmr (D$_2$O) δ: 8.15 (1H, s), 5.53 (1H, d, J=1.4 Hz), 4.0 (1H, m), 3.74 (2H, d, J=5 Hz), 3.25–4.25 (1H, m) and 2.27 ppm (3H, s).

EXAMPLE 93

(1'S,5R,6S, and 1'R,5S,6R) 6-(1'-Hydroxy-1'-propyl)-2-methylpenem-3-carboxylic acid, sodium salt (isomer C)

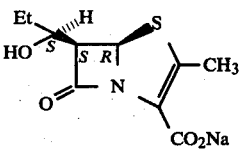

trans 1-t-Butyldimethylsilyl-3-propionyl-4-tritylthio-2-azetidinones

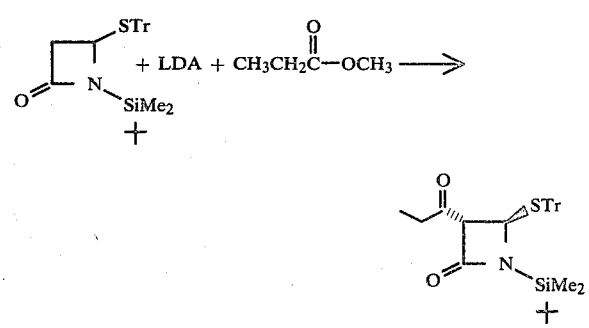

PROCEDURE:

n-BuLi (37.50 ml, 1.6 M/hexane, 60 mmol) was added dropwise under $N_2$ to a cooled (dry ice-acetone bath) and stirred solution of diisopropylamine (8.50 ml, 60 mmol) in dry THF (200 ml). The mixture was stirred in the cold and 1-t-butyldimethylsilyl-4-tritylthio-2-azetidinone (22.9 g, 50 mmol) in dry THF (100 ml) was added. After 15 min, methyl propionate (40 ml, excess) was added and the reaction mixture was kept at −78° for 4 h. Then the cooling bath was removed and the internal temperature was allowed to come to 0° C. (∼40 min). It was poured over ice-HCl (pH ∼6) and extracted with ether. The layers were separated and the aqueous layer was extracted with ether. The combined ether solution was washed with water and brine and dried ($Na_2SO_4$). It was evaporated in vacuo to give an oil in quantitative yield. This contained a mixture of starting material and title compound. It was used as such and purified in the next step. ir (Neat) $\nu_{max}$:

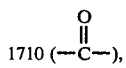
1710 (—C—), 1750 cm$^{-1}$ ($\beta$-lactam).

1-t-Butyldimethylsilyl-3-(1′-hydroxy-1′-propyl)-4-tritylthio-2-azetidinones

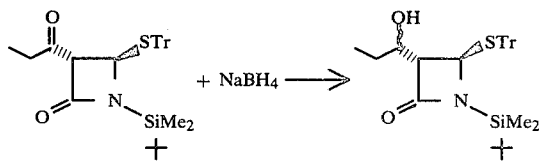

PROCEDURE:

A solution of 1-t-butyldimethylsilyl-3-proprionyl-4-tritylthio-2-azetidinone (26 g, 50 mmol) and sodium borohydride (7.6 g, 200 mmol) in THF (400 ml) was stirred at room temperature for 18 h. It was poured onto ice-HCl (1N) (pH 6) and extracted with ether. The acidic phase was extracted several times with ether and the combined ether solution was washed with brine, dried ($Na_2SO_4$) and evaporated to give an amorphous solid, 25.0 g. This crude product was chromatographed on $SiO_2$ (ACT. 1, 400 g) and eluted first with $CH_2Cl_2$ to give 10.8 g of 1-t-butyldimethylsilyl-4-tritylthio-2-azetidinone. Elution with 20% ether in $CH_2Cl_2$ gave 10.3 g of the title compound as a mixture of two isomeric trans alcohols. This was separated by hplc (Water Associates, System 500), and using 10% EtOAc in $CH_2Cl_2$ as eluent. Isomer C, white solid, 3.8 g; mp (pet. ether) 134°–36° C. $^1$Hmr (CDCl$_3$) δ: 7.1–7.8 (15H, m, STr), 4.35 (H, d), 3.1 (H, dd), 2.5 (H, m), 0.7–1.7 (5H, m), 0.97 (9H, s) and 0.25 ppm (6H, s). Anal. calcd for $C_{31}H_{39}NO_2SSi$: C 71.91, H 7.59, N 2.71; found: C 71.51, H 7.60, N 2.96. Isomer B, white solid, 5.4 g; mp (pentane-pet. ether) 97°–99° C. $^1$Hmr (CDCl$_3$) δ: 7.1–7.8 (15H, m, STr), 4.15 (H, d), 3.4 (H, dd), 3.2 (H, m), 0.7–1.7 (5H, m), 0.85 (9H, s) and 0.1 ppm (6H, s). Total yield of these two alcohols (based on recovered starting material was 67.5%.

(1′S,3S,4R and 1′R,3R,4S) 1-t-butyldimethylsilyl-3-(1′-paranitrobenzyldioxycarbonyl-1′-propyl)-4-tritylthio-2-azetidinone (isomer C).

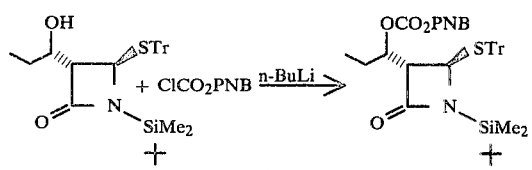

PROCEDURE:

To a cooled (dry ice-acetone bath) solution of (1′S,3S, 4R and 1′R,3R,4S) 1-t-butyldimethylsilyl-3-(1′-hydroxy-1′-propyl)-4-tritylthio-2-azetidinone (isomer C) (3.1 g, 6 mmol) in dry THF (20 ml) was added dropwise under $N_2$ a solution of 1.6 M n-BuLi/hexane (4.88 ml, 7.8 mmol) stirred at −78° C. for 25 min. Paranitrobenzyl chloroformate (1.56 g, 7.2 mmol) in dry THF (10 ml) was then added dropwise and the resulting mixture was stirred at −78° C. for 4 h. It was diluted with ether and washed with NH$_4$Cl solution and brine. The organic phase was dried (Na$_2$SO$_4$) and evaporated to dryness to give 4.2 g of title compound (Quantative yield). $^1$Hmr (CDCl$_3$) δ: 8.2 (2H, d), 7.0–7.7 (17H, m), 5.13 (2H, s), 4.05 (H, d), 3.75 (H, dt), 3.25 (dd), 0.55–1.8 (5H, m), 0.9 (9H, s) and 0.25 ppm (6H, d).

(1′S,3S,4R and 1′R,3R,4S) 3-(1′-paranitrobenzyldioxycarbonyl-1′-propyl)-4-tritylthio-2-azetidinone (isomer C)

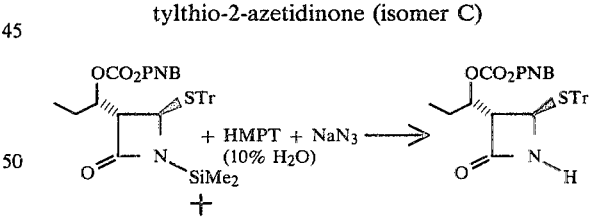

PROCEDURE:

To a cooled (ice bath) solution of (1′S,3S,4R and 1′R,3R,4S) 1-t-butyldimethylsilyl-3-(1′-paranitrobenzyldioxycarbonyl-1′-propyl)-4-tritylthio-2-azetidinone (isomer C) (4.2 g, 6 mmol) in HMPT (40 ml) containing 10% H$_2$O was added sodium azide (0.78 g, 12 mmol). The mixture was stirred at room temperature for 1 h. It was diluted with water (100 ml) and extracted with benzene: pet. ether (1:1) (4×15 ml). The organic phase was washed several times with water (6×30 ml) and brine. It was dried (Na$_2$SO$_4$) and evaporated to dryness to give 3.5 g of a solid (quantitative yield). It was treated with pentane and filtered to give 3.4 g of a pale yellow solid. mp 84°–86° C.; $^1$Hmr (CDCl$_3$) δ: 8.2 (2H, d), 7–7.7 (17H, n), 5.2 2H, s), 4.95 (H, dt), 4.4 (NH), 4.25

(H, d), 3.4 (H, dd), 1.7 (2H, m) and 0.95 ppm (3H, t).
(1'S,3S,4R and 1'R,3R,4S) 3-(1'-paranitrobenzyldioxycarbonyl-1'-propyl)-1-(paranitrobenzyl 2"-hydroxy-2"-hydroxy-2"-acetate)-4-tritylthio-2-azetidinone (isomer C).

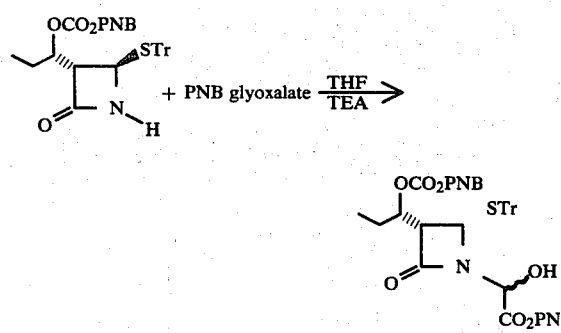

PROCEDURE:

To a solution of (1'S,3S,4R and 1'R,3R,4S) 3-(1'-paranitrobenzyldioxycarbonyl-1'-propyl)-4-tritylthio-2-azetidinone (isomer C) (3.2 g, 5.5 mmol) and paranitrobenzyl glyoxylate hydrate (1.362 g, 6 mmol) in dry THF (50 ml) was added a catalytic amount of TEA (4 drops) and Na$_2$SO$_4$ (to absorb H$_2$O formed). The resulting mixture was stirred at room temperature for 6 h. It was filtered and evaporated to dryness to give 4.35 g of an amorphous solid (quantitative yield). $^1$Hmr (CDCl$_3$) δ: 8.25 (4H, dd), 7–7.9 (19H, m), 5.28 (2H, s), 5.1 (2H, s), 4.8 (H, d), 4.4 (H, dd), 4.1 (H, dt), 3.4 (H, m), 1.1–1.8 (2H, m) and 0.8 ppm (3H, t).

(1'S,3S,4R and 1'R,3R,4S)
3-(1'-paranitrobenzyldioxycarbonyl-1'-propyl)-1-(paranitrobenzyl 2"-chloro-2"-acetate(-4-tritylthio-2-azetidinone (isomer C)

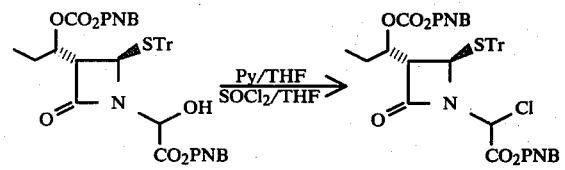

PROCEDURE:

To a cooled (ice salt bath) solution of the above glyoxylate (4.35 g, 5.5 mmol) in dry THF (30 ml) was added 1M py/THF (7 ml, 7 mmol) followed by dropwise addition of 1M SOCl$_2$/THF (7 ml, 7 mmol). The resulting mixture was stirred at the above-indicated temperature for 1 h. It was diluted with benzene (30 ml), stirred in the cold (ice water bath) for 30 min and filtered over Celite-charcoal. The filtrate was evaporated to dryness to give 3.8 g of an amorphous solid (85.3%); $^1$Hmr (CDCl$_3$) δ: 8.15 (4H, d), 6.75–7.7 (19H, m), 5.65 (H, s), 5.2 (2H, s), 5.1 (2H, s), 4.5 (H, m), 3.85 (H, m), 3.4 (H, m), 1.25–2.0 (2H, m) and 0.9 ppm (3H, t).

(1'S,3S,4R and 1'R,3R,4S)
3-(1'-paranitrobenzyldioxycarbonyl-1'-propyl)-1-(paranitrobenzyl 2"-triphenylphosphoranylidene-2"-acetate)-4-tritylthio-2-azetidinone (isomer C)

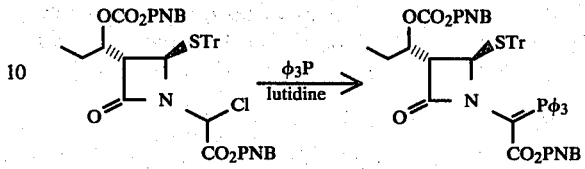

PROCEDURE:

To a solution of the above chloro compound (3.7 g, 4.568 mmol) in dioxane (35 ml) was added φ$_3$P (1.197 g, 5 mmol) and lutidine (0.54 g, 5 mmol). The mixture was heated in an oil bath at 100° C. for 3 days. It was cooled, diluted with ether and washed successively with 1N HCl, 1M NaHCO$_3$ and brine. It was dried (Na$_2$SO$_4$) and filtered over Celite-charcoal. The filtrate was evaporated to dryness to give 3.6 g of an oil. This was chromatographed on SiO$_2$ (120 g) and eluted with benzene, benzene-ether to give 1.45 g of title compound as an amorphous solid (31%); ir (neat) ν$_{max}$: 1750 cm$^{-1}$ (broad).

(1'S,3S,4R and 1'R,3R,4S)
4-acetylthio-3-(1' paranitrobenzyldioxycarbonyl-1'-propyl)-1-(paranitrobenzyl 2"-triphenylphosphoranylidene-2"-acetate)-2-azetidinone (isomer C)

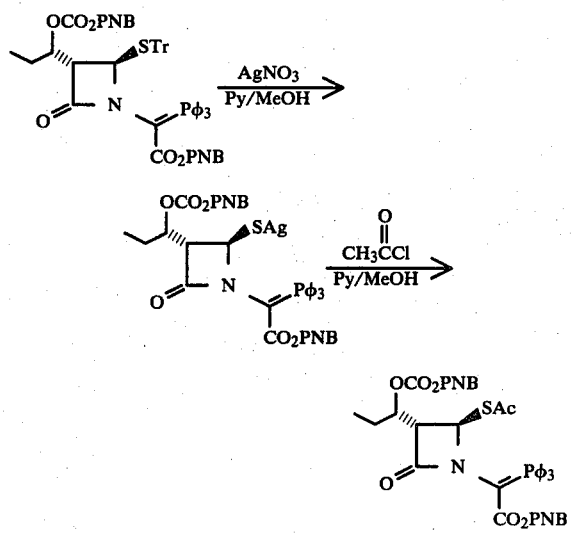

PROCEDURE:

To a hot solution (60° C.) of the above phosphorane (1.4 g, 1.35 mmol) in MeOH (40 ml) was added with stirring a hot solution of AgNO$_3$ (0.3 g, 1.76 mmol) in MeOH (10 ml) followed by pyridine (0.107 g, 0.11 ml, 1.76 mmol). The silver mercaptide began to precipitate immediately. The mixture was stirred at room temperature for 15 min and at 0° C. for 2 h. It was filtered, and the solid washed well with cold MeOH and ether, 1.2 g quantitative yield); mp 113°–115° C. (d); ir (nujol) ν$_{max}$: 1740–1760 cm$^{-1}$ (broad). This solid was used as such. To a cooled (ice bath) solution of the above mercaptide (1.2 g, 1.35 mmol) in CH$_2$Cl$_2$ (15 ml) was added acetyl chloride (0.118 g, 0.107 ml, 1.5 mmol) in CH$_2$Cl$_2$ (2 ml) followed by pyridine (0.119 g, 0.122 ml, 1.5 mmol) in CH$_2$Cl$_2$ (2 ml). The mixture was stirred at 0° C. for 30 min. It was filtered over Celite to remove silver salt and the filtrate was washed successively with HCl (0.5 N), H$_2$O, NaHCO$_3$ (0.5 M) and brine. The CH$_2$Cl$_2$ solution was dried (MgSO$_4$) and evaporated to dryness to give 0.94 g of title compound as an amorphous solid. (83.4%) ir (neat) $\nu_{max}$: 1750 cm$^{-1}$ (broad).

(1'S,5R,6S and 1'R,5S,6R) paranitrobenzyl 6-(1'-paranitrobenzyldioxycarbonyl-1'-propyl)-2-methylpenem-3-carboxylate (isomer C)

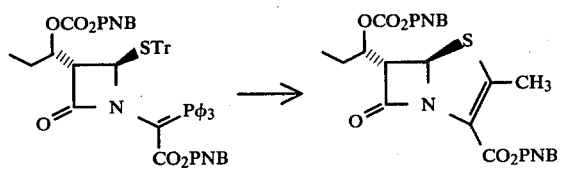

PROCEDURE:

A solution of the above phosphorane (0.4 g, 1.077 mmol) in toluene (35 ml) was heated to reflux and 5 ml of toluene was distilled off. The yellow solution was refluxed for 7.5 h. It was evaporated to dryness to give 0.76 g of a thick oil. This was chromatographed on SiO$_2$ (ACT 1.30 g) and eluted with benzene and benzene-ether to give the title compound as a solid, 0.32 g (53.4%); mp (pentane) 160°–162° C.; $^1$Hmr (CDCl$_3$) δ: 7.3–8.4 (8H, m, aromatic), 5.4 (H,d), 5.3 (4H, benzyls, m), 5.0 (H, dt), 4.0 (H, dd), 2.35 (6H, s), 0.8 (2H, dq) and 1.0 ppm (3H, t).

(1'S,5R,6S and 1'R,5S,6R) 6-(1'-hydroxy-1'-propyl)-2-methylpenem-3-carboxylic acid (isomer C), sodium salt.

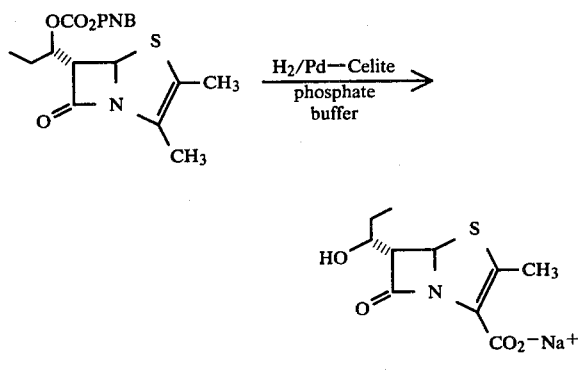

PROCEDURE:

A mixture of the above ester (48 mg, 0.086 mmol) and 30% Pd-Celite (100 mg) in THF (10 ml), Et$_2$O (20 ml), H$_2$O (10 ml) and phosphate buffer (pH7, 2 ml) was hydrogenated at an initial pressure of 50 psi for 23 h. It was filtered over Celite and the layers were separated. The organic layer was washed with H$_2$O (2×5 ml) and the combined water layer was washed with EtOAc (2×10 ml). The aqueous layer was then lyophilized to give the title compound as a white salt, 30 mg; ir (KBr) $\nu_{max}$: 1750 (β-lactam), and 1600–1650 cm$^{-1}$ (broad, —CO$_2^-$); uv $\lambda_{max}$: 258 (ε1105) and 305 (ε1244).

EXAMPLE 94

(1'R,5R,6S and 1'S,5S,6R) 6-(1'-Hydroxy-1'-propyl)-2-methylpenem-3-carboxylic acid, sodium and potassium salts (isomer B)

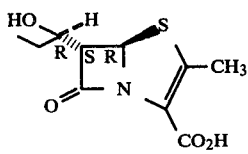

(1'R,3S,4R and 1'S,3R,4S) 1-t'-Butyldimethylsilyl-3-(1'-formyloxy-1'-propyl)-4-tritylthio-2-azetidinone (isomer B)

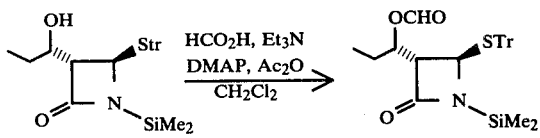

4-Dimethylaminopyridine (DMAP) was prepared according to (a) H. C. Brown et al. Org. Synth. Collect. Vol. 5, 977 (1973) and (b) Helmet Vorbruggen et al. Angew. Chem. Int. Ed., 17, 569, (1978).

PROCEDURE:

To a cooled (0° C.) solution of (1'R,3S,4R and 1'S,3R,4S) 1-t-butyldimethylsilyl-3(1'-hydroxy-1'-propyl)-4-tritylthio-2-azetidinone (isomer B) (3.612 g, 7 mmol) in CH$_2$Cl$_2$ (50 ml) was added Et$_3$N (4.48 ml, 35 mmol), HCO$_2$H (0.63 ml, 16.8 mmol) and DMAP (0.854 g, 7 mmol) followed by dropwise addition of acetic anhydride (7.14 g, 70 mmol). The clear yellow solution was stirred at −40° C. and milky mixture. It was poured onto ice-1 N HCl (pH 6) and the layers were separated. The CH$_2$Cl$_2$ solution was washed with 1 M NaHCO$_3$ and brine. It was dried (Na$_2$SO$_4$) and evaporated to dryness to give 3.8 g of a solid residue. This was treated with pentane and filtered to give 3.7 g of a white solid (96.8%); mp 125°–27° C.; ir (neat) $\nu_{max}$:

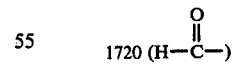

and 1750 cm$^{-1}$ (β-lactam); $^1$Hmr (CDCl$_3$) δ:

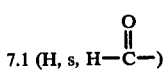

6.8–7.7 (15H, m), 4.8 (H, m), 4.05 (H, d, J=1.5), 3.7 (H, m, J=1.5, J=7), 1.4 (2H, m), 0.95 (9H, s), 0.8 (3H, t) and 0.1 ppm (6H, s); Anal. calcd for C$_{32}$H$_{39}$NO$_3$SSi: C 70.42; H 7.20; N 2.57; found: C 70.20; H 7.33, N 2.73.

(1'R,3S,4R and 1'S,3R,4S) 3-(1'-formyloxy-1'-propyl)-4-tritylthio-2-azetidinone (isomer B)

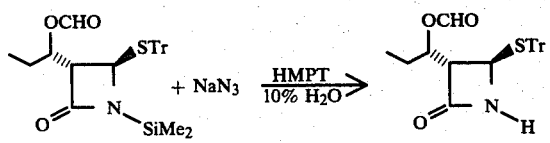

PROCEDURE:

To a cooled (ice bath) solution of (3.7 g, 6.77 mmol) in HMPT (40 ml) containing 10% H$_2$O was added NaN$_3$ (0.91 g, 14 mmol). The mixture was stirred at room temperature for 1.5 h. It was poured onto ice water (200 ml) and extracted with ether (4×40 ml). The ether solution was diluted with pet-ether and washed extensively with water and brine to remove HMPT. It was dried (Na$_2$SO$_4$) and evaporated to dryness to give 2.92 g of a thick colorless oil. (quantitative yield). $^1$Hmr (CDCl$_3$) δ:

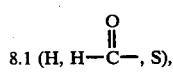

7.1–7.7 (15H, m, —STr), 5.23 (H, m, J=7), 4.38 (H, d, J=2.5), 4.3 (H, —NH), 3.35 (H, dd, J=2.5, J=7), 1.75 (2H, m) and 1.0 ppm (3H, t).

(1'R,3S,4R and 1'S,3R,4S) 3-(1'-formyloxy-1'-ethyl)-1-(paranitrobenzyl 2''-hydroxy-2''-acetate)-4-tritylthio-2-azetidinone (isomer B)

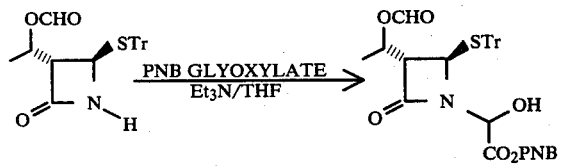

PROCEDURE:

A mixture of 3-(1'-formyloxy-1'-propyl)-4-tritylthio-2-azetidinone (isomer B), (2.9 g, 6.77 mmol), PNB glyoxylate (1.59 g, 7 mmol), Et$_3$N (5 drops) and Na$_2$SO$_4$ (anhydrous, 5.0 g) in THF (50 ml) was stirred at room temperature for 18 h. It was filtered and evaporated to dryness to give an amorphous solid in quantitative yield (4.33 g); $^1$Hmr (CDCl$_3$) δ: 8.2 (2H, d), 7.1–7.8 (18H, m), 5.2 (2H, d), 4.9 (H, m), 4.65 and 4.3 [H, 4.65 (½H,s) 4.3 (½H, s)], 4.2–4.3 (H, d, ½ H at 4.2, ½ H at 4.3), 3.65 (H, m), 1.4 (2H, m) and 0.8 ppm (3H, t).

(1'R,3S,4R and 1'S,3R,4S) 3-(1'-formyloxy-1'-propyl)-1-(paranitrobenzyl 2''-chloro-2''-acetate)-4-tritylthio-2-azetidinone (isomer B)

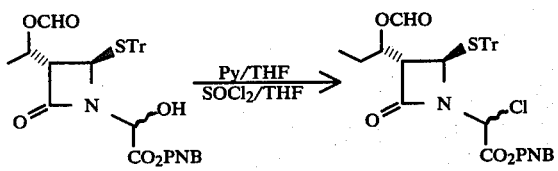

PROCEDURE:

To a cooled (ice salt bath) solution of the above glyoxylate (4.3 g, 6.77 mmol) and 1 M Py/THF (8 ml, 8 mmol) in dry THF (30 ml) was added dropwise 1 M SOCl$_2$/py (8 ml, 8 mmol). The resulting solid mixture was stirred at the above temperature for 1 h. It was diluted with benzene (30 ml) and stirring was continued for 20 min. It was filtered over Celite-charcoal and the filtrate was evaporated to dryness to give 4.1 g of an amorphous solid (92%). ir (neat) ν$_{max}$:

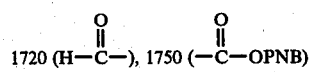

and 1780 cm$^{-1}$ (β-lactam); $^1$Hmr (CDCl$_2$) δ: 8.25 (2H, d),

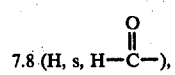

7–7.75 (17H, m), 5.25 (2H, d), 5.0 (H, m), 4.6 (H, s), 4.4 (H, d), 3.7 (H, m), 1.6 (2H, m) and 0.9 ppm (3H, t).

(1'R,3S,4R and 1'S,3R,4S) 3-(1'-formyloxy-1'-propyl)-1-(paranitrobenzyl 2''-triphenylphosphoranylidene-2''-acetate)-4-tritylthio-2-acetidinone (isomer B)

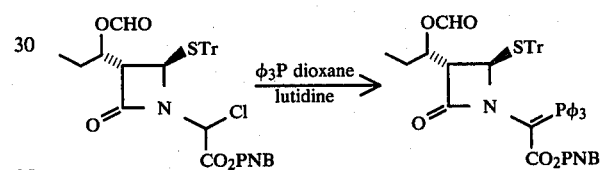

PROCEDURE:

A mixture of the above chloro compound (4.0 g, 6.07 mmol) φ$_3$P (1.834 g, 7 mmol) and lutidine (0.749 g, 7 mmol) in dioxane (40 ml) was heated at 100° C. (oil bath) for 2 days. It was cooled, diluted with ether and washed successively with cold solution of 1 N HCl, 1 M NaHCO$_3$ and brine. The organic solution was dried (Na$_2$SO$_4$) and filtered over Celite-charcoal. It was evaporated to dryness to give an oil which was chromatographed on SiO$_2$ (Act. 1, 200 g) and eluted with benzene and benzene-ether to give 2.60 g of the title compound as an amorphous solid (48.45%); ir (neat) ν$_{max}$:

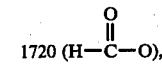

and 1750–1760 cm$^{-1}$ (—CO$_2$PNB and β-lactam).

(1'R,3S,4R and 1'S,3R,4S) 4-acetylthio-3-(1'-formyloxy-1'-propyl)-1-(paranitrobenzyl 2''-triphenylphosphoranylidene-2''-acetate)-2-azetidinone (isomer B)

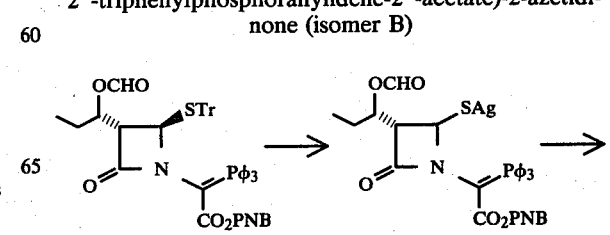

-continued

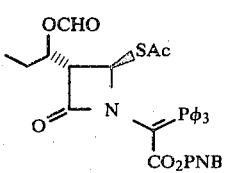

PROCEDURE:

A warm solution (60° C.) of 0.15 M AgNO₃—CH₃OH (8.7 ml, 1.3 mmol) was added to a mixture of the above phosphorane (0.88 g, 1 mmol) and pyridine (0.103 g, 1.3 mmol) in MeOH (5 ml) warmed to 60° C. The mixture was stirred at room temperature for 15 min and at 0° C. for 2 h. It was filtered and washed with cold MeOH to give 0.53 g of the silver mercaptide as a yellow solid (71%) which was used as such. To a cooled (ice bath) mixture of the above mercaptide (0.53 g, 0.71 mmol) and pyridine (0.079 g, 1 mmol) in CH₂Cl₂ (10 ml) was added dropwise CH₃COCl (0.079 g, 1 mmol) in CH₂Cl₂ (5 ml). After stirring at 0° C. for 1 h, it was filtered. The filtrate was washed well with a cold solution of 0.5 M HCl, 0.5 M NaHCO₃ and brine. It was dried (Na₂SO₄) and evaporated to dryness to give 0.43 g of an oil. (63%); ir (neat) $\nu_{max}$:

1700–1760 cm⁻¹ (broad —$\overset{O}{\overset{\|}{C}}$ and β-lactam).

(1'R,3S,4R and 1'S,3R,4S) and acetylthio-3-(1'-hydroxy-1'-propyl-1-(paranitrobenzyl 2''-triphenylphosphoranylide-2''-acetate)-2-azetidinone (isomer B)

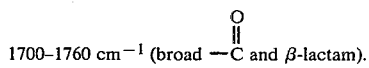

PROCEDURE:

The above formate (1.0 g, 1.45 mmol) in THF (10 ml) was treated at room temperature with HCl/MeOH (10 ml, prepared from 2 ml concentrated HCl and diluted with MeOH to a volume of 24 ml). The mixture was kept at room temperature for 0.5 h. It was basified with 1 M NaHCO₃, extracted with EtOAc solution, washed with brine and dried (Na₂SO₄). It was evaporated to give 0.9 g of crude title compound. This was chromatographed on SiO₂ and eluted with ether and ether:EtOAc (1:1) to give 0.6 g of pure title compound as an amorphous solid (62.5%); ¹Hmr (CDCl₃) δ: 8.25 (2H, d), 7.3–8.1 (17H, m, aromatic), 5.6 (H, m), 5.2 (2H), 4.9 (H), 4.4 (H, m), 2.3 (3H, SAc), 1.5 (2H, m) and 0.9 ppm (3H, t).

(1'R,5R,6S and 1'S,5S,6R) paranitrobenzyl 6-(1'-hydroxy-1'-propyl)-2-methylpenem-3-carboxylate (isomer B)

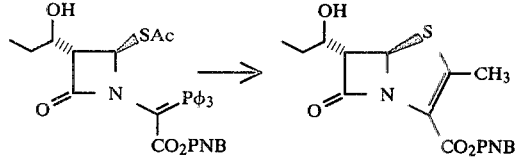

PROCEDURE:

The above phosphorane (0.2 g, 0.3 mmol) in toluene (45 ml) was heated to reflux and 5 ml of toluene was distilled off. The resulting solution was refluxed for 6 h. It was cooled and evaporated to dryness to give 0.2 g of an oil. This was chromatographed on SiO₂ and eluted with ether to give 0.1 g of title compound as a white solid. (87%); mp (pentane) 133°–135° C.; ¹Hmr (CDCl₃) δ: 8.3 (2H, d), 7.6 (2H, d), 5.6 (H, d), 5.35 (2H, d), 4.15 (H, m), 3.8 (H, m), 2.4 (3H, s, CH₃), 2.2 (H, OH), 1.7 (2H, m) and 1.05 ppm (3H, t).

(1'R,5R,6S and 1'S,5S,6R) 6-1'-hydroxy-1'-propyl)-2-methylpenem-3-carboxylic acid (isomer B), mixed K and Na salts

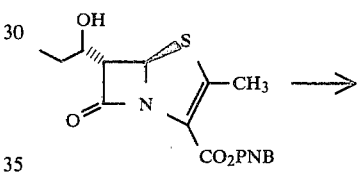

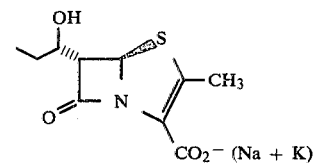

PROCEDURE:

A mixture of the above ester (0.07 g, 0.185 mmol), 30% Pd-Celite (150 mg) and buffer solution (pH 7, 4 ml) in THF (15 ml, Et₂O (25 ml) and deionized water (15 ml was hydrogenated at an initial pressure of 48 psi for 4 h. It was filtered over Celite and the layers were separated. The aqueous layer was washed with ethylacetate and then lyophilized to give 91 mg of a solid; ir (KBr) $\nu_{max}$: 1780 (β-lactam) and 1650 cm⁻¹ (broad, —CO₂⁻); uv H₂O $\lambda_{max}$: 255 (ε 983) and 300 (ε 1092).

EXAMPLE 95

(1'R,5R,6S and 1'S,5S,6R) 6-(1'-Hydroxy-2'-phenylethyl)-2-methylpenem-3-carboxylic acid (isomer B)

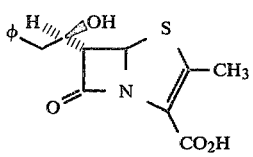

trans 1-(t-butyldimethylsilyl)-3-phenylacetyl-4-tritylthio-2-azetidinone

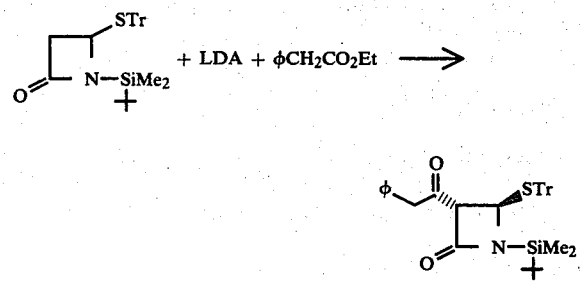

1-t-Butyldimethylsilyl-4-tritylthio-2-azetidinone (18.32 g, 40 mmol) in dry THF (100 ml) was added dropwise under N₂ to a cooled (−78° C.) LDA solution [prepared under N₂, at −78° C. from dropwise addition of 1.6 M n-BuLi (101.25 ml, 162 mmol) to diisopropyl amine (22.95 ml, 162 mmol) in dry THF (150 ml) and stirred at −78° C. for 30 min]. The mixture was stirred at −78° C. for 30 min and ethyl phenylacetate (15.66 g, 15.12 ml 15.12 ml, 93.6 mmol) in dry THF (50 ml) was added and the reaction mixture was stirred at −78° C. for 2 h. It was poured onto ice-1 N HCl (pH 5-6) and extracted with ether several times. The ether solution was washed with brine and dried (Na₂SO₄). It was evaporated to dryness to give 33.7 g of a crude solid. This was dissolved in ether (10 ml) and triturated with pentane (200 ml). The solid was filtered and washed several times with pentane to give 18.3 g of a white solid (79.6%) mp 141–143. ¹Hmr (CDCl₃) δ: 7.0–7.6 (20H, m), 4.8 (H, d), 3.7 (H, d), 3.53 (H, s), 3.43 (H, s) 1.5 (9H, s) and 0.3 ppm (6H, s).

1-(t-butyldimethylsilyl)-3-(1′-hydroxy-2′-phenylethyl)-4-tritylthio-2-azetidinone (2 trans diastereomers)

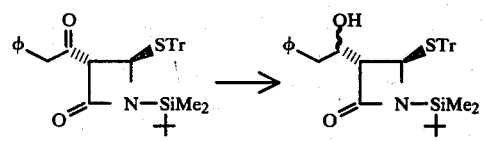

trans 1-(t-butyldimethylsilyl)-3-phenylacetyl-4-tritylthio-2-azetidinone (28.8 g, 50 mmol) and NaBH₄ (0.5 g, 0.25 mole) in THF (200 ml) were stirred at room temperature for 18 h. The mixture was poured onto ice-1N HCl and extracted with CH₂Cl₂. The CH₂Cl₂ solution was washed with brine and dried (Na₂SO₄). It was evaporated to give an amorphous solid (27.7 g). A portion of the solid (23.0 g) was chromatographed on SiO₂ and eluted with hexane:ether to give off-white solid (14.4 g) which was found to be a mixture of (1′R,3S,4R and 1′S,3R,4S) and (1′S,3S,4R and 1′R,3R,4S) isomers in the ratio of 1:1 (60%). ¹Hmr (CDCl₃) δ: 7–7.7 (20H, m), 4.37 (½H, d), 4.18 (½H, d), 3.3–3.8 (H, m), 3.45 (½H, dd), 3.1 (½H, dd), 2.7 (2H, m), 0.87 (9H, d) and 0.25 ppm (6H, s).

1-(t-butyldimethylsilyl)-3-(1′-formyloxy-2′-phenylethyl)-4-tritylthio-2-azetidinone

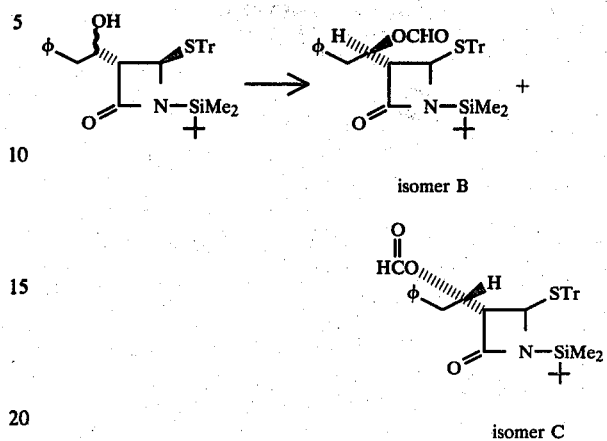

To a cooled (−40° C.) solution of the above mixture of alcohols (14.4 g, 24.9 mmol) in CH₂Cl₂ (250 ml) was added Et₃N (15.93 ml, 125 mmol), HCO₂H (2.24 ml, 59.76 mmol) and DMAP (3.04 g, 24.9 mmol). After stirring for 5 min acetic anhydride (2.35 ml, 249 mmol) was added dropwise. The clear solution was stirred at −40° C. for 15 min whereby it turned into a white cloudy mixture. It was kept at −40° C. for another 45 min (total time 1 h). It was poured onto ice-1N HCl, and the layers separated. The CH₂Cl₂ solution was washed well with cold 1N HCl, H₂O, 1M NaHCO₃ and brine. It was dried (MgSO₄) and evaporated to give 14.0 g of an amorphous solid. This was separated by hplc (Water Associates, System 500) to give: "Isomer B" 6.0 g, mp 172°–73° C. and "Isomer C" 6.0 g mp 188°–89° C. Total yield of pure compound 12.0 g (73.2%). Isomer C: ¹Hmr (CDCl₃) δ: 6.8–7.7 (21H, m), 5.05 (H, dt), 4.05 (CH, d) 3.65 and 3.75 (H, two doublets), 2.7–2.9 (2H, d), 0.88 (9H, s) and 0.2 ppm (6H, s). Isomer B: ¹Hmr (CDCl₃) δ: 7.75 (H, s), 6.9–7.5 (20H, m), 4.3 (H, dt), 3.95 (H, d), 3.37 (H, dd), 2.95 (H, s), 2.85 (H, s), 0.9 (9H, s) and 0.2 ppm (6H, s).

3-(1′-formyloxy-2′-phenylethyl)-4-tritylthio-2-azetidinone (1′R,3S,4R and 1′S,3R,4S enantiomers)

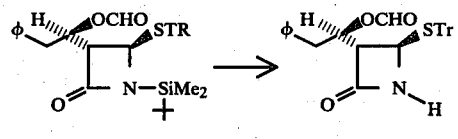

Isomer B

To a cooled (ice bath) solution of the above formate (5.9 g, 9.375 mmol) in HMPT containing 10% water (50 ml) was added NaN₃ (1.3 g, 20 mmol). The mixture was stirred at room temperature for 1.5 h. It was poured onto ice water (300 ml) and extracted with ether (3×100 ml). The ether solution was washed well with water and brine. It was dried (Na₂SO₄) and evaporated to give a solid residue. This was treated with petroleum ether and filtered to give 4.4 g of a white solid (92%) mp 169°–71° C. Anal. calcd for C₃₁H₂₇NO₃S: C 75.43, H 5.51, N 2.84; found: C 75.04, H 5.64, N 2.78. ¹Hmr (CDCl₃) δ: 7.9 (H, s), 7.1–7.6 (20H, m), 5.4 (H, m), 4.6

(H, NH), 4.2 (H, d), 3.3 (H, dd), 3.15 (H, s) and 3.0 (H, s).

3-(1'-formyloxy-2'-phenylethyl)-1-(paranitrobenzyl 2''-hydroxy-2''-acetate)4-tritylthio-2-azetidinone (1'R,3S,4R and 1'S,3R,4S enantiomers)

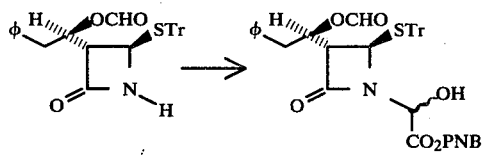

A suspension of PNB glyoxylate (2.37 g, 10.16 mmol) in dry benzene (100 ml) was refluxed under a Dean Stark apparatus (packed with molecular sieve 3Å) for 2 h. Then the above N-H compound (4.2 g, 8.537 mmol) was added and refluxing continued for 1 more h. It was cooled to room temperature $Et_3N$ (0.12 ml, 0.85 mmol) was added and the mixture was stirred at room temperature for 1.5 h. It was evaporated to dryness to give the title compound in quantitative yield as a mixture of two isomeric alcohols. $^1$Hmr ($CDCl_3$) δ: 8.0–8.3 (2H, two doublets), 7.5 and 7.6 (H, two singlets), 7.0–7.4 (20H, m), 5.25 (2H, d), 4.9 (H, OH), 4.25 and 4.35 (H, two doublets), 3.5–4.5 (H, m, broad), 3.1–3.3 (H, m) and 2.9 ppm (2H, m).

3-(1'-formyloxy-2'-phenylethyl)-1-(paranitrobenzyl 2''-chloro-2''-acetate)-4-tritylthio-2-azetidinone (1'R,3S,4R and 1'S,3R,4S enantiomers)

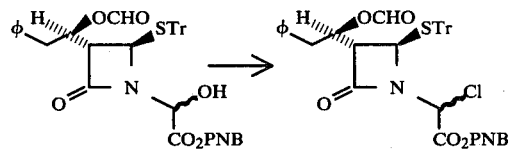

To a cold (ice salt bath) solution of the above glyoxylate (6.0 g, 8.537 mmol) in dry THF (30 ml) was added a 1M solution of pyridine in THF (10 ml, 10 mmol) followed by the dropwise addition of a 1M solution of thionyl chloride in THF (10 ml, 10 mmol). After 1 h at the above temperature it was diluted with benzene (30 ml) and stirring was continued in the cold for 30 min. It was filtered over Celite-charcoal and evaporated to dryness to give 6.0 g of an amorphous solid (98%): $^1$Hmr ($CDCl_3$) δ: 8.2 (2H, m), 7–7.7 (23H, m), 5.8 (H, s), 5.25 (2H, s), 4.35 (H, d), 3.5–4.0 (H, m), 3.3 (H, m) and 2.9 ppm (2H, d).

3-(1'-formyloxy-2'-phenylethyl)-1-(paranitrobenzyl 2''-triphenylphosphoranylidene-2''-acetate)-4-tritylthio-2-azetidinone (1'R,3S,4R and 1S,3R,4S enantiomers)

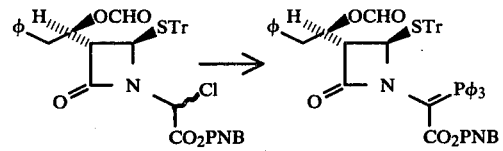

A mixture of the above chloro compound (6.0 g, 8.333 mmol), $\phi_3P$ (2.489 g, 0.5 mmol) and lutidine (1.0165 g, 1.1 ml, 9.5 mmol) in dioxane (50 ml) was heated at 110° C. (bath temp) for 18 h. It was cooled and filtered over Celite. The filtrate was diluted with ethyl acetate and washed with cold 1N HCl, $H_2O$, 1M NaHCO$_3$ and brine. It was dried ($Na_2SO_4$) and evaporated to give 8.0 g of a crude product. This was chromatographed on $SiO_2$ and eluted with ether:hexane (1:1) and ether to give 4.0 g of the title compound. mp (needless from ether) 235°–37° C. (d). (51%); ir (film) $\nu_{max}$: 1720, 1750 cm$^{-1}$.

4-acetylthio-3-(1'-formyloxy-2'-phenylethyl)-1-(paranitrobenzyl 2''-triphenylphosphoranylidene-2''-acetate)-2-azetidinone (1'R,3S,4R and 1'S,3R,4S enantiomers)

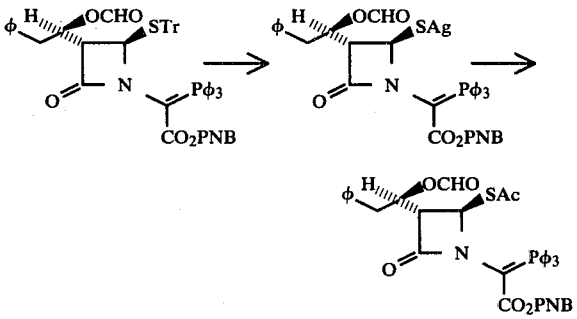

To a refluxing solution of the above phosphorane (3.6 g, 3.8 mmol) and pyridine (0.33 g, 4.2 mmol) in $CH_2Cl_2$ (30 ml) and MeOH (30 ml) was added dropwise a 0.15M $AgNO_3$/MeOH solution (28 ml, 4.2 mmol). The mixture was stirred at room temperature for 2.15 h. It was concentrated to a small volume (~10 ml), cooled and filtered to give the silver mercaptide as a yellow solid (2.3 g, 77%). This mercaptide and pyridine (0.277 g, 3.5 mmol) in ice-cold ($CH_2Cl_2$ (20 ml) was treated dropwise with $CH_3COCl$ (0.27 g, 3.5 mmol) in $CH_2Cl_2$ (5 ml). The mixture was stirred at room temperature for 3 h. It was filtered over Celite and the filtrate was washed with cold 1N HCl, $H_2O$, 1M NaHCO$_3$ and brine. It was dried (MgSO$_4$) and evaporated to dryness to give 1.0 g of an amorphous solid (89.8%). $^1$Hmr ($CDCl_3$) δ: 8.2 (2H, d), 7.0–8.0 (23H, m), 4.5–5.7 (4H, m), 2.6–3.3 (3H, m), and 2.3 ppm (2H, d, SAc).

4-acetylthio-3-(1'-hydroxy-2'-phenylethyl)-1-(paranitrobenzyl 2''-triphenylphosphoranylidene 2''-acetate)-2-azetidinone (1'R,3S,4R and 1'S,3R,4S enantiomers)

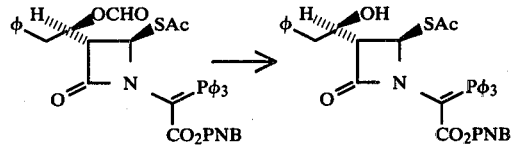

A solution of the above phosphorane (1.8 g, 2.416 mmol) in THF (10 ml) was treated with 1N HCl/MeOH (10 ml) and the mixture was stirred at room temperature for 4 h. It was concentrated to remove methanol, diluted with cold water, basified with 1M NaHCO$_3$ and extracted with CHCl$_3$. The CHCl$_3$ solution was dried (MgSO$_4$) and evaporated to give 1.65 g of an amorphous solid. This was chromatographed on SiO$_2$ and eluted with ether:ethyl acetate to give 1.30 g of the title compound (75%). $^1$Hmr (CDCl$_3$) δ: 8.2 (2H, d), 6.7–8.0 (22H, m), 4.0–6.0 (5H, m), 2.5–3.5 (3H, m) and 2.2 ppm (3H, SAc).

paranitrobenzyl
6-(1'-hydroxy-2'-phenylethyl)-2-methylpenem-3-carboxylate (1'R,5R,6S and 1'S,5S,6R enantiomers)

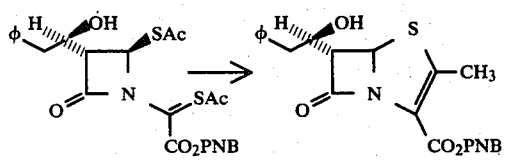

A solution of the above phosphorane (1.2 g, 1.67 mmol) in toluene (80 ml) was heated to reflux (10 ml was distilled off to remove moisture and low boiling point solvent present) for 6 h. It was evaporated to dryness and the crude product was chromatographed on $SiO_2$. The title compound was obtained by eluting the column with ether to give 0.65 g of amorphous solid (89%). $^1$Hmr ($CDCl_3$) δ: 8.2 (2H, d), 7.6 (2H, d), 5.4 (H, d), 5.2–5.4 (2H, d), 4.0–4.5 (H, m), 3.7–4.0 (H, dd), 3.0 (2H, d) and 2.3 ppm (3H, s).

6-(1'-hydroxy-2'-phenylethyl)-2-methylpenem-3-carboxylic acid (1'R,5R,6S and 1'S,5S,6R enantiomers)

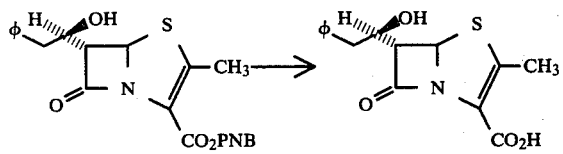

A mixture of the paranitrobenzyl ester (0.33 g, 0.75 mmol), 0.05 M Buffer solution (pH 7, 17.4 ml), THF (30 ml), $Et_2O$ (30 ml), distilled $H_2O$ (60 ml), and 30% Pd/Celite (0.69 g) was hydrogenated at an initial pressure of 50 psi for 24 h. It was filtered over Celite and the organic layer washed with water. The combined water layer was washed several times with EtOAc and it was lyophilized for 18 h to give the title compound as a yellow solid salt. This was treated with a small amount of water, acidified with cold 1N HCl and extracted well with $CHCl_3$. The $CHCl_3$ solution was dried ($MgSO_4$) and evaporated to give a solid residue. This was treated with ether and filtered to give 30 mg of a white solid (13.2%), mp 165°–167° C.; ir (nujol) $\nu_{max}$: 3580 (OH, Sharp), 1660 and 1760 cm$^{-1}$; uv (MeOH) $\lambda_{max}$: 310 (ε 5490) and 254 (ε 4880).

EXAMPLE 96

(1'R,5R,6S and 1'S,5S,6R)
6-(1'-Hydroxyethyl)-2-(2-aminoethoxymethyl)penem-3-carboxylic Acid (isomer B)—Alternate Procedure

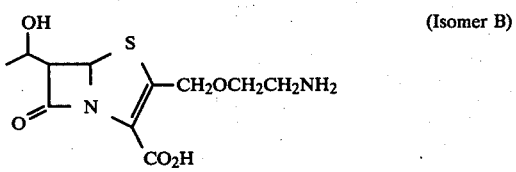
(Isomer B)

(1'R,3S,4R and 1'S,3R,4S)
4-(2-azidoethoxyacetylthio)-3-(1'-hydroxyethyl)-1-(β-trimethylsilylethyl
2''-triphenylphosphoranylidene-2''-acetate)-2-azetidinone

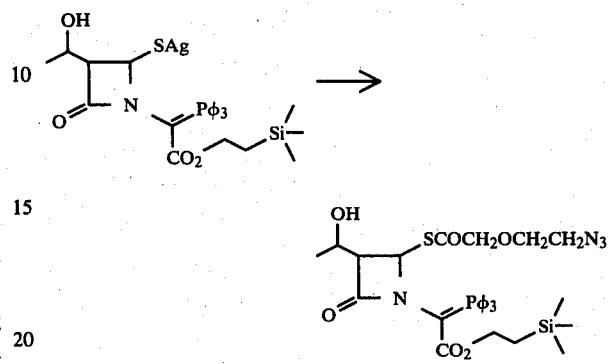

Trimethylsilyl chloride (1.54 ml, 11.8 mmol) was added to a stirred slurry of silver 3-(1'-hydroxyethyl)-1-(β-trimethylsilylethyl 2''-triphenylphosphoranylidene-2''-acetate)-2-azetidinone-4-thiolate (isomer B) (2.48 g, 3.34 mmol), imidazole (136 mg, 2.0 mmol) and triethylamine (1.64 ml, 11.8 mmol) in THF (60 ml) at 0° C. The mixture was stirred at 23° for 18 h. Methylene chloride (60 ml) was added, the mixture cooled to −15° C., pyridine (1.32 ml, 16.4 mmol) and β-azidoethoxyacetyl chloride (1.43 g, 8.70 mmol) added and the mixture stirred at −15° C. for 0.5 h. Ether (60 ml), ethyl acetate (60 ml) and 1M hydrochloric acid (20 ml) were added. The precipitate was removed by filtration and the organic phase was washed with 0.1M hydrochloric acid (100 ml), 1% sodium bicarbonate (100 ml), and saturated sodium chloride. Concentration of the dried solution gave crude title compound as an oil. 85%. ir $\nu_{max}$: 1755 and 1695 cm$^{-1}$.

(1'R,5R,6S and 1'S,5S,6R) β-trimethylsilylethyl 2-β-azidoethoxymethyl-6-(1'-hydroxyethyl)-penem-3-carboxylate (Isomer B)

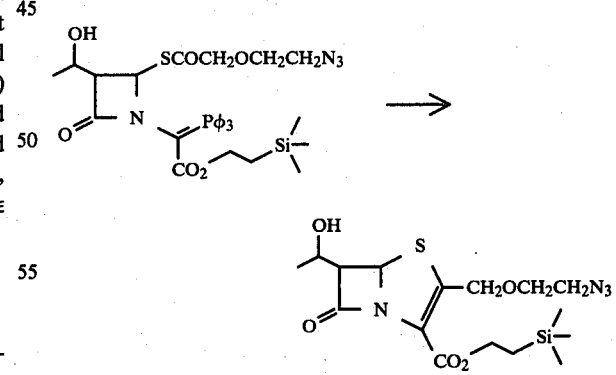

A solution of the above phosphorane (1.3 g) in toluene (200 ml) was heated under reflux for 3 h. Concentration of the solvent on a rotary evaporator gave the crude title compound. Chromatography on silica gel (40 g) eluting with increasing proportions of ether in hexane gave crystalline title compound, 65%. ir$\nu_{max}$: 1760 and 1700 cm$^{-1}$; $^1$Hmr indicated contamination with a second isomer.

(1'R,5R,6S and 1'S,5S,6R)-2-β-azidoethoxymethyl-6-(1'-hydroxyethyl)-penem-3-carboxylic acid (Isomer B).

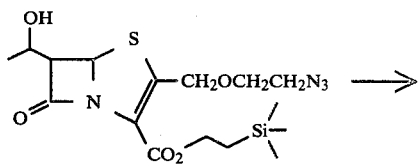

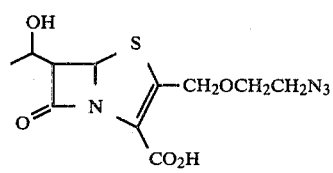

A solution of anhydrous tetrabutylammonium fluoride (3 ml, 1.5 mmol) in THF was added to a solution of the above ester (155 mg, 0.37 mmol) in THF (2 ml) at 0° C. After 5 min at 0° C., water (10 ml) and ethyl acetate (10 ml) were added, the mixture was acidified to pH 3 (1M hydrochloric acid) and the phases separated. The organic phase was extracted with 0.05M sodium bicarbonate, the aqueous extracts acidified to pH 3 with hydrochloric acid and extracted with ethyl acetate. The organic extracts were washed with saturated sodium chloride, dried, concentrated on the rotary evaporator and the residue triturated in ether to give the crude title compound as a solid, 27 mg, 28%. ir $\nu_{max}$: 3500, 1785, 1670 cm$^{-1}$; $^1$Hmr (CDCl$_3$) δ: 1.30 (3H, d, J=6.5, CH$_3$-1'), 2.22 (1H, OH), 3.1–3.9 (5H, m, CH$_2$ and H-6), 3.9–4.4 (1H, m, H-1'), 5.60 (1H, d, J=1, H-5).

(1'R,5R,6S and 1'S,5S,6R) 6-(1'-Hydroxyethyl)-2-(2-aminoethoxymethyl)-penem-3-carboxylic acid (Isomer B)

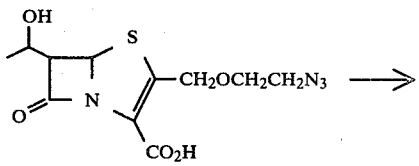

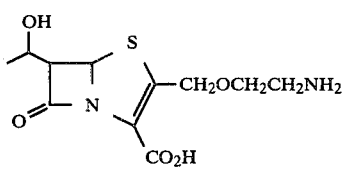

A solution of the above azidocompound (150 mg) in THF (15 ml), ether (15 ml) and water (15 ml) was hydrogenated in a Parr shaker in the presence of 10% Pd/C (150 mg) at an initial H$_2$ pressure of 60 psi. After 3 h the catalyst was removed by filtration over Celite and the aqueous phase was washed with ethyl acetate and lyophilized to give the crude title compound. Purification by hplc (Waters, C$_{18}$ Micro Bondapack Reverse Phase) gave 46.7 mg of pure title compound identical to a previously prepared sample prepared by hydrogenation/hydrogenolysis of the corresponding azido p-nitrobenzyl derivative.

EXAMPLE 97

Alternate Preparation of 4-Tritylthio-1-(p-nitrobenzyl-2'-triphenylphosphoranylidene-2'-acetate)-2-azetidinone

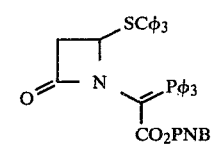

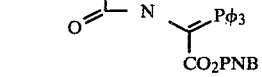

1-(1'-carboxy-1'-hydroxymethyl)-4tritylthio-2-azetidinone triethylanime salt

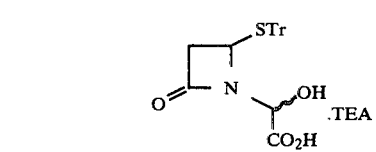

To a solution of 4-tritylthio-2-azetidinone (3.5 g, 10.15 mmol) in tetrahydrofuran (8 ml) was added triethylamine (1.42 ml, 10.15 mmol) and glyoxylic acid hydrate (1.02 g, 10.15 mmol). The mixture was stirred at room temperature with 4Å mol. sieves* (volume of 8 ml) for 1 h and allowed to stand at room temperature overnight. The solidified mixture was diluted with methylene chloride and filtered; the filtrate was evaporated and the residue crystallized from pentane to give 5.18 g (98%) of title compound as a white solid mp 112°–5° C.; ir $\nu_{max}$: 3100–3600, and 1755 cm$^{-1}$; $^1$Hmr (CDCl$_3$) δ: 7.3 (15H, m), 4.92 and 5.10 (1H, 2s), 4.50 (1H, dd, J=8 Hz, J=3 Hz), 3.0 (1H, dd, J=15 Hz, J=7 Hz), 3.1 (6H, q, J=7 Hz), 2.70 (1H, dd, J=15 Hz, J=3 Hz), 2.0–3.5 (2H, m) and 1.21 ppm (9H, t, J=7 Hz).
*Mol. sieves were dried at 150° C. for 18 h.

1-(1'-carboxy-1'-chloromethyl)-4-tritylthio-2-azetidinone

A cooled (ice bath) solution of the triethylamine salt of 1-(1'-carboxy-1'-hydroxymethyl)-4-tritylthio-2-azetidinone (1.04 g, 2.0 mmol) in methylene chloride (5 ml) was treated dropwise, under N$_2$, with thionyl chloride (0.16 ml, 2.2 mmol) in methylene chloride (2 ml). The solution was stirred at room temperature for 20 min and concentrated. The residue was diluted with benzene and filtered over a Celite/charcoal bed. The filtrate was evaporated in vacuo to give 870 mg (quantitative) of the title compound as an amorphous solid. It was used in the next step without further purification. ir$\nu_{max}$: 1775 cm$^{-1}$; $^1$Hmr (CDCl$_3$) δ: 9.22 (1H, bs), 7.27 (15H, m), 5.3 and 5.2 (1H, 2d, J=2 Hz), 4.6 (1H, m) and 2.8 ppm (2H, m).

1-(1'-carbo-p-nitrobenzyloxy-1'-chloromethyl)-4-tritylthio-2-azetidinone

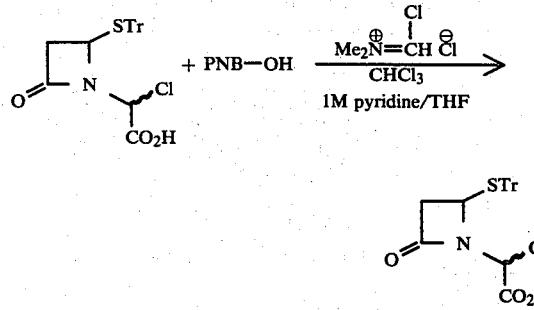

To a cooled (ice bath) solution of DMF (0.17 ml, 2.2 mol) in *chloroform (4.4 ml) was added dropwise oxalyl chloride (0.19 ml, 2.2 mmol). The mixture was stirred 5 min in ice, then 20 min at room temperature. The solution was cooled in an ice bath and treated dropwise with 1-(1'-carboxy-1'-chloromethyl)-4-tritylthio-2-azetidinone (854 mg, 2 mmol) in chloroform (2 ml) followed by a 1M solution of pyridine in tetrahydrofuran (2.2 ml, 2.2 mmol); the solution was stirred at room temperature for 30 min, cooled to 0° C. and treated dropwise with paranitrobenzyl alcohol (370 mg, 2.2 mmol) in tetrahydrofuran/chloroform (1:1, 2 ml) and triethylamine (0.31 ml, 2.2 mmol). The solution was stirred at room temperature for 30 min, then evaporated. The residue was diluted with benzene and filtered over a Celite/charcoal bed and the filtrate was evaporated in vacuo. The crude chloro ester was purified on a silica gel pad (5 g) and eluted with methylene chloride to give 790 mg (70%) of the title compound as a beige powder. Trituration in ether gave a white solid, mp 168°-9° C. ir$\nu_{max}$: 1780, 1760 cm$^{-1}$; $^1$Hmr (CDCl$_3$) δ: 8.15 (2H, d, J=9 Hz), 7.49 (2H, d, J=9 Hz), 7.3 (15H, m), 5.75 and 5.35 (1H, 2s), 5.3 (2H, s), 4.55 (1H, m), 2.8 (2H, m). This compound was identical to an authentic sample prepared by reaction of 4-tritylthio-2-azetidinone with p-nitrobenzyl glyoxylate followed by a thionyl chloride treatment.

*chloroform was left on mol sieves. (3Å) for 18 h before reaction (to remove any trace of alcohol)

EXAMPLE 98

2-(3-Aminocyclopentyl)-penem-3-carboxylic acid, isomers

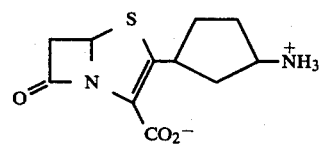

Tetramethyl 1,1,3,4-butanetetracarboxylate

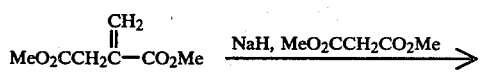

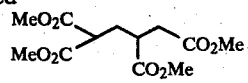

A suspension of sodium hydride in oil (29 g, contains 0.6 mol) was washed with hexane and slurried with diethyl ether (140 ml). A solution of dimethylmalonate (132 g, 1.0 mol) in ether (1050 ml) was added dropwise with stirring (vigorous evolution of hydrogen). The resulting mixture was stirred for 2 h at 23° C. A solution of dimethylitaconate (79 g, 0.50 mol) in ether (320 ml) was added and the mixture was stirred for 18 h at 23° C. The mixture was cooled to 0° C. and cold 1 M hydrochloric acid (600 ml) was added and mixed well. The ether layer was separated and washed with water and saturated NaCl (1 each). The aqueous layers were extracted with ether (500 ml) which was washed with water and saturated NaCl. The combined ether extracts were dried and the solvent was evaporated in vacuo to give an oil, 179 g. The oil was distilled through a Vigreaux column, bp 145°-56° C. (0.5-1.5 torr), to give the title compound, 94.7 g (65% yield); $^1$Hmr (CDCl$_3$) δ: 3.63 (s, 3H, OMe), 3.60 (s, 3H, OMe), 3.57 (s, 3H, OMe), 3.53 (s, 3H, OMe), 3.35 (m, 1H, H-1), 3.2-2.3 (m, 3H, H-3+H-4) and 2.1 ppm (m, 2H, H-2).

Trimethyl 3-oxo-1,2,4-cyclopentanecarboxylate

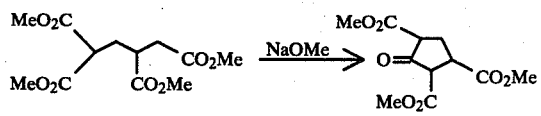

Sodium (8.0, 350 mmol) was added in small pieces to methanol (100 ml). When the formation of sodium methoxide was complete, a solution of tetramethyl 1,1,3,4-butanetetracarboxylate (94.7 g, 327 mmol) in toluene (950 ml) was added. The solution was stirred and heated under reflux for 6.5 h. The solution was cooled to 23° C. and was washed with 350 ml each of 1 M hydrochloric acid and water. The solvent was evaporated in vacuo to give the title compound, 68.8 g (83% yield), as a colorless liquid. ir (liq.) $\nu_{max}$: 1765 (sh), 1730 cm$^{-1}$; $^1$Hmr (CDCl$_3$) δ: 3.75 (br s, 9H, OMe), 4.2-3.2 (m, 2H, H-2+H-4), and 3.0-2.2 ppm (m, 3H, H-1+H-5).

3-Oxocyclopentanecarboxylic acid

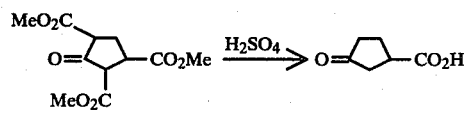

A mixture of trimethyl 3-oxo-1,2,4-cyclopentanecarboxylate (68.8 g, 257 mmol) and 8% sulfuric acid (700 ml) was heated under reflux with stirring for 2 h. The solution was cooled and 25% sodium hydroxide (60 ml) was added (solution pH 1.5). The solution was extracted with EtOAc (500 ml+250 ml). The combined organic extracts were washed with water (back-extracted with more EtOAc) and extracted with 2.5% sodium hydroxide solution (400 ml) (solution pH 10.5). The aqueous extract was cooled to 0° C., acidified to pH 2 with 6M hydrochloric acid (50 ml), and extracted with EtOAc (500 ml). The organic extract was washed with water and saturated NaCl (250 ml each). The combined aqueous was extracted with EtOAc (250 ml). The combined organic extracts were dried and the solvent was evaporated in vacuo to give the title compound as a liquid, 15.3 g (45% yield), mp 59°-60.5° C. (Et$_2$O/hexane). Lit. mp 63° C.); ir (nujol) $\nu_{max}$: 3300-2500, 1730 cm$^{-1}$; $^1$Hmr (CDCl$_3$) δ: 11.62 (s, 1H, CO$_2$H), 3.1 (m, 1H, H-1) and 2.6-2.0 ppm (m, 6H, CH$_2$).

Methyl 3-oxocyclopentanecarboxylate

A solution of 3-oxocyclopentanecarboxylic acid (13.2 g, 103 mmol), MeOH (130 ml) and 98% sulfuric acid (0.1 ml) was heated under reflux with stirring for 1.5 h. The MeOH was evaporated in vacuo. The residue was dissolved in CH$_2$Cl$_2$ (100 ml) and was washed with 1% sodium bicarbonate (50 ml). The solvent was evaporated in vacuo to give the title compound as a liquid, 12.2 g (84% yield); ir (liq.) $\nu_{max}$: 1730-1740 cm$^{-1}$; $^1$Hmr (CDCl$_3$) δ: 3.71 (s, 3H, OMe), 3.2 (m, 1H, H-1) and 2.5-1.9 ppm (m, 6H, CH$_2$).

Methyl 3-hydroxycyclopentanecarboxylate

A solution of methyl 3-oxocyclopentanecarboxylate (9.58 g, 67.5 mmol) in THF (100 ml) was added to a slurry of sodium borohydride (3.8 g, 100 mmol) in THF (100 ml). The mixture was stirred at 23° C. for 2 h, cooled to 0° C. and acidified to pH 6 with 1M hydrochloric acid. The mixture was extracted with EtOAc (2×100 ml) and the organic extracts were washed with water and saturated sodium chloride (100 ml each). The extracts were dried and the solvent was evaporated in vacuo to give the title compound as a colorless liquid, 6.66 g (68% yield), (a mixture of two isomers); ir (liq.) $\nu_{max}$: 3450, 1725 cm$^{-1}$; $^1$Hmr (CDCl$_3$) δ: 4.30 (m, 1H, H-3), 3.70-3.67 (2×s, 3H, OMe), 2.9 (m, 1H, H-1), 2.8 (s, 1H, OH) and 2.3-1.6 ppm (m, 6H, CH$_2$).

Methyl 3-methanesulfonyloxycyclopentanecarboxylate

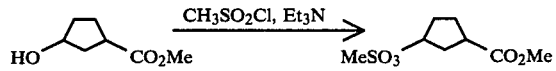

A solution of methanesulfonyl chloride (4.7 ml, 60 mmol) in 25 ml of CH$_2$Cl$_2$ was added dropwise with stirring to a solution of methyl 3-hydroxycyclopentanecarboxylate (6.5 g, 45 mmol) and triethylamine (9.0 ml, 65 mmol) in CH$_2$Cl$_2$ (65 ml) at 0° C. The solution was stirred at 23° C. for 24 h and then washed with water (3×50 ml). The washes were extracted with CH$_2$Cl$_2$ and the combined organic extracts were dried, treated with charcoal and filtered. The solvent was evaporated in vacuo to give the title compound as a yellow liquid, 9.1 g (91% yield), and as a mixture of isomers: ir (liq.) $\nu_{max}$: 1730 cm$^{-1}$; $^1$Hmr (CDCl$_3$) δ: 5.13 (m, 1H, H-3), 3.68 (2×s, 3H, CO$_2$Me), 3.00 (s, 3H, SO$_3$Me), 2.8 (m, 1H, H-1) and 2.4-1.7 ppm (m, 6H, CH$_2$).

Methyl 3-azidocyclopentanecarboxylates

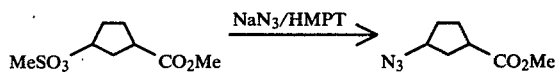

A mixture of methyl 3-methanesulfonyloxycyclopentanecarboxylate (9.0 g, 40.5 mmol), sodium azide (5.2 g, 80 mmol) and HMPT (90 ml) was stirred and heated at 100° C. for 3 h. The cooled mixture was added to water (800 ml) and extracted with diethyl ether (200 ml+3×150 ml). Each ether extract was washed with water (3×75 ml). The combined ether extracts were washed with saturated sodium chloride (200 ml), dried, treated with charcoal and filtered. The solvent was evaporated in vacuo to give crude title compound, 5.2 g. The product was chromatographed (dry column technique) using 125 g of silica and hexane: ether 3:1 as eluant. The two major fractions were re-chromatographed to give isomer—X, 1.84 g and isomer—Y, 0.81 g. Combined yield was 39%. It was not determined which was the cis and which the trans isomer. Spectral data for the two isomers were virtually identical (mixture shows 2 Hz separation of two OMe peaks) ir (liq.) $\nu_{max}$: 2100, 1735 cm$^{-1}$; $^1$Hmr (CDCl$_3$) δ: 4.1 (m, 1H, H-3), 3.76 (s, 3H, OMe), 2.9 (m, 1H, H-1), and 2.4-1.6 ppm (m, 6H, CH$_2$).

3-Azidocyclopentanecarboxylic acids

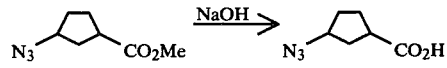

A solution of methyl 3-azidocyclopentanecarboxylate (isomer-X) (1.69 g, 10.0 mmol) in 17 ml each of MeOH and water was stirred vigorously while a 1M sodium hydroxide (10.0 ml) solution was added dropwise. Stirring was continued at 23° C. for 2 h. The MeOH was evaporated in vacuo and the aqueous residue (diluted with 50 ml of water) was washed with ether (30 ml). The solution was acidified to pH 3 with 3M hydrochloric acid and extracted with CH$_2$Cl$_2$ (25 ml+2×15 ml). The extract was dried and the solvent was evaporated in vacuo to give isomer—X of the title compound as a colorless oil, 1.44 g (93% yield); ir (liq.) $\nu_{max}$: 3400-2500, 2090, 1700 cm$^{-1}$; $^1$Hmr (CDCl$_3$) δ: 11.6 (s, 1H, CO$_2$H), 4.07 (m, 1H, H-3), 2.95 (m, 1H, H-1) and 2.4-1.6 ppm (m, 6H, CH$_2$). Isomer—Y (806 mg) was converted into the title isomer—Y in the same manner, 697 mg (94% yield); $^1$Hmr (CDCl$_3$) δ: 11.25 (br, 1H, CO$_2$H), 3.96 (m, 1H, H-3), 2.80 (m, 1H, H-1), and 2.3-1.6 ppm (m, 6H, CH$_2$).

1-(p-Nitrobenzyloxycarbonyl methyl triphenylphosphoranyl)-4-(3-azidocyclopentanethiocarboxylate)-2-azetidinone

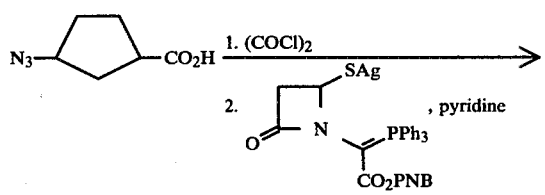

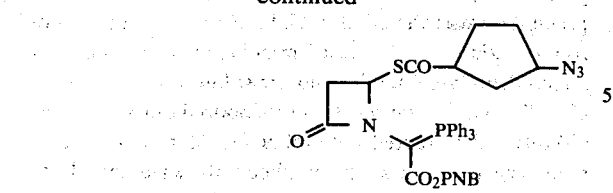

A solution of 3-azidocyclopentanecarboxylic acid (isomer-X) (775 mg, 5.00 mmol) in oxalyl chloride (4 ml) was stirred at 23° C. for 3 h. The excess oxalyl chloride was evaporated in vacuo. The product, as a solution in $CH_2Cl_2$ (10 ml), was added dropwise to a solution of 1-(p-nitrobenzylkoxycarbonyl methyl triphenylphosphoranyl)-4-(silver mercaptidyl)-2-azetidinone (2.91 g, 4.6 mmol) and pyridine (0.40 ml, 5.0 mmol) in $CH_2Cl_2$ (30 ml). The mixture was stirred at 23° C. for 30 min. A solid was removed by filtration and the solution was washed with 1% hydrochloric acid, water and 1% sodium bicarbonate (30 ml each). The solvent was evaporated in vacuo to give the crude product. The product was chromatographed on silica gel (55 g, dry column technique), elution with $Et_2O$: EtOAc 90:10 changing to 75:25. Evaporation of the solvent from the appropriate fractions gave isomer X of the title compound as a yellow powder, 1.20 g, (35% yield). ir (nujol) $\nu_{max}$: 2100, 1760, 1685 cm$^{-1}$; $^1$Hmr (CDCl$_3$), poorly resolved but bands correctly located for PNB, PPh$_3$, and aliphatic regions. Similarly, isomer—Y (697 mg) gave isomer—Y of the title, 1.54 g, (50% yield); $^1$Hmr (CDCl$_3$) very similar to spectrum of isomer—X.

p-Nitrobenzyl 2-(3-azidocyclopentyl)-penem-3-carboxylate

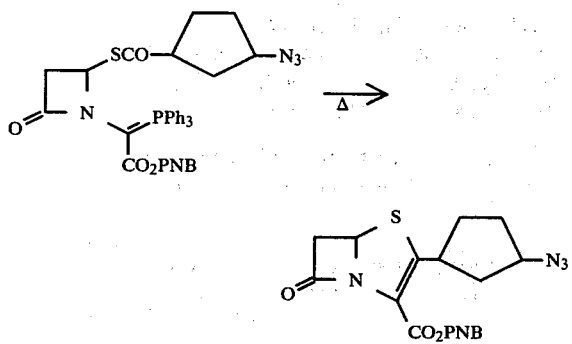

A solution of phosphorane (isomer—X) (1.20 g, 1.73 mmol) and toluene (100 ml) was stirred and heated under reflux for 18 h. The toluene was evaporated in vacuo and the residue was chromatographed on silica gel (30 g, dry column technique). Elution with diethyl ether and evaporation of the solvent from the appropriate fractions gave isomer—X of the title compound, 375 mg (52% yield); mp 124°–125° C. (Et$_2$O); ir (amorphous film) $\nu_{max}$: 2100, 1785, 1705 cm$^{-1}$; $^1$Hmr (CDCl$_3$) δ: 8.28 (d, J=9 Hz, 2H, Ar), 7.60 (d, J=9 Hz, 2H, Ar), 5.60 (q, 1H, H-7), 5.43 & 5.33 (pair of d, J=15 Hz, 2H, benzylic CH$_2$), 4.1 (m, 2H, H-1'+H-3'), 3.80 (dd, $J_{ab}$=16.5 Hz, $J_{bc}$=3.5 Hz, 1H, H-6), 3.50 (dd, $J_{ab}$=16.5 Hz, $J_{ac}$=2 Hz, 1H, H-6), 2.4–1.4 (m, 6H, H-2', 4', -5'), (H-6≡A & B, H-7≡C). Anal. calcd for C$_{18}$H$_{17}$N$_5$O$_5$S: C 52.04, H 4.12, N 16.86, S 7.72; found: C 51.63, H 4.11, N 16.70, S 7.74. Similarly, isomer—Y (1.54 g, 2.22 mmol) in toluene (150 ml) was heated under reflux for 45 h. Chromatography gave isomer—Y of the title compound, 371 mg (40% yield), as an amorphous gum; ir (film) $\nu_{max}$: 2100, 1775, 1705 cm$^{-1}$; $^1$Hmr (CDCl$_3$) δ: 8.20 (d, 2H, Ar), 7.63 (d, 2H, ar), 5.60 (q, 1H, H-7 [C]), 5.40 & 5.27 (pair of d, 2H, benzylic H), 4.1 (m, 2H, H-1' and -3'), 3.80 (dd, $J_{ab}$=16.5 Hz, $J_{bc}$=3.5 Hz, 1H, H-6[B]), 3.50 (dd, $J_{ab}$=16.5 Hz, $J_{ac}$=2 Hz, H-6 [A]) and 2.8–1.5 ppm (m, 6H, H-2',-4'-5').

2-(3-aminocyclopentyl)-penem-3-carboxylic acids

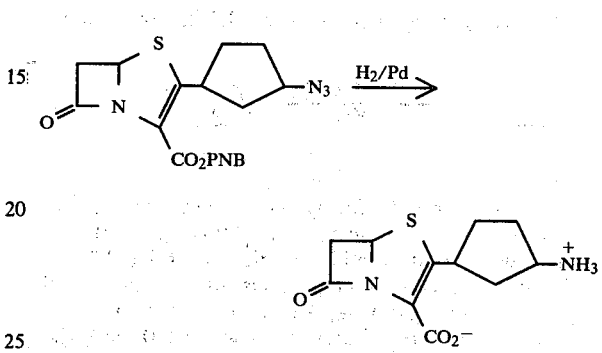

A mixture of p-nitrobenzyl 2-(3-azidocyclopentyl)-penem-3-carboxylate (isomer X) (300 mg, 0.72 mmol), 20 ml each of THF, Et$_2$O and water, and 30% palladium on diatomaceous earth (600 mg) was hydrogenated at 23° C. and 50 psi for 3 h. The catalyst was removed by filtration and the phases were separated. The aqueous phase was washed with ether and freeze-dried to give crude isomer—X of the title compound, 170 mg. The product was separated into two isomers by hplc (C-18 reversed phase column [organosilane on silica gel], water: acetonitrile 95:5). Combined yield 106 mg (58%). Isomer—XA, 45 mg; uv (H$_2$O)$\epsilon_{max}$: 257 (ε3360), 301 (ε4780) mμ; ir (nujol) $\nu_{max}$: 3600–2500, 1765 cm$^{-1}$; $^1$Hmr (D$_2$O, d$_6$-acetone) δ: 5.63 (q, 1H, H-7 [C]), 4.23 (m, 1H, H-3'), 3.87 (m, 1H, H-1'), 3.75 (dd, $J_{ab}$=16.5 Hz, $J_{ac}$=1.5 Hz, 1H, H-6 [A]), 3.37 (dd, $J_{ab}$=16.5 Hz, $J_{bc}$=3.5 Hz, 1H, H-6[B]) and 2.4–1.5 ppm (m, 6H, H-2', -4', -5'). Isomer—XB, 61 mg; uv (H$_2$O) $\lambda_{max}$: 256 (ε2460), 301 (ε3620) mμ; ir (nujol) $\nu_{max}$: 3600–2400, 1765 cm$^{-1}$; $^1$Hmr (D$_2$O) δ: 5.69 (q, 1H, H-7 [C]), 4.25 (m, 1H, H-3'), 3.85 (m, 1H, H-1'), 3.80 (dd, $J_{ab}$=16.5 Hz, $J_{ac}$=3.5 Hz, 1H, H-6 [B]), 3.50 (dd, $J_{ab}$=16.5 $J_{ac}$=1.7 Hz, 1H, H-6 [A]) and 2.5–1.4 ppm (m, 6H, H-2',-4',-5'). Isomer—Y (371 mg, 0.894 mmol) was treated in the same manner as isomer—X to give, after freeze-drying, isomer—Y of the title compound, (33 mg). The product was separated into three isomers by hplc (same conditions as for isomer—X). Combined yield: 11.5 mg (5%). The minor fraction appeared to be one of the—X isomers. Isomer—YA, 6 mg; uv (H$_2$O) $\lambda_{max}$: 255 (ε1980), 301 (2230) mμ; This isomer did not have high enough purity for further work. Isomer—YB, 4.5 mg; uv (H$_2$O) $\lambda_{max}$: 256 (ε3180), 301 (δ4295) m; $^1$Hmr (D$_2$O) δ: 5.66 (q, 1H, H-7 [C]), 4.0 (m, 2H, H-1', -3'), 3.77 (dd, $J_{ab}$=17 Hz, $J_{bc}$=2 Hz, 1H, H-6 [B]), 3.48 (dd, $J_{ab}$=17 Hz, $J_{ac}$=3.5 Hz, 1H, H-6 [A]), and 2.6–1.5 ppm (m, 6H, H-2',-4',-5').

EXAMPLE 99

2-(trans-2-Aminocyclopropyl)-penem-3-carboxylic Acid

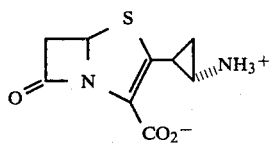

trans-ethyl hydrogen cyclopropane-1,2-dicarboxylate

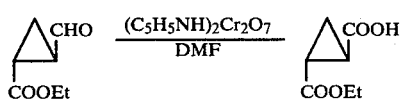

A solution of ethyl 2-formyl-1-cyclopropanecarboxylate (6.465 g, 45.5 mmol) in dry DMF (25 ml) was treated with solid pyridinium dichromate[1] (34.23 g, 90.92 mmol, added in ~5 g portions, addition time of 15 min). The resulting mixture was stirred at room temperature for 15 h. After dilution with water (200 ml), the mixture was extracted with ether (5×20 ml) and the combined organic extracts were washed with 1N HCl and brine. The organic phase was then extracted with saturated NaHCO$_3$ (4×20 ml). The basic extracts were acidified with 10% HCl and extracted with ether (5×20 ml). The combined ether extracts were dried on anhydrous sodium sulfate and evaporated under vacuum to give a clear oil which crystallized on standing: 4.849 g (67%); mp 50–55 (Lit.[2] mp 55°–58° C.); ir $\nu_{max}$(CH$_2$Cl$_2$): 3000 (broad OH of acid), 1725 (C=O of ester) and 1700 cm$^{-1}$ (C=O of acid); $^1$Hmr (CDCl$_3$) δ: 11.36 (1H, s, COOH), 4.15 (2H, q, J=7, CH$_2$—CH$_3$), 2.3–1.9 (2H, m, cyclopropyl), 1.5 (2H, d, J=7, cyclopropyl) and 1.27 ppm (3H, t, J=7, CH$_2$—CH$_3$).

[1] E. J. Corey and G. Schmidt, Tet. Lett. 399 (1979).
[2] K. B. Wiberg, R. K. Barnes & J. Albin, J. Am. Chem. Soc., 79, 4994 (1957).

Ethyl trans-(2-N-carbo-p-nitrobenzyloxyamino) cyclopropane carboxylate

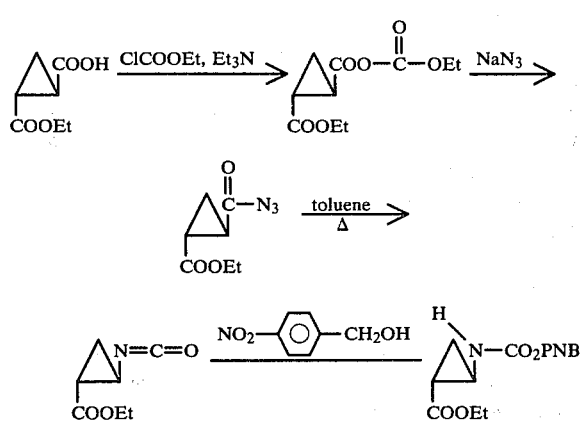

To the trans-ethyl hydrogen cyclopropane-1,2-dicarboxylate (2.254 g, 14.25 mmol) was added water (1 ml) and acetone (5 ml) to complete solubilisation. This solution was cooled to 0° C. and treated with a solution of triethyl amine (1.760 g, 17.4 mmol) in acetone (20 ml). Then a solution of ethyl chloroformate (2.08 g, 19.80 mmol) in acetone (8 ml) was added dropwise over a period of 10 min and the resulting solution with a white precipitate was stirred at 0° C. for 30 min. A solution of sodium azide (1.473 g, 22.67 mmol) in water (6 ml) was added dropwise (10 min) and the solution was stirred at 0° C. for one h. The reaction was poured onto ice water (50 ml) and extracted with ether (3×50 ml). The combined organic phases were washed with water and dried over anhydrous magnesium sulfate. Evaporation of the solvent left the acyl azide as an oil: 2.242 g (86%); ir (film) $\nu_{max}$:2140 (N$_3$), 1733 (C=O of ester) and 1708 cm$^{-1}$ (C=O of acyl azide); $^1$Hmr (CDCl$_3$) δ: 4.17 (2H, q, J=7, CH$_2$CH$_3$), 2.4~2.1 (2H, m, cyclopropyl), 1.58 (2H, d, J=8, cyclopropyl) and 1.28 ppm (3H, t, J=7, CH$_2$—CH$_3$).

The crude acyl azide (2.242 g) in dry toluene (30 ml) was heated at 100° C. for one h. Evaporation of the solvent under vacuum gave an oil [ir (film) $\nu_{max}$: 2280 (N=C=O) and 1725 cm$^{-1}$ (C=O)] which was diluted with dry dioxane (30 ml) and treated with p-nitrobenzyl alcohol (2.291 g, 14.96 mmol). After 9 h at 100° C. and 15 h at 70° C. ir indicated no isocyanate band left. The solvent was evaporated under vacuum and the residue was recrystallized from ether to give 2.213 g (59%) of the carbamate as white needles (the mother liquors contained some more carbamate but separation from the p-nitrobenzyl alcohol was impossible); mp 93.0–93.5° C. (ether-hexanes); ir (KBr) $\nu_{max}$: 3320 (NH, strong), 1720 (sh) (C=O of ester), 1692 (C=O of carbamate) and 1515 cm$^{-1}$ (NO$_2$); $^1$Hmr (CDCl$_3$) δ: 8.21 (2H, d, J$_{Hm,Ho}$=8.8, Hm of p-nitrobenzyl), 7.50 (2H, d, J$_{Ho,Hm}$=8.8, Ho of p-nitrobenryl), 5.2 (2H, s, CH$_2$ of p-nitrobenzyl), 4.9 (1H, broad s, NH), 4.14 (2H, q, J=7.2, CH$_2$—CH$_3$), 3.1 (1H, m, cyclopropyl), 2.0~1.0 (3H, m, cyclopropyl) and 1.25 ppm (3H, t, J=7.2, CH$_2$—CH$_3$); Anal. calcd for C$_{14}$H$_{16}$N$_2$O$_6$: C 54.54, H 5.23, N 9.08; found: C 54.56, H 5.24, N 9.04.

trans-(2-N-carbo-p-nitrobenzyloxy amino) cyclopropane carboxylic acid

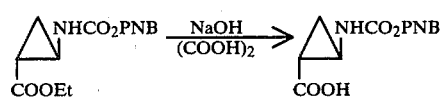

A solution of ethyl trans-(2-N-carbo-p-nitrobenzyloxyamino) cyclopropane carboxylate (1.050 g, 3.40 mmol) in a mixture of methanol (3 ml) and dioxane (1.5 ml) (added for solubility) was cooled to 0° C. and treated with 3.4 ml of a 1 M aqueous solution of sodium hydroxyde. After 15 min at 0° C. and one h at room temperature, the solution was washed with ether (10) and the aqueous phase was cooled again to 0° C. and treated with solid oxalic acid (0.306 g, 3.40 mmol). The aqueous solution was then extracted with dichloromethane (3 ×15 ml). The combined organic extracts were washed once with brine and dried over anhydrous sodium sulfate. Evaporation of the solvent under reduced pressure gave an oil (0.900 g) which was used immediately for the next step: ir (film) $\nu_{max}$:1725 (broad C=O) and 1520 cm$^{-1}$ (NO$_2$).

1'R,2'S,4R and 1'S,2'R,4S; 1'R,2'S,4S and 1'S,2'R,4R) 4-[trans-(2-N-carbo-p-nitrobenzyloxyamino)-1-cyclopropane carboxylthio]-1-(paranitrobenzyl 2''-triphenylphosphornaylidene-2''-acetate)-2-azetidinone.

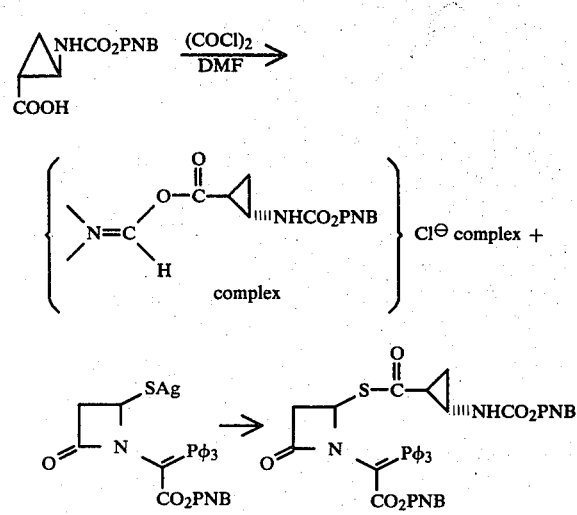

To a cold (-20°C.) solution of dry N,N-dimethyl formamide (0.663 ml, 8.57 mmol) in dry acetonitrile (4 ml) was added oxalyl chloride (250 ml, 2.55 mmol). To this cold suspension was added a solution of trans-(2-N-carbo-p-nitrobenzyloxyamino) cyclo propane carboxylic acid (0.80 g, 2.85 mmol) in dry acetonitrile (3 ml). After 20 min at −20° C., the clear homogeneous reaction mixture was treated dropwise with a solution of (4R and 4S) silver 1-paranitro-benzyl 2'-triphenylphosphoranylidene-2'-acetate)-2-azetidinone-4-thiolate (1.514 g, 2.38 mmol) in dry dichloromethane (3 ml) containing pyridine (0.69 ml, 8.55 mmol). After 15 min at −20° C. and 5 min at room temperature the reaction mixture was poured onto 5% acetic acid and extracted with dichloromethane (4×20 ml). The combined organic phases were washed with saturated NaHCO$_3$ and brine (pH 7). After drying on anhydrous sodium sulfate, evaporation of the solvent gave a red oil (1.040 g) which was chromatographed on 20 g of silicagel. Elution with a mixture of dichloromethane and ethyl acetate (8:2 to 6:4) gave 0.451 g of a complex mixture which was not further investigated. A mixture of CH$_2$Cl$_2$:EtOAc (1:1) then eluted the phosphorane (0.410 g, 27%) as a yellow oil: ir (CH$_2$Cl$_2$) $\nu_{max}$: 3425 (NH), 1752 and 1730 (C=O), 1690 (C=O of thioester), 1625 and 1610 (C=C) and 1525 cm$^{-1}$ (NO$_2$).

1'R,2'S,5R and 1'S,2'R,5'S; 1'R,2'S,5S and 1'S,2'R,5R) paranitrobenzyl 2-[trans-(2-N-carbo p-nitrobenzyloxyamino)-1-cyclopropyl]-penem-3-carboxylate

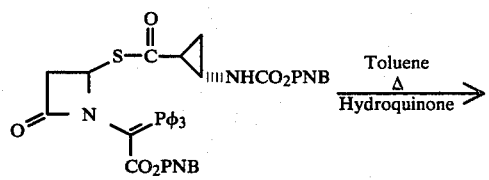

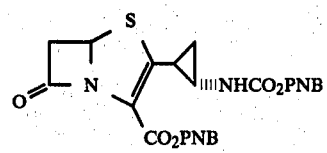

A solution of (1'R,2'S,4R and 1'S,2'R,4S; 1'R,2'S,4S and 1'S,2'R,4R) 4-[trans-(2-N-carbo-p-nitrobenzyloxyamino)-1-cyclopropane carboxylthio]-1-(p-nitrobenzyl 2''-triphenylphosphoranylidene-2''-acetate)-2-azetidinone (0.410 g, 5.0×10$^{-4}$ mol) in dry toluene (40 ml) was maintained at 100° C. for 15 h. Evaporation of the solvent followed by chromatography of the residual oil on 20 g of silicagel (elution C$_6$H$_6$:EtOAc 7:3) gave the penem as a yellow oil (0.112 g, 41%): ir (CH$_2$Cl$_2$) $\nu_{max}$: 3430 (MH), 1792 C=O of β-lactam), 1728 and 1712 (C=O) and 1528 cm$^{-1}$ (NO$_2$); $^1$Hmr (CDCl$_3$) δ: 8.15 (4H, d, J$_{Hm,Ho}$=8.8 Hm of p-nitrobenzyl), 7.56 and 7.45 (4H, 2d, J$_{Ho,Hm}$=8.8 Ho of the two p-nitrobenzyl), 5.6 (1H, m, H-5), 5.5–4.7 (4H, m, overlapping CH$_2$ of the two CH$_2$ of p-nitrobenzyl), 3.8 (1H, dd, J$_{6,5\ cis}$=3.8, J$_{gem}$=16, H-6 cis), 3.42 (1H, dd, J$_{6,5\ trans}$=1.8, J$_{gem}$=16, H-6 trans), ∼3.2–2.6 and ∼1.6–2.1 ppm (4H, m, cyclopropyl).

1'R,2'S,5R and 1'S,2'R,5S; 1'R,2'S,5S and 1'S,2'R,5R 2-(trans-2-aminocyclopropyl)-penem-3-carboxylic acid

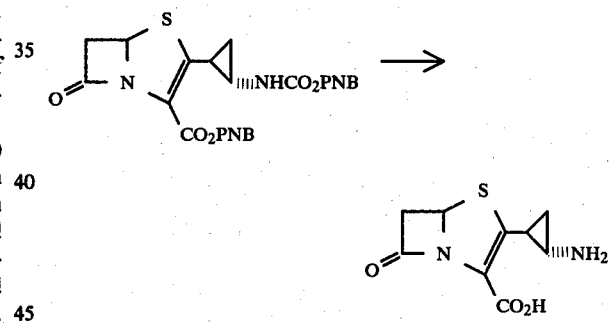

A solution of (1'R,2'S,5R and 1'S,2'R,5S; 1'R,2'S,5S and 1'S,2'R,5R) paranitrobenzyl 2-[trans-(2-N-carbo-p-nitrobenzyloxyamino)-1-cyclopropyl]-penem-3-carboxylate (0.135 g, 2.49×10$^{-4}$ mol) in dimethoxymethane (8 ml), ether (12 ml) and water (10 ml) was hydrogenated over Pd/C (10%) (0.150 mg) at 45 psi for 5 h. The catalyst was then filtered and washed with water and ether (10 ml each). The combined aqueous phases were washed with ether (1×10 ml) and lyophylized to give 0.034 g of brown powder; uv (H$_2$O) λ$_{max}$: 297 (ε 2040). Purification of this material (hplc reverse phase μ-bondapak C-18, one broad peak), gave 0.008 g (14%) of a light brown powder; uv (H$_2$O) λ$_{max}$: 257 (ε 3100), 300.5 (ε 4000); ir (KBr) λ$_{max}$: 1765 cm$^{-1}$ (C=O of β-lactam) (N.B. the product decomposed in the ir beam); $^1$Hmr (D$_2$O) δ: 5.7 (1H, m, H-5), 3.84 (1H, dd, J$_{6,5\ cis}$=3.7, J$_{gem}$=16.7, H-6 cis), 3.47 (1H, dd, J$_{6,5\ trans}$=1.8, J$_{gem}$=16.7, H-6 trans), ∼3.2–2.5 and ∼1.6–2 ppm (4H, m, cyclopropyl). The product is suspected to be very light sensitive and was handled in the dark.

EXAMPLE 100

2-(2'-Aminobutyl)-penem-3-carboxylic Acid

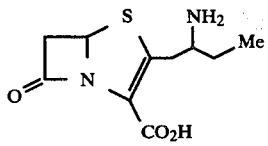

t-Butyl 3-hydroxypentanoate

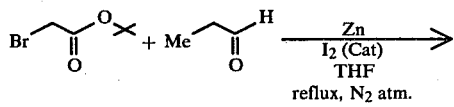

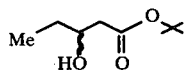

A mixture of zinc (4.25 g, 0.26 mol, granular), a small crystal of iodine and THF (200 ml, freshly distilled over LAH) was refluxed with stirring under a nitrogen atmosphere for 30 min. A portion of the solution (20 ml) of t-butyl α-bromoacetate (35.2 ml, 0.22 mol) and propionaldehyde (10.4 ml, 0.152 mol in THF, 200 ml, freshly distilled over LAH) was added to the above mixture. Within a few minutes the solution became cloudy and the iodine color disappeared. The remainder of the solution was added to the zinc during 30 min, after which the reactants were stirred and heated under reflux for 1 h. The cooled solution was poured into 0.1 N HCL (800 ml) and the pH was adjusted to ~2 with 2 N HCL. The excess of zinc was filtered off and the crude products were extracted into ethyl acetate (3×200 ml). The organic extracts were combined and washed with 8% NaHCO3 (2×200 ml), with water (2×200 ml) and dried over anhydrous MgSO4. The ethyl acetate was evaporated off under reduced pressure to give the crude ester which was purified by distillation, bp 71°–73° C./15 mm, to give colorless liquid (21.3 g, 54.5%). ir (neat) $\nu_{max}$: 3460 (—OH) and 1730 cm$^{-1}$ (C=O of ester), $^1$Hmr (CDCl3) δ: 093 (3H, t), 1.23–1.83 (2H, m), 1.43 (9H, s), 2.32 (2H, d), 3.67 (H, s, OH) and 3.73 ppm (H, m).

[This compound was prepared by a procedure described by D. A. Cornforth et al., J. Che. Soc. C, 2799 (1969)].

t-Butyl-3-tosyloxypentanoate

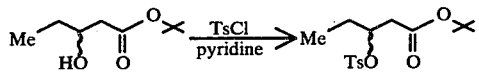

A solution of t-butyl 3-hydroxypentanoate (5.22 g, 0.3 mol) in dry pyridine (10 ml) was treated with p-toluenesulfonyl chloride (6.3 g, 0.33 mol) dissolved in dry pyridine (15 ml). The resulting solution was stirred at room temperature for 24 h and poured into ice-water (300 ml). The oily layer was separated and dissolved in ether (140 ml). This solution was washed with water (3×150 ml) and dried over anhydrous MgSO4. Evaporation of the ether under reduced pressure gave an oil (7.75 g, 78.7%). ir (neat) $\nu_{max}$: 1725 (C=O of ester) and 1178 cm$^{-1}$ (sulfonate); $^1$Hmr (CDCl3) δ: 0.80 (3H, t), 1.38–1.78 (2H, m), 1.42 (9H, s), 2.32–2.62 (2H, m), 2.38 (3H, s), 4.82 (H, m), 7.25 (2H, d) and 7.70 ppm (2H, d). Anal. calcd for C15H24O5S: C 56.94, H 7.65; found: C 58.39, H 7.54.

t-Butyl 3-azidopentanoate

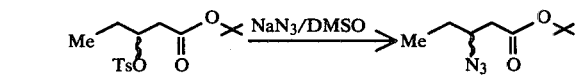

t-Butyl 3-tosyloxypentanoate (7.75 g, 23.6 mmol) was added to a suspension of sodium azide (3.07 g, 47.2 mmol) in dry DMSO (135 ml) and stirred at room temperature for 66 h. The reaction mixture was poured into ice-water (200 ml) and extracted with CH2Cl2 (2×150 ml). The organic extracts were combined, washed with water (4×150 ml) and dried over anhydrous MgSO4. Evaporation of the CH2Cl2 under reduced pressure gave an oil (4.18 g, 89.4%). ir (neat) $\nu_{max}$: 2096 (N3) and 1720 cm$^{-1}$ (C=O of ester); $^1$Hmr (CDCl3) δ: 1.0 (3H, t), 1.27–1.85 (2H, m), 1.48 (9H, s), 2.40 (2H, d) and 3.68 ppm (H, m).

3-Azidopentanoic acid

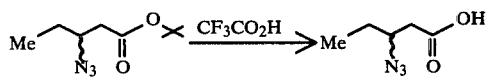

t-Butyl 3-azidopentanoate (1.84 g, 9.23 mmol) was dissolved in 99% trifluroacetic acid (2 ml) and stirred at room temperature for 1 h and evaporated to dryness. The traces of solvent and isobutylene were removed in vacuo to give an oily substance (990 mg, 44.0%). ir (neat) $\nu_{max}$: 3100 (broad, OH), 2100 (N3) and 1710 cm$^{-1}$ (C=O of acid); $^1$Hmr (CDCl3) δ: 1.06 (3H, t), 1.60 (2H, q), 2.57 (2H, d), 3.43 (H, m) and 11.73 ppm (H, s). Anal. calcd for C5H9N3O2: C 41.95, H 6.33; found: C 41.22, H 6.05.

3-Azidopentanoyl chloride

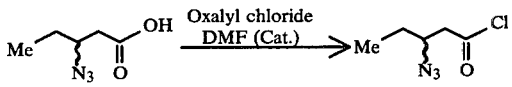

3-Azidopentanoic acid (1.72 g, 12.2 mmol) was dissolved in oxalyl chloride (1.49 ml, 2.22 g, 17.5 mmol) and to this stirring solution was added one drop of DMF. The mixture was stirred at room temperature for 30 min and heated at 80° C. for 40 min. The residue was distilled under vacuum, bp 33° C. (0.1 mm), to give a colorless oil (936 mg, 48.2%); ir (neat) $\nu_{max}$: 2100 (N3), and 1795 cm$^{-1}$ (C=O of acid chloride); $^1$Hmr (CDCl3) δ: 1.03 (3H, t), 1.60 (2H, m), 3.03 (2H, d) and 3.80 ppm (H, m). Anal. calcd for C5H8N3Cl: C 37.16, H 4.99; found: C 37.40, H 4.92.

4-(3'-azidopentanoylthio)-1-(paranitrobenzyl 2''-triphenylphosphoranylidene-2''-acetate)-2-azetidinone

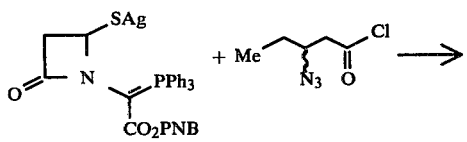

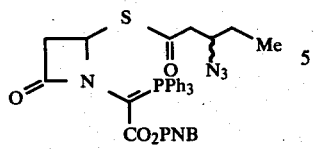

To a solution of silver 1-(paranitrobenzyl 2'-triphenylphosphoranylidene-2'-acetate)-2-azetidinone-4-thiolate (663 mg, 1 mmol) in dry dichloromethane (10 ml) (kept under nitrogen atmosphere and cooled in ice-water bath) was added 3-azidopentanoyl chloride (175 mg, 1.1 mmol) in dry dichloromethane (2 ml). The reaction mixture was stirred at 0° C. for 10 min and 1.5 h at room temperature. The solids were filtered off over a pad of Celite and washed with dichloromethane (10 ml). The filtrate and washings were combined, washed successively with 2% sodium bicarbonate (2×200 ml), and water (2×200 ml) and dried over anhydrous MgSO$_4$. Evaporation under reduced pressure gave a residue which was purified by silica gel column chromatography using 2% MeOH in CH$_2$CL$_2$ as eluent. Combination and evaporation of the appropriate fractions gave a yellow syrup (580 mg, 85.1%). ir (neat) $\nu_{max}$: 2096 (N$_3$), 1750 (shoulder at 1765) (C=O of β-lactam and C=O of p-nitrobenzyl ester) and 1620 cm$^{-1}$ (phosphorane).

paranitrobenzyl 2-(2'-azidobutyl)-penem-3-carboxylate

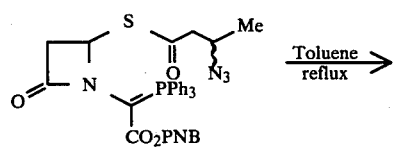

A solution of the above phosphorane (580 mg, 0.85 mmol) in toluene (35 ml) was refluxed for 9 h and evaporated to dryness. The residue (490 mg) was purified on a pad of silica gel using benzene-ether (9.1) as eluent. The product containing fractions were combined and evaporated. The traces of solvent were removed in vacuo to give an oil (202 mg, 58.9%). ir (neat) $\nu_{max}$: 2100 (N$_3$) 1790 (C=O of β-lactam) and 1710 cm$^{-1}$ (C=O of p-nitrobenzyl ester); $^1$Hmr (CDCl$_3$) δ: 1.0 (3H, t), 1.57 (2H, q), 2.38–4.03 (5H, m), 5.35 (2H, d), 5.67 (H, q), 7.60 (2H, d) and 8.18 ppm (2H, d).

2-(2'-aminobutyl)-penem-3-carboxylic acid

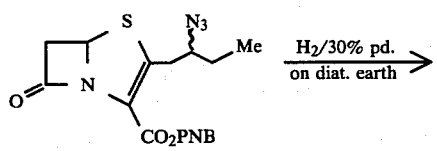

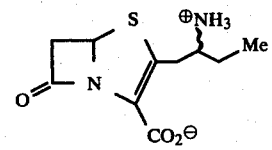

To a solution of paranitrobenzyl 2-(2'-azidobutyl)-penem-3-carboxylate (202 mg 0.50 mmol) in THF (5 ml, freshly distilled over LAH) was successively added ether (5 ml), water (5 ml) and 30% palladium on diatomeceous earth (600 mg). The reaction mixture was shaken at 23° C. for 90 min under 45 psi of hydrogen. The mixture was filtered over a pad of Celite and washed with water. The filtrate and washings were combined and washed with ether-THF (10:1, 22 ml) and with ether-CH$_2$Cl$_2$ (10:1, 22 ml). The aqueous solution was then stirred under high vacuum for 90 min and lyophylized to give a yellowish-green powder (79 mg, 65.2%). The two epimers were separated by hplc (reverse phase. Product containing fractions were combined and lyophylized to give 3 mg of epimer I and 10.5 mg of epimer II as white powders. For epimer I; ir $\nu_{max}$: 1765 (C=O of β-lactam and 1565 cm$^{-1}$ (broad, carboxylate). $^1$Hmr (CDCl$_3$) δ: 1.02 (3H, t, H-4'), 1.78 (2H, q, H-3'), 3.09 (2H, t, H-1'), 3.41 (H, m, H-2'), 3.63 (H, dd, J$_{6,5\ trans}$=1.8 Hz, H-6 trans), 3.75 (H, dd, J$_{6,5\ cis}$=3.6 Hz, H-6 cis) and 5.79 ppm (H, dd, J$_{5,6\ cis}$=3.6 Hz, J$_{5,6\ trans}$=1.8 Hz, H-5); uv (H$_2$O) λ$_{max}$: 309 (ε 4833), 257 (ε 3621). For epimer II; ir $\nu_{max}$:1760 (C=O of β-lactam) and 1570 cm$^{-1}$ (broad, carboxylate: $^1$Hmr (CDCl$_3$) δ: 1.02 (3H, t, H-3'), 1.77 (2H, q, H-3'), 3.13 (2H, t-H-1'), 3.42 (H, m, H-2'), 3.62 (H, dd, H-6 trans), 3.75 (H, dd, H-6) and 5.76 ppm (H, dd, H-5); uv (H$_2$O) λ$_{max}$: 308 (ε 4742), 258 (ε 3267).

EXAMPLE 101

2-(2-Aminoethylsulfinylmethyl) penem-3-carboxylic Acid

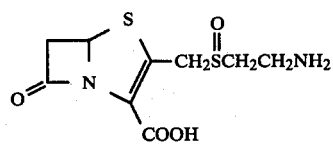

para-nitrobenzyl 2-(2-azidoethylsulfinylmethyl) penem-3-carboxylate

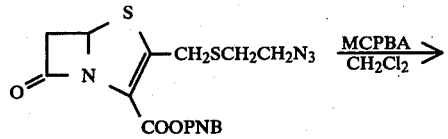

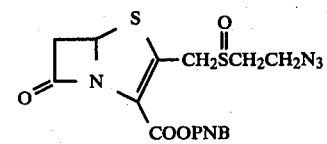

A solution of p-nitrobenzyl 2-azidoethylthiomethyl-penem-3-carboxylate (0.36 g, 0.85 mmol) in CH$_2$Cl$_2$ (30 ml) was cooled to −20° C. under a nitrogen atmosphere and treated dropwise (2 h) with a solution m-chloroperbenzoic acid (0.147 g, 0.85 mmol) in CH$_2$Cl$_2$ (90 ml). The reaction mixture was stirred at −20° C. for 0.5 h, warmed up to room temperature and washed with a saturated NaHCO$_3$ solution and H$_2$O. The organic solution was dried over anhydrous Na$_2$SO$_4$ and concentrated under reduced pressure to an orange residue which was chromatographed over silica gel (silica gel G 60; 9 g; eluent; 25% EtOAc in CH$_2$Cl$_2$, fracton size: 7 ml). Concentration of the appropriate fractions gave a white solid; 0.27 g, mp 128°-31° C., 72.6%. Recrystallization from acetone-ether-pet-ether mixture gave an analytical sample; mp 142° C. dec; calcd for C$_{16}$N$_5$O$_6$S$_2$: C 43.93, H 3.46, N 16.01, S 14.66; found: C 43.79, H 3.44, N 16.02, S 14.63. ir (KBr) $\nu_{max}$: 2110 (N$_3$), 1785 (C=O of β-lactam), 1690 (C=O of PNB ester), 1600, 1560 (C=C), 1520, 1355 cm$^{-1}$ (NO$_2$); uv $\lambda_{max}^{CHCl_3}$:265 (ε 12884), 333 (ε 8764); $^1$Hmr (CDCl$_3$) δ: 2.95 (2H, m, CH$_2$CH$_2$N$_3$), 3.58 (dd, J$_{H-6-H-5\ trans}$=2.0 Hz, J$_{gem}$=16.6 Hz, H-6 trans), 4.33 (center of ABq, J$_{a,b}$=13.4 Hz, H-1'), 4.32 (center of ABq, J$_{a,b}$=13.2 Hz, H-1'), 5.33 (center of ABq, J$_{a,b}$=13.7 Hz, 2H, CH$_2$ of PNB ester), 5.75 (dd, J$_{H-5-H-6\ cis}$=3.6 Hz, J$_{H-5-H-6\ trans}$=2.1 Hz, 1H, H-5), 7.60 (d, J$_{Ho-Hm}$=8.8 Hz, 2H, Ho of PNB ester) and 8.22 (d, J$_{Hm-Ho}$=8.8 Hz, 2H, Hm of PNB ester).

2-(2-aminoethylsulfinylmethyl) penem-3-carboxylic acid

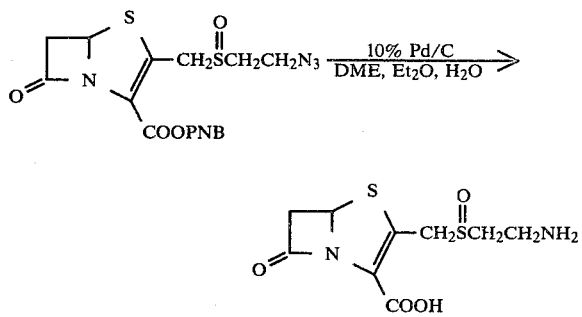

To a solution of paranitrobenzyl 2-(2-ethylsulfinylmethyl) penem-3-carboxylate (57 mg, 0.13 mmol) in dimethoxyethane (20 ml) was successively added Et$_2$O (10 ml), H$_2$O (10 ml) and 10% Pd on charcoal (57 mg). The reaction mixture was hydrogenated under 55 psi for 1.25 h and filtered over a Celite pad. The filtrate was diluted with Et$_2$O; the organic phase was separated and the aqueous solution was washed with Et$_2$O (twice) and lyophilized. The crude orange powder (30 mg) was purified by hplc; lyophylization appropriate fractions gave the title compound as a white powder; 10.4 mg, 29%; uv $\lambda_{max}^{H_2O}$: 313 (ε 4877); ir (KBr) $\nu_{max}$: 1720 (C=O of β-lactam) and 1590 (carboxylate); $^1$Hmr (D$_2$O) δ: 3.0-3.7 (5H, H-6 trans, CH$_2$CH$_2$NH$_3^+$), 3.90 (dd, J$_{H-6-H-5\ cis}$=3.6 Hz, J$_{gem}$=16.9 Hz, 1H, H-6 cis), 5.45 (center of ABq, J$_{a,b}$=13.6 Hz, H-1'), 4.50 (center of ABq, J$_{a,b}$=13.6 Hz, H-1') and 5.8 (m, 1H, H-5).

EXAMPLE 102

(5R) 2'(5'-Aminopentyl)-penem-3-carboxylate

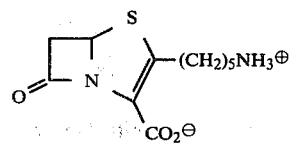

(4R) 4-(6'-azidohexanoylthio)-1-(p-nitrobenzyl 2''-triphenylphosphoranylidene-2''-acetate)-2-azetidinone

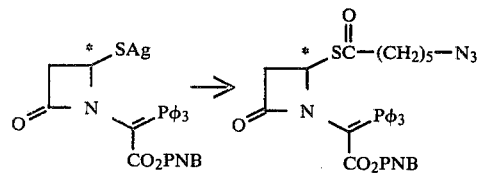

(4R) Silver 1-(p-nitrobenzyl 2'-triphenylphosphoranylidene-2'-acetate)-2-azetidinone-4-thiolate [7.16 g, 10.8 mmol, prepared from the corresponding 5-acetyl derivative with [α]$_D^{25}$+47.9 (C 0.048, CHCl$_3$)] treated as described in Example 87 with 6-azidohexanoyl chloride gave the title compound (34%) with spectral data identical to the authentic 4R and 4S sample.

(5R) p-Nitrobenzyl 2-(5'-azidopentyl)-penem-3-carboxylate

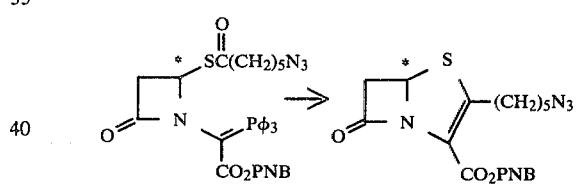

The above (4R)-phosphorane (2.7 g) cyclized as described in Example 87 gave the dextro-title compound (1.12 g, 69%), mp 63°-40° C., [α]$_D^{25}$+108.3 (C 0.026, CHCl$_3$). Spectral data were identical to the authentic 5R and 5S sample.

(5R) 2-(5'-aminopentyl)-penem-3-carboxylic acid

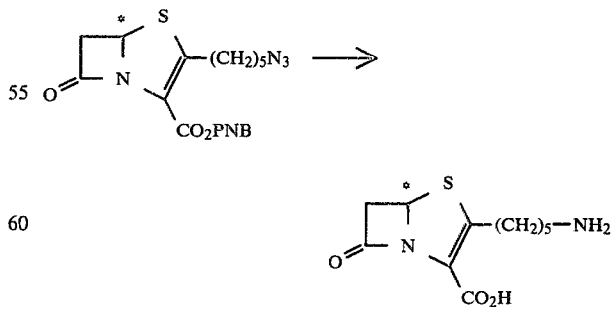

Hydrogenation/hydrogenolysis of the above (5R)-azido-ester (1.08 g) as described in Example 87 (10% Pd/C, dimethoxyethane- Et$_2$O—H$_2$O) gave the title compound (132 mg), [α]$_D^{25}$+187.5 (C 0.033, CHCl$_3$);

uv λ$_{max}$: 300 (ε 5903) and 248 (ε 4311); ir and $^1$Hmr were identical to that of the racemate.

EXAMPLE 103

(4'R,5R,6S and 4'S,5S,6R) 6-(2', 2'-Dimethyl-1',3'-dioxolan-4'-yl)-2-methylpenem-3-carboxylic Acid (Isomer C)

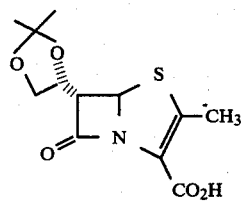

Preparation of

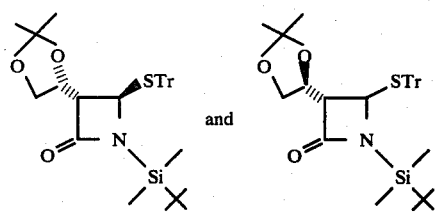

(4'R,3S,4R and 4'S,3R,4S) and (4'S,3S,4R and 4'R,3R,4S)

1-(t-Butyldimethylsilyl)-3-(2',2'-dimthyl-1'-,3'-dioxolan-4'-yl)-4-tritylthio-2-azetidinone ("Isomer C" and "Isomer B")

Ethyl O-(2-methoxy-2-propyl)glycolate[1]

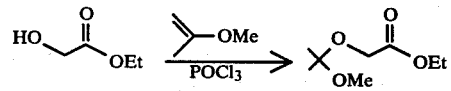

To a solution of ethyl glycolate (15.6 g, 0.150 mol; freshly distilled) and 2-methoxypropene (16.4 g, 0.216 mol; 95% pure)[2] in CH$_2$Cl$_2$ (150 ml) was added at 0°–5° phosphorus oxychloride (3 drops, 35 mg, 0.23 mmol) and the mixture was stirred at 0°–5° for 15 min and at room temperature for 1.5 h. This was then quenched with pyridine (30 drops), stirred 45 min and the solvent evaporated. The residue diluted with pentane (150 ml) was dried over K$_2$CO$_3$. After filtration, the solvent was evaporated yielding 27.89 g (0.158 mol, 100%; 94.9% pure) of the title compound as a colourless oil: $^1$Hmr (CCl$_4$) δ: 1.25 (3H, t, J=7 Hz —CH$_2$CH$_3$), 1.28 (6H, s, Me$_2$), 3.12 (3H, s, —OCH$_3$), 3.88 (2H, s, —OCH$_2$CO—), 4.10 (2H, q, J=7 Hz, —CH$_2$CH$_3$); ir (neat) ν$_{max}$: 1760 and 1735 cm$^{-1}$ (ester).

[1] J. Meinwald et al., Tet. Lett., 4327 (1978)
[2] M. S. Newman and M. C. Vander Zwan, J. Org. Chem., 38, 2910 (1973).

(3S,4R and 3R,4S) 1-(t-Butyldimethylsilyl)-3-(1'-keto-2'-(2''-methoxy-2''-isopropyloxy)-1'-ethyl)-4-tritylthio-2-azetidinone

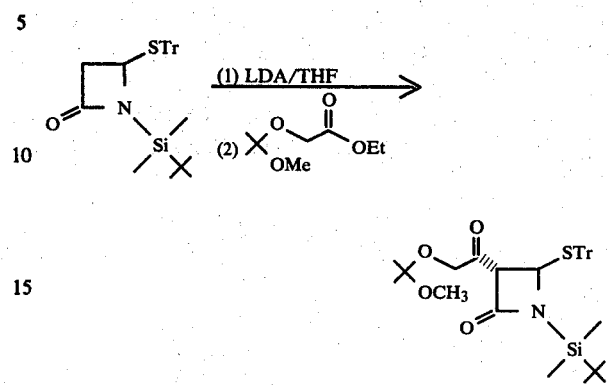

To a stirred solution of diisopropylamine (18.5 ml, 0.134 mol) in THF (400 ml; freshly distilled from LAH) at −78° C. was added n-butyllithium (1.6M in hexane, 90 ml, 0.144 mol) under N$_2$ atmosphere. After 30 min, a solution of 1-(t-butyldimethylsilyl) 4-tritylthio-2-azetidinone (50.0 g, 0.109 mol) in THF (100 ml) was added dropwise over 10 min and the mixture was stirred for 5 min. To this pink solution was added ethyl O-(2-methoxy-2-propyl)glycolate (23.94 g, 0.136 mol) and the mixture was stirred for 1 h. After removing the dry-ice bath saturated NH$_4$Cl solution (200 ml) was added followed by brine (100 ml). The aqueous phase was extracted with Et$_2$O (3×100 ml). The combined organic extracts were washed with brine, dried (Na$_2$SO$_4$) and evaporated yielding 60.95 g (0.103 mol, crude yield 94.6%) of the title compound as a crude orange oil. This crude material was used in the next reaction. A pure sample was obtained by column chromatography (SiO$_2$, eluent: 2% Et$_2$O in benzene); $^1$Hmr (CDCl$_3$) δ: 0.30 (6H, s, Si—CH$_3$), 0.95 (9H, s, t-Bu), 1.12 (3H, s, CH$_3$), 1.15 (3H, s, CH$_3$), 3.15 (3H, s, OCH$_3$), 3.57 (1H, A of AB, J$_{gem}$=17 Hz), 3.77 (1H, d, J=1.6 Hz, H-3), 3.97 (1H, B of AB, J$_{gem}$=17 Hz), 4.83 (1H, d, J=1.6 Hz, H-4); 7.1–7.6 (15H, m, aromatic Hs); ir (neat) ν$_{max}$: 1750, 1725, 1710 cm$^{-1}$ (C=O); tlc, Rf 0.53 (benzene; Et$_2$O=4:1), Rf 0.61 (hexane: EtOAc=2:1).

(3S,4R and 3R,4S) 1-(t-Butyldimethylsilyl)-3-(1'-hydroxy-2'-methoxyisopropyloxyethyl)-4-tritylthio-2-azetidinone (mixture of epimers at C-1')

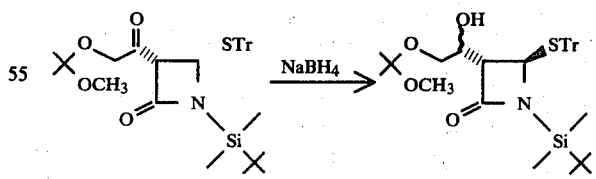

A solution of crude 1-(t-butyldimethylsilyl)-3-(1'-keto-2'-(2''-methoxy-2''-isopropyloxy)-1'-ethyl)-4-tritylthio-2-azetidinone (60.95 g, 0.103 mol) in THF (100 ml) was diluted with abs. EtOH (350 ml) and to this solution was added at 0° C. NaBH$_4$ (4.88 g, 0.156 mol). The mixture was stirred at room temperature for 2 h and quenched by slow addition of brine (280 ml). The mixture was extracted with Et$_2$O (3×150 ml) and the extracts were washed with brine, dried (Na2SO4) and evaporated to yield a yellow residue which was redissolved in CH2Cl2 (500 ml). This was dried (Na2SO4) again and evaporated yielding 57.1 g (0.0966 mol, crude yield 93.8%) of the title compound as a crude yellow foam: [1]Hmr (CDCl4) δ: 0.17 (s, SiCH3), 0.80, 0.87 (2s, Si-tBu), 1.22, 1.25 (2s, CH3), 3.03 (s, OCH3), 4.32 (d, J=2 Hz, H-4), 7.0–7.7 (m, aromatic Hs); ir (neat) $\nu_{max}$ 3460 (OH), 1745 (C=O), 1595 (aromatics): Rf 0.47 and 0.42 (hexanes: EtOAc=2:1). This crude material was used in the next step without purification.

(4′R,3S,4R and 4′S,3R,4S) and (4′S,3S,4R and 4′R,3R,4S)
1-(t-Butyldimethylsilyl)-3-(2′,2′-dimethyl-1′,3′-dioxolan-4′-yl)-4-tritylthio-2-azetidinone. (Isomer C and Isomer B)

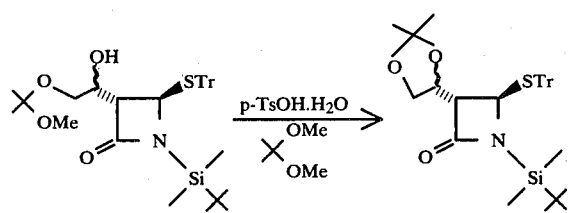

A solution of (3S,4R and 4R,4S) 1-(t-butyldimethylsilyl)-3-(1′-hydroxy-2′-methoxyisopropyloxyethyl)-4-tritylthio-2-azetidinone (mixture of diastereomers at C-1′ (57.1 g, 0.0966 mol; crude) in CH2Cl2 (500 ml) was treated at room temperature with p-toluenesulfonic acid monohydrate (200 mg) and 2,2-dimethoxypropane (20 ml) and then stirred for 1 h. It was washed with sat. NaHCO3 and then brine, dried (Na2SO4) and evaporated yielding 49.64 g (0.0888 mol, crude yield 91.9%) of a mixture of the title compounds (Isomer B and Isomer C) as yellowish foam. This was purified by HPLC (Waters 500 Silicagel; eluent, hexane: EtOAc=9:1) and by crystallization yielding 14.28 g (25.5 mmol, 26.4%) of the title compound (Isomer C) as white crystals; mp 146°–7° C. (pentane); [1]Hmr (CCl4) δ: 0.27 (6H, s, Si—CH3), 0.95 (9H, s, Si—tBu), 1.15 (6H, s, di-Me), 2.5–2.9 (1H, m, H-4′), 2.97 (1H, t, J=1.8 Hz, H-3), 3.25–3.9 (2H, m, H-5′), 4.27 (1H, d, J=1.8 Hz, H-4), 7.1–7.6 (15H, m, aromatic Hs); ir (nujol) $\nu_{max}$: 1750 (C=O) and 1595 cm$^{-1}$ (aromatics); Rf 0.45 (hexanes: EtOAc=4:1) and 14.50 g (25.9 mmol, yield 25.9%) of the title compound (Isomer B) as white crystals: mp 144°–5° C. (Et2O-pentane); [1]Hmr (CCl4) δ: 0.02 (6H, s, SiMe), 0.833 (9H, s, Si—tBu), 1.13, 1.18 (6H, 2s, diMe), 2.5–2.8 (1H, m, H-4′), 3.3–4.1 (2H, m, H-5′), 3.48 (1H, dd, J3,4=1.5 Hz, J3-4′=5.0 Hz, H-3), 3.93 (1H, d, J4-3=1.5 Hz, H-4), 7.1–7.7 (15H, m, aromatic Hs); ir (nujol) $\nu_{max}$: 1650 (C=O) and 1595 cm$^{-1}$ (aromatics); Rf 0.37 (hexanes:EtOAc=4:1). Anal calcd for C33H41NO3SSi: C 70.80, H 7.38, N 2.50, S 5.73; found: (Isomer C) C 70.23, H 7.30, H 7.30; N 2.41, S 5.53 and (Isomer B) C 70.52, H 7.31, N 2.40, S 5.05.

B. Preparation of the Penem Product (Isomer C)

(4′R,3S,4R and 4′S,3R,4S)
3-(2′,2′-Dimethyl-1′,3′-dioxolan-4′-yl)-4-tritylthio-2-azetidinone (Isomer C)

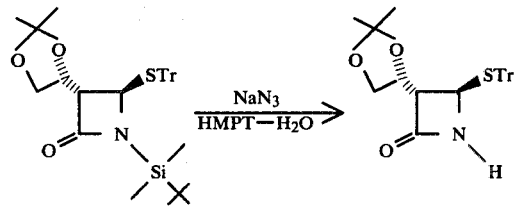

To a stirred solution of (4′R,3S,4R and 4′s,3R,4S) 1-(t-butyl-dimethylsilyl)-3-(2′,2′-dimethyl-1′,3′dioxolan-4′-yl)-4-tritylthio-2-azetidinone (Isomer C)) 14.3 g, 25.6 mmol) in hexamethylphosphoric triamide (230.4 ml) was added slowly (in 20 min) at 0°–5° C. a solution of sodium azide (2.50 g, 38.4 mmol; 1.5 eq) in H2O (25.6 ml). The mixture was stirred at room temperature for 2 h and poured into cold water (2.5 l). The white precipitate formed was collected, washed with H2O and dried yielding 11.26 g (25.3 mmol, crude yield 98.8%) of the title compound as a white solid. A pure material was obtained by crystallization from CH2Cl2—Et2O: mp 192°–3° C. (dec.); [1]Hmr (CDCl3) δ: 1.33, 1.37 (6H, 2s, di-Me), 3.27 (1H, t, J=3 Hz, H-3), 3.8–4.4 (3H, m, H-4′ and H-5′), 4.40 (1H, d, J=3 Hz, H-4), 4.47 (1H, br, NH, D2O exchanged) and 7.1–7.7 ppm (15H, m, aromatic Hs); ir (nujol) $\nu_{max}$: 3220 (NH), 1760 (C=O) and 1950 cm$^{-1}$ (aromatics); Rf 0.31 (hexanes: EtOAc=3:2).

(4′R,3S,4R and 4′S,3R,4S)
3-(2′,2′-Dimethyl-1′,3′-dioxolan-4′-yl)-1-(p-nitrobenzyl 2″-hydroxy-2″-acetate)-4-tritylthio-2-azetidinone (mixture of epimers at C-2″) (Isomer C)

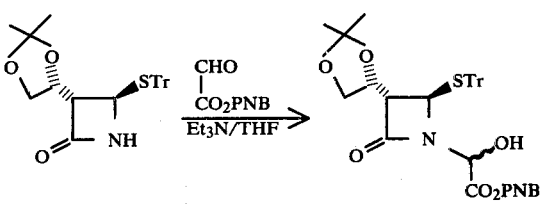

A suspension of p-nitrobenzyl glyoxylate hydrate (6.57 g, 28.95 mmol; 1.15 eq) in benzene (500 ml) was heated at reflux with Dean-Stark trap for 2 h. Evaporation of the solvent gave p-nitrobenzyl glyoxlyate as an oil. A mixture of this oil and (4′R,3S,4R and 4′S,3R,4S) 3-(2′,2′-dimethyl-1′-3′-dioxolan-4′-yl)-4-tritylthio-2-azetidinone (Isomer C) (11.2 g, 25.2 mmol) in THF (350 ml, distilled from LAH) was treated with triethylamine (289 mg, 2.86 mmol) at room temperature under N2 for 18 h (overnight). After evaporation of the solvent, the residue diluted with CH2Cl2 (200 ml) was washed successively with brine containing 1N HCl (2.9 ml) sat NaHCO3 and brine, dried (Na2SO4) and evaporated after addition of Et2O (30 ml) to give 17.2 g (26.3 mmol, crude yield 100%; purity 95.8%) of the title compound as a white foam: Rf 0.40 and 0.30 (benzene:Et2O=3:2). Each isomer was separated by hplc (SiO2, eluent, benzene:Et2O=3:2) and purified by crystallization from CH2Cl2—Et2O. Isomer I: Rf 0.40 (benzene:Et2O=3:2);

mp 153°–4° C.; ¹Hmr (CdCl₃) δ: 1.20 (6H, s, di-Me), 3.1 (2H, m, H-3 and OH), 3.5–4.2 (3H, m, H-4′ and H-5′), 4.55 (1H, d, J=2 Hz, H-4), 5.12 (1H, br, H-2″), 5.30 (2H, s, OCH₂Ar) and 7.1–8.3 ppm (19H, m, aromatic Hs); ir (nujol) $\nu_{max}$: 3370 (OH), 1775 (β-lactam) and 1745 cm⁻¹ (ester); Anal. calcd for $C_{36}H_{34}N_2O_8S$: C 66.04, H 5.23, N 4.28, found: C 65.85, H 5.64, N 4.11. Isomer II: Rf 0.30 (benzene:Et₂O=3:2); mp 164°–5° C.; ¹Hmr (CDCl₃) δ: 1.17 (6H, s, di-Me), ~3.2 (2H, m, H-3 and OH), 3.4–4.0 (3H, m, H-4′ and H-5′), 4.57 (1H, d, J=2 Hz, H-4), 5.23 (1H, br, H-2″), 5.27 (2H, s, —OCH₂Ar), and 7.1–8.3 ppm (19H, m, aromatic Hs); ir (nujol) $\nu_{max}$: 3340 (OH), 1765 (β-lactam) and 1740 cm⁻¹ (ester); Anal. calcd for $C_{36}H_{34}N_2O_8S$: C 66.04, H 5.23, N 4.28, found: C 66.01, H 5.34, N 4.28, S 4.75.

(4′R,3S,4R and 3′S,3R,4S) 3-(2′,2′-Dimethyl-1′,3′-dioxolan-4′-yl)-1-(p-nitrobenzyl 2″-chloro-2″-acetate)-4-tritylthio-2-azetidinone (mixture of epimers at C-2″) (Isomer C)

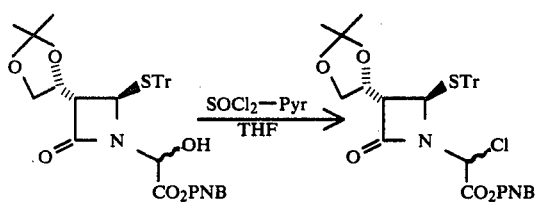

To a stirred solution of (3′R,3S,4R and 4′S,3R,4S) 3-(2′,2′-dimethyl-1′,3′-dioxolan-4′-yl)-1-(p-nitrobenzyl 2″-hydroxy-2″-acetate)-4-tritylthio-2-azetidinone (Isomer C) (17.13 g, 25.07 mmol; mixture of epimers at C-2″) in THF (250 ml) was added at −15° C. under N₂ pyridine (2.84 ml, 35.1 mmol) and then immediately afterwards thionyl chloride (2.20 ml, 30.1 mmol; Anachemia). The mixture was stirred for 20 min at −15° and then the white precipitate was filtered off. After washing with benzene, the filtrates and washings were combined and concentrated. The residue dissolved in benzene (250 ml) was treated with activated charcoal, filtered and evaporated, yielding 17.94 g (26.65 mmol, crude yield 100%; purity 94.1%) of the crude title compound as white foam; Rf 0.76 (benzene:Et₂O=3:2); ¹Hmr (CDCl₃) δ: 1.20 (6H, s, diMe), 3.17 (1H, m, H-3), 3.4–3.9 (3H, m, H-4′ and H-5′), 4.67, 4.72 (1H, 2d, J=2.5 Hz, H-4), 5.30 (2H, s, OCH₂Ar), 5.83 (s, H-2″) and 7.1–8.3 ppm (19 H, m, aromatic Hs); ir (neat) $\nu_{max}$: 1770 cm⁻¹ (β-lactam and ester). This material was used in the next step without purification.

(4′R,3S,4R and 4′S,3R,4S) 3-(2′,2′-Dimethyl-1′,3′-dioxolan-4′-yl)-1-(p-nitrobenzyl 2″-triphenylphosphoranylidene-2″-acetate)-4-tritylthio-2-azetidinone (Isomer C)

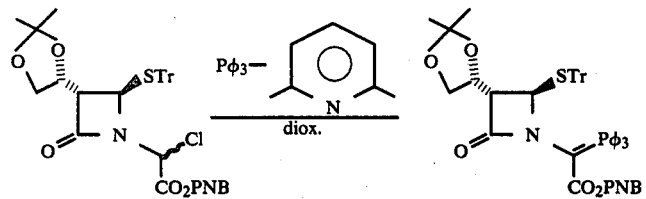

A mixture of (4′R,3S,4R and 4′S,3R,4S) 3-(2′,2′-dimethyl-1′,3′-dioxolan-4′-yl)-1-(p-nitrobenzyl 2″-chloro-2″-acetate)-4-tritylthio-2-azetidinone (Isomer C)

(17.87 g, 25.0 mmol; purity 94.1% mixture of epimers at C-2″), triphenylphosphine (7.27 g, 27.5 mmol) and 2,6-lutidine (3.19 ml, 27.5 mmol) in dioxane (350 ml; distilled from LAH) was heated at reflux under N₂ for 40 h. Evaporation of the solvent in vacuo gave 29.5 g of dark oil which was purified by column chromatography (SiO₂ 330 g; eluent 20–50% Et₂O in benzene), yielding 10.5 g of yellowish solid. This solid was rinsed with Et₂O to give 7.49 g (8.33 mmol), yield 33.3%) of the title compound as slightly yellow crystals, ¹Hmr(CDCl₃) δ: 1.07 (s, di-Me) and 7.1–8.2 ppm (m, aromatic Hs); ir (nujol) $\nu_{max}$: 1760 cm⁻¹ (C=O). An analytical sample was obtained by crystallization from CH₂Cl₂-Et₂O: mp 231°–2° C.; Anal. calcd for $C_{54}H_{47}N_2O_7PS$: C 72.14, H 5.27, N 3.12, S 3.57; found: C 72.18, H 5.43, N 2.98, S 3.41; Rf 0.17 (benzene:Et₂O=1:1).

(4′R,3S,4R and 4′S,3R,4S) Silver 3-(2′,2′-dimethyl-1′,3′-dioxolan-4′-yl)-1-(p-nitrobenzyl 2″-triphenylphosphoranylidene-2″-acetate)-2-azetidinone-4-thiolate (Isomer C)

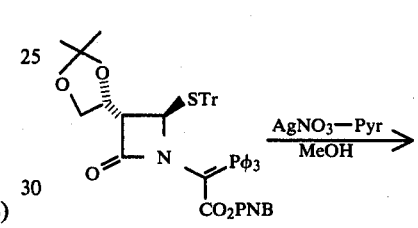

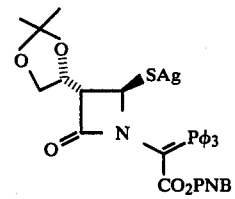

A solution of (4′R,3S,4R and 4′S,3R,4S) 3-(2′,2′-dimethyl-1′,3′-dioxolan-4′-yl)-1-(p-nitrobenzyl 2″-triphenylphosphoranylidene-2″-acetate)-4-tritylthio-2-azetidinone (Isomer C) (319 mg, 0.355 mmol) in CH₂Cl₂ (10 ml) was evaporated to yield an oily residue which was redissolved in hot methanol (8 ml; 60°). To this solution was added at 60° a hot solution of AgNO₃ in MeOH (0.15M, 4.0 ml, 0.60 mmol) and then pyridine (29 μl, 0.36 mmol). The mixture was stirred at room temperature for 5 h and at 0° C. for 1 h. The precipitate was collected and washed with ice-cold methanol and then cold Et₂O, yielding 255 mg (0.334 mmol, yield 94.1%) of the title compound as a brownish solid: ir (nujol) $\nu_{max}$: 1750 cm⁻¹ (s, C=O).

(4'R,3S,4R and 4'S,3R,4S) 3-(2',2'-Dimethyl-1',3'-dioxolan-4'-yl)-1-(p-nitrobenzyl 2''-triphenylphosphoranylidene-2''-acetate)-4-acetylthio-2-azetidinone (Isomer C)

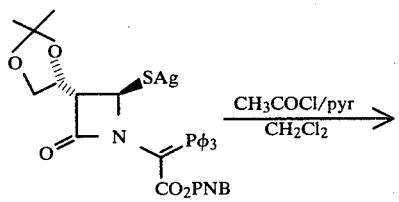

To a solution of (4'R,3S,4R and 4'S,3R,4S) silver 3-(2',2'-dimethyl-1',3'-dioxolan-4'-yl)-1-(p-nitrobenzyl 2''-triphenylphosphoranylidene-2''-acetate)-2-azetidinone-4-thiolate (Isomer C) (254 mg, 0.333 mmol) in CH$_2$Cl$_2$ (15 ml) containing pyridine (100 μl, 1.24 mmol; 3.72 eq) was added at 0°–5° C. acetyl chloride (71 μl, 1.0 mmol; 3.0 eq). The mixture was stirred at 0°–5° C. for 40 min. After filtration of the precipitate over Celite the filtrate was washed successively with brine containing 1N HCl (1.25 ml), sat. NaHCO$_3$ and then brine, dried (Na$_2$SO$_4$) and evaporated, yielding 200 mg of an oil which was crystallized from Et$_2$O to give 155 mg (0.222 mmol, yield 66.7%) of the title compound as white crystals: $^1$Hmr (CDCl$_3$) δ: 1.23 (s, di-Me), 2.20, 2.33 (2s, —SAc) and 7.2–8.3 ppm (m, aromatic Hs): ir (nujol) ν$_{max}$: 1750 (β-lactam and ester) and 1690 cm$^{-1}$ (thioester). An analytical sample was obtained by crystallizaton from CH$_2$Cl$_2$—Et$_2$O: mp 177°–8° C.; Anal. calcd for C$_{37}$H$_{35}$N$_2$O$_8$PS: C 63.60, H 5.05, N 4.01, S 4.59; found: C 63.34, H 5.32, N 3.83, S 4.31; Rf 0.62 (EtOAc).

(4'R,5R,6S and 4'S,4S,6R) p-Nitrobenzyl 6-(2',2'-Dimethyl-1',3'-dioxolan-4'-yl)-2-methylpenem-3-carboxylate (Isomer C)

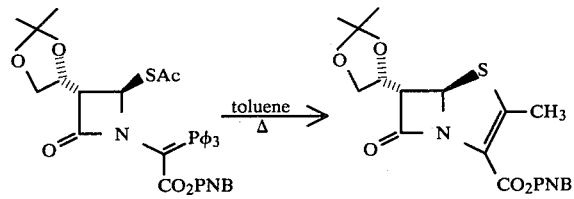

A suspension of (4'R,3S,4R and 4'S,3R,4S) 3-(2',2'-dimethyl-1',3'-dioxolan-4'-yl)-1-(p-nitrobenzyl 2''-triphenylphosphoranylidene-2''-acetate)-4-acetylthio-2-azetidinone (Isomer C) (443 mg, 0.634 mmol) in toluene (70 ml) was heated at reflux under N$_2$ for 6 h. Evaporation of the solvent gave white solid which was purified by column chromatography (SiO$_2$ 10 g; eluent 10% Et$_2$O in benzene) yielding 247 mg (0.587 mmol, yield 92.7%) of the title compound as white solid: $^1$Hmr (CDCl$_3$) δ: 1.42 (6H, s, di-Me), 2.38 (3H, s, 2-CH$_3$), 3.8–4.5 (4H, m, H-6, H-4' and H-5'), 5.02–5.25–5.33–5.57 (2H, AB type, —OCH$_2$Ar), 5.57 (1H, d, J=1.8 Hz, H-5) and 7.52–7.67–8.12–8.27 ppm (4H, A$_2$'B$_2$', aromatic Hs); ir (nujol) ν$_{max}$: 1760 (β-lactam) and 1700 cm$^{-1}$ (ester). An analytical sample was obtained by crystallization from CH$_2$Cl$_2$—Et$_2$O: mp 167°–8° C.; uv (EtOH) λ$_{max}$: 265 (ε 14,000) and 314 mμ (ε 10,000); Anal. calcd for C$_{19}$H$_{20}$N$_2$O$_7$PS: C 54.28, H 4.79, N 6.66, S 7.63; found: C 54.15, H 4.78, N 6.54, S 7.64; Rf 0.62 (benzene-Et$_2$O=1:1).

(4'R,5R,6S and 4'S,5S,6R) 6-(2',2'-Dimethyl-1',3'-dioxolan-4'-yl)-2-methylpenem-3-carboxylic acid (Isomer C)

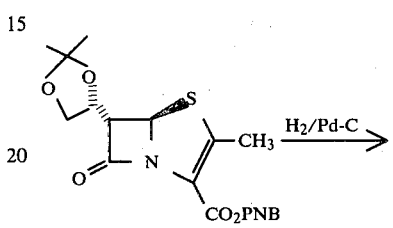

A solution of (4'R,5R,6S and 4'S,5S,6R) p-nitrobenzyl 6-(2',2'-dimethyl-1',3'-dioxolan-4'-yl)-2-methylpenem-3-carboxylate (Isomer C) (195 mg, 0.464 mmol) in THF (20 ml) was mixed with Et$_2$O (20 ml), H$_2$O (20 ml), NaHCO$_3$ (39 mg, 0.46 mmol) and 10% Pd—C (200 mg, Engelhard). This mixture was hydrogenated at 35 psi for 4 h at room temperature. After removal of the catalyst (over Celite), the aqueous layer was washed with EtOAc (×2), saturated with NaCl, acidified with 1N HCl (0.47 ml) and immediately extracted with EtOAc (20 ml×3). The extracts washed with brine were dried (Na$_2$SO$_4$) and evaporated yielding 94 mg of yellowish solid which was rinsed with pentane to give 89 mg (0.31 mmol, yield 67%) of the title compound as yellowish solid: mp 132°–3° C.; Rf 0.60 (Acetone:-HOAc=5:0.7; $^1$Hmr (CDCl$_3$) δ: 1.37, 1.43 (6H, 2s, di-Me), 2.36 (3H, s, 2-CH$_3$), 3.9–4.6 (4H, m, H-6, H-4' and H-5') and 5.59 ppm (1H, d, J=1.7 Hz, H-5); ir (nujol) ν$_{max}$: 1760 (β-lactam) and 1660 cm$^{-1}$ (CO$_2$H); uv (EtOH) λ$_{max}$: 309 (ε 6300) and 263 mμ (ε 3800).

EXAMPLE 104

(4'R,5R,6S and 4'R,5S,6R) 6-(2',2'-Dimethyl-1',3'-dioxolan-4'-yl)-2-methylpenem-3-carboxylic Acid (Isomer B)

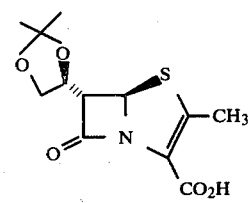

(4'S,3S,4R and 4'R,3R,4S) 3-(2',2'-Dimethyl-1',3'-dioxolan-4'-yl)-4-tritylthio-2-azetidinone (Isomer B)

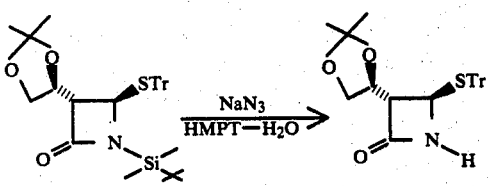

The title compound was prepared as described in Example 103 for the "Isomer C" from (4'S,3S,4R and 4'R,3R,4S) 1-(t-butyldimethylsilyl)-3-(2',2'-dimethyl-1',3'-dioxolan-3'-yl)-4-tritylthio-2-azetidinone (Isomer B) (14.4 g, 25.8 mmol): yield 10.8 g, 24.3 mmol, 94.1%; mp 155° C. (CH₂Cl₂—Et₂O); Rf 0.24 (hexanes:EtOAc=2:1); Hmr (CDCl₃): 1.37, 1.40 (6H, 2s, di-Me), 3.23 (1H, dd, J₃₋₄=2.5 Hz, J₃₋₄'=5 Hz, H-3), 3.7–4.5 (4H, m, H-4',H-5',N—H), 4.50 (1H, d, J=2.5 Hz, H-4) and 7.1–7.6 ppm (15H, m, aromatic Hs); ir (nujol) 3170 (NH) and 1745 cm⁻¹ (C=O); Anal. calcd for $C_{27}H_{27}NO_3S$: C 72.78, H 6.11, N 3.14, S 7.20; found: C 72.16, H 6.11, N 3.14, S 7.17.

(4'S,3S,4R and 4'R,3R,4S) 3-(2',2'-Dimethyl-1',3'-dioxolan-4'-yl)-1-(p-nitrobenzyl 2''-hydroxy-2''-acetate)-4-tritylthio-2-azetidinone (mixture of epimers at C-2'') (Isomer B)

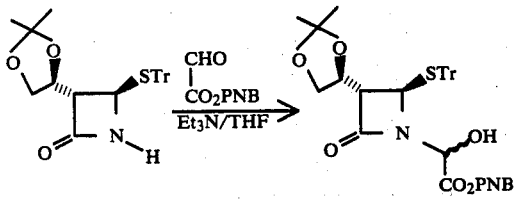

The title compound was prepared as described in Example 103 for the "Isomer C" from (4'S,3S,4R and 4'R,3R,4S) 3-(2',2'-dimethyl-1',3'-dioxolan-4'-yl)-4-tritylthio-2-azetidinone (Isomer B) (10.8 g, 24.3 mmol): yield 15.8 g, 24.1 mmol, 99.3%; yellowish foam; Rf 0.29 and 0.22 (benzene: Et₂O+1:1); ¹Hmr (CDCl₃) δ: 1.28, 1.34 (2s, di-Me), 3.4–4.4 (m, H-3, H-4',H-5', H-2'',OH), 4.39, 4.53 (2d, J=2 Hz, H-4), 5.15, 5.25 (2s, OCH₂Ar) and 7.1–8.3 ppm (m, aromatic Hs); ir (neat) $\nu_{max}$: 3440 (br, OH), 1760 (C=O), 1520, 1350 cm⁻¹ (NO₂).

(4'S,3S,4R and 4'R,3R,4S) 3-(2',2'-Dimethyl-1',3'-dioxolan-4'-yl)-1-(p-nitrobenzyl 2''-chloro-2''-acetate)-4-tritylthio-2-azetidinone (mixture of epimers at C-2'') (Isomer B)

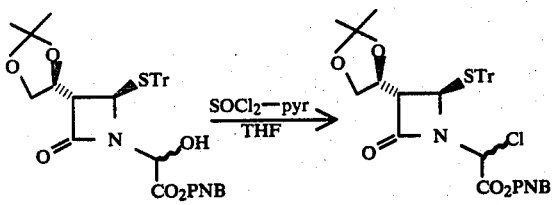

The title compound was prepared as described in Example 103 for the "Isomer C" from (4'S,3S,4R and 4'R,3R,4S) 3-(2',2'-dimethyl-1',3'-dioxolan-4'-yl)-1-(p-nitrobenzyl 2''-hydroxy-2''-acetate)-4-tritylthio-2-azetidinone (Isomer B) (14.9 g, 22.8 mmol; mixture of epimers at C-2''); yield 14.1 g, 20.9 mmol, 91.9%; yellowish foam; Rf 0.52 (benzene:Et₂O=3:2); ¹Hmr (CDCl₃) δ: 1.30, 1.38 (6H, 2s, di-Me), 3.4–4.5 (4H, m, H-3, H-4', H-5'), 4.57 (1H, d, J=3 Hz, H-4) 5.13 (s, H-2''), 5.27 (s, OCH₂Ar) and 7.1–8.3 ppm (19H, m, aromatic Hs); ir (neat) $\nu_{max}$: 1780 cm⁻¹ (β-lactam, ester).

(4'S,3S,4R and 4'R,3R,4S) 3-(2',2'-Dimethyl-1',3'-dioxolan-4'-yl)-1-(p-nitrobenzyl 2''-triphenylphosphoranilidene-2''-acetate)-4-tritylthio-2-azetidinone (Isomer B)

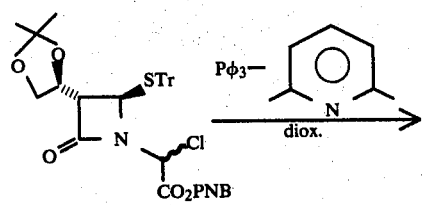

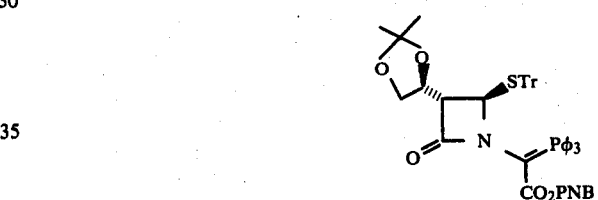

The title compound was prepared as described in Example 103 for the "Isomer C" from (4'S,3S,4R and 3'R,3R,4S) 3-(2',2'-dimethyl-1',3'-dioxolan-4'-yl)-1-(p-nitrobenzyl 2''-chloro-2''-acetate)-4-tritylthio-2-azetidinone (Isomer B) (14.0 g, 20.8 mmol; mixture of epimers at C-2''): yield 4.64 g, 5.16 mmol, 24.8%; mp 190°-95° C. (dec., CH₂Cl₂—Et₂O); ¹Hmr (CDCl₃) δ: 1.12, 1.20, 1.27, 1.35 (4s, di-Me) and 7.0–8.1 ppm (m, aromatic Hs); ir (CH₂Cl₂) $\nu_{max}$: 1750 cm⁻¹ (β-lactam ester); Anal. calcd for $C_{54}H_{47}N_2O_7PS$: C 72.14, H 5.27, N 3.12, S 3.57; found: C 71.90, H 5.57, N 3.07, S 3.56; Rf 0.21 (benzene:Et₂O=1:1).

(4'S,3S,4R and 4'R,3S,4R) Silver 3-(2',2'-dimethyl-1',3'-dioxolan-4'-yl)-1-(p-nitrobenzyl 2''-triphenylphosphoranylidene-2''-acetate)-2-azetidinone-4-triolate (Isomer B)

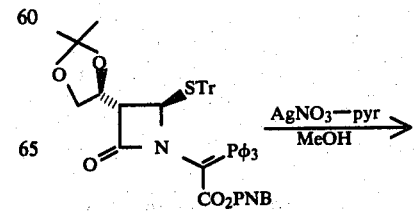

-continued

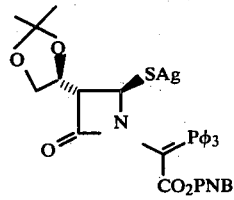

The title compound was prepared as described in Example 103 for the "Isomer C" from (4'S,3S,4R and 4'R,3S,4R) 3-(2',2'-dimethyl-1',3'-dioxolan-4'-yl)-1-(p-nitrobenzyl 2''-triphenylphosphoranylidene-2''-acetate)-4-tritylthio-2-azetidinone (Isomer B) (1.00 g, 1.12 mmol): yield 580 mg, 0.760 mmol, 68.8%; mp 129°–135° C. (dec); ir (nujol) $v_{max}$: 1745 cm$^{-1}$ (β-lactam, ester).

(4'S,3S,4R and 4'R,3R,4S)
3-(2',2'-Dimethyl-1',3'-dioxolan-4'-yl)-1-(p-nitrobenzyl 2''-triphenylphosphoranylidene-2''-acetate)-4-acetylthio-2-azetidinone (Isomer B)

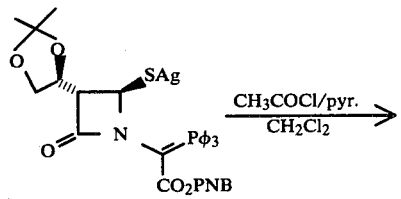

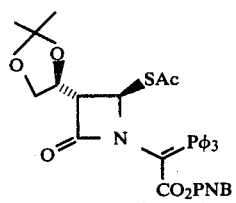

The title compound was prepared as described in Example 103 for the "Isomer C" from (4'S,3S,4R and 4'R,3R,4S) silver 3-(2',2'-dimethyl-1',3'-dioxolan-4'-yl)-1-(p-nitrobenzyl 2''-triphenylphosphoranylidene-2''-acetate)-2-azetidinone-4-thiolate (Isomer B) (2.46 g, 3.22 mmol): yield after purification by column chromatography (SiO$_2$ 32 g, eluent 10%–50% EtOAc in CH$_2$Cl$_2$=1:1); $^1$Hmr (CDCl$_3$) δ: 1.23, 1.27, 1.30 (3s, di-Me), 2.22, 2.33 (2s, SAc) and 7.3–8.3 ppm (m, aromatic Hs); ir (neat) $v_{max}$ 1755 (β-lactam, ester) and 1695 cm$^{-1}$ (thioester).

(4'S,5R,6S and 4'R,5S,6R) p-Nitrobenzyl 6-(2',2'-dimethyl-1',3'-dioxolan-4'-yl)-2-methylpenem-3-carboxylate (Isomer B)

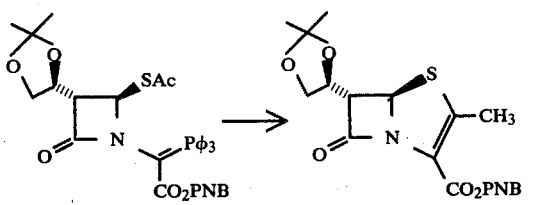

The title compound was prepared as described in Example 103 for the "Isomer C" from (4',S,3S,4R and 4'R,3R,4S) 3-(2',2'-dimethyl-1', 3'-dioxolan-4'-yl)-1-(p-nitrobenzyl 2''-triphenylphosphoranylidene-2''-acetate)-4-acetylthio-2-azetidinone (Isomer B) (200 mg, 0.286 mmol): yield 64 mg, 0.15 mmol, 53%; mp 151°–2° C. (CH$_2$Cl$_2$/Et$_2$O); Rf 0.67 (benzene: Et$_2$O=1:1); $^1$Hmr (CDCl$_3$) δ: 1.29, 1.38 (6H, 2s, di-Me), 2.30 (3H, s, 2-CH$_3$), 3.6–4.4 (4H, m, H-6, H-4', H-5'), 5.00–5.18–5.28–5.46 (4H, ABq, —OCH$_2$Ar), 5.47 (1H, d, J=1.5Hz, H-5) and 7.42–7.55–8.05–8.15 ppm (4H, A$_2$'B$_2$', aromatic Hs); ir (neat) $v_{max}$: 1785 cm$^{-1}$ (β-lactam) and 1710 cm$^{-1}$ (ester); uv (EtOH) $\lambda_{max}$: 266 (ε13,300) and 314 mμ (ε9,700); Anal. calcd C$_{19}$H$_{20}$N$_2$O$_7$S: C 54.28, H 4.79, N 6.66, S 7.63; found: C 54.00 H 4.75, N 6.68, S 7.61.

(4'S,5R,6S and 4'R,5S,6R)
6-(2',2'-Dimethyl-1',3'-dioxolan-4'-yl)-2-methylpenem-3-carboxylic acid (Isomer B)

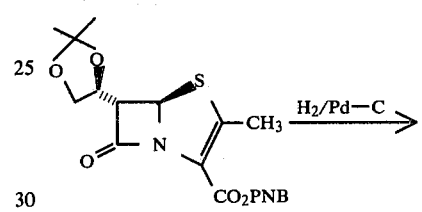

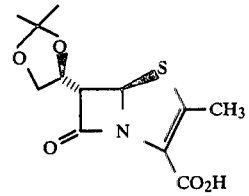

The title compound was prepared as described in Example 103 for the "Isomer C" from (4'S, 5R,6S and 4'R,5S,6R) p-nitrobenzyl 6-(2',2'-dimethyl-1',3'-dioxolan-4'-yl)-2-methylpenem-3-carboxylate (Isomer B) (79 mg, 0.19 mmol): yield after recrystallization from CH$_2$Cl$_2$-pentane 9 mg, 0.032 mmol, 17%; Rf 0.54 (Acetone: HOAc=5:0.5); $^1$Hmr (CDCl$_3$) δ: 1.35, 1.44 (6H, 2s, di-Me), 2.37 (3H, s, 2-CH$_3$), 3.6–4.5 (4H, m, H-6, H-4',H-5') and 5.56 ppm (1H, brs, H-5); ir (neat) $v_{max}$: 1785 cm$^{-1}$ (β-lactam); uv (EtOH) $\lambda_{max}$: 307 (ε4300) and 262 mμ(ε3700).

EXAMPLE 105

(1'R,5R,6S and 1'S,5S,6R)
6-(1'-Hydroxy-2'-methoxymethoxy-2'-ethyl)-2-ethyl)-2-methylpenem-3-carboxylic acid (Isomer C)

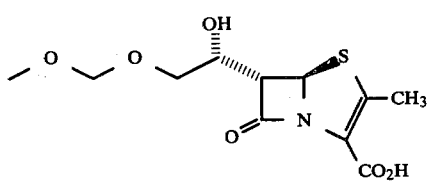

(1'R,3S,4R and 1'S,3R,4S) 3-(1',2'-dihydroxyethyl)-1-(p-nitrobenzyl 2''-triphenylphosphoranylidene-2''-acetate)-4-acetylthio-2-azetidinone (Isomer C)

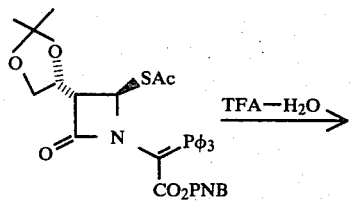

A solution of (4'R,3S,4R and 4'S,3R,4S) 3-(2',2'-dimethyl-1',3'-dioxolan-4'-yl)-1-(p-nitrobenzyl 2''-triphenylphosphoranylidene-2''-acetate)-4-acetylthio-2-azetidinone (Isomer C) (472 mg, 0.676 mmol) in trifluoroacetic acid (1.0 ml) and H₂O (0.1 ml) was left at room temperature for 30 min. The mixture was added dropwise to a cold solution of NaHCO₃ (2.5 g) in H₂O (50 ml) and extracted with CH₂Cl₂ (20 ml × 3). The extracts washed with sat. NaHCO₃ and then brine were dried (Na₂SO₄) and evaporated yielding 458 mg (0.695 mmol, crude yield 100%; purity 97.3%) of the crude title compound as yellowish foam; ¹Hmr (CDCl₃) δ: 2.20, 2.32 (2s, SAc) and 7.2–8.3 ppm (m, aromatic Hs); ir (neat) ν$_{max}$: 3420 (OH), 1745 (β-lactam, ester) and 1690 cm⁻¹ (thioester); Rf 0.16 (EtOAc).

(1'R,3S,4R and 1'S,3R,4S) 3-(1'-Hydroxy-2'-methoxymethoxy-1'-ethyl)-1-(p-nitrobenzyl 2''-triphenylphosphoranylidene-2''-acetate)-4-acetylthio-2-azetidinone (Isomer C)

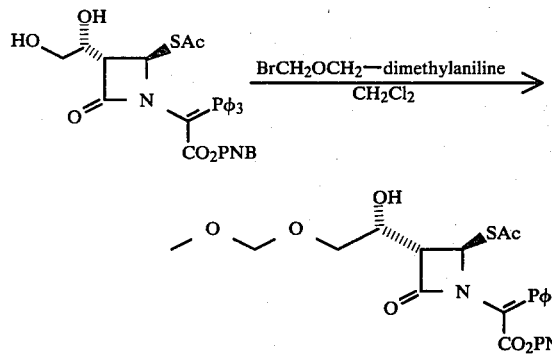

To a solution of (1'R,3S,4R and 1'S,3R,4S) 3-(1',2'-dihydroxyethyl)-1-(p-nitrobenzyl 2''-triphenylphosphoranylidene-2''-acetate)-4-acetylthio-2-azetidinone (Isomer C) (291 mg, 0.430 mmol; purity 97.3%) and bromomethylmethylether (55.2 mg, 0.442 mmol; 4 drops) in CH₂Cl₂ (8 ml) was added at 0° C., N,N'-dimethylaniline (58.8 mg, 0.483 mmol; 5 drops) and the mixture was stirred at room temperature for 20 h. Additional bromomethylmethylether (2 drops) and N,N'-dimethylaniline (2 drops) were added and it was stirred for another 4 h. The mixture diluted with CH₂Cl₂ was washed successively with 1N HCl, sat. NaHCO₃ and brine, dried (Na₂SO₄) and evaporated. The crude residue was purified by hplc (SiO₂, eluent EtOAc) collecting (31 mg, 0.186 mmol, yield 42.2%) of the title compound as an oil: Rf 0.24 (EtOAc); ¹Hmr (CDCl₃) ε: 2.20, 2.32 (2s, SAc), 3.30 (s, OCH₃) 4.52 (s, —OCH₂O—) and 7.4–8.3 ppm (m, aromatic Hs); ir (neat) ν$_{max}$: 3420 (OH), 1755 (br, β-lactam and ester) and 1690 cm⁻¹ (thioester).

(1'R,5R,6S and 1'S,5S,6R) p-Nibrobenzyl 6-(1'-hydroxy-2'-methoxymethoxy-2'-ethyl)-2-methyl-penem-3-carboxylate

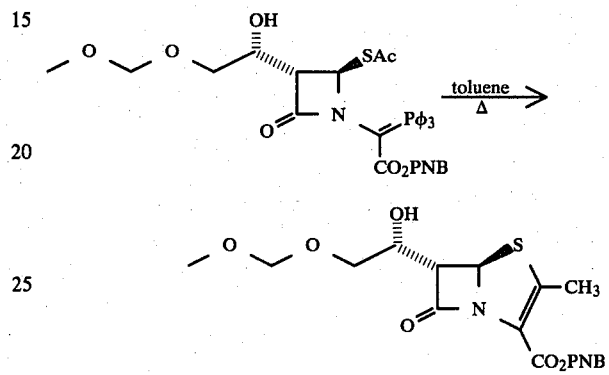

A solution of (1'R,3S,4R and 1'S,3R,4S) 3-(1'-hydroxy-2'-methoxymethoxy-1'-ethyl)-1-(p-nitrobenzyl 2''-triphenylphosphoranylidene-2''-acetate)-4-acetylthio-2-azetidinone (Isomer C) (167 mg, 0.238 mmol) in toluene (30 ml) was heated at reflux under N₂ for 8 h. Evaporation of the solvent in vacuo gave oily residue which was purified by hplc (SiO₂, eluent EtOAc) to give 68 mg (0.16 mmol, yield 67%) of the title compound as an oil: Rf 0.61 (EtOAc), 0.15 (benzene: Et₂O=1:1); ¹Hmr (CDCl₃) δ: 2.38 (3H, s, 2-CH₃), 3.35 (1H, br, OH), 3.40 (3H, s, OCH₃), 3.6–3.8 (2H, m, H-2'), 3.90 (1H, dd, J$_{6-5}$=2Hz, J$_{6-1}$=4Hz, H-6), 4.18 (1H, m, H-1'), 4.67 (2H, s, —OCH₂O—), 5.03–5.27–5.38–5.62 (2H, ABq, OCH₂Ar), 5.65 (1H, d, J=2Hz, H-5) and 7.55–7.70–8.15–8.30 ppm (4H, A₂'B₂', aromatic Hs); ir (neat) ν$_{max}$: 3450 (OH), 1785 (β-lactam), 1710 (ester) and 1520 cm⁻¹ (NO₂); uv (EtOH) λ$_{max}$: 266 (ε13000) and 313 mμ(ε9100); Anal. calcd for C₁₈H₂₀N₂O₈S: C 50.94, H 4.75, N 6.60; found: C 51.13, H 4.77, N 6.36.

(1'R,5R,6S and 1'S,5S,6R) 6-(1'-Hydroxy-2'-methoxymethoxy-2'-ethyl)-2-methyl-penem-3-carboxylic acid (Isomer C)

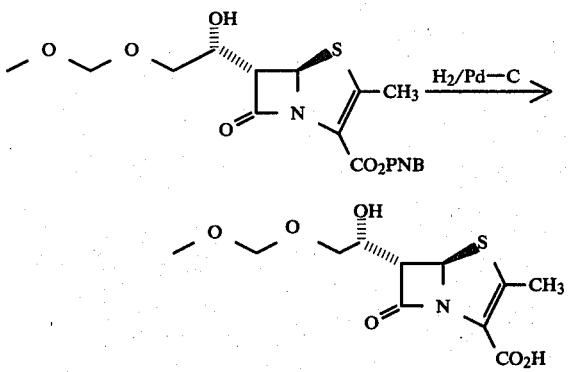

A solution of (1′R,5R,6S and 1′S,5S,6R) p-nitrobenzyl 6-(1′-hydroxy-2′-methoxymethoxy-2′-ethyl)-2-methylpenem-3-carboxylate (Isomer C) (51 mg, 0.12 mmol) in THF (10 ml) was mixed with Et$_2$O (10 ml), H$_2$O (10 ml), NaHCO$_3$ (10 mg, 0.12 mmol) and 10% Pd—C (50 mg; Engelhard). It was hydrogenated at room temperature at 32 psi for 3 h. After filtration of the catalyst over Celite, the aqueous layer separated was washed with Et$_2$O ($\times$3) and saturated with NaCl. The aqueous phase acidified at 0° C. with 0.1N HCl (1.2 ml) was immediately extracted with EtOAc (15ml $\times$3). The extracts were washed with brine, dried (Na$_2$SO$_4$) and evaporated yielding 22 mg of yellowish solid which was rinsed with a small amount of Et$_2$O to give 20 mg (0.069 mmol, yield 58%) of the title compound as slightly yellow solid: $^1$Hmr (DMSO-d$_6$) δ: 2.28 (3H, s, 2-CH$_3$), 3.27 (3H, s, OCH$_3$), 3.49(2H, d, J=6.2Hz, 2′-H), 3.87 (1H, dd, J$_{6-5}$=1.7Hz, J$_{6-1}$=3.3Hz, 6H), 4.58 (2H, s, —OCH$_2$O—) and 5.55 ppm (1H, d, J=1.7 Hz, 5-H); ir (KBr) ν$_{max}$: 3410 (OH), 1755 (⊕-lactam) and 1655 cm$^{-1}$ (CO$_2$H); uv (EtOH) λ$_{max}$: 308 (ε 6800) and 262 mμ(ε 4200), mp 137°-8° C. (dec.).

EXAMPLE 106

(1′S,5R,6S and 1′R,5S,6R) 6-(1′-Hydroxy-2′-methoxymethoxy-2′-ethyl)-2-methylpenem-3-carboxylic acid (Isomer B)

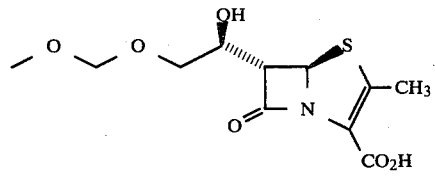

(1′S,3S,4R and 1′R,3R,4S) 3-(1′,2′-dihydroxyethyl)-1-(p-nitrobenzyl 2″-triphenylphosphoranylidene-2″-acetate)-4-acetylthio-2-azetidinone (Isomer B)

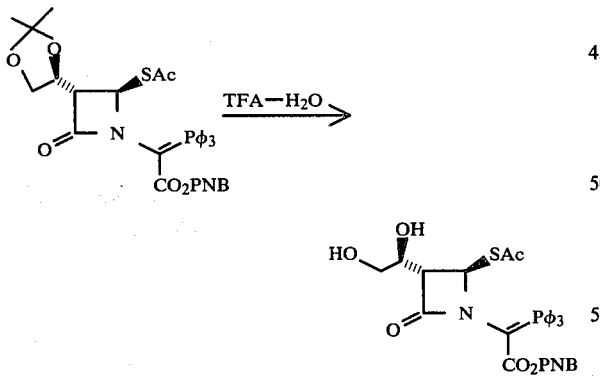

The title compound was prepared as described in Example 105 for the "Isomer C" from (4′S,3S,4R and 4′R,3R,4S) 3-(2′,2′-dimethyl-1′,3′-dioxolan-4′-yl)-1-(p-nitrobenzyl 2″-triphenylphosphoranylidene-2″-acetate)-4-acetylthio-2-azetidinone (Isomer B) (1.03 g, 1.47 mmol): yield 970 mg, 1.47 mmol, 100%; yellowish foam: $^1$Hmr (CDCl$_3$) δ: 2.20, 2.32 (2s, —SAc) and 7.3–8.2 ppm (m, aromatic Hs); ir (neat) ν$_{max}$: 3410 (OH), 1750 (β-lactam, ester) and 1690 cm$^{-1}$ (thioester): Rf 0.16 (EtOAc).

(1′S,3S,4R and 1′R,3R,4S) 3-(1′-Hydroxy-2′-methoxymethoxy-1′-ethyl)-1-(p-nitrobenzyl 2″-triphenylphosphoranylidene-2″-acetate)-4-acetylthio-2-azetidinone (Isomer B)

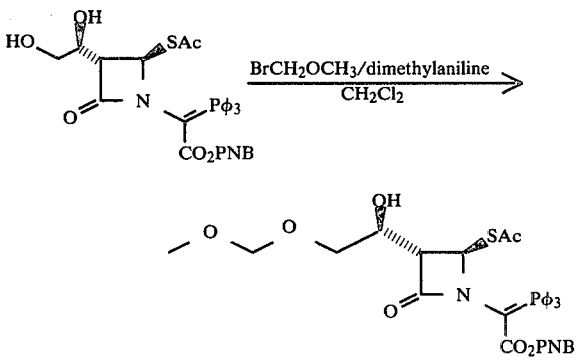

The title compound was prepared as described in Example 105 for the "Isomer C" from (1′s,3S,4R and 1′R,3R,4S) 3-(1′2′-dihydroxyethyl)-1-(p-nitrobenzyl 2″-triphenylphosphoranylidene-2″-acetate)-4-acetylthio-2-azetidinone (Isomer B) (485 mg, 0.736 mmol): yield 205 mg, 0.292 mmol, 39.6%; oil; $^1$Hmr (CDCl$_3$) δ: 2.22, 2.33 (2s, Sac), 3.32 (s, OCH$_3$), 4.57 (s,—OCH$_2$O—) and 7.2–8.3 ppm (m, aromatic Hs); ir (neat) ν$_{max}$: 3420 (OH), 1755 (β-lactam, ester) and 1690 (thioester); Rf 0.32 (EtOAc).

(1′S,5R,6S and 1′R,5S,6R) p-Nitrobenzyl 6-(1′-hydroxy-1′-methoxymethoxy-2′-ethyl)-2-methylpenem-3-carboxylate

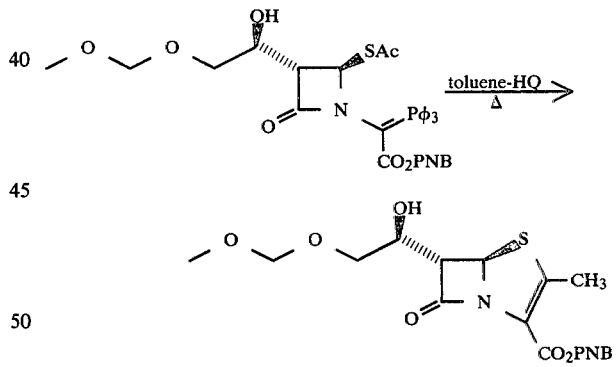

The title compound was prepared as described in Example 105 for the "Isomer C" from (1′S,3S,4R and 1′R,3R,4S) 3-(1′-hydroxy-2-methoxymethoxy-1′-ethyl)-1-(p-nitrobenzyl 2″-triphenylphosphoranylidene-2″-acetate)-4-acetylthio-2-azetidinone (Isomer B) (205 mg, 0.292 mmol) and hydroquinone (10 mg, 0.09 mmol): yield 38 mg, 0.090 mmol, 31%; 152°-4° C.; Rf 0.23 (benzene: Et$_2$O=1:1); $^1$Hmr (CDCl$_3$) δ: 2.37 (3H, s, 2-CH$_3$), 3.40 (3H, s, OCH$_3$), 3.4–3.9 (3H, m, H-6, H-2″), 4.15 (1H, m, H-1′), 4.67 (2H, s, —OCH$_2$O—), 5.10–5.27–5.39–5.56 (2H, ABq, —OCH$_2$Ar), 5.67 (1H, d, J=1.5 Hz, H-5) and 5.55–5.16–8.15–8.27 ppm (4H, A$_2'$B$_2'$, aromatic H$_3$); ir (CH$_2$Cl$_2$ mull) ν$_{max}$: 3370 (OH), 1785 (β-lactam) and 1700 cm$^{-1}$ (ester); uv (THF-EtOH=1:1) λ$_{max}$: 265 (ε 10400) and 314 mμ (ε 7800).

(1'S,5R,6S and 1'R,5S,6R)
6-(1'-Hydroxy-2'-methoxymethoxy-2'-ethyl)-2-methyl-penem-3-carboxylic acid (Isomer B)

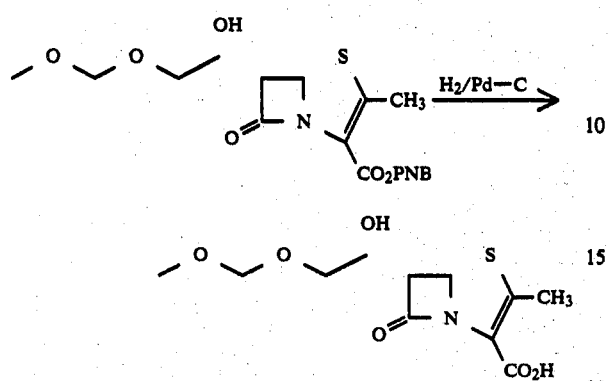

The title compound was prepared as described in Example 105 for the "Isomer C" from (1'S,5R,6S and 1'R,5S,6R) p-nitrobenzyl 6-(1'-hydroxy-2'-methoxyme-thoxy-2'-ethyl)-2-methylpenem-3-carboxylate (Isomer B) (36 mg, 0.085 mmol): yield 7.5 mg, 0.026 mmol, 30%; yellowish crystals; $^1$Hmr (CDCl$_3$) δ: 2.36 (3H, s, 2-CH$_3$), 3.39 (3H, s, OCH$_3$), 3.6-3.9 (3H, m, H-6, H-2'), 4.15 (1H, m, H-1'), 4.66 (2H, s, OCH$_2$O) and 5.67 ppm (1H, d, J=1.4 Hz, H-5); ir (CH$_2$Cl$_2$) $\nu_{max}$: 1785 (β-lactam) and 1675 cm$^{-1}$ (CO$_2$H); uv (EtOH) $\lambda_{max}$: 308 (ε 2900) and 263 mμ (ε 2900).

EXAMPLE 107

2-Benzimidoylaminomethylpenem-3-carboxylic Acid

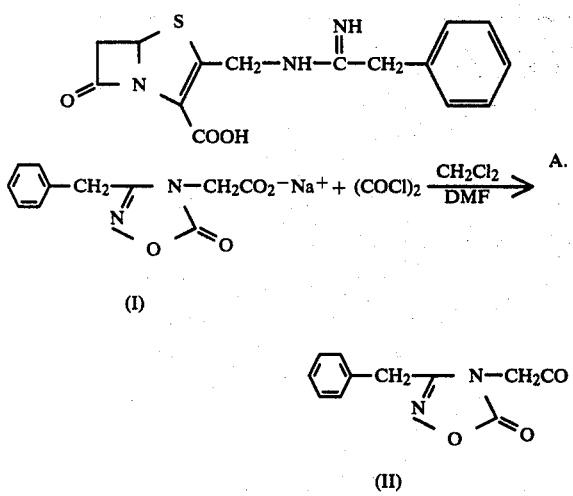

To a suspension of 0.38 g (0.0015 mole) of sodium 3-benzyl-1,2,4-oxadiazol-5-1 -one-4-acetate (I)[1] in 10 ml of methyl chloride, containing 2 drops of DMF, was added at room temperature 0.13 ml (0.0015 mole) of oxalyl chloride, causing the mixture to effervesce. The reaction mixture was stirred at room temperature for 1 hour. The NaCl that had formed was removed by filtration and the filter cake was washed with several small portions of methylene chloride. The solution of acid chloride (II), was used directly.

[1] K. Takács and K. Harsányi, Ber. 103, 2330 (1970).

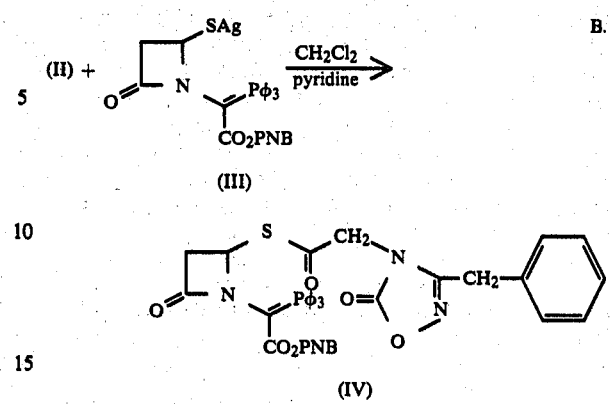

A solution of 1.0 g (0.0015 mole) of (III) and 0.12 ml (0.015 mole) of pyridine in 10 ml of methylene chloride under a nitrogen atmosphere was cooled to 4°. The acid chloride (II) solution was added all at once to the solution of (III) and the reaction mixture was stirred at 4° for 5 minutes, then at room temperature for 1.5 hrs. A thick precipitate formed in the reaction mixture. The mixture was filtered and the filtrate diluted with methylene chloride to a volume to 70-90 ml. The organic phase was then washed successively with 70 ml of 0.1N hydrochloric acid, 80 ml of 1% sodium bicarbonate and 80 ml of water. The methylene chloride phase was dried over magnesium sulfate. The solvent was removed at reduced pressure and the residual oil chromatographed on Mallinckrodt SilicAR CC-7 silica gel using chloroform as the eluant, giving 0.4 g (30.5%) of (IV) as an oil. The infrared and nuclear magnetic resonance spectra were consistent for (IV).

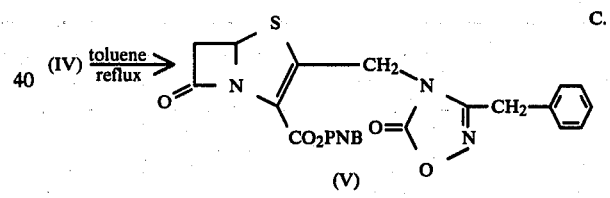

A solution of 0.4 g (0.00045 mole) of IV in 50 ml of toluene was heated at reflux for 4 hrs. The solvent was removed at reduced pressure and the residue chromatographed on Mallinckrodt SilicAR CC-7 silica gel, using 5% ethyl acetate in methylene chloride as eluant, affording 0.15 g (66.6%) of V as an oil which solidified. The infrared and nuclear magnetic resonance spectra were consistent for V. Anal. Calcd for C$_{23}$H$_{18}$N$_4$O$_7$S: C, 55.86; H, 3.67; N, 11.33. Found: C, 56.17; H, 3.76; N, 11.23.

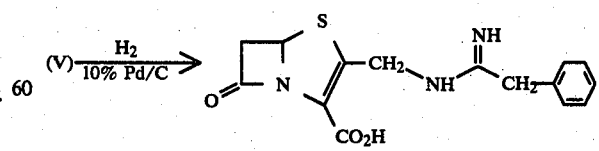

A solution of 0.135 g (0.00027 mole) of V in 40 ml of tetrahydrofuran and 40 ml of anhydrous diethyl ether was added to a slurry of 10% palladium on carbon catalyst in 40 ml of water under a nitrogen atmosphere. The resultant mixture was hydrogenated in a Parr hydrogenation apparatus at room temperature at an initial hydrogen pressure of 52 psi for 3.5 hrs. Hydrogen uptake was 4.5 psi. The catalyst was removed by filtration, washing the filter pad well with water. Additional diethyl ether was added to the filtrate and the phases were separated. The aqueous phase was extracted 3× with diethyl ether. The aqueous phase was then concentrated to dryness at reduced pressure. The residue was chromatographed, using the high pressure liquid chromatography technique, to afford 0.050 g (58%) of the title penem acid; decomp 156°–173°. The infrared and nuclear magnetic resonance spectra were consistent for the desired product. Anal. Calcd for $C_{15}H_{15}N_3O_3S.1.5-H_2O$: C, 52.31; H, 5.27; N, 12.20. Found: C, 51.64; H, 4.95; N, 12.31.

EXAMPLE 108

2-Phenylimidoylaminomethylpenem-3-carboxylic Acid

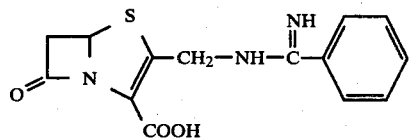

Following the procedure of Example 107 but using an equimolar amount of sodium 3-phenyl-1,2,4-oxadiazol-5-one-4-acetate as the starting material in place of the sodium 3-benzyl-1,2,4-oxadiazol-5-one-4-acetate used therein, there was produced the title product.

BIOLOGICAL DATA

Representative compounds of the present invention were subjected to in vitro antibiotic screening against a variety of microorganisms. Samples of the indicated compounds after solution in water and dilution was Nutrient Broth were found to exhibit the following Minimum Inhibitory Concentration (MIC) in mcg./ml. versus the indicated microorganisms as determined by overnight incubation at 37° C. by the tube dilution method.

| | | M.I.C. in mcg/ml | | |
|---|---|---|---|---|
| | | Compound (Preparation No.) | | |
| Organism | | 2,3 | 4 (+) | 4 (−) |
| Str. pneumoniae | A-9585 | 0.03 | 0.06 | 8 |
| Str. pyogenes | A-9604 | 0.13 | 0.25 | 8 |
| Staph. aureus | A-9537 | 0.13 | 0.5 | 32 |
| Staph. aureus and 50% serum | A-9537 | 8 | 4 | >63 |
| Staph. aureus (Pen-Res) | A-9606 | 1 | 0.5 | >125 |
| Staph. aureus (Meth-Res) | A-15097 | 1 | 1 | >125 |
| Str. faecalis | A-20688 | 32 | 32 | 125 |
| E. coli | A-15119 | 8 | 4 | >125 |
| E. coli | A-20341-1 | 16 | 16 | >125 |
| K. pneumoniae | A-15130 | 16 | 8 | >125 |
| K. pneumoniae | A-20468 | >125 | >125 | >125 |
| Pr. mirabilis | A-9900 | 8 | 4 | >125 |
| *Pr. vulgaris | A-9716 | 8 | 4 | >125 |
| Pr. morganii | A-15153 | 16 | 8 | >125 |
| Pr. rettgeri | A-21205 | 4 | 4 | >125 |
| Ser. marcescens | A-20019 | 8 | 4 | >125 |
| Ent. cloacae | A-9659 | 16 | 8 | >125 |
| Ent. cloacae | A-9656 | 16 | 8 | >125 |
| Ps. aeruginosa | A-9843A | 125 | 32 | >125 |
| Ps. aeruginosa | A-21213 | >125 | 63 | >125 |

*name of this strain changed to *Proteus mirabilis* A-9716

| | M.I.C. in mcg/ml | | | | | | | |
|---|---|---|---|---|---|---|---|---|
| | Compound (Preparation No.) | | | | | | | |
| Organism | 5 | 6 | 7 | 8 | 9 | 10 | 11 | 12 |
| Streptococcus pneumoniae A9585 | >8 16 | .06 | .25 1 | .016 | .03 .016 | .03 | .13 | .5 |
| Streptococcus pyogenes A9604 | >8 32 | .25 | .5 8 | .03 | .25 .13 | .5 | 4 | .5 |
| Staphylococcus aureus A9537 | 125 >125 | .5 | 2 2 | <.008 | .5 .5 | .13 | 16 | 1 |
| Staph aureus +50% Serum A9537 | >63 >63 | 32 | >63 >63 | >63 | 63 63 | 16 | >63 | >63 |
| Staphylococcus aureus A9606 | >125 >125 | 2 | 8 16 | 4 | 8 4 | .5 | 32 | .5 |
| Staphylococcus aureus A15097 | >125 >125 | >125 | 63 63 | >125 | 16 8 | .5 | 63 | 1 |
| Streptococcus faecalis A20688 | >125 >125 | 32 | 16 16 | 32 | 63 32 | 32 | 125 | 63 |
| Escherichia coli A15119 | >125 >125 | 2 | 4 8 | 1 | 1 .5 | 4 | 16 | 63 |
| Escherichia coli A20341-1 | >125 >125 | 125 | >125 >125 | >125 | >125 63 | 125 | 63 | >125 |
| Klebsiella pneumoniae A15130 | >125 >125 | 8 | 63 125 | 32 | 16 16 | 8 | 63 | >125 |
| Klebsiella species A20468 | >125 >125 | >125 | >125 >125 | >125 | >125 >125 | >125 | >125 | >125 |
| Proteus mirabilis A9900 | >125 >125 | 2 | 4 4 | .5 | 1 .5 | 4 | 4 | 16 |
| Proteus vulgaris A9716 | >125 >125 | 2 | 4 4 | 1 | 2 .5 | 4 | 4 | 16 |
| Proteus morganii A15153 | >125 >125 | 4 | 32 63 | 1 | 4 4 | 8 | 63 | 16 |
| Providencia stuartii A21205 | >125 >125 | 2 | 16 16 | 1 | 2 2 | 4 | 1 | 63 |
| Serratia marcescens A20019 | >125 >125 | 4 | 32 63 | 32 | 4 4 | 4 | 4 | >125 |
| Enterobacter cloacae A9659 | >125 >125 | 4 | 32 63 | 16 | 4 4 | 16 | 63 | >125 |

-continued

| M.I.C. in mcg/ml | | | | | | | | |
|---|---|---|---|---|---|---|---|---|
| Enterobacter cloacae A9656 | >125 >125 | 8 | 125 125 | 16 | 16 8 | 16 | 63 | >125 |
| Pseudomonas aeruginosa A9843A | >125 >125 | >125 | >125 >125 | >125 | >125 >125 | >125 | >125 | >125 |
| Pseudomonas aeruginosa A21213 | >125 >125 | >125 | >125 >125 | >125 | >125 >125 | 125 | >125 | >125 |
| Hemophilus influenzae A9833 | — — | — | — — | — | — | — | — | — |
| Haemophilus influenzae A21522 | — — | — | — — | — | — | — | — | — |
| Bacteroides fragilis A20931 | — — | — | — — | — | — | — | — | — |
| Bacteroides fragilis A20929 | — — | — | — — | — | — | — | — | — |

| Organism | Compound (Preparation No.) | | | | | | |
|---|---|---|---|---|---|---|---|
|  | 13 | 14 (Na+ Salt) | 15 | 16 | 17 | 18 | 19 |
| Streptococcus pneumoniae A9585 | 1 | .03 .03 | 1 1 | <.016 .06 | >2 | .06 .06 | .03 |
| Streptococcus pyogenes A9604 | 1 | .06 .06 | 8 8 | <.016 .25 | >2 | .25 .25 | .06 |
| Staphylococcus aureus A9537 | 1 | .5 .25 | 1 .5 | <.016 .13 | >2 | .5 .5 | .03 |
| Staph aureus +50% Serum A9537 | >32 | 32 63 | >63 >63 | >63 >63 | >32 | >63 >63 | 32 |
| Staphylococcus aureus A9606 | 8 | 32 32 | 16 16 | 4 4 | >63 | 1 1 | .5 |
| Staphylococcus aureus A15097 | 16 | >125 >125 | 125 125 | 125 125 | >63 | 16 16 | 125 |
| Streptococcus faecalis A20688 | 32 | 32 32 | 63 63 | 32 32 | >63 | 63 63 | 125 |
| Escherichia coli A15119 | 8 | 16 8 | 16 16 | 63 63 | >63 | 2 2 | 8 |
| Escherichia coli A20341-1 | >63 | >125 >125 | >125 >125 | >125 >125 | >63 | >125 >125 | >125 |
| Klebsiella pneumoniae A15130 | 32 | 125 >125 | >125 >125 | >125 >125 | >63 | 32 32 | 32 |
| Klebsiella species A20468 | >63 | >125 >125 | >125 >125 | >125 >125 | >63 | >125 >125 | >125 |
| Proteus mirabilis A9900 | 4 | 2 1 | 16 16 | 4 8 | >63 | 2 2 | 1 |
| Proteus vulgaris A9716 | 4 | 4 2 | 16 16 | 4 8 | >63 | 2 2 | 2 |
| Proteus morganii A15153 | 32 | 16 16 | 63 63 | 16 16 | >63 | 8 8 | 2 |
| Providencia stuartii A21205 | 4 | 63 63 | 16 32 | 16 16 | >63 | — | — |
| Serratia marcescens A20019 | 16 | 63 125 | 125 63 | 125 125 | >63 | 32 32 | 63 |
| Enterobacter cloacae A9659 | 63 | 32 63 | >125 125 | >125 >125 | >63 | 16 16 | 63 |
| Enterobacter cloacae A9656 | 63 | 125 125 | 125 63 | 125 125 | >63 | 32 32 | 63 |
| Pseudomonas aeruginosa A9843A | >63 | >125 >125 | >125 >125 | >125 >125 | >63 | >125 >125 | >125 |
| Pseudomonas aeruginosa A21213 | >63 | >125 >125 | >125 >125 | >125 >125 | >63 | >125 >125 | >125 |
| Hemophilus influenzae A9833 | — | — | — | — | — | — | — |
| Haemophilus influenzae A21522 | — | — | — | — | — | — | — |
| Bacteroides fragilis A20931 | — | — | — | — | — | — | — |
| Bacteroides fragilis A20929 | — | — | — | — | — | — | — |
| Pseudomonas aeruginosa A20599 | | | | | | — | — |
| Pseudomonas aeruginosa A9925 | | | | | | — | — |
| Pseudomonas aeruginosa A20229 | | | | | | — | — |
| Proteus species A20543 | | | | | | — | — |
| Proteus rettgeri A21203 | | | | | | | 4 4 | 2 |

| Organism | Compound (Preparation No.) | | | | | | | |
|---|---|---|---|---|---|---|---|---|
|  | 20 | 21 | 22 | 23 | 24 | 25 | 26 | 27 |
| Streptococcus pneumoniae | .25 | 2 | .13 | .25 | .25 | 125 | 2 | .13 |

M.I.C. in mcg/ml

| Organism | | | | | | | | |
|---|---|---|---|---|---|---|---|---|
| Streptococcus pyogenes A9585 | 1 | 8 | .25 | .25 | 1 | >125 | 4 | .25 |
| Staphylococcus aureus A9604 | 2 | .06 | .5 | .25 | .13 | 1 | 4 | .5 |
| Staph aureus +50% Serum A9537 | 16 | >63 | 32 | >63 | >63 | 8 | >63 | >63 |
| Staphylococcus aureus A9537 | 4 | 1 | 32 | 32 | 4 | 32 | 125 | 8 |
| Staphylococcus aureus A9606 | 8 | 32 | >125 | 125 | 125 | 4 | >125 | 8 |
| Streptococcus faecalis A15097 | >125 | 32 | 125 | >125 | 63 | 125 | >125 | 4 |
| Escherichia coli A20688 | 16 | 4 | 2 | 16 | 16 | 8 | 32 | 8 |
| Escherichia coli A15119 | 63 | 125 | 125 | >125 | >125 | 2 | >125 | 125 |
| Klebsiella pneumoniae A20341-1 | 63 | 125 | 32 | 125 | 63 | 125 | >125 | 125 |
| Klebsiella species A15130 | >125 | 125 | 125 | >125 | >125 | 4 | >125 | >125 |
| Proteus mirabilis A20468 | 16 | 1 | 16 | 2 | 2 | 8 | 32 | 4 |
| Proteus mirabilis A9900 | — | 2 | 4 | 4 | 2 | 63 | 32 | 4 |
| Proteus morganii A9716 | 32 | 4 | 8 | 63 | 16 | 63 | 63 | 32 |
| Proteus rettgeri A15153 | 32 | 4 | 16 | 32 | 8 | 32 | 32 | 16 |
| Serratia marcescens A21203 | 32 | 63 | 63 | 125 | 32 | 63 | 63 | 63 |
| Enterobacter cloacae A20019 | 63 | 63 | 63 | 125 | 63 | 16 | 63 | 125 |
| Enterobacter cloacae A9659 | 32 | 32 | 63 | >125 | 63 | 16 | 63 | 63 |
| Pseudomonas aeruginosa A9656 | 125 | 125 | 125 | >125 | 125 | 125 | 125 | 125 |
| Pseudomonas aeruginosa A9843A | >125 | 125 | 125 | >125 | 125 | >125 | 125 | 125 |
| Hemophilus influenzae A21213 | — | — | — | — | — | — | — | — |
| Haemophilus influenzae A9833 | — | — | — | — | — | — | — | — |
| Bacteroides fragilis A21522 | — | — | — | — | — | — | — | — |
| Bacteroides fragilis A20931 | — | — | — | — | — | — | — | — |
| A20929 | | | | | | | | |

| Organism | Compound (Example No.) | | | | | | | |
|---|---|---|---|---|---|---|---|---|
| | 1 (cis) | 1 (trans) | 2 | 3 | 4 | 5 | 11 | 13 |
| Streptococcus pneumoniae A9585 | 4 | 2 | 1 | 1 | 1 | .5 | .5 | .25 2 |
| Streptococcus pyogenes A9604 | 4 | 4 | 2 | 4 | 4 | 4 | .5 | 1 8 |
| Staphylococcus aureus A9537 | 8 | 8 | 8 | 2 | 8 | 4 | 1 | .13 .13 |
| Staph aureus +50% Serum A9537 | >63 | >63 | >63 | >63 | >63 | >63 | 63 | >63 >63 |
| Staphylococcus aureus A9606 | 16 | 8 | 4 | 4 | 4 | 9 | .5 | 1 2 |
| Staphylococcus aureus A15097 | 63 | 8 | 8 | 32 | 125 | 63 | 1 | 63 63 |
| Streptococcus faecalis A20688 | 63 | >125 | 63 | 125 | 125 | 125 | 63 | 32 63 |
| Escherichia coli A15119 | 125 | 125 | 32 | 63 | >125 | 63 | 63 | 4 4 |
| Escherichia coli A20341-1 | 125 | 125 | 32 | 63 | >125 | 125 | >125 | 125 125 |
| Klebsiella pneumoniae A15130 | >125 | >125 | 63 | 125 | >125 | 63 | >125 | 63 63 |
| Klebsiella species A20468 | >125 | >125 | >125 | >125 | >125 | >125 | >125 | 125 125 |
| Proteus mirabilis A9900 | 125 | 125 | 63 | 63 | 63 | 63 | 16 | 2 2 |
| Proteus vulgaris A9716 | 63 | — | 63 | 32 | 63 | 32 | 16 | 2 2 |
| Proteus morganii A15153 | >125 | >125 | 63 | 125 | 125 | 125 | 16 | 4 4 |
| Providencia stuartii A21205 | 63 | 63 | 32 | 63 | 125 | 32 | 63 | 4 4 |
| Serratia marcescens | >125 | >125 | 125 | 63 | >125 | 63 | >125 | 32 |

-continued

| | M.I.C. in mcg/ml | | | | | | | |
|---|---|---|---|---|---|---|---|---|
| A20019 | | | | | | | | 63 |
| Enterobacter cloacae A9659 | >125 | >125 | 125 | 125 | >125 | 125 | >125 | 63 |
| Enterobacter cloacae A9656 | >125 | >125 | >125 | 125 | >125 | 125 | >125 — | |
| Pseudomonas aeruginosa A9843A | >125 | >125 | >125 | >125 | — | >125 | >125 | — |
| Pseudomonas aeruginosa A21213 | >125 | >125 | >125 | >125 | — | >125 | >125 | — |
| Hemophilus influenzae A9833 | — | — | — | — | — | — | — | — |
| Haemophilus influenzae A21522 | — | — | — | — | — | — | — | — |
| Bacteroides fragilis A20931 | — | — | — | — | — | — | — | — |
| Bacteroides fragilis A20929 | — | — | — | — | — | — | — | — |

| | Compound (Example No.) | | | | | | | | | |
|---|---|---|---|---|---|---|---|---|---|---|
| Organism | 14 | 15 | 16 | 17 | 16 (5) | 16 (6) | 18 | 19 | 20 | 21 |
| Streptococcus pneumoniae A9585 | .06 | .13 | 1 | >8 | 1 | 2 | 125 | .5 | 8 | .13 |
| Streptococcus pyogenes A9604 | .25 | .5 | 4 | >8 | 2 | 4 | >125 | 2 | 63 | 1 |
| Staphylococcus aureus A9537 | .13 | 1 | 2 | >8 | 4 | 4 | 125 | 4 | >125 | .13 |
| Staph aureus +50% Serum A9537 | 16 | >63 | 32 | >63 | 32 | 63 | >63 | 63 | >63 | >63 |
| Staphylococcus aureus A9606 | — | 32 | 8 | >125 | 32 | 125 | >125 | 8 | >125 | 8 |
| Staphylococcus aureus A15097 | 2 | 125 | 63 | >125 | 63 | 63 | >125 | 63 | >125 | >125 |
| Streptococcus faecalis A20688 | 63 | 63 | >125 | >125 | >63 | 125 | >125 | 125 | >125 | 16 |
| Escherichia coli A15119 | 4 | 16 | 4 | 125 | 16 | 16 | >125 | 8 | >125 | 4 |
| Escherichia coli A20341-1 | 63 | >125 | 16 | >125 | >63 | 125 | >125 | 16 | >125 | 125 |
| Klebsiella pneumoniae A15130 | 16 | 125 | 8 | >125 | 63 | 125 | >125 | 16 | >125 | 16 |
| Klebsiella species A20468 | >125 | >125 | 125 | >125 | >63 | >125 | 125 | >125 | >125 | >125 |
| Proteus mirabilis A9900 | 4 | 16 | 2 | >125 | 8 | 16 | >125 | 16 | >125 | 2 |
| Proteus vulgaris A21559 | | | | | 63 | 32 | | | | |
| Proteus vulgaris A9716 | — | — | — | — | | | — | | — | — |
| Proteus morganii A15153 | 16 | 63 | 1 | >125 | 16 | 32 | 125 | 16 | 125 | 16 |
| Proteus rettgeri A21203 | 4 | 16 | 1 | 125 | 32 | 32 | 125 | 16 | 125 | 4 |
| Serratia marcescens A20019 | 8 | 63 | 8 | >125 | 32 | 63 | >125 | 16 | >125 | 16 |
| Enterobacter cloacae A9659 | 16 | 125 | 8 | >125 | 63 | 63 | >125 | 16 | >125 | 16 |
| Enterobacter cloacae A9656 | 16 | 63 | 8 | >125 | 63 | 63 | >125 | 16 | >125 | 32 |
| Pseudomonas aeruginosa A9843A | 125 | 125 | 1 | 125 | 16 | 32 | 125 | 63 | 125 | 125 |
| Pseudomonas aeruginosa A21213 | 125 | 125 | 1 | 125 | 32 | >125 | 125 | 125 | 125 | 125 |
| Hemophilus influenzae A9833 | — | — | — | — | — | — | — | — | — | — |
| Haemophilus influenzae A21522 | — | — | — | — | — | — | — | — | — | — |
| Bacteroides fragilis A20931 | — | — | — | — | — | — | — | — | — | — |
| Bacteroides fragilis A20929 | — | — | — | — | — | — | — | — | — | — |
| Pseudomonas aeruginosa A20599 | — | — | — | — | | | — | — | — | — |
| Pseudomonas aeruginosa A9925 | — | — | — | — | | | — | — | — | — |
| Pseudomonas aeruginosa A20229 | — | — | — | — | | | — | — | — | — |
| Proteus species A20543 | — | — | — | — | | | — | — | — | — |
| Proteus mirabilis A9716 | — | 16 | 2 | >125 | | | 125 | 16 | 125 | 2 |

-continued

| | M.I.C. in mcg/ml | | | | | | | | | |
|---|---|---|---|---|---|---|---|---|---|---|
| | Compound (Example No.) | | | | | | | | | |
| Organism | 22 | 24 | 25 | 26 | 32 | 34 | 43 | 44 | 45 | 51 |
| Streptococcus pneumoniae A9585 | .25 | 2 | .25 | .016 | .25 | .25 | .016 | 2 | .5 | .25 .25 |
| Streptococcus pyogenes A9604 | 2 | 2 | .25 | .06 | 8 | 2 | .25 | 16 | 1 | 2 1 |
| Staphylococcus aureus A9537 | 2 | 4 | .5 | .13 | 8 | 4 | .03 | 32 | 1 | 2 1 |
| Staph aureus +50% Serum A9537 | 63 | 16 | 8 | 4 | 32 | 63 | 63 | >63 | 63 | 63 >32 |
| Staphylococcus aureus A9606 | 63 | 8 | 1 | 8 | 16 | 4 | 16 | >125 | 4 | 63 32 |
| Staphylococcus aureus A15097 | 125 | >125 | 125 | 125 | 63 | 16 | >125 | >125 | 125 | 125 63 |
| Streptococcus faecalis A20688 | 125 | 63 | 63 | 63 | >125 | 125 | 16 | 125 | 125 | 125 63 |
| Escherichia coli A15119 | 16 | 32 | 4 | .5 | 63 | 4 | 63 | 63 | 125 | 16 8 |
| Escherichia coli A20341-1 | 125 | 125 | 63 | 63 | >125 | 16 | >125 | >125 | 125 | 125 >63 |
| Klebsiella pneumoniae A15130 | 32 | >125 | 16 | 8 | 125 | 32 | >125 | >125 | 125 | 32 32 |
| Klebsiella species A20468 | >125 | 125 | >125 | >125 | >125 | 125 | >125 | >125 | 125 | >125 >63 |
| Proteus mirabilis A9900 | 16 | 63 | 4 | 1 | 63 | 16 | 32 | 63 | 32 | 16 8 |
| Proteus vulgaris A9716 | — | — | — | — | 125 | 16 | — | — | — | — |
| Proteus morganii A15153 | 32 | 125 | 4 | 1 | 125 | 32 | 32 | 125 | 125 | 32 16 |
| Proteus rettgeri A21203 | 16 | 125 | 8 | 2 | 63 | 32 | — | 125 | 63 | 16 8 |
| Serratia marcescens A20019 | 32 | 63 | 4 | 1 | 63 | 32 | 16 | >125 | 125 | 32 16 |
| Enterobacter cloacae A9659 | 16 | 63 | 4 | 2 | 125 | 32 | >125 | >125 | 125 | 16 16 |
| Enterobacter cloacae A9656 | 32 | 125 | 8 | 1 | 125 | 63 | 125 | >125 | 125 | 32 32 |
| Pseudomonas aeruginosa A9843A | 125 | 125 | 16 | 1 | 125 | 125 | >125 | 125 | 125 | 125 63 |
| Pseudomonas aeruginosa A21213 | 125 | >125 | >125 | 125 | 125 | 125 | >125 | 125 | 125 | 125 63 |
| Hemophilus influenzae A9833 | — | >125 | >125 | 125 | — | — | — | — | — | — |
| Haemophilus influenzae A21522 | — | — | — | — | — | — | — | — | — | — |
| Bacteroides fragilis A20931 | — | — | — | — | — | — | — | — | — | — |
| Bacteroides fragilis A20929 | — | — | — | — | — | — | — | — | — | — |
| Pseudomonas aeruginosa A20599 | — | — | — | — | — | — | — | — | — | — |
| Pseudomonas aeruginosa A9925 | — | — | — | — | — | — | — | — | — | — |
| Pseudomonas aeruginosa A20229 | — | — | — | — | — | — | — | — | — | — |
| Proteus species A20543 | — | — | — | — | — | — | — | — | — | — |
| Proteus mirabilis A9716 | 16 | — | — | — | — | — | 16 | 63 | 63 | 16 |
| Providencia stuartii A21205 | — | — | — | — | — | — | 63 | — | — | — |
| Proteus mirabilis A9555 | — | — | — | — | — | — | — | — | — | 63 |

| | Compound (Example No.) | | | | | |
|---|---|---|---|---|---|---|
| Organism | 53 | 54 | 56 | 57 | 58 | 68 |
| Streptococcus pneumoniae A9585 | .06 | 63 | 125 | .06 | .25 | 4 |
| Streptococcus pyogenes A9604 | .13 | 125 | 125 | .13 | 2 | 16 |
| Staphylococcus aureus A9537 | 1 | 32 | >125 | 1 | 4 | 16 |
| Staph aureus +50% Serum A9537 | >63 | 32 | >63 | 16 | 63 | >63 |
| Staphylococcus aureus A9606 | 8 | >125 | >125 | 125 | 4 | 63 |
| Staphylococcus aureus A15097 | 16 | 63 | >125 | >125 | 16 | 63 |
| Streptococcus faecalis | 8 | 63 | >125 | 125 | 125 | 125 |

-continued

| M.I.C. in mcg/ml | | | | | | |
|---|---|---|---|---|---|---|
| A20688 *Escherichia coli* | 2 | 63 | >125 | 16 | 4 | 63 |
| A15119 *Escherichia coli* | 63 | 32 | >125 | >125 | 16 | 63 |
| A20341-1 *Klebsiella pneumoniae* | 16 | >125 | >125 | 125 | 32 | 63 |
| A15130 Klebsiella species | >125 | 63 | >125 | >125 | 125 | 125 |
| A20468 *Proteus mirabilis* | 2 | 125 | >125 | 8 | 16 | 63 |
| A9900 *Proteus vulgaris* | 2 | >125 | >125 | 63 | 16 | 63 |
| A9555 *Proteus morganii* | 8 | 125 | >125 | 32 | 32 | 125 |
| A15153 *Proteus rettgeri* | 2 | 125 | >125 | 16 | 32 | 63 |
| A21203 *Serratia marcescens* | 8 | 125 | >125 | 63 | 32 | 63 |
| A20019 *Enterobacter cloacae* | 16 | 125 | >125 | 125 | 32 | 63 |
| A9659 *Enterobacter cloacae* | 32 | 32 | >125 | 63 | 63 | 63 |
| A9656 *Pseudomonas aeruginosa* | 125 | 125 | 125 | 125 | 125 | 125 |
| A9843A *Pseudomonas aeruginosa* | 125 | 125 | 125 | 125 | 125 | 125 |
| A21213 *Hemophilus influenzae* | — | — | — | — | — | — |
| A9833 *Haemophilus influenzae* | — | — | — | — | — | — |
| A21522 *Bacteroides fragilis* | — | — | — | — | — | — |
| A20931 *Bacteroides fragilis* | — | — | — | — | — | — |
| A20929 | | | | | | |

| Organism | Compound (Example No.) | | | | | | | |
|---|---|---|---|---|---|---|---|---|
| | 59 | 60 | 65 | 79 | 61 | 62 | 64 | 66,96 |
| *Streptococcus pneumoniae* | 32 | .25 | .004 | .016 | .03 | .03 | .016 | .03 |
| A9585 | 32 | .25 | .008 | — | | | | |
| *Streptococcus pyogenes* | 125 | 1 | .004 | .03 | .06 | .5 | .03 | .03 |
| A9604 | 125 | 1 | .008 | — | | | | |
| *Staphylococcus aureus* | — | — | .008 | .06 | .5 | .03 | .06 | .06 |
| A9537 | >125 | 2 | .008 | — | | | | |
| Staph aureus +50% Serum A9537 | — | — | .06 | .25 | 4 | .25 | .13 | .5 |
| | >63 | 8 | .06 | — | | | | |
| *Staphylococcus aureus* | — | — | .06 | .5 | 1 | .25 | .13 | .25 |
| A9606 | >125 | 4 | .06 | — | | | | |
| *Staphylococcus aureus* | — | — | .06 | >63 | 2 | .5 | .25 | 1 |
| A15097 | >125 | 8 | .25 | 125 | | | | |
| *Streptococcus faecalis* | >125 | 63 | .5 | 16 | 2 | 32 | 4 | 4 |
| A20688 | >125 | 63 | .5 | — | | | | |
| *Escherichia coli* | >125 | 16 | .13 | 4 | 2 | 8 | 2 | .5 |
| A15119 | >125 | 16 | .25 | — | | | | |
| *Escherichia coli* | >125 | 16 | <.25 | 16 | 8 | 8 | 2 | .5 |
| A20341-1 | >125 | 16 | .13 | — | | | | |
| *Klebsiella pneumoniae* | >125 | 16 | <.25 | 16 | 8 | 16 | 4 | 2 |
| A15130 | >125 | 16 | .5 | — | | | | |
| Klebsiella species | >125 | 16 | .5 | >63 | 63 | 32 | 4 | 2 |
| A20468 | >125 | 16 | .5 | — | | | | |
| *Proteus mirabilis* | >125 | 32 | <.25 | 8 | 2 | 2 | 4 | 1 |
| A9900 | >125 | 16 | .25 | — | | | | |
| *Proteus vulgaris* | >125 | 16 | <.25 | 16 | 4 | 2 | 2 | 1 |
| A21559 | >125 | 16 | .25 | — | | | | |
| *Proteus morganii* | >125 | 32 | 1 | 16 | 8 | 2 | 4 | 4 |
| A15153 | >125 | 16 | 1 | — | | | | |
| *Proteus rettgeri* | >125 | 16 | <.25 | 8 | 2 | 2 | 4 | 2 |
| A21203 | >125 | 16 | .5 | — | | | | |
| *Serratia marcescens* | >125 | 16 | .5 | 8 | 8 | 16 | 4 | 2 |
| A20019 | >125 | 16 | .5 | — | | | | |
| *Enterobacter cloacae* | >125 | 32 | 4 | 32 | 8 | 32 | 4 | 8 |
| A9659 | >125 | — | 2 | — | | | | |
| *Enterobacter cloacae* | >125 | 16 | .5 | — | 32 | 1 | 16 | 2 |
| A9656 | >125 | — | .5 | — | | | | |
| *Pseudomonas aeruginosa* | >125 | >125 | 16 | — | 63 | 2 | 16 | 16 |
| A9843A | >125 | — | 16 | — | | | | |
| *Pseudomonas aeruginosa* | >125 | >125 | 125 | — | — | — | — | 8 |
| A21213 | >125 | — | 63 | — | | | | |
| *Hemophilus influenzae* | — | — | — | — | — | — | — | — |
| A9833 | — | — | — | — | | | | |
| *Haemophilus influenzae* | — | — | — | — | — | — | — | — |

-continued

| | M.I.C. in mcg/ml | | | | | | | |
|---|---|---|---|---|---|---|---|---|
| A21522 | — | — | — | — | | | | |
| *Bacteroides fragilis* A20931 | — | — | — | — | — | — | — | — |
| *Bacteroides fragilis* A20929 | — | — | — | — | — | — | — | — |

| | Compound (Example No.) | | | | | | | |
|---|---|---|---|---|---|---|---|---|
| Organism | 70 | 72 | 73 | 74 | 75 | 76 | 77 | 78 |
| *Streptococcus pneumoniae* A9585 | >63 | 1 | .13 | .001 | .002 | .03 | .03 | .03 |
| *Streptococcus pyogenes* A9604 | >63 | 2 | .25 | .001 | .016 | .5 | .5 | .06 |
| *Staphylococcus aureus* A9537 | >63 | 4 | .25 | .004 | .06 | 1 | .13 | .13 |
| Staph aureus +50% Serum A9537 | >32 | 63 | 1 | 2 | .5 | >63 | >63 | 2 |
| *Staphylococcus aureus* A9606 | >63 | 32 | 32 | 32 | 63 | 4 | 4 | 16 |
| *Staphylococcus aureus* A15097 | >63 | 63 | 16 | 32 | 4 | 8 | 16 | 8 |
| *Streptococcus faecalis* A20688 | >63 | >125 | 32 | 1 | 4 | 125 | 125 | 16 |
| *Escherichia coli* A15119 | >63 | 125 | 8 | 8 | 1 | 4 | 4 | 2 |
| *Escherichia coli* A20341-1 | >63 | >125 | 125 | 125 | 8 | >125 | >125 | 16 |
| *Klebsiella pneumoniae* A15130 | >63 | >125 | 32 | 32 | 4 | 63 | >125 | 4 |
| *Klebsiella species* A20468 | >63 | >125 | >125 | >125 | >125 | >125 | >125 | >125 |
| *Proteus mirabilis* A9900 | >63 | 125 | 8 | 4 | 1 | 8 | 2 | 4 |
| *Proteus vulgaris* A21559 | >63 | 125 | 32 | 16 | 2 | 8 | 63 | 4 |
| *Proteus morganii* A15153 | >63 | >125 | 32 | 16 | 4 | 16 | 16 | 8 |
| *Proteus rettgeri* A21203 | >63 | 125 | 16 | 16 | 1 | 8 | >125 | 4 |
| *Serratia marcescens* A20019 | >63 | >125 | 16 | 16 | 2 | 16 | >125 | 4 |
| *Enterobacter cloacae* A9659 | >63 | >125 | 63 | 32 | 4 | 16 | >125 | 4 |
| *Enterobacter cloacae* A9656 | >63 | >125 | 32 | 32 | 4 | 16 | 125 | 4 |
| *Pseudomonas aeruginosa* A9843A | >63 | >125 | >125 | >125 | 63 | >125 | >125 | 16 |
| *Pseudomonas aeruginosa* A21213 | >63 | >125 | >125 | >125 | 125 | >125 | >125 | >125 |
| *Hemophilus influenzae* A9833 | — | — | — | — | — | — | — | — |
| *Haemophilus influenzae* A21522 | — | — | — | — | — | — | — | — |
| *Bacteroides fragilis* A20931 | — | — | — | — | — | — | — | — |
| *Bacteroides fragilis* A20929 | — | — | — | — | — | — | — | — |

| | Compound (Example No.) | | | | | | | |
|---|---|---|---|---|---|---|---|---|
| Organism | 80 | 81 | 82 | 83 | 84 | 85 | 86 | 87 |
| *Streptococcus pneumoniae* A9585 | .03 | 2 | .016 | .06 | 1 | .06 | .13 | .008 |
| *Streptococcus pyogenes* A9604 | .06 | 16 | .016 | .13 | 1 | .06 | .13 | .008 |
| *Staphylococcus aureus* A9537 | .06 | 32 | .25 | .5 | 4 | .06 | .13 | .016 |
| Staph aureus +50% Serum A9537 | .25 | >32 | 4 | 8 | 32 | 1 | 1 | .13 |
| *Staphylococcus aureus* A9606 | .5 | 2 | 16 | 32 | 16 | 16 | 32 | 4 |
| *Staphylococcus aureus* A15097 | >63 | 8 | 4 | >125 | >125 | >63 | 125 | 32 |
| *Streptococcus faecalis* A20688 | 16 | 63 | 63 | 125 | >125 | 16 | 32 | 8 |
| *Escherichia coli* A15119 | 4 | 2 | 8 | 2 | 16 | 4 | 2 | 4 |
| *Escherichia coli* A20341-1 | 8 | 32 | 32 | 16 | >125 | 63 | 8 | 16 |
| *Klebsiella pneumoniae* A15130 | 8 | 8 | 32 | 8 | 125 | 32 | 4 | 8 |
| Klebsiella species | >63 | >63 | >125 | >125 | >125 | >63 | >125 | >125 |

-continued

| | \multicolumn{8}{c}{M.I.C. in mcg/ml} |
|---|---|---|---|---|---|---|---|---|
| Proteus mirabilis A9900 | 4 | 4 | 4 | 2 | 8 | 4 | 2 | 4 |
| Proteus vulgaris A21559 | 8 | 16 | 8 | 8 | 63 | >63 | 8 | 16 |
| Proteus morganii A15153 | 16 | 8 | 16 | 4 | 16 | 4 | 8 | 4 |
| Proteus rettgeri A21203 | 8 | 8 | 8 | 4 | 32 | 4 | 2 | 4 |
| Serratia marcescens A20019 | 8 | 8 | 16 | 4 | 63 | 4 | 2 | 2 |
| Enterobacter cloacae A9659 | 16 | 8 | 63 | 16 | 125 | 8 | 8 | 16 |
| Enterobacter cloacae A9656 | 8 | 8 | 32 | 4 | 125 | 8 | 4 | 8 |
| Pseudomonas aeruginosa A9843A | 63 | 63 | >125 | 63 | >125 | 8 | 63 | 32 |
| Pseudomonas aeruginosa A21213 | >63 | >63 | >125 | 63 | >125 | 63 | 125 | >125 |
| Hemophilus influenzae A9833 | — | — | — | — | — | — | — | — |
| Haemophilus influenzae A21522 | — | — | — | — | — | — | — | — |
| Bacteroides fragilis A20931 | — | — | — | — | — | — | — | — |
| Bacteroides fragilis A20929 | — | — | — | — | — | — | — | — |

| | \multicolumn{9}{c}{Compound (Example No.)} |
|---|---|---|---|---|---|---|---|---|---|
| | | | | | | | \multicolumn{3}{c}{98} |
| Organism | 88 | 91 | 92 | 93 | 94 | 95 | isomer A | isomer B | isomer C |
| Streptococcus pneumoniae A9585 | .13 | .25 | .5 | >125 | 1 | 32 | .004 | .008 | .06 |
| Streptococcus pyogenes A9604 | .13 | .25 | .5 | >125 | 16 | 32 | .004 | .008 | .06 |
| Staphylococcus aureus A9537 | .13 | .25 | 8 | >125 | 32 | 125 | .03 | .03 | .13 |
| Staph aureus +50% Serum A9537 | .5 | 16 | 32 | >63 | >63 | >63 | .13 | .25 | 4 |
| Staphylococcus aureus A9606 | 16 | 32 | 16 | >125 | 32 | >125 | 32 | >63 | >63 |
| Staphylococcus aureus A15097 | 16 | >125 | 32 | >125 | >125 | >125 | >63 | >63 | >63 |
| Streptococcus faecalis A20688 | 63 | 63 | >63 | >125 | >125 | >125 | 4 | 8 | 32 |
| Escherichia coli A15119 | 4 | 1 | 32 | >125 | >125 | >125 | 1 | 1 | 2 |
| Escherichia coli A20341-1 | 16 | 63 | 32 | >125 | >125 | >125 | 16 | 16 | 16 |
| Klebsiella pneumoniae A15130 | 8 | 16 | 63 | >125 | >125 | >125 | 4 | 4 | 8 |
| Klebsiella species A20468 | >63 | >125 | 63 | >125 | >125 | >125 | >63 | >63 | >63 |
| Proteus mirabilis A9900 | 4 | 1 | 32 | >125 | >125 | >125 | 1 | 1 | 8 |
| Proteus vulgaris A21559 | 16 | 8 | 32 | >125 | >125 | >125 | 2 | 8 | 16 |
| Proteus morganii A15153 | 8 | 4 | 63 | >125 | >125 | >125 | 4 | 4 | 16 |
| Proteus rettgeri A21203 | 8 | 2 | 32 | >125 | >125 | >125 | 1 | 1 | 4 |
| Serratia marcescens A20019 | 8 | 4 | 63 | >125 | >125 | >125 | 2 | 2 | 8 |
| Enterobacter cloacae A9659 | 32 | 4 | 63 | >125 | >125 | >125 | 4 | 8 | 16 |
| Enterobacter cloacae A9656 | 32 | 2 | 63 | >125 | >125 | >125 | 2 | 2 | 8 |
| Pseudomonas aeruginosa A9843A | 63 | 125 | >63 | >125 | >125 | >125 | >63 | 63 | 32 |
| Pseudomonas aeruginosa A21213 | >63 | 125 | >63 | >125 | >125 | >125 | >63 | >63 | >63 |
| Hemophilus influenzae A9833 | — | — | — | — | — | — | — | — | — |
| Haemophilus influenzae A21522 | — | — | — | — | — | — | — | — | — |
| Bacteroides fragilis A20931 | — | — | — | — | — | — | — | — | — |
| Bacteroides fragilis A20929 | — | — | — | — | — | — | — | — | — |

Compound (Example No.)

-continued

| Organism | 99 | 100 | 101 | 102 | 103 | 104 | 105 | 106 | 107 | 108 |
|---|---|---|---|---|---|---|---|---|---|---|
| *Streptococcus pneumoniae* A9585 | 1 | .25 | .5 | .008 | 63 | 16 | 4 | 32 | .5 | .25 |
| *Streptococcus pyogenes* A9604 | 1 | .25 | .5 | .016 | 63 | 32 | 4 | 32 | .5 | .25 |
| *Staphylococcus aureus* A9537 | 1 | .25 | .5 | .03 | >63 | 63 | >8 | 63 | .5 | .25 |
| Staph aureus +50% Serum A9537 | 16 | 8 | 4 | .25 | >32 | >32 | >32 | >32 | 16 | 16 |
| *Staphylococcus aureus* A9606 | 4 | >32 | 4 | 2 | >63 | 63 | 63 | >63 | 32 | 16 |
| *Staphylococcus aureus* A15097 | 32 | >32 | 63 | 8 | >63 | 63 | >63 | >63 | >63 | >125 |
| *Streptococcus faecalis* A20688 | 63 | >32 | >63 | 4 | >63 | 63 | >63 | >63 | >63 | 125 |
| *Escherichia coli* A15119 | 8 | 4 | 8 | 1 | >63 | >63 | 63 | 63 | 63 | 63 |
| *Escherichia coli* A20341-1 | 63 | 32 | 32 | 16 | >63 | >63 | 63 | 63 | >63 | >125 |
| *Klebsiella pneumoniae* A15130 | 32 | 16 | 32 | 2 | >63 | >63 | 63 | >63 | >63 | 125 |
| *Klebsiella species* A20468 | >63 | >32 | >63 | >63 | >63 | >63 | >63 | >63 | >63 | >125 |
| *Proteus mirabilis* A9900 | 8 | 8 | 8 | 2 | 63 | >63 | >63 | 63 | 63 | 63 |
| *Proteus vulgaris* A21559 | 16 | 16 | 16 | 16 | >63 | >63 | >63 | >63 | 63 | 125 |
| *Proteus morganii* A15153 | 16 | 16 | 16 | 2 | >63 | >63 | >63 | >63 | 63 | 63 |
| *Proteus rettgeri* A21203 | 8 | 8 | 16 | 2 | >63 | 63 | 32 | 63 | 63 | 63 |
| *Serratia marcescens* A20019 | 16 | 8 | 32 | 2 | >63 | >63 | >63 | 63 | 63 | 125 |
| *Enterobacter cloacae* A9659 | 16 | 16 | 32 | 4 | >63 | >63 | 63 | >63 | >63 | 125 |
| *Enterobacter cloacae* A9656 | 16 | 8 | 63 | 2 | >63 | >63 | 63 | 63 | 63 | 125 |
| *Pseudomonas aeruginosa* A9843A | >63 | >32 | 63 | 8 | 63 | 63 | 63 | 63 | 63 | 63 |
| *Pseudomonas aeruginosa* A21213 | >63 | >32 | 63 | >63 | 63 | 63 | 63 | 63 | 63 | 125 |
| *Hemophilus influenzae* A9833 | — | — | — | — | — | — | — | — | — | — |
| *Haemophilus influenzae* A21522 | — | — | — | — | — | — | — | — | — | — |
| *Bacteroides fragilis* A20931 | — | — | — | — | — | — | — | — | — | — |
| *Bacteroides fragilis* A20929 | — | — | — | — | — | — | — | — | — | — |

Representative compounds of the present invention were also tested in vivo in mice and their $PD_{50}$ (dose of compound in mg/kg required to protect 50% of the treated mice against an otherwise lethal infection of a microorganism) values determined with respect to the test organisms shown below.

*E. coli* A15119

| Compound | # of infecting organisms of *E. coli* A15119 | # of treatments | Treatment route | $PD_{50}$ (mg/kg/treatment) |
|---|---|---|---|---|
| Compound of Ex. 73 | $7.4 \times 10^5$ | 2 | IM | 25 |
| Compound of Ex. 98 (isomer A) | $7.8 \times 10^5$ | 2 | IM | 17.4 |
| Compound of Ex. 78 | $7 \times 10^5$ | 2 | IM | 28 |
| Compound of Ex. 75 | $6.5 \times 10^5$ | 2 | PO | >50 |
|  | $6.5 \times 10^5$ | 2 | IM | 25 |

*S. aureus* A9606

| Compound | # of infecting organisms of *S. aureus* A9606 | # of treatments | Treatment route | $PD_{50}$ (mg/kg/treatment) |
|---|---|---|---|---|
| Compound of Prep. 2, 3 | $8 \times 10^8$ | 2 | IM | >50 |
| Compound of Ex. 73 | $8 \times 10^8$ | 2 | IM | 6.3 |

*K. pneumoniae* A15130

| Compound | # of infecting organisms of *K. pneumoniae* A15130 | # of treatments | Treatment route | $PD_{50}$ (mg/kg/treatment) |
|---|---|---|---|---|
| Compound of Prep. 2, 3 | $1.2 \times 10^3$ | 2 | IM | >400 |
| Compound of Ex. 73 | $1.2 \times 10^3$ | 2 | IM | >100 |

S. pneumoniae A9585

| Compound | # of infecting organisms of S. pneumoniae A9585 | # of treatments | Treatment route | PD$_{50}$ (mg/kg/treatment) |
|---|---|---|---|---|
| Compound of Prep. 2, 3 | $3 \times 10^4$ | 2 | IM | >12.5 |
| Compound of Ex. 73 | $3 \times 10^4$ | 2 | IM | 1.2 |
| Compound of Prep. 2, 3 | $3.4 \times 10^4$ | 2 | IM | >50 |
| Compound of Ex. 73 | $3.4 \times 10^4$ | 2 | IM | 1.56 |

Proteus mirabilis A9900

| Compound | # of infecting organisms of P. mirabilis A9900 | # of treatments | Treatment route | PD$_{50}$ (mg/kg/treatment) |
|---|---|---|---|---|
| Compound of Ex. 73 | $1.3 \times 10^7$ | 2 | IM | >100 |

S. pyogenes A9604

| Compound | # of infecting organisms of S. pyogenes A9604 | # of treatments | Treatment route | PD$_{50}$ (mg/kg/treatment) |
|---|---|---|---|---|
| Compound of Prep. 2, 3 | $8 \times 10^3$ | 2 | IM | >12.5 |
| Compound of Ex. 73 | $8 \times 10^3$ | 2 | IM | 0.51 |
| Compound of Prep. 2, 3 | $1.2 \times 10^3$ | 2 | IM | >50 |
| Compound of Ex. 73 | $1.2 \times 10^3$ | 2 | IM | 0.89 |

S. aureus A9537

| Compound | # of infecting organisms of S. aureus A9537 | # of treatments | Treatment route | PD$_{50}$ (mg/kg/treatment) |
|---|---|---|---|---|
| Compound of Ex. 22 | $1.1 \times 10^6$ | 2 | IM | 0.63 |
| Compound of Prep. 2, 3 | $1.1 \times 10^6$ | 2 | IM | 13 |
| Compound of Ex. 65 | $7.8 \times 10^5$ | 2 | IM | 0.12 |
| Compound of Prep. 2, 3 | $7.8 \times 10^5$ | 2 | IM | 13 |
| Compound of Ex. 83 | $1.1 \times 10^6$ | 2 | IM | 3.3 |
| Compound of Prep. 2, 3 | $1.1 \times 10^6$ | 2 | IM | 22 |
| Compound of Ex. 24 | $1 \times 10^6$ | 2 | IM | 0.63 |
| Compound of Ex. 82 | $1 \times 10^6$ | 2 | IM | 1.25 |
| Compound of Ex. 84 | $1 \times 10^6$ | 2 | IM | 33 |
| Compound of Ex. 86 | $1 \times 10^6$ | 2 | IM | 1.9 |
| Compound of Ex. 87 | $1 \times 10^6$ | 2 | IM | 0.12 |
| Compound of Ex. 91 | $9.1 \times 10^5$ | 2 | IM | 9.6 |
| Compound of Ex. 98 (isomer A) | $9.1 \times 10^5$ | 2 | IM | 0.04 |
| Compound of Ex. 98 (isomer B) | $9.1 \times 10^5$ | 2 | IM | 0.12 |
| Compound of Ex. 66 | $1.1 \times 10^6$ | 2 | IM | 0.12 |
| Compound of Ex. 60 | $6.6 \times 10^5$ | 2 | IM | 7.7 |
| Compound of Ex. 75 | $7.3 \times 10^5$ | 2 | IM | 0.4 |
| Compound of Ex. 13 | $7.3 \times 10^5$ | 2 | IM | 12.5 |
| Compound of Ex. 62 | $8.6 \times 10^5$ | 2 | IM | 1.0 |
| Compound of Ex. 73 | $6.8 \times 10^5$ | 2 | IM | 0.2 |
| Compound of Ex. 73 | $1 \times 10^6$ | 2 | IM | 0.2 |
|  | $1 > 10^6$ | 2 | PO | 0.5 |
| Compound of Ex. 74 | $7.3 \times 10^5$ | 2 | IM | 0.82 |
| Compound of Ex. 78 | $1 \times 10^6$ | 2 | IM | 0.63 |
|  | $1 \times 10^6$ | 2 | PO | 2.5 |
| Compound of Ex. 103 | $8 \times 10^5$ | 2 | IM | >5 |
| Compound of Ex. 64 | $8 \times 10^5$ | 2 | IM | 0.04 |
| Compound of Ex. 80 | $8 \times 10^5$ | 2 | IM | 0.6 |
| Compound of Ex. 73 | $8 \times 10^5$ | 2 | IM | 0.2 |
| Compound of Ex. 79 | $8 \times 10^5$ | 2 | IM | 0.8 |

Mouse blood levels after intramuscular administration of representative compounds of the present invention were determined and are reported in the table below.

| | *Mouse Blood Levels in mcg/ml After intramuscular Administration of 40 mg/kg Body Weight | | | | | | |
|---|---|---|---|---|---|---|---|
| | Minutes After Administration | | | | | | |
| Compound | 10 | 20 | 30 | 45 | 60 | 90 | 120 |
| Compound of Ex. 65 | 44.7 | 34.4 | 23.7 | 17.6 | 9.8 | 3.6 | 1 |
| Compound of Ex. 78 | 29.7 | 19.3 | 12.6 | 6.6 | <5.0 | <5.0 | <5 |
| Compound of Ex. 73 | 37.9 | 30.8 | 21.2 | 13.2 | 8.4 | 3.4 | <3 |
| Compound of Ex. 86 | 36 | 26.3 | 16.5 | 7.5 | 4.0 | <3.1 | <3.1 |
| Compound of Ex. 87 | 50.3 | 47.3 | 34.6 | 23.3 | — | — | — |
| Compound of Ex. 24 | 51.4 | 37.1 | 21.8 | 9.4 | 5.0 | <3.1 | <3.1 |
| Compound of Ex. 22 | 36.5 | 39.9 | 31.5 | 16.5 | 11.5 | 5.7 | 3.1 |

*Average of 6 mice

We claim:
1. An intermediate selected from the group consisting of a compound of the formula

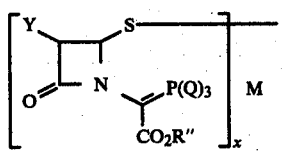

wherein Y is $C_1$–$C_6$ alkyl, $C_1$–$C_6$ alkyl substituted by a hydroxy group or $C_1$–$C_6$ alkyl substituted by a hydroxy group which is protected by a conventional blocking group, Q is phenyl or (lower)alkyl, R" is a conventional carboxyl protecting group, X is 1 or 2 and M is Cu(II), Pb(II) or Hg(II) when X is 2 or Ag(I) when X is 1; and a compound of the formula

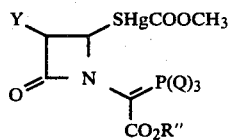

in which Y, Q and R" are as defined above.

2. An intermediate according to claim 1 having the formula

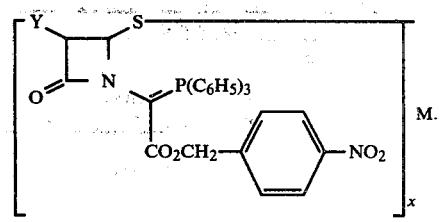

wherein X is 1 or 2, M is Cu(II), Pb(II) or Hg(II) when X is 2 or Ag(I) when X is 1 and Y is α-hydroxyethyl or α-hydroxyethyl in which the hydroxy group is protected by a conventional blocking group.

3. An intermediate according to claim 2 wherein Y is

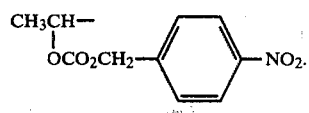

4. An intermediate according to claim 1 having the formula

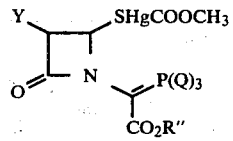

wherein Y is α-hydroxyethyl or α-hydroxyethyl in which the hydroxy group is protected by a conventional blocking group.

* * * * *